(12) United States Patent
zur Megede et al.

(10) Patent No.: US 8,263,394 B2
(45) Date of Patent: Sep. 11, 2012

(54) POLYNUCLEOTIDES ENCODING ANTIGENIC HIV TYPE B POLYPEPTIDES, POLYPEPTIDES, AND USES THEREOF

(75) Inventors: Jan zur Megede, Larkspur, CA (US); Susan W. Barnett, San Francisco, CA (US)

(73) Assignee: Novartis Vaccines & Diagnostics Inc., Emeryville, CA (US)

( * ) Notice: Subject to any disclaimer, the term of this patent is extended or adjusted under 35 U.S.C. 154(b) by 327 days.

(21) Appl. No.: 12/018,413

(22) Filed: Jan. 23, 2008

(65) Prior Publication Data
US 2009/0004733 A1    Jan. 1, 2009

Related U.S. Application Data

(60) Division of application No. 11/100,356, filed on Apr. 6, 2005, now abandoned, which is a continuation-in-part of application No. 10/190,434, filed on Jul. 5, 2002, now abandoned, said application No. 11/100,356 is a continuation-in-part of application No. 10/387,336, filed on Mar. 11, 2003, now Pat. No. 7,348,177, which is a continuation of application No. 09/475,515, filed on Dec. 30, 1999, now Pat. No. 6,602,705.

(60) Provisional application No. 60/349,728, filed on Jan. 16, 2002, provisional application No. 60/316,860, filed on Aug. 31, 2001, provisional application No. 60/168,471, filed on Dec. 1, 1999, provisional application No. 60/114,495, filed on Dec. 31, 1998.

(51) Int. Cl.
*C12N 15/00* (2006.01)
*C12N 15/48* (2006.01)

(52) U.S. Cl. .................. 435/320.1; 536/23.4; 536/23.72

(58) Field of Classification Search ........................ None
See application file for complete search history.

(56) References Cited

U.S. PATENT DOCUMENTS

| | | |
|---|---|---|
| 4,652,639 A | 3/1987 | Stabinsky |
| 4,861,707 A | 8/1989 | Ivanoff et al. |
| RE33,653 E | 7/1991 | Mark et al. |
| 5,032,510 A | 7/1991 | Kovacevic et al. |
| 5,082,767 A | 1/1992 | Hatfield et al. |
| 5,128,319 A | 7/1992 | Arlinghaus |
| 5,130,247 A | 7/1992 | Kniskern et al. |
| 5,156,949 A | 10/1992 | Luciw et al. |
| 5,256,767 A | 10/1993 | Salk et al. |
| 5,304,472 A | 4/1994 | Bass et al. |
| 5,364,773 A | 11/1994 | Paoletti et al. |
| 5,419,900 A | 5/1995 | Lane et al. |
| 5,503,833 A | 4/1996 | Redmond et al. |
| 5,550,280 A | 8/1996 | Dao-Cong et al. |
| 5,637,677 A | 6/1997 | Greene et al. |
| 5,665,569 A | 9/1997 | Ohno |
| 5,665,720 A | 9/1997 | Young et al. |
| 5,670,152 A | 9/1997 | Weiner et al. |
| 5,683,864 A | 11/1997 | Houghton et al. |
| 5,686,078 A | 11/1997 | Becker et al. |
| 5,688,688 A | 11/1997 | Luciw et al. |
| 5,693,755 A | 12/1997 | Buonagurio et al. |
| 5,712,088 A | 1/1998 | Houghton et al. |
| 5,714,596 A | 2/1998 | Houghton et al. |
| 5,728,520 A | 3/1998 | Weiner et al. |
| 5,741,492 A | 4/1998 | Hurwitz et al. |
| 5,750,373 A | 5/1998 | Garrard et al. |
| 5,786,464 A | 7/1998 | Seed |
| 5,792,459 A | 8/1998 | Haigwood |
| 5,795,737 A | 8/1998 | Seed |
| 5,817,637 A | 10/1998 | Weiner et al. |
| 5,837,242 A | 11/1998 | Holliger et al. |
| 5,837,818 A | 11/1998 | Buonagurio et al. |
| 5,840,313 A | 11/1998 | Vahine et al. |
| 5,846,546 A | 12/1998 | Hurwitz |
| 5,853,736 A | 12/1998 | Becker et al. |
| 5,858,675 A | 1/1999 | Hillman et al. |
| 5,859,193 A | 1/1999 | Devare et al. |
| 5,866,320 A | 2/1999 | Rovinski et al. |
| 5,871,747 A | 2/1999 | Gengoux-Sedlik et al. |
| 5,876,724 A | 3/1999 | Girard |
| 5,876,731 A | 3/1999 | Sia et al. |
| 5,879,907 A | 3/1999 | Aberg et al. |
| 5,879,925 A | 3/1999 | Rovinski et al. |
| 5,889,176 A | 3/1999 | Rovinski et al. |
| 5,932,445 A | 8/1999 | Lal et al. |
| 5,951,975 A | 9/1999 | Falo, Jr. et al. |
| 5,955,342 A | 9/1999 | Rovinski et al. |
| 5,965,726 A | 10/1999 | Pavlakis et al. |
| 5,972,596 A | 10/1999 | Pavlakis et al. |

(Continued)

FOREIGN PATENT DOCUMENTS
EP        0187041        7/1986
(Continued)

OTHER PUBLICATIONS

Verma et al. (Nature, 1997, vol. 389, pp. 239-242.*
Barre-Sinoussi et al., "Isolation of a T-lymphotropic retrovirus from a patient at risk for acquired immune deficiency syndrome (AIDS)," *Science 220*, 868-71, 1983.
Kotsopoulou et al., A Rev-Independent Human Immunodeficiency Virus Type 1 (HIV-1)-Based Vector That Exploits a Codon-Optimized HIV-1 gag-pol Gene. *J. Virol.* 74, 4839-52, 2000.
GenBank accession No. AF110965, 2001.
GenBank accession No. AF110967, 2001.
GenBank accession No. AF110968, 2001.
GenBank accession No. AF110975, 2001.
GenBank accession No. M65024, 1993.
Adams at al., "The Expression of Hybrid Hiv:ty Virus-like Particles in Yeast," *Nature* 329:68-70 (1987).

(Continued)

*Primary Examiner* — Mary E Mosher
*Assistant Examiner* — Myron Hill
(74) *Attorney, Agent, or Firm* — Regina Bautista; Helen Lee

(57) ABSTRACT

The present invention relates to polynucleotides encoding immunogenic HIV polypeptides. Uses of the polynucleotides in applications including immunization, generation of packaging cell lines, and production of HIV polypeptides are also described. Polynucleotides encoding antigenic HIV polypeptides are described, as are uses of these polynucleotides and polypeptide products therefrom, including formulations of immunogenic compositions and uses thereof.

10 Claims, 84 Drawing Sheets

U.S. PATENT DOCUMENTS

| | | | |
|---|---|---|---|
| 6,001,977 A | 12/1999 | Chang et al. | |
| 6,004,763 A | 12/1999 | Gengoux et al. | |
| 6,025,125 A | 2/2000 | Rovinski et al. | |
| 6,060,273 A | 5/2000 | Dirks et al. | |
| 6,060,587 A | 5/2000 | Weiner et al. | |
| 6,063,384 A | 5/2000 | Morrow et al. | |
| 6,074,636 A | 6/2000 | Nichols | |
| 6,080,408 A | 6/2000 | Rovinski et al. | |
| 6,087,486 A | 7/2000 | Weiner et al. | |
| 6,090,388 A | 7/2000 | Wang | |
| 6,093,800 A | 7/2000 | Reiter et al. | |
| 6,096,505 A | 8/2000 | Selby et al. | |
| 6,099,847 A | 8/2000 | Tobin et al. | |
| 6,114,148 A | 9/2000 | Seed et al. | |
| 6,132,973 A | 10/2000 | Lal et al. | |
| 6,139,833 A | 10/2000 | Burgess et al. | |
| 6,140,059 A | 10/2000 | Schawaller | |
| 6,146,635 A | 11/2000 | Cano et al. | |
| 6,172,201 B1 | 1/2001 | Weiner et al. | |
| 6,174,666 B1 | 1/2001 | Pavlakis et al. | |
| 6,214,804 B1 | 4/2001 | Felgner et al. | |
| 6,291,157 B1 | 9/2001 | Rovinski et al. | |
| 6,291,664 B1 | 9/2001 | Pavlakis et al. | |
| 6,316,253 B1 | 11/2001 | Innis et al. | |
| 6,331,404 B1 | 12/2001 | Berman et al. | |
| 6,602,705 B1 | 8/2003 | Barnett et al. | |
| 7,622,125 B2 * | 11/2009 | zur Megede et al. | 424/204.1 |

FOREIGN PATENT DOCUMENTS

| | | |
|---|---|---|
| EP | 0199301 A1 | 10/1986 |
| EP | 0242216 | 10/1987 |
| EP | 0314317 A1 | 5/1989 |
| EP | 0449116 B1 | 10/1991 |
| EP | 0617132 A2 | 9/1994 |
| EP | 0449116 B1 | 10/1999 |
| WO | WO 93/23569 | 11/1893 |
| WO | WO 86/03224 | 6/1986 |
| WO | WO 87/02775 | 5/1987 |
| WO | WO 88/00471 | 1/1988 |
| WO | WO 88/10300 | 12/1988 |
| WO | WO 89/01940 | 3/1989 |
| WO | WO 89/02277 | 3/1989 |
| WO | WO 89/02922 | 4/1989 |
| WO | WO 89/03222 | 4/1989 |
| WO | WO 90/00556 | 1/1990 |
| WO | WO 90/02568 | 3/1990 |
| WO | WO 90/03984 | 4/1990 |
| WO | WO 90/10438 | 9/1990 |
| WO | WO 90/11092 | 10/1990 |
| WO | WO 90/11359 | 10/1990 |
| WO | WO 90/12094 | 10/1990 |
| WO | WO 90/15141 | 12/1990 |
| WO | WO 91/04273 | 4/1991 |
| WO | WO 91/06319 | 5/1991 |
| WO | WO 91/07425 | 5/1991 |
| WO | WO 91/07510 | 5/1991 |
| WO | WO 91/13360 | 9/1991 |
| WO | WO 91/13906 | 9/1991 |
| WO | WO 91/15238 | 10/1991 |
| WO | WO 91/15512 | 10/1991 |
| WO | WO 91/16926 | 11/1991 |
| WO | WO 91/18928 | 12/1991 |
| WO | WO 91/19803 | 12/1991 |
| WO | WO 92/03475 | 3/1992 |
| WO | WO 92/04046 | 3/1992 |
| WO | WO 92/05799 | 4/1992 |
| WO | WO 93/02102 | 2/1993 |
| WO | WO 93/04090 | 3/1993 |
| WO | WO 93/08836 | 5/1993 |
| WO | WO 93/14789 | 8/1993 |
| WO | WO 93/20212 | 10/1993 |
| WO | WO 93/21346 | 10/1993 |
| WO | WO 94/04574 | 3/1994 |
| WO | WO 94/07922 | 4/1994 |
| WO | WO 94/11523 | 5/1994 |
| WO | WO 94/13804 | 6/1994 |
| WO | WO 94/15621 | 7/1994 |
| WO | WO 94/16060 | 7/1994 |
| WO | WO 94/16737 | 8/1994 |
| WO | WO 94/18221 | 8/1994 |
| WO | WO 94/20141 | 9/1994 |
| WO | WO 94/20640 | 9/1994 |
| WO | WO 94/22477 | 10/1994 |
| WO | WO 94/26293 | 11/1994 |
| WO | WO 94/29339 | 12/1994 |
| WO | WO 95/03407 | 2/1995 |
| WO | WO 95/04818 | 2/1995 |
| WO | WO 95/11317 | 4/1995 |
| WO | WO 95/11701 | 5/1995 |
| WO | WO 95/24485 | 9/1995 |
| WO | WO 95/25124 | 9/1995 |
| WO | WO 95/27505 | 10/1995 |
| WO | WO 95/29700 | 11/1995 |
| WO | WO 95/33206 | 12/1995 |
| WO | WO 95/33835 | 12/1995 |
| WO | WO 96/02273 | 2/1996 |
| WO | WO 96/02557 | 2/1996 |
| WO | WO 96/04382 | 2/1996 |
| WO | WO 96/09066 | 3/1996 |
| WO | WO 96/09378 | 3/1996 |
| WO | WO 96/16178 | 5/1996 |
| WO | WO 96/20732 | 7/1996 |
| WO | WO 96/23509 | 8/1996 |
| WO | WO 96/25177 | 8/1996 |
| WO | WO 96/30523 | 10/1996 |
| WO | WO 96/40290 | 12/1996 |
| WO | WO 97/03198 | 1/1997 |
| WO | WO 97/11605 | 4/1997 |
| WO | WO 97/26009 | 7/1997 |
| WO | WO 97/31115 | 8/1997 |
| WO | WO 97/48370 | 12/1997 |
| WO | WO 98/08539 | 3/1998 |
| WO | WO 98/12207 | 3/1998 |
| WO | WO 98/34640 | 8/1998 |
| WO | WO 98/41536 | 9/1998 |
| WO | WO 98/41645 | 9/1998 |
| WO | WO 98/43182 | 10/1998 |
| WO | WO 98/48843 | 11/1998 |
| WO | WO 98/59074 | 12/1998 |
| WO | WO 99/02694 | 1/1999 |
| WO | WO 99/06599 | 2/1999 |
| WO | WO 99/09412 | 2/1999 |
| WO | WO 99/12416 | 3/1999 |
| WO | WO 99/13864 | 3/1999 |
| WO | WO 99/16883 | 4/1999 |
| WO | WO 99/27958 | 6/1999 |
| WO | WO 99/33346 | 7/1999 |
| WO | WO 99/41397 | 8/1999 |
| WO | WO 99/41398 | 8/1999 |
| WO | WO 99/52463 | 10/1999 |
| WO | WO 99/53960 | 10/1999 |
| WO | WO 99/67395 | 12/1999 |
| WO | WO 00/08043 | 2/2000 |
| WO | WO 00/15819 | 3/2000 |
| WO | WO 00/18929 | 4/2000 |
| WO | WO 00/21556 | 4/2000 |
| WO | WO 00/29561 | 5/2000 |
| WO | WO 00/39302 * | 7/2000 |
| WO | WO 00/39303 | 7/2000 |
| WO | WO 00/39304 | 7/2000 |
| WO | WO 00/44926 | 8/2000 |
| WO | WO 00/65076 | 11/2000 |
| WO | WO 00/66179 | 11/2000 |
| WO | WO 00/67761 | 11/2000 |
| WO | WO 00/67787 | 11/2000 |
| WO | WO 00/71561 | 11/2000 |
| WO | WO 01/02607 | 1/2001 |
| WO | WO 01/12223 | 2/2001 |
| WO | WO 01/16342 | 3/2001 |
| WO | WO 01/19958 | 3/2001 |
| WO | WO 01/21270 | 3/2001 |
| WO | WO 01/26681 | 4/2001 |
| WO | WO 01/29225 | 4/2001 |
| WO | WO 01/36614 | 5/2001 |
| WO | WO 01/42308 | 6/2001 |
| WO | WO 01/43693 | 6/2001 |

| WO | WO 01/45748 | 6/2001 |
| WO | WO 01/46408 | 6/2001 |
| WO | WO 01/47955 | 7/2001 |
| WO | WO 01/54701 | 8/2001 |
| WO | WO 01/54719 | 8/2001 |
| WO | WO 01/60393 | 8/2001 |
| WO | WO 01/60838 | 8/2001 |
| WO | WO 02/04493 | 1/2002 |
| WO | WO 03/004620 | 1/2003 |

OTHER PUBLICATIONS

Anderson, et al., "Human Gene Therapy," *Nature* 392(6679 Suppl):25-30 (1998).

Arthur, et al., "Serological Responses in Chimpanzees Inoculated with Human Immunodeficiency Virus Glycoprotein (Gp120) Subunit Vaccine," *Proc Natl Acad Sci USA* 84(23):8583-8587 (1987).

Azevedo et al., "Main Features of DNA-Based Immunization Vectors," *Braz J Med Biol Res.* 32(2):147-153 (1999).

Baker et al., "Structures of Bovine and Human Papillomaviruses. Analysis by Cryoelectron Microscopy and Three-dimensional Image Reconstruction," *Biophys. J.* 60:1445-1456(1991).

Barr, et al., "Antigenicity and Immunogenicity of Domains of the Human Immunodeficiency Virus (HIV) Envelope Polypeptide Expressed in the Yeast *Saccharomyces cerevisiae*," *Vaccine* 5(2):90-101 (1987).

Barrett, et al., "Large-scale production and purification of a vaccinia recombinant-derived HIV-1 gp160 and analysis of its immunogenicity," *AIDS Res Hum Retroviruses* 5(2):159-71 (1989).

Beard. W. A., et al.,"Role of the "Helix Clamp" in HIV-1 Reverse Transcriptase Catalytic Cycling as Revealed by Alanine-Scanning Mutagenesis," *Journal of Biological Chemistry* 271(21):12213-12220 (1996).

Berger, P.B., "New Directions in Research: Report from the 10th International Conference on AIDS," *Canadian Medical Association Journal* 152(12):1991-1995 (1995).

Berman, et al., "Human Immunodeficiency Virus Type 1 Challenge of Chimpanzees Immunized with Recombinant Envelope Glycoprotein gp120," *Proc Natl Acad Sci USA* 85(14):5200-5204 (1988).

Berman, et al.. "Expression and Immunogenicity of the Extracellular Domain of the Human Immunodeficiency Virus Type 1 Envelope Glycoprotein, gp160," *J Virol.* 63(8):3489-3498 (1989).

Birx and Redfield, "HIV Vaccine Therapy," *Int J Immunopharmacol.* 13(1):129-132 (1991).

Bolognesi, D.P., "Progress in Vaccines Against AIDS," *Science* 246:1233-1234 (1989).

Borrow, et al., "Virus-Specific CD8+ Cytotoxic T-Lymphocyte Activity Associated with Control of Viremia in Primary Human Immunodeficiency Virus Type 1 Infection," *J Virol.* 68(9):6103-6110 (1994).

Bourgault, et al., "Cytotoxic T-Cell Response and AIDS—Free Survival in Simian Immunodeficiency Virus-Infected Macaques," *AIDS.* 7 (Suppl 2):S73-S79 (1993).

Brown et al., "Chimeric Parvovirus B19 Capsids for the Presentation of Foreign Epitopes," *Virology* 198:477-488 (1994).

Bujacz, G., et al., "The Catalytic Domain of Human immunodeficiency Virus Integrase: Ordered Active Site in the F185H Mutant," *Febs Letters* 398(2-3):175-178 (1996).

Burton et al., "Why Do We Not Have on HIV Vaccine and How Can We Make One?" *Nat Med.* 4(5 Suppl):495-498 (1998).

Carmichael et al., "Quantitative Analysis of the Human Immunodeficiency Virus Type 1 (Hiv-1)-specific Cytotoxic T Lymphocyte (Ctl) Response at Different Stages of Hiv-1 Infection: Differential Ctl Responses to Hiv-1 and Epstein-barr Virus in Late Disease," *J Exp Med.* 177(2):249-256 (1993).

Chazal N. et al., "Phenotypic Characterization of Insertion Mutants of the Human Immunodeficiency Virus Type 1 Gag Precursor Expressed in Recombinant Baculovirus-infected Cells," *Virology* 68(1):111-122 (1994).

Ciernik et al., "Induction of Cytotoxic T Lymphocytes and Antitumor Immunity with Dna Vaccines Expressing Single T Cell Epitopes," *J. Immunol.* 156(7):2369-2375 (1996).

Clavel et al., "Isolation of a New Human Retrovirus from West African Patients with AIDS," *Science* 233:343-346 (1986).

Clavel et al., "Molecular Cloning and Polymorphism of the Human Immune Deficiency Virus Type 2," *Nature* 324:691-695 (1986).

Daar et al., "Transient High Levels of Viremia in Patients with Primary Human Immunodeficiency Virus Type 1 Infection," *N Engl J Med.* 324(14):961-964 (1991).

Davey et al., "Subcutaneous administration of interleukin-2 in human immunodeficiency virus type 1-infected persons," *J Infect Dis.* 175(4):781-789 (1997).

Davies J. F., et al., "Crystal structure of the ribonuclease H domain of HIV-1 reverse transcriptase," *Science* 252(5002):88-95 (1991).

Deminio et al., "Evaluation of Reverse Transcriptase and Protease inhibitors in Two-drug Combinations Against Human Immunodeficiency Virus Replication," *Antimicrob Agents Chemother.* 40(6):1346-1351 (1996).

Desai et al., "Molecular Cloning and Primary Nucleotide Sequence Analysis of a Distinct Human Immunodeficiency Virus Isolate Reveal Significant Divergence in its Genomic Sequence," *Proc. Natl. Acad. Sci. USA* 83:8380-8384 (1986).

Doe et al., "Induction of HIV-1 Envelope (gp120)-Specific Cytotoxic T Lymphocyte Responses in Mice by Recombinant CHO Cell-Derived gp120 is Enhanced by Enzymatic Removal of N-Linked Glycans," *Eur. J. Immunol.* 24:2369-2376 (1994).

Doe, B. and Walker, C.M. "HIV-1 p24 Gag-Specific Cytotoxic T-Lymphocyte Responses in Mice," *AIDS* 10(7):793-794 (1996).

Dyda F., et al., "Crystal Structure of the Catalytic Domain of HIV-1 Integrase: Similarity to Other Polynucteotidyl Transferases," *Science* 266(5193):1981-1986 (1994).

Earl et al., "Isolate-and Group-specific Immune Responses to the Envelope Protein of Human Immunodeficiency Virus Induced by a Live Recombinant Vaccinia Virus in Macaques," *AIDS Res Hum Retroviruses* 5(1):23-32 (1989).

Edelman, R., "Vaccine Adjuvants," *Rev Infect Dis.* 2(3):370-383 (1980).

Engelman, A. et al., "Structure-based Mutagenesis of the Catalytic Domain of Human Immunodeficiency Virus Type 1 Integrase," *Journal of Virology* 71(5):3507-3514 (1997).

Esnouf et al., "Mechanism of Inhibition of HIV-1 Reverse Transcriptase by Nonnucleoside Inhibhors," *Structural Biology* 2(4) 303-308 (1995).

Evans et al., "An Engineered Poliovirus Chimaera Elicits Broadly Reactive Hiv-1 Neutralizing Antibodies," *Nature* 339(6223):385-388 (1989).

Faust et al., "Outpatient Biopsies of the Palatine Tonsil: Access to Lymphoid Tissue for Assessment of Human Immunodeficiency Virus RNA Titers," *Otolaryngol Head Neck Surg.* 114(4):593-598 (1996).

Fennie et al., "Model for Intracellular Folding of the Human Immunodeficiency Virus Type 1 gp120," *J. Virol.* 63(2):639-646 (1989).

Ferre et al., "Combination Therapies Against HIV-1 Infection:Exploring the Concept of Combining Antiretroviral Drug Treatments with HIV-1 Immune-Based Therapies in Asymptomatic Individuals," *AIDS Patient Care STDS* 10(6):357-361 (1996).

Fisher, et al., "Biologically diverse molecular variants within a single HIV-1 isolate," *Nature* 334:444-447 (1988).

Fox et al., "No Winners Against AIDS," *Bio/Technology* 12(2):128 (1994).

Gamier, L. et al., "Particle Size Determinants in the Human Immunodeficiency Virus Type 1 Gag Protein," *J Virol* 72(6):4667-4677 (1998).

Goldgur, Y. et al., "Three New Structures of the Core Domain of HIV-1 Integrase: an Active Site That Binds Magnesium," *Proceedings of the National Academy of Sciences of the United States of America* 95(16):9150-9154 (1998).

Goudsmit et al., "Human Immunodeficiency Virus Type 1 Neutralization Epitope with Conserved Architecture Elicits Early Type-specific Antibodies in Experimentally Infected Chimpanzees," *Proc. Natl. Acad. Sci. USA* 85:4478-4482 (1988).

Greene, "AIDS and the Immune System," *Scientific American Sop.* :99-105 (1993).

Griffiths J.C. et al., "Hybrid Human Immunodeficiency Virus Gag Particles as an Antigen Carrier System: Induction of Cytotoxic T-cell and Humoral Responses by a Gag:V3 Fusion," *J. Virol.* 67(6):3191-3198 (1993).

Grimison B. and Laurence, J., "Immunodominant Epitope Regions of HIV-1 Reverse Transcriptase: Correlations with HIV-1 + Serum IgG Inhibitory to Polymerase Activity and With Disease Progression," *Journal of Acquired/Immune Deficiency Syndromes and Human Retrovirology* 9(1):58-68 (1995).

Gurgo at al., "Envelope Sequences of Two New United States HIV-1 Isolates," *Virology* 164:531-536 (1988).

Gurunathan et al., "CD 40 Ligand/Trimer DNA Enhances Both Humoral and Cellular Immune Responses and Induces Protective Immunity to Infectious and Tumor Challenge," *J Immunol.* 161(9):4563-4571 (1998).

Guyader et al., "Genome Organization and Transactivation of the Human Immunodeficiency Virus Type 2," *Nature* 326:662-669 (1987).

Hagensee et al., "Three-dimensional Structure of Vaccinia Virus-produced Human Papillomavirus Type 1 Capsids," *J. Virol.* 68:4503-4505 (1994).

Hahn et al., "Genetic Variation in HTLV-III/LAV Over Time in Patients with AIDS or at Risk for AIDS," *Science* 232:1548-1553 (1986).

Hammer et al., "Issues in Combination Antiretroviral Therapy: a Review," *J Acquir Immuno Defic Syndr.* 7(Suppl 2):S24-S37 (1994).

Haynes et al., "Update on the Issues of HIV Vaccine Development" *Ann Med.* 28(1):39-41 (1996).

Haynes et al., "Toward an Understanding of the Correlates of Protective Immunity to Hiv Infection" *Science* 271:324-328 (1996).

Heeney et al., "Note-chemokines and Neutralizing Antibody Titers Correlate with Sterilizing Immunity Generated in HIV-1 Vaccinated Macaques," *Proc Natl Acad Sci USA* 95(18):10803-10808 (1998).

Hickman, A. B., et al., "Biophysical and enzymatic properties of the catalytic domain of HIV-1 integrase," *Journal of Biological Chemistry* 269(46):29279-29287 (1994).

Ho et al., "Human Immunodeficiency Virus Neutralizing Antibodies Recognize Several Conserved Domains on the Envelope Glycoproteins," *J Virol.* 61(6):2024-2028 (1987).

Jacobo-Molina, A. et al., "Crystal Structure of Human Immunodeficiency Virus Type 1 Reverse Transcriptase Complexed with Double-stranded DNA at 3.0 A Resolution Shows Bent DNA," *Proceedings of the National Academy of Sciences of the United States of America* 90(13):6320-6324 (1993).

Katz, R. A. and Skalka, A. M., "The Retroviral Enzymes," *Annual Review of Biochemistry* 63: 133-73 (1994).

Keefer, et al., "Safety and Immunogenicity of Env 2-3, a Human Immunodeficiency Virus Type 1 Candidate Vaccine, in Combination with a Novel Adjuvant, MTP-PE/MF59. NIAID AIDS Vaccine Evaluation Group," *AIDS Res Hum Retroviruses.* 12(8):683-693 (1996).

Kirnbauer et al., "Efficient Self-assembly of Human Papillomavirus Type 16 L1 and L1-L2 into Virus-Like Particles," *J. Virol.* 67:6929-6936 (1993).

Klenerman, et al., "Original Antigenic Sin Impairs Cytotoxic T Lymphocyte Responses to Viruses Bearing Variant Epitopes," *Nature* 394(6692):482-485 (1998).

Koff et al., "Development and Testing of AIDS Vaccines," *Science* 241:426-432 (1988).

Koff and Schultz, "Progress and Challenges Toward and AIDS Vaccine: Brother, Can You Spare a Paradigm?" *J. Clinical Immunology* 16(3):127-133 (1996).

Kohl et al., "Active Human Immunodeficiency Virus Protease Is Required for Viral Infectivity," *PNAS USA* 85:4686-4690 (1988).

Kohlstaedt, L. A. et al., "Crystal Structure at 3.5 A Resolution of HIV-1 Reverse Transcsiptase Complexed with an Inhibitor," *Science* 256(5065):1783-1790 (1992).

Koup et al., "Temporal Association of Cellular Immune Responses with the Initial Control of Viremia in Primary Human Immunodeficiency Virus Type 1 Syndrome," *J Virol.* 68(7):4650-4655 (1994).

Kovacs et al., "Increases in CD4 T Lymphocytes with Intermittent Courses of Interleukin-2 in Patients with Human Immunodeficiency Virus Infection," *New England J. Med.* 332(9):567-575 (1995).

Kovacs et al., "Controlled Trial of Interleukin-2 Infusions in Patients Infected with the Human Immunodeficiency Virus," *N Engl J Med.* 335(18):1350-1356 (1996).

Krausslich et al., "Processing of in Vitro-synthesized Gag Precursor Proteins of Human Immunodeficiency Virus (HIV) Type 1 by HIV Proteinase Generated in *Escherichia coli*," *J. Virol.* 62:4393-4397 (1988).

Kreuter J., et al., "Mode of Action of Immunological Adjuvants: Some Physicochemical Factors Influencing the Effectivity of Polyacrylic Adjuvants," *Infect Immun.* 19(2):667-675 (1978).

Krug, M. S. and Berger, S. L., "Reverse Transcriptase from Human Immunodeficiency Virus: a Single Template-primer Binding Site Serves Two Physically Separable Catalytic Functions," *Biochemistry* 30(44):10614-10623 (1991).

Lalvani A. et al., "Rapid effector Function in CD8+ Memory T Cells," *J. Exp. Med.* 186:859-865 (1997).

Lasky et al., "Delineation of a Region of the Human Immunodeficiency Virus Type 1 gp120 Glycoprotein Critical for Interaction with the CD4 Receptor," *Cell* 50(6):975-985 (1987).

Levy et al., "Isolation of Lymphocytopathic Retroviruses from San Francisco Patients with AIDS," *Science* 225:840-842 (1984).

Littman et al., "Unusual Intron in the Immunoglobulin Domain of the Newly Isolated Murine CD4 (L3T4) Gene," *Nature* 325(6103):453-455 (1987).

Looney et al., "Type-restricted Neutralization of Molecular Clones of Human Immunodeficiency Virus," *Science* 241:357-359 (1988).

Maddon et al., "The Isolation and Nucleotide Sequence of a Cdna Encoding the T Cell Surface Protein T4: a New Member of the Immunoglobulin Gene Family," *Cell* 42(1):93-104 (1985).

Maignan, S., et al., "Crystal Structures of the Catalytic Domain of HIV-1 Integrase Free and Complexed with its Metal Cofactor: High Level of Similarity of the Active Site with Other Viral Integrases," *Journal of Molecular Biology* 282(2):359-368 (1998).

Manca et al., "Antigenicity of Hiv-derived T Helper Determinants in the Context of Carrier Recombinant Proteins: Effect on T Helper Cell Repertoire Selection," *Eur J Immunol.* 26(10):2461-2469 (1996).

Mazurnder, A., et al., "Effects of nucleotide analogues on human immunodeficiency virus type 1 integrase." *Molecular Pharmacology* 49(4):621-628 (1996).

Mazza et al., "Recombinant Interleukin-2 (Ril-2) in Acquired Immune Deficiency Syndrome (Aids): Preliminary Report in Patients with Lymphoma Associated with Hiv Infection," *Eur J Haematol.* 49(1):1-6 (1992).

Mcheyzer-Williams, M.G. et al., "Enumeration and Characterization of Memory Cells in the Th Compartment," *Immunol. Rev.* 150:5-21 (1996).

McCluskie, et al., "Route and method of delivery of DNA vaccine Influence Immune responses in mice and non-human primates," *Mol Med.* 5(5):287-300 (1999).

McCornack et al., "HIV Protease Substrate Conformation: Modulation by Cyclophilin A," *FEBS Letts* 414:84-88 (1997).

McMichael, A.J. and O'Callaghan, C.A., "A New Look at T Cells," *J. Exp. Med.* 187(9)1367-1371 (1998).

Modrow et al., "Computer-assisted Analysis of Envelope Protein Sequences of Seven Human Immunodeficiency Virus Isolates: Prediction of Antigenic Epitopes in Conserved and Variable Regions," *J. Virol.* 61(2):570-578 (1987).

Montagnier et al., "Human T-Cell Leukemia Viruses: The Family of Human T-Lymphotropic Retroviruses: Their Role in Malignancies and Association with AIDS," *Gallo, Essex & Gross. eds.*, pp. 363-379 (1984).

Myers et al., "Human Retroviruses and AIDS," published by the Los Alamos National Laboratory, Los Alamos, NM, 1991, pp. I-A-48 to I-A-56 and II-77 to II-88.

Nathanson et al., "Biological Considerations in the Development of a Human Immunodeficiency Virus Vaccine," *J Infect Dis.* 182(2):579-589 (2000).

Novitsky et al., "Molecular Cloning and Phylogenetic Analysis of Human Immunodeficiency Virus Type 1 Subtype C: a Set of 23 Full-Length Clones from Botswana," *J. Virol.* 73(5):4427-4432 (1999).

Nowak and Bangham, "Population Dynamics of Immune Responses to Persistent Viruses," *Science* 272(5258):74-79 (1996).

Odile et al., "Anti-HIV Active Immunization, Evidence for Persistent Cell Mediated Immunity after a 2 Year Follow Up," Eighth International Conference on AIDS/III STD World Congress Amsterdam, The Netherlands Jul. 19-24, 1992, Abstract No. M08 0024.

Okuda et al., "Induction of Potent Humoral and Cell-mediated Immune Responses Following Direct Injection of DNA Encoding the HIV Type 1 Env and Rev gene Products," *AIDS Res Hum Retroviruses.* 11(8):933-943 (1995).

Palanlappan, C. et al., "Mutations Within the Primer Grip Region of HIV-1 Reverse Transcriptase Result in Loss of RNase H Function," *Journal of Biological Chemistry* 272(17):11157-11164 (1997).

Park et al., "Ov erexpression of The Gag-pol Precursor From Human Immunodeficiency Virus Type 1 Proviral Genomes Results in Efficient Proteolytic Processing in the Absence of Virion Production," *J. Virol.* 65:5111 (1991).

Patel et al., "In sights into DNA Polymerization Mechanisms from Structure and Function Analysis of HIV-1 Reverse Transcriptase," *Bio chemistry* 34:5351-5363 (1995).

Perelson, et al., "D ecay Characteristics of Hiv-1-infected Compartments During Combination Therapy," *Nature* 387(6629):188-191 (1997).

Popovic et al., "De tection, Isolation, and Continuous Production of Cytopathic Retroviruses (HTLV-III) from Patients with AIDS and Pre-AIDS," *Science* 224:497-500 (1984).

Pyle et al,. "Immune Response to Immunostimulatory Complexes (ISCOMs) Prepared from Human Immunodeficiency Virus Typo 1 (HIV-1) or the HIV-1 External Envelope Glycoprotein (gp120)," *Vaccine* 7(5):465-473 (1989).

Redfield and Birx, "Hiv-sp ecific Vaccine Therapy: Concepts, Status, and Future Directions," *AIDS Res Hum Retroviruses* 8(6):1051-1058 (1992).

Reicin, A.S. et al., "Linker Insertion Mutations in the Human Immunodeficiency Virus Type 1 Gag Gene: Effects on Virion Particle Assembly, Release, and Infectivity," *J. Virol.* 69(2):642-650 (1995).

Roboy, et al., "Prospect for Prevention of Human Immunodeficiency Virus Infection: Purified 120-kDa Envelope Glycoprotein Induces Neutralizing Antibody," *Proc Nati Acad Sci USA* 83(18):7023-7027 (1986).

Rodgers, D. W. et al., "The Structure of Unliganded Reverse Transcriptase from the Human Immunodeficiency Virus Type 1," *Proceedings of the National Academy of Sciences of the United States of America* 92(4):1222-1226 (1995).

Seag, et al., "Ex tensive Variation of Human Immunodeficiency Virus Type-1 in vivo," *Nature* 334:440-444 (1988).

Seep and Kuritzkes, "Strategies for Continuing Antiretroviral Therapy," *Intl AIDS Society USA* 4(2):16-19 (1996).

Salk et al., "Prospects for the Control of Aids by Immunizing Seropositive Individuals," Nature 327(6122):473-476 (1987).

Schernthaner, et al., "Endosp erm-specific Activity of a Zein Gene Promoter in Transgenic Tobacco Plants," *The EMBO J.* 7:1249-1259 (1988).

Schulhafer et al., "A cquired Immunodeficiency Syndrome: Molecular Biology and its Therapeutic Intervention (review)." *In Vivo* 3(2):61-78 (1989).

Sheng N. and Dennis, D., "A ctive Site Labeling of HIV-1 Reverse Transcriptase," *Biochemistry* 32(18):4938-4942 (1993).

Smith et al., "Blocking of HIV-1 infectivity by a soluble, secreted form of the CD4 antigen," *Science* 238(4834):1704-1707 (1987).

Spence R. A., et al., "Mechanism of Inhibition of HIV-1 Reverse Transcriptase by Nonnucleoside Inhibitors," *Science* 267(5200):988-993 (1995).

Srinivasan et al., "Molecular Characterization of Human Immunodeficiency Virus from Zaire: Nucleotide Sequence Analysis Identifies Conserved and Variable Domains in the Envelope Gene," *Gene* 52:71-82 (1987).

Starcich et al., "Id entificadon and Characterization of Conserved and Variable Regions in the Envelope Gene of HTLV-III/LAV, the Retrovirus of AIDS," *Cell* 45:637-648 (1986).

Steimer et al., "Ge netically Engineered Human Immunodeficiency Envelope Glycoprotein Gp120 Produced in Yeast is the Target of Neutralizing Antibodies," *Vaccines* 87:236-241 (1987).

Sternberg et al., "Prediction of Antigenic Determinants and Secondary Structures of the Major Aids Virus Proteins," *FEBS Letters* 218(2):231-237 (1987).

Tindle et al., "C himeric Hepatitis B Core Antigen Particles Containing B- and Th-epitopes of Human Papillomavirus Type 16 E7 Protein Induce Specific Antibody and T-helper Responses in Immunised Mice," *Virology* 200:547-552 (1994).

Vacca et al., "L-735,524: an Orally Bioavailable Human Immunodeficiency Virus Type 1 Protease Inhibitor," *Proc Natl Acad Sci USA* 91(8):4096-4100 (1994).

Verma et al., "G ene therapy—Promises, Problems and Prospects," *Nature* 389(6648):239-242 (1997).

Vilmer et al., "Isolation of New Lymphotropic Retrovirus from Two Siblings with *Haemophilia B*, One with AIDS," *The Lancer* 1:753 (1984).

Wagner R., et al., "Studies an Processing, Particle Formation, and Immunogenicity of the HIV-1 gag Gene Product: a Possible Component of a HIV Vaccine," *Arch Virol.* 127:117-137 (1992).

Wagner et al., "Ass embly and Extracellular Release of Chimeric HIV-1 PR55gag Retrovirus-like Particles," *Virology* 200:162-175 (1994).

Wagner et al., "C onstruction, Expression, and Immunogenicity of Chimeric HIV-1 Virus-like Particles," *Virology* 220:128-140 (1996).

Wakefield, J. K.et al., "In Vitro Enzymatic Activity of Human Immunodeficiency Virus Type 1 Reverse Transcriptase Mutants in the Highly Conserved YMDD Amino Acid Motif Correlates with the Infectious Potential of the Proviral Genome," *Journal of Virology* 66(1):6806-6812 (1992).

Wan et al., "Au toprocessing: an Essential Step for the Activation of HIV-1 Protease," *Biochem. J.* 316:569-573 (1996).

Wang et al., "In duction of Humoral and Cellular Immune Responses to the Human Immuno-deficiency Type 1 Virus in Nonhuman Primates by in Vivo DNA Inoculation," *Virology* 211(1):102-112 (1995).

Wang C. et al., "A nalysis of Minimal Human Immunodeficiency Virus Type 1 Gag Coding Sequences Capable of Virus-like Particle Assembly and Release," *J Virol* 72(10): 7950-7959 (1898).

Wu X., et al., "Targeting foreign proteins to human immunodeficiency virus particles via fusion with Vpr and Vpx," *J. Virol.* 69(6):3389-3398 (1995).

Yeni et al., "An tiretroviral and Immune-based Therapies: Update," *AIDS* 7(Suppl 1):S173-S184 (1993).

Yenolsky et al., "A Mutant Neomycin Phosphotransferase II Gene Reduces the Resistance of Transformants to Antibiotic Selection Pressure," *Proc. Natl. Acad. Sci. USA* 87:3435-3439 (1990).

Youmo et al., "Nu cleotide Sequence Analysis of the Env Gene of a New Zairian isolate of HIV-1," *AIDS Res Hum Retroviruses* 4(3):165-73 (1988).

Zagury et al., "Progress Report IV on Aids Vaccine in Human: Phase I Clinical Trial in Hiv Infected Patients," *VII International Conference on AIDS*, Florence Jun. 16-21, 1991, Abstract No. M.A. 67.

Zagury et al., "One-year Follow-up of Vaccine Therapy in Hiv-Infected Immune-deficient Individuals: a New Strategy," *J. Acquired Immune Deficiency Syndromes* 5:676-681 (1992).

Zhang Y., et al., "A nalysis of the Assembly Function of the Human Immunodeficiency Virus Type 1 Gag Protein Nucleocapsid Domain," *J Virol* 72(3):1782-1789 (1998).

zur Megede et al., "In creased Expression and Immunogenicity of Sequence-modified Human Immunodeficiency Virus Type 1 Gag Gene," *J Virol.* 74(6):2628-2635 (2000).

Haas et al., "Cyto toxic T-cell responses to HIV-1 reverse transcriptase, integrase and protease", *AIDS* 12:1427-1436 (1998).

Hamajima et al., "The combination of DNA and peptide vaccines induces strong immunities against HIV-1 in both humoral and CMI", 11th International AIDS Conference, Vancouver, British Columbia, Jul. 7-12, 1996; 11(1):6 (abstract No. Mo.A.151) (1996).

Kent et al., "A recombinant ovipoxvirus HIV-1 vaccine expressing interferon-gamma is safe and immunogenic in macaques", *Vaccines* 18:2250-2256 (2000).

Williamson et al., "Designing HIV-1 subtype C vaccines for South Africa", *South African J. Sci.* 96:318-342 (2000).

Calarota et. al., "Immune Responses in Asymptomatic HIV-1—Infected Patients After HIV-DNA Immunization Followed by Highly Active Antiretroviral Treatment", *J Immunology*, (1999) 163(4):2330-2338.

André et al., "Increased Immune Response Elicited by DNA Vaccination with a Synthetic gp120 Sequence with Optimized Codon Usage," *J. Virology* 72(2)1497-1503 (1998).
Bolognesi et al., *Ann. Int. Med.* 8(7):603-611 (1994).
Borsetti et al., *J. Virol.* 72(11):9313-9317 (1998).
Burton et al., *AIDS* 11(Suppl. A):S87-S98 (1997).
Cao et al., J. Virol. 71(12):9808-9812 (1997).
Cheng-Mayer, *PNAS USA* 86:8575-8579 (1989).
D'Souza et al., *J. Infect. Dis.* 175:1056-1062 (1997).
Earl et al., *PNAS USA* 87:648-652 (1990).
Earl et al., *J. Virol.* 65:31-41 (1991).
Fiore et al., *Virol.* 204:297-303 (1994).
Freed, *Virology* 251:1-15 (1998).
Greene, "AIDS and the Immune System," *Scientific American* Sep. :99-105 (1993).
Griffiths J.C. et al., "Hybrid Human Immunodeficiency Virus Gag Partides as an Antigen Carrier System: Induction of Cytotoxic T-cell and Humoral Responses by a Gag:V3 Fusion," *J. Virol.* 67(6):3191-3198 (1993).
Haas et al., *Current Biology* 6(3):315-324 (1996).
Hu et al., *Science* 255:456-459 (1992).
Javaherian et al., *PNAS USA* 86:6786-6792 (1989).
Jeffs et al., *J. Gen. Virol.* 77:1403-1410 (1996).
Kang et al., PNAS USA 88:6171-6175 (1991).
Kwong et al., *Nature* 393:648-659 (1998).
Lu et al., "Immunogenicity of DNA vaccines expressing human immunodeficiency virus type 1 envelope glycoprotein with and without deletions in the V1/2 and V3 regions," *AIDS Research and Human Retroviruses* 14(2):151-155 (1998).
Mammano et al., J. Virol. 68(8):4927-4936 (1994).
Mascola et al., *J. Infect. Dis.* 169:48-54 (1994).
Matsushita et al., *J. Virol* 62:2107-2144 (1988).
Matthews *PNAS USA* 83:9709-9713 (1986).
McDougal et al., *J. Immunol.* 137:2937-2944 (1986).
Montefiori et al., *AIDS Res. Hum. Retroviruses* 15(8):689-698 (1999).
Nara et al., *J. Virol.* 62:2622-2628 (1988).
Palker et al., *PNAS USA* 85:1932-1936 (1988).
Peng et al., *AIDS* 11:587-595 (1997).
Putney et al., *Science* 234:1392-1395 (1986).
Ratner et al., *Nature* 313:277-284 (1985).
Robert-Guroff et al., *Nature* (London) 316:72-74 (1985).
Rushe et al., *PNAS USA* 85:3198-3202 (1988).
Sanchez-Pescador et al., *Science* 227(4686):484-492 (1985).
Schneider et al., "Inactivation of the human immunodeficiency virus type 1 inhibitory elements allows rev-independent expression of gag and gag/protease and particle formation," *J. Virology* 71(7):4892-4903 (1997).
Stamatatos et al., *AIDS Res. Hum. Retroviruses* 14(13)1129-1139 (1998).
Stamatatos et al., "An envelope modification that renders a primary, neutralization-resistant clade B human immunodeficiency virus type 1 isolate highly susceptible to neutralization by sera from other clades," *J. Virolog*) 72(10):7840-7845 (1998).
Thati et al., *J. Virol.* 67(7):3978-3988 (1993).
Trokla et al., *J. Virol.* 69(11):6609-6617 (1995).
Wan et al., "Autoprocessing: an Essential Step for the Activation of HIV-1 Protease," *Biochem. J.* 316:569-573 (1996).
Wang et al., *Virology* 200:524-534 (1994).
Weiss et al., *Nature* (London) 316:69-72 (1985).
Weiss et al., *Nature* (London) 324:572-575 (1986).
Wyatt et al., *J. Virol.* 69(9):5723-5733 (1995).
Wyatt et al., *Nature* 393:705-711 (1998).
Zhu et al., Science 261:1179-1181 (1993).
US 5,766,545, 06/1998, Weiner at al. (withdrawn)

* cited by examiner

8_S_ZA

```
   1 TGGAAGGGTT AATTTACTCC AAGAAAAGGC AAGAAATCCT TGATTTGTGG GTCTATCACA
  61 CACAAGGCTT CTTCCCTGAT TGGCAAAACT ACACACCGGG GCCAGGGGTC AGATATCCAC
 121 TGACCTTTGG ATGGTGCTAC AAGCTAGTGC CAGTTGACCC AGGGGAGGTG GAAGAGGCCA
 181 ACGGAGGAGA AGACAACTGT TTGCTACACC CTATGAGCCA ACATGGAGCA GAGGATGAAG
 241 ATAGAGAAGT ATTAAAGTGG AAGTTTGACA GCCTCCTAGC ACGCAGACAC ATGGCCCGCG
 301 AGCTACATCC GGAGTATTAC AAAGACTGCT GACACAGAAG GGACTTTCCG CCTGGGACTT
 361 TCCACTGGGG CGTTCCGGGA GGTGTGGTCT GGGCGGGACT TGGGAGTGGT CAACCCTCAG
 421 ATGCTGCATA TAAGCAGCTG CTTTTCGCCT GTACTGGGTC TCTCTCGGTA GACCAGATCT
 481 GAGCCTGGGA GCCCTCTGGC TATCTAGGGA ACCCACTGCT TAAGCCTCAA TAAAGCTTGC
 541 CTTGAGTGCT TTAAGTAGTG TGTGCCCATC TGTTGTGTGA CTCTGGTAAC TAGAGATCCC
 601 TCAGACCCTT TGTGGTAGTG TGGAAAATCT CTAGCAGTGG CGCCCGAACA GGGACCAGAA
 661 AGTGAAAGTG AGACCAGAGG AGATCTCTCG ACGCAGGACT CGGCTTGCTG AAGTGCACAC
 721 GGCAAGAGGC GAGAGGGGCG GCTGGTGAGT ACGCCAATTT TACTTGACTA GCGGAGGCTA
 781 GAAGGAGAGA GATGGGTGCG AGAGCGTCAA TATTAAGCGG CGGAAAATTA GATAAATGGG
 841 AAAGAATTAG GTTAAGGCCA GGGGGAAAGA AACATTATAT GTTAAAACAT CTAGTATGGG
 901 CAAGCAGGGA GCTGGAAAGA TTTGCACTTA ACCCTGGCCT GTTAGAAACA TCAGAAGGCT
 961 GTAAACAAAT AATAAAACAG CTACAACCAG CTCTTCAGAC AGGAACAGAG GAACTTAGAT
1021 CATTATTCAA CACAGTAGCA ACTCTCTATT GTGTACATAA AGGGATAGAG GTACGAGACA
1081 CCAAGGAAGC CTTAGACAAG ATAGAGGAAG AACAAAACAA ATGTCAGCAA AAAGCACAAC
1141 AGGCAAAAGC AGCTGACGAA AAGGTCAGTC AAAATTATCC TATAGTACAG AATGCCCAAG
1201 GGCAAATGGT ACACCAAGCT ATATCACCTA GAACATTGAA TGCATGGATA AAAGTAATAG
1261 AGGAAAAGGC TTTCAATCCA GAGGAAATAC CCATGTTTAC AGCATTATCA GAAGGAGCCA
1321 CCCCACAAGA TTTAAACACA ATGTTAAATA CAGTGGGGGG ACATCAAGCA GCCATGCAAA
1381 TGTTAAAAGA TACCATCAAT GAGGAGGCTG CAGAATGGGA TAGGACACAT CCAGTACATG
1441 CAGGGCCTGT TGCACCAGGC CAGATGAGAG AACCAAGGGG AAGTGACATA GCAGGAACTA
1501 CTAGTACCCT TCAGGAACAA ATAGCATGGA TGACAAGTAA TCCACCTATT CCAGTAGAAG
1561 ACATCTATAA AAGATGGATA ATTCTGGGGT TAAATAAAAT AGTAAGAATG TATAGCCCTG
1621 TTAGCATTTT GGACATAAAA CAAGGGCCAA AAGAACCCTT TAGAGACTAT GTAGACCGGT
1681 TCTTTAAAAC CTTAAGAGCT GAACAAGCTA CACAAGATGT AAAGAATTGG ATGACAGACA
1741 CCTTGTTGGT CCAAAATGCG AACCCAGATT GTAAGACCAT TTTAAGAGCA TTAGGACCAG
1801 GGGCCTCATT AGAAGAAATG ATGACAGCAT GTCAGGGAGT GGGAGGACCT AGCCATAAAG
1861 CAAGAGTGTT GGCTGAGGCA ATGAGCCAAG CAAACAGTAA CATACTAGTG CAGAGAAGCA
1921 ATTTTAAAGG CTCTAACAGA ATTATTAAAT GTTTCAACTG TGGCAAAGTA GGGCACATAG
1981 CCAGAAATTG CAGGGCCCCT AGGAAAAAGG GCTGTTGGAA ATGTGGACAG GAAGGACACC
2041 AAATGAAAGA CTGTACTGAG AGGCAGGCTA ATTTTTTAGG GAAAATTTGG CCTTCCCACA
2101 AGGGGAGGCC AGGGAATTTC CTCCAGAACA GACCAGAGCC AACAGCCCCA CCAGCAGAAC
2161 CAACAGCCCC ACCAGCAGAG AGCTTCAGGT TCGAGGAGAC AACCCCCGTG CCGAGGAAGG
2221 AGAAAGAGAG GGAACCTTTA ACTTCCCTCA AATCACTCTT TGGCAGCGAC CCCTTGTCTC
2281 AATAAAAGTA GAGGGCCAGA TAAAGGAGGC TCTCTTAGAC ACAGGAGCAG ATGATACAGT
2341 ATTAGAAGAA ATAGATTTGC CAGGGAAATG GAAACCAAAA ATGATAGGGG GAATTGGAGG
2401 TTTTATCAAA GTAAGACAGT ATGATCAAAT ACTTATAGAA ATTTGTGGAA AAAGGCTAT
2461 AGGTACAGTA TTAGTAGGGC CTACACCAGT CAACATAATT GGAAGAAATC TGTTAACTCA
2521 GCTTGGATGC ACACTAAATT TTCCAATTAG TCCTATTGAA ACTGTACCAG TAAAATTAAA
2581 ACCAGGAATG GATGGCCCAA AGGTCAAACA ATGGCCATTG ACAGAAGAAA AAATAAAAGC
2641 ATTAACAGCA ATTTGTGAGG AAATGGAGAA GGAAGGAAAA ATTACAAAAA TTGGGCCTGA
2701 TAATCCATAT AACACTCCAG TATTTGCCAT AAAAAAGAAG GACAGTACTA AGTGGAGAAA
2761 ATTAGTAGAT TTCAGGGAAC TCAATAAAAG AACTCAAGAC TTTTGGGAAG TTCAATTAGG
2821 AATACCACAC CCAGCAGGAT TAAAAAAGAA AAAATCAGTG ACAGTGCTAG ATGTGGGGGA
2881 TGCATATTTT TCAGTTCCTT TAGATGAAAG CTTCAGGAAA TATACTGCAT TCACCATACC
```

FIGURE 1A

```
2941 TAGTATAAAC AATGAAACAC CAGGGATTAG ATATCAATAT AATGTGCTGC CACAGGGATG
3001 GAAAGGATCA CCAGCAATAT TCCAGAGTAG CATGACAAAA ATCTTAGAGC CCTTCAGAGC
3061 AAAAAATCCA GACATAGTTA TCTATCAATA TATGGATGAC TTGTATGTAG GATCTGACTT
3121 AGAAATAGGG CAACATAGAG CAAAAATAGA AGAGTTAAGG GAACATTTAT TGAAATGGGG
3181 ATTTACAACA CCAGACAAGA AACATCAAAA AGAACCCCCA TTTCTTTGGA TGGGGTATGA
3241 ACTCCATCCT GACAAATGGA CAGTACAACC TATACTGCTG CCAGAAAAGG ATAGTTGGAC
3301 TGTCAATGAT ATACAGAAGT TAGTGGGAAA ATTAAACTGG GCAAGTCAGA TTTACCCAGG
3361 GATTAAAGTA AGGCAACTCT GTAAACTCCT CAGGGGGGCC AAAGCACTAA CAGACATAGT
3421 ACCACTAACT GAAGAAGCAG AATTAGAATT GGCAGAGAAC AGGGAAATTT TAAGAGAACC
3481 AGTACATGGA GTATATTATG ATCCATCAAA AGACTTGATA GCTGAAATAC AGAAACAGGG
3541 GCATGAACAA TGGACATATC AAATTTATCA AGAACCATTT AAAAATCTGA AAACAGGGAA
3601 GTATGCAAAA ATGAGGACTA CCCACACTAA TGATGTAAAA CAGTTAACAG AGGCAGTGCA
3661 AAAAATAGCC ATGGAAAGCA TAGTAATATG GGGAAAGACT CCTAAATTTA GACTACCCAT
3721 CCAAAAAGAA ACATGGGAGA CATGGTGGAC AGACTATTGG CAAGCCACCT GGATCCCTGA
3781 GTGGGAGTTT GTTAATACCC CTCCCCTAGT AAAATTATGG TACCAACTAG AAAAAGATCC
3841 CATAGCAGGA GTAGAAACTT TCTATGTAGA TGGAGCAACT AATAGGGAAG CTAAAATAGG
3901 AAAAGCAGGG TATGTTACTG ACAGAGGAAG GCAGAAAATT GTTACTCTAA CTAACACAAC
3961 AAATCAGAAG ACTGAGTTAC AAGCAATTCA GCTAGCTCTG CAGGATTCAG GATCAGAAGT
4021 AAACATAGTA ACAGACTCAC AGTATGCATT AGGAATCATT CAAGCACAAC CAGATAAGAG
4081 TGACTCAGAG ATATTTAACC AAATAATAGA ACAGTTAATA AACAAGGAAA GAATCTACCT
4141 GTCATGGGTA CCAGCACATA AAGGAATTGG GGGAAATGAA CAAGTAGATA AATTAGTAAG
4201 TAAGGGAATT AGGAAAGTGT TGTTTCTAGA TGGAATAGAT AAAGCTCAAG AAGAGCATGA
4261 AAGGTACCAC AGCAATTGGA GAGCAATGGC TAATGAGTTT AATCTGCCAC CCATAGTAGC
4321 AAAAGAAATA GTAGCTAGCT GTGATAAATG TCAGCTAAAA GGGGAAGCCA TACATGGACA
4381 AGTCGACTGT AGTCCAGGGA TATGGCAATT AGATTGTACC CATTTAGAGG GAAAAATCAT
4441 CCTGGTAGCA GTCCATGTAG CTAGTGGCTA CATGGAAGCA GAGGTTATCC CAGCAGAAAC
4501 AGGACAAGAA ACAGCATATT TTATATTAAA ATTAGCAGGA AGATGGCCAG TCAAAGTAAT
4561 ACATACAGAC AATGGCAGTA ATTTTACCAG TACTGCAGTT AAGGCAGCCT GTTGGTGGGC
4621 AGGTATCCAA CAGGAATTTG GAATTCCCTA CAATCCCCAA AGTCAGGGAG TGGTAGAATC
4681 CATGAATAAA GAATTAAAGA AAATAATAGG ACAAGTAAGA GATCAAGCTG AGCACCTTAA
4741 GACAGCAGTA CAAATGGCAG TATTCATTCA CAATTTTAAA AGAAAAGGGG GAATTGGGGG
4801 GTACAGTGCA GGGGAAAGAA TAATAGACAT AATAGCAACA GACATACAAA CTAAAGAATT
4861 ACAAAAACAA ATTATAAGAA TTCAAAATTT TCGGGTTTAT TACAGAGACA GCAGAGACCC
4921 TATTTGGAAA GGACCAGCCG AACTACTCTG GAAAGGTGAA GGGGTAGTAG TAATAGAAGA
4981 TAAAGGTGAC ATAAAGGTAG TACCAAGGAG GAAAGCAAAA ATCATTAGAG ATTATGGAAA
5041 ACAGATGGCA GGTGCTGATT GTGTGGCAGG TGGACAGGAT GAAGATTAGA GCATGGAATA
5101 GTTTAGTAAA GCACCATATG TATATATCAA GGAGAGCTAG TGGATGGGTC TACAGACATC
5161 ATTTTGAAAG CAGACATCCA AAAGTAAGTT CAGAAGTACA TATCCCATTA GGGGATGCTA
5221 GATTAGTAAT AAAAACATAT TGGGGTTTGC AGACAGGAGA AAGAGATTGG CATTTGGGTC
5281 ATGGAGTCTC CATAGAATGG AGACTGAGAG AATACAGCAC ACAAGTAGAC CCTGACCTGG
5341 CAGACCAGCT AATTCACATG CATTATTTTG ATTGTTTTAC AGAATCTGCC ATAAGACAAG
5401 CCATATTAGG ACACATAGTT TTTCCTAGGT GTGACTATCA AGCAGGACAT AAGAAGGTAG
5461 GATCTCTGCA ATACTTGGCA CTGACAGCAT TGATAAAACC AAAAAAGAGA AAGCCACCTC
5521 TGCCTAGTGT TAGAAAATTA GTAGAGGATA GATGGAACGA CCCCCAGAAG ACCAGGGGCC
5581 GCAGAGGGAA CCATACAATG AATGGACACT AGAGATTCTA GAAGAACTCA AGCAGGAAGC
5641 TGTCAGACAC TTTCCTAGAC CATGGCTCCA TAGCTTAGGA CAATATATCT ATGAAACCTA
5701 TGGGGATACT TGGACGGGAG TTGAAGCTAT AATAAGAGTA CTGCAACAAC TACTGTTCAT
5761 TCATTTCAGA ATTGGATGCC AACATAGCAG AATAGGCATC TTGCGACAGA GAAGAGCAAG
5821 AAATGGAGCC AGTAGATCCT AAACTAAAGC CCTGGAACCA TCCAGGAAGC CAACCTAAAA
5881 CAGCTTGTAA TAATTGCTTT TGCAAACACT GTAGCTATCA TTGTCTAGTT TGCTTTCAGA
```

FIGURE 1B

```
5941 CAAAAGGTTT AGGCATTTCC TATGGCAGGA AGAAGCGGAG ACAGCGACGA AGCGCTCCTC
6001 CAAGTGGTGA AGATCATCAA AATCCTCTAT CAAAGCAGTA AGTACACATA GTAGATGTAA
6061 TGGTAAGTTT AAGTTTATTT AAAGGAGTAG ATTATAGATT AGGAGTAGGA GCATTGATAG
6121 TAGCACTAAT CATAGCAATA ATAGTGTGGA CCATAGCATA TATAGAATAT AGGAAATTGG
6181 TAAGACAAAA GAAAATAGAC TGGTTAATTA AAAGAATTAG GGAAAGAGCA GAAGACAGTG
6241 GCAATGAGAG TGATGGGGAC ACAGAAGAAT TGTCAACAAT GGTGGATATG GGCATCTTA
6301 GGCTTCTGGA TGCTAATGAT TTGTAACACG GAGGACTTGT GGGTCACAGT CTACTATGGG
6361 GTACCTGTGT GGAGAGAAGC AAAAACTACT CTATTCTGTG CATCAGATGC TAAAGCATAT
6421 GAGACAGAAG TGCATAATGT CTGGGCTACA CATGCTTGTG TACCCACAGA CCCCAACCCA
6481 CAAGAAATAG TTTTGGGAAA TGTAACAGAA AATTTTAATA TGTGGAAAAA TAACATGGCA
6541 GATCAGATGC ATGAGGATAT AATCAGTTTA TGGATCAAA GCCTAAAGCC ATGTGTAAAG
6601 TTGACCCCAC TCTGTGTCAC TTTAAACTGT ACAGATACAA ATGTTACAGG TAATAGAACT
6661 GTTACAGGTA ATACAAATGA TACCAATATT GCAAATGCTA CATATAAGTA TGAAGAAATG
6721 AAAAATTGCT CTTTCAATGC AACCACAGAA TTAAGAGATA AGAAACATAA AGAGTATGCA
6781 CTCTTTTATA AACTTGATAT AGTACCACTT AATGAAATA GTAACAACTT ACATATAGA
6841 TTAATAAATT GCAATACCTC AACCATAACA CAAGCCTGTC CAAAGGTCTC TTTTGACCCG
6901 ATTCCTATAC ATTACTGTGC TCCAGCTGAT TATGCGATTC TAAAGTGTAA TAATAAGACA
6961 TTCAATGGGA CAGGACCATG TTATAATGTC AGCACAGTAC AATGTACACA TGGAATTAAG
7021 CCAGTGGTAT CAACTCAACT ACTGTTAAAT GGTAGTCTAG CAGAAGAAGG GATAATAATT
7081 AGATCTGAAA ATTTGACAGA GAATACCAAA ACAATAATAG TACATCTTAA TGAATCTGTA
7141 GAGATTAATT GTACAAGGCC CAACAATAAT ACAAGGAAAA GTGTAAGGAT AGGACCAGGA
7201 CAAGCATTCT ATGCAACAAA TGACGTAATA GGAAACATAA GACAAGCACA TTGTAACATT
7261 AGTACAGATA GATGGAATAA AACTTTACAA CAGGTAATGA AAAAATTAGG AGAGCATTTC
7321 CCTAATAAAA CAATAAAATT TGAACCACAT GCAGGAGGGG ATCTAGAAAT TACAATGCAT
7381 AGCTTTAATT GTAGAGGAGA ATTTTTCTAT TGCAATACAT CAAACCTGTT TAATAGTACA
7441 TACTACCCTA AGAATGGTAC ATACAAATAC AATGGTAATT CAAGCTTACC CATCACACTC
7501 CAATGCAAAA TAAAACAAAT TGTACGCATG TGGCAAGGGG TAGGACAAGC AATGTATGCC
7561 CCTCCCATTG CAGGAAACAT AACATGTAGA TCAAACATCA CAGGAATACT ATTGACACGT
7621 GATGGGGGAT TTAACAACAC AAACAACGAC ACAGAGGAGA CATTCAGACC TGGAGGAGGA
7681 GATATGAGGG ATAACTGGAG AAGTGAATTA TATAAATATA AAGTGGTAGA AATTAAGCCA
7741 TTGGGAATAG CACCCACTAA GGCAAAAAGA AGAGTGGTGC AGAGAAAAA AAGAGCAGTG
7801 GGAATAGGAG CTGTGTTCCT TGGGTTCTTG GGAGCAGCAG GAAGCACTAT GGGCGCAGCG
7861 TCAATAACGC TGACGGTACA GGCCAGACAA CTGTTGTCTG GTATAGTGCA ACAGCAAAGC
7921 AATTTGCTGA AGGCTATAGA GGCGCAACAG CATATGTTGC AACTCACAGT CTGGGGCATT
7981 AAGCAGCTCC AGGCGAGAGT CCTGGCTATA GAAAGATACC TAAAGGATCA ACAGCTCCTA
8041 GGGATTTGGG GCTGCTCTGG AAGACTCATC TGCACCACTG CTGTGCCTTG GAACTCCAGT
8101 TGGAGTAATA AATCTGAAGC AGATATTTGG GATAACATGA CTTGGATGCA GTGGGATAGA
8161 GAATTAATA ATTACACAGA AACAATATTC AGGTTGCTTG AAGACTCGCA AAACCAGCAG
8221 GAAAAGAATG AAAAAGATTT ATTAGAATTG GACAAGTGGA ATAATCTGTG GAATTGGTTT
8281 GACATATCAA ACTGGCTGTG GTATATAAAA ATATTCATAA TGATAGTAGG AGGCTTGATA
8341 GGTTTAAGAA TAATTTTTGC TGTGCTCTCT ATAGTGAATA GAGTTAGGCA GGGATACTCA
8401 CCTTTGTCAT TTCAGACCCT TACCCCAAGC CCGAGGGGAC TCGACAGGCT CGGAGGAATC
8461 GAAGAAGAAG GTGGAGAGCA AGACAGAGAC AGATCCATAC GATTGGTGAG CGGATTCTTG
8521 TCGCTTGCCT GGGACGATCT GCGGAGCCTG TGCCTCTTCA GCTACCACCG CTTGAGAGAC
8581 TTCATATTAA TTGCAGTGAG GCAGTGGAA CTTCTGGGAC ACAGCAGTCT CAGGGGACTA
8641 CAGAGGGGGT GGGAGATCCT TAAGTATCTG GGAAGTCTTG TGCAGTATTG GGTCTAGAG
8701 CTAAAAAAGA GTGCTATTAG TCCGCTTGAT ACCATAGCAA TAGCAGTAGC TGAAGGAACA
8761 GATAGGATTA TAGAATTGGT ACAAGAATT TGTAGAGCTA TCCTCAACAT ACCTAGGAGA
8821 ATAAGACAGG GCTTTGAAGC AGCTTTGCTA TAAAATGGGA GGCAAGTGGT CAAAACGCAG
8881 CATAGTTGGA TGGCCTGCAG TAAGAGAAAG AATGAGAAGA ACTGAGCCAG CAGCAGAGGG
8941 AGTAGGAGCA GCGTCTCAAG ACTTAGATAG ACATGGGGCA CTTACAAGCA GCAACACACC
```

FIGURE 1C

```
9001 TGCTACTAAT GAAGCTTGTG CCTGGCTGCA AGCACAAGAG GAGGACGGAG ATGTAGGCTT
9061 TCCAGTCAGA CCTCAGGTAC CTTTAAGACC AATGACTTAT AAGAGTGCAG TAGATCTCAG
9121 CTTCTTTTTA AAAGAAAAGG GGGGACTGGA AGGGTTAATT TACTCTAGGA AAAGGCAAGA
9181 AATCCTTGAT TTGTGGGTCT ATAACACACA AGGCTTCTTC CCTGATTGGC AAAACTACAC
9241 ATCGGGGCCA GGGGTCCGAT TCCCACTGAC CTTTGGATGG TGCTTCAAGC TAGTACCAGT
9301 TGACCCAAGG GAGGTGAAAG AGGCCAATGA AGGAGAAGAC AACTGTTTGC TACACCCTAT
9361 GAGCCAACAT GGAGCAGAGG ATGAAGATAG AGAAGTATTA AAGTGGAAGT TTGACAGCCT
9421 TCTAGCACAC AGACACATGG CCCGCGAGCT ACATCCGGAG TATTACAAAG ACTGCTGACA
9481 CAGAAGGGAC TTTCCGCCTG GGACTTTCCA CTGGGGCGTT CCGGGAGGTG TGGTCTGGGC
9541 GGGACTTGGG AGTGGTCACC CTCAGATGCT GCATATAAGC AGCTGCTTTT CGCTTGTACT
9601 GGGTCTCTCT CGGTAGACCA GATCTGAGCC TGGGAGCTCT CTGGCTATCT AGGGAACCCA
9661 CTGCTTAGGC CTCAATAAAG CTTGCCTTGA GTGCTCTAAG TAGTGTGTGC CCATCTGTTG
9721 TGTGACTCTG GTAACTAGAG ATCCCTCAGA CCCTTTGTGG TAGTGTGGAA AATCTCTAGC
9781 A
```

FIGURE 1D

↓: is the regions for β-sheet deletions

*: is the N-linked glycosylation sites for subtype C TV1 and TV2. Possible mutation (N→ Q) or deletions can be performed.

```
                      1                                                    50
      SF162      (1)  ----MDAMKRGLCCVLLLCGAVFVSPSAVEKLWVTVYYGVPVWKEATTTL
      TV1.8_2    (1)  MRVMGTQKNCQQWWIWGILGFWMLMICNTEDLWVTVYYGVPVWRDAKTTL
      TV1.8_5    (1)  MRVMGTQKNCQQWWIWGILGFWMLMICNTEDLWVTVYYGVPVWREAKTTL
      TV2.12-5/1 (1)  MRARGILKNYRHWWIWGILGFWMLMICNVKGLWVTVYYGVPVGREAKTTL
      Consensus  (1)  MRVMGTQKNCQQWWIWGILGFWMLMICNVEDLWVTVYYGVPVWREAKTTL 51                                     *             100
      SF162      (47) FCASDAKAYDTEVHNVWATHACVPTDPNPQEIVLENVTENFNMWKNNMVE
      TV1.8_2    (51) FCASDAKAYETEVHNVWATHACVPTDPNPQEIVLGNVTENFNMWKNDMAD
      TV1.8_5    (51) FCASDAKAYETEVHNVWATHACVPTDPNPQEIVLGNVTENFNMWKNNMAD
      TV2.12-5/1 (51) FCASDAKAYEKEVHNVWATHACVPTDPNPQEVLLGNVTENFNMWKNDMVD
      Consensus  (51) FCASDAKAYETEVHNVWATHACVPTDPNPQEIVLGNVTENFNMWKNNMVD β2/V1V2/β3
                      101           ↓              *   *    *    *  * 150
      SF162      (97) QMHEDIISLWDQSLKPCVKLTPLCVTLHCTNLKNATNTK-----SSN---
      TV1.8_2   (101) QMHEDVISLWDQSLKPCVKLTPLCVTLNCIDTNVTGNRTVTGNSTNNTN
      TV1.8_5   (101) QMHEDIISLWDQSLKPCVKLTPLCVTLNCIDTNVTGNRTVTGNSNDTNIS
      TV2.12-5/1(101) QMQEDIISLWDQSLKPCVKLTPLCVTLNCTNATVNYN-------NIS---
      Consensus (101) QMHEDIISLWDQSLKPCVKLTPLCVTLNCTNTNVTGNRTVTGNSNSN  A 151     *  *                                      *200
      SF162     (139) WKEMDRGEIKNCSFKVTTSIRNKMQKEYALFYKLDVVPIDN----DNTSY
      TV1.8_2   (151) TGIYNIEEMKNCSFNATTELRDKKHKEYALFYKRLDIVPLN--ENSDNFTY
      TV1.8_5   (151) NATYKYEEMKNCSFNATTELRDKKHKEYALFYKLDIVPLN--ENSNNFTY
      TV2.12-5/1(141) ------KDMKNCSFYVTTELRDKKKCENALFYRLDIVPLNNRKNGNINNY
      Consensus (151)  A Y   EEMKNCSFNVTTELRDKKHKEYALFYKLDIVPLNN ENSNNFTY

*
                      201   *  ↓                           *    *    250
      SF162     (185) KLTNCNTSVITQACPKVSFEPIPIHYCAPAGEAILKCNDRKFNGSGPCTN
      TV1.8_2   (199) RLINCNTSTITQACPKVSFDPIPIHYCAPAGYAILKCNNKTFNGTGPCYN
      TV1.8_5   (199) RLINCNTSTITQACPKVSFDPIPIHYCAPADYAILKCNNKTFNGTGPCYN
      TV2.12-5/1(185) RLINCNTSAITQACPKVSFDPIPIHYCAPAGYAPLKCNNKTFNGISPCDN
      Consensus (201) RLINCNTSTITQACPKVSFDPIPIHYCAPAGYAILKCNNKTFNGTGPCYN

*
                      251              *                   *           300
      SF162     (235) VSTVQCTHGIRPVVSTQLLLNGSLAEEGVVIRSENFTDNAKTIIVQLKES
      TV1.8_2   (249) VSTVQCTHGIKPVVSTQLLLNGSLAEEGIIIRSENLTENTKTIIVHLNES
      TV1.8_5   (249) VSTVQCTHGIKPVVSTQLLLNGSLAEEGIIIRSENLTENTKTIIVHLNES
      TV2.12-5/1(235) VSTVQCTHGIKPVVSTQLLLNGSLAEEIIIRSENLNNVKTIIVHLNES
      Consensus (251) VSTVQCTHGIKPVVSTQLLLNGSLAEEGIIIRSENLTENTKTIIVHLNES 301*   *                                       *350
      SF162     (285) VEINCTRPNNNTRKSITIGPGRAFYATGDIIGDIRQAHCNISGEKWNNT
      TV1.8_2   (299) VEINCTRPNNNTRKSVRIGPGQAFYATNDVIGDIRQAHCNISTDRWNKTL
      TV1.8_5   (299) VEINCTRPNNNTRKSVRIGPGQAFYATNDVIGDIRQAHCNISTDRWNKTL
      TV2.12-5/1(285) VEIKCIRPGNNTRKSVRIGPGQAFYATGDIIGDIRQAHCNASKNEWNTL
      Consensus (301) VEINCTRPNNNTRKSVRIGPGQAFYATNDIIGNIRQAHCNISTDRWNKTL
```

FIGURE 2A

```
                    351         *                        *      400
     SF162   (335) KQLVTKLQAQFGNKT-IVFKQSSGGDPEIVMHSFNCGGEFFYCNSTQL
   TV1.8_2   (349) QQVMKKLGEHFPNKT-IQFKPHAGGDLEITMHSFNCRGEFFYCNTSNL
   TV1.8_5   (349) QQVMKKLGEHFPNKT-IKFEPHAGGDLLITMHSFNCRGEFFYCNTSNL
 TV2.12-5/1  (335) QRVSQKLGELFPNSTGLKFAPHSGGDLEITTHSFNCGGEFYCNTTDL
  Consensus  (351) QQVMKKLQEHFPNKT IKFKPHAGGDLEITMHSFNCRGEFFYCNTSNLFN 401         *          *       ↓   β20/β21    ↓   450
     SF162   (384) STWNN------IGPN-NINGTYLPCRIKQLINRWQEVGKAMYAPPIRG
   TV1.8_2   (398) STYHS---NNGIYKYNGNSSSPITLQCKIKQLVRMWQGVGQATYAPPIAG
   TV1.8_5   (398) STYFP---KNGIYKYNGNSSLPITLQCKIKQLVRMWQGVGQAMYAPPIAG
 TV2.12-5/1  (385) STYSNGTCTNGICMSN--NIERLTQCRIKQINMWGEVGRAMYAPPIAG
  Consensus  (401) STYHN   NGTYKYNGNSS PITLQCKIKQIIRMWQGVGQAMYAPPIAG

*
                    451         *                 *   *    500
     SF162   (427) QIRCSSNITGLLLTRDGGKEIFNT---TEIFRPGGGDMRDNWRSELYKYK
   TV1.8_2   (445) NITCRSNITGILLTRDSGFNTTNN---TITFRPGGGDMRDNWRSELYKYK
   TV1.8_5   (445) NITCRSNITGILLTRDCGFNNTNNDTEITFRPGGGDMRDNWRSELYKYKV
 TV2.12-5/1  (433) NITCRSNITGILLTRDGGDNNTEI----TFRPGGGDMRDNWRSELYKYKV
  Consensus  (451) NITCRSNITGILLTRDGGFNNTNT TETFRPGGGDMRDNWRSELYKYKV 501                                          550
     SF162   (475) VKIEPLGVAPTKAKRRVVQREKRAVTLGAMFLGFLGAAGSTMGARSLTLT
   TV1.8_2   (493) VEIKPLGIAPTKAKRRVVQREKRAVGIGAVFLGFLGAAGSTMGAASITLT
   TV1.8_5   (495) VEIKPLGIAPTKAKRRVVQREKKAVGIGAVFLGFLGAAGSTMGAASITLT
 TV2.12-5/1  (480) VEIKPLGVAPTKAKRRVVEREKRAVGIGAVLGFLGAAGSTMGAASITLT
  Consensus  (501) VEIKPLGIAPTKAKRRVVQREKRAVGIGAVFLGFLGAAGSTMGAASITLT
                    551                                          600
     SF162   (525) VQARQLLSGIVQQQNNLLRAIEAQQHLLQLTVWGIKQLQARVLAVERYLK
   TV1.8_2   (543) VQARQLLSGIVQQQSNLLKAIEAQQHMLQLTVWGIKQLQARVLAIERYLK
   TV1.8_5   (545) VQARQLLSGIVQQQSNLLKAIEAQQHMLQLTVWGIKQLQARVLAIERYLK
 TV2.12-5/1  (530) VQARQLLSGIVQQQSNLLRAIEAQQHMLQLTVWGIKQLQARVLAIERYLQ
  Consensus  (551) VQARQLLSGIVQQQSNLLKAIEAQQHMLQLTVWGIKQLQARVLAIERYLK 601                *     *         *     650
     SF162   (575) DQQLLGIWGCSGKLICTTAVPWNASWSNKSLDQIWNNMTWMEWEREIDNY
   TV1.8_2   (593) DQQLLGIWGCSGRLICTTAVPWNSSWSNKSEKDIWDNMTWMQWDREISNY
   TV1.8_5   (595) DQQLLGIWGCSGRLICTTAVPWNSSWSNKSEADIWDNMTWMQWDRETNNY
 TV2.12-5/1  (580) DQQLLGIWGCSGKLICTTNVLWNSSWSNKQSDIWDNMTWMQWDREISNY
  Consensus  (601) DQQLLGIWGCSGKLICTTAVPWNSSWSNKSEADIWDNMTWMQWDREISNY
                    651                                          700
     SF162   (625) TNLIYTLIEEDSNQQEKNEQELLELDKWASLWNWFDISKWLWYIKIFIMI
   TV1.8_2   (643) TGLIYNLLEDSQNQQEKNEKDLLELDKWNNLWNWFDISNWPYIKIFIMI
   TV1.8_5   (645) TETIYRLLEDSQNQQEKNEKDLLEIDKWNNLWNWFDISNWLWYIKIFIMI
 TV2.12-5/1  (630) TNTIYRLLEDSQSQQERNEKDLIALDRWNNLWNWLSLNWLWYIKIFIMI
  Consensus  (651) TNTIYRLLEDSQNQQEKNEKDLLELDKWNNLWNWFDISNWLWYIKIFIMI
                    701                                          750
     SF162   (675) VGGLVGLRIVFTVLSIVNRVRQGYSPLSFQTRFPAPRGPDRPEGIEEEGG
   TV1.8_2   (693) VGGLIGLRIIFAVLSIVNRVRQGYSPLSFQTLTPSPRGLDRLGGIEEEGG
   TV1.8_5   (695) VGGLIGLRIIFAVLSIVNRVRQGYSPLSFQTLTPSPRGLDRLGGIEEEGG
 TV2.12-5/1  (680) VGGLIGLRIIFAVLSIVNRVRQGYSPLSLQTLIENPRSPRGLGGIEEEGG
  Consensus  (701) VGGLIGLRIIFAVLSIVNRVRQGYSPLSFQTLTPSPRGPDRLGGIEEEGG
```

FIGURE 2B

```
              751                                                800
     SF162  (725)  ERDRDSSPLHLAIIDDLRSLCLSSYRLRLLLLAARIVLLCR-
    TV1.8_2 (743)  QDRDSIRLVSFLSLADDLRNLCLLSLRLRLFLLAVRAVLLGHS
    TV1.8_5 (745)  QDRDSIRLVSFLSLADDLRSLCLLSLRLRDFLLAVRAVLLGHS
  TV2.12-5/1 (730) QSSSIRLVSGFLSLADDLRSLCLLCLRLRLFLLVVRAVLLGHS
  Consensus  (751) EQDRDRSIRLVSGFLSLAWDDLRSLCLFSYHRLRDFILIAVRAVELLGHS 801                                                850
     SF162  (774)  ------RGWEALKYWGNLLQYWIQELKNSAVSLFDATAIAVAEGTDRIIE
    TV1.8_2 (793)  SLRGLQRGWEILKYLGSLVQYWGLELKKSAISLLDTIAITVAEGTDRIIE
    TV1.8_5 (795)  SLRGLQRGWEILKYLGSLVQYWGLELKKSAISPLDTIAIAVAEGTDRIIE
  TV2.12-5/1 (780) SLRGLQRGWGTLKYLGSLVQYWGLELKKSAINLLDTIAIAVAEGTDRIIE
  Consensus  (801) SLRGLQRGWEILKYLGSLVQYWGLELKKSAISLLDTIAIAVAEGTDRIIE 851                       876
     SF162  (818)  VARIGRAFLHIPRRIRQGFERALL-
    TV1.8_2 (843)  LVQRICRAILNIPRRIRQGFAALL-
    TV1.8_5 (845)  LVQRICRAILNIPRRIRQGFAALL-
  TV2.12-5/1 (830) FLQNICRGIRNVPRRIRQGFEAATQ-
  Consensus  (851) LVQRICRAILNIPRRIRQGFEAALL
```

GagComplPolmut.SF2 (Gag complete, RT mutated, Protease functional; all in frame)

```
GTCGACGCCACCATGGGCGCCCGCGCCAGCGTGCTGAGCGGCGGCGAGCT
GGACAAGTGGGAGAAGATCCGCCTGCGCCCCGGCGGCAAGAAGAAGTAC
AAGCTGAAGCACATCGTGTGGGCCAGCCGCGAGCTGGAGCGCTTCGCCGT
GAACCCCGGCCTGCTGGAGACCAGCGAGGGCTGCCGCCAGATCCTGGGCC
AGCTGCAGCCCAGCCTGCAGACCGGCAGCGAGGAGCTGCGCAGCCTGTAC
AACACCGTGGCCACCCTGTACTGCGTGCACCAGCGCATCGACGTCAAGGA
CACCAAGGAGGCCCTGGAGAAGATCGAGGAGGAGCAGAACAAGTCCAAG
AAGAAGGCCCAGCAGGCCGCCGCCGCCGGCACCGGCAACAGCAGCC
AGGTGAGCCAGAACTACCCCATCGTGCAGAACCTGCAGGGCCAGATGGTG
CACCAGGCCATCAGCCCCCGCACCCTGAACGCCTGGGTGAAGGTGGTGGA
GGAGAAGGCCTTCAGCCCCGAGGTGATCCCCATGTTCAGCGCCCTGAGCG
AGGGCGCCACCCCCCAGGACCTGAACACGATGTTGAACACCGTGGGCGGC
CACCAGGCCGCCATGCAGATGCTGAAGGAGACCATCAACGAGGAGGCCG
CCGAGTGGGACCGCGTGCACCCCGTGCACGCCGGCCCCATCGCCCCCGGC
CAGATGCGCGAGCCCCGCGGCAGCGACATCGCCGGCACCACCAGCACCCT
GCAGGAGCAGATCGGCTGGATGACCAACAACCCCCCCATCCCCGTGGGCG
AGATCTACAAGCGGTGGATCATCCTGGGCCTGAACAAGATCGTGCGGATG
TACAGCCCCACCAGCATCCTGGACATCCGCCAGGGCCCCAAGGAGCCCTT
CCGCGACTACGTGGACCGCTTCTACAAGACCCTGCGCGCTGAGCAGGCCA
GCCAGGACGTGAAGAACTGGATGACCGAGACCCTGCTGGTGCAGAACGC
CAACCCCGACTGCAAGACCATCCTGAAGGCTCTCGGCCCCGCGGCCACCC
TGGAGGAGATGATGACCGCCTGCCAGGGCGTGGGCGGCCCCGGCCACAA
GGCCCGCGTGCTGGCCGAGGCGATGAGCCAGGTGACGAACCCGGCGACC
ATCATGATGCAGCGCGGCAACTTCCGCAACCAGCGGAAGACCGTCAAGTG
CTTCAACTGCGGCAAGGAGGGCCACACCGCCAGGAACTGCCGCGCCCCC
GCAAGAAGGGCTGCTGGCGCTGCGGCCGCGAGGGCCACCAGATGAAGGA
CTGCACCGAGCGCCAGGCCAACTTCCTGGGCAAGATCTGGCCCAGCTACA
AGGGCCGCCCCGGCAACTTCCTGCAGAGCCGCCCCGAGCCCACCGCCCCC
CCCGAGGAGAGCTTCCGCTTCGGCGAGGAGAAGACCACCCCCAGCCAGA
AGCAGGAGCCCATCGACAAGGAGCTGTACCCCCTGACCAGCCTGCGCAGC
CTGTTCGGCAACGACCCCAGCAGCCAGAAAGAATTCAAGGCCCGCGTGCT
GGCCGAGGCGATGAGCCAGGTGACGAACCCGGCGACCATCATGATGCAG
CGCGGCAACTTCCGCAACCAGCGGAAGACCGTCAAGTGCTTCAACTGCGG
CAAGGAGGGCCACACCGCCAGGAACTGCCGCGCCCCCGCAAGAAGGGC
TGCTGGCGCTGCGGCCGCGAAGGACACCAAATGAAAGATTGCACTGAGA
GACAGGCTAATTTCTTCCGCGAGGACCTGGCCTTCCTGCAGGGCAAGGCC
CGCGAGTTCAGCAGCGAGCAGACCCGCGCCAACAGCCCCACCCGCCGCGA
GCTGCAGGTGTGGGGCGGCGAGAACAACAGCCTGAGCGAGGCCGGCGCC
GACCGCCAGGGCACCGTGAGCTTCAACTTCCCCCAGATCACCCTGTGGCA
GCGCCCCCTGGTGACCATCAGGATCGGCGGCCAGCTCAAGGAGGCGCTGC
TCGACACCGGCGCCGACGACACCGTGCTGGAGGAGATGAACCTGCCCGGC
AAGTGGAAGCCCAAGATGATCGGCGGGATCGGGGGCTTCATCAAGGTGC
GGCAGTACGACCAGATCCCCGTGGAGATCTGCGGCCACAAGGCCATCGGC
```

```
ACCGTGCTGGTGGGCCCCACCCCCGTGAACATCATCGGCCGCAACCTGCT
GACCCAGATCGGCTGCACCCTGAACTTCCCCATCAGCCCCATCGAGACGG
TGCCCGTGAAGCTGAAGCCGGGGATGGACGGCCCCAAGGTCAAGCAGTG
GCCCCTGACCGAGGAGAAGATCAAGGCCCTGGTGGAGATCTGCACCGAG
ATGGAGAAGGAGGGCAAGATCAGCAAGATCGGCCCCGAGAACCCCTACA
ACACCCCCGTGTTCGCCATCAAGAAGAAGGACAGCACCAAGTGGCGCAA
GCTGGTGGACTTCCGCGAGCTGAACAAGCGCACCCAGGACTTCTGGGAGG
TGCAGCTGGGCATCCCCACCCCGCCGGCCTGAAGAAGAAGAAGAGCGTG
ACCGTGCTGGACGTGGGCGACGCCTACTTCAGCGTGCCCCTGGACAAGGA
CTTCCGCAAGTACACCGCCTTCACCATCCCCAGCATCAACAACGAGACCC
CCGGCATCCGCTACCAGTACAACGTGCTGCCCCAGGGCTGGAAGGGCAGC
CCCGCCATCTTCCAGAGCAGCATGACCAAGATCCTGGAGCCCTTCCGCAA
GCAGAACCCCGACATCGTGATCTACCAGGCCCCCTGTACGTGGGCAGCG
ACCTGGAGATCGGCCAGCACCGCACCAAGATCGAGGAGCTGCGCCAGCA
CCTGCTGCGCTGGGGCTTCACCACCCCGACAAGAAGCACCAGAAGGAGC
CCCCCTTCCTGCCCATCGAGCTGCACCCCGACAAGTGGACCGTGCAGCCC
ATCATGCTGCCCGAGAAGGACAGCTGGACCGTGAACGACATCCAGAAGCT
GGTGGGCAAGCTGAACTGGGCCAGCCAGATCTACGCCGGCATCAAGGTGA
AGCAGCTGTGCAAGCTGCTGCGCGGCACCAAGGCCCTGACCGAGGTGATC
CCCCTGACCGAGGAGGCCGAGCTGGAGCTGGCCGAGAACCGCGAGATCCT
GAAGGAGCCCGTGCACGAGGTGTACTACGACCCCAGCAAGGACCTGGTG
GCCGAGATCCAGAAGCAGGGCCAGGGCCAGTGGACCTACCAGATCTACC
AGGAGCCCTTCAAGAACCTGAAGACCGGCAAGTACGCCCGCATGCGCGGC
GCCCACACCAACGACGTGAAGCAGCTGACCGAGGCCGTGCAGAAGGTGA
GCACCGAGAGCATCGTGATCTGGGGCAAGATCCCCAAGTTCAAGCTGCCC
ATCCAGAAGGAGACCTGGGAGGCCTGGTGGATGGAGTACTGGCAGGCCA
CCTGGATCCCCGAGTGGGAGTTCGTGAACACCCCCCCCTGGTGAAGCTG
TGGTACCAGCTGGAGAAGGAGCCCATCGTGGGCGCCGAGACCTTCTACGT
GGACGGCGCCGCCAACCGCGAGACCAAGCTGGGCAAGGCCGGCTACGTG
ACCGACCGGGGCCGGCAGAAGGTGGTGAGCATCGCCGACACCACCAACC
AGAAGACCGAGCTGCAGGCCATCCACCTGGCCCTGCAGGACAGCGGCCTG
GAGGTGAACATCGTGACCGACAGCCAGTACGCCCTGGGCATCATCCAGGC
CCAGCCCGACAAGAGCGAGAGCGAGCTGGTGAGCCAGATCATCGAGCAG
CTGATCAAGAAGGAGAAGGTGTACCTGGCCTGGGTGCCCGCCCACAAGGG
CATCGGCGGCAACGAGCAGGTGGACAAGCTGGTGAGCGCCGGCATCCGC
AAGGTGCTGTTCCTGAACGGCATCGATGGCGGCATCGTGATCTACCAGTA
CATGGACGACCTGTACGTGGGCAGCGGCGGCCCTAGGATCGATTAAAAGC
TTCCCGGGGCTAGCACCGGTTCTAGA
```

GagComplPolmutAtt.SF2 (Gag complete, RT mutated, Protease attenuated; all in frame)

```
GTCGACGCCACCATGGGCGCCCGCGCCAGCGTGCTGAGCGGCGGCGAGCT
GGACAAGTGGGAGAAGATCCGCCTGCGCCCCGGCGGCAAGAAGAAGTAC
AAGCTGAAGCACATCGTGTGGGCCAGCCGCGAGCTGGAGCGCTTCGCCGT
GAACCCCGGCCTGCTGGAGACCAGCGAGGGCTGCCGCCAGATCCTGGGCC
AGCTGCAGCCCAGCCTGCAGACCGGCAGCGAGGAGCTGCGCAGCCTGTAC
AACACCGTGGCCACCCTGTACTGCGTGCACCAGCGCATCGACGTCAAGGA
CACCAAGGAGGCCCTGGAGAAGATCGAGGAGGAGCAGAACAAGTCCAAG
AAGAAGGCCCAGCAGGCCGCCGCCGCCGGCACCGGCAACAGCAGCC
AGGTGAGCCAGAACTACCCCATCGTGCAGAACCTGCAGGGCCAGATGGTG
CACCAGGCCATCAGCCCCCGCACCCTGAACGCCTGGGTGAAGGTGGTGGA
GGAGAAGGCCTTCAGCCCCGAGGTGATCCCCATGTTCAGCGCCCTGAGCG
AGGGCGCCACCCCCCAGGACCTGAACACGATGTTGAACACCGTGGGCGGC
CACCAGGCCGCCATGCAGATGCTGAAGGAGACCATCAACGAGGAGGCCG
CCGAGTGGGACCGCGTGCACCCCGTGCACGCCGGCCCCATCGCCCCCGGC
CAGATGCGCGAGCCCCGCGGCAGCGACATCGCCGGCACCACCAGCACCCT
GCAGGAGCAGATCGGCTGGATGACCAACAACCCCCCCATCCCCGTGGGCG
AGATCTACAAGCGGTGGATCATCCTGGGCCTGAACAAGATCGTGCGGATG
TACAGCCCCACCAGCATCCTGGACATCCGCCAGGGCCCCAAGGAGCCCTT
CCGCGACTACGTGGACCGCTTCTACAAGACCCTGCGCGCTGAGCAGGCCA
GCCAGGACGTGAAGAACTGGATGACCGAGACCCTGCTGGTGCAGAACGC
CAACCCCGACTGCAAGACCATCCTGAAGGCTCTCGGCCCCGCGGCCACCC
TGGAGGAGATGATGACCGCCTGCCAGGGCGTGGGCGGCCCCGGCCACAA
GGCCCGCGTGCTGGCCGAGGCGATGAGCCAGGTGACGAACCCGGCGACC
ATCATGATGCAGCGCGGCAACTTCCGCAACCAGCGGAAGACCGTCAAGTG
CTTCAACTGCGGCAAGGAGGGCCACACCGCCAGGAACTGCCGCGCCCCC
GCAAGAAGGGCTGCTGGCGCTGCGGCCGCGAGGGCCACCAGATGAAGGA
CTGCACCGAGCGCCAGGCCAACTTCCTGGGCAAGATCTGGCCCAGCTACA
AGGGCCGCCCCGGCAACTTCCTGCAGAGCCGCCCCGAGCCCACCGCCCCC
CCCGAGGAGAGCTTCCGCTTCGGCGAGGAGAAGACCACCCCCAGCCAGA
AGCAGGAGCCCATCGACAAGGAGCTGTACCCCCTGACCAGCCTGCGCAGC
CTGTTCGGCAACGACCCCAGCAGCCAGAAAGAATTCAAGGCCCGCGTGCT
GGCCGAGGCGATGAGCCAGGTGACGAACCCGGCGACCATCATGATGCAG
CGCGGCAACTTCGCAACCAGCGGAAGACCGTCAAGTGCTTCAACTGCGG
CAAGGAGGGCCACACCGCCAGGAACTGCCGCGCCCCCGCAAGAAGGGC
TGCTGGCGCTGCGGCCGCGAAGGACACCAAATGAAAGATTGCACTGAGA
GACAGGCTAATTTCTTCCGCGAGGACCTGGCCTTCCTGCAGGGCAAGGCC
CGCGAGTTCAGCAGCGAGCAGACCCGCGCCAACAGCCCCACCCGCCGCGA
GCTGCAGGTGTGGGGCGGCGAGAACAACAGCCTGAGCGAGGCCGGCGCC
GACCGCCAGGGCACCGTGAGCTTCAACTTCCCCCAGATCACCCTGTGGCA
GCGCCCCCTGGTGACCATCAGGATCGGCGGCCAGCTCAAGGAGGCGCTGC
TCGACTCCGGCGCCGACGACACCGTGCTGGAGGAGATGAACCTGCCCGGC
AAGTGGAAGCCCAAGATGATCGGCGGGATCGGGGGCTTCATCAAGGTGC
GGCAGTACGACCAGATCCCCGTGGAGATCTGCGGCCACAAGGCCATCGGC
```

ACCGTGCTGGTGGGCCCCACCCCCGTGAACATCATCGGCCGCAACCTGCT
GACCCAGATCGGCTGCACCCTGAACTTCCCCATCAGCCCCATCGAGACGG
TGCCCGTGAAGCTGAAGCCGGGGATGGACGGCCCCAAGGTCAAGCAGTG
GCCCCTGACCGAGGAGAAGATCAAGGCCCTGGTGGAGATCTGCACCGAG
ATGGAGAAGGAGGGCAAGATCAGCAAGATCGGCCCCGAGAACCCCTACA
ACACCCCCGTGTTCGCCATCAAGAAGAAGGACAGCACCAAGTGGCGCAA
GCTGGTGGACTTCCGCGAGCTGAACAAGCGCACCCAGGACTTCTGGGAGG
TGCAGCTGGGCATCCCCACCCCGCCGGCCTGAAGAAGAAGAAGAGCGTG
ACCGTGCTGGACGTGGGCGACGCCTACTTCAGCGTGCCCTGGACAAGGA
CTTCCGCAAGTACACCGCCTTCACCATCCCCAGCATCAACAACGAGACCC
CCGGCATCCGCTACCAGTACAACGTGCTGCCCCAGGGCTGGAAGGGCAGC
CCCGCCATCTTCCAGAGCAGCATGACCAAGATCCTGGAGCCCTTCCGCAA
GCAGAACCCCGACATCGTGATCTACCAGGCCCCCTGTACGTGGGCAGCG
ACCTGGAGATCGGCCAGCACCGCACCAAGATCGAGGAGCTGCGCCAGCA
CCTGCTGCGCTGGGGCTTCACCACCCCGACAAGAAGCACCAGAAGGAGC
CCCCCTTCCTGCCCATCGAGCTGCACCCCGACAAGTGGACCGTGCAGCCC
ATCATGCTGCCCGAGAAGGACAGCTGGACCGTGAACGACATCCAGAAGCT
GGTGGGCAAGCTGAACTGGGCCAGCCAGATCTACGCCGGCATCAAGGTGA
AGCAGCTGTGCAAGCTGCTGCGCGGCACCAAGGCCCTGACCGAGGTGATC
CCCCTGACCGAGGAGGCCGAGCTGGAGCTGGCCGAGAACCGCGAGATCCT
GAAGGAGCCCGTGCACGAGGTGTACTACGACCCCAGCAAGGACCTGGTG
GCCGAGATCCAGAAGCAGGGCCAGGGCCAGTGGACCTACCAGATCTACC
AGGAGCCCTTCAAGAACCTGAAGACCGGCAAGTACGCCCGCATGCGCGGC
GCCCACACCAACGACGTGAAGCAGCTGACCGAGGCCGTGCAGAAGGTGA
GCACCGAGAGCATCGTGATCTGGGGCAAGATCCCCAAGTTCAAGCTGCCC
ATCCAGAAGGAGACCTGGGAGGCCTGGTGGATGGAGTACTGGCAGGCCA
CCTGGATCCCCGAGTGGGAGTTCGTGAACACCCCCCCCTGGTGAAGCTG
TGGTACCAGCTGGAGAAGGAGCCCATCGTGGGCGCCGAGACCTTCTACGT
GGACGGCGCCGCCAACCGCGAGACCAAGCTGGGCAAGGCCGGCTACGTG
ACCGACCGGGGCCGGCAGAAGGTGGTGAGCATCGCCGACACCACCAACC
AGAAGACCGAGCTGCAGGCCATCCACCTGGCCCTGCAGGACAGCGGCCTG
GAGGTGAACATCGTGACCGACAGCCAGTACGCCCTGGGCATCATCCAGGC
CCAGCCCGACAAGAGCGAGAGCGAGCTGGTGAGCCAGATCATCGAGCAG
CTGATCAAGAAGGAGAAGGTGTACCTGGCCTGGGTGCCCGCCCACAAGGG
CATCGGCGGCAACGAGCAGGTGGACAAGCTGGTGAGCGCCGGCATCCGC
AAGGTGCTGTTCCTGAACGGCATCGATGGCGGCATCGTGATCTACCAGTA
CATGGACGACCTGTACGTGGGCAGCGGCGGCCCTAGGATCGATTAAAAGC
TTCCCGGGGCTAGCACCGGTTCTAGA

GagComplPolmutIna.SF2 (Gag complete, RT mutated, Protease inactive; all in frame)

```
GTCGACGCCACCATGGGCGCCCGCGCCAGCGTGCTGAGCGGCGGCGAGCT
GGACAAGTGGGAGAAGATCCGCCTGCGCCCCGGCGGCAAGAAGAAGTAC
AAGCTGAAGCACATCGTGTGGGCCAGCCGCGAGCTGGAGCGCTTCGCCGT
GAACCCCGGCCTGCTGGAGACCAGCGAGGGCTGCCGCCAGATCCTGGGCC
AGCTGCAGCCCAGCCTGCAGACCGGCAGCGAGGAGCTGCGCAGCCTGTAC
AACACCGTGGCCACCCTGTACTGCGTGCACCAGCGCATCGACGTCAAGGA
CACCAAGGAGGCCCTGGAGAAGATCGAGGAGGAGCAGAACAAGTCCAAG
AAGAAGGCCCAGCAGGCCGCCGCCGCCGGCACCGGCAACAGCAGCC
AGGTGAGCCAGAACTACCCCATCGTGCAGAACCTGCAGGGCCAGATGGTG
CACCAGGCCATCAGCCCCCGCACCCTGAACGCCTGGGTGAAGGTGGTGA
GGAGAAGGCCTTCAGCCCCGAGGTGATCCCCATGTTCAGCGCCCTGAGCG
AGGGCGCCACCCCCCAGGACCTGAACACGATGTTGAACACCGTGGGCGGC
CACCAGGCCGCCATGCAGATGCTGAAGGAGACCATCAACGAGGAGGCCG
CCGAGTGGGACCGCGTGCACCCCGTGCACGCCGGCCCCATCGCCCCCGGC
CAGATGCGCGAGCCCCGCGGCAGCGACATCGCCGGCACCACCAGCACCCT
GCAGGAGCAGATCGGCTGGATGACCAACAACCCCCCATCCCCGTGGGCG
AGATCTACAAGCGGTGGATCATCCTGGGCCTGAACAAGATCGTGCGGATG
TACAGCCCCACCAGCATCCTGGACATCGCCAGGGCCCCAAGGAGCCCTT
CCGCGACTACGTGGACCGCTTCTACAAGACCCTGCGCGCTGAGCAGGCCA
GCCAGGACGTGAAGAACTGGATGACCGAGACCCTGCTGGTGCAGAACGC
CAACCCCGACTGCAAGACCATCCTGAAGGCTCTCGGCCCCGCGGCCACCC
TGGAGGAGATGATGACCGCCTGCCAGGGCGTGGGCGGCCCCGGCCACAA
GGCCCGCGTGCTGGCCGAGGCGATGAGCCAGGTGACGAACCCGGCGACC
ATCATGATGCAGCGCGGCAACTTCCGCAACCAGCGGAAGACCGTCAAGTG
CTTCAACTGCGGCAAGGAGGGCCACACCGCCAGGAACTGCCGCGCCCCC
GCAAGAAGGGCTGCTGGCGCTGCGGCCGCGAGGGCCACCAGATGAAGGA
CTGCACCGAGCGCCAGGCCAACTTCCTGGGCAAGATCTGGCCCAGCTACA
AGGGCCGCCCCGGCAACTTCCTGCAGAGCCGCCCCGAGCCCACCGCCCCC
CCCGAGGAGAGCTTCCGCTTCGGCGAGGAGAAGACCACCCCCAGCCAGA
AGCAGGAGCCCATCGACAAGGAGCTGTACCCCCTGACCAGCCTGCGCAGC
CTGTTCGGCAACGACCCCAGCAGCCAGAAGAATTCAAGGCCCGCGTGCT
GGCCGAGGCGATGAGCCAGGTGACGAACCCGGCGACCATCATGATGCAG
CGCGGCAACTTCCGCAACCAGCGGAAGACCGTCAAGTGCTTCAACTGCGG
CAAGGAGGGCCACACCGCCAGGAACTGCCGCGCCCCCGCAAGAAGGGC
TGCTGGCGCTGCGGCCGCGAAGGACACCAAATGAAAGATTGCACTGAGA
GACAGGCTAATTTCTTCCGCGAGGACCTGGCCTTCCTGCAGGGCAAGGCC
CGCGAGTTCAGCAGCGAGCAGACCCGCGCCAACAGCCCCACCCGCCGCGA
GCTGCAGGTGTGGGGCGGCGAGAACAACAGCCTGAGCGAGGCCGGCGCC
GACCGCCAGGGCACCGTGAGCTTCAACTTCCCCCAGATCACCCTGTGGCA
GCGCCCCCTGGTGACCATCAGGATCGGCGGCCAGCTCAAGGAGGCGCTGC
TCGCCACCGGCGCCGACGACACCGTGCTGGAGGAGATGAACCTGCCCGGC
AAGTGGAAGCCCAAGATGATCGGCGGGATCGGGGGCTTCATCAAGGTGC
GGCAGTACGACCAGATCCCCGTGGAGATCTGCGGCCACAAGGCCATCGGC
ACCGTGCTGGTGGGCCCCACCCCCGTGAACATCATCGGCCGCAACCTGCT
```

GACCCAGATCGGCTGCACCCTGAACTTCCCCATCAGCCCCATCGAGACGG
TGCCCGTGAAGCTGAAGCCGGGGATGGACGGCCCCAAGGTCAAGCAGTG
GCCCCTGACCGAGGAGAAGATCAAGGCCCTGGTGGAGATCTGCACCGAG
ATGGAGAAGGAGGGCAAGATCAGCAAGATCGGCCCCGAGAACCCCTACA
ACACCCCCGTGTTCGCCATCAAGAAGAAGGACAGCACCAAGTGGCGCAA
GCTGGTGGACTTCCGCGAGCTGAACAAGCGCACCCAGGACTTCTGGGAGG
TGCAGCTGGGCATCCCCACCCCGCCGGCCTGAAGAAGAAGAAGAGCGTG
ACCGTGCTGGACGTGGGCGACGCCTACTTCAGCGTGCCCTGGACAAGGA
CTTCCGCAAGTACACCGCCTTCACCATCCCCAGCATCAACAACGAGACCC
CCGGCATCCGCTACCAGTACAACGTGCTGCCCCAGGGCTGGAAGGGCAGC
CCCGCCATCTTCCAGAGCAGCATGACCAAGATCCTGGAGCCCTTCCGCAA
GCAGAACCCCGACATCGTGATCTACCAGGCCCCCCTGTACGTGGGCAGCG
ACCTGGAGATCGGCCAGCACCGCACCAAGATCGAGGAGCTGCGCCAGCA
CCTGCTGCGCTGGGGCTTCACCACCCCCGACAAGAAGCACCAGAAGGAGC
CCCCCTTCCTGCCCATCGAGCTGCACCCCGACAAGTGGACCGTGCAGCCC
ATCATGCTGCCCGAGAAGGACAGCTGGACCGTGAACGACATCCAGAAGCT
GGTGGGCAAGCTGAACTGGGCCAGCCAGATCTACGCCGGCATCAAGGTGA
AGCAGCTGTGCAAGCTGCTGCGCGGCACCAAGGCCCTGACCGAGGTGATC
CCCCTGACCGAGGAGGCCGAGCTGGAGCTGGCCGAGAACCGCGAGATCCT
GAAGGAGCCCGTGCACGAGGTGTACTACGACCCCAGCAAGGACCTGGTG
GCCGAGATCCAGAAGCAGGGCCAGGGCCAGTGGACCTACCAGATCTACC
AGGAGCCCTTCAAGAACCTGAAGACCGGCAAGTACGCCCGCATGCGCGGC
GCCCACACCAACGACGTGAAGCAGCTGACCGAGGCCGTGCAGAAGGTGA
GCACCGAGAGCATCGTGATCTGGGGCAAGATCCCCAAGTTCAAGCTGCCC
ATCCAGAAGGAGACCTGGGAGGCCTGGTGGATGGAGTACTGGCAGGCCA
CCTGGATCCCCGAGTGGGAGTTCGTGAACACCCCCCCCTGGTGAAGCTG
TGGTACCAGCTGGAGAAGGAGCCCATCGTGGGCGCCGAGACCTTCTACGT
GGACGGCGCCGCCAACCGCGAGACCAAGCTGGGCAAGGCCGGCTACGTG
ACCGACCGGGGCCGGCAGAAGGTGGTGAGCATCGCCGACACCACCAACC
AGAAGACCGAGCTGCAGGCCATCCACCTGGCCCTGCAGGACAGCGGCCTG
GAGGTGAACATCGTGACCGACAGCCAGTACGCCCTGGGCATCATCCAGGC
CCAGCCCGACAAGAGCGAGAGCGAGCTGGTGAGCCAGATCATCGAGCAG
CTGATCAAGAAGGAGAAGGTGTACCTGGCCTGGGTGCCCGCCCACAAGGG
CATCGGCGGCAACGAGCAGGTGGACAAGCTGGTGAGCGCCGGCATCCGC
AAGGTGCTGTTCCTGAACGGCATCGATGGCGGCATCGTGATCTACCAGTA
CATGGACGACCTGTACGTGGGCAGCGGCGGCCCTAGGATCGATTAAAAGC
TTCCCGGGGCTAGCACCGGTTCTAGA

gagCpolInaTatRevNef.opt_B

GTCGACGCCACCATGGGCGCCCGCGCCAGCGTGCTGAGCGGCGGCGAGCTGGACAAGTGGGAGAAGATC
CGCCTGCGCCCCGGCGGCAAGAAGAAGTACAAGCTGAAGCACATCGTGTGGGCCAGCCGCGAGCTGGAG
CGCTTCGCCGTGAACCCCGGCCTGCTGGAGACCAGCGAGGGCTGCCGCCAGATCCTGGGCCAGCTGCAG
CCCAGCCTGCAGACCGGCAGCGAGGAGCTGCGCAGCCTGTACAACACCGTGGCCACCCTGTACTGCGTG
CACCAGCGCATCGACGTCAAGGACACCAAGGAGGCCCTGGAGAAGATCGAGGAGGAGCAGAACAAGTCC
AAGAAGAAGGCCCAGCAGGCCGCCGCCGCCGCCGGCACCGGCAACAGCAGCCAGGTGAGCCAGAACTAC
CCCATCGTGCAGAACCTGCAGGGCCAGATGGTGCACCAGGCCATCAGCCCCGCACCCTGAACGCCTGG
GTGAAGGTGGTGGAGGAGAAGGCCTTCAGCCCCGAGGTGATCCCCATGTTCAGCGCCCTGAGCGAGGGC
GCCACCCCCCAGGACCTGAACACGATGTTGAACACCGTGGGCGGCCACCAGGCCGCCATGCAGATGCTG
AAGGAGACCATCAACGAGGAGGCCGCCGAGTGGGACCGCGTGCACCCCGTGCACGCCGGCCCCATCGCC
CCCGGCCAGATGCGCGAGCCCCGCGGCAGCGACATCGCCGGCACCACCAGCACCCTGCAGGAGCAGATC
GGCTGGATGACCAACAACCCCCCCATCCCCGTGGGCGAGATCTACAAGCGGTGGATCATCCTGGGCCTG
AACAAGATCGTGCGGATGTACAGCCCCACCAGCATCCTGGACATCCGCCAGGGCCCCAAGGAGCCCTTC
CGCGACTACGTGGACCGCTTCTACAAGACCCTGCGCGCTGAGCAGGCCAGCCAGGACGTGAAGAACTGG
ATGACCGAGACCCTGCTGGTGCAGAACGCCAACCCCGACTGCAAGACCATCCTGAAGGCTCTCGGCCCC
GCGGCCACCCTGGAGGAGATGATGACCGCCTGCCAGGGCGTGGGCGGCCCCGGCCACAAGGCCCGCGTG
CTGGCCGAGGCGATGAGCCAGGTGACGAACCCGGCGACCATCATGATGCAGCGCGGCAACTTCCGCAAC
CAGCGGAAGACCGTCAAGTGCTTCAACTGCGGCAAGGAGGGCCACACCGCCAGGAACTGCCGCGCCCCC
CGCAAGAAGGGCTGCTGGCGCTGCGGCCGCGAGGGCCACCAGATGAAGGACTGCACCGAGCGCCAGGCC
AACTTCCTGGGCAAGATCTGGCCCAGCTACAAGGGCCGCCCCGGCAACTTCCTGCAGAGCCGCCCCGAG
CCCACCGCCCCCCCCGAGGAGAGCTTCCGCTTCGGCGAGGAGAAGACCACCCCCAGCCAGAAGCAGGAG
CCCATCGACAAGGAGCTGTACCCCCTGACCAGCCTGCGCAGCCTGTTCGGCAACGACCCCAGCAGCCAG
AAAGAATTCAAGGCCCGCGTGCTGGCCGAGGCGATGAGCCAGGTGACGAACCCGGCGACCATCATGATG
CAGCGCGGCAACTTCCGCAACCAGCGGAAGACCGTCAAGTGCTTCAACTGCGGCAAGGAGGGCCACACC
GCCAGGAACTGCCGCGCCCCCCGCAAGAAGGGCTGCTGGCGCTGCGGCCGCGAAGGACACCAAATGAAA
GATTGCACTGAGAGACAGGCTAATTTCTTCCGCGAGGACCTGGCCTTCCTGCAGGGCAAGGCCCGCGAG
TTCAGCAGCGAGCAGACCCGCGCCAACAGCCCCACCCGCCGCGAGCTGCAGGTGTGGGGCGGCGAGAAC
AACAGCCTGAGCGAGGCCGGCGCCGACCGCCAGGGCACCGTGAGCTTCAACTTCCCCCAGATCACCCTG
TGGCAGCGCCCCCTGGTGACCATCAGGATCGGCGGCCAGCTCAAGGAGGCGCTGCTCGCCACCGGCGCC
GACGACACCGTGCTGGAGGAGATGAACCTGCCCGGCAAGTGGAAGCCCAAGATGATCGGCGGGATCGGG
GGCTTCATCAAGGTGCGGCAGTACGACCAGATCCCCGTGGAGATCTGCGGCCACAAGGCCATCGGCACC
GTGCTGGTGGGCCCCACCCCCGTGAACATCATCGGCCGCAACCTGCTGACCCAGATCGGCTGCACCCTG
AACTTCCCCATCAGCCCCATCGAGACGGTGCCCGTGAAGCTGAAGCCGGGGATGGACGGCCCCAAGGTC
AAGCAGTGGCCCCTGACCGAGGAGAAGATCAAGGCCCTGGTGGAGATCTGCACCGAGATGGAGAAGGAG
GGCAAGATCAGCAAGATCGGCCCCGAGAACCCCTACAACACCCCCGTGTTCGCCATCAAGAAGAAGGAC
AGCACCAAGTGGCGCAAGCTGGTGGACTTCCGCGAGCTGAACAAGCGCACCCAGGACTTCTGGGAGGTG
CAGCTGGGCATCCCCCACCCCGCCGGCCTGAAGAAGAAGAAGAGCGTGACCGTGCTGGACGTGGGCGAC
GCCTACTTCAGCGTGCCCCTGGACAAGGACTTCCGCAAGTACACCGCCTTCACCATCCCCAGCATCAAC
AACGAGACCCCCGGCATCCGCTACCAGTACAACGTGCTGCCCCAGGGCTGGAAGGGCAGCCCCGCCATC
TTCCAGAGCAGCATGACCAAGATCCTGGAGCCCTTCCGCAAGCAGAACCCCGACATCGTGATCTACCAG
GCCCCCCTGTACGTGGGCAGCGACCTGGAGATCGGCCAGCACCGCACCAAGATCGAGGAGCTGCGCCAG
CACCTGCTGCGCTGGGGCTTCACCACCCCCGACAAGAAGCACCAGAAGGAGCCCCCCTTCCTGCCCATC
GAGCTGCACCCCGACAAGTGGACCGTGCAGCCCATCATGCTGCCCGAGAAGGACAGCTGGACCGTGAAC
GACATCCAGAAGCTGGTGGGCAAGCTGAACTGGGCCAGCCAGATCTACGCCGGCATCAAGGTGAAGCAG
CTGTGCAAGCTGCTGCGCGGCACCAAGGCCCTGACCGAGGTGATCCCCCTGACCGAGGAGGCCGAGCTG
GAGCTGGCCGAGAACCGCGAGATCCTGAAGGAGCCCGTGCACGAGGTGTACTACGACCCCAGCAAGGAC
CTGGTGGCCGAGATCCAGAAGCAGGGCCAGGGCCAGTGGACCTACCAGATCTACCAGGAGCCCTTCAAG
AACCTGAAGACCGGCAAGTACGCCCGCATGCGCGGCGCCCACACCAACGACGTGAAGCAGCTGACCGAG
GCCGTGCAGAAGGTGAGCACCGAGAGCATCGTGATCTGGGGCAAGATCCCCAAGTTCAAGCTGCCCATC
CAGAAGGAGACCTGGGAGGCCTGGTGGATGGAGTACTGGCAGGCCACCTGGATCCCCGAGTGGGAGTTC
GTGAACACCCCCCCCCTGGTGAAGCTGTGGTACCAGCTGGAGAAGGAGCCCATCGTGGGCGCCGAGACC
TTCTACGTGGACGGCGCCGCCAACCGCGAGACCAAGCTGGGCAAGGCCGGCTACGTGACCGACCGGGGC
CGGCAGAAGGTGGTGAGCATCGCCGACACCACCAACCAGAAGACCGAGCTGCAGGCCATCCACCTGGCC
CTGCAGGACAGCGGCCTGGAGGTGAACATCGTGACCGACAGCCAGTACGCCCTGGGCATCATCCAGGCC

```
CAGCCCGACAAGAGCGAGAGCGAGCTGGTGAGCCAGATCATCGAGCAGCTGATCAAGAAGGAGAAGGTG
TACCTGGCCTGGGTGCCCGCCCACAAGGGCATCGGCGGCAACGAGCAGGTGGACAAGCTGGTGAGCGCC
GGCATCCGCAAGGTGCTGTTCCTGAACGGCATCGATGGCGGCATCGTGATCTACCAGTACATGGACGAC
CTGTACGTGGGCAGCGGCGGCCCTAGGGAGCCCGTGGACCCCGCCTGGAGCCCTGGAAGCACCCCGGC
AGCCAGCCCAAGACCGCCGGCACCAACTGCTACTGCAAGAAGTGCTGCTTCCACTGCCAGGTGAGCTTC
ATCACCAAGGGCCTGGGCATCAGCTACGGCCGCAAGAAGCGCCGCCAGCGCCGCCGCGCCCCCCCCGAC
AGCGAGGTGCACCAGGTGAGCCTGCCCAAGCAGCCCGCCAGCCAGCCCAGGGCGACCCCACCGGCCCC
AAGGAGAGCAAGAAGAAGGTGGAGCGCGAGACCGAGACCGACCCCGTGCACCCCGGGGCCGGCCGCAGC
GGCGACAGCGACGAGGAGCTGCTGCAGACCGTGCGCTTCATCAAGTTCCTGTACCAGAGCAACCCCCTG
CCCAGCCCCAAGGGCACCCGCCAGGCCGACCTGAACCGCCGCCGCCGCTGGCGCGAGCGCCAGCGCCAG
ATCCAGAGCATCAGCGCCTGGATCATCAGCACCCACCTGGGCCGCAGCACCGAGCCCGTGCCCCTGCAG
CTGCCCCCCGACCTGCGCCTGAACCTGGACTGCAGCGAGGACTGCGGCACCAGCGGCACCCAGGGCGTG
GGCAGCCCCCAGGTGCTGGGCGAGAGCCCCGCCGTGCTGGACAGCGGCACCAAGGAGCTCGAGGCCGGC
AAGTGGAGCAAGCGCATGAGCGGCTGGAGCGCCGTGCGCGAGCGCATGAAGCGCGCCGAGCCCGCCGAG
CCCGCCGCCGACGGCGTGGGCGCCGTGAGCCGCGACCTGGAGAAGCACGGCGCCATCACCAGCAGCAAC
ACCGCCGCCAACAACGCCGACTGCGCCTGGCTGGAGGCCCAGGAGGACGAGGACGTGGGCTTCCCCGTG
CGCCCCCAGGTGCCCCTGCGCCCCATGACCTACAAGGCCGCCCTGGACCTGAGCCACTTCCTGAAGGAG
AAGGGCGGCCTGGAGGGCCTGATCTACAGCCAGAAGCGCCAGGACATCCTGGACCTGTGGATCCACCAC
ACCCAGGGCTACTTCCCCGGCTGGCAGAACTACACCCCCGGCCCCGGCATCCGCTACCCCCTGACCTTC
GGCTGGTGCTTCAAGCTGGTGCCCGTGGACCCCGACTACGTGGAGGAGGCCAACGCCGGCGAGAACAAC
AGCCTGCTGCACCCCATGAGCCAGCACGGCATGGACGACCCCGAGAAGGAGGTGCTGGTGTGGCGCTTC
GACAGCCGCCTGGCCTTCCACCACATGGCCCGCGAGCTGCACCCCGAGTACTACAAGGACTGCGATTAA
AAGCTTCCCGGGGCTAGCACCGGTTCTAGA
```

GagPolmutAtt.SF2 (Gag, RT mutated, Protease attenuated; all in frame)

```
GTCGACGCCACCATGGGCGCCCGCGCCAGCGTGCTGAGCGGCGGCGAGCT
GGACAAGTGGGAGAAGATCCGCCTGCGCCCCGGCGGCAAGAAGAAGTAC
AAGCTGAAGCACATCGTGTGGGCCAGCCGCGAGCTGGAGCGCTTCGCCGT
GAACCCCGGCCTGCTGGAGACCAGCGAGGGCTGCCGCCAGATCCTGGGCC
AGCTGCAGCCCAGCCTGCAGACCGGCAGCGAGGAGCTGCGCAGCCTGTAC
AACACCGTGGCCACCCTGTACTGCGTGCACCAGCGCATCGACGTCAAGGA
CACCAAGGAGGCCCTGGAGAAGATCGAGGAGGAGCAGAACAAGTCCAAG
AAGAAGGCCCAGCAGGCCGCCGCCGCCGGCACCGGCAACAGCAGCC
AGGTGAGCCAGAACTACCCCATCGTGCAGAACCTGCAGGGCCAGATGGTG
CACCAGGCCATCAGCCCCCGCACCCTGAACGCCTGGGTGAAGGTGGTGGA
GGAGAAGGCCTTCAGCCCCGAGGTGATCCCCATGTTCAGCGCCCTGAGCG
AGGGCGCCACCCCCCAGGACCTGAACACGATGTTGAACACCGTGGGCGGC
CACCAGGCCGCCATGCAGATGCTGAAGGAGACCATCAACGAGGAGGCCG
CCGAGTGGGACCGCGTGCACCCCGTGCACGCCGGCCCCATCGCCCCCGGC
CAGATGCGCGAGCCCCGCGGCAGCGACATCGCCGGCACCACCAGCACCCT
GCAGGAGCAGATCGGCTGGATGACCAACAACCCCCCATCCCCGTGGGCG
AGATCTACAAGCGGTGGATCATCCTGGGCCTGAACAAGATCGTGCGGATG
TACAGCCCCACCAGCATCCTGGACATCCGCCAGGGCCCCAAGGAGCCCTT
CCGCGACTACGTGGACCGCTTCTACAAGACCCTGCGCGCTGAGCAGGCCA
GCCAGGACGTGAAGAACTGGATGACCGAGACCCTGCTGGTGCAGAACGC
CAACCCCGACTGCAAGACCATCCTGAAGGCTCTCGGCCCCGCGGCCACCC
TGGAGGAGATGATGACCGCCTGCCAGGGCGTGGGCGGCCCCGGCCACAA
GGCCCGCGTGCTGGCCGAGGCGATGAGCCAGGTGACGAACCCGGCGACC
ATCATGATGCAGCGCGGCAACTTCCGCAACCAGCGGAAGACCGTCAAGTG
CTTCAACTGCGGCAAGGAGGGCCACACCGCCAGGAACTGCCGCGCCCCC
GCAAGAAGGGCTGCTGGCGCTGCGGCCGCGAAGGACACCAAATGAAAGA
TTGCACTGAGAGACAGGCTAATTTCTTCCGCGAGGACCTGGCCTTCCTGCA
GGGCAAGGCCCGCGAGTTCAGCAGCGAGCAGACCCGCGCCAACAGCCCC
ACCCGCCGCGAGCTGCAGGTGTGGGGCGGCGAGAACAACAGCCTGAGCG
AGGCCGGCGCCGACCGCCAGGGCACCGTGAGCTTCAACTTCCCCCAGATC
ACCCTGTGGCAGCGCCCCCTGGTGACCATCAGGATCGGCGGCCAGCTCAA
GGAGGCGCTGCTCGACTCCGGCGCCGACGACACCGTGCTGGAGGAGATGA
ACCTGCCCGGCAAGTGGAAGCCCAAGATGATCGGCGGGATCGGGGGCTTC
ATCAAGGTGCGGCAGTACGACCAGATCCCCGTGGAGATCTGCGGCCACAA
GGCCATCGGCACCGTGCTGGTGGGCCCCACCCCCGTGAACATCATCGGCC
GCAACCTGCTGACCCAGATCGGCTGCACCCTGAACTTCCCCATCAGCCCC
ATCGAGACGGTGCCCGTGAAGCTGAAGCCGGGGATGGACGGCCCCAAGG
TCAAGCAGTGGCCCCTGACCGAGGAGAAGATCAAGGCCCTGGTGGAGATC
TGCACCGAGATGGAGAAGGAGGGCAAGATCAGCAAGATCGGCCCCGAGA
ACCCCTACAACACCCCCGTGTTCGCCATCAAGAAGAAGGACAGCACCAAG
TGGCGCAAGCTGGTGGACTTCCGCGAGCTGAACAAGCGCACCCAGGACTT
CTGGGAGGTGCAGCTGGGCATCCCCCACCCCGCCGGCCTGAAGAAGAAGA
AGAGCGTGACCGTGCTGGACGTGGGCGACGCCTACTTCAGCGTGCCCCTG
GACAAGGACTTCCGCAAGTACACCGCCTTCACCATCCCCAGCATCAACAA
CGAGACCCCCGGCATCCGCTACCAGTACAACGTGCTGCCCCAGGGCTGGA
```

AGGGCAGCCCCGCCATCTTCCAGAGCAGCATGACCAAGATCCTGGAGCCC
TTCCGCAAGCAGAACCCCGACATCGTGATCTACCAGGCCCCCCTGTACGT
GGGCAGCGACCTGGAGATCGGCCAGCACCGCACCAAGATCGAGGAGCTG
CGCCAGCACCTGCTGCGCTGGGGCTTCACCACCCCCGACAAGAAGCACCA
GAAGGAGCCCCCCTTCCTGCCCATCGAGCTGCACCCCGACAAGTGGACCG
TGCAGCCCATCATGCTGCCCGAGAAGGACAGCTGGACCGTGAACGACATC
CAGAAGCTGGTGGGCAAGCTGAACTGGGCCAGCCAGATCTACGCCGGCAT
CAAGGTGAAGCAGCTGTGCAAGCTGCTGCGCGGCACCAAGGCCCTGACCG
AGGTGATCCCCCTGACCGAGGAGGCCGAGCTGGAGCTGGCCGAGAACCG
CGAGATCCTGAAGGAGCCCGTGCACGAGGTGTACTACGACCCCAGCAAGG
ACCTGGTGGCCGAGATCCAGAAGCAGGGCCAGGGCCAGTGGACCTACCA
GATCTACCAGGAGCCCTTCAAGAACCTGAAGACCGGCAAGTACGCCCGCA
TGCGCGGCGCCCACACCAACGACGTGAAGCAGCTGACCGAGGCCGTGCA
GAAGGTGAGCACCGAGAGCATCGTGATCTGGGGCAAGATCCCCAAGTTCA
AGCTGCCCATCCAGAAGGAGACCTGGGAGGCCTGGTGGATGGAGTACTGG
CAGGCCACCTGGATCCCCGAGTGGGAGTTCGTGAACACCCCCCCCCTGGT
GAAGCTGTGGTACCAGCTGGAGAAGGAGCCCATCGTGGGCGCCGAGACCT
TCTACGTGGACGGCGCCGCCAACCGCGAGACCAAGCTGGGCAAGGCCGG
CTACGTGACCGACCGGGGCCGGCAGAAGGTGGTGAGCATCGCCGACACC
ACCAACCAGAAGACCGAGCTGCAGGCCATCCACCTGGCCCTGCAGGACAG
CGGCCTGGAGGTGAACATCGTGACCGACAGCCAGTACGCCCTGGGCATCA
TCCAGGCCCAGCCCGACAAGAGCGAGAGCGAGCTGGTGAGCCAGATCAT
CGAGCAGCTGATCAAGAAGGAGAAGGTGTACCTGGCCTGGGTGCCCGCCC
ACAAGGGCATCGGCGGCAACGAGCAGGTGGACAAGCTGGTGAGCGCCGG
CATCCGCAAGGTGCTGTTCCTGAACGGCATCGATGGCGGCATCGTGATCT
ACCAGTACATGGACGACCTGTACGTGGGCAGCGGCGGCCCTAGGATCGAT
TAAAAGCTTCCCGGGGCTAGCACCGGTGAATTC

GagPolmutIna.SF2 (Gag, RT mutated, Protease inactive; all in frame)

GTCGACGCCACCATGGGCGCCCGCGCCAGCGTGCTGAGCGGCGGCGAGCT
GGACAAGTGGGAGAAGATCCGCCTGCGCCCCGGCGGCAAGAAGAAGTAC
AAGCTGAAGCACATCGTGTGGGCCAGCCGCGAGCTGGAGCGCTTCGCCGT
GAACCCCGGCCTGCTGGAGACCAGCGAGGGCTGCCGCCAGATCCTGGGCC
AGCTGCAGCCCAGCCTGCAGACCGGCAGCGAGGAGCTGCGCAGCCTGTAC
AACACCGTGGCCACCCTGTACTGCGTGCACCAGCGCATCGACGTCAAGGA
CACCAAGGAGGCCCTGGAGAAGATCGAGGAGGAGCAGAACAAGTCCAAG
AAGAAGGCCCAGCAGGCCGCCGCCGCCGGCACCGGCAACAGCAGCC
AGGTGAGCCAGAACTACCCCATCGTGCAGAACCTGCAGGGCCAGATGGTG
CACCAGGCCATCAGCCCCGCACCCTGAACGCCTGGGTGAAGGTGGTGGA
GGAGAAGGCCTTCAGCCCCGAGGTGATCCCCATGTTCAGCGCCCTGAGCG
AGGGCGCCACCCCCCAGGACCTGAACACGATGTTGAACACCGTGGGCGGC
CACCAGGCCGCCATGCAGATGCTGAAGGAGACCATCAACGAGGAGGCCG
CCGAGTGGGACCGCGTGCACCCCGTGCACGCCGGCCCCATCGCCCCCGGC
CAGATGCGCGAGCCCCGCGGCAGCGACATCGCCGGCACCACCAGCACCCT
GCAGGAGCAGATCGGCTGGATGACCAACAACCCCCCATCCCCGTGGGCG
AGATCTACAAGCGGTGGATCATCCTGGGCCTGAACAAGATCGTGCGGATG
TACAGCCCCACCAGCATCCTGGACATCCGCCAGGGCCCCAAGGAGCCCTT
CCGCGACTACGTGGACCGCTTCTACAAGACCCTGCGCGCTGAGCAGGCCA
GCCAGGACGTGAAGAACTGGATGACCGAGACCCTGCTGGTGCAGAACGC
CAACCCCGACTGCAAGACCATCCTGAAGGCTCTCGGCCCCGCGGCCACCC
TGGAGGAGATGATGACCGCCTGCCAGGGCGTGGGCGGCCCCGGCCACAA
GGCCCGCGTGCTGGCCGAGGCGATGAGCCAGGTGACGAACCCGGCGACC
ATCATGATGCAGCGCGGCAACTTCCGCAACCAGCGGAAGACCGTCAAGTG
CTTCAACTGCGGCAAGGAGGGCCACACCGCCAGGAACTGCCGCGCCCCC
GCAAGAAGGGCTGCTGGCGCTGCGGCCGCGAAGGACACCAAATGAAAGA
TTGCACTGAGAGACAGGCTAATTTCTTCCGCGAGGACCTGGCCTTCCTGCA
GGGCAAGGCCCGCGAGTTCAGCAGCGAGCAGACCCGCGCCAACAGCCCC
ACCCGCCGCGAGCTGCAGGTGTGGGGCGGCGAGAACAACAGCCTGAGCG
AGGCCGGCGCCGACCGCCAGGGCACCGTGAGCTTCAACTTCCCCCAGATC
ACCCTGTGGCAGCGCCCCCTGGTGACCATCAGGATCGGCGGCCAGCTCAA
GGAGGCGCTGCTCGCCACCGGCGCCGACGACACCGTGCTGGAGGAGATG
AACCTGCCCGGCAAGTGGAAGCCCAAGATGATCGGCGGGATCGGGGGCTT
CATCAAGGTGCGGCAGTACGACCAGATCCCCGTGGAGATCTGCGGCCACA
AGGCCATCGGCACCGTGCTGGTGGGCCCCACCCCCGTGAACATCATCGGC
CGCAACCTGCTGACCCAGATCGGCTGCACCCTGAACTTCCCCATCAGCCCC
ATCGAGACGGTGCCCGTGAAGCTGAAGCCGGGGATGGACGGCCCCAAGG
TCAAGCAGTGGCCCCTGACCGAGGAGAAGATCAAGGCCCTGGTGGAGATC
TGCACCGAGATGGAGAAGGAGGGCAAGATCAGCAAGATCGGCCCCGAGA
ACCCCTACAACACCCCCGTGTTCGCCATCAAGAAGAAGGACAGCACCAAG
TGGCGCAAGCTGGTGGACTTCCGCGAGCTGAACAAGCGCACCCAGGACTT
CTGGGAGGTGCAGCTGGGCATCCCCCACCCCGCCGGCCTGAAGAAGAAGA
AGAGCGTGACCGTGCTGGACGTGGGCGACGCCTACTTCAGCGTGCCCCTG
GACAAGGACTTCCGCAAGTACACCGCCTTCACCATCCCCAGCATCAACAA
CGAGACCCCCGGCATCCGCTACCAGTACAACGTGCTGCCCCAGGGCTGGA

```
AGGGCAGCCCCGCCATCTTCCAGAGCAGCATGACCAAGATCCTGGAGCCC
TTCCGCAAGCAGAACCCCGACATCGTGATCTACCAGGCCCCCCTGTACGT
GGGCAGCGACCTGGAGATCGGCCAGCACCGCACCAAGATCGAGGAGCTG
CGCCAGCACCTGCTGCGCTGGGGCTTCACCACCCCCGACAAGAAGCACCA
GAAGGAGCCCCCCTTCCTGCCCATCGAGCTGCACCCCGACAAGTGGACCG
TGCAGCCCATCATGCTGCCCGAGAAGGACAGCTGGACCGTGAACGACATC
CAGAAGCTGGTGGGCAAGCTGAACTGGGCCAGCCAGATCTACGCCGGCAT
CAAGGTGAAGCAGCTGTGCAAGCTGCTGCGCGGCACCAAGGCCCTGACCG
AGGTGATCCCCCTGACCGAGGAGGCCGAGCTGGAGCTGGCCGAGAACCG
CGAGATCCTGAAGGAGCCCGTGCACGAGGTGTACTACGACCCCAGCAAGG
ACCTGGTGGCCGAGATCCAGAAGCAGGGCCAGGGCCAGTGGACCTACCA
GATCTACCAGGAGCCCTTCAAGAACCTGAAGACCGGCAAGTACGCCCGCA
TGCGCGGCGCCCACACCAACGACGTGAAGCAGCTGACCGAGGCCGTGCA
GAAGGTGAGCACCGAGAGCATCGTGATCTGGGGCAAGATCCCCAAGTTCA
AGCTGCCCATCCAGAAGGAGACCTGGGAGGCCTGGTGGATGGAGTACTGG
CAGGCCACCTGGATCCCCGAGTGGGAGTTCGTGAACACCCCCCCCTGGT
GAAGCTGTGGTACCAGCTGGAGAAGGAGCCCATCGTGGGCGCCGAGACCT
TCTACGTGGACGGCGCCGCCAACCGCGAGACCAAGCTGGGCAAGGCCGG
CTACGTGACCGACCGGGGCCGGCAGAAGGTGGTGAGCATCGCCGACACC
ACCAACCAGAAGACCGAGCTGCAGGCCATCCACCTGGCCCTGCAGGACAG
CGGCCTGGAGGTGAACATCGTGACCGACAGCCAGTACGCCCTGGGCATCA
TCCAGGCCCAGCCCGACAAGAGCGAGAGCGAGCTGGTGAGCCAGATCAT
CGAGCAGCTGATCAAGAAGGAGAAGGTGTACCTGGCCTGGGTGCCCGCCC
ACAAGGGCATCGGCGGCAACGAGCAGGTGGACAAGCTGGTGAGCGCCGG
CATCCGCAAGGTGCTGTTCCTGAACGGCATCGATGGCGGCATCGTGATCT
ACCAGTACATGGACGACCTGTACGTGGGCAGCGGCGGCCCTAGGATCGAT
TAAAAGCTTCCCGGGGCTAGCACCGGTGAATTC
```

GagProtInaRTmut.SF2 (Gag, Protease inactive, RT mutated; all in frame fusion protein)

```
GCCACCATGGGCGCCCGCGCCAGCGTGCTGAGCGGCGGCGAGCTGGACA
AGTGGGAGAAGATCCGCCTGCGCCCCGGCGGCAAGAAGAAGTACAAGCT
GAAGCACATCGTGTGGGCCAGCCGCGAGCTGGAGCGCTTCGCCGTGAACC
CCGGCCTGCTGGAGACCAGCGAGGGCTGCCGCCAGATCCTGGGCCAGCTG
CAGCCCAGCCTGCAGACCGGCAGCGAGGAGCTGCGCAGCCTGTACAACAC
CGTGGCCACCCTGTACTGCGTGCACCAGCGCATCGACGTCAAGGACACCA
AGGAGGCCCTGGAGAAGATCGAGGAGGAGCAGAACAAGTCCAAGAAGAA
GGCCCAGCAGGCCGCCGCCGCCGGCACCGGCAACAGCAGCCAGGTG
AGCCAGAACTACCCCATCGTGCAGAACCTGCAGGGCCAGATGGTGCACCA
GGCCATCAGCCCCGCACCCTGAACGCCTGGGTGAAGGTGGTGGAGGAGA
AGGCCTTCAGCCCCGAGGTGATCCCCATGTTCAGCGCCCTGAGCGAGGGC
GCCACCCCCCAGGACCTGAACACGATGTTGAACACCGTGGGCGGCCACCA
GGCCGCCATGCAGATGCTGAAGGAGACCATCAACGAGGAGGCCGCCGAG
TGGGACCGCGTGCACCCCGTGCACGCCGGCCCCATCGCCCCCGGCCAGAT
GCGCGAGCCCCGCGGCAGCGACATCGCCGGCACCACCAGCACCCTGCAGG
AGCAGATCGGCTGGATGACCAACAACCCCCCATCCCCGTGGGCGAGATC
TACAAGCGGTGGATCATCCTGGGCCTGAACAAGATCGTGCGGATGTACAG
CCCCACCAGCATCCTGGACATCGCCAGGGCCCCAAGGAGCCCTTCCGCG
ACTACGTGGACCGCTTCTACAAGACCCTGCGCGCTGAGCAGGCCAGCCAG
GACGTGAAGAACTGGATGACCGAGACCCTGCTGGTGCAGAACGCCAACCC
CGACTGCAAGACCATCCTGAAGGCTCTCGGCCCCGCGGCCACCCTGGAGG
AGATGATGACCGCCTGCCAGGGCGTGGGCGGCCCCGGCCACAAGGCCCGC
GTGCTGGCCGAGGCGATGAGCCAGGTGACGAACCCGGCGACCATCATGAT
GCAGCGCGGCAACTTCCGCAACCAGCGGAAGACCGTCAAGTGCTTCAACT
GCGGCAAGGAGGGCCACACCGCCAGGAACTGCCGCGCCCCCGCAAGAA
GGGCTGCTGGCGCTGCGGCCGCGAGGGCCACCAGATGAAGGACTGCACC
GAGCGCCAGGCCAACTTCCTGGGCAAGATCTGGCCCAGCTACAAGGGCCG
CCCCGGCAACTTCCTGCAGAGCCGCCCCGAGCCCACCGCCCCCCCGAGG
AGAGCTTCCGCTTCGGCGAGGAGAAGACCACCCCCAGCCAGAAGCAGGA
GCCCATCGACAAGGAGCTGTACCCCCTGACCAGCCTGCGCAGCCTGTTCG
GCAACGACCCCAGCAGCCAGAAAGAATTCCCCCAGATCACCCTGTGGCAG
CGCCCCCTGGTGACCATCAGGATCGGCGGCCAGCTCAAGGAGGCGCTGCT
CGCCACCGGCGCCGACGACACCGTGCTGGAGGAGATGAACCTGCCCGGCA
AGTGGAAGCCCAAGATGATCGGCGGGATCGGGGGCTTCATCAAGGTGCG
GCAGTACGACCAGATCCCCGTGGAGATCTGCGGCCACAAGGCCATCGGCA
CCGTGCTGGTGGGCCCCACCCCCGTGAACATCATCGGCCGCAACCTGCTG
ACCCAGATCGGCTGCACCCTGAACTTCCCCATCAGCCCCATCGAGACGGT
GCCCGTGAAGCTGAAGCCGGGGATGGACGGCCCCAAGGTCAAGCAGTGG
CCCCTGACCGAGGAGAAGATCAAGGCCCTGGTGGAGATCTGCACCGAGAT
GGAGAAGGAGGGCAAGATCAGCAAGATCGGCCCCGAGAACCCCTACAAC
ACCCCCGTGTTCGCCATCAAGAAGAAGGACAGCACCAAGTGGCGCAAGCT
GGTGGACTTCCGCGAGCTGAACAAGCGCACCCAGGACTTCTGGGAGGTGC
AGCTGGGCATCCCCCACCCCGCCGGCCTGAAGAAGAAGAAGAGCGTGAC
CGTGCTGGACGTGGGCGACGCCTACTTCAGCGTGCCCCTGGACAAGGACT
```

TCCGCAAGTACACCGCCTTCACCATCCCCAGCATCAACAACGAGACCCCC
GGCATCCGCTACCAGTACAACGTGCTGCCCCAGGGCTGGAAGGGCAGCCC
CGCCATCTTCCAGAGCAGCATGACCAAGATCCTGGAGCCCTTCCGCAAGC
AGAACCCCGACATCGTGATCTACCAGGCCCCCCTGTACGTGGGCAGCGAC
CTGGAGATCGGCCAGCACCGCACCAAGATCGAGGAGCTGCGCCAGCACCT
GCTGCGCTGGGGCTTCACCACCCCCGACAAGAAGCACCAGAAGGAGCCCC
CCTTCCTGCCCATCGAGCTGCACCCCGACAAGTGGACCGTGCAGCCCATC
ATGCTGCCCGAGAAGGACAGCTGGACCGTGAACGACATCCAGAAGCTGGT
GGGCAAGCTGAACTGGGCCAGCCAGATCTACGCCGGCATCAAGGTGAAG
CAGCTGTGCAAGCTGCTGCGCGGCACCAAGGCCCTGACCGAGGTGATCCC
CCTGACCGAGGAGGCCGAGCTGGAGCTGGCCGAGAACCGCGAGATCCTG
AAGGAGCCCGTGCACGAGGTGTACTACGACCCCAGCAAGGACCTGGTGGC
CGAGATCCAGAAGCAGGGCCAGGGCCAGTGGACCTACCAGATCTACCAG
GAGCCCTTCAAGAACCTGAAGACCGGCAAGTACGCCCGCATGCGCGGCGC
CCACACCAACGACGTGAAGCAGCTGACCGAGGCCGTGCAGAAGGTGAGC
ACCGAGAGCATCGTGATCTGGGGCAAGATCCCCAAGTTCAAGCTGCCCAT
CCAGAAGGAGACCTGGGAGGCCTGGTGGATGGAGTACTGGCAGGCCACC
TGGATCCCCGAGTGGGAGTTCGTGAACACCCCCCCCTGGTGAAGCTGTG
GTACCAGCTGGAGAAGGAGCCCATCGTGGGCGCCGAGACCTTCTACGTGG
ACGGCGCCGCCAACCGCGAGACCAAGCTGGGCAAGGCCGGCTACGTGAC
CGACCGGGGCCGGCAGAAGGTGGTGAGCATCGCCGACACCACCAACCAG
AAGACCGAGCTGCAGGCCATCCACCTGGCCCTGCAGGACAGCGGCCTGGA
GGTGAACATCGTGACCGACAGCCAGTACGCCCTGGGCATCATCCAGGCCC
AGCCCGACAAGAGCGAGAGCGAGCTGGTGAGCCAGATCATCGAGCAGCT
GATCAAGAAGGAGAAGGTGTACCTGGCCTGGGTGCCCGCCCACAAGGGC
ATCGGCGGCAACGAGCAGGTGGACAAGCTGGTGAGCGCCGGCATCCGCA
AGGTGCTCTAAATCTAGA

GagProtInaRTmutTatRevNef.opt_B

```
GCCACCATGGGCGCCCGCGCCAGCGTGCTGAGCGGCGGCGAGCTGGACAAGTGGGAGAAGATCCGCCTG
CGCCCCGGCGGCAAGAAGAAGTACAAGCTGAAGCACATCGTGTGGGCCAGCCGCGAGCTGGAGCGCTTC
GCCGTGAACCCCGGCCTGCTGGAGACCAGCGAGGGCTGCCGCCAGATCCTGGGCCAGCTGCAGCCCAGC
CTGCAGACCGGCAGCGAGGAGCTGCGCAGCCTGTACAACACCGTGGCCACCCTGTACTGCGTGCACCAG
CGCATCGACGTCAAGGACACCAAGGAGGCCCTGGAGAAGATCGAGGAGGAGCAGAACAAGTCCAAGAAG
AAGGCCCAGCAGGCCGCCGCCGCCGGCACCGGCAACAGCAGCCAGGTGAGCCAGAACTACCCCATC
GTGCAGAACCTGCAGGGCCAGATGGTGCACCAGGCCATCAGCCCCGCACCCTGAACGCCTGGGTGAAG
GTGGTGGAGGAGAAGGCCTTCAGCCCCGAGGTGATCCCCATGTTCAGCGCCCTGAGCGAGGGCGCCACC
CCCCAGGACCTGAACACGATGTTGAACACCGTGGGCGGCCACCAGGCCGCCATGCAGATGCTGAAGGAG
ACCATCAACGAGGAGGCCGCCGAGTGGGACCGCGTGCACCCCGTGCACGCCGGCCCCATCGCCCCCGGC
CAGATGCGCGAGCCCCGCGGCAGCGACATCGCCGGCACCACCAGCACCCTGCAGGAGCAGATCGGCTGG
ATGACCAACAACCCCCCCATCCCCGTGGGCGAGATCTACAAGCGGTGGATCATCCTGGGCCTGAACAAG
ATCGTGCGGATGTACAGCCCCACCAGCATCCTGGACATCCGCCAGGGCCCCAAGGAGCCCTTCCGCGAC
TACGTGGACCGCTTCTACAAGACCCTGCGCGCTGAGCAGGCCAGCCAGGACGTGAAGAACTGGATGACC
GAGACCCTGCTGGTGCAGAACGCCAACCCCGACTGCAAGACCATCCTGAAGGCTCTCGGCCCGCGGCC
ACCCTGGAGGAGATGATGACCGCCTGCCAGGGCGTGGGCGGCCCCGGCCACAAGGCCCGCGTGCTGGCC
GAGGCGATGAGCCAGGTGACGAACCCGGCGACCATCATGATGCAGCGCGGCAACTTCCGCAACCAGCGG
AAGACCGTCAAGTGCTTCAACTGCGGCAAGGAGGGCCACACCGCCAGGAACTGCCGCGCCCCCCGCAAG
AAGGGCTGCTGGCGCTGCGGCCGCGAGGGCCACCAGATGAAGGACTGCACCGAGCGCCAGGCCAACTTC
CTGGGCAAGATCTGGCCCAGCTACAAGGGCCGCCCCGGCAACTTCCTGCAGAGCCGCCCCGAGCCCACC
GCCCCCCCCGAGGAGAGCTTCCGCTTCGGCGAGGAGAAGACCACCCCCAGCCAGAAGCAGGAGCCCATC
GACAAGGAGCTGTACCCCCTGACCAGCCTGCGCAGCCTGTTCGGCAACGACCCCAGCAGCCAGAAAGAA
TTCCCCCAGATCACCCTGTGGCAGCGCCCCCTGGTGACCATCAGGATCGGCGGCCAGCTCAAGGAGGCG
CTGCTCGCCACCGGCGCCGACGACACCGTGCTGGAGGAGATGAACCTGCCCGGCAAGTGGAAGCCCAAG
ATGATCGGCGGGATCGGGGGCTTCATCAAGGTGCGGCAGTACGACCAGATCCCCGTGGAGATCTGCGGC
CACAAGGCCATCGGCACCGTGCTGGTGGGCCCCACCCCCGTGAACATCATCGGCCGCAACCTGCTGACC
CAGATCGGCTGCACCCTGAACTTCCCCATCAGCCCCATCGAGACGGTGCCCGTGAAGCTGAAGCCGGGG
ATGGACGGCCCCAAGGTCAAGCAGTGGCCCCTGACCGAGGAGAAGATCAAGGCCCTGGTGGAGATCTGC
ACCGAGATGGAGAAGGAGGGCAAGATCAGCAAGATCGGCCCCGAGAACCCCTACAACACCCCCGTGTTC
GCCATCAAGAAGAAGGACAGCACCAAGTGGCGCAAGCTGGTGGACTTCCGCGAGCTGAACAAGCGCACC
CAGGACTTCTGGGAGGTGCAGCTGGGCATCCCCCACCCCGCCGGCCTGAAGAAGAAGAAGAGCGTGACC
GTGCTGGACGTGGGCGACGCCTACTTCAGCGTGCCCCTGGACAAGGACTTCCGCAAGTACACCGCCTTC
ACCATCCCCAGCATCAACAACGAGACCCCCGGCATCCGCTACCAGTACAACGTGCTGCCCCAGGGCTGG
AAGGGCAGCCCCGCCATCTTCCAGAGCAGCATGACCAAGATCCTGGAGCCCTTCCGCAAGCAGAACCCC
GACATCGTGATCTACCAGGCCCCCCTGTACGTGGGCAGCGACCTGGAGATCGGCCAGCACCGCACCAAG
ATCGAGGAGCTGCGCCAGCACCTGCTGCGCTGGGGCTTCACCACCCCCGACAAGAAGCACCAGAAGGAG
CCCCCCTTCCTGCCCATCGAGCTGCACCCCGACAAGTGGACCGTGCAGCCCATCATGCTGCCCGAGAAG
GACAGCTGGACCGTGAACGACATCCAGAAGCTGGTGGGCAAGCTGAACTGGGCCAGCCAGATCTACGCC
GGCATCAAGGTGAAGCAGCTGTGCAAGCTGCTGCGCGGCACCAAGGCCCTGACCGAGGTGATCCCCCTG
ACCGAGGAGGCCGAGCTGGAGCTGGCCGAGAACCGCGAGATCCTGAAGGAGCCCGTGCACGAGGTGTAC
TACGACCCCAGCAAGGACCTGGTGGCCGAGATCCAGAAGCAGGGCCAGGGCCAGTGGACCTACCAGATC
TACCAGGAGCCCTTCAAGAACCTGAAGACCGGCAAGTACGCCCGCATGCGCGGCGCCCACACCAACGAC
GTGAAGCAGCTGACCGAGGCCGTGCAGAAGGTGAGCACCGAGAGCATCGTGATCTGGGGCAAGATCCCC
AAGTTCAAGCTGCCCATCCAGAAGGAGACCTGGGAGGCCTGGTGGATGGAGTACTGGCAGGCCACCTGG
ATCCCCGAGTGGGAGTTCGTGAACACCCCCCCCTGGTGAAGCTGTGGTACCAGCTGGAGAAGGAGCCC
ATCGTGGGCGCCGAGACCTTCTACGTGGACGGCGCCGCCAACCGCGAGACCAAGCTGGGCAAGGCCGGC
TACGTGACCGACCGGGCCGGCAGAAGGTGGTGAGCATCGCCGACACCACCAACCAGAAGACCGAGCTG
CAGGCCATCCACCTGGCCCTGCAGGACAGCGGCCTGGAGGTGAACATCGTGACCGACAGCCAGTACGCC
CTGGGCATCATCCAGGCCCAGCCCGACAAGAGCGAGAGCGAGCTGGTGAGCCAGATCATCGAGCAGCTG
ATCAAGAAGGAGAAGGTGTACCTGGCCTGGGTGCCCGCCCACAAGGGCATCGGCGGCAACGAGCAGGTG
GACAAGCTGGTGAGCGCCGGCATCCGCAAGGTGCTCAAGCTTGAGCCCGTGGACCCCGCCTGGAGCCC
TGGAAGCACCCCGGCAGCCAGCCCAAGACCGCCGGCACCAACTGCTACTGCAAGAAGTGCTGCTTCCAC
TGCCAGGTGAGCTTCATCACCAAGGGCCTGGGCATCAGCTACGGCCGCAAGAAGCGCCGCCAGCGCCGC
CGCGCCCCCCCGACAGCGAGGTGCACCAGGTGAGCCTGCCCAAGCAGCCCGCCAGCCAGCCCCAGGGC
```

```
GACCCCACCGGCCCCAAGGAGAGCAAGAAGAAGGTGGAGCGCGAGACCGAGACCGACCCCGTGCACCCC
GGGGCCGGCCGCAGCGGCGACAGCGACGAGGAGCTGCTGCAGACCGTGCGCTTCATCAAGTTCCTGTAC
CAGAGCAACCCCCTGCCCAGCCCCAAGGGCACCCGCCAGGCCGACCTGAACCGCCGCCGCCGCTGGCGC
GAGCGCCAGCGCCAGATCCAGAGCATCAGCGCCTGGATCATCAGCACCCACCTGGGCCGCAGCACCGAG
CCCGTGCCCCTGCAGCTGCCCCCCGACCTGCGCCTGAACCTGGACTGCAGCGAGGACTGCGGCACCAGC
GGCACCCAGGGCGTGGGCAGCCCCCAGGTGCTGGGCGAGAGCCCCGCCGTGCTGGACAGCGGCACCAAG
GAGCTCGAGGCCGGCAAGTGGAGCAAGCGCATGAGCGGCTGGAGCGCCGTGCGCGAGCGCATGAAGCGC
GCCGAGCCCGCCGAGCCCGCCGCCGACGGCGTGGGCGCCGTGAGCCGCGACCTGGAGAAGCACGGCGCC
ATCACCAGCAGCAACACCGCCGCCAACAACGCCGACTGCGCCTGGCTGGAGGCCCAGGAGGACGAGGAC
GTGGGCTTCCCCGTGCGCCCCCAGGTGCCCCTGCGCCCCATGACCTACAAGGCCGCCCTGGACCTGAGC
CACTTCCTGAAGGAGAAGGGCGGCCTGGAGGGCCTGATCTACAGCCAGAAGCGCCAGGACATCCTGGAC
CTGTGGATCCACCACACCCAGGGCTACTTCCCCGGCTGGCAGAACTACACCCCGGCCCCGGCATCCGC
TACCCCCTGACCTTCGGCTGGTGCTTCAAGCTGGTGCCCGTGGACCCCGACTACGTGGAGGAGGCCAAC
GCCGGCGAGAACAACAGCCTGCTGCACCCCATGAGCCAGCACGGCATGGACGACCCCGAGAAGGAGGTG
CTGGTGTGGCGCTTCGACAGCCGCCTGGCCTTCCACCACATGGCCCGCGAGCTGCACCCCGAGTACTAC
AAGGACTGCTAA
```

GagRTmut.SF2 (Gag, RT mutated; all in frame fusion protein)

```
GTCGACGCCACCATGGGCGCCCGCGCCAGCGTGCTGAGCGGCGGCGAGCT
GGACAAGTGGGAGAAGATCCGCCTGCGCCCCGGCGGCAAGAAGAAGTAC
AAGCTGAAGCACATCGTGTGGGCCAGCCGCGAGCTGGAGCGCTTCGCCGT
GAACCCCGGCCTGCTGGAGACCAGCGAGGGCTGCCGCCAGATCCTGGGCC
AGCTGCAGCCCAGCCTGCAGACCGGCAGCGAGGAGCTGCGCAGCCTGTAC
AACACCGTGGCCACCCTGTACTGCGTGCACCAGCGCATCGACGTCAAGGA
CACCAAGGAGGCCCTGGAGAAGATCGAGGAGGAGCAGAACAAGTCCAAG
AAGAAGGCCCAGCAGGCCGCCGCCGCCGGCACCGGCAACAGCAGCC
AGGTGAGCCAGAACTACCCCATCGTGCAGAACCTGCAGGGCCAGATGGTG
CACCAGGCCATCAGCCCCCGCACCCTGAACGCCTGGGTGAAGGTGGTGGA
GGAGAAGGCCTTCAGCCCCGAGGTGATCCCCATGTTCAGCGCCCTGAGCG
AGGGCGCCACCCCCCAGGACCTGAACACGATGTTGAACACCGTGGGCGGC
CACCAGGCCGCCATGCAGATGCTGAAGGAGACCATCAACGAGGAGGCCG
CCGAGTGGGACCGCGTGCACCCCGTGCACGCCGGCCCCATCGCCCCCGGC
CAGATGCGCGAGCCCCGCGGCAGCGACATCGCCGGCACCACCAGCACCCT
GCAGGAGCAGATCGGCTGGATGACCAACAACCCCCCATCCCCGTGGGCG
AGATCTACAAGCGGTGGATCATCCTGGGCCTGAACAAGATCGTGCGGATG
TACAGCCCCACCAGCATCCTGGACATCCGCCAGGGCCCCAAGGAGCCCTT
CCGCGACTACGTGGACCGCTTCTACAAGACCCTGCGCGCTGAGCAGGCCA
GCCAGGACGTGAAGAACTGGATGACCGAGACCCTGCTGGTGCAGAACGC
CAACCCCGACTGCAAGACCATCCTGAAGGCTCTCGGCCCCGCGGCCACCC
TGGAGGAGATGATGACCGCCTGCCAGGGCGTGGGCGGCCCCGGCCACAA
GGCCCGCGTGCTGGCCGAGGCGATGAGCCAGGTGACGAACCCGGCGACC
ATCATGATGCAGCGCGGCAACTTCCGCAACCAGCGGAAGACCGTCAAGTG
CTTCAACTGCGGCAAGGAGGGCCACACCGCCAGGAACTGCCGCGCCCCC
GCAAGAAGGGCTGCTGGCGCTGCGGCCGCGAGGGCCACCAGATGAAGGA
CTGCACCGAGCGCCAGGCCAACTTCCTGGGCAAGATCTGGCCCAGCTACA
AGGGCCGCCCCGGCAACTTCCTGCAGAGCCGCCCCGAGCCCACCGCCCCC
CCCGAGGAGAGCTTCCGCTTCGGCGAGGAGAAGACCACCCCCAGCCAGA
AGCAGGAGCCCATCGACAAGGAGCTGTACCCCCTGACCAGCCTGCGCAGC
CTGTTCGGCAACGACCCCAGCAGCCAGAAAGAATTCCCCATCAGCCCCAT
CGAGACGGTGCCCGTGAAGCTGAAGCCGGGGATGGACGGCCCCAAGGTC
AAGCAGTGGCCCCTGACCGAGGAGAAGATCAAGGCCCTGGTGGAGATCT
GCACCGAGATGGAGAAGGAGGGCAAGATCAGCAAGATCGGCCCCGAGAA
CCCCTACAACACCCCCGTGTTCGCCATCAAGAAGAAGGACAGCACCAAGT
GGCGCAAGCTGGTGGACTTCCGCGAGCTGAACAAGCGCACCCAGGACTTC
TGGGAGGTGCAGCTGGGCATCCCCCACCCCGCCGGCCTGAAGAAGAAGA
AGAGCGTGACCGTGCTGGACGTGGGCGACGCCTACTTCAGCGTGCCCCTG
GACAAGGACTTCCGCAAGTACACCGCCTTCACCATCCCCAGCATCAACAA
CGAGACCCCCGGCATCCGCTACCAGTACAACGTGCTGCCCCAGGGCTGGA
AGGGCAGCCCCGCCATCTTCCAGAGCAGCATGACCAAGATCCTGGAGCCC
TTCCGCAAGCAGAACCCCGACATCGTGATCTACCAGGCCCCCTGTACGT
GGGCAGCGACCTGGAGATCGGCCAGCACCGCACCAAGATCGAGGAGCTG
CGCCAGCACCTGCTGCGCTGGGGCTTCACCACCCCCGACAAGAAGCACCA
GAAGGAGCCCCCCTTCCTGCCCATCGAGCTGCACCCCGACAAGTGGACCG
```

TGCAGCCCATCATGCTGCCCGAGAAGGACAGCTGGACCGTGAACGACATC
CAGAAGCTGGTGGGCAAGCTGAACTGGGCCAGCCAGATCTACGCCGGCAT
CAAGGTGAAGCAGCTGTGCAAGCTGCTGCGCGGCACCAAGGCCCTGACCG
AGGTGATCCCCCTGACCGAGGAGGCCGAGCTGGAGCTGGCCGAGAACCG
CGAGATCCTGAAGGAGCCCGTGCACGAGGTGTACTACGACCCCAGCAAGG
ACCTGGTGGCCGAGATCCAGAAGCAGGGCCAGGGCCAGTGGACCTACCA
GATCTACCAGGAGCCCTTCAAGAACCTGAAGACCGGCAAGTACGCCCGCA
TGCGCGGCGCCCACACCAACGACGTGAAGCAGCTGACCGAGGCCGTGCA
GAAGGTGAGCACCGAGAGCATCGTGATCTGGGGCAAGATCCCCAAGTTCA
AGCTGCCCATCCAGAAGGAGACCTGGGAGGCCTGGTGGATGGAGTACTGG
CAGGCCACCTGGATCCCCGAGTGGGAGTTCGTGAACACCCCCCCCCTGGT
GAAGCTGTGGTACCAGCTGGAGAAGGAGCCCATCGTGGGCGCCGAGACCT
TCTACGTGGACGGCGCCGCCAACCGCGAGACCAAGCTGGGCAAGGCCGG
CTACGTGACCGACCGGGGCCGGCAGAAGGTGGTGAGCATCGCCGACACC
ACCAACCAGAAGACCGAGCTGCAGGCCATCCACCTGGCCCTGCAGGACAG
CGGCCTGGAGGTGAACATCGTGACCGACAGCCAGTACGCCCTGGGCATCA
TCCAGGCCCAGCCCGACAAGAGCGAGAGCGAGCTGGTGAGCCAGATCAT
CGAGCAGCTGATCAAGAAGGAGAAGGTGTACCTGGCCTGGGTGCCCGCCC
ACAAGGGCATCGGCGGCAACGAGCAGGTGGACAAGCTGGTGAGCGCCGG
CATCCGCAAGGTGCTCTAAATCTAGA

Figure 15

GagTatRevNef.opt_B

GCCACCATGGGCGCCCGCGCCAGCGTGCTGAGCGGCGGCGAGCTGGACAAGTGGGAGAAGATCCGCCTG
CGCCCCGGCGGCAAGAAGAAGTACAAGCTGAAGCACATCGTGTGGGCCAGCCGCGAGCTGGAGCGCTTC
GCCGTGAACCCCGGCCTGCTGGAGACCAGCGAGGGCTGCCGCCAGATCCTGGGCCAGCTGCAGCCCAGC
CTGCAGACCGGCAGCGAGGAGCTGCGCAGCCTGTACAACACCGTGGCCACCCTGTACTGCGTGCACCAG
CGCATCGACGTCAAGGACACCAAGGAGGCCCTGGAGAAGATCGAGGAGGAGCAGAACAAGTCCAAGAA
AAGGCCCAGCAGGCCGCCGCCGCCGGCACCGGCAACAGCAGCCAGGTGAGCCAGAACTACCCCATC
GTGCAGAACCTGCAGGGCCAGATGGTGCACCAGGCCATCAGCCCCGCACCCTGAACGCCTGGGTGAAG
GTGGTGGAGGAGAAGGCCTTCAGCCCCGAGGTGATCCCCATGTTCAGCGCCCTGAGCGAGGGCGCCACC
CCCCAGGACCTGAACACGATGTTGAACACCGTGGGCGGCCACCAGGCCGCCATGCAGATGCTGAAGGAG
ACCATCAACGAGGAGGCCGCCGAGTGGGACCGCGTGCACCCCGTGCACGCCGGCCCCATCGCCCCCGGC
CAGATGCGCGAGCCCCGCGGCAGCGACATCGCCGGCACCACCAGCACCCTGCAGGAGCAGATCGGCTGG
ATGACCAACAACCCCCCCATCCCCGTGGGCGAGATCTACAAGCGGTGGATCATCCTGGGCCTGAACAAG
ATCGTGCGGATGTACAGCCCCACCAGCATCCTGGACATCCGCCAGGGCCCCAAGGAGCCCTTCCGCGAC
TACGTGGACCGCTTCTACAAGACCCTGCGCGCTGAGCAGGCCAGCCAGGACGTGAAGAACTGGATGACC
GAGACCCTGCTGGTGCAGAACGCCAACCCCGACTGCAAGACCATCCTGAAGGCTCTCGGCCCCGCGGCC
ACCCTGGAGGAGATGATGACCGCCTGCCAGGGCGTGGGCGGCCCCGGCCACAAGGCCCGCGTGCTGGCC
GAGGCGATGAGCCAGGTGACGAACCCGGCGACCATCATGATGCAGCGCGGCAACTTCCGCAACCAGCGG
AAGACCGTCAAGTGCTTCAACTGCGGCAAGGAGGGCCACACCGCCAGGAACTGCCGCGCCCCCGCAAG
AAGGGCTGCTGGCGCTGCGGCCGCGAGGGCCACCAGATGAAGGACTGCACCGAGCGCCAGGCCAACTTC
CTGGGCAAGATCTGGCCCAGCTACAAGGGCCGCCCCGGCAACTTCCTGCAGAGCCGCCCCGAGCCCACC
GCCCCCCCGAGGAGAGCTTCCGCTTCGGCGAGGAGAAGACCACCCCCAGCCAGAAGCAGGAGCCCATC
GACAAGGAGCTGTACCCCCTGACCAGCCTGCGCAGCCTGTTCGGCAACGACCCCAGCAGCCAGGAATTC
GAGCCCGTGGACCCCGCCTGGAGCCCTGGAAGCACCCCGGCAGCCAGCCCAAGACCGCCGGCACCAAC
TGCTACTGCAAGAAGTGCTGCTTCCACTGCCAGGTGAGCTTCATCACCAAGGGCCTGGGCATCAGCTAC
GGCCGCAAGAAGCGCCGCCAGCGCCGCCGCGCCCCCCCCGACAGCGAGGTGCACCAGGTGAGCCTGCCC
AAGCAGCCCGCCAGCCAGCCCCAGGGCGACCCCACCGGCCCCAAGGAGAGCAAGAAGAAGGTGGAGCGC
GAGACCGAGACCGACCCCGTGCACCCCGGGCCGGCCGCAGCGGCGACAGCGACGAGGAGCTGCTGCAG
ACCGTGCGCTTCATCAAGTTCCTGTACCAGAGCAACCCCCTGCCCAGCCCCAAGGGCACCCGCCAGGCC
GACCTGAACCGCCGCCGCCGCTGGCGCGAGCGCCAGCGCCAGATCCAGAGCATCAGCGCCTGGATCATC
AGCACCCACCTGGGCCGCAGCACCGAGCCCGTGCCCCTGCAGCTGCCCCCGACCTGCGCCTGAACCTG
GACTGCAGCGAGGACTGCGGCACCAGCGGCACCCAGGGCGTGGGCAGCCCCAGGTGCTGGGCGAGAGC
CCCGCCGTGCTGGACAGCGGCACCAAGGAGCTCGAGGCCGGCAAGTGGAGCAAGCGCATGAGCGGCTGG
AGCGCCGTGCGCGAGCGCATGAAGCGCGCCGAGCCGCCGAGCCCGCCGCCGACGGCGTGGGCGCCGTG
AGCCGCGACCTGGAGAAGCACGGCGCCATCACCAGCAGCAACACCGCCGCCAACAACGCCGACTGCGCC
TGGCTGGAGGCCCAGGAGGACGAGGACGTGGGCTTCCCCGTGCGCCCCCAGGTGCCCCTGCGCCCCATG
ACCTACAAGGCCGCCCTGGACCTGAGCCACTTCCTGAAGGAGAAGGGCGGCCTGGAGGGCCTGATCTAC
AGCCAGAAGCGCCAGGACATCCTGGACCTGTGGATCCACCACACCCAGGGCTACTTCCCCGGCTGGCAG
AACTACACCCCGGCCCCGGCATCCGCTACCCCCTGACCTTCGGCTGGTGCTTCAAGCTGGTGCCCGTG
GACCCCGACTACGTGGAGGAGGCCAACGCCGGCGAGAACAACAGCCTGCTGCACCCCATGAGCCAGCAC
GGCATGGACGACCCCGAGAAGGAGGTGCTGGTGTGGCGCTTCGACAGCCGCCTGGCCTTCCACCACATG
GCCCGCGAGCTGCACCCCGAGTACTACAAGGACTGCTAA

Figure 16 gp140.modSF162.CwtLmod

```
   1 atgcgcgtga tgggca

Figure 17 gp140.modSF162.CwtLnat

```
   1 atgagagtga tggggacaca gaagaattgt caacaatggt ggatatgggg catcttaggc
  61 ttctggatgc taatgatttg tagcgccgtg gagaagctgt gggtgaccgt gtactacggc
 121 gtgcccgtgt ggaaggaggc caccaccacc ctgttctgcg ccagcgacgc caaggcctac
 181 gacaccgagg tgcacaacgt gtgggccacc cacgcctgcg tgcccaccga ccccaacccc
 241 caggagatcg tgctggagaa cgtgaccgag aacttcaaca tgtggaagaa caacatggtg
 301 gagcagatgc acgaggacat catcagcctg tgggaccaga gcctgaagcc ctgcgtgaag
 361 ctgacccccc tgtgcgtgac cctgcactgc accaacctga gaacgccac caacaccaag
 421 agcagcaact ggaaggagat ggaccgcggc gagatcaaga actgcagctt caaggtgacc
 481 accagcatcc gcaacaagat gcagaaggag tacgccctgt tctacaagct ggacgtggtg
 541 cccatcgaca cgacaacac cagctacaag ctgatcaact gcaacaccag cgtgatcacc
 601 caggcctgcc ccaaggtgag cttcgagccc atccccatcc actactgcgc ccccgccggc
 661 ttcgccatcc tgaagtgcaa cgacaagaag ttcaacggca gcggccctg caccaacgtg
 721 agcaccgtgc agtgcaccca cggcatccgc ccgtggtga gcacccagct gctgctgaac
 781 ggcagcctgg ccgaggaggg cgtggtgatc cgcagcgaga acttcaccga caacgccaag
 841 accatcatcg tgcagctgaa ggagagcgtg gagatcaact gcacccgccc caacaacaac
 901 acccgcaaga gcatcaccat cggccccggc cgcgccttct acgccaccgg cgacatcatc
 961 ggcgacatcc gccaggccca ctgcaacatc agcggcgaga agtggaacaa cacccctgaag
1021 cagatcgtga ccaagctgca ggcccagttc ggcaacaaga ccatcgtgtt caagcagagc
1081 agcggcggcg accccgagat cgtgatgcac agcttcaact gcggcggcga gttcttctac
1141 tgcaacagca cccagctgtt caacagcacc tggaacaaca ccatcggccc caacaacacc
1201 aacggcacca tcaccctgcc ctgccgcatc aagcagatca tcaaccgctg gcaggaggtg
1261 ggcaaggcca tgtacgcccc ccccatccgc ggccagatcc gctgcagcag caacatcacc
1321 ggcctgctgc tgacccgcga cggcggcaag gagatcagca caccaccga gatcttccgc
1381 cccggcggcg gcgacatgcg cgacaactgg cgcagcgagc tgtacaagta caaggtggtg
1441 aagatcgagc ccctgggcgt ggcccccacc aaggccaagc gccgcgtggt gcagcgcgag
1501 aagcgcgccg tgaccctggg cgccatgttc ctgggcttcc tgggcgccgc cggcagcacc
1561 atgggcgccc gcagcctgac cctgaccgtg caggcccgcc agctgctgag cggcatcgtg
1621 cagcagcaga acaacctgct gcgcgccatc gaggcccagc agcacctgct gcagctgacc
1681 gtgtggggca tcaagcagct gcaggcccgc gtgctggccg tggagcgcta cctgaaggac
1741 cagcagctgc tgggcatctg ggctgcagc ggcaagctga tctgcaccac cgccgtgccc
1801 tggaacgcca gctggagcaa caagagcctg gaccagatct ggaacaacat gacctggatg
1861 gagtgggagc gcgagatcga caactacacc aacctgatct acacctgat cgaggagagc
1921 cagaaccagc aggagaagaa cgagcaggag ctgctggagc tggacaagtg ggccagcctg
1981 tggaactggt tcgacatcag caagtggctg tggtacatct aactcgag
```

Figure 18 gp160.modSF162.delV2.mut7

```
   1 atggatgcaa tgaagagagg gctctgctgt gtgctgctgc tgtgtggagc agtcttcgtt
  61 tcgcccagcg ccgtggagaa gctgtgggtg accgtgtact acggcgtgcc cgtgtggaag
 121 gaggccacca ccaccctgtt ctgcgccagc gacgccaagg cctacgacac cgaggtgcac
 181 aacgtgtggg ccacccacgc ctgcgtgccc accgacccca accccagga gatcgtgctg
 241 gagaacgtga ccgagaactt caacatgtgg aagaacaaca tggtggagca gatgcacgag
 301 gacatcatca gcctgtggga ccagagcctg aagccctgcg tgaagctgac cccctgtgc
 361 gtgaccctgc actgcaccaa cctgaagaac gccaccaaca ccaagagcag caactggaag
 421 gagatggacc gcggcgagat caagaactgc agcttcaagg tgggcgccgg caagctgatc
 481 aactgcaaca ccagcgtgat cacccaggcc tgccccaagg tgagcttcga gcccatcccc
 541 atccactact gcgccccgc cggcttcgcc atcctgaagt gcaacgacaa gaagttcaac
 601 ggcagcggcc cctgcaccaa cgtgagcacc gtgcagtgca cccacggcat ccgccccgtg
 661 gtgagcaccc agctgctgct gaacggcagc ctggccgagg agggcgtggt gatccgcagc
 721 gagaacttca ccgacaacgc caagaccatc atcgtgcagc tgaaggagag cgtggagatc
 781 aactgcaccc gccccaacaa caacacccgc aagagcatca ccatcggccc cggccgcgcc
 841 ttctacgcca ccggcgacat catcggcgac atcgccagg cccactgcaa catcagcggc
 901 gagaagtgga acaacaccct gaagcagatc gtgaccaagc tgcaggccca gttcggcaac
 961 aagaccatcg tgttcaagca gagcagcggc ggcgacccccg agatcgtgat gcacagcttc
1021 aactgcggcg gcgagttctt ctactgcaac agcacccagc tgttcaacag cacctggaac
1081 aacaccatcg gccccaacaa caccaacggc accatcaccc tgccctgccg catcaagcag
1141 atcatcaacc gctggcagga ggtgggcaag gccatgtacg cccccccat ccgcggccag
1201 atccgctgca gcagcaacat caccggcctg ctgctgaccc gcgacggcgg caaggagatc
1261 agcaacacca ccgagatctt ccgccccggc ggcggcgaca tgcgcgacaa ctggcgcagc
1321 gagctgtaca agtacaaggt ggtgaagatc gagcccctgg gcgtggcccc caccaaggcc
1381 atcagcagcg tggtgcagag cgagaagagc ccgtgaccc tgggcgccat gttcctgggc
1441 ttcctgggcg ccgccggcag caccatgggc gcccgcagcc tgaccctgac cgtgcaggcc
1501 cgccagctgc tgagcggcat cgtgcagcag cagaacaacc tgctgcgcgc catcgaggcc
1561 cagcagcacc tgctgcagct gaccgtgtgg ggcatcaagc agctgcaggc ccgcgtgctg
1621 gccgtggagc gctacctgaa ggaccagcag ctgctgggca tctggggctg cagcggcaag
1681 ctgatctgca ccaccgccgt gccctggaac gccagctgga caacaagag cctggaccag
1741 atctggaaca acatgacctg gatggagtgg gagcgcgaga tcgacaacta caccaacctg
1801 atctacaccc tgatcgagga gagccagaac cagcaggaga gaacgagca ggagctgctg
1861 gagctggaca gtgggccag cctgtggaac tggttcgaca tcagcaagtg gctgtggtac
1921 atcaagatct tcatcatgat cgtgggcggc ctggtgggcc tgcgcatcgt gttcaccgtg
1981 ctgagcatcg tgaaccgcgt gcgccagggc tacagccccc tgagcttcca gacccgcttc
2041 cccgcccccc gcggccccga ccgccccgag ggcatcgagg aggagggcgg cgagcgcgac
2101 cgcgaccgca gcagccccct ggtgcacggc ctgctggccc tgatctggga cgacctgcgc
2161 agcctgtgcc tgttcagcta ccaccgcctg cgcgacctga tcctgatcgc cgcccgcatc
2221 gtggagctgc tgggccgccg cggctggag gccctgaagt actggggcaa cctgctgcag
2281 tactggatcc aggagctgaa gaacagcgcc gtgagcctgt tcgacgccat cgccatcgcc
2341 gtggccgagg gcaccgaccg catcatcgag gtggcccagc gcatcggccg cgccttcctg
2401 cacatccccc gccgcatccg ccagggcttc gagcgcgccc tgctgtaa
```

Figure 19 gp160.modSF162.delV2.mut8

```
   1 atggatgcaa tgaagagagg gctctgctgt gtgctgctgc tgtgtggagc agtcttcgtt
  61 tcgcccagcg ccgtggagaa gctgtgggtg accgtgtact acggcgtgcc cgtgtggaag
 121 gaggccacca ccaccctgtt ctgcgccagc gacgccaagg cctacgacac cgaggtgcac
 181 aacgtgtggg ccacccacgc ctgcgtgccc accgacccca accccagga gatcgtgctg
 241 gagaacgtga ccgagaactt caacatgtgg aagaacaaca tggtggagca gatgcacgag
 301 gacatcatca gcctgtggga ccagagcctg aagccctgcg tgaagctgac cccctgtgc
 361 gtgaccctgc actgcaccaa cctgaagaac gccaccaaca ccaagagcag caactggaag
 421 gagatggacc gcggcgagat caagaactgc agcttcaagg tgggcgccgg caagctgatc
 481 aactgcaaca ccagcgtgat cacccaggcc tgccccaagg tgagcttcga gcccatcccc
 541 atccactact gcgccccgc cggcttcgcc atcctgaagt gcaacgacaa gaagttcaac
 601 ggcagcggcc cctgcaccaa cgtgagcacc gtgcagtgca cccacggcat ccgccccgtg
 661 gtgagcaccc agctgctgct gaacggcagc ctggccgagg agggcgtggt gatccgcagc
 721 gagaacttca ccgacaacgc caagaccatc atcgtgcagc tgaaggagag cgtggagatc
 781 aactgcaccc gccccaacaa caacacccgc aagagcatca ccatcggccc cggccgcgcc
 841 ttctacgcca ccggcgacat catcggcgac atccgccagg cccactgcaa catcagcggc
 901 gagaagtgga acaacaccct gaagcagatc gtgaccaagc tgcaggccca gttcggcaac
 961 aagaccatcg tgttcaagca gagcagcggc ggcgacccg agatcgtgat gcacagcttc
1021 aactgcggcg gcgagttctt ctactgcaac agcacccagc tgttcaacag cacctggaac
1081 aacaccatcg cccccaacaa caccaacggc accatcaccc tgccctgccg catcaagcag
1141 atcatcaacc gctggcagga ggtgggcaag gccatgtacg ccccccccat ccgcggccag
1201 atccgctgca gcagcaacat caccggcctg ctgctgaccc gcgacggcgg caaggagatc
1261 agcaacacca ccgagatctt ccgccccggc ggcggcgaca tgcgcgacaa ctggcgcagc
1321 gagctgtaca agtacaaggt ggtgaagatc gagcccctgg gcgtggcccc caccatcgcc
1381 atcagcagcg tggtgcagag cgagaagagc gccgtgaccc tgggcgccat gttcctgggc
1441 ttcctgggcg ccgccggcag caccatgggc gcccgcagcc tgaccctgac cgtgcaggcc
1501 cgccagctgc tgagcggcat cgtgcagcag cagaacaacc tgctgcgcgc catcgaggcc
1561 cagcagcacc tgctgcagct gaccgtgtgg ggcatcaagc agctgcaggc cgcgtgctg
1621 gccgtggagc gctacctgaa ggaccagcag ctgctgggca tctgggctg cagcggcaag
1681 ctgatctgca ccaccgccgt gccctggaac gccagctgga gcaacaagag cctggaccag
1741 atctggaaca acatgacctg gatggagtgg gagcgcgaga tcgacaacta caccaacctg
1801 atctacaccc tgatcgagga gagccagaac cagcaggaga gaacgagca ggagctgctg
1861 gagctggaca gtgggccag cctgtggaac tggttcgaca tcagcaagtg gctgtggtac
1921 atcaagatct tcatcatgat cgtgggcggc ctggtgggcc tgcgcatcgt gttcaccgtg
1981 ctgagcatcg tgaaccgcgt gcgccagggc tacagccccc tgagcttcca gacccgcttc
2041 cccgccccc gcggccccga ccgcccgag ggcatcgagg aggagggcgg cgagcgcgac
2101 cgcgaccgca gcgccccct ggtgcacggc ctgctggccc tgatctggga cgacctgcgc
2161 agcctgtgcc tgttcagcta ccaccgcctg cgcgacctga tcctgatcgc cgcccgcatc
2221 gtggagctgc tgggccgccg cggctggagg ccctgaagt actgggcaa cctgctgcag
2281 tactggatcc aggagctgaa gaacagcgcc gtgagcctgt cgacgccat cgccatcgcc
2341 gtggccgagg caccgaccg catcatcgag gtggcccagc gcatcggccg cgccttcctg
2401 cacatccccc gccgcatccg ccagggcttc gagcgcgccc tgctgtaa
```

Figure 20 int.opt.mut.SF2

TTCCTGAACGGCATCGACAAGGCCCAGGAGGAGCACGAGAAGTACCACAGCAACTGGCGCGCCATGGCC
AGCGACTTCAACCTGCCCCCCGTGGTGGCCAAGGAGATCGTGGCCAGCGCCGACAAGTGCCAGCTGAAG
GGCGAGGCCATGCACGGCCAGGTGGACTGCAGCCCCGGCATCTGGCAGCTGGCCTGCACCCACCTGGAG
GGCAAGATCATCCTGGTGGCCGTGCACGTGGCCAGCGGCTACATCGAGGCCGAGGTGATCCCCGCCGAG
ACCGGCCAGGAGACCGCCTACTTCCTGCTGAAGCTGGCCGGCCGCTGGCCCGTGAAGACCATCCACACC
GCCAACGGCAGCAACTTCACCAGCACCACCGTGAAGGCCGCCTGCTGGTGGGCCGGCATCAAGCAGGAG
TTCGGCATCCCCTACAACCCCCAGAGCCAGGGCGTGGTGGCGAGCATGAACAACGAGCTGAAGAAGATC
ATCGGCCAGGTGCGCGACCAGGCCGAGCACCTGAAGACCGCCGTGCAGATGGCCGTGTTCATCCACAAC
TTCAAGCGCAAGGGCGGCATCGGCGGCTACAGCGCCGGCGAGCGCATCGTGGACATCATCGCCACCGAC
ATCCAGACCAAGGAGCTGCAGAAGCAGATCACCAAGATCCAGAACTTCCGCGTGTACTACCGCGACAAC
AAGGACCCCCTGAAGGGCCCCGCCAAGCTGCTGTGGAAGGGCGAGGGCGCCGTGGTGATCCAGGACAAC
AGCGACATCAAGGTGGTGCCCCGCCGCAAGGCCAAGATCATCCGCGACTACGGCAAGCAGATGGCCGGC
GACGACTGCGTGGCCAGCCGCCAGGACGAGGAC

Figure 21 int.opt.SF2

TTCCTGAACGGCATCGACAAGGCCCAGGAGGAGCACGAGAAGTACCACAGCAACTGGCGCGCCATGGCC
AGCGACTTCAACCTGCCCCCCGTGGTGGCCAAGGAGATCGTGGCCAGCTGCGACAAGTGCCAGCTGAAG
GGCGAGGCCATGCACGGCCAGGTGGACTGCAGCCCCGGCATCTGGCAGCTGGACTGCACCCACCTGGAG
GGCAAGATCATCCTGGTGGCCGTGCACGTGGCCAGCGGCTACATCGAGGCCGAGGTGATCCCCGCCGAG
ACCGGCCAGGAGACCGCCTACTTCCTGCTGAAGCTGGCCGGCCGCTGGCCCGTGAAGACCATCCACACC
GACAACGGCAGCAACTTCACCAGCACCACCGTGAAGGCCGCCTGCTGGTGGGCCGGCATCAAGCAGGAG
TTCGGCATCCCCTACAACCCCCAGAGCCAGGGCGTGGTGGAGAGCATGAACAACGAGCTGAAGAAGATC
ATCGGCCAGGTGCGCGACCAGGCCGAGCACCTGAAGACCGCCGTGCAGATGGCCGTGTTCATCCACAAC
TTCAAGCGCAAGGGCGGCATCGGCGGCTACAGCGCCGGCGAGCGCATCGTGGACATCATCGCCACCGAC
ATCCAGACCAAGGAGCTGCAGAAGCAGATCACCAAGATCCAGAACTTCCGCGTGTACTACCGCGACAAC
AAGGACCCCCTGTGGAAGGGCCCCGCCAAGCTGCTGTGGAAGGGCGAGGGCGCCGTGGTGATCCAGGAC
AACAGCGACATCAAGGTGGTGCCCCGCCGCAAGGCCAAGATCATCCGCGACTACGGCAAGCAGATGGCC
GGCGACGACTGCGTGGCCAGCCGCCAGGACGAGGAC

Figure 22 nef.D125G.-myr.opt.SF162

ATGGCCGGCAAGTGGAGCAAGCGCATGAGCGGCTGGAGCGCCGTGCGCGAGCGCATGAAGCGCGCCGAG
CCCGCCGAGCCCGCCGCCGACGGCGTGGGCGCCGTGAGCCGCGACCTGGAGAAGCACGGCGCCATCACC
AGCAGCAACACCGCCGCCAACAACGCCGACTGCGCCTGGCTGGAGGCCCAGGAGGACGAGGACGTGGGC
TTCCCCGTGCGCCCCCAGGTGCCCCTGCGCCCCATGACCTACAAGGCCGCCCTGGACCTGAGCCACTTC
CTGAAGGAGAAGGGCGGCCTGGAGGGCCTGATCTACAGCCAGAAGCGCCAGGACATCCTGGACCTGTGG
ATCCACCACACCCAGGGCTACTTCCCCGGCTGGCAGAACTACACCCCCGGCCCCGGCATCCGCTACCCC
CTGACCTTCGGCTGGTGCTTCAAGCTGGTGCCCGTGGACCCCGACTACGTGGAGGAGGCCAACGCCGGC
GAGAACAACAGCCTGCTGCACCCCATGAGCCAGCACGGCATGGACGACCCCGAGAAGGAGGTGCTGGTG
TGGCGCTTCGACAGCCGCCTGGCCTTCCACCACATGGCCCGCGAGCTGCACCCCGAGTACTACAAGGAC
TGC

Figure 23 nef.D107G.-myr18.opt.SF162 (dbl.mutant)

ATGAAGCGCGCCGAGCCCGCCGAGCCCGCCGCCGACGGCGTGGGCGCCGTGAGCCGC
GACCTGGAGAAGCACGGCGCCATCACCAGCAGCAACACCGCCGCCAACAACGCCGAC
TGCGCCTGGCTGGAGGCCCAGGAGGACGAGGACGTGGGCTTCCCCGTGCGCCCCAG
GTGCCCCTGCGCCCCATGACCTACAAGGCCGCCCTGGACCTGAGCCACTTCCTGAAG
GAGAAGGGCGGCCTGGAGGGCCTGATCTACAGCCAGAAGCGCCAGGACATCCTGGAC
CTGTGGATCCACCACACCCAGGGCTACTTCCCCGGCTGGCAGAACTACACCCCCGGC
CCCGGCATCCGCTACCCCCTGACCTTCGGCTGGTGCTTCAAGCTGGTGCCCGTGGAC
CCCGACTACGTGGAGGAGGCCAACGCCGGCGAGAACAACAGCCTGCTGCACCCCATG
AGCCAGCACGGCATGGACGACCCCGAGAAGGAGGTGCTGGTGTGGCGCTTCGACAGC
CGCCTGGCCTTCCACCACATGGCCCGCGAGCTGCACCCCGAGTACTACAAGGACTGC

Figure 24 nef.opt.D125G.SF162

ATGGGCGGCAAGTGGAGCAAGCGCATGAGCGGCTGGAGCGCCGTGCGCGAGCGCATGAAGCGCGCCGAG
CCCGCCGAGCCCGCCGCCGACGGCGTGGGCGCCGTGAGCCGCGACCTGGAGAAGCACGGCGCCATCACC
AGCAGCAACACCGCCGCCAACAACGCCGACTGCGCCTGGCTGGAGGCCCAGGAGGACGAGGACGTGGGC
TTCCCCGTGCGCCCCCAGGTGCCCCTGCGCCCCATGACCTACAAGGCCGCCCTGGACCTGAGCCACTTC
CTGAAGGAGAAGGGCGGCCTGGAGGGCCTGATCTACAGCCAGAAGCGCCAGGACATCCTGGACCTGTGG
ATCCACCACACCCAGGGCTACTTCCCCGGCTGGCAGAACTACACCCCCGGCCCCGGCATCCGCTACCCC
CTGACCTTCGGCTGGTGCTTCAAGCTGGTGCCCGTGGACCCCGACTACGTGGAGGAGGCCAACGCCGGC
GAGAACAACAGCCTGCTGCACCCCATGAGCCAGCACGGCATGGACGACCCCGAGAAGGAGGTGCTGGTG
TGGCGCTTCGACAGCCGCCTGGCCTTCCACCACATGGCCCGCGAGCTGCACCCCGAGTACTACAAGGAC
TGC

Figure 25 nef.opt.SF162

ATGGGCGGCAAGTGGAGCAAGCGCATGAGCGGCTGGAGCGCCGTGCGCGAGCGCATGAA
GCGCGCCGAGCCCGCCGAGCCCGCCGCCGACGGCGTGGGCGCCGTGAGCCGCGACCTGG
AGAAGCACGGCGCCATCACCAGCAGCAACACCGCCGCCAACAACGCCGACTGCGCCTGG
CTGGAGGCCCAGGAGGACGAGGACGTGGGCTTCCCCGTGCGCCCCAGGTGCCCCTGCGC
CCCATGACCTACAAGGCCGCCCTGGACCTGAGCCACTTCCTGAAGGAGAAGGGCGGCCTG
GAGGGCCTGATCTACAGCCAGAAGCGCCAGGACATCCTGGACCTGTGGATCCACCACACC
CAGGGCTACTTCCCCGACTGGCAGAACTACACCCCCGGCCCCGGCATCCGCTACCCCCTG
ACCTTCGGCTGGTGCTTCAAGCTGGTGCCCGTGGACCCCGACTACGTGGAGGAGGCCAAC
GCCGGCGAGAACAACAGCCTGCTGCACCCCATGAGCCAGCACGGCATGGACGACCCCGA
GAAGGAGGTGCTGGTGTGGCGCTTCGACAGCCGCCTGGCCTTCCACCACATGGCCCGCGA
GCTGCACCCCGAGTACTACAAGGACTGC

Figure 26 p15RnaseH.opt.SF2

TACGTGGACGGCGCCGCCAACCGCGAGACCAAGCTGGGCAAGGCCGGCTACGTGACCGA
CCGGGGCCGGCAGAAGGTGGTGAGCATCGCCGACACCACCAACCAGAAGACCGAGCTGC
AGGCCATCCACCTGGCCCTGCAGGACAGCGGCCTGGAGGTGAACATCGTGACCGACAGCC
AGTACGCCCTGGGCATCATCCAGGCCCAGCCCGACAAGAGCGAGAGCGAGCTGGTGAGC
CAGATCATCGAGCAGCTGATCAAGAAGGAGAAGGTGTACCTGGCCTGGGTGCCCGCCCAC
AAGGGCATCGGCGGCAACGAGCAGGTGGACAAGCTGGTGAGCGCCGGCATCCGCAAGGT
GCTG

Figure 27 p2Pol.opt.YMWM.SF2

GCCACCATGGCCGAGGCGATGAGCCAGGTGACGAACCCGGCGACCATCATGATGCAGCGCGGCAACTTC
CGCAACCAGCGGAAGACCGTCAAGTGCTTCAACTGCGGCAAGGAGGGCCACACCGCCAGGAACTGCCGC
GCCCCCCGCAAGAAGGGCTGCTGGCGCTGCGGCCGCGAAGGACACCAAATGAAAGATTGCACTGAGAGA
CAGGCTAATTTCTTCCGCGAGGACCTGGCCTTCCTGCAGGGCAAGGCCCGCGAGTTCAGCAGCGAGCAG
ACCCGCGCCAACAGCCCCACCCGCCGCGAGCTGCAGGTGTGGGCGGCGAGAACAACAGCCTGAGCGAG
GCCGGCGCCGACCGCCAGGGCACCGTGAGCTTCAACTTCCCCCAGATCACCCTGTGGCAGCGCCCCCTG
GTGACCATCAGGATCGGCGGCCAGCTCAAGGAGGCGCTGCTCGCCACCGGCGCCGACGACACCGTGCTG
GAGGAGATGAACCTGCCCGGCAAGTGGAAGCCCAAGATGATCGGCGGGATCGGGGGCTTCATCAAGGTG
CGGCAGTACGACCAGATCCCCGTGGAGATCTGCGGCCACAAGGCCATCGGCACCGTGCTGGTGGGCCCC
ACCCCCGTGAACATCATCGGCCGCAACCTGCTGACCCAGATCGGCTGCACCCTGAACTTCCCCATCAGC
CCCATCGAGACGGTGCCCGTGAAGCTGAAGCCGGGGATGGACGGCCCCAAGGTCAAGCAGTGGCCCCTG
ACCGAGGAGAAGATCAAGGCCCTGGTGGAGATCTGCACCGAGATGGAGAAGGAGGGCAAGATCAGCAAG
ATCGGCCCCGAGAACCCCTACAACACCCCCGTGTTCGCCATCAAGAAGAAGGACAGCACCAAGTGGCGC
AAGCTGGTGGACTTCCGCGAGCTGAACAAGCGCACCCAGGACTTCTGGGAGGTGCAGCTGGGCATCCCC
CACCCCGCCGGCCTGAAGAAGAAGAAGAGCGTGACCGTGCTGGACGTGGGCGACGCCTACTTCAGCGTG
CCCCTGGACAAGGACTTCCGCAAGTACACCGCCTTCACCATCCCCAGCATCAACAACGAGACCCCCGGC
ATCCGCTACCAGTACAACGTGCTGCCCCAGGGCTGGAAGGGCAGCCCCGCCATCTTCCAGAGCAGCATG
ACCAAGATCCTGGAGCCCTTCCGCAAGCAGAACCCCGACATCGTGATCTACCAGGCCCCCCTGTACGTG
GGCAGCGACCTGGAGATCGGCCAGCACCGCACCAAGATCGAGGAGCTGCGCCAGCACCTGCTGCGCTGG
GGCTTCACCACCCCCGACAAGAAGCACCAGAAGGAGCCCCCCTTCCTGCCCATCGAGCTGCACCCCGAC
AAGTGGACCGTGCAGCCCATCATGCTGCCCGAGAAGGACAGCTGGACCGTGAACGACATCCAGAAGCTG
GTGGGCAAGCTGAACTGGGCCAGCCAGATCTACGCCGGCATCAAGGTGAAGCAGCTGTGCAAGCTGCTG
CGCGGCACCAAGGCCCTGACCGAGGTGATCCCCCTGACCGAGGAGGCCGAGCTGGAGCTGGCCGAGAAC
CGCGAGATCCTGAAGGAGCCCGTGCACGAGGTGTACTACGACCCCAGCAAGGACCTGGTGGCCGAGATC
CAGAAGCAGGGCCAGGGCCAGTGGACCTACCAGATCTACCAGGAGCCCTTCAAGAACCTGAAGACCGGC
AAGTACGCCCGCATGCGCGGCGCCCACACCAACGACGTGAAGCAGCTGACCGAGGCCGTGCAGAAGGTG
AGCACCGAGAGCATCGTGATCTGGGGCAAGATCCCCAAGTTCAAGCTGCCCATCCAGAAGGAGACCTGG
GAGGCCTGGTGGATGGAGTACTGGCAGGCCACCTGGATCCCCGAGTGGGAGTTCGTGAACACCCCCCCC
CTGGTGAAGCTGTGGTACCAGCTGGAGAAGGAGCCCATCGTGGGCGCCGAGACCTTCTACGTGGACGGC
GCCGCCAACCGCGAGACCAAGCTGGGCAAGGCCGGCTACGTGACCGACCGGGGCCGGCAGAAGGTGGTG
AGCATCGCCGACACCACCAACCAGAAGACCGAGCTGCAGGCCATCCACCTGGCCCTGCAGGACAGCGGC
CTGGAGGTGAACATCGTGACCGACAGCCAGTACGCCCTGGGCATCATCCAGGCCCAGCCCGACAAGAGC
GAGAGCGAGCTGGTGAGCCAGATCATCGAGCAGCTGATCAAGAAGGAGAAGGTGTACCTGGCCTGGGTG
CCCGCCCACAAGGGCATCGGCGGCAACGAGCAGGTGGACAAGCTGGTGAGCGCCGGCATCCGCAAGGTG
CTGTTCCTGAACGGCATCGATGGCGGCATCGTGATCTACCAGTACATGGACGACCTGTACGTGGGCAGC
GGCGGCCCTAGGATCGATTAAAAGCTTCCCGGGGCTAGCACCGGT

Figure 28 p2PolInaopt.YM.SF2

GCCACCATGGCCGAGGCGATGAGCCAGGTGACGAACCCGGCGACCATCATGATGCAGCGCGGCAACTTC
CGCAACCAGCGGAAGACCGTCAAGTGCTTCAACTGCGGCAAGGAGGGCCACACCGCCAGGAACTGCCGC
GCCCCCCGCAAGAAGGGCTGCTGGCGCTGCGGCCGCGAAGGACACCAAATGAAAGATTGCACTGAGAGA
CAGGCTAATTTCTTCCGCGAGGACCTGGCCTTCCTGCAGGGCAAGGCCCGCGAGTTCAGCAGCGAGCAG
ACCCGCGCCAACAGCCCCACCCGCCGCGAGCTGCAGGTGTGGGGCGGCGAGAACAACAGCCTGAGCGAG
GCCGGCGCCGACCGCCAGGGCACCGTGAGCTTCAACTTCCCCCAGATCACCCTGTGGCAGCGCCCCCTG
GTGACCATCAGGATCGGCGGCCAGCTCAAGGAGGCGCTGCTCGCCACCGGCGCCGACGACACCGTGCTG
GAGGAGATGAACCTGCCCGGCAAGTGGAAGCCCAAGATGATCGGCGGGATCGGGGGCTTCATCAAGGTG
CGGCAGTACGACCAGATCCCCGTGGAGATCTGCGGCCACAAGGCCATCGGCACCGTGCTGGTGGGCCCC
ACCCCCGTGAACATCATCGGCCGCAACCTGCTGACCCAGATCGGCTGCACCCTGAACTTCCCCATCAGC
CCCATCGAGACGGTGCCCGTGAAGCTGAAGCCGGGGATGGACGGCCCCAAGGTCAAGCAGTGGCCCCTG
ACCGAGGAGAAGATCAAGGCCCTGGTGGAGATCTGCACCGAGATGGAGAAGGAGGGCAAGATCAGCAAG
ATCGGCCCCGAGAACCCCTACAACACCCCCGTGTTCGCCATCAAGAAGAAGGACAGCACCAAGTGGCGC
AAGCTGGTGGACTTCCGCGAGCTGAACAAGCGCACCCAGGACTTCTGGGAGGTGCAGCTGGGCATCCCC
CACCCCGCCGGCCTGAAGAAGAAGAAGAGCGTGACCGTGCTGGACGTGGGCGACGCCTACTTCAGCGTG
CCCCTGGACAAGGACTTCCGCAAGTACACCGCCTTCACCATCCCCAGCATCAACAACGAGACCCCCGGC
ATCCGCTACCAGTACAACGTGCTGCCCCAGGGCTGGAAGGGCAGCCCCGCCATCTTCCAGAGCAGCATG
ACCAAGATCCTGGAGCCCTTCCGCAAGCAGAACCCCGACATCGTGATCTACCAGGCCCCCCTGTACGTG
GGCAGCGACCTGGAGATCGGCCAGCACCGCACCAAGATCGAGGAGCTGCGCCAGCACCTGCTGCGCTGG
GGCTTCACCACCCCCGACAAGAAGCACCAGAAGGAGCCCCCCTTCCTGTGGATGGGCTACGAGCTGCAC
CCCGACAAGTGGACCGTGCAGCCCATCATGCTGCCCGAGAAGGACAGCTGGACCGTGAACGACATCCAG
AAGCTGGTGGGCAAGCTGAACTGGGCCAGCCAGATCTACGCCGGCATCAAGGTGAAGCAGCTGTGCAAG
CTGCTGCGCGGCACCAAGGCCCTGACCGAGGTGATCCCCCTGACCGAGGAGGCCGAGCTGGAGCTGGCC
GAGAACCGCGAGATCCTGAAGGAGCCCGTGCACGAGGTGTACTACGACCCCAGCAAGGACCTGGTGGCC
GAGATCCAGAAGCAGGGCCAGGGCCAGTGGACCTACCAGATCTACCAGGAGCCCTTCAAGAACCTGAAG
ACCGGCAAGTACGCCCGCATGCGCGGCGCCCACACCAACGACGTGAAGCAGCTGACCGAGGCCGTGCAG
AAGGTGAGCACCGAGAGCATCGTGATCTGGGGCAAGATCCCCAAGTTCAAGCTGCCCATCCAGAAGGAG
ACCTGGGAGGCCTGGTGGATGGAGTACTGGCAGGCCACCTGGATCCCCGAGTGGGAGTTCGTGAACACC
CCCCCCCTGGTGAAGCTGTGGTACCAGCTGGAGAAGGAGCCCATCGTGGGCGCCGAGACCTTCTACGTG
GACGGCGCCGCCAACCGCGAGACCAAGCTGGGCAAGGCCGGCTACGTGACCGACCGGGCCGGCAGAAG
GTGGTGAGCATCGCCGACACCACCAACCAGAAGACCGAGCTGCAGGCCATCCACCTGGCCCTGCAGGAC
AGCGGCCTGGAGGTGAACATCGTGACCGACAGCCAGTACGCCCTGGGCATCATCCAGGCCCAGCCCGAC
AAGAGCGAGAGCGAGCTGGTGAGCCAGATCATCGAGCAGCTGATCAAGAAGGAGAAGGTGTACCTGGCC
TGGGTGCCCGCCCACAAGGGCATCGGCGGCAACGAGCAGGTGGACAAGCTGGTGAGCGCCGGCATCCGC
AAGGTGCTGTTCCTGAACGGCATCGATGGCGGCATCGTGATCTACCAGTACATGGACGACCTGTACGTG
GGCAGCGGCGGCCCTAGGATCGATTAAAAGCTTCCCGGGGCTAGCACCGGT

Figure 29 p2Polopt.SF2

```
GCCACCATGGCCGAGGCGATGAGCCAGGTGACGAACCCGGCGACCATCATGATGCAGCGCGGCAACTTC
CGCAACCAGCGGAAGACCGTCAAGTGCTTCAACTGCGGCAAGGAGGGCCACACCGCCAGGAACTGCCGC
GCCCCCCGCAAGAAGGGCTGCTGGCGCTGCGGCCGCGAAGGACACCAAATGAAAGATTGCACTGAGAGA
CAGGCTAATTTCTTCCGCGAGGACCTGGCCTTCCTGCAGGGCAAGGCCCGCGAGTTCAGCAGCGAGCAG
ACCCGCGCCAACAGCCCCACCCGCCGCGAGCTGCAGGTGTGGGCGGCGAGAACAACAGCCTGAGCGAG
GCCGGCGCCGACCGCCAGGGCACCGTGAGCTTCAACTTCCCCCAGATCACCCTGTGGCAGCGCCCCCTG
GTGACCATCAGGATCGGCGGCCAGCTCAAGGAGGCGCTGCTCGACACCGGCGCCGACGACACCGTGCTG
GAGGAGATGAACCTGCCCGGCAAGTGGAAGCCCAAGATGATCGGCGGGATCGGGGGCTTCATCAAGGTG
CGGCAGTACGACCAGATCCCCGTGGAGATCTGCGGCCACAAGGCCATCGGCACCGTGCTGGTGGGCCCC
ACCCCCGTGAACATCATCGGCCGCAACCTGCTGACCCAGATCGGCTGCACCCTGAACTTCCCCATCAGC
CCCATCGAGACGGTGCCCGTGAAGCTGAAGCCGGGATGGACGGCCCCAAGGTCAAGCAGTGGCCCCTG
ACCGAGGAGAAGATCAAGGCCCTGGTGGAGATCTGCACCGAGATGGAGAAGGAGGGCAAGATCAGCAAG
ATCGGCCCCGAGAACCCCTACAACACCCCCGTGTTCGCCATCAAGAAGAAGGACAGCACCAAGTGGCGC
AAGCTGGTGGACTTCCGCGAGCTGAACAAGCGCACCCAGGACTTCTGGGAGGTGCAGCTGGGCATCCCC
CACCCCGCCGGCCTGAAGAAGAAGAAGAGCGTGACCGTGCTGGACGTGGGCGACGCCTACTTCAGCGTG
CCCCTGGACAAGGACTTCCGCAAGTACACCGCCTTCACCATCCCCAGCATCAACAACGAGACCCCCGGC
ATCCGCTACCAGTACAACGTGCTGCCCCAGGGCTGGAAGGGCAGCCCCGCCATCTTCCAGAGCAGCATG
ACCAAGATCCTGGAGCCCTTCCGCAAGCAGAACCCCGACATCGTGATCTACCAGTACATGGACGACCTG
TACGTGGGCAGCGACCTGGAGATCGGCCAGCACCGCACCAAGATCGAGGAGCTGCGCCAGCACCTGCTG
CGCTGGGGCTTCACCACCCCCGACAAGAAGCACCAGAAGGAGCCCCCCTTCCTGTGGATGGGCTACGAG
CTGCACCCCGACAAGTGGACCGTGCAGCCCATCATGCTGCCCGAGAAGGACAGCTGGACCGTGAACGAC
ATCCAGAAGCTGGTGGGCAAGCTGAACTGGGCCAGCCAGATCTACGCCGGCATCAAGGTGAAGCAGCTG
TGCAAGCTGCTGCGCGGCACCAAGGCCCTGACCGAGGTGATCCCCCTGACCGAGGAGGCCGAGCTGGAG
CTGGCCGAGAACCGCGAGATCCTGAAGGAGCCCGTGCACGAGGTGTACTACGACCCCAGCAAGGACCTG
GTGGCCGAGATCCAGAAGCAGGGCCAGGGCCAGTGGACCTACCAGATCTACCAGGAGCCCTTCAAGAAC
CTGAAGACCGGCAAGTACGCCCGCATGCGCGGCGCCCACACCAACGACGTGAAGCAGCTGACCGAGGCC
GTGCAGAAGGTGAGCACCGAGAGCATCGTGATCTGGGGCAAGATCCCCAAGTTCAAGCTGCCCATCCAG
AAGGAGACCTGGGAGGCCTGGTGGATGGAGTACTGGCAGGCCACCTGGATCCCCGAGTGGGAGTTCGTG
AACACCCCCCCCCTGGTGAAGCTGTGGTACCAGCTGGAGAAGGAGCCCATCGTGGGCGCCGAGACCTTC
TACGTGGACGGCGCCGCCAACCGCGAGACCAAGCTGGGCAAGGCCGGCTACGTGACCGACCGGGGCCGG
CAGAAGGTGGTGAGCATCGCCGACACCACCAACCAGAAGACCGAGCTGCAGGCCATCCACCTGGCCCTG
CAGGACAGCGGCCTGGAGGTGAACATCGTGACCGACAGCCAGTACGCCCTGGGCATCATCCAGGCCCAG
CCCGACAAGAGCGAGAGCGAGCTGGTGAGCCAGATCATCGAGCAGCTGATCAAGAAGGAGAAGGTGTAC
CTGGCCTGGGTGCCCGCCCACAAGGGCATCGGCGGCAACGAGCAGGTGGACAAGCTGGTGAGCGCCGGC
ATCCGCAAGGTGCTGTTCCTGAACGGCATCGATGGCGGCATCGTGATCTACCAGTACATGGACGACCTG
TACGTGGGCAGCGGCGGCCCTAGGATCGATTAAAAGCTTCCCGGGGCTAGCACCGGT
```

Figure 30 p2PolTatRevNef.opt.native_B

```
ATGGCCGAGGCGATGAGCCAGGTGACGAACCCGGCGACCATCATGATGCAGCGCGGCAACTTCCGCAAC
CAGCGGAAGACCGTCAAGTGCTTCAACTGCGGCAAGGAGGGCCACACCGCCAGGAACTGCCGCGCCCC
CGCAAGAAGGGCTGCTGGCGCTGCGGCCGCGAAGGACACCAAATGAAAGATTGCACTGAGAGACAGGCT
AATTTCTTCCGCGAGGACCTGGCCTTCCTGCAGGGCAAGGCCCGCGAGTTCAGCAGCGAGCAGACCCGC
GCCAACAGCCCCACCCGCCGCGAGCTGCAGGTGTGGGCGGCGAGAACAACAGCCTGAGCGAGGCCGGC
GCCGACCGCCAGGGCACCGTGAGCTTCAACTTCCCCCAGATCACCCTGTGGCAGCGCCCCCTGGTGACC
ATCAGGATCGGCGGCCAGCTCAAGGAGGCGCTGCTCGACACCGGCGCCGACGACACCGTGCTGGAGGAG
ATGAACCTGCCCGGCAAGTGGAAGCCCAAGATGATCGGCGGGATCGGGGGCTTCATCAAGGTGCGGCAG
TACGACCAGATCCCCGTGGAGATCTGCGGCCACAAGGCCATCGGCACCGTGCTGGTGGGCCCCACCCCC
GTGAACATCATCGGCCGCAACCTGCTGACCCAGATCGGCTGCACCCTGAACTTCCCCATCAGCCCCATC
GAGACGGTGCCCGTGAAGCTGAAGCCGGGGATGGACGGCCCCAAGGTCAAGCAGTGGCCCCTGACCGAG
GAGAAGATCAAGGCCCTGGTGGAGATCTGCACCGAGATGGAGAAGGAGGGCAAGATCAGCAAGATCGGC
CCCGAGAACCCCTACAACACCCCCGTGTTCGCCATCAAGAAGAAGGACAGCACCAAGTGGCGCAAGCTG
GTGGACTTCCGCGAGCTGAACAAGCGCACCCAGGACTTCTGGGAGGTGCAGCTGGGCATCCCCACCCC
GCCGGCCTGAAGAAGAAGAAGAGCGTGACCGTGCTGGACGTGGGCGACGCCTACTTCAGCGTGCCCCTG
GACAAGGACTTCCGCAAGTACACCGCCTTCACCATCCCCAGCATCAACAACGAGACCCCCGGCATCCGC
TACCAGTACAACGTGCTGCCCCAGGGCTGGAAGGGCAGCCCCGCCATCTTCCAGAGCAGCATGACCAAG
ATCCTGGAGCCCTTCCGCAAGCAGAACCCCGACATCGTGATCTACCAGTACATGGACGACCTGTACGTG
GGCAGCGACCTGGAGATCGGCCAGCACCGCACCAAGATCGAGGAGCTGCGCCAGCACCTGCTGCGCTGG
GGCTTCACCACCCCCGACAAGAAGCACCAGAAGGAGCCCCCCTTCCTGTGGATGGGCTACGAGCTGCAC
CCCGACAAGTGGACCGTGCAGCCCATCATGCTGCCCGAGAAGGACAGCTGGACCGTGAACGACATCCAG
AAGCTGGTGGGCAAGCTGAACTGGGCCAGCCAGATCTACGCCGGCATCAAGGTGAAGCAGCTGTGCAAG
CTGCTGCGCGGCACCAAGGCCCTGACCGAGGTGATCCCCCTGACCGAGGAGGCCGAGCTGGAGCTGGCC
GAGAACCGCGAGATCCTGAAGGAGCCCGTGCACGAGGTGTACTACGACCCCAGCAAGGACCTGGTGGCC
GAGATCCAGAAGCAGGGCCAGGGCCAGTGGACCTACCAGATCTACCAGGAGCCCTTCAAGAACCTGAAG
ACCGGCAAGTACGCCCGCATGCGCGGCGCCCACACCAACGACGTGAAGCAGCTGACCGAGGCCGTGCAG
AAGGTGAGCACCGAGAGCATCGTGATCTGGGGCAAGATCCCCAAGTTCAAGCTGCCCATCCAGAAGGAG
ACCTGGGAGGCCTGGTGGATGGAGTACTGGCAGGCCACCTGGATCCCCGAGTGGGAGTTCGTGAACACC
CCCCCCCTGGTGAAGCTGTGGTACCAGCTGGAGAAGGAGCCCATCGTGGGCGCCGAGACCTTCTACGTG
GACGGCGCCGCCAACCGCGAGACCAAGCTGGGCAAGGCCGGCTACGTGACCGACGGGGCCGGCAGAAG
GTGGTGAGCATCGCCGACACCACCAACCAGAAGACCGAGCTGCAGGCCATCCACCTGGCCCTGCAGGAC
AGCGGCCTGGAGGTGAACATCGTGACCGACAGCCAGTACGCCCTGGGCATCATCCAGGCCCAGCCCGAC
AAGAGCGAGAGCGAGCTGGTGAGCCAGATCATCGAGCAGCTGATCAAGAAGGAGAAGGTGTACCTGGCC
TGGGTGCCCGCCCACAAGGGCATCGGCGGCAACGAGCAGGTGGACAAGCTGGTGAGCGCCGGCATCCGC
AAGGTGCTGgaattcGAGCCCGTGGACCCCGCCTGGAGCCCTGGAAGCACCCCGGCAGCCAGCCCAAG
ACCGCCTGCACCAACTGCTACTGCAAGAAGTGCTGCTTCCACTGCCAGGTGTGCTTCATCACCAAGGGC
CTGGGCATCAGCTACGGCCGCAAGAAGCGCCGCCAGCGCCGCCGCGCCCCCCCCGACAGCGAGGTGCAC
CAGGTGAGCCTGCCCAAGCAGCCCGCCAGCCAGCCCCAGGGCGACCCCACCGGCCCCAAGGAGAGCAAG
AAGAAGGTGGAGCGCGAGACCGAGACCGACCCCGTGCACCCCGGGCCGGCCGCAGCGGCGACAGCGAC
GAGGAGCTGCTGCAGACCGTGCGCTTCATCAAGTTCCTGTACCAGAGCAACCCCCTGCCCAGCCCCAAG
GGCACCCGCCAGGCCGCCGCAACCGCCGCCGCCGCTGGCGCGAGCGCCAGCGCCAGATCCAGAGCATC
AGCGCCTGGATCATCAGCACCCACCTGGGCCGCAGCACCGAGCCCGTGCCCCTGCAGCTGCCCCCCCTG
GAGCGCCTGAACCTGGACTGCAGCGAGGACTGCGGCACCAGCGGCACCCAGGGCGTGGGCAGCCCCCAG
GTGCTGGGCGAGAGCCCCGCCGTGCTGGACAGCGGCACCAAGGAGCTCGAGGGCGGCAAGTGGAGCAAG
CGCATGAGCGGCTGGAGCGCCGTGCGCGAGCGCATGAAGCGCGCCGAGCCCGCCGAGCCCGCCGCCGAC
GGCGTGGGCGCCGTGAGCCGCGACCTGGAGAAGCACGGCGCCATCACCAGCAGCAACACCGCCGCCAAC
AACGCCGACTGCGCCTGGCTGGAGGCCCAGGAGGACGAGGACGTGGGCTTCCCCGTGCGCCCCCAGGTG
CCCCTGCGCCCCATGACCTACAAGGCCGCCCTGGACCTGAGCCACTTCCTGAAGGAGAAGGGCGGCCTG
GAGGGCCTGATCTACAGCCAGAAGCGCCAGGACATCCTGGACCTGTGGATCCACCACACCCAGGGCTAC
TTCCCCGACTGGCAGAACTACACCCCCGGCCCCGGCATCCGCTACCCCCTGACCTTCGGCTGGTGCTTC
AAGCTGGTGCCCGTGGACCCCGACTACGTGGAGGAGGCCAACGCCGGCGAGAACAACAGCCTGCTGCAC
CCCATGAGCCAGCACGGCATGGACGACCCCGAGAAGGAGGTGCTGGTGTGGCGCTTCGACAGCCGCCTG
GCCTTCCACCACATGGCCCGCGAGCTGCACCCCGAGTACTACAAGGACTGC
```

p2PolTatRevNef.opt_B

```
GCCACCATGGCCGAGGCGATGAGCCAGGTGACGAACCCGGCGACCATCATGATGCAGCGCGGCAACTTC
CGCAACCAGCGGAAGACCGTCAAGTGCTTCAACTGCGGCAAGGAGGGCCACACCGCCAGGAACTGCCGC
GCCCCCCGCAAGAAGGGCTGCTGGCGCTGCGGCCGCGAAGGACACCAAATGAAAGATTGCACTGAGAGA
CAGGCTAATTTCTTCCGCGAGGACCTGGCCTTCCTGCAGGGCAAGGCCCGCGAGTTCAGCAGCGAGCAG
ACCCGCGCCAACAGCCCCACCCGCCGCGAGCTGCAGGTGTGGGGCGGCGAGAACAACAGCCTGAGCGAG
GCCGGCGCCGACCGCCAGGGCACCGTGAGCTTCAACTTCCCCCAGATCACCCTGTGGCAGCGCCCCCTG
GTGACCATCAGGATCGGCGGCCAGCTCAAGGAGGCGCTGCTCGCCACCGGCGCCGACGACACCGTGCTG
GAGGAGATGAACCTGCCCGGCAAGTGGAAGCCCAAGATGATCGGCGGGATCGGGGGCTTCATCAAGGTG
CGGCAGTACGACCAGATCCCCGTGGAGATCTGCGGCCACAAGGCCATCGGCACCGTGCTGGTGGGCCCC
ACCCCCGTGAACATCATCGGCCGCAACCTGCTGACCCAGATCGGCTGCACCCTGAACTTCCCCATCAGC
CCCATCGAGACGGTGCCCGTGAAGCTGAAGCCGGGGATGGACGGCCCCAAGGTCAAGCAGTGGCCCCTG
ACCGAGGAGAAGATCAAGGCCCTGGTGGAGATCTGCACCGAGATGGAGAAGGAGGGCAAGATCAGCAAG
ATCGGCCCCGAGAACCCCTACAACACCCCCGTGTTCGCCATCAAGAAGAAGGACAGCACCAAGTGGCGC
AAGCTGGTGGACTTCCGCGAGCTGAACAAGCGCACCCAGGACTTCTGGGAGGTGCAGCTGGGCATCCCC
CACCCCGCCGGCCTGAAGAAGAAGAAGAGCGTGACCGTGCTGGACGTGGGCGACGCCTACTTCAGCGTG
CCCCTGGACAAGGACTTCCGCAAGTACACCGCCTTCACCATCCCCAGCATCAACAACGAGACCCCCGGC
ATCCGCTACCAGTACAACGTGCTGCCCCAGGGCTGGAAGGGCAGCCCCGCCATCTTCCAGAGCAGCATG
ACCAAGATCCTGGAGCCCTTCCGCAAGCAGAACCCCGACATCGTGATCTACCAGGCCCCCCTGTACGTG
GGCAGCGACCTGGAGATCGGCCAGCACCGCACCAAGATCGAGGAGCTGCGCCAGCACCTGCTGCGCTGG
GGCTTCACCACCCCCGACAAGAAGCACCAGAAGGAGCCCCCCTTCCTGCCCATCGAGCTGCACCCCGAC
AAGTGGACCGTGCAGCCCATCATGCTGCCCGAGAAGGACAGCTGGACCGTGAACGACATCCAGAAGCTG
GTGGGCAAGCTGAACTGGGCCAGCCAGATCTACGCCGGCATCAAGGTGAAGCAGCTGTGCAAGCTGCTG
CGCGGCACCAAGGCCCTGACCGAGGTGATCCCCCTGACCGAGGAGGCCGAGCTGGAGCTGGCCGAGAAC
CGCGAGATCCTGAAGGAGCCCGTGCACGAGGTGTACTACGACCCCAGCAAGGACCTGGTGGCCGAGATC
CAGAAGCAGGGCCAGGGCCAGTGGACCTACCAGATCTACCAGGAGCCCTTCAAGAACCTGAAGACCGGC
AAGTACGCCCGCATGCGCGGCGCCCACACCAACGACGTGAAGCAGCTGACCGAGGCCGTGCAGAAGGTG
AGCACCGAGAGCATCGTGATCTGGGGCAAGATCCCCAAGTTCAAGCTGCCCATCCAGAAGGAGACCTGG
GAGGCCTGGTGGATGGAGTACTGGCAGGCCACCTGGATCCCCGAGTGGGAGTTCGTGAACACCCCCCCC
CTGGTGAAGCTGTGGTACCAGCTGGAGAAGGAGCCCATCGTGGGCGCCGAGACCTTCTACGTGGACGGC
GCCGCCAACCGCGAGACCAAGCTGGGCAAGGCCGGCTACGTGACCGACCGGGGCCGGCAGAAGGTGGTG
AGCATCGCCGACACCACCAACCAGAAGACCGAGCTGCAGGCCATCCACCTGGCCCTGCAGGACAGCGGC
CTGGAGGTGAACATCGTGACCGACAGCCAGTACGCCCTGGGCATCATCCAGGCCCAGCCCGACAAGAGC
GAGAGCGAGCTGGTGAGCCAGATCATCGAGCAGCTGATCAAGAAGGAGAAGGTGTACCTGGCCTGGGTG
CCCGCCCACAAGGGCATCGGCGGCAACGAGCAGGTGGACAAGCTGGTGAGCGCCGGCATCCGCAAGGTG
CTGTTCCTGAACGGCATCGATGGCGGCATCGTGATCTACCAGTACATGGACGACCTGTACGTGGGCAGC
GGCGGCCCTAGGGAGCCCGTGGACCCCGCCTGGAGCCCTGGAAGCACCCCGGCAGCCAGCCCAAGACC
GCCGGCACCAACTGCTACTGCAAGAAGTGCTGCTTCCACTGCCAGGTGAGCTTCATCACCAAGGGCCTG
GGCATCAGCTACGGCCGCAAGAAGCGCCGCAGCGCCGCCGCCCCCCCGACAGCGAGGTGCACCAG
GTGAGCCTGCCCAAGCAGCCCGCCAGCCAGCCCCAGGGCGACCCCACCGGCCCCAAGGAGAGCAAGAAG
AAGGTGGAGCGCGAGACCGAGACCGACCCCGTGCACCCCGGGGCCGGCCGCAGCGGCGACAGCGACGAG
GAGCTGCTGCAGACCGTGCGCTTCATCAAGTTCCTGTACCAGAGCAACCCCCTGCCCAGCCCCAAGGGC
ACCCGCCAGGCCGACCTGAACCGCCGCCGCCGCTGGCGCGAGCGCCAGCGCCAGATCCAGAGCATCAGC
GCCTGGATCATCAGCACCCACCTGGGCCGCAGCACCGAGCCCGTGCCCCTGCAGCTGCCCCCCGACCTG
CGCCTGAACCTGGACTGCAGCGAGGACTGCGGCACCAGCGGCACCCAGGGCGTGGGCAGCCCCCAGGTG
CTGGGCGAGAGCCCCGCCGTGCTGGACAGCGGCACCAAGGAGCTCGAGGCCGGCAAGTGGAGCAAGCGC
ATGAGCGGCTGGAGCGCCGTGCGCGAGCGCATGAAGCGCGCCGAGCCCGCCGAGCCCGCCGCCGACGGC
GTGGGCGCCGTGAGCCGCGACCTGGAGAAGCACGGCGCCATCACCAGCAGCAACACCGCCGCCAACAAC
GCCGACTGCGCCTGGCTGGAGGCCCAGGAGGACGAGGACGTGGGCTTCCCCGTGCGCCCCCAGGTGCCC
CTGCGCCCCATGACCTACAAGGCCGCCCTGGACCTGAGCCACTTCCTGAAGGAGAAGGGCGGCCTGGAG
GGCCTGATCTACAGCCAGAAGCGCCAGGACATCCTGGACCTGTGGATCCACCACACCCAGGGCTACTTC
CCCGGCTGGCAGAACTACACCCCCGGCCCCGGCATCCGCTACCCCCTGACCTTCGGCTGGTGCTTCAAG
CTGGTGCCCGTGGACCCCGACTACGTGGAGGAGGCCAACGCCGGCGAGAACAACAGCCTGCTGCACCCC
ATGAGCCAGCACGGCATGGACGACCCCGAGAAGGAGGTGCTGGTGTGGCGCTTCGACAGCCGCCTGGCC
```

TTCCACCACATGGCCCGCGAGCTGCACCCCGAGTACTACAAGGACTGCGATTAAAAGCTTCCCGGGGCT
AGCACCGGT

Figure 32 pol.opt.SF2 (native, start at p6Pol until 6aa Integrase)

```
TTCTTCCGCGAGGACCTGGCCTTCCTGCAGGGCAAGGCCCGCGAGTTCAGCAGCGAGCAGACCCGCGCC
AACAGCCCCACCCGCCGCGAGCTGCAGGTGTGGGGCGGCGAGAACAACAGCCTGAGCGAGGCCGGCGCC
GACCGCCAGGGCACCGTGAGCTTCAACTTCCCCCAGATCACCCTGTGGCAGCGCCCCCTGGTGACCATC
AGGATCGGCGGCCAGCTCAAGGAGGCGCTGCTCGACACCGGCGCCGACGACACCGTGCTGGAGGAGATG
AACCTGCCCGGCAAGTGGAAGCCCAAGATGATCGGCGGGATCGGGGGCTTCATCAAGGTGCGGCAGTAC
GACCAGATCCCCGTGGAGATCTGCGGCCACAAGGCCATCGGCACCGTGCTGGTGGGCCCCACCCCCGTG
AACATCATCGGCCGCAACCTGCTGACCCAGATCGGCTGCACCCTGAACTTCCCCATCAGCCCCATCGAG
ACGGTGCCCGTGAAGCTGAAGCCGGGGATGGACGGCCCCAAGGTCAAGCAGTGGCCCCTGACCGAGGAG
AAGATCAAGGCCCTGGTGGAGATCTGCACCGAGATGGAGAAGGAGGGCAAGATCAGCAAGATCGGCCCC
GAGAACCCCTACAACACCCCCGTGTTCGCCATCAAGAAGAAGGACAGCACCAAGTGGCGCAAGCTGGTG
GACTTCCGCGAGCTGAACAAGCGCACCCAGGACTTCTGGGAGGTGCAGCTGGGCATCCCCACCCCGCC
GGCCTGAAGAAGAAGAAGAGCGTGACCGTGCTGGACGTGGGCGACGCCTACTTCAGCGTGCCCCTGGAC
AAGGACTTCCGCAAGTACACCGCCTTCACCATCCCCAGCATCAACAACGAGACCCCCGGCATCCGCTAC
CAGTACAACGTGCTGCCCCAGGGCTGGAAGGGCAGCCCCGCCATCTTCCAGAGCAGCATGACCAAGATC
CTGGAGCCCTTCCGCAAGCAGAACCCCGACATCGTGATCTACCAGTACATGGACGACCTGTACGTGGGC
AGCGACCTGGAGATCGGCCAGCACCGCACCAAGATCGAGGAGCTGCGCCAGCACCTGCTGCGCTGGGGC
TTCACCACCCCCGACAAGAAGCACCAGAAGGAGCCCCCCTTCCTGTGGATGGGCTACGAGCTGCACCCC
GACAAGTGGACCGTGCAGCCCATCATGCTGCCCGAGAAGGACAGCTGGACCGTGAACGACATCCAGAAG
CTGGTGGGCAAGCTGAACTGGGCCAGCCAGATCTACGCCGGCATCAAGGTGAAGCAGCTGTGCAAGCTG
CTGCGCGGCACCAAGGCCCTGACCGAGGTGATCCCCCTGACCGAGGAGGCCGAGCTGGAGCTGGCCGAG
AACCGCGAGATCCTGAAGGAGCCCGTGCACGAGGTGTACTACGACCCCAGCAAGGACCTGGTGGCCGAG
ATCCAGAAGCAGGGCCAGGGCCAGTGGACCTACCAGATCTACCAGGAGCCCTTCAAGAACCTGAAGACC
GGCAAGTACGCCCGCATGCGCGGCGCCCACACCAACGACGTGAAGCAGCTGACCGAGGCCGTGCAGAAG
GTGAGCACCGAGAGCATCGTGATCTGGGGCAAGATCCCCAAGTTCAAGCTGCCCATCCAGAAGGAGACC
TGGGAGGCCTGGTGGATGGAGTACTGGCAGGCCACCTGGATCCCCGAGTGGGAGTTCGTGAACACCCCC
CCCCTGGTGAAGCTGTGGTACCAGCTGGAGAAGGAGCCCATCGTGGGCGCCGAGACCTTCTACGTGGAC
GGCGCCGCCAACCGCGAGACCAAGCTGGGCAAGGCCGGCTACGTGACCGACCGGGGCCGGCAGAAGGTG
GTGAGCATCGCCGACACCACCAACCAGAAGACCGAGCTGCAGGCCATCCACCTGGCCCTGCAGGACAGC
GGCCTGGAGGTGAACATCGTGACCGACAGCCAGTACGCCCTGGGCATCATCCAGGCCCAGCCCGACAAG
AGCGAGAGCGAGCTGGTGAGCCAGATCATCGAGCAGCTGATCAAGAAGGAGAAGGTGTACCTGGCCTGG
GTGCCCGCCCACAAGGGCATCGGCGGCAACGAGCAGGTGGACAAGCTGGTGAGCGCCGGCATCCGCAAG
GTGCTG
```

Figure 33 prot.opt.SF2 (native):

CCCCAGATCACCCTGTGGCAGCGCCCCCTGGTGACCATCAGGATCGGCGGCCAGCTCAAGGAGGCGCTG
CTCGACACCGGCGCCGACGACACCGTGCTGGAGGAGATGAACCTGCCCGGCAAGTGGAAGCCCAAGATG
ATCGGCGGGATCGGGGGCTTCATCAAGGTGCGGCAGTACGACCAGATCCCCGTGGAGATCTGCGGCCAC
AAGGCCATCGGCACCGTGCTGGTGGGCCCCACCCCCGTGAACATCATCGGCCGCAACCTGCTGACCCAG
ATCGGCTGCACCCTGAACTTC

Figure 34 protIna.opt.SF2 (mutant, Protease non-functional):

```
CCCCAGATCACCCTGTGGCAGCGCCCCCTGGTGACCATCAGGATCGGCGGCCAGCTCAAGGAGGCGCTG
CTCGCCACCGGCGCCGACGACACCGTGCTGGAGGAGATGAACCTGCCCGGCAAGTGGAAGCCCAAGATG
ATCGGCGGGATCGGGGGCTTCATCAAGGTGCGGCAGTACGACCAGATCCCCGTGGAGATCTGCGGCCAC
AAGGCCATCGGCACCGTGCTGGTGGGCCCCACCCCCGTGAACATCATCGGCCGCAACCTGCTGACCCAG
ATCGGCTGCACCCTGAACTTC
```

Figure 35 protInaRT.YM.opt.SF2

CCCCAGATCACCCTGTGGCAGCGCCCCCTGGTGACCATCAGGATCGGCGGCCAGCTCAAGGAGGCGCTG
CTCGCCACCGGCGCCGACGACACCGTGCTGGAGGAGATGAACCTGCCCGGCAAGTGGAAGCCCAAGATG
ATCGGCGGGATCGGGGGCTTCATCAAGGTGCGGCAGTACGACCAGATCCCCGTGGAGATCTGCGGCCAC
AAGGCCATCGGCACCGTGCTGGTGGGCCCCACCCCCGTGAACATCATCGGCCGCAACCTGCTGACCCAG
ATCGGCTGCACCCTGAACTTCCCCATCAGCCCCATCGAGACGGTGCCCGTGAAGCTGAAGCCGGGGATG
GACGGCCCCAAGGTCAAGCAGTGGCCCCTGACCGAGGAGAAGATCAAGGCCCTGGTGGAGATCTGCACC
GAGATGGAGAAGGAGGGCAAGATCAGCAAGATCGGCCCCGAGAACCCCTACAACACCCCCGTGTTCGCC
ATCAAGAAGAAGGACAGCACCAAGTGGCGCAAGCTGGTGGACTTCCGCGAGCTGAACAAGCGCACCCAG
GACTTCTGGGAGGTGCAGCTGGGCATCCCCCACCCCGCCGGCCTGAAGAAGAAGAAGAGCGTGACCGTG
CTGGACGTGGGCGACGCCTACTTCAGCGTGCCCCTGGACAAGGACTTCCGCAAGTACACCGCCTTCACC
ATCCCCAGCATCAACAACGAGACCCCCGGCATCCGCTACCAGTACAACGTGCTGCCCCAGGGCTGGAAG
GGCAGCCCCGCCATCTTCCAGAGCAGCATGACCAAGATCCTGGAGCCCTTCCGCAAGCAGAACCCCGAC
ATCGTGATCTACCAGGCCCCCCTGTACGTGGGCAGCGACCTGGAGATCGGCCAGCACCGCACCAAGATC
GAGGAGCTGCGCCAGCACCTGCTGCGCTGGGGCTTCACCACCCCCGACAAGAAGCACCAGAAGGAGCCC
CCCTTCCTGTGGATGGGCTACGAGCTGCACCCCGACAAGTGGACCGTGCAGCCCATCATGCTGCCCGAG
AAGGACAGCTGGACCGTGAACGACATCCAGAAGCTGGTGGGCAAGCTGAACTGGGCCAGCCAGATCTAC
GCCGGCATCAAGGTGAAGCAGCTGTGCAAGCTGCTGCGCGGCACCAAGGCCCTGACCGAGGTGATCCCC
CTGACCGAGGAGGCCGAGCTGGAGCTGGCCGAGAACCGCGAGATCCTGAAGGAGCCCGTGCACGAGGTG
TACTACGACCCCAGCAAGGACCTGGTGGCCGAGATCCAGAAGCAGGGCCAGGGCCAGTGGACCTACCAG
ATCTACCAGGAGCCCTTCAAGAACCTGAAGACCGGCAAGTACGCCCGCATGCGCGGCGCCCACACCAAC
GACGTGAAGCAGCTGACCGAGGCCGTGCAGAAGGTGAGCACCGAGAGCATCGTGATCTGGGGCAAGATC
CCCAAGTTCAAGCTGCCCATCCAGAAGGAGACCTGGGAGGCCTGGTGGATGGAGTACTGGCAGGCCACC
TGGATCCCCGAGTGGGAGTTCGTGAACACCCCCCCCTGGTGAAGCTGTGGTACCAGCTGGAGAAGGAG
CCCATCGTGGGCGCCGAGACCTTCTACGTGGACGGCGCCGCCAACCGCGAGACCAAGCTGGGCAAGGCC
GGCTACGTGACCGACCGGGGCCGGCAGAAGGTGGTGAGCATCGCCGACACCACCAACCAGAAGACCGAG
CTGCAGGCCATCCACCTGGCCCTGCAGGACAGCGGCCTGGAGGTGAACATCGTGACCGACAGCCAGTAC
GCCCTGGGCATCATCCAGGCCCAGCCCGACAAGAGCGAGAGCGAGCTGGTGAGCCAGATCATCGAGCAG
CTGATCAAGAAGGAGAAGGTGTACCTGGCCTGGGTGCCCGCCCACAAGGGCATCGGCGGCAACGAGCAG
GTGGACAAGCTGGTGAGCGCCGGCATCCGCAAGGTGCTG

Figure 36 protInaRT.YMWM.opt.SF2

CCCCAGATCACCCTGTGGCAGCGCCCCCTGGTGACCATCAGGATCGGCGGCCAGCTCAAGGAGGCGCTG
CTCGCCACCGGCGCCGACGACACCGTGCTGGAGGAGATGAACCTGCCCGGCAAGTGGAAGCCCAAGATG
ATCGGCGGGATCGGGGGCTTCATCAAGGTGCGGCAGTACGACCAGATCCCCGTGGAGATCTGCGGCCAC
AAGGCCATCGGCACCGTGCTGGTGGGCCCCACCCCCGTGAACATCATCGGCCGCAACCTGCTGACCCAG
ATCGGCTGCACCCTGAACTTCCCCCAGATCACCCTGTGGCAGCGCCCCCTGGTGACCATCAGGATCGGC
GGCCAGCTCAAGGAGGCGCTGCTCGACACCGGCGCCGACGACACCGTGCTGGAGGAGATGAACCTGCCC
GGCAAGTGGAAGCCCAAGATGATCGGCGGGATCGGGGGCTTCATCAAGGTGCGGCAGTACGACCAGATC
CCCGTGGAGATCTGCGGCCACAAGGCCATCGGCACCGTGCTGGTGGGCCCCACCCCCGTGAACATCATC
GGCCGCAACCTGCTGACCCAGATCGGCTGCACCCTGAACTTCCCCATCAGCCCCATCGAGACGGTGCCC
GTGAAGCTGAAGCCGGGGATGGACGGCCCCAAGGTCAAGCAGTGGCCCCTGACCGAGGAGAAGATCAAG
GCCCTGGTGGAGATCTGCACCGAGATGGAGAAGGAGGGCAAGATCAGCAAGATCGGCCCCGAGAACCCC
TACAACACCCCCGTGTTCGCCATCAAGAAGAAGGACAGCACCAAGTGGCGCAAGCTGGTGGACTTCCGC
GAGCTGAACAAGCGCACCCAGGACTTCTGGGAGGTGCAGCTGGGCATCCCCCACCCCGCCGGCCTGAAG
AAGAAGAAGAGCGTGACCGTGCTGGACGTGGGCGACGCCTACTTCAGCGTGCCCCTGGACAAGGACTTC
CGCAAGTACACCGCCTTCACCATCCCCAGCATCAACAACGAGACCCCCGGCATCCGCTACCAGTACAAC
GTGCTGCCCCAGGGCTGGAAGGGCAGCCCCGCCATCTTCCAGAGCAGCATGACCAAGATCCTGGAGCCC
TTCCGCAAGCAGAACCCCGACATCGTGATCTACCAGGCCCCCCTGTACGTGGGCAGCGACCTGGAGATC
GGCCAGCACCGCACCAAGATCGAGGAGCTGCGCCAGCACCTGCTGCGCTGGGGCTTCACCACCCCCGAC
AAGAAGCACCAGAAGGAGCCCCCCTTCCTGCCCATCGAGCTGCACCCCGACAAGTGGACCGTGCAGCCC
ATCATGCTGCCCGAGAAGGACAGCTGGACCGTGAACGACATCCAGAAGCTGGTGGGCAAGCTGAACTGG
GCCAGCCAGATCTACGCCGGCATCAAGGTGAAGCAGCTGTGCAAGCTGCTGCGCGGCACCAAGGCCCTG
ACCGAGGTGATCCCCCTGACCGAGGAGGCCGAGCTGGAGCTGGCCGAGAACCGCGAGATCCTGAAGGAG
CCCGTGCACGAGGTGTACTACGACCCCAGCAAGGACCTGGTGGCCGAGATCCAGAAGCAGGGCCAGGGC
CAGTGGACCTACCAGATCTACCAGGAGCCCTTCAAGAACCTGAAGACCGGCAAGTACGCCCGCATGCGC
GGCGCCCACACCAACGACGTGAAGCAGCTGACCGAGGCCGTGCAGAAGGTGAGCACCGAGAGCATCGTG
ATCTGGGGCAAGATCCCCAAGTTCAAGCTGCCCATCCAGAAGGAGACCTGGGAGGCCTGGTGGATGGAG
TACTGGCAGGCCACCTGGATCCCCGAGTGGGAGTTCGTGAACACCCCCCCCCTGGTGAAGCTGTGGTAC
CAGCTGGAGAAGGAGCCCATCGTGGGCGCCGAGACCTTCTACGTGGACGGCGCCGCCAACCGCGAGACC
AAGCTGGGCAAGGCCGGCTACGTGACCGACCGGGGCCGGCAGAAGGTGGTGAGCATCGCCGACACCACC
AACCAGAAGACCGAGCTGCAGGCCATCCACCTGGCCCTGCAGGACAGCGGCCTGGAGGTGAACATCGTG
ACCGACAGCCAGTACGCCCTGGGCATCATCCAGGCCCAGCCCGACAAGAGCGAGAGCGAGCTGGTGAGC
CAGATCATCGAGCAGCTGATCAAGAAGGAGAAGGTGTACCTGGCCTGGGTGCCCGCCCACAAGGGCATC
GGCGGCAACGAGCAGGTGGACAAGCTGGTGAGCGCCGGCATCCGCAAGGTGCTG

Figure 37

ProtInaRTmut.SF2 (Protease inactive, RT mutated)

GTCGACGCCACCATGCCCCAGATCACCCTGTGGCAGCGCCCCCTGGTGAC
CATCAGGATCGGCGGCCAGCTCAAGGAGGCGCTGCTCGCCACCGGCGCCG
ACGACACCGTGCTGGAGGAGATGAACCTGCCCGGCAAGTGGAAGCCCAA
GATGATCGGCGGGATCGGGGGCTTCATCAAGGTGCGGCAGTACGACCAGA
TCCCCGTGGAGATCTGCGGCCACAAGGCCATCGGCACCGTGCTGGTGGGC
CCCACCCCCGTGAACATCATCGGCCGCAACCTGCTGACCCAGATCGGCTG
CACCCTGAACTTCCCCATCAGCCCCATCGAGACGGTGCCCGTGAAGCTGA
AGCCGGGGATGGACGGCCCCAAGGTCAAGCAGTGGCCCCTGACCGAGGA
GAAGATCAAGGCCCTGGTGGAGATCTGCACCGAGATGGAGAAGGAGGGC
AAGATCAGCAAGATCGGCCCCGAGAACCCCTACAACACCCCCGTGTTCGC
CATCAAGAAGAAGGACAGCACCAAGTGGCGCAAGCTGGTGGACTTCCGC
GAGCTGAACAAGCGCACCCAGGACTTCTGGGAGGTGCAGCTGGGCATCCC
CCACCCCGCCGGCCTGAAGAAGAAGAAGAGCGTGACCGTGCTGGACGTG
GGCGACGCCTACTTCAGCGTGCCCTGGACAAGGACTTCCGCAAGTACAC
CGCCTTCACCATCCCCAGCATCAACAACGAGACCCCCGGCATCCGCTACC
AGTACAACGTGCTGCCCCAGGGCTGGAAGGGCAGCCCCGCCATCTTCCAG
AGCAGCATGACCAAGATCCTGGAGCCCTTCCGCAAGCAGAACCCCGACAT
CGTGATCTACCAGGCCCCCCTGTACGTGGGCAGCGACCTGGAGATCGGCC
AGCACCGCACCAAGATCGAGGAGCTGCGCCAGCACCTGCTGCGCTGGGGC
TTCACCACCCCCGACAAGAAGCACCAGAAGGAGCCCCCCTTCCTGCCCAT
CGAGCTGCACCCCGACAAGTGGACCGTGCAGCCCATCATGCTGCCCGAGA
AGGACAGCTGGACCGTGAACGACATCCAGAAGCTGGTGGGCAAGCTGAA
CTGGGCCAGCCAGATCTACGCCGGCATCAAGGTGAAGCAGCTGTGCAAGC
TGCTGCGCGGCACCAAGGCCCTGACCGAGGTGATCCCCCTGACCGAGGAG
GCCGAGCTGGAGCTGGCCGAGAACCGCGAGATCCTGAAGGAGCCCGTGC
ACGAGGTGTACTACGACCCCAGCAAGGACCTGGTGGCCGAGATCCAGAA
GCAGGGCCAGGGCCAGTGGACCTACCAGATCTACCAGGAGCCCTTCAAGA
ACCTGAAGACCGGCAAGTACGCCCGCATGCGCGGCGCCCACACCAACGAC
GTGAAGCAGCTGACCGAGGCCGTGCAGAAGGTGAGCACCGAGAGCATCG
TGATCTGGGGCAAGATCCCCAAGTTCAAGCTGCCCATCCAGAAGGAGACC
TGGGAGGCCTGGTGGATGGAGTACTGGCAGGCCACCTGGATCCCCGAGTG
GGAGTTCGTGAACACCCCCCCCTGGTGAAGCTGTGGTACCAGCTGGAGA
AGGAGCCCATCGTGGGCGCCGAGACCTTCTACGTGGACGGCGCCGCCAAC
CGCGAGACCAAGCTGGGCAAGGCCGGCTACGTGACCGACCGGGGCCGGC
AGAAGGTGGTGAGCATCGCCGACACCACCAACCAGAAGACCGAGCTGCA
GGCCATCCACCTGGCCCTGCAGGACAGCGGCCTGGAGGTGAACATCGTGA
CCGACAGCCAGTACGCCCTGGGCATCATCCAGGCCCAGCCCGACAAGAGC
GAGAGCGAGCTGGTGAGCCAGATCATCGAGCAGCTGATCAAGAAGGAGA
AGGTGTACCTGGCCTGGGTGCCCGCCCACAAGGGCATCGGCGGCAACGAG
CAGGTGGACAAGCTGGTGAGCGCCGGCATCCGCAAGGTGCTCTAAATCTA
GA

Figure 38 protRT.opt.SF2

CCCCAGATCACCCTGTGGCAGCGCCCCCTGGTGACCATCAGGATCGGCGGCCAGCTCAAGGAGGCGCTG
CTCGACACCGGCGCCGACGACACCGTGCTGGAGGAGATGAACCTGCCCGGCAAGTGGAAGCCCAAGATG
ATCGGCGGGATCGGGGGCTTCATCAAGGTGCGGCAGTACGACCAGATCCCCGTGGAGATCTGCGGCCAC
AAGGCCATCGGCACCGTGCTGGTGGGCCCCACCCCGTGAACATCATCGGCCGCAACCTGCTGACCCAG
ATCGGCTGCACCCTGAACTTCCCCATCAGCCCCATCGAGACGGTGCCCGTGAAGCTGAAGCCGGGGATG
GACGGCCCCAAGGTCAAGCAGTGGCCCCTGACCGAGGAGAAGATCAAGGCCCTGGTGGAGATCTGCACC
GAGATGGAGAAGGAGGGCAAGATCAGCAAGATCGGCCCCGAGAACCCCTACAACACCCCGTGTTCGCC
ATCAAGAAGAAGGACAGCACCAAGTGGCGCAAGCTGGTGGACTTCCGCGAGCTGAACAAGCGCACCCAG
GACTTCTGGGAGGTGCAGCTGGGCATCCCCACCCCGCCGGCCTGAAGAAGAAGAAGAGCGTGACCGTG
CTGGACGTGGGCGACGCCTACTTCAGCGTGCCCCTGGACAAGGACTTCCGCAAGTACACCGCCTTCACC
ATCCCCAGCATCAACAACGAGACCCCCGGCATCCGCTACCAGTACAACGTGCTGCCCCAGGGCTGGAAG
GGCAGCCCCGCCATCTTCCAGAGCAGCATGACCAAGATCCTGGAGCCCTTCCGCAAGCAGAACCCCGAC
ATCGTGATCTACCAGTACATGGACGACCTGTACGTGGGCAGCGACCTGGAGATCGGCCAGCACCGCACC
AAGATCGAGGAGCTGCGCCAGCACCTGCTGCGCTGGGGCTTCACCACCCCCGACAAGAAGCACCAGAAG
GAGCCCCCCTTCCTGTGGATGGGCTACGAGCTGCACCCCGACAAGTGGACCGTGCAGCCCATCATGCTG
CCCGAGAAGGACAGCTGGACCGTGAACGACATCCAGAAGCTGGTGGGCAAGCTGAACTGGGCCAGCCAG
ATCTACGCCGGCATCAAGGTGAAGCAGCTGTGCAAGCTGCTGCGCGGCACCAAGGCCCTGACCGAGGTG
ATCCCCCTGACCGAGGAGGCCGAGCTGGAGCTGGCCGAGAACCGCGAGATCCTGAAGGAGCCCGTGCAC
GAGGTGTACTACGACCCCAGCAAGGACCTGGTGGCCGAGATCCAGAAGCAGGGCCAGGGCCAGTGGACC
TACCAGATCTACCAGGAGCCCTTCAAGAACCTGAAGACCGGCAAGTACGCCCGCATGCGCGGCGCCCAC
ACCAACGACGTGAAGCAGCTGACCGAGGCCGTGCAGAAGGTGAGCACCGAGAGCATCGTGATCTGGGGC
AAGATCCCCAAGTTCAAGCTGCCCATCCAGAAGGAGACCTGGGAGGCCTGGTGGATGGAGTACTGGCAG
GCCACCTGGATCCCCGAGTGGGAGTTCGTGAACACCCCCCCCTGGTGAAGCTGTGGTACCAGCTGGAG
AAGGAGCCCATCGTGGGCGCCGAGACCTTCTACGTGGACGGCGCCGCCAACCGCGAGACCAAGCTGGGC
AAGGCCGGCTACGTGACCGACCGGGGCCGGCAGAAGGTGGTGAGCATCGCCGACACCACCAACCAGAAG
ACCGAGCTGCAGGCCATCCACCTGGCCCTGCAGGACAGCGGCCTGGAGGTGAACATCGTGACCGACAGC
CAGTACGCCCTGGGCATCATCCAGGCCCAGCCCGACAAGAGCGAGAGCGAGCTGGTGAGCCAGATCATC
GAGCAGCTGATCAAGAAGGAGAAGGTGTACCTGGCCTGGGTGCCCGCCCACAAGGGCATCGGCGGCAAC
GAGCAGGTGGACAAGCTGGTGAGCGCCGGCATCCGCAAGGTGCTG

Figure 39

ProtRT.TatRevNef.opt_B

```
ATGCCCCAGATCACCCTGTGGCAGCGCCCCCTGGTGACCATCAGGATCGGCGGCCAGCTCAAGGAGGCG
CTGCTCGCCACCGGCGCCGACGACACCGTGCTGGAGGAGATGAACCTGCCCGGCAAGTGGAAGCCCAAG
ATGATCGGCGGGATCGGGGGCTTCATCAAGGTGCGGCAGTACGACCAGATCCCCGTGGAGATCTGCGGC
CACAAGGCCATCGGCACCGTGCTGGTGGGCCCCACCCCCGTGAACATCATCGGCCGCAACCTGCTGACC
CAGATCGGCTGCACCCTGAACTTCCCCATCAGCCCCATCGAGACGGTGCCCGTGAAGCTGAAGCCGGGG
ATGGACGGCCCCAAGGTCAAGCAGTGGCCCCTGACCGAGGAGAAGATCAAGGCCCTGGTGGAGATCTGC
ACCGAGATGGAGAAGGAGGGCAAGATCAGCAAGATCGGCCCCGAGAACCCCTACAACACCCCCGTGTTC
GCCATCAAGAAGAAGGACAGCACCAAGTGGCGCAAGCTGGTGGACTTCCGCGAGCTGAACAAGCGCACC
CAGGACTTCTGGGAGGTGCAGCTGGGCATCCCCCACCCCGCCGGCCTGAAGAAGAAGAAGAGCGTGACC
GTGCTGGACGTGGGCGACGCCTACTTCAGCGTGCCCCTGGACAAGGACTTCCGCAAGTACACCGCCTTC
ACCATCCCCAGCATCAACAACGAGACCCCCGGCATCCGCTACCAGTACAACGTGCTGCCCCAGGGCTGG
AAGGGCAGCCCCGCCATCTTCCAGAGCAGCATGACCAAGATCCTGGAGCCCTTCCGCAAGCAGAACCCC
GACATCGTGATCTACCAGCCCCCTGTACGTGGGCAGCGACCTGGAGATCGGCCAGCACCGCACCAAG
ATCGAGGAGCTGCGCCAGCACCTGCTGCGCTGGGGCTTCACCACCCCCGACAAGAAGCACCAGAAGGAG
CCCCCCTTCCTGCCCCATCGAGCTGCACCCCGACAAGTGGACCGTGCAGCCCATCATGCTGCCCGAGAAG
GACAGCTGGACCGTGAACGACATCCAGAAGCTGGTGGGCAAGCTGAACTGGGCCAGCCAGATCTACGCC
GGCATCAAGGTGAAGCAGCTGTGCAAGCTGCTGCGCGGCACCAAGGCCCTGACCGAGGTGATCCCCCTG
ACCGAGGAGGCCGAGCTGGAGCTGGCCGAGAACCGCGAGATCCTGAAGGAGCCCGTGCACGAGGTGTAC
TACGACCCCAGCAAGGACCTGGTGGCCGAGATCCAGAAGCAGGGCCAGGGCCAGTGGACCTACCAGATC
TACCAGGAGCCCTTCAAGAACCTGAAGACCGGCAAGTACGCCCGCATGCGCGGCGCCCACACCAACGAC
GTGAAGCAGCTGACCGAGGCCGTGCAGAAGGTGAGCACCGAGAGCATCGTGATCTGGGGCAAGATCCCC
AAGTTCAAGCTGCCCATCCAGAAGGAGACCTGGGAGGCCTGGTGGATGGAGTACTGGCAGGCCACCTGG
ATCCCCGAGTGGGAGTTCGTGAACACCCCCCCCCTGGTGAAGCTGTGGTACCAGCTGGAGAAGGAGCCC
ATCGTGGGCGCCGAGACCTTCTACGTGGACGGCGCCGCCAACCGCGAGACCAAGCTGGGCAAGGCCGGC
TACGTGACCGACCGGGGCCGGCAGAAGGTGGTGAGCATCGCCGACACCACCAACCAGAAGACCGAGCTG
CAGGCCATCCACCTGGCCCTGCAGGACAGCGGCCTGGAGGTGAACATCGTGACCGACAGCCAGTACGCC
CTGGGCATCATCCAGGCCCAGCCCGACAAGAGCGAGAGCGAGCTGGTGAGCCAGATCATCGAGCAGCTG
ATCAAGAAGGAGAAGGTGTACCTGGCCTGGGTGCCCGCCCACAAGGGCATCGGCGGCAACGAGCAGGTG
GACAAGCTGGTGAGCGCCGGCATCCGCAAGGTGCTCGAATTCGAGCCCGTGGACCCCCGCCTGGAGCCC
TGGAAGCACCCCGGCAGCCAGCCCAAGACCGCCGGCACCAACTGCTACTGCAAGAAGTGCTGCTTCCAC
TGCCAGGTGAGCTTCATCACCAAGGGCCTGGGCATCAGCTACGGCCGCAAGAAGCGCCGCCAGCGCCGC
CGCGCCCCCCCGACAGCGAGGTGCACCAGGTGAGCCTGCCCAAGCAGCCCGCCAGCCAGCCCCAGGGC
GACCCCACCGGCCCCAAGGAGAGCAAGAAGAAGGTGGAGCGCGAGACCGAGACCGACCCCGTGCACCCC
GGGGCCGGCCGCAGCGGCGACAGCGACGAGGAGCTGCTGCAGACCGTGCGCTTCATCAAGTTCCTGTAC
CAGAGCAACCCCCTGCCCAGCCCCAAGGGCACCCGCCAGGCCGACCTGAACCGCCGCCGCCGCTGGCGC
GAGCGCCAGCGCCAGATCCAGAGCATCAGCGCCTGGATCATCAGCACCCACCTGGGCCGCAGCACCGAG
CCCGTGCCCCTGCAGCTGCCCCCGACCTGCGCCTGAACCTGGACTGCAGCGAGGACTGCGGCACCAGC
GGCACCCAGGGCGTGGGCAGCCCCCAGGTGCTGGGCGAGAGCCCCGCCGTGCTGGACAGCGGCACCAAG
GAGCTCGAGGCCGGCAAGTGGAGCAAGCGCATGAGCGGCTGGAGCGCCGTGCGCGAGCGCATGAAGCGC
GCCGAGCCCGCCGAGCCCGCCGCCGACGGCGTGGGCGCCGTGAGCCGCGACCTGGAGAAGCACGGCGCC
ATCACCAGCAGCAACACCGCCGCCAACAACGCCGACTGCGCCTGGCTGGAGGCCCAGGAGGACGAGGAC
GTGGGCTTCCCCGTGCGCCCCCAGGTGCCCCTGCGCCCCATGACCTACAAGGCCGCCCTGGACCTGAGC
CACTTCCTGAAGGAGAAGGGCGGCCTGGAGGGCCTGATCTACAGCCAGAAGCGCCAGGACATCCTGGAC
CTGTGGATCCACCACACCCAGGGCTACTTCCCCGGCTGGCAGAACTACACCCCCGGCCCCGGCATCCGC
TACCCCCTGACCTTCGGCTGGTGCTTCAAGCTGGTGCCCGTGGACCCCGACTACGTGGAGGAGGCCAAC
GCCGGCGAGAACAACAGCCTGCTGCACCCCATGAGCCAGCACGGCATGGACGACCCCGAGAAGGAGGTG
CTGGTGTGGCGCTTCGACAGCCGCCTGGCCTTCCACCACATGGCCCGCGAGCTGCACCCCGAGTACTAC
AAGGACTGC
```

Figure 40

ProtRTTatRevNef.opt_B

```
GCCACCATGCCCCAGATCACCCTGTGGCAGCGCCCCCTGGTGACCATCAGGATCGGCGGCCAGCTCAAG
GAGGCGCTGCTCGCCACCGGCGCCGACGACACCGTGCTGGAGGAGATGAACCTGCCCGGCAAGTGGAAG
CCCAAGATGATCGGCGGGATCGGGGGCTTCATCAAGGTGCGGCAGTACGACCAGATCCCCGTGGAGATC
TGCGGCCACAAGGCCATCGGCACCGTGCTGGTGGGCCCCACCCCCGTGAACATCATCGGCCGCAACCTG
CTGACCCAGATCGGCTGCACCCTGAACTTCCCCATCAGCCCCATCGAGACGGTGCCCGTGAAGCTGAAG
CCGGGGATGGACGGCCCCAAGGTCAAGCAGTGGCCCCTGACCGAGGAGAAGATCAAGGCCCTGGTGGAG
ATCTGCACCGAGATGGAGAAGGAGGGCAAGATCAGCAAGATCGGCCCCGAGAACCCCTACAACACCCCC
GTGTTCGCCATCAAGAAGAAGGACAGCACCAAGTGGCGCAAGCTGGTGGACTTCCGCGAGCTGAACAAG
CGCACCCAGGACTTCTGGGAGGTGCAGCTGGGCATCCCCCACCCCGCCGGCCTGAAGAAGAAGAAGAGC
GTGACCGTGCTGGACGTGGGCGACGCCTACTTCAGCGTGCCCCTGGACAAGGACTTCCGCAAGTACACC
GCCTTCACCATCCCCAGCATCAACAACGAGACCCCCGGCATCCGCTACCAGTACAACGTGCTGCCCCAG
GGCTGGAAGGGCAGCCCCGCCATCTTCCAGAGCAGCATGACCAAGATCCTGGAGCCCTTCCGCAAGCAG
AACCCCGACATCGTGATCTACCAGGCCCCCCTGTACGTGGGCAGCGACCTGGAGATCGGCCAGCACCGC
ACCAAGATCGAGGAGCTGCGCCAGCACCTGCTGCGCTGGGGCTTCACCACCCCCGACAAGAAGCACCAG
AAGGAGCCCCCCTTCCTGCCCATCGAGCTGCACCCCGACAAGTGGACCGTGCAGCCCATCATGCTGCCC
GAGAAGGACAGCTGGACCGTGAACGACATCCAGAAGCTGGTGGGCAAGCTGAACTGGGCCAGCCAGATC
TACGCCGGCATCAAGGTGAAGCAGCTGTGCAAGCTGCTGCGCGGCACCAAGGCCCTGACCGAGGTGATC
CCCCTGACCGAGGAGGCCGAGCTGGAGCTGGCCGAGAACCGCGAGATCCTGAAGGAGCCCGTGCACGAG
GTGTACTACGACCCCAGCAAGGACCTGGTGGCCGAGATCCAGAAGCAGGGCCAGGGCCAGTGGACCTAC
CAGATCTACCAGGAGCCCTTCAAGAACCTGAAGACCGGCAAGTACGCCCGCATGCGCGGCGCCCACACC
AACGACGTGAAGCAGCTGACCGAGGCCGTGCAGAAGGTGAGCACCGAGAGCATCGTGATCTGGGGCAAG
ATCCCCAAGTTCAAGCTGCCCATCCAGAAGGAGACCTGGGAGGCCTGGTGGATGGAGTACTGGCAGGCC
ACCTGGATCCCCGAGTGGGAGTTCGTGAACACCCCCCCCCTGGTGAAGCTGTGGTACCAGCTGGAGAAG
GAGCCCATCGTGGGCGCCGAGACCTTCTACGTGGACGGCGCCGCCAACCGCGAGACCAAGCTGGGCAAG
GCCGGCTACGTGACCGACCGGGGCCGGCAGAAGGTGGTGAGCATCGCCGACACCACCAACCAGAAGACC
GAGCTGCAGGCCATCCACCTGGCCCTGCAGGACAGCGGCCTGGAGGTGAACATCGTGACCGACAGCCAG
TACGCCCTGGGCATCATCCAGGCCCAGCCCGACAAGAGCGAGAGCGAGCTGGTGAGCCAGATCATCGAG
CAGCTGATCAAGAAGGAGAAGGTGTACCTGGCCTGGGTGCCCGCCCACAAGGGCATCGGCGGCAACGAG
CAGGTGGACAAGCTGGTGAGCGCCGGCATCCGCAAGGTGCTCGAATTCGAGCCCGTGGACCCCGCCTG
GAGCCCTGGAAGCACCCCGGCAGCCAGCCCAAGACCGCCGGCACCAACTGCTACTGCAAGAAGTGCTGC
TTCCACTGCCAGGTGAGCTTCATCACCAAGGGCCTGGGCATCAGCTACGGCCGCAAGAAGCGCCGCCAG
CGCCGCCGCGCCCCCCCCGACAGCGAGGTGCACCAGGTGAGCCTGCCCAAGCAGCCCGCCAGCCAGCCC
CAGGGCGACCCCACCGGCCCCAAGGAGAGCAAGAAGAAGGTGGAGCGCGAGACCGAGACCGACCCCGTG
CACCCCGGGGCCGGCCGCAGCGGCGACAGCGACGAGGAGCTGCTGCAGACCGTGCGCTTCATCAAGTTC
CTGTACCAGAGCAACCCCCTGCCCAGCCCCAAGGGCACCCGCCAGGCCGACCTGAACCGCCGCCGCCGC
TGGCGCGAGCGCCAGCGCCAGATCCAGAGCATCAGCGCCTGGATCATCAGCACCCACCTGGGCCGCAGC
ACCGAGCCCGTGCCCCTGCAGCTGCCCCCCGACCTGCGCCTGAACCTGGACTGCAGCGAGGACTGCGGC
ACCAGCGGCACCCAGGGCGTGGGCAGCCCCCAGGTGCTGGGCGAGAGCCCCGCCGTGCTGGACAGCGGC
ACCAAGGAGCTCGAGGCCGGCAAGTGGAGCAAGCGCATGAGCGGCTGGAGCGCCGTGCGCGAGCGCATG
AAGCGCGCCGAGCCCGCCGAGCCCGCCGCCGACGGCGTGGGCGCCGTGAGCCGCGACCTGGAGAAGCAC
GGCGCCATCACCAGCAGCAACACCGCCGCCAACAACGCCGACTGCGCCTGGCTGGAGGCCCAGGAGGAC
GAGGACGTGGGCTTCCCCGTGCGCCCCCAGGTGCCCCTGCGCCCCATGACCTACAAGGCCGCCCTGGAC
CTGAGCCACTTCCTGAAGGAGAAGGGCGGCCTGGAGGGCCTGATCTACAGCCAGAAGCGCCAGGACATC
CTGGACCTGTGGATCCACCACACCCAGGGCTACTTCCCCGGCTGGCAGAACTACACCCCCGGCCCCGGC
ATCCGCTACCCCCTGACCTTCGGCTGGTGCTTCAAGCTGGTGCCCGTGGACCCCGACTACGTGGAGGAG
GCCAACGCCGGCGAGAACAACAGCCTGCTGCACCCCATGAGCCAGCACGGCATGGACGACCCCGAGAAG
GAGGTGCTGGTGTGGCGCTTCGACAGCCGCCTGGCCTTCCACCACATGGCCCGCGAGCTGCACCCCGAG
TACTACAAGGACTGCGATTAA
```

Figure 41 rev.exon1_2.M5/10.opt.SF162

ATGGCCGGCCGCAGCGGCGACAGCGACGAGGAGCTGCTGCAGACCGTGCGCTTCATCAAGTTCCTGTAC
CAGAGCAACCCCCTGCCCAGCCCCAAGGGCACCCGCCAGGCCGACCTGAACCGCCGCCGCCGCTGGCGC
GAGCGCCAGCGCCAGATCCAGAGCATCAGCGCCTGGATCATCAGCACCCACCTGGGCCGCAGCACCGAG
CCCGTGCCCCTGCAGCTGCCCCCCGACCTGCGCCTGAACCTGGACTGCAGCGAGGACTGCGGCACCAGC
GGCACCCAGGGCGTGGGCAGCCCCCAGGTGCTGGGCGAGAGCCCCGCCGTGCTGGACAGCGGCACCAAG
GAG

Figure 42 rev.exon1_2.opt.SF162

ATGGCCGGCCGCAGCGGCGACAGCGACGAGGAGCTGCTGCAGACCGTGCGCTTCATCAAGTTCCTGTAC
CAGAGCAACCCCCTGCCCAGCCCCAAGGGCACCCGCCAGGCCCGCCGCAACCGCCGCCGCCGCTGGCGC
GAGCGCCAGCGCCAGATCCAGAGCATCAGCGCCTGGATCATCAGCACCCACCTGGGCCGCAGCACCGAG
CCCGTGCCCCTGCAGCTGCCCCCCCTGGAGCGCCTGAACCTGGACTGCAGCGAGGACTGCGGCACCAGC
GGCACCCAGGGCGTGGGCAGCCCCCAGGTGCTGGGCGAGAGCCCCGCCGTGCTGGACAGCGGCACCAAG
GAG

Figure 43

RT.opt.SF2 (mutant)

GCCACCATGCCCCAGATCACCCTGTGGCAGCGCCCCCTGGTGACCATCAGGATCGGCGGCCAGCTCAAG
GAGGCGCTGCTCGCCACCGGCGCCGACGACACCGTGCTGGAGGAGATGAACCTGCCCGGCAAGTGGAAG
CCCAAGATGATCGGCGGGATCGGGGGCTTCATCAAGGTGCGGCAGTACGACCAGATCCCCGTGGAGATC
TGCGGCCACAAGGCCATCGGCACCGTGCTGGTGGGCCCCACCCCCGTGAACATCATCGGCCGCAACCTG
CTGACCCAGATCGGCTGCACCCTGAACTTCCCCATCAGCCCCATCGAGACGGTGCCCGTGAAGCTGAAG
CCGGGGATGGACGGCCCCAAGGTCAAGCAGTGGCCCCTGACCGAGGAGAAGATCAAGGCCCTGGTGGAG
ATCTGCACCGAGATGGAGAAGGAGGGCAAGATCAGCAAGATCGGCCCCGAGAACCCCTACAACACCCCC
GTGTTCGCCATCAAGAAGAAGGACAGCACCAAGTGGCGCAAGCTGGTGGACTTCCGCGAGCTGAACAAG
CGCACCCAGGACTTCTGGGAGGTGCAGCTGGGCATCCCCACCCCGCCGGCCTGAAGAAGAAGAAGAGC
GTGACCGTGCTGGACGTGGGCGACGCCTACTTCAGCGTGCCCCTGGACAAGGACTTCCGCAAGTACACC
GCCTTCACCATCCCCAGCATCAACAACGAGACCCCCGGCATCCGCTACCAGTACAACGTGCTGCCCCAG
GGCTGGAAGGGCAGCCCCGCCATCTTCCAGAGCAGCATGACCAAGATCCTGGAGCCCTTCCGCAAGCAG
AACCCCGACATCGTGATCTACCAGGCCCCCTGTACGTGGGCAGCGACCTGGAGATCGGCCAGCACCGC
ACCAAGATCGAGGAGCTGCGCCAGCACCTGCTGCGCTGGGGCTTCACCACCCCCGACAAGAAGCACCAG
AAGGAGCCCCCCTTCCTGCCCATCGAGCTGCACCCCGACAAGTGGACCGTGCAGCCCATCATGCTGCCC
GAGAAGGACAGCTGGACCGTGAACGACATCCAGAAGCTGGTGGGCAAGCTGAACTGGGCCAGCCAGATC
TACGCCGGCATCAAGGTGAAGCAGCTGTGCAAGCTGCTGCGCGGCACCAAGGCCCTGACCGAGGTGATC
CCCCTGACCGAGGAGGCCGAGCTGGAGCTGGCCGAGAACCGCGAGATCCTGAAGGAGCCCGTGCACGAG
GTGTACTACGACCCCAGCAAGGACCTGGTGGCCGAGATCCAGAAGCAGGGCCAGGGCCAGTGGACCTAC
CAGATCTACCAGGAGCCCTTCAAGAACCTGAAGACCGGCAAGTACGCCCGCATGCGCGGCGCCCACACC
AACGACGTGAAGCAGCTGACCGAGGCCGTGCAGAAGGTGAGCACCGAGAGCATCGTGATCTGGGGCAAG
ATCCCCAAGTTCAAGCTGCCCATCCAGAAGGAGACCTGGGAGGCCTGGTGGATGGAGTACTGGCAGGCC
ACCTGGATCCCCGAGTGGGAGTTCGTGAACACCCCCCCCTGGTGAAGCTGTGGTACCAGCTGGAGAAG
GAGCCCATCGTGGGCGCCGAGACCTTCTACGTGGACGGCGCCGCCAACCGCGAGACCAAGCTGGGCAAG
GCCGGCTACGTGACCGACCGGGGCCGGCAGAAGGTGGTGAGCATCGCCGACACCACCAACCAGAAGACC
GAGCTGCAGGCCATCCACCTGGCCCTGCAGGACAGCGGCCTGGAGGTGAACATCGTGACCGACAGCCAG
TACGCCCTGGGCATCATCCAGGCCCAGCCCGACAAGAGCGAGAGCGAGCTGGTGAGCCAGATCATCGAG
CAGCTGATCAAGAAGGAGAAGGTGTACCTGGCCTGGGTGCCCGCCCACAAGGGCATCGGCGGCAACGAG
CAGGTGGACAAGCTGGTGAGCGCCGGCATCCGCAAGGTGCTCTAA

Figure 44

RT.opt.SF2 (native)

```
GCCACCATGCCCCAGATCACCCTGTGGCAGCGCCCCTGGTGACCATCAGGATCGGCGGCCAGCTCAAG
GAGGCGCTGCTCGACACCGGCGCCGACGACACCGTGCTGGAGGAGATGAACCTGCCCGGCAAGTGGAAG
CCCAAGATGATCGGCGGGATCGGGGGCTTCATCAAGGTGCGGCAGTACGACCAGATCCCCGTGGAGATC
TGCGGCCACAAGGCCATCGGCACCGTGCTGGTGGGCCCCACCCCCGTGAACATCATCGGCCGCAACCTG
CTGACCCAGATCGGCTGCACCCTGAACTTCCCCATCAGCCCCATCGAGACGGTGCCCGTGAAGCTGAAG
CCGGGGATGGACGGCCCCAAGGTCAAGCAGTGGCCCCTGACCGAGGAGAAGATCAAGGCCCTGGTGGAG
ATCTGCACCGAGATGGAGAAGGAGGGCAAGATCAGCAAGATCGGCCCCGAGAACCCCTACAACACCCCC
GTGTTCGCCATCAAGAAGAAGGACAGCACCAAGTGGCGCAAGCTGGTGGACTTCCGCGAGCTGAACAAG
CGCACCCAGGACTTCTGGGAGGTGCAGCTGGGCATCCCCCACCCCGCCGGCCTGAAGAAGAAGAAGAGC
GTGACCGTGCTGGACGTGGGCGACGCCTACTTCAGCGTGCCCCTGGACAAGGACTTCCGCAAGTACACC
GCCTTCACCATCCCCAGCATCAACAACGAGACCCCCGGCATCCGCTACCAGTACAACGTGCTGCCCCAG
GGCTGGAAGGGCAGCCCCGCCATCTTCCAGAGCAGCATGACCAAGATCCTGGAGCCCTTCCGCAAGCAG
AACCCCGACATCGTGATCTACCAGTACATGGACGACCTGTACGTGGGCAGCGACCTGGAGATCGGCCAG
CACCGCACCAAGATCGAGGAGCTGCGCCAGCACCTGCTGCGCTGGGGCTTCACCACCCCCGACAAGAAG
CACCAGAAGGAGCCCCCCTTCCTGTGGATGGGCTACGAGCTGCACCCCGACAAGTGGACCGTGCAGCCC
ATCATGCTGCCCGAGAAGGACAGCTGGACCGTGAACGACATCCAGAAGCTGGTGGGCAAGCTGAACTGG
GCCAGCCAGATCTACGCCGGCATCAAGGTGAAGCAGCTGTGCAAGCTGCTGCGCGGCACCAAGGCCCTG
ACCGAGGTGATCCCCCTGACCGAGGAGGCCGAGCTGGAGCTGGCCGAGAACCGCGAGATCCTGAAGGAG
CCCGTGCACGAGGTGTACTACGACCCCAGCAAGGACCTGGTGGCCGAGATCCAGAAGCAGGGCCAGGGC
CAGTGGACCTACCAGATCTACCAGGAGCCCTTCAAGAACCTGAAGACCGGCAAGTACGCCCGCATGCGC
GGCGCCCACACCAACGACGTGAAGCAGCTGACCGAGGCCGTGCAGAAGGTGAGCACCGAGAGCATCGTG
ATCTGGGGCAAGATCCCCAAGTTCAAGCTGCCCATCCAGAAGGAGACCTGGGAGGCCTGGTGGATGGAG
TACTGGCAGGCCACCTGGATCCCCGAGTGGGAGTTCGTGAACACCCCCCCCTGGTGAAGCTGTGGTAC
CAGCTGGAGAAGGAGCCCATCGTGGGCGCCGAGACCTTCTACGTGGACGGCGCCGCCAACCGCGAGACC
AAGCTGGGCAAGGCCGGCTACGTGACCGACGGGGCCGGCAGAAGGTGGTGAGCATCGCCGACACCACC
AACCAGAAGACCGAGCTGCAGGCCATCCACCTGGCCCTGCAGGACAGCGGCCTGGAGGTGAACATCGTG
ACCGACAGCCAGTACGCCCTGGGCATCATCCAGGCCCAGCCCGACAAGAGCGAGAGCGAGCTGGTGAGC
CAGATCATCGAGCAGCTGATCAAGAAGGAGAAGGTGTACCTGGCCTGGGTGCCCGCCCACAAGGGCATC
GGCGGCAACGAGCAGGTGGACAAGCTGGTGAGCGCCGGCATCCGCAAGGTGCTGTAA
```

Figure 45

RTmut.SF2 (RT mutated)

GTCGACGCCACCATGCCCATCAGCCCCATCGAGACGGTGCCCGTGAAGCT
GAAGCCGGGGATGGACGGCCCCAAGGTCAAGCAGTGGCCCCTGACCGAG
GAGAAGATCAAGGCCCTGGTGGAGATCTGCACCGAGATGGAGAAGGAGG
GCAAGATCAGCAAGATCGGCCCCGAGAACCCCTACAACACCCCCGTGTTC
GCCATCAAGAAGAAGGACAGCACCAAGTGGCGCAAGCTGGTGGACTTCC
GCGAGCTGAACAAGCGCACCCAGGACTTCTGGGAGGTGCAGCTGGGCATC
CCCCACCCCGCCGGCCTGAAGAAGAAGAAGAGCGTGACCGTGCTGGACGT
GGGCGACGCCTACTTCAGCGTGCCCTGGACAAGGACTTCCGCAAGTACA
CCGCCTTCACCATCCCCAGCATCAACAACGAGACCCCCGGCATCCGCTAC
CAGTACAACGTGCTGCCCCAGGGCTGGAAGGGCAGCCCCGCCATCTTCCA
GAGCAGCATGACCAAGATCCTGGAGCCCTTCCGCAAGCAGAACCCCGACA
TCGTGATCTACCAGGCCCCCTGTACGTGGGCAGCGACCTGGAGATCGGC
CAGCACCGCACCAAGATCGAGGAGCTGCGCCAGCACCTGCTGCGCTGGGG
CTTCACCACCCCCGACAAGAAGCACCAGAAGGAGCCCCCCTTCCTGCCCA
TCGAGCTGCACCCCGACAAGTGGACCGTGCAGCCCATCATGCTGCCCGAG
AAGGACAGCTGGACCGTGAACGACATCCAGAAGCTGGTGGGCAAGCTGA
ACTGGGCCAGCCAGATCTACGCCGGCATCAAGGTGAAGCAGCTGTGCAAG
CTGCTGCGCGGCACCAAGGCCCTGACCGAGGTGATCCCCCTGACCGAGGA
GGCCGAGCTGGAGCTGGCCGAGAACCGCGAGATCCTGAAGGAGCCCGTG
CACGAGGTGTACTACGACCCCAGCAAGGACCTGGTGGCCGAGATCCAGAA
GCAGGGCCAGGGCCAGTGGACCTACCAGATCTACCAGGAGCCCTTCAAGA
ACCTGAAGACCGGCAAGTACGCCCGCATGCGCGGCGCCCACACCAACGAC
GTGAAGCAGCTGACCGAGGCCGTGCAGAAGGTGAGCACCGAGAGCATCG
TGATCTGGGGCAAGATCCCCAAGTTCAAGCTGCCCATCCAGAAGGAGACC
TGGGAGGCCTGGTGGATGGAGTACTGGCAGGCCACCTGGATCCCCGAGTG
GGAGTTCGTGAACACCCCCCCCTGGTGAAGCTGTGGTACCAGCTGGAGA
AGGAGCCCATCGTGGGCGCCGAGACCTTCTACGTGGACGGCGCCGCCAAC
CGCGAGACCAAGCTGGGCAAGGCCGGCTACGTGACCGACCGGGGCCGGC
AGAAGGTGGTGAGCATCGCCGACACCACCAACCAGAAGACCGAGCTGCA
GGCCATCCACCTGGCCCTGCAGGACAGCGGCCTGGAGGTGAACATCGTGA
CCGACAGCCAGTACGCCCTGGGCATCATCCAGGCCCAGCCCGACAAGAGC
GAGAGCGAGCTGGTGAGCCAGATCATCGAGCAGCTGATCAAGAAGGAGA
AGGTGTACCTGGCCTGGGTGCCCGCCCACAAGGGCATCGGCGGCAACGAG
CAGGTGGACAAGCTGGTGAGCGCCGGCATCCGCAAGGTGCTCTAAAGAAT
TC

Figure 46 tat.exon1_2.opt.C22/37.SF2

ATGGAGCCCGTGGACCCCCGCCTGGAGCCCTGGAAGCACCCCGGCAGCCAGCCCAAGACCGCCGGCACC
AACTGCTACTGCAAGAAGTGCTGCTTCCACTGCCAGGTGAGCTTCATCACCAAGGGCCTGGGCATCAGC
TACGGCCGCAAGAAGCGCCGCCAGCGCCGCCGCGCCCCCCCCGACAGCGAGGTGCACCAGGTGAGCCTG
CCCAAGCAGCCCGCCAGCCAGCCCCAGGGCGACCCCACCGGCCCCAAGGAGAGCAAGAAGAAGGTGGAG
CGCGAGACCGAGACCGACCCCGTGCAC

Figure 47 tat.exon1_2.opt.C37.SF2

ATGGAGCCCGTGGACCCCCGCCTGGAGCCCTGGAAGCACCCCGGCAGCCAGCCCAAGACCGCCTGCACC
AACTGCTACTGCAAGAAGTGCTGCTTCCACTGCCAGGTGAGCTTCATCACCAAGGGCCTGGGCATCAGC
TACGGCCGCAAGAAGCGCCGCCAGCGCCGCCGCGCCCCCCCGACAGCGAGGTGCACCAGGTGAGCCTG
CCCAAGCAGCCCGCCAGCCAGCCCCAGGGCGACCCCACCGGCCCCAAGGAGAGCAAGAAGAAGGTGGAG
CGCGAGACCGAGACCGACCCCGTGCAC

Figure 48

TatRevNef.opt.native.SF162

ATGGAGCCCGTGGACCCCCGCCTGGAGCCCTGGAAGCACCCCGGCAGCCAGCCCAAGACCGCCTGCACC
AACTGCTACTGCAAGAAGTGCTGCTTCCACTGCCAGGTGTGCTTCATCACCAAGGGCCTGGGCATCAGC
TACGGCCGCAAGAAGCGCCGCCAGCGCCGCCGCGCCCCCCCCGACAGCGAGGTGCACCAGGTGAGCCTG
CCCAAGCAGCCCGCCAGCCAGCCCCAGGGCGACCCCACCGGCCCCAAGGAGAGCAAGAAGAAGGTGGAG
CGCGAGACCGAGACCGACCCCGTGCACCCCGGGGCCGGCCGCAGCGGCGACAGCGACGAGGAGCTGCTG
CAGACCGTGCGCTTCATCAAGTTCCTGTACCAGAGCAACCCCCTGCCCAGCCCCAAGGGCACCCGCCAG
GCCCGCCGCAACCGCCGCCGCCGCTGGCGCGAGCGCCAGCGCCAGATCCAGAGCATCAGCGCCTGGATC
ATCAGCACCCACCTGGGCCGCAGCACCGAGCCCGTGCCCTGCAGCTGCCCCCCCTGGAGCGCCTGAAC
CTGGACTGCAGCGAGGACTGCGGCACCAGCGGCACCCAGGGCGTGGGCAGCCCCCAGGTGCTGGGCGAG
AGCCCCGCCGTGCTGGACAGCGGCACCAAGGAGCTCGAGGGCGGCAAGTGGAGCAAGCGCATGAGCGGC
TGGAGCGCCGTGCGCGAGCGCATGAAGCGCGCCGAGCCCGCCGAGCCCGCCGCCGACGGCGTGGGCGCC
GTGAGCCGCGACCTGGAGAAGCACGGCGCCATCACCAGCAGCAACACCGCCGCCAACAACGCCGACTGC
GCCTGGCTGGAGGCCCAGGAGGACGAGGACGTGGGCTTCCCCGTGCGCCCCCAGGTGCCCCTGCGCCCC
ATGACCTACAAGGCCGCCCTGGACCTGAGCCACTTCCTGAAGGAGAAGGGCGGCCTGGAGGGCCTGATC
TACAGCCAGAAGCGCCAGGACATCCTGGACCTGTGGATCCACCACACCCAGGGCTACTTCCCCGACTGG
CAGAACTACACCCCCGGCCCCGGCATCCGCTACCCCCTGACCTTCGGCTGGTGCTTCAAGCTGGTGCCC
GTGGACCCCGACTACGTGGAGGAGGCCAACGCCGGCGAGAACAACAGCCTGCTGCACCCCATGAGCCAG
CACGGCATGGACGACCCCGAGAAGGAGGTGCTGGTGTGGCGCTTCGACAGCCGCCTGGCCTTCCACCAC
ATGGCCCGCGAGCTGCACCCCGAGTACTACAAGGACTGC

Figure 49

TatRevNef.opt.SF162

ATGGAGCCCGTGGACCCCCGCCTGGAGCCCTGGAAGCACCCCGGCAGCCAGCCCAAGACCGCCGGCACC
AACTGCTACTGCAAGAAGTGCTGCTTCCACTGCCAGGTGAGCTTCATCACCAAGGGCCTGGGCATCAGC
TACGGCCGCAAGAAGCGCCGCCAGCGCCGCGCGCCCCCCCGACAGCGAGGTGCACCAGGTGAGCCTG
CCCAAGCAGCCCGCCAGCCAGCCCCAGGGCGACCCCACCGGCCCCAAGGAGAGCAAGAAGAAGGTGGAG
CGCGAGACCGAGACCGACCCCGTGCACCCCGGGGCCGGCCGCAGCGGCGACAGCGACGAGGAGCTGCTG
CAGACCGTGCGCTTCATCAAGTTCCTGTACCAGAGCAACCCCCTGCCCAGCCCCAAGGGCACCCGCCAG
GCCGACCTGAACCGCCGCCGCCGCTGGCGCGAGCGCCAGCGCCAGATCCAGAGCATCAGCGCCTGGATC
ATCAGCACCCACCTGGGCCGCAGCACCGAGCCCGTGCCCTGCAGCTGCCCCCCGACCTGCGCCTGAAC
CTGGACTGCAGCGAGGACTGCGGCACCAGCGGCACCCAGGGCGTGGGCAGCCCCCAGGTGCTGGGCGAG
AGCCCCGCCGTGCTGGACAGCGGCACCAAGGAGCTCGAGGCCGGCAAGTGGAGCAAGCGCATGAGCGGC
TGGAGCGCCGTGCGCGAGCGCATGAAGCGCGCCGAGCCCGCCGAGCCCGCCGCCGACGGCGTGGGCGCC
GTGAGCCGCGACCTGGAGAAGCACGGCGCCATCACCAGCAGCAACACCGCCGCCAACAACGCCGACTGC
GCCTGGCTGGAGGCCCAGGAGGACGAGGACGTGGGCTTCCCCGTGCGCCCCAGGTGCCCCTGCGCCCC
ATGACCTACAAGGCCGCCCTGGACCTGAGCCACTTCCTGAAGGAGAAGGGCGGCCTGGAGGGCCTGATC
TACAGCCAGAAGCGCCAGGACATCCTGGACCTGTGGATCCACCACACCCAGGGCTACTTCCCCGGCTGG
CAGAACTACACCCCCGGCCCCGGCATCCGCTACCCCCTGACCTTCGGCTGGTGCTTCAAGCTGGTGCCC
GTGGACCCCGACTACGTGGAGGAGGCCAACGCCGGCGAGAACAACAGCCTGCTGCACCCCATGAGCCAG
CACGGCATGGACGACCCCGAGAAGGAGGTGCTGGTGTGGCGCTTCGACAGCCGCCTGGCCTTCCACCAC
ATGGCCCGCGAGCTGCACCCCGAGTACTACAAGGACTGC

Figure 50

TatRevNefGag_B

```
GCCACCATGGAGCCCGTGGACCCCCGCCTGGAGCCCTGGAAGCACCCCGGCAGCCAGCCCAAGACCGCC
GGCACCAACTGCTACTGCAAGAAGTGCTGCTTCCACTGCCAGGTGAGCTTCATCACCAAGGGCCTGGGC
ATCAGCTACGGCCGCAAGAAGCGCCGCCAGCGCCGCCGCGCCCCCCCGACAGCGAGGTGCACCAGGTG
AGCCTGCCCAAGCAGCCCGCCAGCCAGCCCCAGGGCGACCCCACCGGCCCCAAGGAGAGCAAGAAGAAG
GTGGAGCGCGAGACCGAGACCGACCCCGTGCACCCCGGGGCCGGCCGCAGCGGCGACAGCGACGAGGAG
CTGCTGCAGACCGTGCGCTTCATCAAGTTCCTGTACCAGAGCAACCCCCTGCCCAGCCCCAAGGGCACC
CGCCAGGCCGACCTGAACCGCCGCCGCCGCTGGCGCGAGCGCCAGCGCCAGATCCAGAGCATCAGCGCC
TGGATCATCAGCACCCACCTGGGCCGCAGCACCGAGCCCGTGCCCCTGCAGCTGCCCCCCGACCTGCGC
CTGAACCTGGACTGCAGCGAGGACTGCGGCACCAGCGGCACCCAGGGCGTGGGCAGCCCCAGGTGCTG
GGCGAGAGCCCCGCCGTGCTGGACAGCGGCACCAAGGAGCTCGAGGCCGGCAAGTGGAGCAAGCGCATG
AGCGGCTGGAGCGCCGTGCGCGAGCGCATGAAGCGCGCCGAGCCCGCCGAGCCCGCCGCCGACGGCGTG
GGCGCCGTGAGCCGCGACCTGGAGAAGCACGGCGCCATCACCAGCAGCAACACCGCCGCCAACAACGCC
GACTGCGCCTGGCTGGAGGCCAGGAGGACGAGGACGTGGGCTTCCCCGTGCGCCCCAGGTGCCCCTG
CGCCCCATGACCTACAAGGCCGCCCTGGACCTGAGCCACTTCCTGAAGGAGAAGGGCGGCCTGGAGGGC
CTGATCTACAGCCAGAAGCGCCAGGACATCCTGGACCTGTGGATCCACCACACCCAGGGCTACTTCCCC
GGCTGGCAGAACTACACCCCCGGCCCCGGCATCCGCTACCCCCTGACCTTCGGCTGGTGCTTCAAGCTG
GTGCCCGTGGACCCCGACTACGTGGAGGAGGCCAACGCCGGCGAGAACAACAGCCTGCTGCACCCCATG
AGCCAGCACGGCATGGACGACCCCGAGAAGGAGGTGCTGGTGTGGCGCTTCGACAGCCGCCTGGCCTTC
CACCACATGGCCCGCGAGCTGCACCCCGAGTACTACAAGGACTGCGAATTCGGCGCCCGCGCCAGCGTG
CTGAGCGGCGGCGAGCTGGACAAGTGGGAGAAGATCCGCCTGCGCCCCGGCGGCAAGAAGAAGTACAAG
CTGAAGCACATCGTGTGGGCCAGCCGCGAGCTGGAGCGCTTCGCCGTGAACCCCGGCCTGCTGGAGACC
AGCGAGGGCTGCCGCCAGATCCTGGGCCAGCTGCAGCCCAGCCTGCAGACCGGCAGCGAGGAGCTGCGC
AGCCTGTACAACACCGTGGCCACCCTGTACTGCGTGCACCAGCGCATCGACGTCAAGGACACCAAGGAG
GCCCTGGAGAAGATCGAGGAGGAGCAGAACAAGTCCAAGAAGAAGGCCCAGCAGGCCGCCGCCGCCGCC
GGCACCGGCAACAGCAGCCAGGTGAGCCAGAACTACCCCATCGTGCAGAACCTGCAGGGCCAGATGGTG
CACCAGGCCATCAGCCCCCGCACCCTGAACGCCTGGGTGAAGGTGGTGGAGGAGAAGGCCTTCAGCCCC
GAGGTGATCCCCATGTTCAGCGCCCTGAGCGAGGGCGCCACCCCCCAGGACCTGAACACGATGTTGAAC
ACCGTGGGCGGCCACCAGGCCGCCATGCAGATGCTGAAGGAGACCATCAACGAGGAGGCCGCCGAGTGG
GACCGCGTGCACCCCGTGCACGCCGGCCCCATCGCCCCCGGCCAGATGCGCGAGCCCCGCGGCAGCGAC
ATCGCCGGCACCACCAGCACCCTGCAGGAGCAGATCGGCTGGATGACCAACAACCCCCCCATCCCCGTG
GGCGAGATCTACAAGCGGTGGATCATCCTGGGCCTGAACAAGATCGTGCGGATGTACAGCCCCACCAGC
ATCCTGGACATCCGCCAGGGCCCCAAGGAGCCCTTCCGCGACTACGTGGACCGCTTCTACAAGACCCTG
CGCGCTGAGCAGGCCAGCCAGGACGTGAAGAACTGGATGACCGAGACCCTGCTGGTGCAGAACGCCAAC
CCCGACTGCAAGACCATCCTGAAGGCTCTCGGCCCCGCGGCCACCCTGGAGGAGATGATGACCGCCTGC
CAGGGCGTGGGCGGCCCCGGCCACAAGGCCCGCGTGCTGGCCGAGGCGATGAGCCAGGTGACGAACCCG
GCGACCATCATGATGCAGCGCGGCAACTTCCGCAACCAGCGGAAGACCGTCAAGTGCTTCAACTGCGGC
AAGGAGGGCCACACCGCCAGGAACTGCCGCGCCCCCGCAAGAAGGGCTGCTGGCGCTGCGGCCGCGAG
GGCCACCAGATGAAGGACTGCACCGAGCGCCAGGCCAACTTCCTGGGCAAGATCTGGCCCAGCTACAAG
GGCCGCCCCGGCAACTTCCTGCAGAGCCGCCCCGAGCCCACCGCCCCCCCGAGGAGAGCTTCCGCTTC
GGCGAGGAGAAGACCACCCCCAGCCAGAAGCAGGAGCCCATCGACAAGGAGCTGTACCCCCTGACCAGC
CTGCGCAGCCTGTTCGGCAACGACCCCAGCAGCCAGTAA
```

TatRevNefgagCpolIna_B

```
GTCGACGCCACCATGGAGCCCGTGGACCCCCGCCTGGAGCCCTGGAAGCACCCCGGCAGCCAGCCCAAG
ACCGCCGGCACCAACTGCTACTGCAAGAAGTGCTGCTTCCACTGCCAGGTGAGCTTCATCACCAAGGGC
CTGGGCATCAGCTACGGCCGCAAGAAGCGCCGCCAGCGCCGCCGCGCCCCCCCGACAGCGAGGTGCAC
CAGGTGAGCCTGCCCAAGCAGCCCGCCAGCCAGCCCCAGGGCGACCCCACCGGCCCCAAGGAGAGCAAG
AAGAAGGTGGAGCGCGAGACCGAGACCGACCCCGTGCACCCCGGGGCCGGCCGCAGCGGCGACAGCGAC
GAGGAGCTGCTGCAGACCGTGCGCTTCATCAAGTTCCTGTACCAGAGCAACCCCCTGCCCAGCCCCAAG
GGCACCCGCCAGGCCGACCTGAACCGCCGCCGCCGCTGGCGCGAGCGCCAGCGCCAGATCCAGAGCATC
AGCGCCTGGATCATCAGCACCCACCTGGGCCGCAGCACCGAGCCCGTGCCCCTGCAGCTGCCCCCCGAC
CTGCGCCTGAACCTGGACTGCAGCGAGGACTGCGGCACCAGCGGCACCCAGGGCGTGGGCAGCCCCAG
GTGCTGGGCGAGAGCCCCGCCGTGCTGGACAGCGGCACCAAGGAGCTCGAGGCCGGCAAGTGGAGCAAG
CGCATGAGCGGCTGGAGCGCCGTGCGCGAGCGCATGAAGCGCGCCGAGCCCGCCGAGCCCGCCGCCGAC
GGCGTGGGCGCCGTGAGCCGCGACCTGGAGAAGCACGGCGCCATCACCAGCAGCAACACCGCCGCCAAC
AACGCCGACTGCGCCTGGCTGGAGGCCCAGGAGGACGAGGACGTGGGCTTCCCCGTGCGCCCCAGGTG
CCCCTGCGCCCCATGACCTACAAGGCCGCCCTGGACCTGAGCCACTTCCTGAAGGAGAAGGGCGGCCTG
GAGGGCCTGATCTACAGCCAGAAGCGCCAGGACATCCTGGACCTGTGGATCCACCACACCCAGGGCTAC
TTCCCCGGCTGGCAGAACTACACCCCCGGCCCCGGCATCCGCTACCCCCTGACCTTCGGCTGGTGCTTC
AAGCTGGTGCCCGTGGACCCCGACTACGTGGAGGAGGCCAACGCCGGCGAGAACAACAGCCTGCTGCAC
CCCATGAGCCAGCACGGCATGGACGACCCCGAGAAGGAGGTGCTGGTGTGGCGCTTCGACAGCCGCCTG
GCCTTCCACCACATGGCCCGCGAGCTGCACCCCGAGTACTACAAGGACTGCCTCGAGGGCGCCCGCGCC
AGCGTGCTGAGCGGCGGCGAGCTGGACAAGTGGGAGAAGATCCGCCTGCGCCCCGGCGGCAAGAAGAAG
TACAAGCTGAAGCACATCGTGTGGGCCAGCCGCGAGCTGGAGCGCTTCGCCGTGAACCCCGGCCTGCTG
GAGACCAGCGAGGGCTGCCGCCAGATCCTGGGCCAGCTGCAGCCCAGCCTGCAGACCGGCAGCGAGGAG
CTGCGCAGCCTGTACAACACCGTGGCCACCCTGTACTGCGTGCACCAGCGCATCGACGTCAAGGACACC
AAGGAGGCCCTGGAGAAGATCGAGGAGGAGCAGAACAAGTCCAAGAAGAAGGCCCAGCAGGCCGCCGCC
GCCGCCGGCACCGGCAACAGCAGCCAGGTGAGCCAGAACTACCCCATCGTGCAGAACCTGCAGGGCCAG
ATGGTGCACCAGGCCATCAGCCCCCGCACCCTGAACGCCTGGGTGAAGGTGGTGGAGGAGAAGGCCTTC
AGCCCCGAGGTGATCCCCATGTTCAGCGCCCTGAGCGAGGGCGCCACCCCCCAGGACCTGAACACGATG
TTGAACACCGTGGGCGGCCACCAGGCCGCCATGCAGATGCTGAAGGAGACCATCAACGAGGAGGCCGCC
GAGTGGGACCGCGTGCACCCCGTGCACGCCGGCCCCATCGCCCCGGCCAGATGCGCGAGCCCCGCGGC
AGCGACATCGCCGGCACCACCAGCACCCTGCAGGAGCAGATCGGCTGGATGACCAACAACCCCCCCATC
CCCGTGGGCGAGATCTACAAGCGGTGGATCATCCTGGGCCTGAACAAGATCGTGCGGATGTACAGCCCC
ACCAGCATCCTGGACATCCGCCAGGGCCCCAAGGAGCCCTTCCGCGACTACGTGGACCGCTTCTACAAG
ACCCTGCGCGCTGAGCAGGCCAGCCAGGACGTGAAGAACTGGATGACCGAGACCCTGCTGGTGCAGAAC
GCCAACCCCGACTGCAAGACCATCCTGAAGGCTCTCGGCCCCGCGGCCACCCTGGAGGAGATGATGACC
GCCTGCCAGGGCGTGGGCGGCCCCGGCCACAAGGCCCGCGTGCTGGCCGAGGCGATGAGCCAGGTGACG
AACCCGGCGACCATCATGATGCAGCGCGGCAACTTCCGCAACCAGCGGAAGACCGTCAAGTGCTTCAAC
TGCGGCAAGGAGGGCCACACCGCCAGGAACTGCCGCGCCCCCCGCAAGAAGGGCTGCTGGCGCTGCGGC
CGCGAGGGCCACCAGATGAAGGACTGCACCGAGCGCCAGGCCAACTTCCTGGGCAAGATCTGGCCCAGC
TACAAGGGCCGCCCCGGCAACTTCCTGCAGAGCCGCCCCGAGCCCACCGCCCCCCCGAGGAGAGCTTC
CGCTTCGGCGAGGAGAAGACCACCCCCAGCCAGAAGCAGGAGCCCATCGACAAGGAGCTGTACCCCCTG
ACCAGCCTGCGCAGCCTGTTCGGCAACGACCCCAGCAGCCAGAAAGAATTCAAGGCCCGCGTGCTGGCC
GAGGCGATGAGCCAGGTGACGAACCCGGCGACCATCATGATGCAGCGCGGCAACTTCCGCAACCAGCGG
AAGACCGTCAAGTGCTTCAACTGCGGCAAGGAGGGCCACACCGCCAGGAACTGCCGCGCCCCCGCAAG
AAGGGCTGCTGGCGCTGCGGCCGCGAAGGACACCAAATGAAAGATTGCACTGAGAGACAGGCTAATTTC
TTCCGCGAGGACCTGGCCTTCCTGCAGGGCAAGGCCCGCGAGTTCAGCAGCGAGCAGACCCGCGCCAAC
AGCCCCACCCGCCGCGAGCTGCAGGTGTGGGCGGCGAGAACAACAGCCTGAGCGAGGCCGGCGCCGAC
CGCCAGGGCACCGTGAGCTTCAACTTCCCCCAGATCACCCTGTGGCAGCGCCCCCTGGTGACCATCAGG
ATCGGCGGCCAGCTCAAGGAGGCGCTGCTCGCCACCGGCGCCGACGACACCGTGCTGGAGGAGATGAAC
CTGCCCGGCAAGTGGAAGCCCAAGATGATCGGCGGGATCGGGGGCTTCATCAAGGTGCGGCAGTACGAC
CAGATCCCCGTGGAGATCTGCGGCCACAAGGCCATCGGCACCGTGCTGGTGGGCCCCACCCCCGTGAAC
ATCATCGGCCGCAACCTGCTGACCCAGATCGGCTGCACCCTGAACTTCCCCATCAGCCCCATCGAGACG
GTGCCCGTGAAGCTGAAGCCGGGGATGGACGGCCCCAAGGTCAAGCAGTGGCCCCTGACCGAGGAGAAG
ATCAAGGCCCTGGTGGAGATCTGCACCGAGATGGAGAAGGAGGGCAAGATCAGCAAGATCGGCCCCGAG
AACCCCTACAACACCCCCGTGTTCGCCATCAAGAAGAAGGACAGCACCAAGTGGCGCAAGCTGGTGGAC
```

TTCCGCGAGCTGAACAAGCGCACCCAGGACTTCTGGGAGGTGCAGCTGGGCATCCCCCACCCCGCCGGC
CTGAAGAAGAAGAAGAGCGTGACCGTGCTGGACGTGGGCGACGCCTACTTCAGCGTGCCCCTGGACAAG
GACTTCCGCAAGTACACCGCCTTCACCATCCCCAGCATCAACAACGAGACCCCCGGCATCCGCTACCAG
TACAACGTGCTGCCCCAGGGCTGGAAGGGCAGCCCCGCCATCTTCCAGAGCAGCATGACCAAGATCCTG
GAGCCCTTCCGCAAGCAGAACCCCGACATCGTGATCTACCAGGCCCCCTGTACGTGGGCAGCGACCTG
GAGATCGGCCAGCACCGCACCAAGATCGAGGAGCTGCGCCAGCACCTGCTGCGCTGGGGCTTCACCACC
CCCGACAAGAAGCACCAGAAGGAGCCCCCCTTCCTGCCCATCGAGCTGCACCCCGACAAGTGGACCGTG
CAGCCCATCATGCTGCCCGAGAAGGACAGCTGGACCGTGAACGACATCCAGAAGCTGGTGGGCAAGCTG
AACTGGGCCAGCCAGATCTACGCCGGCATCAAGGTGAAGCAGCTGTGCAAGCTGCTGCGCGGCACCAAG
GCCCTGACCGAGGTGATCCCCCTGACCGAGGAGGCCGAGCTGGAGCTGGCCGAGAACCGCGAGATCCTG
AAGGAGCCCGTGCACGAGGTGTACTACGACCCCAGCAAGGACCTGGTGGCCGAGATCCAGAAGCAGGGC
CAGGGCCAGTGGACCTACCAGATCTACCAGGAGCCCTTCAAGAACCTGAAGACCGGCAAGTACGCCCGC
ATGCGCGGCGCCCACACCAACGACGTGAAGCAGCTGACCGAGGCCGTGCAGAAGGTGAGCACCGAGAGC
ATCGTGATCTGGGGCAAGATCCCCAAGTTCAAGCTGCCCATCCAGAAGGAGACCTGGGAGGCCTGGTGG
ATGGAGTACTGGCAGGCCACCTGGATCCCCGAGTGGGAGTTCGTGAACACCCCCCCCTGGTGAAGCTG
TGGTACCAGCTGGAGAAGGAGCCCATCGTGGGCGCCGAGACCTTCTACGTGGACGGCGCCGCCAACCGC
GAGACCAAGCTGGGCAAGGCCGGCTACGTGACCGACCGGGGCCGGCAGAAGGTGGTGAGCATCGCCGAC
ACCACCAACCAGAAGACCGAGCTGCAGGCCATCCACCTGGCCCTGCAGGACAGCGGCCTGGAGGTGAAC
ATCGTGACCGACAGCCAGTACGCCCTGGGCATCATCCAGGCCCAGCCCGACAAGAGCGAGAGCGAGCTG
GTGAGCCAGATCATCGAGCAGCTGATCAAGAAGGAGAAGGTGTACCTGGCCTGGGTGCCCGCCCACAAG
GGCATCGGCGGCAACGAGCAGGTGGACAAGCTGGTGAGCGCCGGCATCCGCAAGGTGCTGTTCCTGAAC
GGCATCGATGGCGGCATCGTGATCTACCAGTACATGGACGACCTGTACGTGGGCAGCGGCGGCCCTAGG
ATCGATTAAAAGCTTCCCGGGGCTAGCACCGGTTCTAGA

TatRevNefGagProtInaRTmut_B

```
GCCACCATGGAGCCCGTGGACCCCCGCCTGGAGCCCTGGAAGCACCCCGGCAGCCAGCCCAAGACCGCC
GGCACCAACTGCTACTGCAAGAAGTGCTGCTTCCACTGCCAGGTGAGCTTCATCACCAAGGGCCTGGGC
ATCAGCTACGGCCGCAAGAAGCGCCGCCAGCGCCGCCGCGCCCCCCCCGACAGCGAGGTGCACCAGGTG
AGCCTGCCCAAGCAGCCCGCCAGCCAGCCCCAGGGCGACCCCACCGGCCCCAAGGAGAGCAAGAAGAAG
GTGGAGCGCGAGACCGAGACCGACCCCGTGCACCCCGGGGCCGGCCGCAGCGGCGACAGCGACGAGGAG
CTGCTGCAGACCGTGCGCTTCATCAAGTTCCTGTACCAGAGCAACCCCCTGCCCAGCCCCAAGGGCACC
CGCCAGGCCGACCTGAACCGCCGCCGCCGCTGGCGCGAGCGCCAGCGCCAGATCCAGAGCATCAGCGCC
TGGATCATCAGCACCCACCTGGGCCGCAGCACCGAGCCCGTGCCCTGCAGCTGCCCCCGACCTGCGC
CTGAACCTGGACTGCAGCGAGGACTGCGGCACCAGCGGCACCCAGGGCGTGGGCAGCCCCAGGTGCTG
GGCGAGAGCCCCGCCGTGCTGGACAGCGGCACCAAGGAGCTCGAGGCCGGCAAGTGGAGCAAGCGCATG
AGCGGCTGGAGCGCCGTGCGCGAGCGCATGAAGCGCGCCGAGCCCGCCGAGCCCGCCGCCGACGGCGTG
GGCGCCGTGAGCCGCGACCTGGAGAAGCACGGCGCCATCACCAGCAGCAACACCGCCGCCAACAACGCC
GACTGCGCCTGGCTGGAGGCCCAGGAGGACGAGGACGTGGGCTTCCCCGTGCGCCCCCAGGTGCCCCTG
CGCCCCATGACCTACAAGGCCGCCCTGGACCTGAGCCACTTCCTGAAGGAGAAGGGCGGCCTGGAGGGC
CTGATCTACAGCCAGAAGCGCCAGGACATCCTGGACCTGTGGATCCACCACACCCAGGGCTACTTCCCC
GGCTGGCAGAACTACACCCCCGGCCCCGGCATCCGCTACCCCCTGACCTTCGGCTGGTGCTTCAAGCTG
GTGCCCGTGGACCCCGACTACGTGGAGGAGGCCAACGCCGGCGAGAACAACAGCCTGCTGCACCCCATG
AGCCAGCACGGCATGGACGACCCCGAGAAGGAGGTGCTGGTGTGGCGCTTCGACAGCCGCCTGGCCTTC
CACCACATGGCCCGCGAGCTGCACCCCGAGTACTACAAGGACTGCAAGCTTGGCGCCCGCGCCAGCGTG
CTGAGCGGCGGCGAGCTGGACAAGTGGGAGAAGATCCGCCTGCGCCCCGGCGGCAAGAAGAAGTACAAG
CTGAAGCACATCGTGTGGGCCAGCCGCGAGCTGGAGCGCTTCGCCGTGAACCCCGGCCTGCTGGAGACC
AGCGAGGGCTGCCGCCAGATCCTGGGCCAGCTGCAGCCCAGCCTGCAGACCGGCAGCGAGGAGCTGCGC
AGCCTGTACAACACCGTGGCCACCCTGTACTGCGTGCACCAGCGCATCGACGTCAAGGACACCAAGGAG
GCCCTGGAGAAGATCGAGGAGGAGCAGAACAAGTCCAAGAAGAAGGCCCAGCAGGCCGCCGCCGCCGCC
GGCACCGGCAACAGCAGCCAGGTGAGCCAGAACTACCCCATCGTGCAGAACCTGCAGGGCCAGATGGTG
CACCAGGCCATCAGCCCCCGCACCCTGAACGCCTGGGTGAAGGTGGTGGAGGAGAAGGCCTTCAGCCCC
GAGGTGATCCCCATGTTCAGCGCCCTGAGCGAGGGCGCCACCCCCCAGGACCTGAACACGATGTTGAAC
ACCGTGGGCGGCCACCAGGCCGCCATGCAGATGCTGAAGGAGACCATCAACGAGGAGGCCGCCGAGTGG
GACCGCGTGCACCCCGTGCACGCCGGCCCCATCGCCCCCGGCCAGATGCGCGAGCCCCGCGGCAGCGAC
ATCGCCGGCACCACCAGCACCCTGCAGGAGCAGATCGGCTGGATGACCAACAACCCCCCCATCCCCGTG
GGCGAGATCTACAAGCGGTGGATCATCCTGGGCCTGAACAAGATCGTGCGGATGTACAGCCCCACCAGC
ATCCTGGACATCCGCCAGGGCCCCAAGGAGCCCTTCCGCGACTACGTGGACCGCTTCTACAAGACCCTG
CGCGCTGAGCAGGCCAGCCAGGACGTGAAGAACTGGATGACCGAGACCCTGCTGGTGCAGAACGCCAAC
CCCGACTGCAAGACCATCCTGAAGGCTCTCGGCCCCGCGGCCACCCTGGAGGAGATGATGACCGCCTGC
CAGGGCGTGGGCGGCCCCGGCCACAAGGCCCGCGTGCTGGCCGAGGCGATGAGCCAGGTGACGAACCCG
GCGACCATCATGATGCAGCGCGGCAACTTCCGCAACCAGCGGAAGACCGTCAAGTGCTTCAACTGCGGC
AAGGAGGGCCACACCGCCAGGAACTGCCGCGCCCCCGCAAGAAGGGCTGCTGGCGCTGCGGCCGCGAG
GGCCACCAGATGAAGGACTGCACCGAGCGCCAGGCCAACTTCCTGGGCAAGATCTGGCCCAGCTACAAG
GGCCGCCCCGGCAACTTCCTGCAGAGCCGCCCCGAGCCCACCGCCCCCCCCGAGGAGAGCTTCCGCTTC
GGCGAGGAGAAGACCACCCCCAGCCAGAAGCAGGAGCCCATCGACAAGGAGCTGTACCCCCTGACCAGC
CTGCGCAGCCTGTTCGGCAACGACCCCAGCAGCCAGAAAGAATTCCCCCAGATCACCCTGTGGCAGCGC
CCCCTGGTGACCATCAGGATCGGCGGCCAGCTCAAGGAGGCGCTGCTCGCCACCGGCGCCGACGACACC
GTGCTGGAGGAGATGAACCTGCCCGGCAAGTGGAAGCCCAAGATGATCGGCGGGATCGGGGCTTCATC
AAGGTGCGGCAGTACGACCAGATCCCCGTGGAGATCTGCGGCCACAAGGCCATCGGCACCGTGCTGGTG
GGCCCCACCCCCGTGAACATCATCGGCCGCAACCTGCTGACCCAGATCGGCTGCACCCTGAACTTCCCC
ATCAGCCCCATCGAGACGGTGCCCGTGAAGCTGAAGCCGGGGATGGACGGCCCCAAGGTCAAGCAGTGG
CCCCTGACCGAGGAGAAGATCAAGGCCCTGGTGGAGATCTGCACCGAGATGGAGAAGGAGGGCAAGATC
AGCAAGATCGGCCCCGAGAACCCCTACAACACCCCCGTGTTCGCCATCAAGAAGAAGGACAGCACCAAG
TGGCGCAAGCTGGTGGACTTCCGCGAGCTGAACAAGCGCACCCAGGACTTCTGGGAGGTGCAGCTGGGC
ATCCCCCACCCCGCCGGCCTGAAGAAGAAGAAGAGCGTGACCGTGCTGGACGTGGGCGACGCCTACTTC
AGCGTGCCCCTGGACAAGGACTTCCGCAAGTACACCGCCTTCACCATCCCCAGCATCAACAACGAGACC
CCCGGCATCCGCTACCAGTACAACGTGCTGCCCCAGGGCTGGAAGGGCAGCCCCGCCATCTTCCAGAGC
AGCATGACCAAGATCCTGGAGCCCTTCCGCAAGCAGAACCCCGACATCGTGATCTACCAGGCCCCCTG
TACGTGGGCAGCGACCTGGAGATCGGCCAGCACCGCACCAAGATCGAGGAGCTGCGCCAGCACCTGCTG
```

```
CGCTGGGGCTTCACCACCCCCGACAAGAAGCACCAGAAGGAGCCCCCCTTCCTGCCCATCGAGCTGCAC
CCCGACAAGTGGACCGTGCAGCCCATCATGCTGCCCGAGAAGGACAGCTGGACCGTGAACGACATCCAG
AAGCTGGTGGGCAAGCTGAACTGGGCCAGCCAGATCTACGCCGGCATCAAGGTGAAGCAGCTGTGCAAG
CTGCTGCGCGGCACCAAGGCCCTGACCGAGGTGATCCCCCTGACCGAGGAGGCCGAGCTGGAGCTGGCC
GAGAACCGCGAGATCCTGAAGGAGCCCGTGCACGAGGTGTACTACGACCCCAGCAAGGACCTGGTGGCC
GAGATCCAGAAGCAGGGCCAGGGCCAGTGGACCTACCAGATCTACCAGGAGCCCTTCAAGAACCTGAAG
ACCGGCAAGTACGCCCGCATGCGCGGCGCCCACACCAACGACGTGAAGCAGCTGACCGAGGCCGTGCAG
AAGGTGAGCACCGAGAGCATCGTGATCTGGGGCAAGATCCCCAAGTTCAAGCTGCCCATCCAGAAGGAG
ACCTGGGAGGCCTGGTGGATGGAGTACTGGCAGGCCACCTGGATCCCCGAGTGGGAGTTCGTGAACACC
CCCCCCCTGGTGAAGCTGTGGTACCAGCTGGAGAAGGAGCCCATCGTGGGCGCCGAGACCTTCTACGTG
GACGGCGCCGCCAACCGCGAGACCAAGCTGGGCAAGGCCGGCTACGTGACCGACCGGGGCCGGCAGAAG
GTGGTGAGCATCGCCGACACCACCAACCAGAAGACCGAGCTGCAGGCCATCCACCTGGCCCTGCAGGAC
AGCGGCCTGGAGGTGAACATCGTGACCGACAGCCAGTACGCCCTGGGCATCATCCAGGCCCAGCCCGAC
AAGAGCGAGAGCGAGCTGGTGAGCCAGATCATCGAGCAGCTGATCAAGAAGGAGAAGGTGTACCTGGCC
TGGGTGCCCGCCCACAAGGGCATCGGCGGCAACGAGCAGGTGGACAAGCTGGTGAGCGCCGGCATCCGC
AAGGTGCTCTAA
```

Figure 53

TatRevNefp2Pol.opt_B

```
GCCACCATGGAGCCCGTGGACCCCCGCCTGGAGCCCTGGAAGCACCCCGGCAGCCAGCCCAAGACCGCC
GGCACCAACTGCTACTGCAAGAAGTGCTGCTTCCACTGCCAGGTGAGCTTCATCACCAAGGGCCTGGGC
ATCAGCTACGGCCGCAAGAAGCGCCGCCAGCGCCGCCGCGCCCCCCCCGACAGCGAGGTGCACCAGGTG
AGCCTGCCCAAGCAGCCCGCCAGCCAGCCCCAGGGCGACCCCACCGGCCCCAAGGAGAGCAAGAAGAAG
GTGGAGCGCGAGACCGAGACCGACCCCGTGCACCCGGGGCCGGCCGCAGCGGCGACAGCGACGAGGAG
CTGCTGCAGACCGTGCGCTTCATCAAGTTCCTGTACCAGAGCAACCCCCTGCCCAGCCCCAAGGGCACC
CGCCAGGCCGACCTGAACCGCCGCCGCCGCTGGCGCGAGCGCCAGCGCCAGATCCAGAGCATCAGCGCC
TGGATCATCAGCACCCACCTGGGCCGCAGCACCGAGCCCGTGCCCCTGCAGCTGCCCCCCGACCTGCGC
CTGAACCTGGACTGCAGCGAGGACTGCGGCACCAGCGGCACCCAGGGCGTGGGCAGCCCCAGGTGCTG
GGCGAGAGCCCCGCCGTGCTGGACAGCGGCACCAAGGAGCTCGAGGCCGGCAAGTGGAGCAAGCGCATG
AGCGGCTGGAGCGCCGTGCGCGAGCGCATGAAGCGCGCCGAGCCCGCCGAGCCCGCCGCCGACGGCGTG
GGCGCCGTGAGCCGCGACCTGGAGAAGCACGGCGCCATCACCAGCAGCAACACCGCCGCCAACAACGCC
GACTGCGCCTGGCTGGAGGCCCAGGAGGACGAGGACGTGGGCTTCCCCGTGCGCCCCCAGGTGCCCCTG
CGCCCCATGACCTACAAGGCCGCCCTGGACCTGAGCCACTTCCTGAAGGAGAAGGGCGGCCTGGAGGGC
CTGATCTACAGCCAGAAGCGCCAGGACATCCTGGACCTGTGGATCCACCACACCCAGGGCTACTTCCCC
GGCTGGCAGAACTACACCCCCGGCCCCGGCATCCGCTACCCCCTGACCTTCGGCTGGTGCTTCAAGCTG
GTGCCCGTGGACCCCGACTACGTGGAGGAGGCCAACGCCGGCGAGAACAACAGCCTGCTGCACCCCATG
AGCCAGCACGGCATGGACGACCCCGAGAAGGAGGTGCTGGTGTGGCGCTTCGACAGCCGCCTGGCCTTC
CACCACATGGCCCGCGAGCTGCACCCCGAGTACTACAAGGACTGCGAATTCGCCGAGGCGATGAGCCAG
GTGACGAACCCGGCGACCATCATGATGCAGCGCGGCAACTTCCGCAACCAGCGGAAGACCGTCAAGTGC
TTCAACTGCGGCAAGGAGGGCCACACCGCCAGGAACTGCCGCGCCCCCGCAAGAAGGGCTGCTGGCGC
TGCCGGCCGCGAAGGACACCAAATGAAAGATTGCACTGAGAGACAGGCTAATTTCTTCCGCGAGGACCTG
GCCTTCCTGCAGGGCAAGGCCCGCGAGTTCAGCAGCGAGCAGACCCGCGCCAACAGCCCCACCCGCCGC
GAGCTGCAGGTGTGGGCGGCGAGAACAACAGCCTGAGCGAGGCCGGCGCCGACCGCCAGGGCACCGTG
AGCTTCAACTTCCCCCAGATCACCCTGTGGCAGCGCCCCCTGGTGACCATCAGGATCGGCGGCCAGCTC
AAGGAGGCGCTGCTCGCCACCGGCGCCGACGACACCGTGCTGGAGGAGATGAACCTGCCCGGCAAGTGG
AAGCCCAAGATGATCGGCGGGATCGGGGGCTTCATCAAGGTGCGGCAGTACGACCAGATCCCCGTGGAG
ATCTGCGGCCACAAGGCCATCGGCACCGTGCTGGTGGGCCCCACCCCCGTGAACATCATCGGCCGCAAC
CTGCTGACCCAGATCGGCTGCACCCTGAACTTCCCCATCAGCCCCATCGAGACGGTGCCCGTGAAGCTG
AAGCCGGGGATGGACGGCCCCAAGGTCAAGCAGTGGCCCCTGACCGAGGAGAAGATCAAGGCCCTGGTG
GAGATCTGCACCGAGATGGAGAAGGAGGGCAAGATCAGCAAGATCGGCCCCGAGAACCCCTACAACACC
CCCGTGTTCGCCATCAAGAAGAAGGACAGCACCAAGTGGCGCAAGCTGGTGGACTTCCGCGAGCTGAAC
AAGCGCACCCAGGACTTCTGGGAGGTGCAGCTGGGCATCCCCACCCCGCCGGCCTGAAGAAGAAGAAG
AGCGTGACCGTGCTGGACGTGGGCGACGCCTACTTCAGCGTGCCCCTGGACAAGGACTTCCGCAAGTAC
ACCGCCTTCACCATCCCCAGCATCAACAACGAGACCCCCGGCATCCGCTACCAGTACAACGTGCTGCCC
CAGGGCTGGAAGGGCAGCCCCGCCATCTTCCAGAGCAGCATGACCAAGATCCTGGAGCCCTTCCGCAAG
CAGAACCCCGACATCGTGATCTACCAGGCCCCCCTGTACGTGGGCAGCGACCTGGAGATCGGCCAGCAC
CGCACCAAGATCGAGGAGCTGCGCCAGCACCTGCTGCGCTGGGGCTTCACCACCCCCGACAAGAAGCAC
CAGAAGGAGCCCCCCTTCCTGCCCATCGAGCTGCACCCCGACAAGTGGACCGTGCAGCCCATCATGCTG
CCCGAGAAGGACAGCTGGACCGTGAACGACATCCAGAAGCTGGTGGGCAAGCTGAACTGGGCCAGCCAG
ATCTACGCCGGCATCAAGGTGAAGCAGCTGTGCAAGCTGCTGCGCGGCACCAAGGCCCTGACCGAGGTG
ATCCCCCTGACCGAGGAGGCCGAGCTGGAGCTGGCCGAGAACCGCGAGATCCTGAAGGAGCCCGTGCAC
GAGGTGTACTACGACCCCAGCAAGGACCTGGTGGCCGAGATCCAGAAGCAGGGCCAGGGCCAGTGGACC
TACCAGATCTACCAGGAGCCCTTCAAGAACCTGAAGACCGGCAAGTACGCCCGCATGCGCGGCGCCCAC
ACCAACGACGTGAAGCAGCTGACCGAGGCCGTGCAGAAGGTGAGCACCGAGAGCATCGTGATCTGGGGC
AAGATCCCCAAGTTCAAGCTGCCCATCCAGAAGGAGACCTGGGAGGCCTGGTGGATGGAGTACTGGCAG
GCCACCTGGATCCCCGAGTGGGAGTTCGTGAACACCCCCCCCCTGGTGAAGCTGTGGTACCAGCTGGAG
AAGGAGCCCATCGTGGGCGCCGAGACCTTCTACGTGGACGGCGCCGCCAACCGCGAGACCAAGCTGGGC
AAGGCCGGCTACGTGACCGACCGGGGCCGGCAGAAGGTGGTGAGCATCGCCGACACCACCAACCAGAAG
ACCGAGCTGCAGGCCATCCACCTGGCCCTGCAGGACAGCGGCCTGGAGGTGAACATCGTGACCGACAGC
CAGTACGCCCTGGGCATCATCCAGGCCCAGCCCGACAAGAGCGAGAGCGAGCTGGTGAGCCAGATCATC
GAGCAGCTGATCAAGAAGGAGAAGGTGTACCTGGCCTGGGTGCCCGCCCACAAGGGCATCGGCGGCAAC
GAGCAGGTGGACAAGCTGGTGAGCGCCGGCATCCGCAAGGTGCTGTAA
```

Figure 54

TatRevNef.ProtRT.opt_B

GCCACCATGGAGCCCGTGGACCCCCGCCTGGAGCCCTGGAAGCACCCCGGCAGCCAGCCCAAGACCGCC
GGCACCAACTGCTACTGCAAGAAGTGCTGCTTCCACTGCCAGGTGAGCTTCATCACCAAGGGCCTGGGC
ATCAGCTACGGCCGCAAGAAGCGCCGCCAGCGCCGCCGCGCCCCCCCCGACAGCGAGGTGCACCAGGTG
AGCCTGCCCAAGCAGCCCGCCAGCCAGCCCCAGGGCGACCCCACCGGCCCCAAGGAGAGCAAGAAGAAG
GTGGAGCGCGAGACCGAGACCGACCCCGTGCACCCCGGGGCCGGCCGCAGCGGCGACAGCGACGAGGAG
CTGCTGCAGACCGTGCGCTTCATCAAGTTCCTGTACCAGAGCAACCCCCTGCCCAGCCCCAAGGGCACC
CGCCAGGCCGACCTGAACCGCCGCCGCCGCTGGCGCGAGCGCCAGCGCAGATCCAGAGCATCAGCGCC
TGGATCATCAGCACCCACCTGGGCCGCAGCACCGAGCCCGTGCCCCTGCAGCTGCCCCCCGACCTGCGC
CTGAACCTGGACTGCAGCGAGGACTGCGGCACCAGCGGCACCCAGGGCGTGGGCAGCCCCAGGTGCTG
GGCGAGAGCCCCGCCGTGCTGGACAGCGGCACCAAGGAGCTCGAGGCCGGCAAGTGGAGCAAGCGCATG
AGCGGCTGGAGCGCCGTGCGCGAGCGCATGAAGCGCGCCGAGCCCGCCGAGCCCGCCGCCGACGGCGTG
GGCGCCGTGAGCCGCCGACCTGGAGAAGCACGGCGCCATCACCAGCAGCAACACCGCCGCCAACAACGCC
GACTGCGCCTGGCTGGAGGCCCAGGAGGACGAGGACGTGGGCTTCCCCGTGCGCCCCCAGGTGCCCCTG
CGCCCCATGACCTACAAGGCCGCCCTGGACCTGAGCCACTTCCTGAAGGAGAAGGGCGGCCTGGAGGGC
CTGATCTACAGCCAGAAGCGCCAGGACATCCTGGACCTGTGGATCCACCACACCCAGGGCTACTTCCCC
GGCTGGCAGAACTACACCCCCGGCCCCGGCATCCGCTACCCCCTGACCTTCGGCTGGTGCTTCAAGCTG
GTGCCCGTGGACCCCGACTACGTGGAGGAGGCCAACGCCGGCGAGAACAACAGCCTGCTGCACCCCATG
AGCCAGCACGGCATGGACGACCCCGAGAAGGAGGTGCTGGTGTGGCGCTTCGACAGCCGCCTGGCCTTC
CACCACATGGCCCGCGAGCTGCACCCCGAGTACTACAAGGACTGCGAATTCCCCCAGATCACCCTGTGG
CAGCGCCCCCTGGTGACCATCAGGATCGGCGGCCAGCTCAAGGAGGCGCTGCTCGCCACCGGCGCCGAC
GACACCGTGCTGGAGGAGATGAACCTGCCCGGCAAGTGGAAGCCCAAGATGATCGGCGGGATCGGGGGC
TTCATCAAGGTGCGGCAGTACGACCAGATCCCCGTGGAGATCTGCGGCCACAAGGCCATCGGCACCGTG
CTGGTGGGCCCCACCCCCGTGAACATCATCGGCCGCAACCTGCTGACCCAGATCGGCTGCACCCTGAAC
TTCCCCATCAGCCCCATCGAGACGGTGCCCGTGAAGCTGAAGCCGGGGATGGACGGCCCCAAGGTCAAG
CAGTGGCCCCTGACCGAGGAGAAGATCAAGGCCCTGGTGGAGATCTGCACCGAGATGGAGAAGGAGGGC
AAGATCAGCAAGATCGGCCCCGAGAACCCCTACAACACCCCCGTGTTCGCCATCAAGAAGAAGGACAGC
ACCAAGTGGCGCAAGCTGGTGGACTTCCGCGAGCTGAACAAGCGCACCCAGGACTTCTGGGAGGTGCAG
CTGGGCATCCCCCACCCCGCCGGCCTGAAGAAGAAGAAGAGCGTGACCGTGCTGGACGTGGGCGACGCC
TACTTCAGCGTGCCCCTGGACAAGGACTTCCGCAAGTACACCGCCTTCACCATCCCCAGCATCAACAAC
GAGACCCCCGGCATCCGCTACCAGTACAACGTGCTGCCCCAGGGCTGGAAGGGCAGCCCCGCCATCTTC
CAGAGCAGCATGACCAAGATCCTGGAGCCCTTCCGCAAGCAGAACCCCGACATCGTGATCTACCAGGCC
CCCCTGTACGTGGGCAGCGACCTGGAGATCGGCCAGCACCGCACCAAGATCGAGGAGCTGCGCCAGCAC
CTGCTGCGCTGGGGCTTCACCACCCCCGACAAGAAGCACCAGAAGGAGCCCCCCTTCCTGCCCATCGAG
CTGCACCCCGACAAGTGGACCGTGCAGCCCATCATGCTGCCCGAGAAGGACAGCTGGACCGTGAACGAC
ATCCAGAAGCTGGTGGGCAAGCTGAACTGGGCCAGCCAGATCTACGCCGGCATCAAGGTGAAGCAGCTG
TGCAAGCTGCTGCGCGGCACCAAGGCCCTGACCGAGGTGATCCCCCTGACCGAGGAGGCCGAGCTGGAG
CTGGCCGAGAACCGCGAGATCCTGAAGGAGCCCGTGCACGAGGTGTACTACGACCCCAGCAAGGACCTG
GTGGCCGAGATCCAGAAGCAGGGCCAGGGCCAGTGGACCTACCAGATCTACCAGGAGCCCTTCAAGAAC
CTGAAGACCGGCAAGTACGCCCGCATGCGCGGCGCCCACACCAACGACGTGAAGCAGCTGACCGAGGCC
GTGCAGAAGGTGAGCACCGAGAGCATCGTGATCTGGGGCAAGATCCCCAAGTTCAAGCTGCCCATCCAG
AAGGAGACCTGGGAGGCCTGGTGGATGGAGTACTGGCAGGCCACCTGGATCCCCGAGTGGGAGTTCGTG
AACACCCCCCCCCTGGTGAAGCTGTGGTACCAGCTGGAGAAGGAGCCCATCGTGGGCGCCGAGACCTTC
TACGTGGACGGCGCCGCCAACCGCGAGACCAAGCTGGGCAAGGCCGGCTACGTGACCGACCGGGGCCGG
CAGAAGGTGGTGAGCATCGCCGACACCACCAACCAGAAGACCGAGCTGCAGGCCATCCACCTGGCCCTG
CAGGACAGCGGCCTGGAGGTGAACATCGTGACCGACAGCCAGTACGCCCTGGGCATCATCCAGGCCCAG
CCCGACAAGAGCGAGAGCGAGCTGGTGAGCCAGATCATCGAGCAGCTGATCAAGAAGGAGAAGGTGTAC
CTGGCCTGGGTGCCCGCCCACAAGGGCATCGGCGGCAACGAGCAGGTGGACAAGCTGGTGAGCGCCGGC
ATCCGCAAGGTGCTCTAA

Figure 55 vif.opt.SF2

ATGGAGAACCGCTGGCAGGTGATGATCGTGTGGCAGGTGGACCGCATGCGCATCCGCACCTGGAAGAGC
CTGGTGAAGCACCACATGTACATCAGCAAGAAGGCCAAGGGCTGGTTCTACCGCCACCACTACGAGAGC
ACCCACCCCGCGTGAGCAGCGAGGTGCACATCCCCCTGGGCGACGCCAAGCTGGTGATCACCACCTAC
TGGGGCCTGCACACCGGCGAGCGCGAGTGGCACCTGGGCCAGGGCGTGGCCATCGAGTGGCGCAAGAAG
AAGTACAGCACCCAGGTGGACCCCGGCCTGGCCGACCAGCTGATCCACCTGCACTACTTCGACTGCTTC
AGCGAGAGCGCCATCAAGAACGCCATCCTGGGCTACCGCGTGAGCCCCGCTGCGAGTACCAGGCCGGC
CACAACAAGGTGGGCAGCCTGCAGTACCTGGCCCTGGCCGCCCTGATCACCCCCAAGAAGACCAAGCCC
CCCCTGCCCAGCGTGAAGAAGCTGACCGAGGACCGCTGGAACAAGCCCCAGAAGACCAAGGGCCACCGC
GGCAGCCACACCATGAACGGCCAC

Figure 56 vpr.opt.SF2

ATGGAGCAGGCCCCCGAGGACCAGGGCCCCCAGCGCGAGCCCTACAACGAGTGGACCCTGGAGCTGCTG
GAGGAGCTGAAGCGCGAGGCCGTGCGCCACTTCCCCCGCCCCTGGCTGCACAGCCTGGGCCAGTACATC
TACGAGACCTACGGCGACACCTGGGCCGGCGTGGAGGCCATCATCCGCATCCTGCAGCAGCTGCTGTTC
ATCCACTTCCGCATCGGCTGCCAGCACAGCCGCATCGGCATCATCCAGCAGCGCCGCGCCCGCCGCAAC
GGCGCCAGCCGCAGC

Figure 57 vpu.opt.SF162

ATGCAGCCCCTGCAGATCCTGGCCATCGTGGCCCTGGTGGTGGCCGCCATCATCGCCATCGTGGTGTGG
ACCATCGTGTACATCGAGTACCGCAAGATCCTGCGCCAGCGCAAGATCGACCGCCTGATCGACCGCATC
ACCGAGCGCGCCGAGGACAGCGGCAACGAGAGCGAGGGCGACCAGGAGGAGCTGAGCGCCCTGGTGGAG
CGCGGCCACCTGGCCCCCTGGGACGTGGACGACCTG

FIGURE 58 (SEQ ID NO:61)

gp140modSF162.GM135-154-186-195

```
   1 atggatgcaa tgaagagagg gctctgctgt gtgctgctgc tgtgtggagc agtcttcgtt
  61 tcgcccagcg ccgtggagaa gctgtgggtg accgtgtact acggcgtgcc cgtgtggaag
 121 gaggccacca ccaccctgtt ctgcgccagc gacgccaagg cctacgacac cgaggtgcac
 181 aacgtgtggg ccacccacgc ctgcgtgccc accgacccca accccagga gatcgtgctg
 241 gagaacgtga ccgagaactt caacatgtgg aagaacaaca tggtggagca gatgcacgag
 301 gacatcatca gcctgtggga ccagagcctg aagccctgcg tgaagctgac ccccctgtgc
 361 gtgacccctgc actgcaccaa cctgaagcag gccaccaaca ccaagagcag caactggaag
 421 gagatggacc gcggcgagat caagcagtgc agcttcaagg tgaccaccag catccgcaac
 481 aagatgcaga aggagtacgc cctgttctac aagctggacg tggtgcccat cgacaacgac
 541 cagaccagct acaagctgat caactgccag accagcgtga tcacccaggc ctgccccaag
 601 gtgagcttcg agcccatccc catccactac tgcgcccccg ccggcttcgc catcctgaag
 661 tgcaacgaca agaagttcaa cggcagcggc ccctgcacca acgtgagcac cgtgcagtgc
 721 acccacggca tccgccccgt ggtgagcacc cagctgctgc tgaacggcag cctggccgag
 781 gagggcgtgg tgatccgcag cgagaacttc accgacaacg ccaagaccat catcgtgcag
 841 ctgaaggaga gcgtggagat caactgcacc cgccccaaca acaacacccg caagagcatc
 901 accatcggcc ccggccgcgc cttctacgcc accggcgaca tcatcggcga catccgccag
 961 gcccactgca acatcagcgg cgagaagtgg aacaacaccc tgaagcagat cgtgaccaag
1021 ctgcaggccc agttcggcaa caagaccatc gtgttcaagc agagcagcgg cggcgacccc
1081 gagatcgtga tgcacagctt caactgcggc ggcgagttct tctactgcaa cagcacccag
1141 ctgttcaaca gcacctggaa caacaccatc ggccccaaca acaccaacgg caccatcacc
1201 ctgccctgcc gcatcaagca gatcatcaac cgctggcagg aggtgggcaa ggccatgtac
1261 gcccccccca tccgcggcca gatccgctgc agcagcaaca tcaccggcct gctgctgacc
1321 cgcgacggcg gcaaggagat cagcaacacc accgagatct ccgccccgg cggcggcgac
1381 atgcgcgaca ctggcgcag cgagctgtac aagtacaagg tgtgaagat cgagcccctg
1441 ggcgtggccc ccaccaaggc caagcgccgc gtggtgcagc gcgagaagcg cgccgtgacc
1501 ctgggcgcca tgttcctggg cttcctgggc gccgccggca gcaccatggg cgcccgcagc
1561 ctgaccctga ccgtgcaggc ccgccagctg ctgagcggca tcgtgcagca gcagaacaac
1621 ctgctgcgcg ccatcgaggc ccagcagcac ctgctgcagc tgaccgtgtg gggcatcaag
1681 cagctgcagg cccgcgtgct ggccgtggag cgctacctga aggaccagca gctgctgggc
1741 atctggggct gcagcggcaa gctgatctgc accaccgccg tgccctggaa cgccagctgg
1801 agcaacaaga gcctggacca gatctggaac aacatgacct ggatggagtg ggagcgcgag
1861 atcgacaact acaccaacct gatctacacc ctgatcgagg agagccagaa ccagcaggag
1921 aagaacgagc aggagctgct ggagctggac aagtgggcca gcctgtggaa ctggttcgac
1981 atcagcaagt ggctgtggta catctaa
```

FIGURE 59 (SEQ ID NO:62)

gp140modSF162.GM154

```
   1 atggatgcaa tgaagagagg gctctgctgt gtgctgctgc tgtgtggagc agtcttcgtt
  61 tcgcccagcg ccgtggagaa gctgtgggtg accgtgtact acggcgtgcc cgtgtggaag
 121 gaggccacca ccaccctgtt ctgcgccagc gacgccaagg cctacgacac cgaggtgcac
 181 aacgtgtggg ccacccacgc ctgcgtgccc accgacccca cccccagga gatcgtgctg
 241 gagaacgtga ccgagaactt caacatgtgg aagaacaaca tggtggagca gatgcacgag
 301 gacatcatca gcctgtggga ccagagcctg aagccctgcg tgaagctgac cccctgtgc
 361 gtgaccctgc actgcaccaa cctgaagaac gccaccaaca ccaagagcag caactggaag
 421 gagatggacc gcggcgagat caagcagtgc agcttcaagg tgaccaccag catccgcaac
 481 aagatgcaga aggagtacgc cctgttctac aagctggacg tggtgcccat cgacaacgac
 541 aacaccagct acaagctgat caactgcaac accagcgtga tcacccaggc ctgccccaag
 601 gtgagcttcg agcccatccc catccactac tgcgcccccg ccggcttcgc catcctgaag
 661 tgcaacgaca gaagttcaa cggcagcggc cctgcacca acgtgagcac cgtgcagtgc
 721 acccacggca tccgccccgt ggtgagcacc cagctgctgc tgaacggcag cctggccgag
 781 gagggcgtgg tgatccgcag cgagaacttc accgacaacg ccaagaccat catcgtgcag
 841 ctgaaggaga gcgtggagat caactgcacc cgccccaaca caacacccg caagagcatc
 901 accatcggcc ccggccgcgc cttctacgcc accggcgaca tcatcggcga catccgccag
 961 gcccactgca acatcagcgg cgagaagtgg aacaacaccc tgaagcagat cgtgaccaag
1021 ctgcaggccc agttcggcaa caagaccatc gtgttcaagc agagcagcgg cggcgacccc
1081 gagatcgtga tgcacagctt caactgcggc ggcgagttct tctactgcaa cagcacccag
1141 ctgttcaaca gcacctggaa caacaccatc ggccccaaca acaccaacgg caccatcacc
1201 ctgccctgcc gcatcaagca gatcatcaac cgctggcagg aggtgggcaa ggccatgtac
1261 gcccccccca tccgcggcca gatccgctgc agcagcaaca tcaccggcct gctgctgacc
1321 cgcgacggcg gcaaggagat cagcaacacc accgagatct ccgccccgg cggcggcgac
1381 atgcgcgaca actggcgcag cgagctgtac aagtacaagg tggtgaagat cgagcccctg
1441 ggcgtggccc ccaccaaggc caagcgccgc gtggtgcagc gcgagaagcg cgccgtgacc
1501 ctgggcgcca tgttcctggg cttcctgggc gccgccggca gcaccatggg cgcccgcagc
1561 ctgaccctga ccgtgcaggc ccgccagctg ctgagcggca tcgtgcagca gcagaacaac
1621 ctgctgcgcg ccatcgaggc ccagcagcac ctgctgcagc tgaccgtgtg gggcatcaag
1681 cagctgcagg cccgcgtgct ggccgtggag cgctacctga aggaccagca gctgctgggc
1741 atctggggct gcagcggcaa gctgatctgc accaccgccg tgccctggaa cgccagctgg
1801 agcaacaaga gcctggacca gatctggaac aacatgacct ggatggagtg ggagcgcgag
1861 atcgacaact acaccaacct gatctacacc ctgatcgagg agagccagaa ccagcaggag
1921 aagaacgagc aggagctgct ggagctggac aagtgggcca gcctgtggaa ctggttcgac
1981 atcagcaagt ggctgtggta catctaa
```

FIGURE 60 (SEQ ID NO:63)

gp140modSF162.Gm154-186-195

```
   1 atggatgcaa tgaagagagg gctctgctgt gtgctgctgc tgtgtggagc agtcttcgtt
  61 tcgcccagcg ccgtggagaa gctgtgggtg accgtgtact acggcgtgcc cgtgtggaag
 121 gaggccacca ccaccctgtt ctgcgccagc gacgccaagg cctacgacac cgaggtgcac
 181 aacgtgtggg ccacccacgc ctgcgtgccc accaccccca cccccagga gatcgtgctg
 241 gagaacgtga ccgagaactt caacatgtgg aagaacaaca tggtggagca gatgcacgag
 301 gacatcatca gcctgtggga ccagagcctg aagccctgcg tgaagctgac ccccctgtgc
 361 gtgaccctgc actgcaccaa cctgaagaac gccaccaaca ccaagagcag caactggaag
 421 gagatggacc gcggcgagat caagcagtgc agcttcaagg tgaccaccag catccgcaac
 481 aagatgcaga aggagtacgc cctgttctac aagctggacg tggtgcccat cgacaacgac
 541 cagaccagct acaagctgat caactgccag accagcgtga tcacccaggc ctgccccaag
 601 gtgagcttcg agcccatccc catccactac tgcgccccg ccggcttcgc catcctgaag
 661 tgcaacgaca agaagttcaa cggcagcggc ccctgcacca acgtgagcac cgtgcagtgc
 721 acccacggca tccgccccgt ggtgagcacc cagctgctgc tgaacggcag cctggccgag
 781 gagggcgtgg tgatccgcag cgagaacttc accgacaacg ccaagaccat catcgtgcag
 841 ctgaaggaga gcgtggagat caactgcacc cgccccaaca acaacacccg caagagcatc
 901 accatcggcc ccggccgcgc cttctacgcc accggcgaca tcatcggcga catccgccag
 961 gcccactgca acatcagcgg cgagaagtgg aacaacaccc tgaagcagat cgtgaccaag
1021 ctgcaggccc agttcggcaa caagaccatc gtgttcaagc agagcagcgg cggcgacccc
1081 gagatcgtga tgcacagctt caactgcggc ggcgagttct ctactgcaa cagcacccag
1141 ctgttcaaca gcacctggaa caacaccatc ggccccaaca acaccaacgg caccatcacc
1201 ctgccctgcc gcatcaagca gatcatcaac cgctggcagg aggtgggcaa ggccatgtac
1261 gccccccca tccgcggcca gatccgctgc agcagcaaca tcaccggcct gctgctgacc
1321 cgcgacggcg gcaaggagat cagcaacacc accgagatct ccgccccgg cggcggcgac
1381 atgcgcgaca actggcgcag cgagctgtac aagtacaagg tggtgaagat cgagcccctg
1441 ggcgtggccc ccaccaaggc caagcgccgc gtggtgcagc gcgagaagcg cgccgtgacc
1501 ctgggcgcca tgttcctggg cttcctgggc gccgccggca gcaccatggg cgcccgcagc
1561 ctgaccctga ccgtgcaggc ccgccagctg ctgagcggca tcgtgcagca gcagaacaac
1621 ctgctgcgcg ccatcgaggc ccagcagcac ctgctgcagc tgaccgtgtg gggcatcaag
1681 cagctgcagg cccgcgtgct ggccgtggag cgctacctga aggaccagca gctgctgggc
1741 atctggggct gcagcggcaa gctgatctgc accaccgccg tgccctggaa cgccagctgg
1801 agcaacaaga gcctggacca gatctggaac aacatgacct ggatggagtg ggagcgcgag
1861 atcgacaact acaccaacct gatctacacc ctgatcgagg agagccagaa ccagcaggag
1921 aagaacgagc aggagctgct ggagctggac aagtgggcca gcctgtggaa ctggttcgac
1981 atcagcaagt ggctgtggta catctaa
```

FIGURE 61 (SEQ ID NO:64)

gp140mut7.modSF162.GM154

```
   1 atggatgcaa tgaagagagg gctctgctgt gtgctgctgc tgtgtggagc agtcttcgtt
  61 tcgcccagcg ccgtggagaa gctgtgggtg accgtgtact acggcgtgcc cgtgtggaag
 121 gaggccacca ccaccctgtt ctgcgccagc gacgccaagg cctacgacac cgaggtgcac
 181 aacgtgtggg ccacccacgc ctgcgtgccc accgacccca cccccagga gatcgtgctg
 241 gagaacgtga ccgagaactt caacatgtgg aagaacaaca tggtggagca gatgcacgag
 301 gacatcatca gcctgtggga ccagagcctg aagccctgcg tgaagctgac cccctgtgc
 361 gtgaccctgc actgcaccaa cctgaagaac gccaccaaca ccaagagcag caactggaag
 421 gagatggacc gcggcgagat caagcagtgc agcttcaagg tgaccaccag catccgcaac
 481 aagatgcaga aggagtacgc cctgttctac aagctggacg tggtgcccat cgacaacgac
 541 aacaccagct acaagctgat caactgcaac accagcgtga tcacccaggc ctgccccaag
 601 gtgagcttcg agcccatccc catccactac tgcgcccccg ccggcttcgc catcctgaag
 661 tgcaacgaca gaagttcaa cggcagcggc cctgcacca acgtgagcac cgtgcagtgc
 721 acccacggca tccgccccgt ggtgagcacc cagctgctgc tgaacggcag cctggccgag
 781 gagggcgtgg tgatccgcag cgagaacttc accgacaacg ccaagaccat catcgtgcag
 841 ctgaaggaga gcgtggagat caactgcacc cgccccaaca acaacacccg caagagcatc
 901 accatcggcc ccggccgcgc cttctacgcc accggcgaca tcatcggcga catccgccag
 961 gcccactgca acatcagcgg cgagaagtgg aacaacaccc tgaagcagat cgtgaccaag
1021 ctgcaggccc agttcggcaa caagaccatc gtgttcaagc agagcagcgg cggcgacccc
1081 gagatcgtga tgcacagctt caactgcggc ggcgagttct tctactgcaa cagcacccag
1141 ctgttcaaca gcacctggaa caacaccatc ggccccaaca acaccaacgg caccatcacc
1201 ctgccctgcc gcatcaagca gatcatcaac cgctggcagg aggtgggcaa ggccatgtac
1261 gccccccca tccgcggcca gatccgctgc agcagcaaca tcaccggcct gctgctgacc
1321 cgcgacggcg gcaaggagat cagcaacacc accgagatct ccgccccgg cggcggcgac
1381 atgcgcgaca actggcgcag cgagctgtac aagtacaagg tggtgaagat cgagcccctg
1441 ggcgtggccc ccaccaaggc catcagcagc gtggtgcaga gcgagaagag cgccgtgacc
1501 ctgggcgcca tgttcctggg cttcctgggc gccgccggca gcaccatggg cgcccgcagc
1561 ctgacccctga ccgtgcaggc ccgccagctg ctgagcggca tcgtgcagca gcagaacaac
1621 ctgctgcgcg ccatcgaggc ccagcagcac ctgctgcagc tgaccgtgtg gggcatcaag
1681 cagctgcagg cccgcgtgct ggccgtggag cgctacctga aggaccagca gctgctgggc
1741 atctggggct gcagcggcaa gctgatctgc accaccgccg tgccctggaa cgccagctgg
1801 agcaacaaga gcctggacca gatctggaac aacatgacct ggatggagtg ggagcgcgag
1861 atcgacaact acaccaacct gatctacacc ctgatcgagg agagccagaa ccagcaggag
1921 aagaacgagc aggagctgct ggagctggac aagtgggcca gcctgtggaa ctggttcgac
1981 atcagcaagt ggctgtggta catctaa
```

```
Translation of:                    101
     gp140modSF162       (101) DIISLWDQSLKPCVKLTPLCVTLHCTNLKNATNTKSSNWKEMDRGEIKNC
     gp140.modSF162.GM154 (101) DIISLWDQSLKPCVKLTPLCVTLHCTNLKNATNTKSSNWKEMDRGEIKQC
gp140.modSF162.GM154-186-195 (101) DIISLWDQSLKPCVKLTPLCVTLHCTNLKNATNTKSSNWKEMDRGEIKQC
gp140.modSF162.GM135-154-186-195 (101) DIISLWDQSLKPCVKLTPLCVTLHCTNLKQATNTKSSNWKEMDRGEIKQC
              Consensus   (101) DIISLWDQSLKPCVKLTPLCVTLHCTNLKNATNTKSSNWKEMDRGEIKQC Translation of:                    151                                          200
     gp140modSF162       (151) SFKVTTSIRNKMQKEYALFYKLDVVPIDNDNTSYKLINCNTSVITQACPK
     gp140.modSF162.GM154 (151) SFKVTTSIRNKMQKEYALFYKLDVVPIDNDNTSYKLINCNTSVITQACPK
gp140.modSF162.GM154-186-195 (151) SFKVTTSIRNKMQKEYALFYKLDVVPIDNDQTSYKLINCQTSVITQACPK
gp140.modSF162.GM135-154-186-195 (151) SFKVTTSIRNKMQKEYALFYKLDVVPIDNDQTSYKLINCQTSVITQACPK
              Consensus   (151) SFKVTTSIRNKMQKEYALFYKLDVVPIDNDNTSYKLINCNTSVITQACPK
```

| Group | Animal | % Virus Inhibition | | | |
|---|---|---|---|---|---|
| | | Post-2$^{nd}$ DNA (1:20) | Post-2$^{nd}$ - DNA (1:100) | Post-Prot (1:100) | Post-Prot (1:500) |
| 1 | 1 | 0 | 60 | 0 | 17 |
| | 2 | 34 | 59 | 50 | 21 |
| | 3 | 0 | 0 | 12 | 38 |
| | 4 | 95 | 92 | 83 | 57 |
| 2 | 5 | 100 | 69 | 99 | 99 |
| | 6 | 0 | 28 | 27 | 35 |
| | 7 | 0 | 0 | 43 | 0 |
| | 8 | 95 | 38 | 79 | 74 |
| 3 | 9 | 40 | 0 | 61 | 26 |
| | 10 | 0 | 0 | 0 | 0 |
| | 11 | 94 | 41 | 91 | 57 |
| | 12 | 0 | 0 | 12 | 19 |
| 4 | 13 | 100 | 86 | 78 | 18 |
| | 14 | 20 | 0 | 68 | 0 |
| | 15 | 99 | 70 | 100 | 31 |
| | 16 | 0 | 33 | 0 | 24 |
| 5 | 17 | 100 | 67 | 100 | 75 |
| | 18 | 69 | 36 | 100 | 53 |
| | 19 | 58 | 33 | NA | NA |
| | 20 | 99 | 80 | 92 | 39 |
| 6 | 21 | NA | NA | NA | NA |
| | 22 | 78 | 12 | 100 | 88 |
| | 23 | 67 | 63 | 92 | 17 |
| | 24 | 70 | 62 | 77 | 0 |
| 7 | 29 | 100 | 100 | 74 | 68 |
| | 30 | 81 | 63 | 55 | 28 |
| | 31 | 100 | 79 | 100 | 91 |
| | 32 | 100 | 78 | 100 | 45 |
| Sub B positive serum | 20480 | 100 | 100 | 100 | 100 |

Figure 67

| Group | Animal | % Virus Inhibition | | ELISA Titer |
|---|---|---|---|---|
| | | TV1 | TV2 | |
| 1 | 1 | 0 | 38 | 19716 |
| | 2 | 25 | 67 | 37994 |
| | 3 | 0 | 0 | 7529 |
| | 4 | 0 | 79 | 41963 |
| 2 | 5 | 30 | 51 | 112768 |
| | 6 | 0 | 0 | 57677 |
| | 7 | 23 | 9 | 26247 |
| | 8 | 47 | 78 | 90376 |
| 3 | 9 | 0 | 42 | 62004 |
| | 10 | 13 | 0 | 5741 |
| | 11 | 0 | 36# | 53599 |
| | 12 | 21 | 12 | 37597 |
| 4 | 13 | 0 | 22# | 45543 |
| | 14 | 0 | 0 | 24885 |
| | 15 | 0 | 17# | 87556 |
| | 16 | 28# | 59 | 19838 |
| 5 | 17 | 72 | 80 | 124618 |
| | 18 | 0 | 77 | 143905 |
| | 19 | NA | NA | NA |
| | 20 | 19 | 56# | 91808 |
| 6 | 21 | NA | NA | NA |
| | 22 | 34 | 44 | 31413 |
| | 23 | 51 | 50# | 62925 |
| | 24 | 22 | 31# | 28620 |
| | 29 | 0 | 9 | 62604 |
| | 30 | 0 | 50# | 15932 |
| | 31 | 0 | 58 | 22418 |
| | 32 | 41 | 0 | 21119 |
| Sub B positive pool | | 46 | 56 | NA |
| Sub C positive pool | | 36 | 85 | NA |

Figure 68

| Group | Animal | % Virus Inhibition | | | ELISA titer |
|---|---|---|---|---|---|
| | | TV1 | Du174 | SF162 | |
| 1 | 1 | 28 | 20 | 12 | 19716 |
| | 2 | 33 | 19 | 9 | 37994 |
| | 3 | 0 | 0 | 0 | 7529 |
| | 4 | 52 | 61 | 79 | 41963 |
| 2 | 5 | 33 | 0 | 95 | 112768 |
| | 6 | 3 | 0 | 14 | 57677 |
| | 7 | 0 | 0 | 0 | 26247 |
| | 8 | 54 | 0 | 86 | 90376 |
| 3 | 9 | 0 | 52 | 73 | 62004 |
| | 10 | 0 | 58 | 15 | 5741 |
| | 11 | 0 | 0 | 71 | 53599 |
| | 12 | 0 | 0 | 0 | 37597 |
| 4 | 13 | 15 | 0 | 69 | 45543 |
| | 14 | 0 | 0 | 0 | 24885 |
| | 15 | 0 | 13 | 0 | 87556 |
| | 16 | 14 | 0 | 0 | 19838 |
| 5 | 17 | 0 | 0 | 0 | 124618 |
| | 18 | 0 | 0 | 30 | 143905 |
| | 19 | NA | NA | NA | NA |
| | 20 | 63 | 0 | 56 | 91808 |
| 6 | 21 | NA | NA | NA | NA |
| | 22 | 24 | NV | 38 | 31413 |
| | 23 | 7 | 65 | 76 | 62925 |
| | 24 | 0 | NV | NV | 28620 |
| 7 | 29 | 32 | 0 | 82 | 62604 |
| | 30 | 6 | NV | 0 | 15932 |
| | 31 | 0 | 0 | 98 | 22418 |
| | 32 | 34 | 0 | 0 | 21119 |

POLYNUCLEOTIDES ENCODING ANTIGENIC HIV TYPE B POLYPEPTIDES, POLYPEPTIDES, AND USES THEREOF

CROSS-REFERENCE TO RELATED APPLICATIONS

This application is a division of Ser. No. 11/100,356 filed Apr. 6, 2005, now abandoned, which is a continuation-in-part of Ser. No. 10/190,434 filed Jul. 5, 2002, now abandoned, which claims the benefit of Ser. No. 60/349,728 filed Jan. 16, 2002 and Ser. No. 60/316,860 filed Aug. 31, 2001. Ser. No. and Ser. No. 10/387,336 filed Mar. 11, 2003. Said Ser. No. 11/100,356 is also a continuation-in-part of Ser. No. 10/387, 336 filed Mar. 11, 2003, now U.S. Pat. No. 7,348,177, which is a continuation of Ser. No. 09/475,515 filed on Dec. 30, 1999 now U.S. Pat. No. 6,602,705, and which claims the benefit of Ser. No. 60/114,495 filed Dec. 31, 1998 and Ser. No. 60/168,471 filed Dec. 1, 1999. Each of these applications is incorporated herein by reference in its entirety.

BACKGROUND OF THE INVENTION

Acquired immune deficiency syndrome (AIDS) is recognized as one of the greatest health threats facing modern medicine. There is, as yet, no cure for this disease.
In 1983-1984, three groups independently identified the suspected etiological agent of AIDS. See, e.g., Barre-Sinoussi et al. (1983) Science 220:868-871; Montagnier et al, in Human T-Cell Leukemia Viruses (Gallo, Essex & Gross eds., 1984) Vilmer et al. (1984) The Lancet 1:753; Popovic et al. (1984) Science 224:497-500; Levy et al. (1984) Science 225:840-842. These isolates were variously called lymphadenopathy-associated virus (LAV), human T-cell lymphotrophic virus type III (HTLV-III), or AIDS-associated retrovirus (ARV). All of these isolates are strains of the same virus, and were later collectively named Human Immunodeficiency Virus (HIV). With the isolation of a related AIDS-causing virus, the strains originally called HIV are now termed HIV-1 and the related virus is called HIV-2 See, e.g., Guyader et al. (1987) Nature 326:662-669; Brun-Vezinet et al. (1986) Science 233: 343-346; Clavel et al. (1986) Nature 324:691-695.

A great deal of information has been gathered about the HIV virus, however, to date an effective vaccine has not been identified. Several targets for vaccine development have been examined including the env and Gag gene products encoded by HIV. Gag gene products include, but are not limited to, Gag-polymerase and Gag-protease. Env gene products include, but are not limited to, monomeric gp120 polypeptides, oligomeric gp140 polypeptides and gp160 polypeptides.

Haas, et al., (*Current Biology* 6(3):315-324, 1996) suggested that selective codon usage by HIV-1 appeared to account for a substantial fraction of the inefficiency of viral protein synthesis. Andre, et al., (*J. Virol.* 72(2): 1497-1503, 1998) described an increased immune response elicited by DNA vaccination employing a synthetic gp120 sequence with modified codon usage. Schneider, et al., (*J Virol.* 71(7): 4892-4903, 1997) discuss inactivation of inhibitory (or instability) elements (INS) located within the coding sequences of the Gag and Gag-protease coding sequences.

The Gag proteins of HIV-1 are necessary for the assembly of virus-like particles. HIV-1 Gag proteins are involved in many stages of the life cycle of the virus including, assembly, virion maturation after particle release, and early post-entry steps in virus replication. The roles of HIV-1 Gag proteins are numerous and complex (Freed, E. O., *Virology* 251:1-15, 1998).

Wolf, et al., (PCT International Application, WO 96/30523, published 3 Oct. 1996; European Patent Application, Publication No. 0 449 116 A1, published 2 Oct. 1991) have described the use of altered pr55 Gag of HIV-1 to act as a non-infectious retroviral-like particulate carrier, in particular, for the presentation of immunologically important epitopes. Wang, et al., (*Virology* 200:524-534, 1994) describe a system to study assembly of HIV Gag-β-galactosidase fusion proteins into virions. They describe the construction of sequences encoding HIV Gag-β-galactosidase fusion proteins, the expression of such sequences in the presence of HIV Gag proteins, and assembly of these proteins into virus particles.

Shiver, et al., (PCT International Application, WO 98/34640, published 13 Aug. 1998) described altering HIV-1 (CAM1) Gag coding sequences to produce synthetic DNA molecules encoding HIV Gag and modifications of HIV Gag. The codons of the synthetic molecules were codons preferred by a projected host cell.

Recently, use of HIV Env polypeptides in immunogenic compositions has been described. (see, U.S. Pat. No. 5,846, 546 to Hurwitz et al., issued Dec. 8, 1998, describing immunogenic compositions comprising a mixture of at least four different recombinant virus that each express a different HIV env variant; and U.S. Pat. No. 5,840,313 to Vahlne et al., issued Nov. 24, 1998, describing peptides which correspond to epitopes of the HIV-1 gp120 protein). In addition, U.S. Pat. No. 5,876,731 to Sia et al, issued Mar. 2, 1999 describes candidate vaccines against HIV comprising an amino acid sequence of a T-cell epitope of Gag linked directly to an amino acid sequence of a B-cell epitope of the V3 loop protein of an HIV-1 isolate containing the sequence GPGR.

SUMMARY OF THE INVENTION

Described herein are novel HIV sequences, polypeptides encoded by these novel sequences, and synthetic expression cassettes generated from these and other HIV sequences. In one aspect, the present invention relates to improved HIV expression cassettes. In a second aspect, the present invention relates to generating an immune response in a subject using the expression cassettes of the present invention. In a further aspect, the present invention relates to generating an immune response in a subject using the expression cassettes of the present invention, as well as, polypeptides encoded by the expression cassettes of the present invention. In another aspect, the present invention relates to enhanced vaccine technologies for the induction of potent neutralizing antibodies and/or cellular immune responses against HIV in a subject.

In certain embodiments, the present invention relates to synthetic polynucleotides and/or expression cassettes encoding HIV polypeptides, including, but not limited to, Env, Gag, Pol, RT, Int, Prot, Vpr, Vpu, Vif, Nef, Tat, Rev and/or fragments or combinations thereof. In addition, the present invention also relates to improved expression of HIV polypeptides and production of virus-like particles. Synthetic expression cassettes encoding the HIV polypeptides (e.g., Gag-, pol-, protease (prot)-, reverse transcriptase, integrase, RNAseH, Tat, Rev, Nef, Vpr, Vpu, Vif and/or Env-containing polypeptides) are described, as are uses of the expression cassettes. Mutations in some of the genes are described that reduce or eliminate the activity of the gene product without adversely affecting the ability of the gene product to generate an immune response. Exemplary synthetic polynucleotides include, but are not limited to, GagComplPolmut.SF2 (SEQ ID NO:9), GagComplPolmutAtt.SF2 (SEQ ID NO:10), GagComplPolmutIna.SF2 (SEQ ID NO:11), gagCpolIna-TatRevNef.opt_B (SEQ ID NO:12), GagPolmutAtt.SF2 (SEQ ID NO:13), GagPolmutIna.SF2 (SEQ ID NO:14), GagProtInaRTmut.SF2 (SEQ ID NO:15), GagProtInaRTmutTatRevNef.opt_B (SEQ ID NO:16), GagRTmut.SF2 (SEQ ID NO:17), GagTatRevNef.opt_B (SEQ ID NO:18), gp140.modSF162.CwtLmod (SEQ ID NO:19), gp140.modSF162.CwtLnat (SEQ ID NO:20), gp160.modSF162.delV2.mut7 (SEQ ID NO:21), gp160.modSF162.delV2.mut8 (SEQ ID NO:22), int.opt.mut.SF2 (SEQ ID NO:23), int.opt.SF2 (SEQ ID NO:24), nef.D125G.-myr.opt.SF162 (SEQ ID NO:25), nef.D107G.-myr18.opt.SF162 (SEQ ID NO:26), nef.opt.D125G.SF162 (SEQ ID NO:27), nef.opt.SF162 (SEQ ID NO:28), p15RnaseH.opt.SF2 (SEQ ID NO:29), p2Pol.opt.YMWM.SF2 (SEQ ID NO:30), p2PolInaopt.YM.SF2 (SEQ ID NO:31), p2Polopt.SF2 (SEQ ID NO:32), p2PolTatRevNef.opt.native_B (SEQ ID NO:33), p2PolTatRevNef.opt_B (SEQ ID NO:34), pol.opt.SF2 (SEQ ID NO:35), prot.opt.SF2 (SEQ ID NO:36), protIna.opt.SF2 (SEQ ID NO:37), protInaRT.YM.opt.SF2 (SEQ ID NO:38), protInaRT.YMWM.opt.SF2 (SEQ ID NO:39), ProtInaRTmut.SF2 (SEQ ID NO:40), protRT.opt.SF2 (SEQ ID NO:41), ProtRT.TatRevNef.opt_B (SEQ ID NO:42), ProtRT-TatRevNef.opt_B (SEQ ID NO:43), rev.exon1_2.M5-10.opt.SF162 (SEQ ID NO:44), rev.exon1_2.opt.SF162 (SEQ ID NO:45), RT.opt.SF2 (mutant) (SEQ ID NO:46), RT.opt.SF2 (native) (SEQ ID NO:47), RTmut.SF2 (SEQ ID NO:48), tat.exon1_2.opt.C22-37.SF2 (SEQ ID NO:49), tat.exon1_2.opt.C37.SF2 (SEQ ID NO:50), TatRevNef.opt.native.SF162 (SEQ ID NO:51), TatRevNef.opt.SF162 (SEQ ID NO:52), TatRevNefGag B (SEQ ID NO:53), TatRevNefgagCpolIna B (SEQ ID NO:54), TatRevNefGagProtInaRTmut B (SEQ ID NO:55), TatRevNefp2Pol.opt_B, (SEQ ID NO:56) TatRevNefprotRTopt B (SEQ ID NO:57), vif.opt.SF2 (SEQ ID NO:58), vpr.opt.SF2 (SEQ ID NO:59), and vpu.opt.SF162 (SEQ ID NO:60).

Thus, one aspect of the present invention relates to expression cassettes and polynucleotides contained therein. The expression cassettes typically include an HIV-polypeptide encoding sequence inserted into an expression vector backbone. In one embodiment, an expression cassette comprises a polynucleotide sequence encoding one or more polypeptides, wherein the polynucleotide sequence comprises a sequence having between about 85% to 100% and any integer values therebetween, for example, at least about 85%, preferably about 90%, more preferably about 95%, and more preferably about 98% sequence identity to the sequences taught in the present specification.

The polynucleotides encoding the HIV polypeptides of the present invention may also include sequences encoding additional polypeptides. Such additional polynucleotides encoding polypeptides may include, for example, coding sequences for other viral proteins (e.g., hepatitis B or C or other HIV proteins, such as, polynucleotide sequences encoding an HIV Gag polypeptide, polynucleotide sequences encoding an HIV Env polypeptide and/or polynucleotides encoding one or more of vif, vpr, tat, rev, vpu and nef); cytokines or other transgenes.

In one embodiment, the sequence encoding the HIV Pol polypeptide(s) can be modified by deletions of coding regions corresponding to reverse transcriptase and integrase. Such deletions in the polymerase polypeptide can also be made such that the polynucleotide sequence preserves T-helper cell and CTL epitopes. Other antigens of interest may be inserted into the polymerase as well.

In another embodiment, an expression cassette comprises a polynucleotide sequence encoding a polypeptide, for example, GagComplIPolmut.SF2 (SEQ ID NO:9), GagComplPolmutAtt.SF2 (SEQ ID NO:10), GagComplPolmutIna.SF2 (SEQ ID NO:11), gagCpolInaTatRevNef.opt_B (SEQ ID NO:12), GagPolmutAtt.SF2 (SEQ ID NO:13), GagPolmutIna.SF2 (SEQ ID NO:14), GagProtInaRTmut.SF2 (SEQ ID NO:15), GagProtInaRTmutTatRevNef.opt_B (SEQ ID NO:16), GagRTmut.SF2, (SEQ ID NO:17), GagTatRevNef.opt_B (SEQ ID NO:18), gp140.modSF162.CwtLmod (SEQ ID NO:19), gp140.modSF162.CwtLnat (SEQ ID NO:20), gp160.modSF162.delV2.mut7 (SEQ ID NO:21), gp160.modSF162.delV2.mut8 (SEQ ID NO:22), int.opt.mut.SF2 (SEQ ID NO:23), int.opt.SF2 (SEQ ID NO:24), nef.D125G.-myr.opt.SF162 (SEQ ID NO:25), nef.D107G.-myr18.opt.SF162 (SEQ ID NO:26), nef.opt.D125G.SF162 (SEQ ID NO:27), nef.opt.SF162 (SEQ ID NO:28), p15RnaseH.opt.SF2 (SEQ ID NO:29), p2Pol.opt.YMWM.SF2 (SEQ ID NO:30), p2PolInaopt.YM.SF2, (SEQ ID NO:31) p2Polopt.SF2 (SEQ ID NO:32), p2PolTatRevNef.opt.native_B (SEQ ID NO:33), p2PolTatRevNef.opt_B (SEQ ID NO:34), pol.opt.SF2 (SEQ ID NO:35), prot.opt.SF2 (SEQ ID NO:36), protIna.opt.SF2 (SEQ ID NO:37), protInaRT.YM.opt.SF2 (SEQ ID NO:38), protInaRT.YMWM.opt.SF2 (SEQ ID NO:39), ProtInaRTmut.SF2 (SEQ ID NO:40), protRT.opt.SF2 (SEQ ID NO:41), ProtRT.TatRevNef.opt_B (SEQ ID NO:42), ProtRT-TatRevNef.opt_B (SEQ ID NO:43), rev.exon1_2.M5-10.opt.SF162 (SEQ ID NO:44), rev.exon1_2.opt.SF162 (SEQ ID NO:45), RT.opt.SF2 (mutant) (SEQ ID NO:46), RT.opt.SF2 (native) (SEQ ID NO:47), RTmut.SF2 (SEQ ID NO:48), tat.exon1_2.opt.C22-37.SF2 (SEQ ID NO:49), tat.exon1_2. opt.C37.SF2 (SEQ ID NO:50), TatRevNef.opt.native.SF162 (SEQ ID NO:51), TatRevNef.opt.SF162 (SEQ ID NO:52), TatRevNefGag B (SEQ ID NO:53), TatRevNefgagCpolIna B (SEQ ID NO:54), TatRevNefGagProtInaRTmut B (SEQ ID NO:55), TatRevNefp2Pol.opt_B (SEQ ID NO:56), TatRevNefprotRTopt B (SEQ ID NO:57), vif.opt.SF2 (SEQ ID NO:58), vpr.opt.SF2 (SEQ ID NO:59), and vpu.opt.SF162 (SEQ ID NO:60), wherein the polynucleotide sequence encoding the polypeptide comprises a sequence having between about 85% to 100% and any integer values therebetween, for example, at least about 85%, preferably about 90%, more preferably about 95%, and most preferably about 98% sequence identity to the sequences taught in the present specification.

The native and synthetic polynucleotide sequences encoding the HIV polypeptides of the present invention typically have between about 85% to 100% and any integer values therebetween, for example, at least about 85%, preferably about 90%, more preferably about 95%, and more preferably about 98% sequence identity to the sequences taught herein. Further, in certain embodiments, the polynucleotide sequences encoding the HIV polypeptides of the invention will exhibit 100% sequence identity to the sequences taught herein.

The polynucleotides of the present invention can be produced by recombinant techniques, synthetic techniques, or combinations thereof.

The present invention further includes recombinant expression systems for use in selected host cells, wherein the recombinant expression systems employ one or more of the polynucleotides and expression cassettes of the present invention. In such systems, the polynucleotide sequences are operably linked to control elements compatible with expression in the selected host cell. Numerous expression control elements are known to those in the art, including, but not limited to, the following: transcription promoters, transcription enhancer elements, transcription termination signals, polyadenylation sequences, sequences for optimization of initiation of translation, and translation termination sequences. Exemplary transcription promoters include, but are not limited to those derived from CMV, CMV+intron A, SV40, RSV, HIV-Ltr, MMLV-ltr, and metallothionein.

In another aspect the invention includes cells comprising one or more of the expression cassettes of the present invention where the polynucleotide sequences are operably linked to control elements compatible with expression in the selected cell. In one embodiment such cells are mammalian cells. Exemplary mammalian cells include, but are not limited to, BHK, VERO, HT1080, 293, RD, COS-7, and CHO cells. Other cells, cell types, tissue types, etc., that may be useful in the practice of the present invention include, but are not limited to, those obtained from the following: insects (e.g., *Trichoplusia ni* (Tn5) and Sf9), bacteria, yeast, plants, antigen presenting cells (e.g., macrophage, monocytes, dendritic cells, B-cells, T-cells, stem cells, and progenitor cells thereof), primary cells, immortalized cells, tumor-derived cells.

In a further aspect, the present invention includes compositions for generating an immunological response, where the composition typically comprises at least one of the expression cassettes of the present invention and may, for example, contain combinations of expression cassettes such as one or more expression cassettes carrying a Pol-derived-polypeptide-encoding polynucleotide, one or more expression cassettes carrying a Gag-derived-polypeptide-encoding polynucleotide, one or more expression cassettes carrying accessory polypeptide-encoding polynucleotides (e.g., native or synthetic vpu, vpr, nef, vif, tat, rev), and/or one or more expression cassettes carrying an Env-derived-polypeptide-encoding polynucleotide. Such compositions may further contain an adjuvant or adjuvants. The compositions may also contain one or more HIV polypeptides. The HIV polypeptides may correspond to the polypeptides encoded by the expression cassette(s) in the composition, or may be different from those encoded by the expression cassettes. In compositions containing both expression cassettes (or polynucleotides of the present invention) and polypeptides, various expression cassettes of the present invention can be mixed and/or matched with various HIV polypeptides described herein.

In another aspect the present invention includes methods of immunization of a subject. In the method any of the above described compositions are into the subject under conditions that are compatible with expression of the expression cassette(s) in the subject. In one embodiment, the expression cassettes (or polynucleotides of the present invention) can be introduced using a gene delivery vector. The gene delivery vector can, for example, be a non-viral vector or a viral vector. Exemplary viral vectors include, but are not limited to eucaryotic layered vector initiation systems, Sindbis-virus (or other alphavirus) derived vectors, retroviral vectors, and lentiviral vectors. Other exemplary vectors include, but are not limited to, pCMVKm2, pCMV6a, pCMV-link, and pCMVPLEdhfr. Compositions useful for generating an immunological response can also be delivered using a particulate carrier (e.g., PLG or CTAB-PLG microparticles). Further, such compositions can be coated on, for example, gold or tungsten particles and the coated particles delivered to the subject using, for example, a gene gun. The compositions can also be formulated as liposomes. In one embodiment of this method, the subject is a mammal and can, for example, be a human.

In a further aspect, the invention includes methods of generating an immune response in a subject. Any of the expression cassettes described herein can be expressed in a suitable cell to provide for the expression of the HIV polypeptides encoded by the polynucleotides of the present invention. The polypeptide(s) are then isolated (e.g., substantially purified) and administered to the subject in an amount sufficient to elicit an immune response. In certain embodiments, the methods comprise administration of one or more of the expression cassettes or polynucleotides of the present invention, using any of the gene delivery techniques described herein. In other embodiments, the methods comprise co-administration of one or more of the expression cassettes or polynucleotides of the present invention and one or more polypeptides, wherein the polypeptides can be expressed from these polynucleotides or can be other HIV polypeptides. In other embodiments, the methods comprise co-administration of multiple expression cassettes or polynucleotides of the present invention. In still further embodiments, the methods comprise co-administration of multiple polypeptides, for example polypeptides expressed from the polynucleotides of the present invention and/or other HIV polypeptides.

The invention further includes methods of generating an immune response in a subject, where cells of a subject are transfected with any of the above-described expression cassettes or polynucleotides of the present invention, under conditions that permit the expression of a selected polynucleotide and production of a polypeptide of interest (e.g., encoded by any expression cassette of the present invention). By this method an immunological response to the polypeptide is elicited in the subject. Transfection of the cells may be performed ex vivo and the transfected cells are reintroduced into the subject. Alternately, or in addition, the cells may be transfected in vivo in the subject. The immune response may be humoral and/or cell-mediated (cellular). In a further embodiment, this method may also include administration of an HIV polypeptides before, concurrently with, and/or after introduction of the expression cassette into the subject.

The polynucleotides of the present invention may be employed singly or in combination. The polynucleotides of the present invention, encoding HIV-derived polypeptides, may be expressed in a variety of ways, including, but not limited to the following: a polynucleotide encoding a single gene product (or portion thereof) expressed from a promoter; multiple polynucleotides encoding a more than one gene product (or portion thereof) (e.g., polycistronic coding sequences); multiple polynucleotides in-frame to produce a single polyprotein; and, multiple polynucleotides in-frame to produce a single polyprotein wherein the polyprotein has protein cleavage sites between one or more of the polypeptides comprising the polyprotein.

These and other embodiments of the present invention will readily occur to those of ordinary skill in the art in view of the disclosure herein.

BRIEF DESCRIPTION OF THE FIGURES

FIGS. 1A to 1D depict the nucleotide sequence of HIV Type C 8__5_TV1_C.ZA (SEQ ID NO:1; referred to herein as TV1). Various regions are shown in Table A.

FIGS. 2A-C depicts an alignment of Env polypeptides from various HIV isolates (SF162, SEQ ID NO:2; TV1.8__2, SEQ ID NO:3; TV1.8__5, SEQ ID NO:4; TV2.12-5/1, SEQ ID NO:5; Consensus Sequence, SEQ ID NO:6). The regions between the arrows indicate regions (of TV1 and TV2 clones, both HIV Type C isolates) in the beta and/or bridging sheet region(s) that can be deleted and/or truncated. The "*" denotes N-linked glycosylation sites (of TV1 and TV2 clones), one or more of which can be modified (e.g., deleted and/or mutated).

FIG. 6, sheets 1 and 2, presents the sequence of GagComplPolmut.SF2 (SEQ ID NO:9).

FIG. 7, sheets 1 and 2, presents the sequence of GagComplPolmutAtt.SF2 (SEQ ID NO:10).

FIG. 8, sheets 1 and 2, presents the sequence of GagComplPolmutIna.SF2 (SEQ ID NO:11).

FIG. 9, sheets 1 and 2, presents the sequence of gagCpolInaTatRevNef.opt_B (SEQ ID NO:12).

FIG. 10, sheets 1 and 2, presents the sequence of GagPolmutAtt.SF2 (SEQ ID NO:13).

FIG. 11, sheets 1 and 2, presents the sequence of GagPolmutIna.SF2 (SEQ ID NO:14).

FIG. 12, sheets 1 and 2, presents the sequence of GagProtInaRTmut.SF2 (SEQ ID NO:15).

FIG. 13, sheets 1 and 2, presents the sequence of GagProtInaRTmutTatRevNef.opt_B (SEQ ID NO:16).

FIG. 14, sheets 1 and 2, presents the sequence of GagRTmut.SF2 (SEQ ID NO:17).

FIG. 15, presents the sequence of GagTatRevNef.opt_B (SEQ ID NO:18).

FIG. 16, presents the sequence of gp140.modSF162.CwtLmod (SEQ ID NO:19).

FIG. 17, presents the sequence of gp140.modSF162.CwtLnat (SEQ ID NO:20).

FIG. 18, presents the sequence of gp160.modSF162.delV2.mut7 (SEQ ID NO:21).

FIG. 19, presents the sequence of gp160.modSF162.delV2.mut8 (SEQ ID NO:22).

FIG. 20, presents the sequence of int.opt.mut.SF2 (SEQ ID NO:23).

FIG. 21, presents the sequence of int.opt.SF2 (SEQ ID NO:24).

FIG. 22, presents the sequence of nef.D125G.-myr.opt.SF162 (SEQ ID NO:25).

FIG. 23, presents the sequence of nef.D107G.-myr18.opt.SF162 (SEQ ID NO:26).

FIG. 24, presents the sequence of nef.opt.D125G.SF162 (SEQ ID NO:27).

FIG. 25, presents the sequence of nef.opt.SF162 (SEQ ID NO:28).

FIG. 26, presents the sequence of p15RnaseH.opt.SF2 (SEQ ID NO:29).

FIG. 27, presents the sequence of p2Pol.opt.YMWM.SF2 (SEQ ID NO:30).

FIG. 28, presents the sequence of p2PolInaopt.YM.SF2 (SEQ ID NO:31).

FIG. 29, presents the sequence of p2Polopt.SF2 (SEQ ID NO:32).

FIG. 30, presents the sequence of p2PolTatRevNef.opt.native_B (SEQ ID NO:33).

FIG. 31, sheets 1 and 2, presents the sequence of p2PolTatRevNef.opt_B (SEQ ID NO:34).

FIG. 32, presents the sequence of pol.opt.SF2 (SEQ ID NO:35).

FIG. 33, presents the sequence of prot.opt.SF2 (SEQ ID NO:36).

FIG. 34, presents the sequence of protIna.opt.SF2 (SEQ ID NO:37).

FIG. 35, presents the sequence of protInaRT.YM.opt.SF2 (SEQ ID NO:38).

FIG. 36, presents the sequence of protInaRT.YMWM.opt.SF2 (SEQ ID NO:39).

FIG. 37, presents the sequence of ProtInaRTmut.SF2 (SEQ ID NO:40).

FIG. 38, presents the sequence of protRT.opt.SF2 (SEQ ID NO:41).

FIG. 39, presents the sequence of ProtRT.TatRevNef.opt_B (SEQ ID NO:42).

FIG. 40, presents the sequence of ProtRTTatRevNef.opt_B (SEQ ID NO:43).

FIG. 41, presents the sequence of rev.exon1_2.M5-10.opt.SF162 (SEQ ID NO:44).

FIG. 42, presents the sequence of rev.exon1_2.opt.SF162 (SEQ ID NO:45).

FIG. 43, presents the sequence of RT.opt.SF2 (mutant) (SEQ ID NO:46).

FIG. 44, presents the sequence of RT.opt.SF2 (native) (SEQ ID NO:47).

FIG. 45, presents the sequence of RTmut.SF2 (SEQ ID NO:48).

FIG. 46, presents the sequence of tat.exon1_2.opt.C22-37.SF2 (SEQ ID NO:49).

FIG. 47, presents the sequence of tat.exon1_2.opt.C37.SF2 (SEQ ID NO:50).

FIG. 48, presents the sequence of TatRevNef.opt.native.SF162 (SEQ ID NO:51).

FIG. 49, presents the sequence of TatRevNef.opt.SF162 (SEQ ID NO:52).

FIG. 50, presents the sequence of TatRevNefGag B (SEQ ID NO:53).

FIG. 51, sheets 1 and 2, presents the sequence of TatRevNefgagCpolIna B (SEQ ID NO:54).

FIG. 52, sheets 1 and 2, presents the sequence of TatRevNefGagProtInaRTmut B (SEQ ID NO:55).

FIG. 53, presents the sequence of TatRevNefp2Pol.opt_B (SEQ ID NO:56).

FIG. 54, presents the sequence of TatRevNefprotRTopt B (SEQ ID NO:57).

FIG. 55, presents the sequence of vif.opt.SF2 (SEQ ID NO:58).

FIG. 56, presents the sequence of vpr.opt.SF2 (SEQ ID NO:59).

FIG. 57, presents the sequence of vpu.opt.SF162 (SEQ ID NO:60).

FIG. 58, presents the sequence of gp140modSF162.GM135-154-186-195 (SEQ ID NO:61).

FIG. 59, presents the sequence of gp140modSF162.GM154 (SEQ ID NO:62).

FIG. 60, presents the sequence of gp140modSF162.GM154-186-195 (SEQ ID NO:63).

FIG. 61, presents the sequence of gp140mut7.modSF162.GM154 (SEQ ID NO:64).

FIG. 62 depicts alignment of amino acid sequences of various Env glycosylation mutants (GM), including amino acid translation of gp140modSF162 (SEQ ID NO:65); translation of gp140.modSF162.GM154 (SEQ ID NO:66); translation of gp140.modSF162.GM154-186-195 (SEQ ID NO:67); and gp140.modSF162.GM135-154-186-195 (SEQ ID NO:68).

FIG. 66 presents data of neutralizing antibody responses against subtype B SF162 EnvdV2 strain in rabbits immunized with subtype C TV1 Env in a DNA prime protein boost regimen.

FIG. 67 presents data of neutralizing antibody responses against subtype C primary strains, TV1 and TV2 in 5.25 reporter cell assay after a single protein boost.

FIG. 68 presents data of neutralizing antibody responses against subtype C, TV1 and Du174, and subtype B, SF162 after a single protein boost (as measured by Duke PBMC assay).

DETAILED DESCRIPTION OF THE INVENTION

Figure 3:
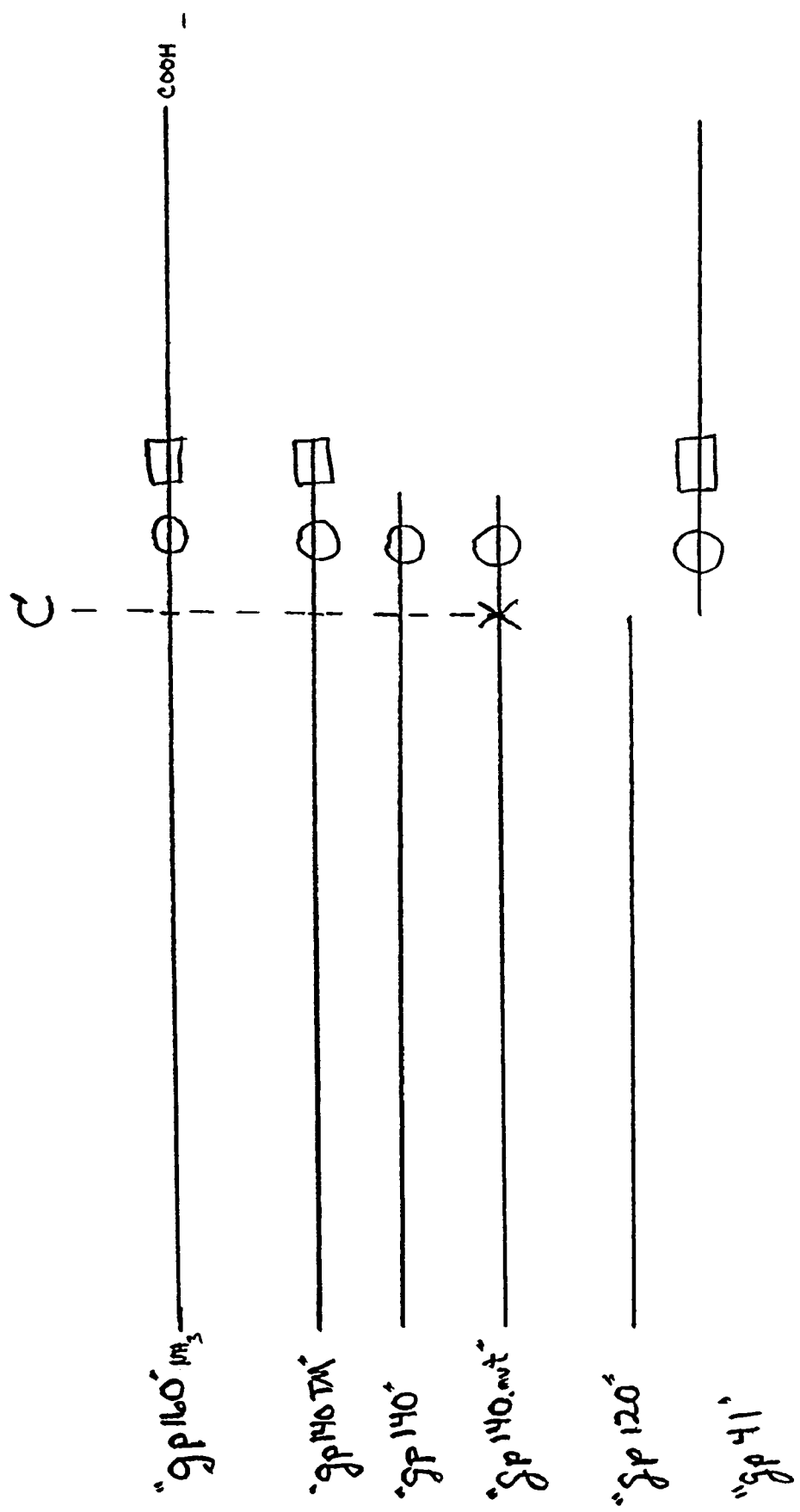
FIG. 3 presents a schematic diagram showing the relationships between the following forms of the HIV Env polypeptide: gp160, gp140, gp120, and gp41.
Figure 4:
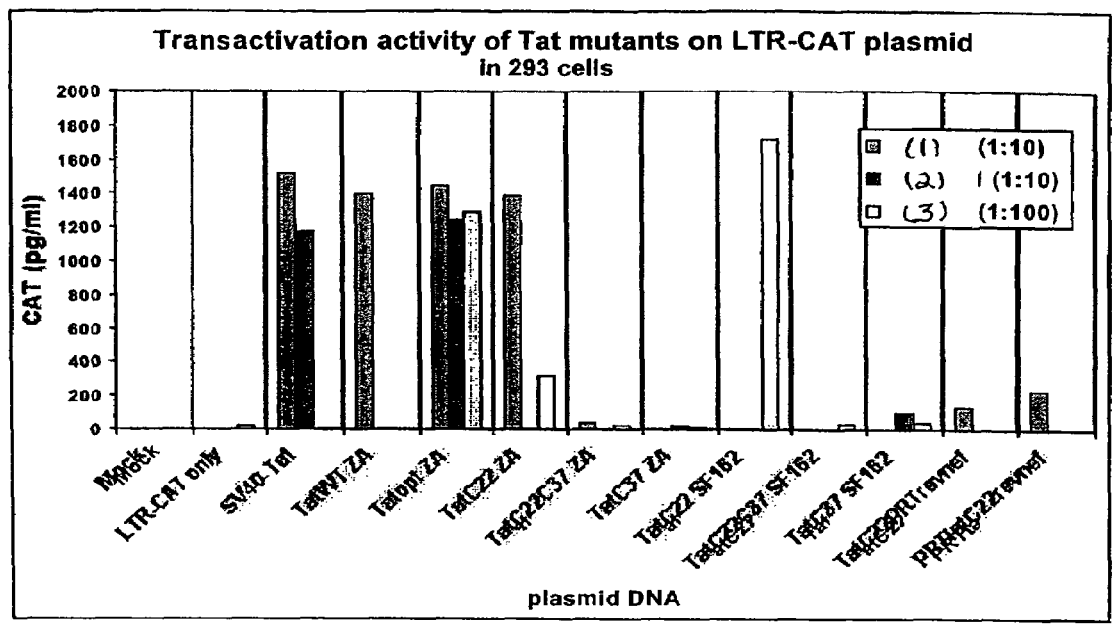
FIG. 4 presents exemplary data concerning transactivation activity of Tat mutants on LTR-CAT plasmid expression in 293 cells.

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); and *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Short Protocols in Molecular Biology*, 4th ed. (Ausubel et al. eds., 1999, John Wiley & Sons); *Molecular Biology Techniques: An Intensive Laboratory Course*, (Ream et al., eds., 1998, Academic Press); PCR (*Introduction to Biotechniques Series*), 2nd ed. (Newton & Graham eds., 1997, Springer Verlag).

All publications, patents and patent applications cited herein, whether supra or infra, are hereby incorporated by reference in their entirety.

As used in this specification, the singular forms "a," "an" and "the" include plural references unless the content clearly dictates otherwise. Thus, for example, reference to "an antigen" includes a mixture of two or more such agents.

1. DEFINITIONS

In describing the present invention, the following terms will be employed, and are intended to be defined as indicated below.

"Synthetic" sequences, as used herein, refers to HIV polypeptide-encoding polynucleotides whose expression has been modified as described herein, for example, by codon substitution, altered activities, and/or inactivation of inhibitory sequences. "Wild-type" or "native" sequences, as used herein, refers to polypeptide encoding sequences that are essentially as they are found in nature, e.g., Gag, Pol, Vif, Vpr, Tat, Rev, Vpu, Env and/or Nef encoding sequences as found in HIV isolates, e.g., SF162, SF2, AF110965, AF110967, AF110968, AF110975, 8_5_TV1_C.ZA, 8_2_TV1_C.ZA or 12-5_1_TV2_C.ZA. The various regions of the HIV genome are shown in Table A, with numbering relative to 8_5_TV1_C.ZA (FIGS. 1A-1D). Thus, the term "Pol" refers to one or more of the following polypeptides: polymerase (p6Pol); protease (prot); reverse transcriptase (p66RT or RT); RNAseH (p15RNAseH); and/or integrase (p31Int or Int). Identification of gene regions for any selected HIV isolate can be performed by one of ordinary skill in the art based on the teachings presented herein and the information known in the art, for example, by performing alignments relative to 8_5_TV1_C.ZA (FIGS. 1A-1D) or alignment to other known HIV isolates, for example, Subtype β isolates with gene regions (e.g., SF2, GenBank Accession number K02007; SF162, GenBank Accession Number M38428, both herein incorporated by reference) and Subtype C isolates with gene regions (e.g., GenBank Accession Number AF110965 and GenBank Accession Number AF110975, both herein incorporated by reference).

As used herein, the term "virus-like particle" or "VLP" refers to a nonreplicating, viral shell, derived from any of several viruses discussed further below. VLPs are generally composed of one or more viral proteins, such as, but not limited to those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art and discussed more fully below. The presence of VLPs following recombinant expression of viral proteins can be detected using conventional techniques known in the art, such as by electron microscopy, X-ray crystallography, and the like. See, e.g., Baker et al., *Biophys. J.* (1991) 60:1445-1456; Hagensee et al., *J. Virol.* (1994) 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

By "particle-forming polypeptide" derived from a particular viral protein is meant a full-length or near full-length viral protein, as well as a fragment thereof, or a viral protein with internal deletions, which has the ability to form VLPs under conditions that favor VLP formation. Accordingly, the polypeptide may comprise the full-length sequence, fragments, truncated and partial sequences, as well as analogs and precursor forms of the reference molecule. The term therefore intends deletions, additions and substitutions to the sequence, so long as the polypeptide retains the ability to form a VLP. Thus, the term includes natural variations of the specified polypeptide since variations in coat proteins often occur between viral isolates. The term also includes deletions, additions and substitutions that do not naturally occur in the reference protein, so long as the protein retains the ability to form a VLP. Preferred substitutions are those which are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids.

The term "HIV polypeptide" refers to any amino acid sequence that exhibits sequence homology to native HIV polypeptides (e.g., Gag, Env, Prot, Pol, RT, Int, vif, vpr, vpu, tat, rev, nef and/or combinations thereof) and/or which is functional. Non-limiting examples of functions that may be exhibited by HIV polypeptides include, use as immunogens (e.g., to generate a humoral and/or cellular immune response), use in diagnostics (e.g, bound by suitable antibodies for use in ELISAs or other immunoassays) and/or polypeptides which exhibit one or more biological activities associated with the wild type or synthetic HIV polypeptide. For example, as used herein, the term "Gag polypeptide" may refer to a polypeptide that is bound by one or more anti-Gag antibodies; elicits a humoral and/or cellular immune response; and/or exhibits the ability to form particles.

An "antigen" refers to a molecule containing one or more epitopes (either linear, conformational or both) that will stimulate a host's immune system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

For purposes of the present invention, antigens can be derived from any of several known viruses, bacteria, parasites and fungi, as described more fully below. The term also intends any of the various tumor antigens. Furthermore, for purposes of the present invention, an "antigen" refers to a protein which includes modifications, such as deletions, additions and substitutions (generally conservative in nature), to the native sequence, so long as the protein maintains the ability to elicit an immunological response, as defined herein. These modifications may be deliberate, as through site-directed mutagenesis, or may be accidental, such as through mutations of hosts which produce the antigens.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376. Recent methods of measuring cell-mediated immune response include measurement of intracellular cytokines or cytokine secretion by T-cell populations, or by measurement of epitope specific T-cells (e.g., by the tetramer technique)(reviewed by McMichael, A. J., and O'Callaghan, C. A., *J. Exp. Med.* 187(9)1367-1371, 1998; Mcheyzer-Williams, M. G., et al, *Immunol. Rev.* 150: 5-21, 1996; Lalvani, A., et al, *J. Exp. Med.* 186:859-865, 1997).

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic composition" is a composition that comprises an antigenic molecule where administration of the composition to a subject results in the development in the subject of a humoral and/or a cellular immune response to the antigenic molecule of interest. The immunogenic composition can be introduced directly into a recipient subject, such as by injection, inhalation, oral, intranasal and mucosal (e.g., intra-rectally or intra-vaginally) administration.

By "subunit vaccine" is meant a vaccine composition which includes one or more selected antigens but not all antigens, derived from or homologous to, an antigen from a pathogen of interest such as from a virus, bacterium, parasite or fungus. Such a composition is substantially free of intact pathogen cells or pathogenic particles, or the lysate of such cells or particles. Thus, a "subunit vaccine" can be prepared from at least partially purified (preferably substantially purified) immunogenic polypeptides from the pathogen, or analogs thereof. The method of obtaining an antigen included in the subunit vaccine can thus include standard purification techniques, recombinant production, or synthetic production.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence such as a stop codon may be located 3' to the coding sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences. For example, the sequences and/or vectors described herein may also include one or more additional sequences that may optimize translation and/or termination including, but not limited to, a Kozak sequence (e.g., GCCACC placed in front (5') of the ATG of the codon-optimized wild-type leader or any other suitable leader sequence (e.g., tpa1, tpa2, wtLnat (native wild-type leader)) or a termination sequence (e.g., TAA or, preferably, TAAA placed after (3') the coding sequence.

A "polynucleotide coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon, for example, at or near the 5' terminus and a translation stop codon, for example, at or near the 3' terminus. Exemplary coding sequences are the modified viral polypeptide-coding sequences of the present invention. The coding regions of the polynucleotide sequences of the present invention are identifiable by one of skill in the art and may, for example, be easily identified by performing translations of all three frames of the polynucleotide and identifying the frame corresponding to the encoded polypeptide, for example, a synthetic nef polynucleotide of the present invention encodes a nef-derived polypeptide. A transcription termination sequence may be located 3' to the coding sequence. Typical "control elements", include, but are not limited to, transcription regulators, such as promoters, transcription enhancer elements, transcription termination signals, and polyadenylation sequences; and translation regulators, such as sequences for optimization of initiation of translation, e.g., Shine-Dalgarno (ribosome binding site) sequences, Kozak sequences (i.e., sequences for the optimization of translation, located, for example, 5' to the coding sequence), leader sequences, translation initiation codon (e.g., ATG), and translation termination sequences. In certain embodiments, one or more translation regulation or initiation sequences (e.g., the leader sequence) are derived from wild-type translation initiation sequences, i.e., sequences that regulate translation of the coding region in their native state. Wild-type leader sequences that have been modified, using the methods described herein, also find use in the present invention. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

A "nucleic acid" molecule can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used inter-changeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

One of skill in the art can readily determine the proper search parameters to use for a given sequence, exemplary preferred Smith Waterman based parameters are presented above. For example, the search parameters may vary based on the size of the sequence in question. Thus, for the polynucleotide sequences of the present invention the length of the polynucleotide sequence disclosed herein is searched against a selected database and compared to sequences of essentially the same length to determine percent identity. For example, a representative embodiment of the present invention would include an isolated polynucleotide comprising X contiguous nucleotides, wherein (i) the X contiguous nucleotides have at least about a selected level of percent identity relative to Y contiguous nucleotides of one or more of the sequences described herein (e.g., in Table C) or fragment thereof, and (ii) for search purposes X equals Y, wherein Y is a selected reference polynucleotide of defined length (for example, a length of from 15 nucleotides up to the number of nucleotides present in a selected full-length sequence).

The sequences of the present invention can include fragments of the sequences, for example, from about 15 nucleotides up to the number of nucleotides present in the full-length sequences described herein (e.g., see the Figures), including all integer values falling within the above-described range. For example, fragments of the polynucleotide sequences of the present invention may be 30-60 nucleotides, 60-120 nucleotides, 120-240 nucleotides, 240-480 nucleotides, 480-1000 nucleotides, and all integer values therebetween.

The synthetic expression cassettes (and purified polynucleotides) of the present invention include related polynucleotide sequences having about 80% to 100%, greater than 80-85%, preferably greater than 90-92%, more preferably greater than 95%, and most preferably greater than 98% up to 100% (including all integer values falling within these described ranges) sequence identity to the synthetic expression cassette and/or polynucleotide sequences disclosed herein (for example, to the sequences of the present invention) when the sequences of the present invention are used as the query sequence against, for example, a database of sequences.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., supra or Ausubel et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., form amide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., supra or Ausubel et al., supra).

A first polynucleotide is "derived from" second polynucleotide if it has the same or substantially the same basepair sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

Generally, a viral polypeptide is "derived from" a particular polypeptide of a virus (viral polypeptide) if it is (i) encoded by an open reading frame of a polynucleotide of that virus (viral polynucleotide), or (ii) displays sequence identity to polypeptides of that virus as described above.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence. Further, polyproteins can be constructed by fusing in-frame two or more polynucleotide sequences encoding polypeptide or peptide products. Further, polycistronic coding sequences may be produced by placing two or more polynucleotide sequences encoding polypeptide products adjacent each other, typically under the control of one promoter, wherein each polypeptide coding sequence may be modified to include sequences for internal ribosome binding sites.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

By "nucleic acid immunization" is meant the introduction of a nucleic acid molecule encoding one or more selected antigens into a host cell, for the in vivo expression of an antigen, antigens, an epitope, or epitopes. The nucleic acid molecule can be introduced directly into a recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

"Gene transfer" or "gene delivery" refers to methods or systems for reliably inserting DNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from alphaviruses, pox viruses and vaccinia viruses. When used for immunization, such gene delivery expression vectors may be referred to as vaccines or vaccine vectors.

"T lymphocytes" or "T cells" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring gene sequences to target cells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors.

Transfer of a "suicide gene" (e.g., a drug-susceptibility gene) to a target cell renders the cell sensitive to compounds or compositions that are relatively nontoxic to normal cells. Moolten, F. L. (1994) Cancer Gene Ther. 1:279-287. Examples of suicide genes are thymidine kinase of herpes simplex virus (HSV-tk), cytochrome P450 (Manome et al. (1996) Gene Therapy 3:513-520), human deoxycytidine kinase (Manome et al. (1996) Nature Medicine 2(5):567-573) and the bacterial enzyme cytosine deaminase (Dong et al. (1996) Human Gene Therapy 7:713-720). Cells which express these genes are rendered sensitive to the effects of the relatively nontoxic prodrugs ganciclovir (HSV-tk), cyclophosphamide (cytochrome P450 2B1), cytosine arabinoside (human deoxycytidine kinase) or 5-fluorocytosine (bacterial cytosine deaminase). Culver et al. (1992) Science 256:1550-1552, Huber et al. (1994) Proc. Natl. Acad. Sci. USA 91:8302-8306.

A "selectable marker" or "reporter marker" refers to a nucleotide sequence included in a gene transfer vector that has no therapeutic activity, but rather is included to allow for simpler preparation, manufacturing, characterization or testing of the gene transfer vector.

A "specific binding agent" refers to a member of a specific binding pair of molecules wherein one of the molecules specifically binds to the second molecule through chemical and/or physical means. One example of a specific binding agent is an antibody directed against a selected antigen.

By "subject" is meant any member of the subphylum chordata, including, without limitation, humans and other primates, including non-human primates such as rhesus macaque, chimpanzees and other apes and monkey species;

farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

By "physiological pH" or a "pH in the physiological range" is meant a pH in the range of approximately 7.0 to 8.0 inclusive, more typically in the range of approximately 7.2 to 7.6 inclusive.

As used herein, "treatment" refers to any of (i) the prevention of infection or reinfection, as in a traditional vaccine, (ii) the reduction or elmination of symptoms, and (iii) the substantial or complete elimination of the pathogen in question. Treatment may be effected prophylactically (prior to infection) or therapeutically (following infection).

By "co-administration" is meant administration of more than one composition or molecule. Thus, co-administration includes concurrent administration or sequentially administration (in any order), via the same or different routes of administration. Non-limiting examples of co-administration regimes include, co-administration of nucleic acid and polypeptide; co-administration of different nucleic acids (e.g., different expression cassettes as described herein and/or different gene delivery vectors); and co-administration of different polypeptides (e.g. different HIV polypeptides and/or different adjuvants). The term also encompasses multiple administrations of one of the co-administered molecules or compositions (e.g., multiple administrations of one or more of the expression cassettes described herein followed by one or more administrations of a polypeptide-containing composition). In cases where the molecules or compositions are delivered sequentially, the time between each administration can be readily determined by one of skill in the art in view of the teachings herein.

"Lentiviral vector", and "recombinant lentiviral vector" refer to a nucleic acid construct which carries, and within certain embodiments, is capable of directing the expression of a nucleic acid molecule of interest. The lentiviral vector include at least one transcriptional promoter/enhancer or locus defining element(s), or other elements which control gene expression by other means such as alternate splicing, nuclear RNA export, post-translational modification of messenger, or post-transcriptional modification of protein. Such vector constructs must also include a packaging signal, long terminal repeats (LTRS) or portion thereof, and positive and negative strand primer binding sites appropriate to the retrovirus used (if these are not already present in the retroviral vector). Optionally, the recombinant lentiviral vector may also include a signal which directs polyadenylation, selectable markers such as Neo, TK, hygromycin, phleomycin, histidinol, or DHFR, as well as one or more restriction sites and a translation termination sequence. By way of example, such vectors typically include a 5' LTR, a tRNA binding site, a packaging signal, an origin of second strand DNA synthesis, and a 3'LTR or a portion thereof "Lentiviral vector particle" as utilized within the present invention refers to a lentivirus which carries at least one gene of interest. The retrovirus may also contain a selectable marker. The recombinant lentivirus is capable of reverse transcribing its genetic material (RNA) into DNA and incorporating this genetic material into a host cell's DNA upon infection. Lentiviral vector particles may have a lentiviral envelope, a non-lentiviral envelope (e.g., an ampho or VSV-G envelope), or a chimeric envelope.

"Nucleic acid expression vector" or "Expression cassette" refers to an assembly which is capable of directing the expression of a sequence or gene of interest. The nucleic acid expression vector includes a promoter which is operably linked to the sequences or gene(s) of interest. Other control elements may be present as well. Expression cassettes described herein may be contained within a plasmid construct. In addition to the components of the expression cassette, the plasmid construct may also include a bacterial origin of replication, one or more selectable markers, a signal which allows the plasmid construct to exist as singe-stranded DNA (e.g., a M13 origin of replication), a multiple cloning site, and a "mammalian" origin of replication (e.g., a SV40 or adenovirus origin of replication).

"Packaging cell" refers to a cell which contains those elements necessary for production of infectious recombinant retrovirus which are lacking in a recombinant retroviral vector. Typically, such packaging cells contain one or more expression cassettes which are capable of expressing proteins which encode Gag, pol and env proteins.

"Producer cell" or "vector producing cell" refers to a cell which contains all elements necessary for production of recombinant retroviral vector particles.

2. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2.1. The HIV Genome

The HIV genome and various polypeptide-encoding regions are shown in Table A. The nucleotide positions are given relative to 8_5_TV1_C.ZA (FIG. 1; an HIV Type C isolate). However, it will be readily apparent to one of ordinary skill in the art in view of the teachings of the present disclosure how to determine corresponding regions in other HIV strains or variants (e.g., isolates $HIV_{IIIb}$, $HIV_{SF2}$, HIV-$1_{SF162}$, HIV-$1_{SF170}$, $HIV_{LAV}$, $HIV_{LAI}$, $HIV_{MN}$, HIV-$1_{CM235}$, HIV-$1_{US4}$, other HIV-1 strains from diverse subtypes (e.g., subtypes, A through G, and O), HIV-2 strains and diverse subtypes (e.g., HIV-$2_{UC1}$ and HIV-$2_{UC2}$), and simian immunodeficiency virus (SIV). (See, e.g., Virology, 3rd Edition (W. K. Joklik ed. 1988); *Fundamental Virology*, 2nd Edition (B. N. Fields and D. M. Knipe, eds. 1991); *Virology*, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify the various regions).

TABLE A

Regions of the HIV Genome relative to 8_5_TV1_C.ZA

| Region | Position in nucleotide sequence |
|---|---|
| 5'LTR | 1-636 |
| U3 | 1-457 |
| R | 458-553 |
| U5 | 554-636 |
| NFkB II | 340-348 |
| NFkB I | 354-362 |
| Sp1 III | 379-388 |
| Sp1 II | 390-398 |
| Sp1 I | 400-410 |
| TATA Box | 429-433 |
| TAR | 474-499 |
| Poly A signal | 529-534 |
| PBS | 638-655 |
| p7 binding region, packaging signal | 685-791 |
| Gag: | 792-2285 |
| p17 | 792-1178 |
| p24 | 1179-1871 |
| Cyclophilin A bdg. | 1395-1505 |
| MHR | 1632-1694 |
| p2 | 1872-1907 |
| p7 | 1908-2072 |
| Frameshift slip | 2072-2078 |
| p1 | 2073-2120 |
| p6Gag | 2121-2285 |
| Zn-motif I | 1950-1991 |
| Zn-motif II | 2013-2054 |
| Pol: | 2072-5086 |
| p6Pol | 2072-2245 |
| Prot | 2246-2542 |
| p66RT | 2543-4210 |
| p15RNaseH | 3857-4210 |
| p31Int | 4211-5086 |
| Vif: | 5034-5612 |
| Hydrophilic region | 5292-5315 |
| Vpr: | 5552-5839 |
| Oligomerization | 5552-5677 |
| Amphipathic a-helix | 5597-5653 |
| Tat: | 5823-6038 and 8417-8509 |
| Tat-1 exon | 5823-6038 |
| Tat-2 exon | 8417-8509 |
| N-terminal domain | 5823-5885 |
| Trans-activation domain | 5886-5933 |
| Transduction domain | 5961-5993 |
| Rev: | 5962-6037 and 8416-8663 |
| Rev-1 exon | 5962-6037 |
| Rev-2 exon | 8416-8663 |
| High-affinity bdg. site | 8439-8486 |
| Leu-rich effector domain | 8562-8588 |
| Vpu: | 6060-6326 |
| Transmembrane domain | 6060-6161 |
| Cytoplasmic domain | 6162-6326 |
| Env (gp160): | 6244-8853 |
| Signal peptide | 6244-6324 |
| gp120 | 6325-7794 |
| V1 | 6628-6729 |
| V2 | 6727-6852 |
| V3 | 7150-7254 |
| V4 | 7411-7506 |
| V5 | 7663-7674 |
| C1 | 6325-6627 |
| C2 | 6853-7149 |
| C3 | 7255-7410 |
| C4 | 7507-7662 |
| C5 | 7675-7794 |
| CD4 binding | 7540-7566 |
| gp41 | 7795-8853 |
| Fusion peptide | 7789-7842 |
| Oligomerization domain | 7924-7959 |
| N-terminal heptad repeat | 7921-8028 |
| C-terminal heptad repeat | 8173-8280 |
| Immunodominant region | 8023-8076 |
| Nef: | 8855-9478 |

TABLE A-continued

Regions of the HIV Genome relative to 8_5_TV1_C.ZA

| Region | Position in nucleotide sequence |
|---|---|
| Myristoylation | 8858-8875 |
| SH3 binding | 9062-9091 |
| Polypurine tract | 9128-9154 |
| SH3 binding | 9296-9307 |

It will be readily apparent that one of skill in the art can readily align any sequence to that shown in Table A to determine relative locations of any particular HIV gene. For example, using one of the alignment programs described herein (e.g., BLAST), other HIV genomic sequences can be aligned with 8_5_TV1_C.ZA (Table A) and locations of genes determined. Polypeptide sequences can be similarly aligned. For example, FIGS. 2A-2C shows the alignment of Env polypeptide sequences from various strains, relative to SF-162. As described in detail in co-owned WO/39303 (herein incorporated by reference), Env polypeptides (e.g., gp120, gp140 and gp160) include a "bridging sheet" comprised of 4 anti-parallel b-strands (b-2, b-3, b-20 and b-21) that form a b-sheet. Extruding from one pair of the b-strands (b-2 and b-3) are two loops, V1 and V2. The b-2 sheet occurs at approximately amino acid residue 113 (Cys) to amino acid residue 117 (Thr) while b-3 occurs at approximately amino acid residue 192 (Ser) to amino acid residue 194 (Ile), relative to SF-162. The "V1/V2 region" occurs at approximately amino acid positions 120 (Cys) to residue 189 (Cys), relative to SF-162. Extruding from the second pair of b-strands (b-20 and b-21) is a "small-loop" structure, also referred to herein as "the bridging sheet small loop." The locations of both the small loop and bridging sheet small loop can be determined relative to HXB-2 following the teachings herein and in WO/39303. Also shown by arrows in FIG. 2A-C are approximate sites for deletions sequence from the beta sheet region. The "*" denotes N-glycosylation sites that can be mutated following the teachings of the present specification.

2.2.0 Synthetic Expression Cassettes

One aspect of the present invention is the generation of HIV-1 coding sequences, and related sequences, for example having improved expression relative to the corresponding wild-type sequences.

2.2.1 Modification of HIV-1 Nucleic Acid Coding Sequences

First, the HIV-1 codon usage pattern was modified so that the resulting nucleic acid coding sequence was comparable to codon usage found in highly expressed human genes. The HIV codon usage reflects a high content of the nucleotides A or T of the codon-triplet. The effect of the HIV-1 codon usage is a high AT content in the DNA sequence that results in a decreased translation ability and instability of the mRNA. In comparison, highly expressed human codons prefer the nucleotides G or C. The HIV coding sequences were modified to be comparable to codon usage found in highly expressed human genes.

Second, there are inhibitory (or instability) elements (INS) located within the coding sequences of, for example, the Gag coding sequences. The RRE is a secondary RNA structure that interacts with the HIV encoded Rev-protein to overcome the expression down-regulating effects of the INS. To overcome the post-transcriptional activating mechanisms of RRE and Rev, the instability elements can be inactivated by introducing multiple point mutations that do not alter the reading frame of the encoded proteins.

Third, for some genes the coding sequence has been altered such that the polynucleotide coding sequence encodes a gene product that is inactive or non-functional (e.g., inactivated polymerase, protease, tat, rev, nef, vif, vpr, and/or vpu gene products). Example 1 describes some exemplary mutations. Example 8 presents information concerning functional analysis of mutated Tat, Rev and Nef antigens.

The synthetic coding sequences are assembled by methods known in the art, for example by companies such as the Midland Certified Reagent Company (Midland, Tex.).

Modification of the Gag polypeptide coding sequences results in improved expression relative to the wild-type coding sequences in a number of mammalian cell lines (as well as other types of cell lines, including, but not limited to, insect cells).

Some exemplary polynucleotide sequences encoding Gag-containing polypeptides are GagComplPolmut.SF2, GagComplPolmutAtt.SF2, GagComplPolmutIna.SF2, gagCpolInaTatRevNef.opt_B, GagPolmutAtt.SF2, GagPolmutIna.SF2, GagProtInaRTmut.SF2, GagProtInaRTmutTatRevNef.opt_B, GagRTmut.SF2, and GagTatRevNef.opt_B.

Similarly, the present invention also includes synthetic Env-encoding polynucleotides and modified Env proteins, for example, gp140.modSF162.CwtLmod, gp140.modSF162.CwtLnat, gp160.modSF162.delV2.mut7, and gp160.modSF162.delV2.mut8.

The codon usage pattern for Env was modified as described above for Gag so that the resulting nucleic acid coding sequence was comparable to codon usage found in highly expressed human genes. Experiments performed in support of the present invention show that the synthetic Env sequences were capable of higher level of protein production relative to the native Env sequences.

Modification of the Env polypeptide coding sequences results in improved expression relative to the wild-type coding sequences in a number of mammalian cell lines (as well as other types of cell lines, including, but not limited to, insect cells). Similar Env polypeptide coding sequences can be obtained, modified and tested for improved expression from a variety of isolates, including those described above for Gag.

Further modifications of Env include, but are not limited to, generating polynucleotides that encode Env polypeptides having mutations and/or deletions therein. For instance, the hypervariable regions, V1 and/or V2, can be deleted as described herein. Additionally, other modifications, for example to the bridging sheet region and/or to N-glycosylation sites within Env can also be performed following the teachings of the present specification. (see, FIG. 2A-C, as well as WO 00/39303, WO 00/39302, WO 00/39304, WO 02/04493 all herein incorporated by reference in their entireties). Various combinations of these modifications can be employed to generate synthetic expression cassettes as described herein.

The present invention also includes expression cassettes which include synthetic Pol sequences. As noted above, "Pol" includes, but is not limited to, the protein-encoding regions comprising polymerase, protease, reverse transcriptase and/or integrase-containing sequences (Wan et al (1996) *Biochem. J.* 316:569-573; Kohl et al. (1988) *PNAS USA* 85:4686-4690; Krausslich et al. (1988) *J. Virol.* 62:4393-4397; Coffin, "Retroviridae and their Replication" in Virology, pp1437-1500 (Raven, N.Y., 1990); Patel et. al. (1995) *Biochemistry* 34:5351-5363). Thus, the synthetic expression cassettes exemplified herein include one or more of these regions and one or more changes to the resulting amino acid sequences.

Some exemplary polynucleotide sequences encoding Pol-derived polypeptides are presented in Table C.

The codon usage pattern for Pol was modified as described above for Gag and Env so that the resulting nucleic acid coding sequence was comparable to codon usage found in highly expressed human genes.

Constructs may be modified in various ways. For example, the expression constructs may include a sequence that encodes the first 6 amino acids of the integrase polypeptide. This 6 amino acid region is believed to provide a cleavage recognition site recognized by HIV protease (see, e.g., McCornack et al. (1997) *FEBS Letts* 414:84-88). Constructs may include a multiple cloning site (MCS) for insertion of one or more transgenes, typically at the 3' end of the construct. In addition, a cassette encoding a catalytic center epitope derived from the catalytic center in RT is typically included 3' of the sequence encoding 6 amino acids of integrase. This cassette encodes Ile 178 through Serine 191 of RT and may be added to keep this well conserved region as a possible CTL epitope. Further, the constructs contain an insertion mutations to preserve the reading frame. (see, e.g., Park et al. (1991) *J. Virol.* 65:5111).

In certain embodiments, the catalytic center and/or primer grip region of RT are modified. The catalytic center and primer grip regions of RT are described, for example, in Patel et al. (1995) *Biochem.* 34:5351 and Palaniappan et al. (1997) *J. Biol. Chem.* 272(17): 11157. For example, wild type sequence encoding the amino acids YMDD at positions 183-185 of p66 RT, numbered relative to AF110975, may be replaced with sequence encoding the amino acids "AP". Further, the primer grip region (amino acids WMGY, residues 229-232 of p66RT, numbered relative to AF110975) may be replaced with sequence encoding the amino acids "PI."

For the Pol sequence, the changes in codon usage are typically restricted to the regions up to the −1 frameshift and starting again at the end of the Gag reading frame; however, regions within the frameshift translation region can be modified as well. Finally, inhibitory (or instability) elements (INS) located within the coding sequences of the protease polypeptide coding sequence can be altered as well.

Experiments can be performed in support of the present invention to show that the synthetic Pol sequences were capable of higher level of protein production relative to the native Pol sequences. Modification of the Pol polypeptide coding sequences results in improved expression relative to the wild-type coding sequences in a number of mammalian cell lines (as well as other types of cell lines, including, but not limited to, insect cells). Similar Pol polypeptide coding sequences can be obtained, modified and tested for improved expression from a variety of isolates, including those described above for Gag and Env.

The present invention also includes expression cassettes which include synthetic sequences derived HIV genes other than Gag, Env and Pol, including but not limited to, regions within Gag, Env, Pol, as well as, GagComplPolmut.SF2, GagComplPolmutAtt.SF2, GagComplPolmutIna.SF2, gagCpolInaTatRevNef.opt_B, GagPolmutAtt.SF2, GagPolmutIna.SF2, GagProtInaRTmut.SF2, GagProtInaRTmutTatRevNef.opt_B, GagRTmut.SF2, GagTatRevNef.opt_B, gp140.modSF162.CwtLmod, gp140.modSF162.CwtLnat, gp160.modSF162.delV2.mut7, gp160.modSF162.delV2.mut8, int.opt.mut.SF2, int.opt.SF2, nef.D125G.-myr.opt.SF162, nef.D107G.-myr18.opt.SF162, nef.opt.D125G.SF162, nef.opt.SF162, p15RnaseH.opt.SF2, p2Pol.opt.YMWM.SF2, p2PolInaopt.YM.SF2, p2Polopt.SF2, p2PolTatRevNef.opt.native_B, p2PolTatRevNef.opt_B, pol.opt.SF2, prot.opt.SF2, protIna.opt.SF2, protInaRT.YM.opt.SF2, protInaRT.YMW-M.opt.SF2, ProtInaRTmut.SF2, protRT.opt.SF2, ProtRT.TatRevNef.opt_B, ProtRTTatRevNef.opt_B, rev.exon1_2.M5-10.opt.SF162, rev.exon1_2.opt.SF162, RT.opt.SF2 (mutant), RT.opt.SF2 (native), RTmut.SF2, tat.exon1_2.opt.C22-37.SF2, tat.exon1_2.opt.C37.SF2, TatRevNef.opt.native.SF162, TatRevNef.opt.SF162, TatRevNefGag B, TatRevNefgagCpolIna B, TatRevNefGagProtInaRTmut B, TatRevNefp2Pol.opt_B, TatRevNefprotRTopt B, vif.opt.SF2, vpr.opt.SF2, and vpu.opt.SF162. Sequences obtained from other strains can be manipulated in similar fashion following the teachings of the present specification. As noted above, the codon usage pattern is modified as described above for Gag, Env and Pol so that the resulting nucleic acid coding sequence is comparable to codon usage found in highly expressed human genes. Typically these synthetic sequences are capable of higher level of protein production relative to the native sequences and that modification of the wild-type polypeptide coding sequences results in improved expression relative to the wild-type coding sequences in a number of mammalian cell lines (as well as other types of cell lines, including, but not limited to, insect cells). Furthermore, the nucleic acid sequence can also be modified to introduce mutations into one or more regions of the gene, for instance to alter the function of the gene product (e.g., render the gene product non-functional) and/or to eliminate site modifications (e.g., the myristoylation site in Nef).

Synthetic expression cassettes, derived from HIV Type B coding sequences, exemplified herein include, but are not limited to, those comprising one or more of the following synthetic polynucleotides: GagComplPolmut.SF2, GagComplPolmutAtt.SF2, GagComplPolmutIna.SF2, gagCpolInaTatRevNef.opt_B, GagPolmutAtt.SF2, GagPolmutIna.SF2, GagProtInaRTmut.SF2, GagProtInaRTmutTatRevNef.opt_B, GagRTmut.SF2, GagTatRevNef.opt_B, gp140.modSF162.CwtLmod, gp140.modSF162.CwtLnat, gp160.modSF162.delV2.mut7, gp160.modSF162.delV2.mut8, int.opt.mut.SF2, int.opt.SF2, nef.D125G.-myr.opt.SF162, nef.D107G.-myr18.opt.SF162, nef.opt.D125G.SF162, nef.opt.SF162, p15RnaseH.opt.SF2, p2Pol.opt.YMWM.SF2, p2PolInaopt.YM.SF2, p2Polopt.SF2, p2PolTatRevNef.opt.native_B, p2PolTatRevNef.opt_B, pol.opt.SF2, prot.opt.SF2, protIna.opt.SF2, protInaRT.YM.opt.SF2, protInaRT.YMWM.opt.SF2, ProtInaRTmut.SF2, protRT.opt.SF2, ProtRT.TatRevNef.opt_B, ProtRTTatRevNef.opt_B, rev.exon1__2.M5-10.opt.SF162, rev.exon1__2.opt.SF162, RT.opt.SF2 (mutant), RT.opt.SF2 (native), RTmut.SF2, tat.exon1__2.opt.C22-37.SF2, tat.exon1__2.opt.C37.SF2, TatRevNef.opt.native.SF162, TatRevNef.opt.SF162, TatRevNefGag B, TatRevNefgagCpolIna B, TatRevNefGagProtInaRTmut B, TatRevNefp2Pol.opt_B, TatRevNefprotRTopt B, vif.opt.SF2, vpr.opt.SF2, and vpu.opt.SF162.

Gag-complete refers to in-frame polyproteins comprising, e.g., Gag and pol, wherein the p6 portion of Gag is present.

Additional sequences that may be employed in some aspects of the present invention have been described in WO 00/39302, WO 00/39303, WO 00/39304, and WO 02/04493, all of which are herein incorporated by reference in their entireties.

2.2.2 Further Modification of Sequences Including HIV Nucleic Acid Coding Sequences The HIV polypeptide-encoding expression cassettes described herein may also contain one or more further sequences encoding, for example, one or more transgenes. Further sequences (e.g., transgenes) useful in the practice of the present invention include, but are not limited to, further sequences are those encoding further viral epitopes/antigens {including but not limited to, HCV antigens (e.g., E1, E2; Houghton, M., et al., U.S. Pat. No. 5,714,596, issued Feb. 3, 1998; Houghton, M., et al., U.S. Pat. No. 5,712,088, issued Jan. 27, 1998; Houghton, M., et al., U.S. Pat. No. 5,683,864, issued Nov. 4, 1997; Weiner, A. J., et al., U.S. Pat. No. 5,728,520, issued Mar. 17, 1998; Weiner, A. J., et al., U.S. Pat. No. 5,766,845, issued Jun. 16, 1998; Weiner, A. J., et al., U.S. Pat. No. 5,670,152, issued Sep. 23, 1997; all herein incorporated by reference), HIV antigens (e.g., derived from one or more HIV isolate); and sequences encoding tumor antigens/epitopes. Further sequences may also be derived from non-viral sources, for instance, sequences encoding cytokines such interleukin-2 (IL-2), stem cell factor (SCF), interleukin 3 (IL-3), interleukin 6 (IL-6), interleukin 12 (IL-12), G-CSF, granulocyte macrophage-colony stimulating factor (GM-CSF), interleukin-1 alpha (IL-1I), interleukin-11 (IL-11), MIP-1I, tumor necrosis factor (TNF), leukemia inhibitory factor (LIF), c-kit ligand, thrombopoietin (TPO) and flt3 ligand, commercially available from several vendors such as, for example, Genzyme (Framingham, Mass.), Genentech (South San Francisco, Calif.), Amgen (Thousand Oaks, Calif.), R&D Systems and Immunex (Seattle, Wash.). Additional sequences are described below. Also, variations on the orientation of the Gag and other coding sequences, relative to each other, are described below.

HIV polypeptide coding sequences can be obtained from other HIV isolates, see, e.g., Myers et al. Los Alamos Database, Los Alamos National Laboratory, Los Alamos, N. Mex. (1992); Myers et al., *Human Retroviruses and Aids,* 1997, Los Alamos, N. Mex.: Los Alamos National Laboratory. Synthetic expression cassettes can be generated using such coding sequences as starting material by following the teachings of the present specification.

Further, the synthetic expression cassettes of the present invention include related polypeptide sequences having greater than 85%, preferably greater than 90%, more preferably greater than 95%, and most preferably greater than 98% sequence identity to the polypeptides encoded by the synthetic expression cassette sequences disclosed herein.

Exemplary expression cassettes and modifications are set forth in Example 1.

2.2.3 Expression of Synthetic Sequences Encoding HIV-1 Polypeptides and Related Polypeptides Synthetic HIV-encoding sequences (expression cassettes) of the present invention can be cloned into a number of different expression vectors to evaluate levels of expression and, in the case of Gag-containing constructs, production of VLPs. The synthetic DNA fragments for HIV polypeptides can be cloned into eucaryotic expression vectors, including, a transient expression vector, CMV-promoter-based mammalian vectors, and a shuttle vector for use in baculovirus expression systems. Corresponding wild-type sequences can also be cloned into the same vectors.

These vectors can then be transfected into a several different cell types, including a variety of mammalian cell lines (293, RD, COS-7, and CHO, cell lines available, for example, from the A.T.C.C.). The cell lines are then cultured under appropriate conditions and the levels of any appropriate polypeptide product can be evaluated in supernatants. (see, Table A). For example, p24 can be used to evaluate Gag expression; gp160, gp140 or gp120 can be used to evaluate Env expression; p6pol can be used to evaluate Pol expression; prot can be used to evaluate protease; p15 for RNAseH; p31 for Integrase; and other appropriate polypeptides for Vif, Vpr, Tat, Rev, Vpu and Nef. Further, modified polypeptides can also be used, for example, other Env polypeptides include, but are not limited to, for example, native gp160, oligomeric gp140, monomeric gp120 as well as modified and/or synthetic sequences of these polypeptides. The results of these assays demonstrate that expression of synthetic HIV polypeptide-encoding sequences are significantly higher than corresponding wild-type sequences.

Further, Western Blot analysis can be used to show that cells containing the synthetic expression cassette produce the expected protein at higher per-cell concentrations than cells containing the native expression cassette. The HIV proteins can be seen in both cell lysates and supernatants. The levels of production are significantly higher in cell supernatants for cells transfected with the synthetic expression cassettes of the present invention.

Fractionation of the supernatants from mammalian cells transfected with the synthetic expression cassette can be used to show that the cassettes provide superior production of HIV proteins and, in the case of Gag, VLPs, relative to the wild-type sequences.

Efficient expression of these HIV-containing polypeptides in mammalian cell lines provides the following benefits: the polypeptides are free of baculovirus contaminants; production by established methods approved by the FDA; increased purity; greater yields (relative to native coding sequences); and a novel method of producing the Sub HIV-containing polypeptides in CHO cells which is not feasible in the absence of the increased expression obtained using the constructs of the present invention. Exemplary Mammalian cell lines include, but are not limited to, BHK, VERO, HT1080, 293, 293T, RD, COS-7, CHO, Jurkat, HUT, SUPT, C8166, MOLT4/clone8, MT-2, MT-4, H9, PM1, CEM, and CEMX174 (such cell lines are available, for example, from the A.T.C.C.).

A synthetic Gag expression cassette of the present invention will also exhibit high levels of expression and VLP production when transfected into insect cells. Synthetic expression cassettes described herein also demonstrate high levels of expression in insect cells. Further, in addition to a higher total protein yield, the final product from the synthetic polypeptides consistently contains lower amounts of contaminating baculovirus proteins than the final product from the native sequences.

Further, synthetic expression cassettes of the present invention can also be introduced into yeast vectors which, in turn, can be transformed into and efficiently expressed by yeast cells (*Saccharomyces cerevisea*; using vectors as described in Rosenberg, S, and Tekamp-Olson, P., U.S. Pat. No. RE35,749, issued, Mar. 17, 1998, herein incorporated by reference).

In addition to the mammalian and insect vectors, the synthetic expression cassettes of the present invention can be incorporated into a variety of expression vectors using selected expression control elements. Appropriate vectors and control elements for any given cell an be selected by one having ordinary skill in the art in view of the teachings of the present specification and information known in the art about expression vectors.

For example, a synthetic expression cassette can be inserted into a vector which includes control elements operably linked to the desired coding sequence, which allow for the expression of the gene in a selected cell-type. For example, typical promoters for mammalian cell expression include the SV40 early promoter, a CMV promoter such as the CMV immediate early promoter (a CMV promoter can include intron A), RSV, HIV-Ltr, the mouse mammary tumor virus LTR promoter (MMLV-ltr), the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook, et al., supra, as well as a bovine growth hormone terminator sequence. Introns, containing splice donor and acceptor sites, may also be designed into the constructs for use with the present invention (Chapman et al., *Nuc. Acids Res*. (1991) 19:3979-3986).

Enhancer elements may also be used herein to increase expression levels of the mammalian constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence (Chapman et al., *Nuc. Acids Res*. (1991) 19:3979-3986).

The desired synthetic polypeptide encoding sequences can be cloned into any number of commercially available vectors to generate expression of the polypeptide in an appropriate host system. These systems include, but are not limited to, the following: baculovirus expression {Reilly, P. R., et al., *Baculovirus Expression Vectors: A Laboratory Manual* (1992); Beames, et al., *Biotechniques* 11:378 (1991); Pharmingen; Clontech, Palo Alto, Calif.)}, vaccinia expression {Earl, P. L., et al., "Expression of proteins in mammalian cells using vaccinia" In *Current Protocols in Molecular Biology* (F. M. Ausubel, et al. Eds.), Greene Publishing Associates & Wiley Interscience, New York (1991); Moss, B., et al., U.S. Pat. No. 5,135,855, issued 4 Aug. 1992}, expression in bacteria {Ausubel, F. M., et al., *Current Protocols in Molecular Biology*, John Wiley and Sons, Inc., Media Pa.; Clontech}, expression in yeast {Rosenberg, S, and Tekamp-Olson, P., U.S. Pat. No. RE35,749, issued, Mar. 17, 1998, herein incorporated by reference; Shuster, J. R., U.S. Pat. No. 5,629,203, issued May 13, 1997, herein incorporated by reference; Gellissen, G., et al., *Antonie Van Leeuwenhoek,* 62(1-2):79-93 (1992); Romanos, M. A., et al., Yeast 8(6):423-488 (1992); Goeddel, D. V., *Methods in Enzymology* 185 (1990); Guthrie, C., and G. R. Fink, *Methods in Enzymology* 194 (1991)}, expression in mammalian cells {Clontech; Gibco-BRL, Ground Island, N.Y.; e.g., Chinese hamster ovary (CHO) cell lines (Haynes, J., et al., *Nuc. Acid. Res.* 11:687-706 (1983); 1983, Lau, Y. F., et al., *Mol. Cell. Biol.* 4:1469-1475 (1984); Kaufman, R. J., "Selection and coamplification of heterologous genes in mammalian cells," in *Methods in Enzymology*, vol. 185, pp 537-566. Academic Press, Inc., San Diego Calif. (1991)}, and expression in plant cells {plant cloning vectors, Clontech Laboratories, Inc., Palo Alto, Calif., and Pharmacia LKB Biotechnology, Inc., Pistcataway, N.J.; Hood, E., et al., *J. Bacteriol.* 168:1291-1301 (1986); Nagel, R., et al., *FEMS Microbiol. Lett.* 67:325 (1990); An, et al., "Binary Vectors", and others in *Plant Molecular Biology Manual A*3: 1-19 (1988); Miki, B. L. A., et al., pp. 249-265, and others in *Plant DNA Infectious Agents* (Hohn, T., et al., eds.) Springer-Verlag, Wien, Austria, (1987); *Plant Molecular Biology: Essential Techniques*, P. G. Jones and J. M. Sutton, New York, J. Wiley, 1997; Miglani, Gurbachan *Dictionary of Plant Genetics and Molecular Biology*, New York, Food Products Press, 1998; Henry, R. J., *Practical Applications of Plant Molecular Biology*, New York, Chapman & Hall, 1997}.

Also included in the invention is an expression vector, containing coding sequences and expression control elements which allow expression of the coding regions in a suitable host. The control elements generally include a promoter, translation initiation codon, and translation and transcription termination sequences, and an insertion site for introducing the insert into the vector. Translational control elements have been reviewed by M. Kozak (e.g., Kozak, M., *Mamm. Genome* 7(8):563-574, 1996; Kozak, M., *Biochimie* 76(9):815-821, 1994; Kozak, M., *J Cell Biol* 108(2):229-241, 1989; Kozak, M., and Shatkin, A. J., *Methods Enzymol* 60:360-375, 1979).

Expression in yeast systems has the advantage of commercial production. Recombinant protein production by vaccinia and CHO cell line have the advantage of being mammalian expression systems. Further, vaccinia virus expression has several advantages including the following: (i) its wide host range; (ii) faithful post-transcriptional modification, processing, folding, transport, secretion, and assembly of recombinant proteins; (iii) high level expression of relatively soluble recombinant proteins; and (iv) a large capacity to accommodate foreign DNA.

The recombinantly expressed polypeptides from synthetic HIV polypeptide-encoding expression cassettes are typically isolated from lysed cells or culture media. Purification can be carried out by methods known in the art including salt fractionation, ion exchange chromatography, gel filtration, size-exclusion chromatography, size-fractionation, and affinity chromatography. Immunoaffinity chromatography can be employed using antibodies generated based on, for example, HIV antigens.

Advantages of expressing the proteins of the present invention using mammalian cells include, but are not limited to, the following: well-established protocols for scale-up production; the ability to produce VLPs; cell lines are suitable to meet good manufacturing process (GMP) standards; culture conditions for mammalian cells are known in the art.

Synthetic HIV 1 polynucleotides are described herein, see, for example, the figures. Various forms of the different embodiments of the invention, described herein, may be combined.

Exemplary expression assays are set forth in Example 2. Exemplary conditions for Western Blot analysis are presented in Example 3.

2.3.0 Production of Virus-Like Particles and Use of the Constructs of the Present Invention to Create Packaging Cell Lines.

The group-specific antigens (Gag) of human immunodeficiency virus type-1 (HIV-1) self-assemble into noninfectious virus-like particles (VLP) that are released from various eucaryotic cells by budding (reviewed by Freed, E. O., *Virology* 251:1-15, 1998). The Gag-containing synthetic expression cassettes of the present invention provide for the production of HIV-Gag virus-like particles (VLPs) using a variety of different cell types, including, but not limited to, mammalian cells.

Viral particles can be used as a matrix for the proper presentation of an antigen entrapped or associated therewith to the immune system of the host.

2.3.1 VLP Production Using the Synthetic Expression Cassettes of the Present Invention The Gag-containing synthetic expression cassettes of the present invention may provide superior production of both Gag proteins and VLPs, relative to native Gag coding sequences. Further, electron microscopic evaluation of VLP production can be used to show that free and budding immature virus particles of the expected size are produced by cells containing the synthetic expression cassettes.

Using the synthetic expression cassettes of the present invention, rather than native Gag coding sequences, for the production of virus-like particles provide several advantages. First, VLPs can be produced in enhanced quantity making isolation and purification of the VLPs easier. Second, VLPs can be produced in a variety of cell types using the synthetic expression cassettes, in particular, mammalian cell lines can be used for VLP production, for example, CHO cells. Production using CHO cells provides (i) VLP formation; (ii) correct myristoylation and budding; (iii) absence of non-Macmillian cell contaminants (e.g., insect viruses and/or cells); and (iv) ease of purification. The synthetic expression cassettes of the present invention are also useful for enhanced expression in cell-types other than mammalian cell lines. For example, infection of insect cells with baculovirus vectors encoding the synthetic expression cassettes results in higher levels of total Gag protein yield and higher levels of VLP production (relative to wild-coding sequences). Further, the final product from insect cells infected with the baculovirus-Gag synthetic expression cassettes consistently contains lower amounts of contaminating insect proteins than the final product when wild-coding sequences are used.

VLPs can spontaneously form when the particle-forming polypeptide of interest is recombinantly expressed in an appropriate host cell. Thus, the VLPs produced using the synthetic expression cassettes of the present invention are conveniently prepared using recombinant techniques. As discussed below, the Gag polypeptide encoding synthetic expression cassettes of the present invention can include other polypeptide coding sequences of interest (for example, HIV protease, HIV polymerase, Env; synthetic Env). Expression of such synthetic expression cassettes yields VLPs comprising the Gag polypeptide, as well as, the polypeptide of interest.

Once coding sequences for the desired particle-forming polypeptides have been isolated or synthesized, they can be cloned into any suitable vector or replicon for expression. Numerous cloning vectors are known to those of skill in the art, and the selection of an appropriate cloning vector is a matter of choice. See, generally, Sambrook et al, supra. The vector is then used to transform an appropriate host cell. Suitable recombinant expression systems include, but are not limited to, bacterial, mammalian, baculovirus/insect, vaccinia, Semliki Forest virus (SFV), Alphaviruses (such as, Sindbis, Venezuelan Equine Encephalitis (VEE)), mammalian, yeast and *Xenopus* expression systems, well known in the art. Particularly preferred expression systems are mammalian cell lines, vaccinia, Sindbis, eucaryotic layered vector initiation systems (e.g., U.S. Pat. No. 6,015,686, U.S. Pat. No. 5,814,482, U.S. Pat. No. 6,015,694, U.S. Pat. No. 5,789,245, EP 1029068A2, WO 9918226A2/A3, EP 00907746A2, WO 9738087A2, all herein incorporated by reference in their entireties), insect and yeast systems.

The synthetic DNA fragments for the expression cassettes of the present invention, e.g., Pol, Gag, Env, Tat, Rev, Nef, Vif, Vpr, and/or Vpu, may be cloned into the following eucaryotic expression vectors: pCMVKm2, for transient expression assays and DNA immunization studies, the pCMVKm2 vector is derived from pCMV6a (Chapman et al., *Nuc. Acids Res.* (1991) 19:3979-3986) and comprises a kanamycin selectable marker, a ColE1 origin of replication, a CMV promoter enhancer and Intron A, followed by an insertion site for the synthetic sequences described below followed by a polyadenylation signal derived from bovine growth hormone—the pCMVKm2 vector differs from the pCMV-link vector only in that a polylinker site is inserted into pCMVKm2 to generate pCMV-link; pESN2dhfr and pCMVPLEdhfr, for expression in Chinese Hamster Ovary (CHO) cells; and, pAcC13, a shuttle vector for use in the Baculovirus expression system (pAcC13, is derived from pAcC12 which is described by Munemitsu S., et al., *Mol Cell Biol.* 10(11):5977-5982, 1990).

Briefly, construction of pCMVPLEdhfr was as follows.

To construct a DHFR cassette, the EMCV IRES (internal ribosome entry site) leader was PCR-amplified from pCite-4a+ (Novagen, Inc., Milwaukee, Wis.) and inserted into pET-23d (Novagen, Inc., Milwaukee, Wis.) as an Xba-Nco fragment to give pET-EMCV. The dhfr gene was PCR-amplified from pESN2dhfr to give a product with a Gly-Gly-Gly-Ser spacer in place of the translation stop codon and inserted as an Nco-BamH1 fragment to give pET-E-DHFR. Next, the attenuated neo gene was PCR amplified from a pSV2Neo (Clontech, Palo Alto, Calif.) derivative and inserted into the unique BamH1 site of pET-E-DHFR to give pET-E-DHFR/Neo$_{(m2)}$. Finally the bovine growth hormone terminator from pcDNA3 (Invitrogen, Inc., Carlsbad, Calif.) was inserted downstream of the neo gene to give pET-E-DHFR/Neo$_{(m2)}$ BGHt. The EMCV-dhfr/neo selectable marker cassette fragment was prepared by cleavage of pET-E-DHFR/Neo$_{(m2)}$ BGHt.

In one vector construct the CMV enhancer/promoter plus Intron A was transferred from pCMV6a (Chapman et al., *Nuc. Acids Res.* (1991) 19:3979-3986) as a HindIII-Sal1 fragment into pUC19 (New England Biolabs, Inc., Beverly, Mass.). The vector backbone of pUC19 was deleted from the Nde1 to the Sap1 sites. The above described DHFR cassette was added to the construct such that the EMCV IRES followed the CMV promoter. The vector also contained an amp$^r$ gene and an SV40 origin of replication.

A number of mammalian cell lines are known in the art and include immortalized cell lines available from the American Type Culture Collection (A.T.C.C.), such as, but not limited to, Chinese hamster ovary (CHO) cells, HeLa cells, baby hamster kidney (BHK) cells, monkey kidney cells (COS), as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*. See, e.g., Summers and Smith, *Texas Agricultural Experiment Station Bulletin No.* 1555 (1987).

Viral vectors can be used for the production of particles in eucaryotic cells, such as those derived from the pox family of viruses, including vaccinia virus and avian poxvirus. Additionally, a vaccinia based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. Alternately, T7 can be added as a purified protein or enzyme as in the "Progenitor" system (Studier and Moffatt, *J. Mol. Biol.* (1986) 189:113-130). The method provides for high level, transient, cytoplasmic production of large quantities of RNA and its translation product(s).

Depending on the expression system and host selected, the VLPS are produced by growing host cells transformed by an expression vector under conditions whereby the particle-forming polypeptide is expressed and VLPs can be formed. The selection of the appropriate growth conditions is within the skill of the art. If the VLPs are formed intracellularly, the cells are then disrupted, using chemical, physical or mechanical means, which lyse the cells yet keep the VLPs substantially intact. Such methods are known to those of skill in the art and are described in, e.g., *Protein Purification Applications: A Practical Approach*, (E.L.V. Harris and S. Angal, Eds., 1990).

The particles are then isolated (or substantially purified) using methods that preserve the integrity thereof, such as, by gradient centrifugation, e.g., cesium chloride (CsCl) sucrose gradients, pelleting and the like (see, e.g., Kirnbauer et al. *J. Virol.* (1993) 67:6929-6936), as well as standard purification techniques including, e.g., ion exchange and gel filtration chromatography.

VLPs produced by cells containing the synthetic expression cassettes of the present invention can be used to elicit an immune response when administered to a subject. One advantage of the present invention is that VLPs can be produced by mammalian cells carrying the synthetic expression cassettes at levels previously not possible. As discussed above, the VLPs can comprise a variety of antigens in addition to the Gag polypeptide (e.g., Gag-protease, Gag-polymerase, Env, synthetic Env, etc.). Purified VLPs, produced using the synthetic expression cassettes of the present invention, can be administered to a vertebrate subject, usually in the form of vaccine compositions. Combination vaccines may also be used, where such vaccines contain, for example, an adjuvant subunit protein (e.g., Env). Administration can take place using the VLPs formulated alone or formulated with other antigens. Further, the VLPs can be administered prior to, concurrent with, or subsequent to, delivery of the synthetic expression cassettes for DNA immunization (see below) and/or delivery of other vaccines. Also, the site of VLP administration may be the same or different as other vaccine compositions that are being administered. Gene delivery can be accomplished by a number of methods including, but are not limited to, immunization with DNA, alphavirus vectors, pox virus vectors, and vaccinia virus vectors.

VLP immune-stimulating (or vaccine) compositions can include various excipients, adjuvants, carriers, auxiliary substances, modulating agents, and the like. The immune stimulating compositions will include an amount of the VLP/antigen sufficient to mount an immunological response. An appropriate effective amount can be determined by one of skill in the art. Such an amount will fall in a relatively broad range that can be determined through routine trials and will generally be an amount on the order of about 0.1 μg to about 1000 μg, more preferably about 1 μg to about 300 μg, of VLP/antigen.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; McGee J P, et al., *J Microencapsul.* 14(2):197-210, 1997; O'Hagan D T, et al., *Vaccine* 11(2): 149-54, 1993. Such carriers are well known to those of ordinary skill in the art. Additionally, these carriers may function as immunostimulating agents ("adjuvants"). Furthermore, the antigen may be conjugated to a bacterial toxoid, such as toxoid from diphtheria, tetanus, cholera, etc., as well as toxins derived from *E. coli*.

Adjuvants may also be used to enhance the effectiveness of the compositions. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) oligonucleotides or polymeric molecules encoding immunostimulatory CpG motifs (Davis, H. L., et al., *J. Immunology* 160:870-876, 1998; Sato, Y. et al., *Science* 273:352-354, 1996) or complexes of antigens/oligonucleotides {Polymeric molecules include double and single stranded RNA and DNA, and backbone modifications thereof, for example, methylphosphonate linkages; or (7) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (8) other substances that act as immunostimulating agents to enhance the effectiveness of the composition. Further, such polymeric molecules include alternative polymer backbone structures such as, but not limited to, polyvinyl backbones (Pitha, *Biochem Biophys Acta*, 204:39, 1970a; Pitha, *Biopolymers,* 9:965, 1970b), and morpholino backbones (Summerton, J., et al., U.S. Pat. No. 5,142,047, issued Aug. 25, 1992; Summerton, J., et al., U.S. Pat. No. 5,185,444 issued Feb. 9, 1993). A variety of other charged and uncharged polynucleotide analogs have been reported. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates).}; and (7) other substances that act as immunostimulating agents to enhance the effectiveness of the VLP immune-stimulating (or vaccine) composition. Alum, CpG oligonucleotides, and MF59 are preferred.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(1'-2'-dipaltoyl-sn-glycero-3-huydroxyphosphoryloxy)-ethylamine (MTP-PE), etc.

Dosage treatment with the VLP composition may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least in part, be determined by the need of the subject and be dependent on the judgment of the practitioner.

If prevention of disease is desired, the antigen carrying VLPs are generally administered prior to primary infection with the pathogen of interest. If treatment is desired, e.g., the reduction of symptoms or recurrences, the VLP compositions are generally administered subsequent to primary infection.

2.3.2 Using the Synthetic Expression Cassettes of the Present Invention to Create Packaging Cell Lines A number of viral based systems have been developed for use as gene transfer vectors for mammalian host cells. For example, retroviruses (in particular, lentiviral vectors) provide a convenient platform for gene delivery systems. A coding sequence of interest (for example, a sequence useful for gene therapy applications) can be inserted into a gene delivery vector and packaged in retroviral particles using techniques known in the art. Recombinant virus can then be isolated and delivered to cells of the subject either in vivo or ex vivo. A number of retroviral systems have been described, including, for example, the following: (U.S. Pat. No. 5,219, 740; Miller et al. (1989) *BioTechniques* 7:980; Miller, A. D. (1990) *Human Gene Therapy* 1:5; Scarpa et al. (1991) *Virology* 180:849; Burns et al. (1993) *Proc. Natl. Acad. Sci. USA* 90:8033; Boris-Lawrie et al. (1993) *Cur. Opin. Genet. Develop.* 3:102; GB 2200651; EP 0415731; EP 0345242; WO 89/02468; WO 89/05349; WO 89/09271; WO 90/02806; WO 90/07936; WO 90/07936; WO 94/03622; WO 93/25698; WO 93/25234; WO 93/11230; WO 93/10218; WO 91/02805; in U.S. Pat. No. 5,219,740; U.S. Pat. No. 4,405,712; U.S. Pat. No. 4,861,719; U.S. Pat. No. 4,980,289 and U.S. Pat. No. 4,777,127; in U.S. Ser. No. 07/800,921; and in Vile (1993) *Cancer Res* 53:3860-3864; Vile (1993) *Cancer Res* 53:962-967; Ram (1993) *Cancer Res* 53:83-88; Takamiya (1992) *J Neurosci Res* 33:493-503; Baba (1993) *J Neurosurg* 79:729-735; Mann (1983) *Cell* 33:153; Cane (1984) *Proc Natl Acad Sci USA* 81; 6349; and Miller (1990) *Human Gene Therapy* 1.

In other embodiments, gene transfer vectors can be constructed to encode a cytokine or other immunomodulatory molecule. For example, nucleic acid sequences encoding native IL-2 and gamma-interferon can be obtained as described in U.S. Pat. Nos. 4,738,927 and 5,326,859, respectively, while useful muteins of these proteins can be obtained as described in U.S. Pat. No. 4,853,332. Nucleic acid sequences encoding the short and long forms of mCSF can be obtained as described in U.S. Pat. Nos. 4,847,201 and 4,879,227, respectively. In particular aspects of the invention, retroviral vectors expressing cytokine or immunomodulatory genes can be produced as described herein (for example, employing the packaging cell lines of the present invention) and in International Application No. PCT US 94/02951, entitled "Compositions and Methods for Cancer Immunotherapy."

Examples of suitable inimunomodulatory molecules for use herein include the following: IL-1 and IL-2 (Karupiah et al. (1990) *J. Immunology* 144:290-298, Weber et al. (1987) *J. Exp. Med.* 166:1716-1733, Gansbacher et al. (1990) *J. Exp. Med.* 172:1217-1224, and U.S. Pat. No. 4,738,927); IL-3 and IL-4 (Tepper et al. (1989) *Cell* 57:503-512, Golumbek et al. (1991) *Science* 254:713-716, and U.S. Pat. No. 5,017,691); IL-5 and IL-6 (Brakenhof et al. (1987) *J. Immunol.* 139:4116-4121, and International Publication No. WO 90/06370); IL-7 (U.S. Pat. No. 4,965,195); IL-8, IL-9, IL-10, IL-11, IL-12, and IL-13 (*Cytokine Bulletin*, Summer 1994); IL-14 and IL-15; alpha interferon (Finter et al. (1991) *Drugs* 42:749-765, U.S. Pat. Nos. 4,892,743 and 4,966,843, International Publication No. WO 85/02862, Nagata et al. (1980) *Nature* 284:316-320, Familletti et al. (1981) *Methods in Enz.* 78:387-394, Twu et al. (1989) *Proc. Natl. Acad. Sci. USA* 86:2046-2050, and Faktor et al. (1990) *Oncogene* 5:867-872); beta-interferon (Seif et al. (1991) *J. Virol.* 65:664-671); gamma-interferons (Radford et al. (1991) *The American Society of Hepatology* 20082015, Watanabe et al. (1989) *Proc. Natl. Acad. Sci. USA* 86:9456-9460, Gansbacher et al. (1990) *Cancer Research* 50:7820-7825, Maio et al. (1989) *Can. Immunol. Immunother.* 30:34-42, and U.S. Pat. Nos. 4,762,791 and 4,727,138); G-CSF (U.S. Pat. Nos. 4,999,291 and 4,810,643); GM-CSF (International Publication No. WO 85/04188).

Immunomodulatory factors may also be agonists, antagonists, or ligands for these molecules. For example, soluble forms of receptors can often behave as antagonists for these types of factors, as can mutated forms of the factors themselves.

Nucleic acid molecules that encode the above-described substances, as well as other nucleic acid molecules that are advantageous for use within the present invention, may be readily obtained from a variety of sources, including, for example, depositories such as the American Type Culture Collection, or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), A.T.C.C. Deposit No. 39656 (which contains sequences encoding TNF), A.T.C.C. Deposit No. 20663 (which contains sequences encoding alpha-interferon), A.T.C.C. Deposit Nos. 31902, 31902 and 39517 (which contain sequences encoding beta-interferon), A.T.C.C. Deposit No. 67024 (which contains a sequence which encodes Interleukin-1b), A.T.C.C. Deposit Nos. 39405, 39452, 39516, 39626 and 39673 (which contain sequences encoding Interleukin-2), A.T.C.C. Deposit Nos. 59399, 59398, and 67326 (which contain sequences encoding Interleukin-3), A.T.C.C. Deposit No. 57592 (which contains sequences encoding Interleukin-4), A.T.C.C. Deposit Nos. 59394 and 59395 (which contain sequences encoding Interleukin-5), and A.T.C.C. Deposit No. 67153 (which contains sequences encoding Interleukin-6).

Plasmids containing cytokine genes or immunomodulatory genes (International Publication Nos. WO 94/02951 and WO 96/21015, both of which are incorporated by reference in their entirety) can be digested with appropriate restriction enzymes, and DNA fragments containing the particular gene of interest can be inserted into a gene transfer vector using standard molecular biology techniques. (See, e.g., Sambrook et al., supra., or Ausubel et al. (eds) *Current Protocols in Molecular Biology*, Greene Publishing and Wiley-Interscience).

Polynucleotide sequences coding for the above-described molecules can be obtained using recombinant methods, such as by screening cDNA and genomic libraries from cells expressing the gene, or by deriving the gene from a vector known to include the same. For example, plasmids which contain sequences that encode altered cellular products may be obtained from a depository such as the A.T.C.C., or from commercial sources. Plasmids containing the nucleotide sequences of interest can be digested with appropriate restriction enzymes, and DNA fragments containing the nucleotide sequences can be inserted into a gene transfer vector using standard molecular biology techniques.

Alternatively, cDNA sequences for use with the present invention may be obtained from cells which express or contain the sequences, using standard techniques, such as phenol extraction and PCR of cDNA or genomic DNA. See, e.g., Sambrook et al., supra, for a description of techniques used to obtain and isolate DNA. Briefly, mRNA from a cell which expresses the gene of interest can be reverse transcribed with reverse transcriptase using oligo-dT or random primers. The single stranded cDNA may then be amplified by PCR (see U.S. Pat. Nos. 4,683,202, 4,683,195 and 4,800,159, see also *PCR Technology: Principles and Applications for DNA Amplification*, Erlich (ed.), Stockton Press, 1989)) using oligonucleotide primers complementary to sequences on either side of desired sequences.

The nucleotide sequence of interest can also be produced synthetically, rather than cloned, using a DNA synthesizer (e.g., an Applied Biosystems Model 392 DNA Synthesizer, available from ABI, Foster City, Calif.). The nucleotide sequence can be designed with the appropriate codons for the expression product desired. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

The synthetic expression cassettes of the present invention can be employed in the construction of packaging cell lines for use with retroviral vectors.

One type of retrovirus, the murine leukemia virus, or "MLV", has been widely utilized for gene therapy applications (see generally Mann et al. (*Cell* 33:153, 1993), Cane and Mulligan (*Proc, Nat'l. Acad. Sci. USA* 81:6349, 1984), and Miller et al., *Human Gene Therapy* 1:5-14, 1990.

Lentiviral vectors typically, comprise a 5' lentiviral LTR, a tRNA binding site, a packaging signal, a promoter operably linked to one or more genes of interest, an origin of second strand DNA synthesis and a 3' lentiviral LTR, wherein the lentiviral vector contains a nuclear transport element. The nuclear transport element may be located either upstream (5') or downstream (3') of a coding sequence of interest (for example, a synthetic Gag or Env expression cassette of the present invention). Within certain embodiments, the nuclear transport element is not RRE. Within one embodiment the packaging signal is an extended packaging signal. Within other embodiments the promoter is a tissue specific promoter, or, alternatively, a promoter such as CMV. Within other embodiments, the lentiviral vector further comprises an internal ribosome entry site.

A wide variety of lentiviruses may be utilized within the context of the present invention, including for example, lentiviruses selected from the group consisting of HIV, HIV-1, HIV-2, FIV and SIV.

Within yet another aspect of the invention, host cells (e.g., packaging cell lines) are provided which contain any of the expression cassettes described herein. For example, within one aspect packaging cell line are provided comprising an expression cassette that comprises a sequence encoding synthetic Gag-polymerase, and a nuclear transport element, wherein the promoter is operably linked to the sequence encoding Gag-polymerase. Packaging cell lines may further comprise a promoter and a sequence encoding tat, rev, or an envelope, wherein the promoter is operably linked to the sequence encoding tat, rev, Env or sequences encoding modified versions of these proteins. The packaging cell line may further comprise a sequence encoding any one or more of other HIV gene encoding sequences.

In one embodiment, the expression cassette (carrying, for example, the synthetic Gag-polymerase) is stably integrated. The packaging cell line, upon introduction of a lentiviral vector, typically produces particles. The promoter regulating expression of the synthetic expression cassette may be inducible. Typically, the packaging cell line, upon introduction of a lentiviral vector, produces particles that are essentially free of replication competent virus.

Packaging cell lines are provided comprising an expression cassette which directs the expression of a synthetic Gag-polymerase gene or comprising an expression cassette which directs the expression of a synthetic Env genes described herein. (See, also, Andre, S., et al., *Journal of Virology* 72(2): 1497-1503, 1998; Haas, J., et al., *Current Biology* 6(3):315-324, 1996) for a description of other modified Env sequences). A lentiviral vector is introduced into the packaging cell line to produce a vector producing cell line.

As noted above, lentiviral vectors can be designed to carry or express a selected gene(s) or sequences of interest. Lentiviral vectors may be readily constructed from a wide variety of lentiviruses (see RNA Tumor Viruses, Second Edition, Cold Spring Harbor Laboratory, 1985). Representative examples of lentiviruses included HIV, HIV-1, HIV-2, FIV and SIV. Such lentiviruses may either be obtained from patient isolates, or, more preferably, from depositories or collections such as the American Type Culture Collection, or isolated from known sources using available techniques.

Portions of the lentiviral gene delivery vectors (or vehicles) may be derived from different viruses. For example, in a given recombinant lentiviral vector, LTRs may be derived from an HIV, a packaging signal from SIV, and an origin of second strand synthesis from HrV-2. Lentiviral vector constructs may comprise a 5' lentiviral LTR, a tRNA binding site, a packaging signal, one or more heterologous sequences, an origin of second strand DNA synthesis and a 3' LTR, wherein said lentiviral vector contains a nuclear transport element that is not RRE.

Briefly, Long Terminal Repeats ("LTRs") are subdivided into three elements, designated U5, R and U3. These elements contain a variety of signals which are responsible for the biological activity of a retrovirus, including for example, promoter and enhancer elements which are located within U3. LTRs may be readily identified in the provirus (integrated DNA form) due to their precise duplication at either end of the genome. As utilized herein, a 5' LTR should be understood to include a 5' promoter element and sufficient LTR sequence to allow reverse transcription and integration of the DNA form of the vector. The 3' LTR should be understood to include a polyadenylation signal, and sufficient LTR sequence to allow reverse transcription and integration of the DNA form of the vector.

The tRNA binding site and origin of second strand DNA synthesis are also important for a retrovirus to be biologically active, and may be readily identified by one of skill in the art. For example, retroviral tRNA binds to a tRNA binding site by Watson-Crick base pairing, and is carried with the retrovirus genome into a viral particle. The tRNA is then utilized as a primer for DNA synthesis by reverse transcriptase. The tRNA binding site may be readily identified based upon its location just downstream from the 5'LTR. Similarly, the origin of second strand DNA synthesis is, as its name implies, important for the second strand DNA synthesis of a retrovirus. This region, which is also referred to as the poly-purine tract, is located just upstream of the 3'LTR.

In addition to a 5' and 3' LTR, tRNA binding site, and origin of second strand DNA synthesis, recombinant retroviral vector constructs may also comprise a packaging signal, as well as one or more genes or coding sequences of interest. In addition, the lentiviral vectors have a nuclear transport element which, in preferred embodiments is not RRE. Representative examples of suitable nuclear transport elements include the element in Rous sarcoma virus (Ogert, et al., *J. ViroL.* 70, 3834-3843, 1996), the element in Rous sarcoma virus (Liu & Mertz, *Genes & Dev.*, 9, 1766-1789, 1995) and the element in the genome of simian retrovirus type I (Zolotukhin, et al., *J. Virol.* 68, 7944-7952, 1994). Other potential elements include the elements in the histone gene (Kedes, *Annu. Rev. Biochem.* 48, 837-870, 1970), the α-interferon gene (Nagata et al., *Nature* 287, 401-408, 1980), the β-adrenergic receptor gene (Koilka, et al., *Nature* 329, 75-79, 1987), and the c-Jun gene (Hattorie, et al., *Proc. Natl. Acad. Sci. USA* 85, 9148-9152, 1988).

Recombinant lentiviral vector constructs typically lack both Gag-polymerase and Env coding sequences. Recombinant lentiviral vector typically contain less than 20, preferably 15, more preferably 10, and most preferably 8 consecutive nucleotides found in Gag-polymerase and Env genes. One advantage of the present invention is that the synthetic Gag-polymerase expression cassettes, which can be used to construct packaging cell lines for the recombinant retroviral vector constructs, have little homology to wild-type Gag-polymerase sequences and thus considerably reduce or eliminate the possibility of homologous recombination between the synthetic and wild-type sequences.

Lentiviral vectors may also include tissue-specific promoters to drive expression of one or more genes or sequences of interest.

Lentiviral vector constructs may be generated such that more than one gene of interest is expressed. This may be accomplished through the use of di- or oligo-cistronic cassettes (e.g., where the coding regions are separated by 80 nucleotides or less, see generally Levin et al., *Gene* 108:167-174, 1991), or through the use of Internal Ribosome Entry Sites ("IRES").

Packaging cell lines suitable for use with the above described recombinant retroviral vector constructs may be readily prepared given the disclosure provided herein. Briefly, the parent cell line from which the packaging cell line is derived can be selected from a variety of mammalian cell lines, including for example, 293, RD, COS-7, CHO, BHK, VERO, HT1080, and myeloma cells.

After selection of a suitable host cell for the generation of a packaging cell line, one or more expression cassettes are introduced into the cell line in order to complement or supply in trans components of the vector which have been deleted.

Representative examples of suitable synthetic HIV polynucleotide sequences have been described herein for use in expression cassettes of the present invention. As described above, the native and/or synthetic coding sequences may also be utilized in these expression cassettes.

Utilizing the above-described expression cassettes, a wide variety of packaging cell lines can be generated. For example, within one aspect packaging cell line are provided comprising an expression cassette that comprises a sequence encoding synthetic Gag-polymerase, and a nuclear transport element, wherein the promoter is operably linked to the sequence encoding Gag-polymerase. Within other aspects, packaging cell lines are provided comprising a promoter and a sequence encoding tat, rev, Env, or other HIV antigens or epitopes derived therefrom, wherein the promoter is operably linked to the sequence encoding tat, rev, Env, or the HIV antigen or epitope. Within further embodiments, the packaging cell line may comprise a sequence encoding any one or more of tat, rev, nef, vif, vpu or vpr. For example, the packaging cell line may contain only tat, rev, nef, vif, vpu, or vpr alone, tat rev and nef, nef and vif, nef and vpu, nef and vpr, vif and vpu, vif and vpr, vpu and vpr, nef vif and vpu, nef vif and vpr, nef vpu and vpr, vif vpu and vpr, all four of nef, vif, vpu, and vpr, etc.

In one embodiment, the expression cassette is stably integrated. Within another embodiment, the packaging cell line, upon introduction of a lentiviral vector, produces particles. Within further embodiments the promoter is inducible. Within certain preferred embodiments of the invention, the packaging cell line, upon introduction of a lentiviral vector, produces particles that are free of replication competent virus.

The synthetic cassettes containing modified coding sequences are transfected into a selected cell line. Transfected cells are selected that (i) carry, typically, integrated, stable copies of the HIV coding sequences, and (ii) are expressing acceptable levels of these polypeptides (expression can be evaluated by methods known in the prior art in view of the teachings of the present disclosure). The ability of the cell line to produce VLPs may also be verified.

A sequence of interest is constructed into a suitable viral vector as discussed above. This defective virus is then transfected into the packaging cell line. The packaging cell line provides the viral functions necessary for producing virus-like particles into which the defective viral genome, containing the sequence of interest, are packaged. These VLPs are then isolated and can be used, for example, in gene delivery or gene therapy.

Further, such packaging cell lines can also be used to produce VLPs alone, which can, for example, be used as adjuvants for administration with other antigens or in vaccine compositions. Also, co-expression of a selected sequence of interest encoding a polypeptide (for example, an antigen) in the packaging cell line can also result in the entrapment and/or association of the selected polypeptide in/with the VLPs.

Various forms of the different embodiments of the present invention (e.g., synthetic constructs) may be combined.

2.4.0 DNA Immunization and Gene Delivery

A variety of HIV polypeptide antigens, particularly HIV antigens, can be used in the practice of the present invention. HIV antigens can be included in DNA immunization constructs containing, for example, a synthetic Env expression cassettes, a synthetic Gag expression cassette, a synthetic pol-derived polypeptide expression cassette, a synthetic expression cassette comprising sequences encoding one or more accessory or regulatory genes (e.g., tat, rev, nef, vif, vpu, vpr), and/or a synthetic Gag expression cassette fused in-frame to a coding sequence for the polypeptide antigen (synthetic or wild-type), where expression of the construct results in VLPs presenting the antigen of interest.

HIV antigens of particular interest to be used in the practice of the present invention include pol, tat, rev, nef, vif, vpu, vpr, and other HIV-1 (also known as HTLV-III, LAV, ARV, etc.) antigens or epitopes derived therefrom, including, but not limited to, antigens such as gp120, gp41, gp160 (both native and modified); Gag; and pol from a variety of isolates including, but not limited to, $HIV_{IIIb}$, $HIV_{SF2}$, $HIV-1_{SF162}$, $HIV-1_{SF170}$, $HIV_{LAV}$, $HIV_{LAI}$, $HIV_{MN}$, $HIV-1_{CM235}$, $HIV-1_{US4}$, other HIV-1 strains from diverse subtypes (e.g., subtypes, A through G, and O), HIV-2 strains and diverse subtypes (e.g., $HIV-2_{UC1}$ and $HIV-2_{UC2}$). See, e.g., Myers, et al., Los Alamos Database, Los Alamos National Laboratory, Los Alamos, N. Mex.; Myers, et al., *Human Retroviruses and Aids,* 1990, Los Alamos, N. Mex.: Los Alamos National Laboratory. These antigens may be synthetic (as described herein) or wild-type.

To evaluate efficacy, DNA immunization using synthetic expression cassettes of the present invention can be performed, for example, as follows. Mice are immunized with a tat/rev/nef synthetic expression cassette. Other mice are immunized with a tat/rev/nef wild type expression cassette. Mouse immunizations with plasmid-DNAs typically show that the synthetic expression cassettes provide a clear improvement of immunogenicity relative to the native expression cassettes. Also, a second boost immunization will induce a secondary immune response, for example, after approximately two weeks. Further, the results of CTL assays typically show increased potency of synthetic expression cassettes for induction of cytotoxic T-lymphocyte (CTL) responses by DNA immunization.

Exemplary primate studies directed at the evaluation of neutralizing antibodies and cellular immune responses against HIV are described below.

It is readily apparent that the subject invention can be used to mount an immune response to a wide variety of antigens and hence to treat or prevent infection, particularly HIV infection.

2.4.1 Delivery of the Synthetic Expression Cassettes of the Present Invention

Polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from cells and tissues containing the same, using standard techniques, such as phenol extraction and PCR of cDNA or genomic DNA. See, e.g., Sambrook et al., supra, for a description of techniques used to obtain and isolate DNA. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence is assembled from overlapping oligonucleotides prepared by standard methods and assembled into a complete coding sequence. See, e.g., Edge, *Nature* (1981) 292:756; Nambair et al., *Science* (1984) 223: 1299; Jay et al., *J. Biol. Chem.* (1984) 259:6311; Stemmer, W. P. C., (1995) *Gene* 164:49-53.

Next, the gene sequence encoding the desired antigen can be inserted into a vector containing a synthetic expression cassette of the present invention. In one embodiment, polynucleotides encoding selected antigens are separately cloned into expression vectors (e.g., Env-coding polynucleotide in a first vector, Gag-coding polynucleotide in a second vector, Pol-derived polypeptide-coding polynucleotide in a third vector, tat-, rev-, nef-, vif-, vpu-, vpr-coding polynucleotides in further vectors, etc.). In certain embodiments, the antigen is inserted into or adjacent a synthetic Gag coding sequence such that when the combined sequence is expressed it results in the production of VLPs comprising the Gag polypeptide and the antigen of interest, e.g., Env (native or modified) or other antigen(s) (native or modified) derived from HIV. Insertions can be made within the coding sequence or at either end of the coding sequence (5', amino terminus of the expressed Gag polypeptide; or 3', carboxy terminus of the expressed Gag polypeptide)(Wagner, R., et al., *Arch Virol.* 127:117-137, 1992; Wagner, R., et al., *Virology* 200:162-175, 1994; Wu, X., et al., *J. Virol.* 69(6):3389-3398, 1995; Wang, C-T., et al., *Virology* 200:524-534, 1994; Chazal, N., et al., *Virology* 68(1):111-122, 1994; Griffiths, J. C., et al., *J. Virol.* 67(6): 3191-3198, 1993; Reicin, A. S., et al., *J. Virol.* 69(2):642-650, 1995).

Up to 50% of the coding sequences of p55Gag can be deleted without affecting the assembly to virus-like particles and expression efficiency (Borsetti, A., et al, *J. Virol.* 72(11): 9313-9317, 1998; Garnier, L., et al., *J Virol* 72(6):4667-4677, 1998; Zhang, Y., et al., *J Virol* 72(3):1782-1789, 1998; Wang, C., et al., *J Virol* 72(10): 7950-7959, 1998). In one embodiment of the present invention, immunogenicity of the high level expressing synthetic Gag expression cassettes can be increased by the insertion of different structural or non-structural HIV antigens, multi-epitope cassettes, or cytokine sequences into deleted regions of Gag sequence. Such deletions may be generated following the teachings of the present invention and information available to one of ordinary skill in the art. One possible advantage of this approach, relative to using full-length sequences fused to heterologous polypeptides, can be higher expression/secretion efficiency of the expression product.

When sequences are added to the amino terminal end of Gag, the polynucleotide can contain coding sequences at the 5' end that encode a signal for addition of a myristic moiety to the Gag-containing polypeptide (e.g., sequences that encode Met-Gly).

The ability of Gag-containing polypeptide constructs to form VLPs can be empirically determined following the teachings of the present specification.

The synthetic expression cassettes can also include control elements operably linked to the coding sequence, which allow for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence.

Enhancer elements may also be used herein to increase expression levels of the mammalian constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence.

Furthermore, plasmids can be constructed which include a chimeric antigen-coding gene sequences, encoding, e.g., multiple antigens/epitopes of interest, for example derived from more than one viral isolate.

Typically the antigen coding sequences precede or follow the synthetic coding sequence and the chimeric transcription unit will have a single open reading frame encoding both the antigen of interest and the synthetic coding sequences. Alternatively, multi-cistronic cassettes (e.g., bi-cistronic cassettes) can be constructed allowing expression of multiple antigens from a single mRNA using the EMCV IRES, or the like (Example 7).

In one embodiment of the present invention, a nucleic acid immunizing composition may comprise, for example, the following: a first expression vector comprising a Gag expression cassette, a second vector comprising an Env expression cassette, and a third expression vector comprising a Pol expression cassette, or one or more coding region of Pol (e.g., Prot, RT, RNase, Int), wherein further antigen coding sequences may be associated with the Pol expression, such antigens may be obtained, for example, from accessory genes (e.g., vpr, vpu, vif), regulatory genes (e.g., nef, tat, rev), or portions of the Pol sequences (e.g., Prot, RT, RNase, Int)). In another embodiment, a nucleic acid immunizing composition may comprise, for example, an expression cassette comprising any of the synthetic polynucleotide sequences of the present invention. In another embodiment, a nucleic acid immunizing composition may comprise, for example, an expression cassette comprising coding sequences for a number of HIV genes (or sequences derived from such genes) wherein the coding sequences are in-frame and under the control of a single promoter, for example, Gag-Env constructs, Tat-Rev-Nef constructs, P2Pol-tat-rev-nef constructs, etc. The synthetic coding sequences of the present invention may be combined in any number of combinations depending on the coding sequence products (i.e., HIV polypeptides) to which, for example, an immunological response is desired to be raised. In yet another embodiment, synthetic coding sequences for multiple HIV-derived polypeptides may be constructed into a polycistronic message under the control of a single promoter wherein IRES are placed adjacent the coding sequence for each encoded polypeptide.

Once complete, the constructs are used for nucleic acid immunization using standard gene delivery protocols. Methods for gene delivery are known in the art. See, e.g., U.S. Pat. Nos. 5,399,346, 5,580,859, 5,589,466. Genes can be delivered either directly to the vertebrate subject or, alternatively, delivered ex vivo, to cells derived from the subject and the cells reimplanted in the subject.

A number of viral based systems have been developed for gene transfer into mammalian cells. For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219, 740; Miller and Rosman, *BioTechniques* (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Temin, *Cur. Opin. Genet. Develop.* (1993) 3:102-109.

A number of adenovirus vectors have also been described. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J. Virol.* (1994) 68:933-940; Barr et al., *Gene Therapy* (1994) 1:51-58; Berkner, K. L. *BioTechniques* (1988) 6:616-629; and Rich et al., *Human Gene Therapy* (1993) 4:461-476).

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., *Molec. Cell. Biol.* (1988) 8:3988-3996; Vincent et al., Vaccines 90 (1990) (Cold Spring Harbor Laboratory Press); Carter, B. J. *Current Opinion in Biotechnology* (1992) 3:533-539; Muzyczka, N. *Current Topics in Microbiol. and Immunol.* (1992) 158:97-129; Kotin, R. M. *Human Gene Therapy* (1994) 5:793-801; Shelling and Smith, *Gene Therapy* (1994) 1:165-169; and Zhou et al., *J. Exp. Med.* (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules encoding the antigens of interest include those derived from the pox family of viruses, including vaccinia virus and avian poxvirus. By way of example, vaccinia virus recombinants expressing the genes can be constructed as follows. The DNA encoding the particular synthetic HIV polypeptide coding sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the coding sequences of interest into the viral genome. The resulting TK⁻ recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., *J. Biol. Chem.* (1993) 268:6866-6869 and Wagner et al., *Proc. Natl. Acad. Sci. USA* (1992) 89:6099-6103, can also be used for gene delivery.

Members of the Alphavirus genus, such as, but not limited to, vectors derived from the Sindbis, Semliki Forest, and Venezuelan Equine Encephalitis viruses, will also find use as viral vectors for delivering the polynucleotides of the present invention (for example, a synthetic Gag-polypeptide encoding expression cassette). For a description of Sindbis-virus derived vectors useful for the practice of the instant methods, see, Dubensky et al., *J. Virol.* (1996) 70:508-519; and International Publication Nos. WO 95/07995 and WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference. Preferred expression systems include, but are not limited to, eucaryotic layered vector initiation systems (e.g., U.S. Pat. No. 6,015,686, U.S. Pat. No. 5,814,482, U.S. Pat. No. 6,015,694, U.S. Pat. No. 5,789,245, EP 1029068A2, WO 9918226A2/A3, EP 00907746A2, WO 9738087A2, all herein incorporated by reference in their entireties).

A vaccinia based infection/transfection system can be conveniently used to provide for inducible, transient expression of the coding sequences of interest in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, *Proc. Natl. Acad. Sci. USA* (1990) 87:6743-6747; Fuerst et al., *Proc. Natl. Acad. Sci. USA* (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, *J. Mol. Biol.* (1986) 189:113-130; Deng and Wolff, *Gene* (1994) 143:245-249; Gao et al., *Biochem. Biophys. Res. Commun.* (1994) 200:1201-1206; Gao and Huang, *Nuc. Acids Res.* (1993) 21:2867-2872; Chen et al., *Nuc. Acids Res.* (1994) 22:2114-2120; and U.S. Pat. No. 5,135,855.

Delivery of the expression cassettes of the present invention can also be accomplished using eucaryotic expression vectors comprising CMV-derived elements, such vectors include, but are not limited to, the following: pCMVKm2, pCMV-link pCMVPLEdhfr, and pCMV6a (all described above).

Synthetic expression cassettes of interest can also be delivered without a viral vector. For example, the synthetic expression cassette can be packaged in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1-17; Straubinger et al., in *Methods of Enzymology* (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Felgner et al., *Proc. Natl. Acad. Sci. USA* (1987) 84:7413-7416); mRNA (Malone et al., *Proc. Natl. Acad. Sci. USA* (1989) 86:6077-6081); and purified transcription factors (Debs et al., *J. Biol. Chem.* (1990) 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphosphatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., *Proc. Natl. Acad. Sci. USA* (1978) 75:4194-4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA and/or protein antigen(s) can also be delivered in cochleate lipid compositions similar to those described by Papahadjopoulos et al., *Biochem. Biophys. Acta.* (1975) 394: 483-491. See, also, U.S. Pat. Nos. 4,663,161 and 4,871,488.

The synthetic expression cassette of interest may also be encapsulated; adsorbed to, or associated with, particulate carriers. Such carriers present multiple copies of a selected antigen to the immune system and promote trapping and retention of antigens in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; McGee J P, et al., *J Microencapsul.* 14(2):197-210, 1997; O'Hagan D T, et al., *Vaccine* 11(2):149-54, 1993. Suitable microparticles may also be manufactured in the presence of charged detergents, such as anionic or cationic detergents, to yield microparticles with a surface having a net negative or a net positive charge. For example, microparticles manufactured with anionic detergents, such as hexadecyltrimethylammonium bromide (CTAB), i.e. CTAB-PLG microparticles, adsorb negatively charged macromolecules, such as DNA. (see, e.g., Int'l Application Number PCT/US99/17308).

Furthermore, other particulate systems and polymers can be used for the in vivo or ex vivo delivery of the gene of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Feigner, P. L., *Advanced Drug Delivery Reviews* (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten, are especially useful for delivering synthetic expression cassettes of the present invention. The particles are coated with the synthetic expression cassette(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744. Also, needle-less injection systems can be used (Davis, H. L., et al, *Vaccine* 12:1503-1509, 1994; Bioject, Inc., Portland, Oreg.).

Recombinant vectors carrying a synthetic expression cassette of the present invention are formulated into compositions for delivery to the vertebrate subject. These compositions may either be prophylactic (to prevent infection) or therapeutic (to treat disease after infection). The compositions will comprise a "therapeutically effective amount" of the gene of interest such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials.

The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, and the like, may be present in such vehicles. Certain facilitators of nucleic acid uptake and/or expression can also be included in the compositions or coadministered, such as, but not limited to, bupivacaine, cardiotoxin and sucrose.

Once formulated, the compositions of the invention can be administered directly to the subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) (with or without the corresponding antigen) in liposomes, and direct microinjection of the DNA into nuclei.

Direct delivery of synthetic expression cassette compositions in vivo will generally be accomplished with or without viral vectors, as described above, by injection using either a conventional syringe or a gene gun, such as the Accell® gene delivery system (PowderJect Technologies, Inc., Oxford, England). The constructs can be injected either subcutaneously, epidermally, intradermally, intramucosally such as nasally, rectally and vaginally, intraperitoneally, intravenously, orally or intramuscularly. Delivery of DNA into cells of the epidermis is particularly preferred as this mode of administration provides access to skin-associated lymphoid cells and provides for a transient presence of DNA in the recipient. Other modes of administration include oral and pulmonary administration, suppositories, needle-less injection, transcutaneous and transdermal applications. Dosage treatment may be a single dose schedule or a multiple dose schedule. Administration of nucleic acids may also be combined with administration of peptides or other substances.

Exemplary immunogenicity studies are presented in Examples 4, 5, 6, 9, 10, 11, and 12.

2.4.2 Ex vivo Delivery of the Synthetic Expression Cassettes of the Present Invention In one embodiment, T cells, and related cell types (including but not limited to antigen presenting cells, such as, macrophage, monocytes, lymphoid cells, dendritic cells, B-cells, T-cells, stem cells, and progenitor cells thereof), can be used for ex vivo delivery of the synthetic expression cassettes of the present invention. T cells can be isolated from peripheral blood lymphocytes (PBLs) by a variety of procedures known to those skilled in the art. For example, T cell populations can be "enriched" from a population of PBLs through the removal of accessory and B cells. In particular, T cell enrichment can be accomplished by the elimination of non-T cells using anti-MHC class II monoclonal antibodies. Similarly, other antibodies can be used to deplete specific populations of non-T cells. For example, anti-Ig antibody molecules can be used to deplete B cells and anti-MacI antibody molecules can be used to deplete macrophages.

T cells can be further fractionated into a number of different subpopulations by techniques known to those skilled in the art. Two major subpopulations can be isolated based on their differential expression of the cell surface markers CD4 and CD8. For example, following the enrichment of T cells as described above, CD4+ cells can be enriched using antibodies specific for CD4 (see Coligan et al., supra). The antibodies may be coupled to a solid support such as magnetic beads. Conversely, CD8+ cells can be enriched through the use of antibodies specific for CD4 (to remove CD4+ cells), or can be isolated by the use of CD8 antibodies coupled to a solid support. CD4 lymphocytes from HIV-1 infected patients can be expanded ex vivo, before or after transduction as described by Wilson et. al. (1995) J. Infect. Dis. 172:88.

Following purification of T cells, a variety of methods of genetic modification known to those skilled in the art can be performed using non-viral or viral-based gene transfer vectors constructed as described herein. For example, one such approach involves transduction of the purified T cell population with vector-containing supernatant of cultures derived from vector producing cells. A second approach involves co-cultivation of an irradiated monolayer of vector-producing cells with the purified T cells. A third approach involves a similar co-cultivation approach; however, the purified T cells are pre-stimulated with various cytokines and cultured 48 hours prior to the co-cultivation with the irradiated vector producing cells. Pre-stimulation prior to such transduction increases effective gene transfer (Nolta et al. (1992) Exp. Hematol. 20:1065). Stimulation of these cultures to proliferate also provides increased cell populations for re-infusion into the patient. Subsequent to co-cultivation, T cells are collected from the vector producing cell monolayer, expanded, and frozen in liquid nitrogen.

Gene transfer vectors, containing one or more synthetic expression cassette of the present invention (associated with appropriate control elements for delivery to the isolated T cells) can be assembled using known methods and following the guidance of the present specification.

Selectable markers can also be used in the construction of gene transfer vectors. For example, a marker can be used which imparts to a mammalian cell transduced with the gene transfer vector resistance to a cytotoxic agent. The cytotoxic agent can be, but is not limited to, neomycin, aminoglycoside, tetracycline, chloramphenicol, sulfonamide, actinomycin, netropsin, distamycin A, anthracycline, or pyrazinamide. For example, neomycin phosphotransferase II imparts resistance to the neomycin analogue geneticin (G418).

The T cells can also be maintained in a medium containing at least one type of growth factor prior to being selected. A variety of growth factors are known in the art which sustain the growth of a particular cell type. Examples of such growth factors are cytokine mitogens such as rIL-2, IL-10, IL-12, and IL-15, which promote growth and activation of lymphocytes. Certain types of cells are stimulated by other growth factors such as hormones, including human chorionic gonadotropin (hCG) and human growth hormone. The selection of an appropriate growth factor for a particular cell population is readily accomplished by one of skill in the art.

For example, white blood cells such as differentiated progenitor and stem cells are stimulated by a variety of growth factors. More particularly, IL-3, IL-4, IL-5, IL-6, IL-9, GM-CSF, M-CSF, and G-CSF, produced by activated $T_H$ and activated macrophages, stimulate myeloid stem cells, which then differentiate into pluripotent stem cells, granulocyte-monocyte progenitors, eosinophil progenitors, basophil progenitors, megakaryocytes, and erythroid progenitors. Differentiation is modulated by growth factors such as GM-CSF, IL-3, IL-6, IL-11, and EPO.

Pluripotent stem cells then differentiate into lymphoid stem cells, bone marrow stromal cells, T cell progenitors, B cell progenitors, thymocytes, $T_H$ Cells, $T_C$ cells, and B cells. This differentiation is modulated by growth factors such as IL-3, IL-4, IL-6, IL-7, GM-CSF, M-CSF, G-CSF, IL-2, and IL-5.

Granulocyte-monocyte progenitors differentiate to monocytes, macrophages, and neutrophils. Such differentiation is modulated by the growth factors GM-CSF, M-CSF, and IL-8. Eosinophil progenitors differentiate into eosinophils. This process is modulated by GM-CSF and IL-5.

The differentiation of basophil progenitors into mast cells and basophils is modulated by GM-CSF, IL-4, and IL-9. Megakaryocytes produce platelets in response to GM-CSF, EPO, and IL-6. Erythroid progenitor cells differentiate into red blood cells in response to EPO.

Thus, during activation by the CD3-binding agent, T cells can also be contacted with a mitogen, for example a cytokine such as IL-2. In particularly preferred embodiments, the IL-2 is added to the population of T cells at a concentration of about 50 to 100 µg/ml. Activation with the CD3-binding agent can be carried out for 2 to 4 days.

Once suitably activated, the T cells are genetically modified by contacting the same with a suitable gene transfer vector under conditions that allow for transfection of the vectors into the T cells. Genetic modification is carried out when the cell density of the T cell population is between about $0.1 \times 10^6$ and $5 \times 10^6$, preferably between about $0.5 \times 10^6$ and $2 \times 10^6$. A number of suitable viral and nonviral-based gene transfer vectors have been described for use herein.

After transduction, transduced cells are selected away from non-transduced cells using known techniques. For example, if the gene transfer vector used in the transduction includes a selectable marker which confers resistance to a cytotoxic agent, the cells can be contacted with the appropriate cytotoxic agent, whereby non-transduced cells can be negatively selected away from the transduced cells. If the selectable marker is a cell surface marker, the cells can be contacted with a binding agent specific for the particular cell surface marker, whereby the transduced cells can be positively selected away from the population. The selection step can also entail fluorescence-activated cell sorting (FACS) techniques, such as where FACS is used to select cells from the population containing a particular surface marker, or the selection step can entail the use of magnetically responsive particles as retrievable supports for target cell capture and/or background removal.

More particularly, positive selection of the transduced cells can be performed using a FACS cell sorter (e.g. a FACSVantage™ Cell Sorter, Becton Dickinson Immunocytometry Systems, San Jose, Calif.) to sort and collect transduced cells expressing a selectable cell surface marker. Following transduction, the cells are stained with fluorescent-labeled antibody molecules directed against the particular cell surface marker. The amount of bound antibody on each cell can be measured by passing droplets containing the cells through the cell sorter. By imparting an electromagnetic charge to droplets containing the stained cells, the transduced cells can be separated from other cells. The positively selected cells are then harvested in sterile collection vessels. These cell sorting procedures are described in detail, for example, in the FACSVantage™ Training Manual, with particular reference to sections 3-11 to 3-28 and 10-1 to 10-17.

Positive selection of the transduced cells can also be performed using magnetic separation of cells based on expression or a particular cell surface marker. In such separation techniques, cells to be positively selected are first contacted with specific binding agent (e.g., an antibody or reagent the interacts specifically with the cell surface marker). The cells are then contacted with retrievable particles (e.g., magnetically responsive particles) which are coupled with a reagent that binds the specific binding agent (that has bound to the positive cells). The cell-binding agent-particle complex can then be physically separated from non-labeled cells, for example using a magnetic field. When using magnetically responsive particles, the labeled cells can be retained in a container using a magnetic filed while the negative cells are removed. These and similar separation procedures are known to those of ordinary skill in the art.

Expression of the vector in the selected transduced cells can be assessed by a number of assays known to those skilled in the art. For example, Western blot or Northern analysis can be employed depending on the nature of the inserted nucleotide sequence of interest. Once expression has been established and the transformed T cells have been tested for the presence of the selected synthetic expression cassette, they are ready for infusion into a patient via the peripheral blood stream.

The invention includes a kit for genetic modification of an ex vivo population of primary mammalian cells. The kit typically contains a gene transfer vector coding for at least one selectable marker and at least one synthetic expression cassette contained in one or more containers, ancillary reagents or hardware, and instructions for use of the kit.

2.4.3 Further Delivery Regimes

Any of the polynucleotides (e.g., expression cassettes) or polypeptides described herein (delivered by any of the methods described above) can also be used in combination with other DNA delivery systems and/or protein delivery systems. Non-limiting examples include co-administration of these molecules, for example, in prime-boost methods where one or more molecules are delivered in a "priming" step and, subsequently, one or more molecules are delivered in a "boosting" step. In certain embodiments, the delivery of one or more nucleic acid-containing compositions and is followed by delivery of one or more nucleic acid-containing compositions and/or one or more polypeptide-containing compositions (e.g., polypeptides comprising HIV antigens). In other embodiments, multiple nucleic acid "primes" (of the same or different nucleic acid molecules) can be followed by multiple polypeptide "boosts" (of the same or different polypeptides). Other examples include multiple nucleic acid administrations and multiple polypeptide administrations.

In any method involving co-administration, the various compositions can be delivered in any order. Thus, in embodiments including delivery of multiple different compositions or molecules, the nucleic acids need not be all delivered before the polypeptides. For example, the priming step may include delivery of one or more polypeptides and the boosting comprises delivery of one or more nucleic acids and/or one more polypeptides. Multiple polypeptide administrations can be followed by multiple nucleic acid administrations or polypeptide and nucleic acid administrations can be performed in any order. In any of the embodiments described herein, the nucleic acid molecules can encode all, some or none of the polypeptides. Thus, one or more or the nucleic acid molecules (e.g., expression cassettes) described herein and/or one or more of the polypeptides described herein can be co-administered in any order and via any administration routes. Therefore, any combination of polynucleotides and/or polypeptides described herein can be used to generate elicit an immune reaction.

3.0 Improved HIV-1 Gag and Pol Expression Cassettes

While not desiring to be bound by any particular model, theory, or hypothesis, the following information is presented to provide a more complete understanding of the present invention.

The world health organization (WHO) estimated the number of people worldwide that are infected with HIV-1 to exceed 36.1 million. The development of a safe and effective HIV vaccine is therefore essential at this time. Recent studies have demonstrated the importance of CTL in controlling the HIV-1 replication in infected patients. Furthermore, CTL reactivity with multiple HIV antigens will be necessary for the effective control of virus replication. Experiments performed in support of the present invention suggest that the inclusion of HIV-1 Gag and Pol, beside Env for the induction of neutralizing antibodies, into the vaccine is useful.

To increase the potency of HIV-1 vaccine candidates, codon modified Gag and Pol expression cassettes were designed, either for Gag alone or Gag plus Pol. To evaluate possible differences in expression and potency, the expression of these constructs was analyzed and immunogenicity studies carried out in mice.

Several expression cassettes encoding Gag and Pol were designed, including, but not limited to, the following: Gag-Protease, GagPolΔintegrase with frameshift (gagFSpol), and GagPolΔintegrase in-frame (gagpol). Versions of GagPolΔ-integrase in-frame were also designed with attenuated (Att) or non-functional Protease (Ina). The nucleic acid sequences were codon modified to correspond to the codon usage of highly expressed human genes. Mice were immunized with titrated DNA doses and humoral and cellular immune responses evaluated by ELISA and intracellular cytokine staining (Example 10).

The immune responses in mice has been seen to be correlated with relative levels of expression in vitro. Vaccine studies in rhesus monkeys will further address immune responses and expression levels in vivo.

4.0 Enhanced Vaccine Technologies for the Induction of Potent Neutralizing Antibodies and Cellular Immune Responses Against HIV.

While not desiring to be bound by any particular model, theory, or hypothesis, the following information is presented to provide a more complete understanding of the present invention.

Protection against HIV infection will likely require potent and broadly reactive pre-existing neutralizing antibodies in vaccinated individuals exposed to a virus challenge. Although cellular immune responses are desirable to control viremia in those who get infected, protection against infection has not been demonstrated for vaccine approaches that rely exclusively on the induction of these responses. For this reason, experiments performed in support of the present invention use prime-boost approaches that employ novel V-deleted envelope antigens from primary HIV isolates (e.g., R5 subtype B (HIV-$1_{SF162}$) and subtype C(HIV-$1_{TV1}$) strains). These antigens were delivered by enhanced DNA [polyactide co-glycolide (PLG) microparticle formulations or electroporation] or alphavirus replicon particle-based vaccine approaches, followed by booster immunizations with Env proteins in MF59 adjuvant. Efficient in vivo expression of plasmid encoded genes by electrical permeabilization has been described (see, e.g., Zucchelli et al. (2000) *J. Virol.* 74:11598-11607; Banga et al. (1998) *Trends Biotechnol.* 10:408-412; Heller et al. (1996) *Febs Lett.* 389:225-228; Mathiesen et al. (1999) *Gene Ther.* 4:508-514; Mir et al. (1999) *Proc. Nat'l Acad. Sci. USA* 8:4262-4267; Nishi et al. (1996) *Cancer Res.* 5:1050-1055). Both native and V-deleted monomeric (gp120) and oligomeric (o-gp140) forms of protein from the SF162 strain were tested as boosters. All protein preparations were highly purified and extensively characterized by biophysical and immunochemical methodologies. Results from rabbit and primate immunogenicity studies indicated that, whereas neutralizing antibody responses could be consistently induced against the parental non-V2-deleted SF162 virus, the induction of responses against heterologous HIV strains improved with deletion of the V2 loop of the immunogens. Moreover, using these prime-boost vaccine regimens, potent HIV antigen-specific CD4+ and CD8+T-cell responses were also demonstrated.

Based on these findings, V2-deleted envelope DNA and protein vaccines were chosen for advancement toward clinical evaluation. Similar approaches for immunization may be employed using, for example, nucleic acid immunization employing the synthetic HIV polynucleotides of the present invention coupled with corresponding or heterologous HIV-derived polypeptide boosts.

One embodiment of this aspect of the present invention may be described generally as follows. Antigens are selected for the vaccine composition(s). Env polypeptides are typically employed in a first antigenic composition used to induce an immune response. Further, Gag polypeptides are typically employed in a second antigenic composition used to induce an immune response. The second antigenic composition may include further HIV-derived polypeptide sequences, including, but not limited to, Pol, Tat, Rev, Nef, Vif, Vpr, and/or Vpu sequences. A DNA prime vaccination is typically performed with the first and second antigenic compositions. Further DNA vaccinations with one or more of the antigenic compositions may also be included at selected time intervals. The prime is typically followed by at least one boost. The boost may, for example, include adjuvanted HIV-derived polypeptides (e.g., corresponding to those used for the DNA vaccinations), coding sequences for HIV-derived polypeptides (e.g., corresponding to those used for the DNA vaccinations) encoded by a viral vector, further DNA vaccinations, and/or combinations of the foregoing. In one embodiment, a DNA prime is administered with a first antigenic composition (e.g., a DNA construct encoding an Envelope polypeptide) and second antigenic composition (e.g., a DNA construct encoding a Gag polypeptide, a Pol polypeptide, a Tat polypeptide, a Nef polypeptide, and a Rev polypeptide). The DNA construct for use in the prime may, for example, comprise a CMV promoter operably linked to the polynucleotide encoding the polypeptide sequence. The DNA prime is followed by a boost, for example, an adjuvanted Envelope polypeptide boost and a viral vector boost (where the viral vector encodes, e.g., a Gag polypeptide, a Pol polypeptide, a Tat polypeptide, a Nef polypeptide, and a Rev polypeptide). Alternately (or in addition), the boost may be an adjuvanted Gag polypeptide, Pol polypeptide, Tat polypeptide, Nef polypeptide, and Rev polypeptide boost and a viral vector boost (where the viral vector encodes, e.g., an Envelope polypeptide). The boost may include all polypeptide antigens which were encoded in the DNA prime; however, this is not required. Further, different polypeptide antigens may be used in the boost relative to the initial vaccination and visa versa. Further, the initial vaccination may be a viral vector rather than a DNA construct.

Some factors that may be considered in HIV envelope vaccine design are as follows. Envelope-based vaccines have demonstrated protection against infection in non-human primate models. Passive antibody studies have demonstrated protection against HIV infection in the presence of neutralizing antibodies against the virus challenge stock. Vaccines that exclude Env generally confer less protective efficacy. Experiments performed in support of the present invention have demonstrated that monomeric gp120 protein-derived from the SF2 lab strain provided neutralization of HIV-1 lab strains and protection against virus challenges in primate models. Primary gp120 protein derived from That E field strains provided cross-subtype neutralization of lab strains. Primary sub-type B oligomeric o-gp140 protein provided partial neutralization of subtype B primary (field) isolates. Primary sub-type B o-gp140ΔV2 DNA prime plus protein boost provided potent neutralization of diverse subtype B primary isolates and protection against virus challenge in primate models. Primary sub-type C o-gp140 and o-gp140ΔV2 likely provide similar results to those just described for sub-type B.

Vaccine strategies for induction of potent, broadly reactive, neutralizing antibodies may be assisted by construction of Envelope polypeptide structures that expose conserved neutralizing epitopes, for example, variable-region deletions and de-glycosylations, envelope protein-receptor complexes, rational design based on crystal structure (e.g., β-sheet deletions), and gp41-fusion domain based immunogens.

Stable CHO cell lines for envelope protein production have been developed using optimized envelope polypeptide coding sequences, including, but not limited to, the following: gp120, o-gp140, gp120ΔV2, o-gp140ΔV2, gp120ΔV1V2, o-gp140ΔV1V2.

In addition, following prime-boost regimes (such as those described above) appear to be beneficial to help reduce viral load in infected subjects, as well as possibly slow or prevent progression of HIV-related disease (relative to untreated subjects).

Exemplary antigenic compositions and immunogenicity studies are presented in Examples 9, 10, 11, and 12.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Generation of Synthetic Expression Cassettes

A. Generating Synthetic Polynucleotides

The polynucleotide sequences of the present invention were manipulated to maximize expression of their gene products. The order of the following steps may vary.

First, the HIV-1 codon usage pattern was modified so that the resulting nucleic acid coding sequence was comparable to codon usage found in highly expressed human genes. The HIV codon usage reflects a high content of the nucleotides A or T of the codon-triplet. The effect of the HIV-1 codon usage is a high AT content in the DNA sequence that results in a high AU content in the RNA and in a decreased translation ability and instability of the mRNA. In comparison, highly expressed human codons prefer the nucleotides G or C. The wild-type sequences were modified to be comparable to codon usage found in highly expressed human genes.

Second, for some genes non-functional variants were created. In the following table (Table B) mutations affecting the activity of several HIV genes are disclosed. AU references cited are herein incorporated by reference.

TABLE B

| Gene | "Region" | Exemplary Mutations |
| --- | --- | --- |
| Pol | prot | Att = Reduced activity by attenuation of Protease (Thr26Ser) (e.g., Konvalinka et al., 1995, J Virol 69: 7180-86)<br>Ina = Mutated Protease, nonfunctional enzyme (Asp25Ala)(e.g., Konvalinka et al., 1995, J Virol 69: 7180-86) |

TABLE B-continued

| Gene | "Region" | Exemplary Mutations |
| --- | --- | --- |
| | RT | YM = Deletion of catalytic center (YMDD_AP; SEQ ID NO: 7) (e.g., Biochemistry, 1995, 34, 5351, Patel et. al.)<br>WM = Deletion of primer grip region (WMGY_PI; SEQ ID NO: 8)) (e.g., J Biol Chem, 272, 17, 11157, Palaniappan, et. al., 1997) |
| | RNase | no direct mutations, RnaseH is affected by "WM" mutation in RT |
| | Integrase | 1) Mutation of HHCC domain, Cys40Ala (e.g., Wiskerchen et. al., 1995, J Virol, 69: 376).<br>2.) Inactivation catalytic center, Asp64Ala, Asp116Ala, Glu152Ala (e.g., Wiskerchen et. al., 1995, J Virol, 69: 376).<br>3) Inactivation of minimal DNA binding domain (MDBD), deletion of Trp235(e.g., Ishikawa et. al., 1999, J Virol, 73: 4475).<br>Constructs int.opt.mut.SF2 and int.opt.mut_C (South Africa TV1) both contain all these mutations (1, 2, and 3) |
| Env | | Mutations in cleavage site (e.g., mut1-4, 7)<br>Mutations in glycosylation site (e.g., GM mutants, for example, change Q residue in V1 and/or V2 to N residue; may also be designated by residue altered in sequence) |
| Tat | | Mutants of Tat in transactivation domain (e.g., Caputo et al., 1996, Gene Ther. 3: 235)<br>cys22 mutant (Cys22Gly) = TatC22<br>cys37 mutant (Cys37Ser) = TatC37<br>cys22/37 double mutant = TatC22/37 |
| Rev | | Mutations in Rev domains (e.g., Thomas et al., 1998, J Virol. 72: 2935-44)<br>Mutation in RNA binding-nuclear localization ArgArg38,39AspLeu = M5<br>Mutation in activation domain LeuGlu78,79AspLeu = M10 |
| Nef | | Mutations of myristoyilation signal and in oligomerization domain:<br>1. Single point mutation myristoyilation signal: Gly-to-Ala = -Myr<br>2. Deletion of N-terminal first 18 (sub-type B, e.g., SF162) or 19 (sub-type C, e.g., South Africa clones) amino acids: -Myr18 or -Myr19 (respectively) (e.g., Peng and Robert-Guroff, 2001, Immunol Letters 78: 195-200)<br>Single point mutation oligomerization: (e.g., Liu et al., 2000, J Virol 74: 5310-19)<br>Asp125Gly (sub B SF162) or Asp124Gly (sub C South Africa clones)<br>Mutations affecting (1) infectivity (replication) of HIV-virions and/or (2) CD4 down regulation. (e.g., Lundquist et al. (2002) J Virol. 76(9): 4625-33) |
| Vif | | Mutations of Vif:<br>e.g., Simon et al., 1999, J Virol 73: 2675-81 |
| Vpr | | Mutations of Vpr:<br>e.g., Singh et al., 2000, J Virol 74: 10650-57 |
| Vpu | | Mutations of Vpu:<br>e.g., Tiganos et al., 1998, Virology 251: 96-107 |

Constructs comprising some of these mutations are described herein. Vif, vpr and vpu synthetic constructs are described. Reducing or eliminating the function of the associated gene products can be accomplished employing the teachings set forth in the above table, in view of the teachings of the present specification.

In one embodiment of the invention, the full length coding region of the Gag-polymerase sequence is included with the synthetic Gag sequences in order to increase the number of epitopes for virus-like particles expressed by the synthetic, optimized Gag expression cassette. Because synthetic HIV-1 Gag-polymerase expresses the potentially deleterious functional enzymes reverse transcriptase (RT) and integrase (INT) (in addition to the structural proteins and protease), it is important to inactivate RT and INT functions. Several in-frame deletions in the RT and INT reading frame can be made to achieve catalytic nonfunctional enzymes with respect to their RT and INT activity. {Jay. A. Levy (Editor) (1995) *The Retroviridae*, Plenum Press, New York. ISBN 0-306-45033X. Pages 215-20; Grimison, B. and Laurence, J. (1995), *Journal Of Acquired Immune Deficiency Syndromes and Human Retrovirology* 9(1):58-68; Wakefield, J. K., et al., (1992) *Journal Of Virology* 66(11):6806-6812; Esnouf, R., et al., (1995) *Nature Structural Biology* 2(4):303-308; Maignan, S., et al., (1998) *Journal Of Molecular Biology* 282(2):359-368; Katz, R. A. and Skalka, A. M. (1994) *Annual Review Of Biochemistry* 73 (1994); Jacobo-Molina, A., et al., (1993) *Proceedings Of the National Academy Of Sciences Of the United States Of America* 90(13):6320-6324; Hickman, A. B., et al., (1994) *Journal Of Biological Chemistry* 269(46):29279-29287; Goldgur, Y., et al., (1998) *Proceedings Of the National Academy Of Sciences Of the United States Of America* 95(16): 9150-9154; Goette, M., et al., (1998) *Journal Of Biological Chemistry* 273(17):10139-10146; Gorton, J. L., et al., (1998) *Journal of Virology* 72(6):5046-5055; Engelman, A., et al., (1997) *Journal Of Virology* 71(5):3507-3514; Dyda, F., et al., *Science* 266(5193):1981-1986; Davies, J. F., et al., (1991) *Science* 252(5002):88-95; Bujacz, G., et al., (1996) *Febs Letters* 398(2-3): 175-178; Beard, W. A., et al., (1996) *Journal Of Biological Chemistry* 271(21):12213-12220; Kohlstaedt, L. A., et al., (1992) *Science* 256(5065):1783-1790; Krug, M. S, and Berger, S. L. (1991) *Biochemistry* 30(44):10614-10623; Mazumder, A., et al., (1996) *Molecular Pharmacology* 49(4): 621-628; Palaniappan, C., et al., (1997) *Journal Of Biological Chemistry* 272(17): 11157-11164; Rodgers, D. W., et al., (1995) *Proceedings Of the National Academy Of Sciences Of the United States Of America* 92(4):1222-1226; Sheng, N. and Dennis, D. (1993) *Biochemistry* 32(18):4938-4942; Spence, R. A., et al., (1995) *Science* 267(5200):988-993.}

Furthermore selected B- and/or T-cell epitopes can be added to the Gag-polymerase constructs within the deletions of the RT- and INT-coding sequence to replace and augment any epitopes deleted by the functional modifications of RT and INT. Alternately, selected B- and T-cell epitopes (including CTL epitopes) from RT and INT can be included in a minimal VLP formed by expression of the synthetic Gag or synthetic GagProt cassette, described above. (For descriptions of known HIV B- and T-cell epitopes see, HIV Molecular Immunology Database CTL Search Interface; Los Alamos Sequence Compendia, 1987-1997; Internet address: http://hiv-web.lanl.gov/immunology/index.html.)

In another aspect, the present invention comprises Env coding sequences that include, but are not limited to, polynucleotide sequences encoding the following HIV-encoded polypeptides: gp160, gp140, and gp120 (see, e.g., U.S. Pat. No. 5,792,459 for a description of the HIV-$1_{SF2}$ ("SF2") Env polypeptide). The relationships between these polypeptides is shown schematically in FIG. 3 (in the figure: the polypeptides are indicated as lines, the amino and carboxy termini are indicated on the gp160 line; the open circle represents the oligomerization domain; the open square represents a transmembrane spanning domain (TM); and "c" represents the location of a cleavage site, in gp140.mut the "X" indicates that the cleavage site has been mutated such that it no longer functions as a cleavage site). The polypeptide gp160 includes the coding sequences for gp120 and gp41. The polypeptide gp41 is comprised of several domains including an oligomerization domain (OD) and a transmembrane spanning domain (TM). In the native envelope, the oligomerization domain is required for the non-covalent association of three gp41 polypeptides to form a trimeric structure: through non-covalent interactions with the gp41 trimer (and itself), the gp120 polypeptides are also organized in a trimeric structure. A cleavage site (or cleavage sites) exists approximately between the polypeptide sequences for gp120 and the polypeptide sequences corresponding to gp41. This cleavage site(s) can be mutated to prevent cleavage at the site. The resulting gp140 polypeptide corresponds to a truncated form of gp160 where the transmembrane spanning domain of gp41 has been deleted. This gp140 polypeptide can exist in both monomeric and oligomeric (i.e. trimeric) forms by virtue of the presence of the oligomerization domain in the gp41 moiety. In the situation where the cleavage site has been mutated to prevent cleavage and the transmembrane portion of gp41 has been deleted the resulting polypeptide product is designated "mutated" gp140 (e.g., gp140.mut). As will be apparent to those in the field, the cleavage site can be mutated in a variety of ways. (See, also, WO 00/39302).

Wild-type HIV coding sequences (e.g., Gag, Env, Pol, tat, rev, nef, vpr, vpu, vif, etc.) can be selected from any known HIV isolate and these sequences manipulated to maximize expression of their gene products following the teachings of the present invention. The wild-type coding region maybe modified in one or more of the following ways. In one embodiment, sequences encoding hypervariable regions of Env, particularly V1 and/or V2 were deleted. In other embodiments, mutations were introduced into sequences, for example, encoding the cleavage site in Env to abrogate the enzymatic cleavage of oligomeric gp140 into gp120 monomers. (See, e.g., Earl et al. (1990) *PNAS USA* 87:648-652; Earl et al. (1991) *J. Virol.* 65:31-41). In yet other embodiments, hypervariable region(s) were deleted, N-glycosylation sites were removed and/or cleavage sites mutated. As discussed above, different mutations may be introduced into the coding sequences of different genes (see, e.g., Table B). For example, Tat coding sequences were modified according to the teachings of the present specification, for example to affect the transactivation domain of the gene product (e.g., replacing a cystein residue at position 22 with a glycine, Caputo et al. (1996) *Gene Therapy* 3:235).

To create the synthetic coding sequences of the present invention the gene cassettes are designed to comprise the entire coding sequence of interest. Synthetic gene cassettes are constructed by oligonucleotide synthesis and PCR amplification to generate gene fragments. Primers are chosen to provide convenient restriction sites for subcloning. The resulting fragments are then ligated to create the entire desired sequence which is then cloned into an appropriate vector. The final synthetic sequences are (i) screened by restriction endonuclease digestion and analysis, (ii) subjected to DNA sequencing in order to confirm that the desired sequence has been obtained and (iii) the identity and integrity of the expressed protein confirmed by SDS-PAGE and Western blotting. The synthetic coding sequences are assembled at Chiron Corp. (Emeryville, Calif.) or by the Midland Certified Reagent Company (Midland, Tex.).

Percent identity to the synthetic sequences of the present invention can be determined, for example, using the Smith-Waterman search algorithm (Time Logic, Incline Village, Nev.), with the following exemplary parameters: weight matrix=nuc4×4hb; gap opening penalty=20, gap extension penalty=5, reporting threshold=1; alignment threshold=20.

Various forms of the different embodiments of the present invention (e.g., constructs) may be combined.

Exemplary embodiments of the synthetic polynucleotides of the present invention include, but are not limited to, the sequences presented in Table C.

TABLE C

Type B Synthetic, Codon Optimized Polynucleotides

| Name | Figure Number | Description (encoding) |
| --- | --- | --- |
| GagComplPolmut.SF2 (SEQ ID NO: 9) | 6 | Gag complete, RT mutated, Protease functional; all in frame |
| GagComplPolmutAtt.SF2 (SEQ ID NO: 10) | 7 | Gag complete, RT mutated, Protease attenuated; all in frame |
| GagComplPolmutIna.SF2 (SEQ ID NO: 11) | 8 | Gag complete, RT mutated, Protease non-functional; all in frame |
| gagCpolInaTatRevNef.opt_B (SEQ ID NO: 12) | 9 | Gag complete, protease non-functional, RT mutated, tat mutated, rev mutated, nef mutated; all in frame |
| GagPolmutAtt.SF2 (SEQ ID NO: 13) | 10 | Gag, RT mutated, Protease attenuated; all in frame |
| GagPolmutIna.SF2 (SEQ ID NO: 14) | 11 | Gag, RT mutated, Protease non-functional; all in frame |
| GagProtInaRTmut.SF2 (SEQ ID NO: 15) | 12 | Gag, Protease non-functional, RT mutated; all in frame |
| GagProtInaRTmutTatRevNef.opt_B (SEQ ID NO: 16) | 13 | Gag, protease non-functional, RT mutated, tat mutated, rev mutated, nef mutated; all in frame |
| GagRTmut.SF2 (SEQ ID NO: 17) | 14 | Gag, RT mutated; all in frame |
| GagTatRevNef.opt_B (SEQ ID NO: 18) | 15 | Gag, tat mutated, rev mutated, nef mutated; all in frame |
| gp140.modSF162.CwtLmod (SEQ ID NO: 19) | 16 | gp140 derived from SF162 with a HIV Type C (TV1) optimized leader sequence |
| gp140.modSF162.CwtLnat (SEQ ID NO: 20) | 17 | gp140 derived from SF162 with a HIV Type C (TV1) native leader sequence |
| gp160.modSF162.delV2.mut7 (SEQ ID NO: 21) | 18 | gp160 derived from SF162, deletion of V2 loop, mutated cleavage site |
| gp160.modSF162.delV2.mut8 (SEQ ID NO: 22) | 19 | gp160 derived from SF162, deletion of V2 loop, mutated cleavage site |
| int.opt.mut.SF2 (SEQ ID NO: 23) | 20 | integrase mutated |
| int.opt.SF2 (SEQ ID NO: 24) | 21 | integrase |
| nef.D125G.-myr.opt.SF162 (SEQ ID NO: 25) | 22 | nef mutated, myristoyilation defective |
| nef.D107G.-myr18.opt.SF162 (SEQ ID NO: 26) | 23 | nef mutated, myristoyilation defective |
| nef.opt.D125G.SF162 (SEQ ID NO: 27) | 24 | nef mutated |
| nef.opt.SF162 (SEQ ID NO: 28) | 25 | nef |
| p15RnaseH.opt.SF2 (SEQ ID NO: 29) | 26 | p15 RNase H; in-frame |
| p2Pol.opt.YMWM.SF2 (SEQ ID NO: 30) | 27 | p2 pol mutated (RT YM, WM) |
| p2PolInaopt.YM.SF2 (SEQ ID NO: 31) | 28 | p2 pol, protease non-functional, RT YM; all in frame |
| p2Polopt.SF2 (SEQ ID NO: 32) | 29 | p2 pol; all in frame |
| p2PolTatRevNef.opt.native_B (SEQ ID NO: 33) | 30 | p2 pol tat rev nef; all native; all in frame |
| p2PolTatRevNef.opt_B (SEQ ID NO: 34) | 31 | p2 pol, protease mutated, RT mutated, tat mutated, rev mutated, nef, mutated; all in frame |
| pol.opt.SF2 (SEQ ID NO: 35) | 32 | pol |
| prot.opt.SF2 (SEQ ID NO: 36) | 33 | protease |
| protIna.opt.SF2 (SEQ ID NO: 37) | 34 | protease non-functional |
| protInaRT.YM.opt.SF2 (SEQ ID NO: 38) | 35 | protease non-functional, RT YM mutated; all in frame |
| protInaRT.YMWM.opt.SF2 (SEQ ID NO: 39) | 36 | protease non-functional, RT YM WM mutated; all in frame |

TABLE C-continued

Type B Synthetic, Codon Optimized Polynucleotides

| Name | Figure Number | Description (encoding) |
|---|---|---|
| ProtInaRTmut.SF2 (SEQ ID NO: 40) | 37 | Protease inactive, RT mutated; all in frame |
| protRT.opt.SF2 (SEQ ID NO: 41) | 38 | protease RT; all in frame |
| ProtRT.TatRevNef.opt_B (SEQ ID NO: 42) | 39 | protease mutated, RT mutated, tat mutated, rev mutated, nef, mutated; all in frame |
| ProtRTTatRevNef.opt_B (SEQ ID NO: 43) | 40 | protease mutated, RT mutated, tat mutated, rev mutated, nef, mutated; all in frame |
| rev.exon1_2.M5-10.opt.SF162 (SEQ ID NO: 44) | 41 | rev exon 1 and 2 in-frame, rev mutated |
| rev.exon1_2.opt.SF162 (SEQ ID NO: 45) | 42 | rev exon 1 and 2 in-frame |
| RT.opt.SF2 (mutant) (SEQ ID NO: 46) | 43 | RT mutant |
| RT.opt.SF2 (native) (SEQ ID NO: 47) | 44 | RT native |
| RTmut.SF2 (SEQ ID NO: 48) | 45 | RT mutated |
| tat.exon1_2.opt.C22-37.SF2 (SEQ ID NO: 49) | 46 | tat exon 1 and 2 in-frame, tat mutated |
| tat.exon1_2.opt.C37.SF2 (SEQ ID NO: 50) | 47 | tat exon 1 and 2 in-frame, tat mutated |
| TatRevNef.opt.native.SF162 (SEQ ID NO: 51) | 48 | tat native, rev native, nef native; all in frame |
| TatRevNef.opt.SF162 (SEQ ID NO: 52) | 49 | tat mutated, rev mutated, nef mutated; all in frame |
| TatRevNefGag B (SEQ ID NO: 53) | 50 | tat mutated, rev mutated, nef mutated, gag; all in frame |
| TatRevNefgagCpolIna B (SEQ ID NO: 54) | 51 | tat mutated, rev mutated, nef mutated, gag complete, protease non-functional, RT mutated; all in frame |
| TatRevNefGagProtInaRTmut B (SEQ ID NO: 55) | 52 | tat mutated, rev mutated, nef mutated, gag, protease non-functional, RT mutant; all in frame |
| TatRevNefp2Pol.opt_B (SEQ ID NO: 56) | 53 | tat mutated, rev mutated, nef mutated, p2 pol, protease mutated, RT mutated; all in frame |
| TatRevNefprotRTopt B (SEQ ID NO: 57) | 54 | tat mutated, rev mutated, nef mutated, protease mutated, RT mutated; all in frame |
| vif.opt.SF2 (SEQ ID NO: 58) | 55 | optimized vif derived from SF2 |
| vpr.opt.SF2 (SEQ ID NO: 59) | 56 | optimized vpr derived from SF2 |
| vpu.opt.SF162 (SEQ ID NO: 60) | 57 | optimized vpu derived from SF162 |

{In Table C, .mut or .mut7 or .mut 8 = envelope mutated in cellular protease cleavage site between gp120/gp41 (i.e., to prevent cleavage; e.g., better for purifying protein)}

B. Creating Expression Cassettes Comprising the Synthetic Polynucleotides of the Present Invention.

The synthetic DNA fragments of the present invention are cloned into the following expression vectors: pCMVKm2, for transient expression assays and DNA immunization studies, the pCMVKm2 vector was derived from pCMV6a (Chapman et al., *Nuc. Acids Res.* (1991) 19:3979-3986) and comprises a kanamycin selectable marker, a ColE1 origin of replication, a CMV promoter enhancer and Intron A, followed by an insertion site for the synthetic sequences described below followed by a polyadenylation signal derived from bovine growth hormone—the pCMVKm2 vector differs from the pCMV-link vector only in that a polylinker site was inserted into pCMVKm2 to generate pCMV-link; pESN2dhfr and pCMV-PLEdhfr (also known as pCMVIII), for expression in Chinese Hamster Ovary (CHO) cells; and, pAcC13, a shuttle vector for use in the Baculovirus expression system (pAcC13, was derived from pAcC12 which was described by Munemitsu S., et al., *Mol Cell Biol.* 10(11):5977-5982, 1990). See, also co-owned WO 00/39302, WO 00/39303, WO 00/39304, and WO 02/04493, for a description of these vectors, all herein incorporated by reference in their entireties.

Briefly, construction of pCMVPLEdhfr (pCMVIII) was as follows. To construct a DHFR cassette, the EMCV IRES (internal ribosome entry site) leader was PCR-amplified from pCite-4a+ (Novagen, Inc., Milwaukee, Wis.) and inserted into pET-23d (Novagen, Inc., Milwaukee, Wis.) as an Xba-Nco fragment to give pET-EMCV. The dhfr gene was PCR-amplified from pESN2dhfr to give a product with a Gly-Gly-Gly-Ser spacer in place of the translation stop codon and inserted as an Nco-BamH1 fragment to give pET-E-DHFR. Next, the attenuated neo gene was PCR amplified from a pSV2Neo (Clontech, Palo Alto, Calif.) derivative and inserted into the unique BamH1 site of pET-E-DHFR to give pET-E-DHFR/

Neo$_{(m2)}$. Then, the bovine growth hormone terminator from pcDNA3 (Invitrogen, Inc., Carlsbad, Calif.) was inserted downstream of the neo gene to give pET-E-DHFR/Neo$_{(m2)}$ BGHt. The EMCV-dhfr/neo selectable marker cassette fragment was prepared by cleavage of pET-E-DHFR/Neo$_{(m2)}$ BGHt. The CMV enhancer/promoter plus Intron A was transferred from pCMV6a (Chapman et al., *Nuc. Acids Res.* (1991) 19:3979-3986) as a HindIII-Sal1 fragment into pUC19 (New England Biolabs, Inc., Beverly, Mass.). The vector backbone of pUC19 was deleted from the Nde1 to the Sap1 sites. The above described DHFR cassette was added to the construct such that the EMCV IRES followed the CMV promoter to produce the final construct. The vector also contained an amp$^r$ gene and an SV40 origin of replication.

Expression vectors of the present invention contain one or more of the synthetic coding sequences disclosed herein, e.g., shown in the Figures. When the expression cassette contains more than one coding sequence the coding sequences may all be in-frame to generate one polyprotein; alternately, the more than one polypeptide coding sequences may comprise a polycistronic message where, for example, an IRES is placed 5' to each polypeptide coding sequence.

Example 2

Expression Assays for the Synthetic Coding Sequences

The wild-type sequences are cloned into expression vectors having the same features as the vectors into which the synthetic HIV-derived sequences were cloned.

Expression efficiencies for various vectors carrying the wild-type (any known isolated) and corresponding synthetic sequence(s) are evaluated as follows. Cells from several mammalian cell lines (293, RD, COS-7, and CHO; all obtained from the American Type Culture Collection, 10801 University Boulevard, Manassas, Va. 20110-2209) are transfected with 2 µg of DNA in transfection reagent LT1 (PanVera Corporation, 545 Science Dr., Madison, Wis.). The cells are incubated for 5 hours in reduced serum medium (Opti-MEM, Gibco-BRL, Gaithersburg, Md.). The medium is then replaced with normal medium as follows: 293 cells, IMDM, 10% fetal calf serum, 2% glutamine (BioWhittaker, Walkersville, Md.); RD and COS-7 cells, D-MEM, 10% fetal calf serum, 2% glutamine (Opti-MEM, Gibco-BRL, Gaithersburg, Md.); and CHO cells, Ham's F-12, 10% fetal calf serum, 2% glutamine (Opti-MEM, Gibco-BRL, Gaithersburg, Md.). The cells are incubated for either 48 or 60 hours. Supernatants are harvested and filtered through 0.45 µm syringe filters and, optionally, stored at −20° C.

Supernatants are evaluated using the Coulter p24-assay (Coulter Corporation, Hialeah, Fla., US), using 96-well plates coated with a suitable monoclonal antibody directed against an HIV antigen (e.g. a murine monoclonal directed again an HIV core antigen). The appropriate HIV antigen binds to the coated wells and biotinylated antibodies against HIV recognize the bound antigen. Conjugated strepavidin-horseradish peroxidase reacts with the biotin. Color develops from the reaction of peroxidase with TMB substrate. The reaction is terminated by addition of 4N $H_2SO_4$. The intensity of the color is directly proportional to the amount of HIV antigen in a sample.

Chinese hamster ovary (CHO) cells are also transfected with plasmid DNA encoding the synthetic HIV polypeptides described herein (e.g., pESN2dhfr or pCMVIII vector backbone) using Mirus TransIT-LT1 polyamine transfection reagent (Pan Vera) according to the manufacturers instructions and incubated for 96 hours. After 96 hours, media is changed to selective media (F12 special with 250 µg/ml G418) and cells are split 1:5 and incubated for an additional 48 hours. Media is changed every 5-7 days until colonies start forming at which time the colonies are picked, plated into 96 well plates and screened by Capture ELISA. Positive clones are expanded in 24 well plates and are screened several times for HIV protein production by Capture ELISA, as described above. After reaching confluency in 24 well plates, positive clones are expanded to T25 flasks (Corning, Corning, N.Y.). These are screened several times after confluency and positive clones are expanded to T75 flasks.

Positive T75 clones are frozen in LN2 and the highest expressing clones are amplified with 0-5 µM methotrexate (MTX) at several concentrations and plated in 100 mm culture dishes. Plates are screened for colony formation and all positive closed are again expanded as described above. Clones are expanded an amplified and screened at each step capture ELISA. Positive clones are frozen at each methotrexate level. Highest producing clones are grown in perfusion bioreactors (3 L, 100 L) for expansion and adaptation to low serum suspension culture conditions for scale-up to larger bioreactors.

Data from experiments performed in support of the present invention show that the synthetic HIV expression cassettes provided dramatic increases in production of their protein products, relative to the native (wild-type) sequences, when expressed in a variety of cell lines and that stably transfected CHO cell lines, which express the desired HIV polypeptide(s), may be produced. Production of HIV polypeptides using CHO cells provides (i) correct glycosylation patterns and protein conformation (as determined by binding to panel of MAbs); (ii) correct binding to CD4 receptor molecules; (iii) absence of non-mammalian cell contaminants (e.g., insect viruses and/or cells); and (iv) ease of purification.

Example 3

Western Blot Analysis of Expression

Western blot analysis of cells transfected with the HIV expression cassettes described herein are performed essentially as described in co-owned WO 00/39302. Briefly, human 293 cells are transfected as described in Example 2 with pCMV6a-based vectors containing native or synthetic HIV expression cassettes. Cells are cultivated for 60 hours post-transfection. Supernatants are prepared as described. Cell lysates are prepared as follows. The cells are washed once with phosphate-buffered saline, lysed with detergent [1% NP40 (Sigma Chemical Co., St. Louis, Mo.) in 0.1 M Tris-HCl, pH 7.5], and the lysate transferred into fresh tubes. SDS-polyacrylamide gels (pre-cast 8-16%; Novex, San Diego, Calif.) are loaded with 20 µl of supernatant or 12.5 µl of cell lysate. A protein standard is also loaded (5 µl, broad size range standard; BioRad Laboratories, Hercules, Calif.). Electrophoresis is carried out and the proteins are transferred using a BioRad Transfer Chamber (BioRad Laboratories, Hercules, Calif.) to Immobilon P membranes (Millipore Corp., Bedford, Mass.) using the transfer buffer recommended by the manufacturer (Millipore), where the transfer is performed at 100 volts for 90 minutes. The membranes are exposed to HIV-1-positive human patient serum and immunostained using o-phenylenediamine dihydrochloride (OPD; Sigma).

The results of the immunoblotting analysis are used to show that cells containing the synthetic HIV expression cassette produce the expected HIV-polypeptide(s) at higher per-cell concentrations than cells containing the native expression cassette.

Example 4

In Vivo Immunogenicity of Synthetic HIV Expression Cassettes

A. Immunization

To evaluate the immunogenicity of the synthetic HIV expression cassettes, a mouse study may be performed. The plasmid DNA, e.g., pCMVKM2 carrying an expression cassette comprising a synthetic sequence of the present invention, is diluted to the following final concentrations in a total injection volume of 100 µl: 20 µg, 2 µg, 0.2 µg, and 0.02 µg. To overcome possible negative dilution effects of the diluted DNA, the total DNA concentration in each sample is brought up to 20 µg using the vector (pCMVKM2) alone. As a control, plasmid DNA comprising an expression cassette encoding the native, corresponding polypeptide is handled in the same manner. Twelve groups of four Balb/c mice (Charles River, Boston, Mass.) are intramuscularly immunized (50 µl per leg, intramuscular injection into the tibialis anterior) using varying dosages.

B. Humoral Immune Response

The humoral immune response is checked with a suitable anti-HIV antibody ELISAs (enzyme-linked immunosorbent assays) of the mice sera 0 and 4 weeks post immunization (groups 5-12) and, in addition, 6 and 8 weeks post immunization, respectively, 2 and 4 weeks post second immunization (groups 1-4).

The antibody titers of the sera are determined by anti-HIV antibody ELISA. Briefly, sera from immunized mice were screened for antibodies directed against an appropriate HIV protein (e.g., HIV p55 for Gag). ELISA microtiter plates are coated with 0.2 µg of HIV protein per well overnight and washed four times; subsequently, blocking is done with PBS-0.2% Tween (Sigma) for 2 hours. After removal of the blocking solution, 100 µl of diluted mouse serum is added. Sera are tested at 1/25 dilutions and by serial 3-fold dilutions, thereafter. Microtiter plates are washed four times and incubated with a secondary, peroxidase-coupled anti-mouse IgG antibody (Pierce, Rockford, Ill.). ELISA plates are washed and 100 µl of 3, 3', 5,5'-tetramethyl benzidine (TMB; Pierce) was added per well. The optical density of each well is measured after 15 minutes. The titers reported are the reciprocal of the dilution of serum that gave a half-maximum optical density (O.D.).

The results of the mouse immunizations with plasmid-DNAs are used to show that the synthetic expression cassettes provide improvement of immunogenicity relative to the native expression cassettes. Also, the second boost immunization induces a secondary immune response after two weeks (groups 1-3).

C. Cellular Immune Response

The frequency of specific cytotoxic T-lymphocytes (CTL) is evaluated by a standard chromium release assay of peptide pulsed Balb/c mouse CD4 cells. HIV protein-expressing vaccinia virus infected CD-8 cells are used as a positive control (vv-protein). Briefly, spleen cells (Effector cells, E) are obtained from the BALB/c mice (immunized as described above). The cells are cultured, restimulated, and assayed for CTL activity against, e.g., Gag peptide-pulsed target cells as described (Doe, B., and Walker, C. M., *AIDS* 10(7):793-794, 1996). Cytotoxic activity is measured in a standard $^{51}$Cr release assay. Target (T) cells are cultured with effector (E) cells at various E:T ratios for 4 hours and the average cpm from duplicate wells is used to calculate percent specific $^{51}$Cr release.

Cytotoxic T-cell (CTL) activity is measured in splenocytes recovered from the mice immunized with HIV DNA constructs described herein. Effector cells from the DNA-immunized animals exhibit specific lysis of HIV peptide-pulsed SV-BALB (MHC matched) targets cells indicative of a CTL response. Target cells that are peptide-pulsed and derived from an MHC-unmatched mouse strain (MC57) are not lysed. The results of the CTL assays are used to show increased potency of synthetic HIV expression cassettes for induction of cytotoxic T-lymphocyte (CTL) responses by DNA immunization.

Example 5

In Vivo Immunogenicity of Synthetic HIV Expression Cassettes

A. General Immunization Methods

To evaluate the immunogenicity of the synthetic HIV expression cassettes, studies using guinea pigs, rabbits, mice, rhesus macaques and baboons are performed. The studies are typically structured as follows: DNA immunization alone (single or multiple); DNA immunization followed by protein immunization (boost); DNA immunization followed by Sindbis particle immunization; immunization by Sindbis particles alone.

B. Guinea Pigs

Experiments may be performed using guinea pigs as follows. Groups comprising six guinea pigs each are immunized intramuscularly or mucosally at 0, 4, and 12 weeks with plasmid DNAs encoding expression cassettes comprising one or more the sequences described herein. The animals are subsequently boosted at approximately 18 weeks with a single dose (intramuscular, intradermally or mucosally) of the HIV protein encoded by the sequence(s) of the plasmid boost and/or other HIV proteins. Antibody titers (geometric mean titers) are measured at two weeks following the third DNA immunization and at two weeks after the protein boost. These results are used to demonstrate the usefulness of the synthetic constructs to generate immune responses, as well as, the advantage of providing a protein boost to enhance the immune response following DNA immunization.

C. Rabbits

Experiments may be performed using rabbits as follows. Rabbits are immunized intramuscularly, mucosally, or intradermally (using a Bioject needless syringe) with plasmid DNAs encoding the HIV proteins described herein. The nucleic acid immunizations are followed by protein boosting after the initial immunization. Typically, constructs comprising the synthetic HIV-polypeptide-encoding polynucleotides of the present invention are highly immunogenic and generate substantial antigen binding antibody responses after only 2 immunizations in rabbits.

D. Humoral Immune Response

In any immunized animal model, the humoral immune response is checked in serum specimens from the immunized animals with an anti-HIV antibody ELISAs (enzyme-linked immunosorbent assays) at various times post-immunization. The antibody titers of the sera are determined by anti-HIV antibody ELISA as described above. Briefly, sera from immunized animals are screened for antibodies directed against the HIV polypeptide/protein(s) encoded by the DNA and/or polypeptide used to immunize the animals. Wells of ELISA microtiter plates are coated overnight with the selected HIV polypeptide/protein and washed four times; subsequently, blocking is done with PBS-0.2% Tween (Sigma) for 2 hours. After removal of the blocking solution, 100 µl of diluted mouse serum is added. Sera are tested at 1/25 dilutions and by serial 3-fold dilutions, thereafter. Microtiter plates are washed four times and incubated with a secondary, peroxidase-coupled anti-mouse IgG antibody (Pierce, Rockford, Ill.). ELISA plates are washed and 100 µl of 3,3',5,5'-tetramethyl benzidine (TMB; Pierce) was added per well. The optical density of each well is measured after 15 minutes. Titers are typically reported as the reciprocal of the dilution of serum that gave a half-maximum optical density (O.D.).

Cellular immune response may also be evaluated.

Example 6

Figure 5:
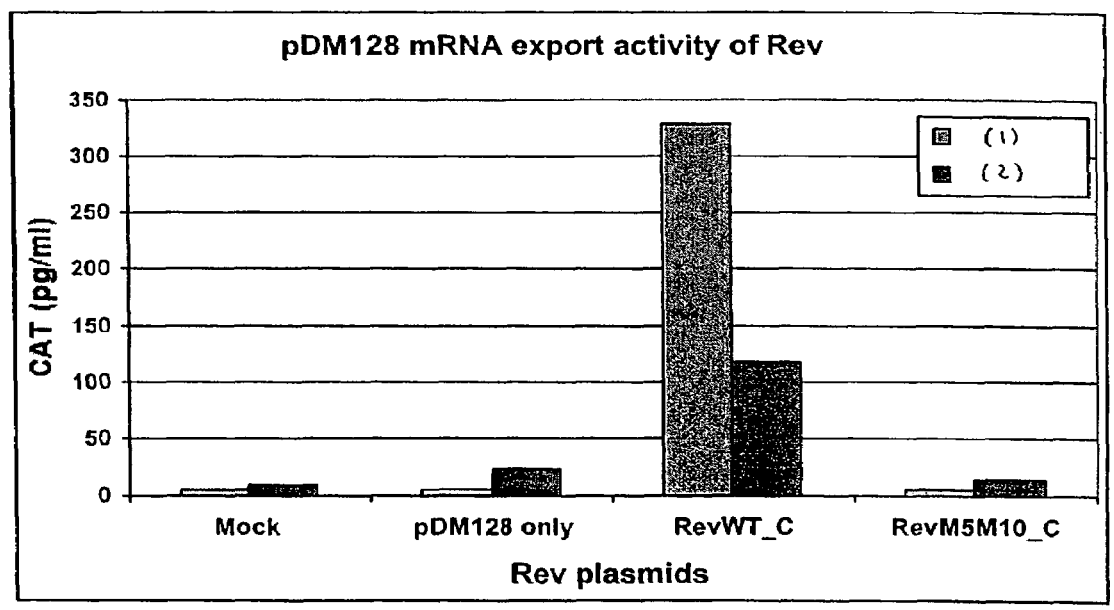
FIG. 5 presents exemplary data concerning export activity of Rev mutants monitored by CAT expression.

DNA-Immunization of Baboons and Rhesus Macaques Using Expression Cassettes Comprising the Synthetic HIV Polynucleotides of the Present Invention A. Baboons Four baboons are immunized 3 times (weeks 0, 4 and 8) bilaterally, intramuscular into the quadriceps or mucosally using the gene delivery vehicles described herein. The animals are bled two weeks after each immunization and an HIV antibody ELISA is performed with isolated plasma. The ELISA is performed-essentially as described above except the second antibody-conjugate is an anti-human IgG, g-chain specific, peroxidase conjugate (Sigma Chemical Co., St. Louis, Md. 63178) used at a dilution of 1:500. Fifty g/mil yeast extract may be added to the dilutions of plasma samples and antibody conjugate to reduce non-specific background due to preexisting yeast antibodies in the baboons. Lymphoproliferative responses to are observed in baboons two weeks post-fourth immunization (at week 14), and enhanced substantially post-boosting with HIV-polypeptide (at week 44 and 76). Such proliferation results are indicative of induction of T-helper cell functions.

B. Rhesus Macaques

The improved potency of the synthetic, codon-modified HIV-polypeptide encoding polynucleotides of the present invention, when constructed into expression plasmids may be confirmed in rhesus macaques. Typically, the macaques have detectable HIV-specific CTL after two or three 1 mg doses of modified HIV polynucleotide. In sum, these results demonstrate that the synthetic HIV DNA is immunogenic in non-human primates. Neutralizing antibodies may also detected.

Example 7

Co-Transfection of Monocistronic and Multicistronic Constructs

The present invention includes co-transfection with multiple, monocistronic expression cassettes, as well as, co-transfection with one or more multi-cistronic expression cassettes, or combinations thereof.

Such constructs, in a variety of combinations, may be transfected into 293T cells for transient transfection studies.

For example, a bicistronic construct may be made where the coding sequences for the different HIV polypeptides are under the control of a single CMV promoter and, between the two coding sequences, an IRES (internal ribosome entry site (EMCV IRES); Kozak, M., Critical Reviews in Biochemistry and Molecular Biology 27(45):385-402, 1992; Witherell, G. W., et al., Virology 214:660-663, 1995) sequence is introduced after the first HIV coding sequence and before the second HIV coding sequence.

Supernatants collected from cell culture are tested for the presence of the HIV proteins and indicate that appropriate proteins are expressed in the transfected cells (e.g., if an Env coding sequence was present the corresponding Env protein was detected; if a Gag coding sequence was present the corresponding Gag protein was detected, etc).

The production of chimeric VLPs by these cell lines may be determined using electron microscopic analysis. (See, e.g., co-owned WO 00/39302).

Example 8

Accessory Gene Components for an HIV-1 Vaccine

Functional Analysis of Mutated Tat, Rev and Nef Type C Antigens

The HIV-1 regulatory and accessory genes have received increased attention as components of HIV vaccines due to their role in viral pathogenesis, the high ratio of highly conserved CTL epitopes and their early expression in the viral life cycle. Because of various undesirable properties of these genes, questions regarding their safety and suitability as vaccine components have been raised. Experiments performed in support of the present invention have analyzed candidate HIV-1 subtype C tat, rev, and nef mutants for efficient expression and inactivation of potential deleterious functions. Other HIV subtype accessory genes may be evaluated similarly.

Sequence-modified, mutant tat, rev, and nef genes coding for consensus Tat, Rev and Nef proteins of South African HIV-1 subtype C were constructed using overlapping synthetic oligonucleotides and PCR-based site-directed mutagenesis. Constructs of the wild-type genes of the isolates closely resembling the respective consensus sequences were also made by PCR. In vitro expression of the constructs was analyzed by western blotting. The trans-activation activity of the Tat mutants and nuclear RNA export activity of the Rev mutants were studied after transfection of various cell lines using reporter-gene-based functionality assays.

In vitro expression of all constructs was demonstrated by western blotting using antigen specific mouse serum generated by DNA vaccination of mice with Tat, Rev, or Nef-expression plasmids. Expression levels of the sequence-modified genes were significantly higher than the wild-type genes.

Subtype B and C Tat cDNA was mutated to get TatC22, TatC37, and TatC22/37. Tat activity assays in three cell lines (RD, HeLa and 293). In the background of the subtype C consensus Tat, a single mutation at C22 was insufficient to inactivate LTR-dependent CAT expression. In contrast, this activity was significantly impaired in RD, 293 and HeLa cells using the single mutation, C37, or the double mutation, C22C37 (see Table B). Corresponding results were obtained for Tat mutants derived from subtype B strains.

Exemplary results are presented in FIG. 4 for transactivation activity of Tat mutants on LTR-CAT plasmid in 293 cells. Three independent assays were performed for each construct (FIG. 4, legend (1), (2), (3)).

The subtype C constructs TatC22ProtRTTatRevNef and ProtRTTatC22RevNef showed reduced Tat activity when compared to TatC22 alone, probably due to structural changes caused by the fusion protein.

For Rev constructs, to test for the loss of function, a CAT assay with a reporter plasmid including native or mutated Rev was used. As shown in FIG. 5, compared to wild-type Rev, the mRNA export function of the subtype C Rev with a double mutation, M5M10 (see Table B), was significantly lower. The background levels are shown in the "mock" data and the pDM128 reporter plasmid without Rev data. Two independent assays were performed for each construct (FIG. 5, legend (1), (2)).

Assays to measure Nef-specific functions may also be performed (Nef mutations are described in Table B). For example, FACs analysis is used to look for the presence of MHC1 and CD4 on cell surfaces. Cells are assayed in the presence and absence of Nef expression (for controls), as well as using the synthetic polynucleotides of the present invention that encode native nef protein and mutated nef protein. Down-regulation of MHC1 and CD4 expression indicates that the nef gene product is not functional, i.e., if nef is non-functional there is no down regulation.

These data demonstrate the impaired functionality of tat and rev DNA immunogens that may form part of a multi-component HIV-1 subtype C vaccine. In contrast to previous published data by other groups, the C22 mutation did not sufficiently inactivate the transactivation function of Tat. The C37 mutation appeared to be required for inactivation of subtype C and subtype B Tat proteins.

Example 9

Evaluation of Immunogenicity of Various HIV Polypeptide Encoding Plasmids

As noted above, the immunogenicity of any of the polynucleotides or expression cassettes described herein is readily evaluated. In the following table (Table D) are exemplified procedures involving a comparison of the immunogenicity of subtype B and C envelope plasmids, both individually and as a mixed-subtype vaccine, using electroporation, in rabbits. It will be apparent that such methods are equally applicable to any other HIV polypeptide.

TABLE D

| Grp | Animal | Imm'n # | Adjuvant | Immunogen | Total Dose | Vol/ Site | Sites/ Animal | Route |
|---|---|---|---|---|---|---|---|---|
| 1 | 1-4 | 1, 2 | — | pCMV 160 TV1 DNA | 1.0 mg | 0.5 ml | 2 | IM/Quad (Electro) |
| | | 3 | — | pCMV 160 TV1 DNA | 1.0 mg | 0.5 ml | 2 | IM/Quad (Electro) |
| | | | MF59C | Protein TBD | 0.05 mg | 0.5 ml | 2 | IM/Glut |
| 2 | 5-8 | 1, 2 | — | pCMV 160 dV2 TV1 DNA | 1.0 mg | 0.5 ml | 2 | IM/Quad (Electro) |
| | | 3 | — | pCMV 160 dV2 TV1 DNA | 1.0 mg | 0.5 ml | 2 | IM/Quad (Electro) |
| | | | MF59C | Protein TBD | 0.05 mg | 0.5 ml | 2 | IM/Glut |
| 3 | 9-12 | 1, 2 | — | pCMV 160 dV1/V2 TV1 DNA | 1.0 mg | 0.5 ml | 2 | IM/Quad (Electro) |
| | | 3 | — | pCMV 160 dV1/V2 TV1 DNA | 1.0 mg | 0.5 ml | 2 | IM/Quad (Electro) |
| | | | MF59C | Protein TBD | 0.05 mg | 0.5 ml | 2 | IM/Glut |
| 4 | 13-16 | 1, 2 | — | pCMV 140 TV1 DNA | 1.0 mg | 0.5 ml | 2 | IM/Quad (Electro) |
| | | 3 | — | pCMV 140 TV1 DNA | 1.0 mg | 0.5 ml | 2 | IM/Quad (Electro) |
| | | | MF59C | Protein TBD | 0.05 mg | 0.5 ml | 2 | IM/Glut |
| 5 | 17-20 | 1, 2 | — | pCMV140dV2TV1 DNA | 1.0 mg | 0.5 ml | 2 | IM/Quad (Electro) |
| | | 3 | — | pCMV140dV2TV1 DNA | 1.0 mg | 0.5 ml | 2 | IM/Quad (Electro) |
| | | | MF59C | Protein TBD | 0.05 mg | 0.5 ml | 2 | IM/Glut |
| 6 | 21-24 | 1, 2 | — | pCMV 140 dV1/V2 TV1 DNA | 1.0 mg | 0.5 ml | 2 | IM/Quad (Electro) |
| | | 3 | — | pCMV 140 dV1/V2 TV1 DNA | 1.0 mg | 0.5 ml | 2 | IM/Quad (Electro) |
| | | | MF59C | Protein TBD | 0.05 mg | 0.5 ml | 2 | IM/Glut |
| 7 | 25-28 | 1, 2 | — | pSIN140dV2SF162 DNA | 1.0 mg | 0.5 ml | 2 | IM/Quad (Electro) |
| | | 3 | — | pSIN 140 dV2 SF162 DNA | 1.0 mg | 0.5 ml | 2 | IM/Quad (Electro) |
| | | | MF59C | Protein TBD | 0.05 mg | 0.5 ml | 2 | IM/Glut |
| 8 | 29-32 | 1, 2 | — | pCMV 140 dV2 SF162 DNA | 1.0 mg | 0.5 ml | 2 | IM/Quad (Electro) |
| | | 3 | — | pCMV 140 dV2 SF162 DNA | 1.0 mg | 0.5 ml | 2 | IM/Quad (Electro) |
| | | | MF59C | Protein TBD | 0.05 mg | 0.5 ml | 2 | IM/Glut |
| 9 | 33-36 | 1, 2 | — | pCMV 140 Q154 SF162 DNA | 1.0 mg | 0.5 ml | 2 | IM/Quad (Electro) |
| | | 3 | — | pCMV 140 Q154 SF162 DNA | 1.0 mg | 0.5 ml | 2 | IM/Quad (Electro) |
| | | | MF59C | Protein TBD | 0.05 mg | 0.5 ml | 2 | IM/Glut |
| 10 | 37-40 | 1, 2 | — | pCMV 140 dV2 SF162 DNA | 1.0 mg | 0.5 ml | 2 | IM/Quad (Electro) |
| | | | | pCMV 140 dV2 TV1 DNA | 1.0 mg | | | |

TABLE D-continued

| Grp | Animal | Imm'n # | Adjuvant | Immunogen | Total Dose | Vol/ Site | Sites/ Animal | Route |
|---|---|---|---|---|---|---|---|---|
| | | 3 | — | pCMV 140 dV2 SF162 DNA | 1.0 mg | 0.5 ml | 2 | IM/Quad (Electro) |
| | | | | pCMV 140 dV2 TV1 DNA | 1.0 mg | | | |
| | | | MF59C | Protein TBD | 0.05 mg | 0.5 ml | 2 | IM/Glut |
| 11 | 41-44 | 1, 2 | — | pCMV 140 dV2 SF162 DNA | 1.0 mg | 0.5 ml | 2 | IM/Quad (Electro) |
| | | | | pCMV 140 dV2 TV1 DNA | 1.0 mg | | | |
| | | 3 | — | pCMV 140 dV2 SF162 DNA | 1.0 mg | 0.5 ml | 2 | IM/Quad (Electro) |
| | | | | pCMV 140 dV2 TV1 DNA | 1.0 mg | | | |
| | | | MF59C | Protein TBD | 0.05 mg | 0.5 ml | 2 | IM/Glut |

The MF59C adjuvant is a microfluidized emulsion containing 5% squalene, 0.5% tween 80, 0.5% span 85, in 10 mM citrate pH 6, stored in 10 mL aliquots at 4° C.

Immunogens are prepared as described in the following table (Table E) for administration to animals in the various groups. Concentrations may vary from those described in the table, for example depending on the sequences and/or proteins being used.

TABLE E

| Group | Preparation |
|---|---|
| 1-9 | Immunization 1-3: pCMV and pSIN based plasmid DNA in Saline + Electroporation<br>Subtype B and C plasmids will be provided frozen at a concentration of 1.0 mg/ml in sterile 0.9% saline. Store at −80° C. until use. Thaw DNA at room temperature; the material should be clear or slightly opaque, with no particulate matter. Animals will be shaved prior to immunization, under sedation of 1× dose IP (by animal weight) of Ketamine-Xylazine (80 mg/ml-4 mg/ml). Immunize each rabbit with 0.5 ml DNA mixture per side (IM/Quadriceps), 1.0 ml per animal. Follow the DNA injection with Electroporation using a 6-needle circular array with 1 cm diameter, 1 cm needle length. Electroporation pulses were given at 20 V/mm, 50 ms pulse length, 1 pulse/s.<br>Immunization 3: Protein Immunization<br>Proteins will be provided at 0.1 mg/ml in citrate buffer. Store at −80° C. until use. Thaw at room temperature; material should be clear with no particulate matter. Add equal volume of MF59C adjuvant to thawed protein and mix well by inverting the tube. Immunize each rabbit with 0.5 ml adjuvanted protein per side, IM/Glut for a total of 1.0 ml per animal. Use material within 1 hour of the addition of adjuvant. |
| | Immunization 1-3: Combined subtype B and C plasmid DNA in Saline<br>The immunogen will be provided at 2.0 mg/ml total DNA (1 mg/ml of each plasmid) in sterile 0.9% saline. Store at −80° C. until use. Thaw DNA at room temperature; the material should be clear or slightly opaque, with no particulate matter. Animals will be shaved prior to immunization, under sedation of 1× dose IP (by animal weight) of Ketamine-Xylazine (80 mg/ml-4 mg/ml). Immunize each rabbit with 0.5 ml DNA mixture per side (IM/Quadriceps), 1.0 ml per animal. Follow the DNA injection with Electroporation using a 6-needle circular array with 1 cm diameter, 1 cm needle length. Electroporation pulses were given at 20 V/mm, 50 ms pulse length, 1 pulse/s. |
| 10-11 | Immunization 3: Protein Immunization<br>Proteins will be provided at 0.1 mg/ml in citrate buffer. Store at −80° C. until use. Thaw at room temperature; material should be clear with no particulate matter. Add equal volume of MF59C adjuvant to thawed protein and mix well by inverting the tube. Immunize each rabbit with 0.5 ml adjuvanted protein per side, IM/Glut for a total of 1.0 ml per animal. Use material within 1 hour of the addition of adjuvant. |

The immunization (Table F) and bleeding (Table G) schedules are as follows:

TABLE F

| | Imm'n: | | | |
|---|---|---|---|---|
| | 1 | 2 | 3 | 3 |
| | Weeks: | | | |
| Group | 0 | 4 | 16 | 16 |
| 1 | pCMV 160 TV1 DNA | pCMV 160 TV1 DNA | pCMV 160 TV1 DNA | Protein + MF59C |
| 2 | pCMV 160 dV2 TV1 DNA | pCMV 160 dV2 TV1 DNA | pCMV 160 dV2 TV1 DNA | Protein + MF59C |
| 3 | pCMV 160 dV1/V2 TV1 DNA | pCMV 160 dV1/V2 TV1 DNA | pCMV 160 dV1/V2 TV1 DNA | Protein + MF59C |
| 4 | pCMV 140 TV1 DNA | pCMV 140 TV1 DNA | pCMV 140 TV1 DNA | Protein + MF59C |
| 5 | pCMV 140 dV2 TV1 DNA | pCMV 140 dV2 TV1 DNA | pCMV 140 dV2 TV1 DNA | Protein + MF59C |
| 6 | pCMV 140 dV1/V2 TV1 DNA | pCMV 140 dV1/V2 TV1 DNA | pCMV 140 dV1/V2 TV1 DNA | Protein + MF59C |
| 7 | pSIN 140 dV2 SF162 DNA | pSIN 140 dV2 SF162 DNA | pSIN 140 dV2 SF162 DNA | Protein + MF59C |
| 8 | pCMV 140 dV2 SF162 DNA | pCMV 140 dV2 SF162 DNA | pCMV 140 dV2 SF162 DNA | Protein + MF59C |
| 9 | pCMV 140 Q154 SF162 DNA | pCMV 140 Q154 SF162 DNA | pCMV 140 Q154 SF162 DNA | Protein + MF59C |
| 10 | pCMV 140 dV2 SF162 DNA + pCMV 140 dV2 TV1 DNA | pCMV 140 dV2 SF162 DNA + pCMV 140 dV2 TV1 DNA | pCMV 140 dV2 SF162 DNA + pCMV 140 dV2 TV1 DNA | Protein + MF59C |
| 11 | pCMV 140 dV2 SF162 DNA + pCMV 140 dV1/V2 TV1 DNA | pCMV 140 dV2 SF162 DNA + pCMV 140 dV1/V2 TV1 DNA | pCMV 140 dV2 SF162 DNA + pCMV 140 dV1/V2 TV1 DNA | Protein + MF59C |

TABLE G

| | Bleed: | | | | | |
|---|---|---|---|---|---|---|
| | 0 | 1 | 2 | 3 | 4 | 5 |
| | | | | Week: | | |
| | −3 | 4 | 6 | 8 | 12 | 16 |
| Sample: | Clotted Bld. for Serum | Clotted Bld. for Serum | Clotted Bld. for Serum | Clotted Bld. for Serum | Clotted Bld. for Serum | Clotted Bld. for Serum |
| Volume: | 20 cc each | 20 cc each | 20 cc each | 20 cc each | 20 cc each | 20 cc each |
| Method: | AA/MEV | AA/MEV | AA/MEV | AA/MEV | AA/MEV | AA/MEV |
| | Bleed: | | | | | |
| | | 6 | 7 | 8 | 9 | 10 |
| | | | | Week: | | |
| | | 18 | 20 | 24 | 28 | TBD |
| Sample: | | Clotted Bld. for Serum | Clotted Bld. for Serum | Clotted Bld. for Serum | Clotted Bld. for Serum | Clotted Bld. for Serum |
| Volume: | | 20 cc each | 20 cc each | 20 cc each | 20 cc each | 20 cc each |
| Method: | | AA/MEV | AA/MEV | AA/MEV | AA/MEV | CP |

Example 10

Mice Immunization Studies with Gag and Pol Constructs

Figure 63:
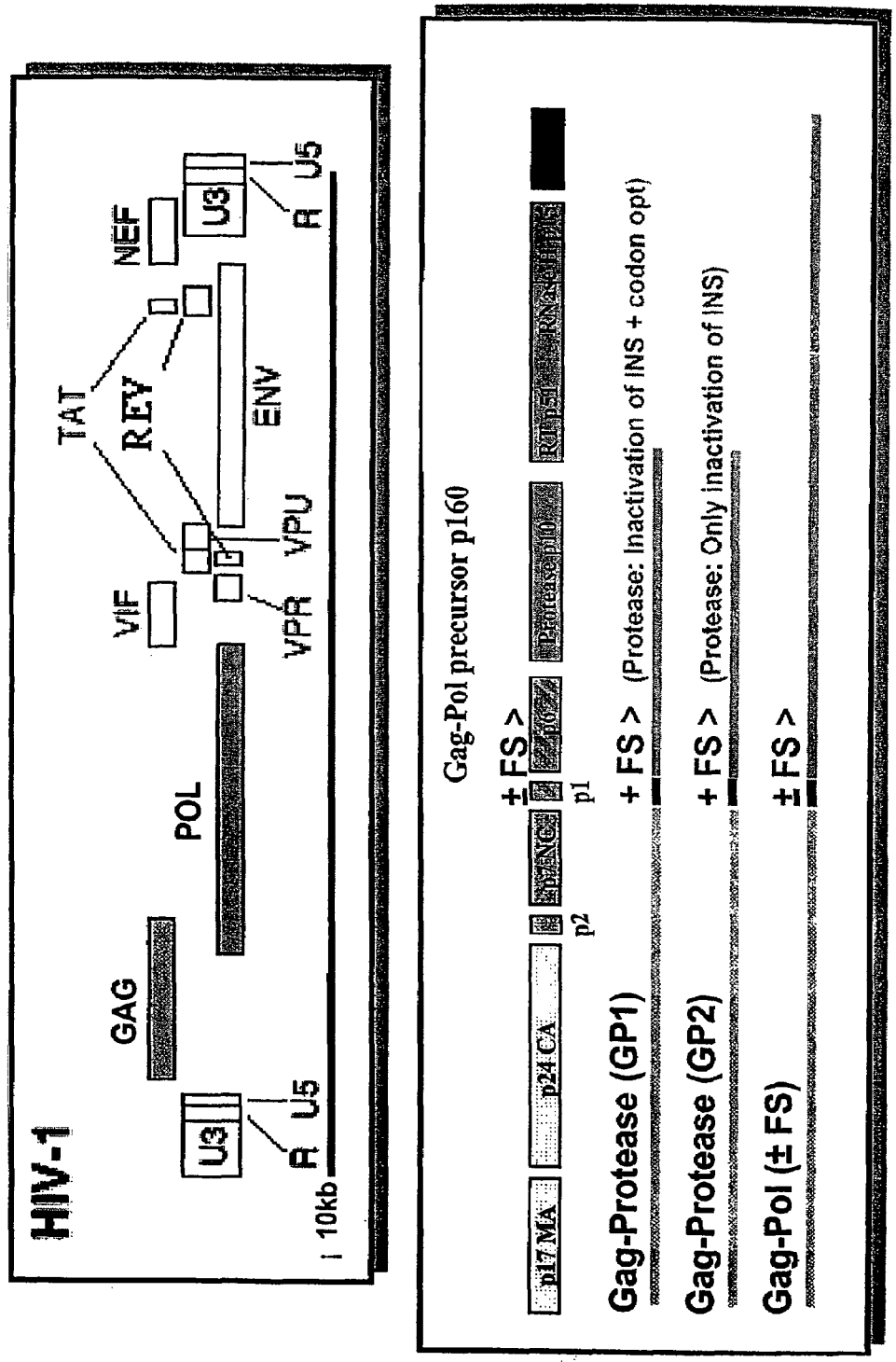
FIG. 63 presents an overview of genome organization of HIV-1 and useful subgenomic fragments.

Cellular and Humoral immune responses were evaluated in mice (essentially as described in Example 4) for the following constructs: Gag, GagProtease (+FS) (GP1, protease codon optimized and inactivation of INS; GP2, protease only inactivation of INS), GagPolΔintegrase with frameshift (gagFSpol), and GagPolΔintegrase in-frame (GagPol) (see FIG. 63). Versions of GagPolΔintegrase in-frame were also designed with attenuated (GagPolAtt) or non-functional Protease (GagPolIna).

In vitro expression data showed comparable expression of p55Gag and p66RT using Gag alone, GagProtease(+FS), GagFSpol and GagPolIna. Constructs with fully functional or attenuated protease (GagPol or GagPolAtt) were less efficient in expression of p55Gag and p66RT, possibly due to cytotoxic effects of protease.

DNA immunization of mice using Gag vs. GP1 and GP2 in pCMV vectors was performed intramuscularly in the tibialis anterior. Mice were immunized at the start of the study (0 week) and 4 weeks later. Bleeds were performed at 0, 4, and 6 weeks. DNA doses used were as follows: 20 μg, 2 μg, 0.2 μg, and 0.02 μg.

DNA immunization of mice using Gag vs. gagFSpol in pCMV vectors was performed intramuscularly in the tibialis anterior. Mice were immunized at the start of the study (0 week) and challenged 4 weeks later with recombinant vaccinia virus encoding Gag (rVVgag). Bleeds were performed at 0 and 4 weeks. DNA doses used were as follows: 20 μg, 2 μg, 0.2 μg, and 0.02 μg.

DNA immunization of mice using Gag vs. gagFSpol and gagpol in pCMV vectors was performed intramuscularly in the tibialis anterior. Mice were immunized at the start of the study (0 week) and challenged 4 weeks later with recombinant vaccinia virus encoding Gag (rVVgag). Bleeds were performed at 0 and 4 weeks. DNA doses used were as follows: 2 μg, 0.2 μg, 0.02 μg, and 0.002 μg.

Cellular immune responses against Gag were comparable for all tested variants, for example, Gag, GagProtease, gagFSpol and GagPolIna all had comparable potencies.

Humoral immune responses to Gag were also comparable with the exception of GP2 and especially GP1. Humoral immune responses were weaker in constructs comprising functional or attenuated proteases which may be due to less efficient secretion of p55Gag caused by overactive protease.

In vitro and in vivo experiments, performed in support of the present invention, suggest that the expression and immunogenicity of Gag was comparable with all constructs. Exceptions were GagPol in-frame with fully functional or attenuated protease. This may be the result of cytotoxic effects of protease. The immune response in mice correlated with relative levels of expression in vitro.

Example 111

Protein Expression, Immunogenicity, and Generation of Neutralizing Antibodies Using Type C Derived Envelope Polypeptides Envelope (Env) vaccines derived from the subtype C primary isolate, TV1, recovered from a South African individual, were tested in rabbits as follows. Gene cassettes were designed to express the gp120 (surface antigen), gp140 (surface antigen plus ectodomain of transmembrane protein, gp41), and full-length (gp120 plus gp41) gp160 forms of the HIV-1 envelope polyprotein with and without deletions of the variable loop regions, V2 and V1V2. All of the genes were sequence-modified to enhance expression of the encoded Env glycoproteins in a Rev-independent fashion and they were subsequently cloned into pCMV-based plasmid vectors for DNA vaccine and protein production applications as described above. The sequences were codon optimized as described herein. Briefly, all the modified envelope genes were cloned into the Chiron pCMVlink plasmid vector, preferably into EcoRI/XhoI sites.

A. Protein Expression

Full-length (gp160), truncated gp140 (Env ectodomain only) and gp120 native versions of the TV1 Env antigen were produced from the expression cassettes described herein. The gp140 encoding sequences were transiently transfected into 293T cells. The expression levels of the gene products were evaluated by an in-house antigen capture ELISA. Envelope genes constructed from the native sequences of TV001c8.2, TV001c8.5 and TV002c12.1 expressed the correct proteins in vitro, with gp140TV001c8.2 exhibiting the highest level of expression. In addition, the Env protein expressed from the TV1-derived clone 8.2 was found to bind the CD4 receptor protein indicating that this feature of the expressed protein is maintained in a functional conformation. The receptor binding properties/functionality of the expressed TV1 gp160 protein result was also confirmed by a cell-fusion assay.

Total expression increased approximately 10-fold for synthetic gp140 constructs compared with the native gp140 gene cassettes. Both the modified gp120 and gp140 variants secreted high amounts of protein in the supernatant. In addition, the V2 and V1V2 deleted forms of gp140 expressed approximately 2-fold more protein than the intact gp140. Overall, the expression levels of synthetic gp140 gene variants increased 10 to 26-fold compared with the gp140 gene with native sequences.

In sum, each synthetic construct tested showed more than 10-fold increased levels of expression relative to those using the native coding sequences. Moreover, all expressed proteins were of the expected molecular weights and were shown to bind CD4. Stable CHO cell lines were derived and small-scale protein purification methods were used to produce small quantities of each of the undeleted and V-deleted oligomeric forms (o-gp140) of these proteins for vaccine studies.

B. Neutralization Properties of TV001 and TV002 Viral Isolates

The transient expression experiment showed that the envelope genes derived from the TV001 and TV002 virus isolates expressed the desired protein products. Relative neutralization sensitivities of these two viral strains using sera from 18 infected South African individuals (subtypes B and C) were as follows. At a 1:10 serum dilution, the TV2 strain was neutralized by 18 of 18 sera; at 1:50, 16 of 18; at 1:250, 15/18. In comparison, the TV1 isolate was neutralized by 15 of 18 at 1:10; only 6 of 18 at 1:50; and none of the specimens at 1:250. In addition, the TV001 patient serum showed neutralization activity against the TV002 isolate at all dilutions tested. In contrast, the TV002 showed neutralization of TV001 only at the 1:10 serum dilution. These results suggest that TV001 isolate is capable of inducing a broader and more potent neutralizing antibody response in its infected host than TV002.

C. Immunogenicity of the Modified TV1 Env DNA and Protein Antigens in Rabbit Studies TV1 Env DNA (comprising the synthetic expression cassettes) and protein vaccines were administered as shown in the following Table H.

TABLE H

| Groups | Plasmid DNA (0, 4, and 20 wks) | Protein boost (20 wks) |
|---|---|---|
| 1 | pCMVgp160.TV1 | o-gp140.TV1 |
| 2 | pCMVgp160dV2.TV1 | o-gp140dV2.TV1 |
| 3 | pCMVgp160dV1V2.TV1 | o-gp140dV1V2.TV1 |
| 4 | pCMVgp140.TV1 | o-gp140.TV1 |
| 5 | pCMVgp140dV2.TV1 | o-gp140dV2.TV1 |
| 6 | pCMVgp140dV1V2.TV1 | o-gp140dV1V2.TV1 |
| 7 | pCMVgp140dV2.SF162 | o-gp140dV2.SF162 |

Seven groups of 4 rabbits per group were immunized with the designated plasmid DNA and oligomeric Env protein antigens. Three doses of DNA, 1 mg of DNA per animal per immunization, were administered intramuscularly by needle injection followed by electroporation on weeks 0, 4, and 20 weeks. A single dose of 100 ug of Env protein in MF59 adjuvant also was given intramuscularly in a separate site at 20 weeks.

The DNA immunization used subtype C sequence-modified genes (TV1)—gp160, gp160dV2, gp160dV1V2, gp140, gp140dV2 and gp140dV1V2—as well as a subtype B SF162 sequence modified gp140dV2. DNA immunizations were performed at 0, 4, and 20 weeks by needle injection by the intramuscular route using electroporation to facilitate transfection of the muscle cells and of resident antigen presenting cells.

A single Env protein booster (in MF59 adjuvant) was given at 20 weeks by intramuscular injection at a separate site. Antibody titers were evaluated by ELISA following each successive immunization. Serum specimens were collected at 0, 4, 6, 8, 12, 22, and 24 weeks. Serum antibody titers were measured on ELISA. 96-well plates were coated with a protein in a concentration of 1 ug/ml. Serum samples were diluted serially 3-fold. Goat anti-rabbit peroxidase conjugate (1:20,000) was used for detection. TMB was used as the substrate, and the antibody titers were read at 0.6 OD at 450 nm.

Neutralizing antibody responses against PBMC-grown R5HIV-1 strains were monitored in the sera collected from the immunized rabbits using two different assays in two different laboratories, the 5.25 reporter cell-line based assay at Chiron and the PBMC-based assay of David Montefiori at Duke University. Results are shown in FIGS. 66, 67, and 68. The Chiron assay was conducted essentially as follows. Neutralizing antibody responses against the PBMC-grown subtype C TV001 and TV002 strains were measured using an in-house reporter cell line assay that uses the 5.25 cell line. This cell has CD4, CCR5, CXCR4 and BONZO receptor/co-receptors on its cell membrane. The parental CEM cell line was derived from a 4-year-old Caucasian female with acute lymphoblastic leukemia, which was fused with the human B cell line 721.174, creating CEMx174. LTR-GFP was transfected into the cells after the CCR5 gene (about 1.1 kb) was cloned into the BamH-I (5') and Sal-I (3') of the pBABE puro retroviral vector, and subsequently introduced into the CEMx174. The green fluorescence protein (GFP) of the cells was detected by flow cytometer (FACScan). For the virus neutralization assay, 50 ul of titrated virus and 50 ul of diluted immune or pre-immune serum were incubated at room temperature for one hour. This mixture was added into wells with $10^4$/ml cells plated in a 24 well plate, and incubated at 37° C. for 5 to 7 days. The cells were then fixed with 2% of formaldehyde after washing with PBS. Fifteen thousand events (cells) were collected for each sample on a Becton Dickinson FACScan using Cellquest software. The data presented were the mean of the triplicate wells. The percent neutralization was calculated compared to the virus control using the following equation: % virus Inhibition=(virus control−experimental)/(virus control−cell control)×100. Any virus inhibition observed in the pre-bleed has been subtracted for each individual animal. Values>50% are considered positive and are highlighted in gray.

In FIG. 67, the "#" indicates that animals had high levels of virus inhibition in pre-bleed serum (>20% virus inhibition) that impacted the magnitude of the observed inhibition and in some cases, our ability to score the serum as a positive or negative for the presence of significant neutralizing antibody activity (<50% inhibition).

For the data presented in FIG. 68, serum samples were collected after a single protein boost (post-third) were screened in triplicate at a 1:8 dilution with virus (1:24 after addition of cells). Values shown are the % reduction in p24 synthesis relative to that in the corresponding pre-bleed control samples. Zero values indicate no or negative values were measured. NV, not valid due to virus inhibition in pre-immune serum. Neutralization was considered positive when p24 was reduced by at least 80%; these samples are highlighted in dark gray. Sample with lighter gray shading showed at least a 50% reduction in p24 synthesis.

Figure 64:
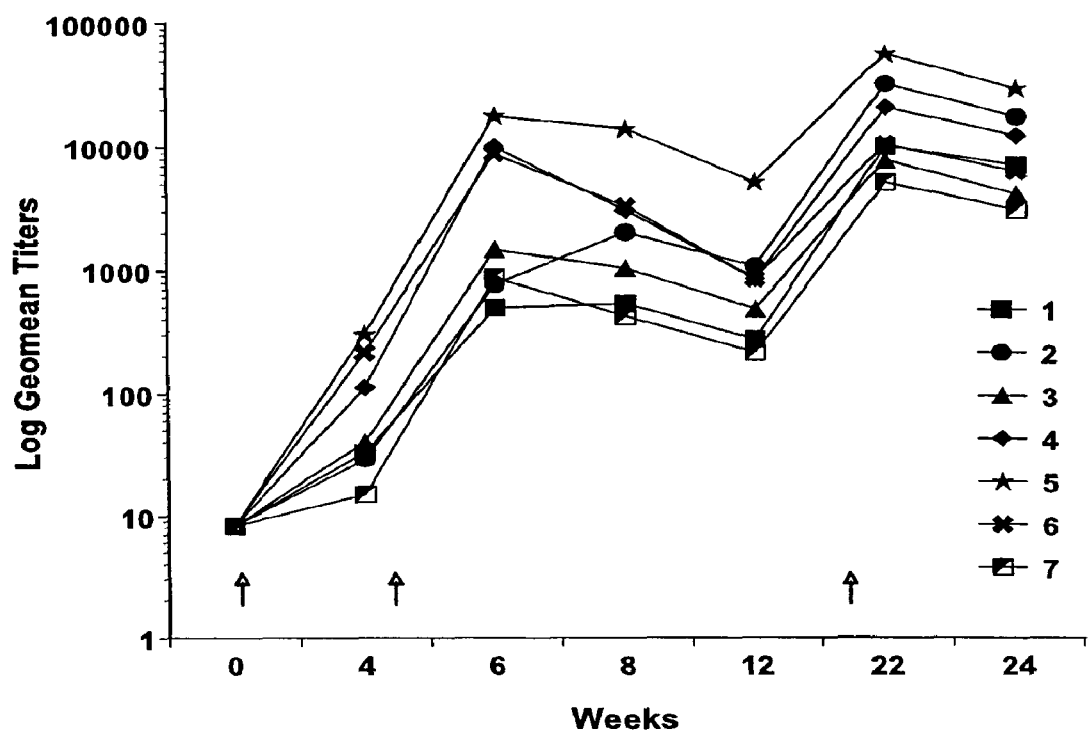
FIG. 64 presents antibody titer data from immunized rabbits following immunization with HIV Envelope DNA constructs and protein.

FIG. 64 shows the ELISA data when plates were coated with the monomeric gp120.TV1 protein. This protein is homologous to the subtype C genes used for the immunization. All immunization groups produced high antibody titers after the second DNA immunization. The groups immunized with gp140 forms of DNA have relatively higher geometric mean antibody titers as compared to the groups using gp160 forms after both first and second DNA immunizations. Both the gp140.TV1 and gp140dV1V2.TV1 genes produced high antibody titers at about $10^4$ at two weeks post second DNA; the gp140dV2.TV1 plasmid yielded the highest titers of antibodies ($>10^4$) at this time point and all others. The binding antibody titers to the gp120.TV1 protein were higher for the group immunized with the homologous gp140dV2.TV1 genes than that with the heterologous gp140dV2.SF162 gene which showed titers of about $10^3$. All the groups, showed some decline in antibody titers by 8 weeks post the second DNA immunization. Following the DNA plus protein booster at 20 weeks, all groups reached titers above that previously observed after the second DNA immunization (0.5-1.0 log increases were observed). After the protein boost, all animals receiving the o-gp140dV2.TV1 protein whether primed by the gp140dV2.TV1 or gp160dV2.TV1 DNA, showed the highest Ab titers.

Figure 65:
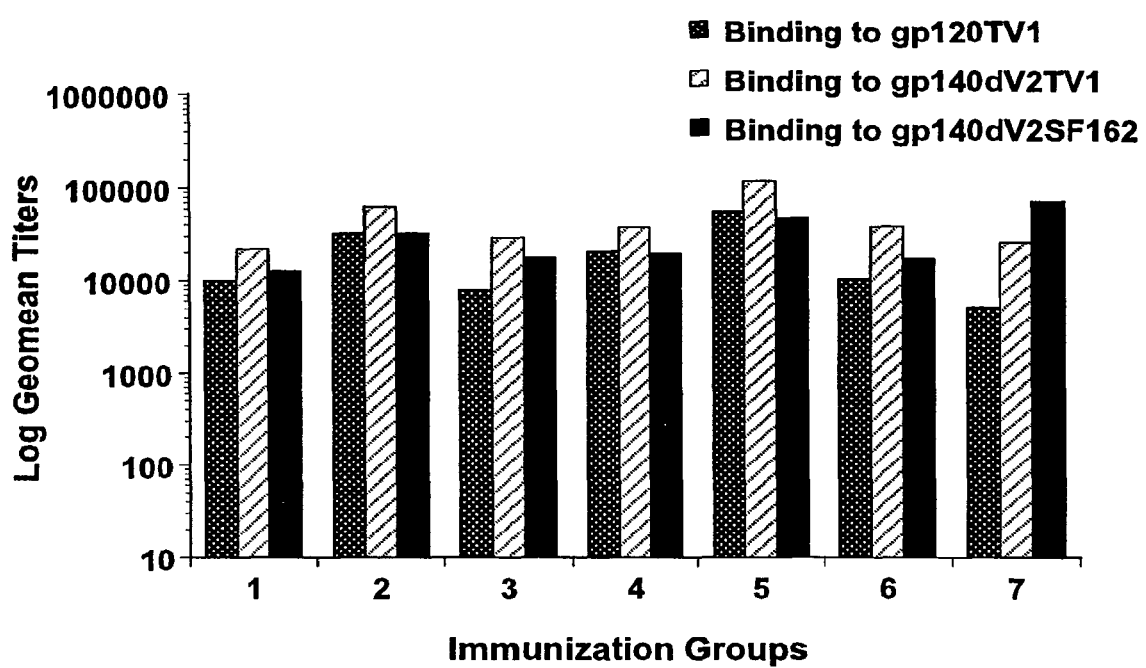
FIG. 65 presents a comparison of ELISA titers against subtype B and C Envelope proteins in rabbit sera collected after three DNA immunizations and a single protein boost.

Binding antibody titers were also measured using ELISA plates coated with either oligomeric subtype C o-gp140dV2.TV1 or subtype B o-gp140dV2.SF162 proteins (FIG. 65). For all the TV1 Env immunized groups, the antibody titers measured using the oligomeric protein, o-gp140dV2.TV1 were higher than those measured using the monomeric (non-V2-deleted) protein, gp120.TV1. In fact, for these groups, the titers observed with the heterologous subtype B o-gp140dV2.SF162 protein were comparable to or greater than those measured with the subtype C TV1 gp120. Nevertheless, all groups immunized with subtype C immunogens showed higher titers binding to the subtype C o-gp140dV2.TV1 protein than to the subtype B protein gp140dV2.SF162. Conversely, the group immunized with the gp140dV2.SF162 immunogen showed higher antibody titers with the oligomeric subtype B protein relative its subtype C counterpart. Overall, all three assays demonstrated that high antibody cross-reactive antibodies were generated by the subtype CTV1-based DNA and protein immunogens.

The results indicate that the subtype C TV1-derived Env DNA and protein antigens are immunogenic inducing high titers of antibodies in immunized rabbits and substantial evidence of neutralizing antibodies against both subtype B and subtype C R5 virus strains. In particular, the gp140dV2.TV1 antigens have induced consistent neutralizing responses against the subtype B SF162EnvDV2 and subtype C TV2 strains. Thus, TV1-based Env DNA and protein-based antigens are immunogenic and induce high titer antibody responses reactive with both subtype C and subtype B HIV-1 Env antigens. Neutralizing antibody responses against the neutralization sensitive subtype B R5 HIV-1$_{SF162DV2}$ strain were observed in some groups after only two DNA immunizations. Following a single booster immunization with Env protein, the majority of rabbits in groups that received V2-deleted forms of the TV1 Env showed neutralization activity against the closely related subtype C TV2 primary strain.

Example 12

Immunological Responses in Rhesus Macaques

Cellular and humoral immune responses were evaluated in three groups of rhesus macaques (each group was made up of four animals) in an immunization study structured as shown in Table I. The route of administration for the immunizing composition was electroporation in each case. Antibody titers are shown in Table I for two weeks post-second immunization.

TABLE I

| Group | Formulation of Immunizing Composition* | Animal # | Titer |
|---|---|---|---|
| 1 | pCMVgag (3.5 mg) + pCMVenv (2.0 mg) | A | 3325 |
| | | B | 4000 |
| | | C (previously immunized with HCV core ISCOMS, rVVC core E1) | 1838 |
| | | D (previously immunized with HCV core ISCOMS, rVVC core E1) | 1850 |
| 2 | pCMVgag (3.5 mg) + pCMVpol (4.2 mg) | A (previously immunized with HCV core ISCOMS, rVVC core E1, p55gag$_{LAI}$(VLP)) | 525 |
| | | B | 5313 |
| | | C | 6450 |
| | | D | 5713 |
| 3 | pCMVgag-pol (5.0 mg) | A (previously immunized with HCV core ISCOMS, rVVC core E1, pCMVgagSF2) | 0 |
| | | B (previously immunized with rVVC/E1, pCMV Epo-Epi, HIV/HCV-VLP, pCMVgagSF2, pUCgp120 SF2) | 1063 |
| | | C | 513 |
| | | D (previously immunized with rVVC/E1, HIV/HCV-VLP) | 713 |

*pCMVgag = pCMVKm2.GagMod Type C Botswana
pCMVenv = pCMVLink.gp140env.dV2.TV1 (Type C)
pCMVpol = pCMVKm2.p2Pol.mut.Ina Type C Botswana
pCMVgag-pol = pCMVKm2.gagCpol.mut.Ina Type C Botswana Pre-immune sera were obtained at week 0 before the first immunization. The first immunization was given at week 0. The second immunization was given at week 4. The first bleed was performed at 2 weeks post-second immunization (i.e., at week 6). A third immunization will be given at week 8 and a fourth at week 16. Animals 2A, 3A, 3B and 3D had been vaccinated previously (approximately 4 years or more) with gag plasmid DNA or gag VLP (subtype B).

Bulk CTL, $^{51}$Cr-release assays, and flow cell cytometry methods were used to obtain the data in Tables J and K. Reagents used for detecting gag- and pol-specific T-cells were (i) synthetic, overlapping peptides spanning "gagCpol"

antigen (n=377), typically the peptides were pools of 15-mers with overlap by 11, the pools were as follows, pool 1, n=1-82, pool 2, n=83-164, pool 3, n=165-271, pool 4, n=272-377, accordingly pools 1 and 2 are "gag"-specific, and pools 3 and 4 are "pol"-specific, and (ii) recombinant vaccinia virus (rVV), for example, rVVgag965, rVVp2Pol975 (contains p2p7gag975), and VV$_{wr}$parent.

Gag-specific IFNγ+CD8+T-cells, Gag-specific IFNγ+CD4+T-cells, Pol-specific IFNγ+CD8+T-cells, and Pol-specific IFNγ+CD4+T-cells in blood were determined for each animal described in Table I above, post second immunization. The results are presented in Tables J and K. It is possible that some of the pol-specific activity shown in Table K was directed against p2p7gag.

TABLE J

Gag Assay Results

| Group/ Animal | Immunizing Composition | Gag Specific CD4+ Responses | | | | Gag Specific CD8+ Responses | | |
|---|---|---|---|---|---|---|---|---|
| | | LPA(SI) | | | Flow | CTL | | Flow |
| | | p55 | Pool 1 | Pool 2 | IFNg+ | Pool 1 | Pool 2 | IFNg+ |
| 1A | pCMVgag pCMVenv | 3.3 | 5.9 | 3.8 | 496 | minus | minus | 225 |
| 1B | pCMVgag pCMVenv | 11.8 | 4.4 | 1.5 | 786 | minus | minus | 160 |
| 1C | pCMVgag pCMVenv | 5.7 | 1.1 | 2.4 | 361 | plus | plus | 715 |
| 1D | pCMVgag pCMVenv | 6.5 | 3.1 | 1.6 | 500 | plus | ? | 596 |
| 2A | pCMVgag pCMVpol | 4.8 | 4.8 | 1.6 | 405 | plus | minus | 1136 |
| 2B | pCMVgag pCMVpol | 12.5 | 6.8 | 3.3 | 1288 | plus | minus | 2644 |
| 2C | pCMVgag pCMVpol | 6 | 3.8 | 2.1 | 776 | minus | minus | 0 |
| 2D | pCMVgag pCMVpol | 18.9 | 13.5 | 5.4 | 1351 | minus | minus | 145 |
| 3A | pCMV gagpol | 12.2 | 7 | 1.5 | 560 | plus | plus | 3595 |
| 3B | pCMV gagpol | 2.7 | 5.6 | 1.3 | 508 | plus | ? | 3256 |
| 3C | pCMV gagpol | 11.6 | 5 | 1.2 | 289 | minus | ? | 617 |
| 3D | pCMV gagpol | 1.5 | 1.2 | 1.4 | 120 | minus | minus | 277 |

? = might be positive on rVVp2Pol.

TABLE K

Pol Assay Results

| Group/ Animal | Immunizing Composition | Pol Specific CD4+ Response | | | Pol Specific CD8+ Responses | | |
|---|---|---|---|---|---|---|---|
| | | LPA(SI) | | Flow | CTL | | Flow |
| | | Pool 3 | Pool 4 | IFNg+ | Pool 3 | Pool 4 | IFNg+ |
| 1A | pCMVgag pCMVenv | 1 | 1.2 | 0 | minus | minus | 0 |
| 1B | pCMVgag pCMVenv | 1 | 1 | 0 | minus | minus | 0 |
| 1C | pCMVgag pCMVenv | 1 | 1.1 | 0 | minus | minus | 0 |
| 1D | pCMVgag pCMVenv | 1.2 | 1.3 | 0 | minus | minus | 262 |
| 2A | pCMVgag pCMVpol | 1.1 | 0.9 | 92 | minus | minus | 459 |
| 2B | pCMVgag pCMVpol | 2.5 | 1.8 | 107 | minus | minus | 838 |
| 2C | pCMVgag pCMVpol | 1.2 | 1.1 | 52 | plus | minus | 580 |
| 2D | pCMVgag pCMVpol | 2.5 | 2.7 | 113 | plus | plus | 5084 |
| 3A | pCMV gagpol | 2.7 | 2.4 | 498 | minus | minus | 3631 |
| 3B | pCMV gagpol | 1.1 | 1 | 299 | minus | minus | 1346 |

TABLE K-continued

| | | Pol Assay Results | | | | |
|---|---|---|---|---|---|---|
| | | Pol Specific CD4+ Response | | | Pol Specific CD8+ Responses | |
| | | LPA(SI) | | Flow | CTL | Flow |
| Group/ Animal | Immunizing Composition | Pool 3 | Pool 4 | IFNg+ | Pool 3 | Pool 4 | IFNg+ |
| 3C | pCMV gagpol | 2.1 | 1.4 | 369 | minus | minus | 399 |
| 3D | pCMV gagpol | 1.3 | 1.8 | 75 | minus | minus | 510 |

These results support that the constructs of the present invention are capable of generating specific cellular and humoral responses against the selected HIV-polypeptide antigens.

Although preferred embodiments of the subject invention have been described in some detail, it is understood that obvious variations can be made without departing from the spirit and the scope of the invention as defined by the appended claims.

SEQUENCE LISTING

<160> NUMBER OF SEQ ID NOS: 68

<210> SEQ ID NO 1
<211> LENGTH: 9781
<212> TYPE: DNA
<213> ORGANISM: Artificial Sequence
<220> FEATURE:
<223> OTHER INFORMATION: Description of Artificial Sequence:
      8_5_TV1_C.ZA

<400> SEQUENCE: 1

```
tggaagggtt aatttactcc aagaaaaggc aagaaatcct tgatttgtgg gtctatcaca      60
cacaaggctt cttccctgat tggcaaaact acacaccggg ccagggtc agatatccac       120 tgacctttgg atggtgctac aagctagtgc cagttgaccc aggggaggtg gaagaggcca    180
acggaggaga agacaactgt ttgctacacc ctatgagcca acatggagca gaggatgaag    240
atagagaagt attaaagtgg aagtttgaca gcctcctagc acgcagacac atggcccgcg   300
agctacatcc ggagtattac aaagactgct gacacagaag gactttccg cctgggactt     360 tccactgggg cgttccggga ggtgtggtct gggcgggact tgggagtggt caaccctcag    420
atgctgcata taagcagctg cttttcgcct gtactgggtc tctctcggta gaccagatct    480
gagcctggga gccctctggc tatctaggga acccactgct taagcctcaa taaagcttgc    540
cttgagtgct ttaagtagtg tgtgcccatc tgttgtgtga ctctggtaac tagagatccc   600
tcagaccctt tgtggtagtg tggaaaatct ctagcagtgg cgcccgaaca gggaccagaa    660
agtgaaagtg agaccagagg agatctctcg acgcaggact cggcttgctg aagtgcacac    720
ggcaagaggc gagaggggcg gctggtgagt acgccaattt tacttgacta gcggaggcta    780
gaaggagaga gatgggtgcg agagcgtcaa tattaagcgg cggaaaatta gataaatggg    840
aaagaattag gttaaggcca gggggaaaga aacattatat gttaaaacat ctagtatggg    900
caagcaggga gctggaaaga tttgcactta accctggcct gttagaaaca tcagaaggct    960
gtaaacaaat aataaaacag ctacaaccag ctcttcagac aggaacagag gaacttagat    1020
cattattcaa cacagtagca actctctatt gtgtacataa agggatagag gtacgagaca    1080
```

```
ccaaggaagc cttagacaag atagaggaag aacaaaacaa atgtcagcaa aaagcacaac      1140
aggcaaaagc agctgacgaa aaggtcagtc aaaattatcc tatagtacag aatgcccaag      1200
ggcaaatggt acaccaagct atatcaccta gaacattgaa tgcatggata aaagtaatag      1260
aggaaaaggc tttcaatcca gaggaaatac ccatgtttac agcattatca gaaggagcca      1320
ccccacaaga tttaaacaca atgttaaata cagtggggggg acatcaagca gccatgcaaa     1380
tgttaaaaga taccatcaat gaggaggctg cagaatggga taggacacat ccagtacatg      1440
cagggcctgt tgcaccaggc cagatgagag aaccaagggg aagtgacata gcaggaacta      1500
ctagtaccct tcaggaacaa atagcatgga tgacaagtaa tccacctatt ccagtagaag      1560
acatctataa aagatggata attctggggt taaataaaat agtaagaatg tatagccctg      1620
ttagcatttt ggacataaaa caagggccaa agaacccctt tagagactat gtagaccggt      1680
tctttaaaac cttaagagct gaacaagcta cacaagatgt aaagaattgg atgacagaca      1740
ccttgttggt ccaaaatgcg aacccagatt gtaagaccat tttaagagca ttaggaccag      1800
gggcctcatt agaagaaatg atgacagcat gtcagggagt gggaggacct agccataaag      1860
caagagtgtt ggctgaggca atgagccaag caaacagtaa catactagtg cagagaagca      1920
attttaaagg ctctaacaga attattaaat gtttcaactg tggcaaagta gggcacatag      1980
ccagaaattg cagggcccct aggaaaaagg gctgttggaa atgtggacag gaaggacacc      2040
aaatgaaaga ctgtactgag aggcaggcta attttttagg gaaaatttgg ccttcccaca      2100
aggggaggcc agggaatttc ctccagaaca gaccagagcc aacagccca ccagcagaac       2160 caacagcccc accagcagag agcttcaggt tcgaggagac aaccccgtg ccgaggaagg       2220 agaaagagag ggaacccttta acttccctca aatcactctt tggcagcgac cccttgtctc      2280
aataaaagta gagggccaga taaaggaggc tctcttagac acaggagcag atgatacagt      2340
attagaagaa atagatttgc cagggaaatg gaaaccaaaa atgatagggg gaattggagg      2400
ttttatcaaa gtaagacagt atgatcaaat acttatagaa atttgtggaa aaaaggctat      2460
aggtacagta ttagtagggc ctacaccagt caacataatt ggaagaaatc tgttaactca      2520
gcttggatgc acactaaatt ttccaattag tcctattgaa actgtaccag taaaattaaa      2580
accaggaatg gatggcccaa aggtcaaaca atggccattg acagaagaaa aaataaaagc      2640
attaacagca atttgtgagg aaatggaaaa ggaaggaaaa attacaaaaa ttgggcctga      2700
taatccatat aacactccag tatttgccat aaaaaagaag gacagtacta agtggagaaa      2760
attagtagat ttcagggaac tcaataaaag aactcaagac ttttgggaag ttcaattagg      2820
aataccacac ccagcaggat taaaaaagaa aaatcagtg acagtgctag atgtggggga      2880
tgcatatttt tcagttcctt tagatgaaag cttcaggaaa tatactgcat tcaccatacc      2940
tagtataaac aatgaaacac cagggattag atatcaatat aatgtgctgc cacagggatg      3000
gaaaggatca ccagcaatat tccagagtag catgacaaaa atcttagagc ccttcagagc      3060
aaaaaatcca gacatagtta tctatcaata tatggatgac ttgtatgtag gatctgactt      3120
agaaataggg caacatagag caaaaataga gagttaagg gaacatttat tgaaatgggg      3180
atttacaaca ccagacaaga aacatcaaaa agaaccccca tttctttgga tggggtatga      3240
actccatcct gacaaatgga cagtacaacc tatactgctg ccagaaaagg atagttggac      3300
tgtcaatgat atacagaagt tagtgggaaa attaaactgg gcaagtcaga tttacccagg      3360
gattaaagta aggcaactct gtaaactcct cagggggggcc aaagcactaa cagacatagt      3420
accactaact gaagaagcag aattagaatt ggcagagaac agggaaattt taagagaacc      3480
```

```
agtacatgga gtatattatg atccatcaaa agacttgata gctgaaatac agaaacaggg    3540
gcatgaacaa tggacatatc aaatttatca agaaccattt aaaaatctga aaacagggaa    3600
gtatgcaaaa atgaggacta cccacactaa tgatgtaaaa cagttaacag aggcagtgca    3660
aaaaatagcc atgaaagca tagtaatatg gggaaagact cctaaattta gactacccat     3720
ccaaaaagaa acatgggaga catggtggac agactattgg caagccacct ggatccctga    3780
gtgggagttt gttaataccc ctcccctagt aaaattatgg taccaactag aaaaagatcc    3840
catagcagga gtagaaactt tctatgtaga tggagcaact aatagggaag ctaaaatagg    3900
aaaagcaggg tatgttactg acagaggaag gcagaaaatt gttactctaa ctaacacaac    3960
aaatcagaag actgagttac aagcaattca gctagctctg caggattcag gatcagaagt    4020
aaacatagta acagactcac agtatgcatt aggaatcatt caagcacaac cagataagag    4080
tgactcagag atatttaacc aaataataga acagttaata aacaaggaaa gaatctacct    4140
gtcatgggta ccagcacata aaggaattgg gggaaatgaa caagtagata aattagtaag    4200
taagggaatt aggaaagtgt tgtttctaga tggaatagat aaagctcaag aagagcatga    4260 aagtaccac agcaattgga gagcaatggc taatgagttt aatctgccac ccatagtagc     4320
aaaagaaata gtagctagct gtgataaatg tcagctaaaa ggggaagcca tacatggaca    4380
agtcgactgt agtccaggga tatggcaatt agattgtacc catttagagg gaaaaatcat    4440
cctggtagca gtccatgtag ctagtggcta catggaagca gaggttatcc cagcagaaac    4500
aggacaagaa acagcatatt ttatattaaa attagcagga agatggccag tcaaagtaat    4560
acatacagac aatggcagta atttcaccag tactgcagtt aaggcagcct gttggtgggc    4620
aggtatccaa caggaatttg gaattcccta caatccccaa agtcagggag tggtagaatc    4680
catgaataaa gaattaaaga aaataatagg acaagtaaga gatcaagctg agcaccttaa    4740
gacagcagta caaatggcag tattcattca caattttaaa agaaaagggg gaattggggg    4800
gtacagtgca ggggaaagaa taatagacat aatagcaaca gacatacaaa ctaaagaatt    4860
acaaaaacaa attataagaa ttcaaaattt tcgggtttat tacagagaca gcagagaccc    4920
tatttggaaa ggaccagccg aactactctg gaaaggtgaa ggggtagtag taatagaaga    4980
taaaggtgac ataaaggtag taccaaggag gaaagcaaaa atcattagag attatggaaa    5040
acagatggca ggtgctgatt gtgtggcagg tggacaggat gaagattaga gcatggaata    5100
gtttagtaaa gcaccatatg tatatatcaa ggagagctag tggatgggtc tacagacatc    5160
attttgaaag cagacatcca aaagtaagtt cagaagtaca tatcccatta ggggatgcta    5220
gattagtaat aaaaacatat tggggtttgc agacaggaga agagattgg catttgggtc    5280 atggagtctc catagaatgg agactgagag aatacagcac acaagtagac cctgacctgg    5340
cagaccagct aattcacatg cattattttg attgttttac agaatctgcc ataagacaag    5400
ccatattagg acacatagtt tttcctaggt gtgactatca agcaggacat aagaaggtag    5460
gatctctgca atacttggca ctgacagcat tgataaaacc aaaaaagaga agccacctc     5520 tgcctagtgt tagaaaatta gtagaggata gatggaacga ccccccagaag accaggggcc    5580 gcagagggaa ccatacaatg aatggacact agagattcta gaagaactca agcaggaagc    5640
tgtcagacac tttcctagac catggctcca tagcttagga caatatatct atgaaaccta    5700
tggggatact tggacgggag ttgaagctat aataagagta ctgcaacaac tactgttcat    5760
tcatttcaga attggatgcc aacatagcag aataggcatc ttgcgacaga gaagagcaag    5820
aaatggagcc agtagatcct aaactaaagc cctggaacca tccaggaagc caacctaaaa    5880
```

```
cagcttgtaa taattgcttt tgcaaacact gtagctatca ttgtctagtt tgctttcaga    5940
caaaaggttt aggcatttcc tatggcagga agaagcggag acagcgacga agcgctcctc    6000
caagtggtga agatcatcaa aatcctctat caaagcagta agtacacata gtagatgtaa    6060
tggtaagttt aagtttattt aaaggagtag attatagatt aggagtagga gcattgatag    6120
tagcactaat catagcaata atagtgtgga ccatagcata tatagaatat aggaaattgg    6180
taagacaaaa gaaaatagac tggttaatta aaagaattag ggaaagagca gaagacagtg    6240
gcaatgagag tgatggggac acagaagaat tgtcaacaat ggtggatatg gggcatctta    6300
ggcttctgga tgctaatgat ttgtaacacg gaggacttgt gggtcacagt ctactatggg    6360
gtacctgtgt ggagagaagc aaaaactact ctattctgtg catcagatgc taaagcatat    6420
gagacagaag tgcataatgt ctgggctaca catgcttgtg tacccacaga ccccaaccca    6480
caagaaatag ttttgggaaa tgtaacagaa aattttaata tgtggaaaaa taacatggca    6540
gatcagatgc atgaggatat aatcagttta tgggatcaaa gcctaaagcc atgtgtaaag    6600
ttgaccccac tctgtgtcac tttaaactgt acagatacaa atgttacagg taatagaact    6660
gttacaggta atacaaatga taccaatatt gcaaatgcta catataagta tgaagaaatg    6720
aaaaattgct ctttcaatgc aaccacagaa ttaagagata agaaacataa agagtatgca    6780 ctctttttata aacttgatat agtaccactt aatgaaaata gtaacaactt tacatataga    6840
ttaataaatt gcaataccctc aaccataaca caagcctgtc caaggtctc ttttgacccg    6900 attcctatac attactgtgc tccagctgat tatgcgattc taaagtgtaa taataagaca    6960
ttcaatggga caggaccatg ttataatgtc agcacagtac aatgtacaca tggaattaag    7020
ccagtggtat caactcaact actgttaaat ggtagtctag cagaagaagg gataataatt    7080
agatctgaaa atttgacaga gaataccaaa acaataatag tacatcttaa tgaatctgta    7140
gagattaatt gtacaaggcc caacaataat acaaggaaaa gtgtaaggat aggaccagga    7200
caagcattct atgcaacaaa tgacgtaata ggaaacataa gacaagcaca ttgtaacatt    7260
agtacagata gatggaataa aactttacaa caggtaatga aaaaattagg agagcatttc    7320
cctaataaaa caataaaatt tgaaccacat gcaggagggg atctagaaat tacaatgcat    7380
agctttaatt gtagaggaga atttttctat tgcaatacat caaacctgtt taatagtaca    7440
tactacccta agaatggtac atacaaatac aatggtaatt caagcttacc catcacactc    7500
caatgcaaaa taaaacaaat tgtacgcatg tggcaagggg taggacaagc aatgtatgcc    7560
cctcccattg caggaaacat aacatgtaga tcaaacatca caggaatact attgacacgt    7620
gatgggggat ttaacaacac aaacaacgac acagaggaga cattcagacc tggaggagga    7680
gatatgaggg ataactggag aagtgaatta tataaatata agtggtagaa attaagccat    7740 tgggaatag cacccactaa ggcaaaaaga agagtggtgc agagaaaaaa aagagcagtg    7800
ggaataggag ctgtgttcct tgggttcttg ggagcagcag gaagcactat gggcgcagcg    7860
tcaataacgc tgacggtaca ggccagacaa ctgttgtctg gtatagtgca acagcaaagc    7920
aatttgctga aggctataga ggcgcaacag catatgttgc aactcacagt ctggggcatt    7980
aagcagctcc aggcgagagt cctggctata gaaagatacc taaaggatca acagctccta    8040
gggatttggg gctgctctgg aagactcatc tgcaccactg ctgtgccttg gaactccagt    8100
tggagtaata aatctgaagc agatatttgg gataacatga cttggatgca gtgggataga    8160
gaaattaata attacacaga acaatattc aggttgcttg aagactcgca aaaccagcag    8220
gaaaagaatg aaaaagattt attagaattg gacaagtgga ataatctgtg gaattggttt    8280
```

-continued

```
gacatatcaa actggctgtg gtatataaaa atattcataa tgatagtagg aggcttgata    8340
ggtttaagaa taattttttgc tgtgctctct atagtgaata gagttaggca gggatactca    8400
cctttgtcat ttcagaccct taccccaagc ccgagggggac tcgacaggct cggaggaatc    8460
gaagaagaag gtggagagca agacagagac agatccatac gattggtgag cggattcttg    8520
tcgcttgcct gggacgatct gcggagcctg tgcctcttca gctaccaccg cttgagagac    8580
ttcatattaa ttgcagtgag ggcagtggaa cttctgggac acagcagtct caggggacta    8640 cagaggggt gggagatcct taagtatctg ggaagtcttg tgcagtattg gggtctagag    8700 ctaaaaaga gtgctattag tccgcttgat accatagcaa tagcagtagc tgaaggaaca    8760
gataggatta tagaattggt acaaagaatt tgtagagcta tcctcaacat acctaggaga    8820
ataagacagg gctttgaagc agctttgcta taaaatggga ggcaagtggt caaaacgcag    8880
catagttgga tggcctgcag taagagaaag aatgagaaga actgagccag cagcagaggg    8940
agtaggagca gcgtctcaag acttagatag acatggggca cttacaagca gcaacacacc    9000
tgctactaat gaagcttgtg cctggctgca agcacaagag gaggacggag atgtaggctt    9060
tccagtcaga cctcaggtac ctttaagacc aatgacttat aagagtgcag tagatctcag    9120
cttcttttta aaagaaaagg ggggactgga agggttaatt tactctagga aaaggcaaga    9180
aatccttgat ttgtgggtct ataacacaca aggcttcttc cctgattggc aaaactacac    9240
atcgggccca ggggtccgat tcccactgac ctttggatgg tgcttcaagc tagtaccagt    9300
tgacccaagg gaggtgaaag aggccaatga aggagaagac aactgtttgc tacaccctat    9360
gagccaacat ggagcagagg atgaagatag agaagtatta aagtggaagt ttgacagcct    9420
tctagcacac agacacatgg cccgcgagct acatccggag tattacaaag actgctgaca    9480
cagaagggac tttccgcctg ggactttcca ctggggcgtt ccgggaggtg tggtctgggc    9540
gggacttggg agtggtcacc ctcagatgct gcatataagc agctgctttt cgcttgtact    9600
gggtctctct cggtagacca gatctgagcc tgggagctct ctggctatct agggaaccca    9660
ctgcttaggc ctcaataaag cttgccttga gtgctctaag tagtgtgtgc ccatctgttg    9720
tgtgactctg gtaactagag atccctcaga cccctttgtgg tagtgtggaa aatctctagc    9780
a                                                                    9781
```

<210> SEQ ID NO 2
<211> LENGTH: 842
<212> TYPE: PRT
<213> ORGANISM: Artificial Sequence
<220> FEATURE:
<223> OTHER INFORMATION: Description of Artificial Sequence: SF162

<400> SEQUENCE: 2

```
Met Asp Ala Met Lys Arg Gly Leu Cys Cys Val Leu Leu Leu Cys Gly
  1               5                  10                  15

Ala Val Phe Val Ser Pro Ser Ala Val Glu Lys Leu Trp Val Thr Val
             20                  25                  30

Tyr Tyr Gly Val Pro Val Trp Lys Glu Ala Thr Thr Thr Leu Phe Cys
         35                  40                  45

Ala Ser Asp Ala Lys Ala Tyr Asp Thr Glu Val His Asn Val Trp Ala
     50                  55                  60

Thr His Ala Cys Val Pro Thr Asp Pro Asn Pro Gln Glu Ile Val Leu
 65                  70                  75                  80

Glu Asn Val Thr Glu Asn Phe Asn Met Trp Lys Asn Asn Met Val Glu
                 85                  90                  95
```

```
Gln Met His Glu Asp Ile Ile Ser Leu Trp Asp Gln Ser Leu Lys Pro
            100                 105                 110

Cys Val Lys Leu Thr Pro Leu Cys Val Thr Leu His Cys Thr Asn Leu
        115                 120                 125

Lys Asn Ala Thr Asn Thr Lys Ser Ser Asn Trp Lys Glu Met Asp Arg
130                 135                 140

Gly Glu Ile Lys Asn Cys Ser Phe Lys Val Thr Thr Ser Ile Arg Asn
145                 150                 155                 160

Lys Met Gln Lys Glu Tyr Ala Leu Phe Tyr Lys Leu Asp Val Val Pro
                165                 170                 175

Ile Asp Asn Asp Asn Thr Ser Tyr Lys Leu Ile Asn Cys Asn Thr Ser
            180                 185                 190

Val Ile Thr Gln Ala Cys Pro Lys Val Ser Phe Glu Pro Ile Pro Ile
        195                 200                 205

His Tyr Cys Ala Pro Ala Gly Phe Ala Ile Leu Lys Cys Asn Asp Lys
    210                 215                 220

Lys Phe Asn Gly Ser Gly Pro Cys Thr Asn Val Ser Thr Val Gln Cys
225                 230                 235                 240

Thr His Gly Ile Arg Pro Val Val Ser Thr Gln Leu Leu Leu Asn Gly
                245                 250                 255

Ser Leu Ala Glu Glu Gly Val Val Ile Arg Ser Glu Asn Phe Thr Asp
            260                 265                 270

Asn Ala Lys Thr Ile Ile Val Gln Leu Lys Glu Ser Val Glu Ile Asn
        275                 280                 285

Cys Thr Arg Pro Asn Asn Asn Thr Arg Lys Ser Ile Thr Ile Gly Pro
    290                 295                 300

Gly Arg Ala Phe Tyr Ala Thr Gly Asp Ile Ile Gly Asp Ile Arg Gln
305                 310                 315                 320

Ala His Cys Asn Ile Ser Gly Glu Lys Trp Asn Asn Thr Leu Lys Gln
                325                 330                 335

Ile Val Thr Lys Leu Gln Ala Gln Phe Gly Asn Lys Thr Ile Val Phe
            340                 345                 350

Lys Gln Ser Ser Gly Gly Asp Pro Glu Ile Val Met His Ser Phe Asn
        355                 360                 365

Cys Gly Gly Glu Phe Phe Tyr Cys Asn Ser Thr Gln Leu Phe Asn Ser
    370                 375                 380

Thr Trp Asn Asn Thr Ile Gly Pro Asn Asn Thr Asn Gly Thr Ile Thr
385                 390                 395                 400

Leu Pro Cys Arg Ile Lys Gln Ile Ile Asn Arg Trp Gln Glu Val Gly
                405                 410                 415

Lys Ala Met Tyr Ala Pro Pro Ile Arg Gly Gln Ile Arg Cys Ser Ser
            420                 425                 430

Asn Ile Thr Gly Leu Leu Leu Thr Arg Asp Gly Gly Lys Glu Ile Ser
        435                 440                 445

Asn Thr Thr Glu Ile Phe Arg Pro Gly Gly Gly Asp Met Arg Asp Asn
    450                 455                 460

Trp Arg Ser Glu Leu Tyr Lys Tyr Lys Val Val Lys Ile Glu Pro Leu
465                 470                 475                 480

Gly Val Ala Pro Thr Lys Ala Lys Arg Val Val Gln Arg Glu Lys
                485                 490                 495

Arg Ala Val Thr Leu Gly Ala Met Phe Leu Gly Phe Leu Gly Ala Ala
            500                 505                 510

Gly Ser Thr Met Gly Ala Arg Ser Leu Thr Leu Thr Val Gln Ala Arg
        515                 520                 525
```

```
Gln Leu Leu Ser Gly Ile Val Gln Gln Asn Asn Leu Leu Arg Ala
        530                 535                 540

Ile Glu Ala Gln Gln His Leu Leu Gln Leu Thr Val Trp Gly Ile Lys
545                 550                 555                 560

Gln Leu Gln Ala Arg Val Leu Ala Val Glu Arg Tyr Leu Lys Asp Gln
                565                 570                 575

Gln Leu Leu Gly Ile Trp Gly Cys Ser Gly Lys Leu Ile Cys Thr Thr
            580                 585                 590

Ala Val Pro Trp Asn Ala Ser Trp Ser Asn Lys Ser Leu Asp Gln Ile
            595                 600                 605

Trp Asn Asn Met Thr Trp Met Glu Trp Glu Arg Glu Ile Asp Asn Tyr
        610                 615                 620

Thr Asn Leu Ile Tyr Thr Leu Ile Glu Glu Ser Gln Asn Gln Gln Glu
625                 630                 635                 640

Lys Asn Glu Gln Glu Leu Leu Glu Leu Asp Lys Trp Ala Ser Leu Trp
                645                 650                 655

Asn Trp Phe Asp Ile Ser Lys Trp Leu Trp Tyr Ile Lys Ile Phe Ile
            660                 665                 670

Met Ile Val Gly Gly Leu Val Gly Leu Arg Ile Val Phe Thr Val Leu
        675                 680                 685

Ser Ile Val Asn Arg Val Arg Gln Gly Tyr Ser Pro Leu Ser Phe Gln
690                 695                 700

Thr Arg Phe Pro Ala Pro Arg Gly Pro Asp Arg Pro Glu Gly Ile Glu
705                 710                 715                 720

Glu Glu Gly Gly Glu Arg Asp Arg Asp Arg Ser Ser Pro Leu Val His
                725                 730                 735

Gly Leu Leu Ala Leu Ile Trp Asp Asp Leu Arg Ser Leu Cys Leu Phe
            740                 745                 750

Ser Tyr His Arg Leu Arg Asp Leu Ile Leu Ile Ala Ala Arg Ile Val
        755                 760                 765

Glu Leu Leu Gly Arg Arg Gly Trp Glu Ala Leu Lys Tyr Trp Gly Asn
        770                 775                 780

Leu Leu Gln Tyr Trp Ile Gln Glu Leu Lys Asn Ser Ala Val Ser Leu
785                 790                 795                 800

Phe Asp Ala Ile Ala Ile Ala Val Ala Glu Gly Thr Asp Arg Ile Ile
                805                 810                 815

Glu Val Ala Gln Arg Ile Gly Arg Ala Phe Leu His Ile Pro Arg Arg
            820                 825                 830

Ile Arg Gln Gly Phe Glu Arg Ala Leu Leu
        835                 840

<210> SEQ ID NO 3
<211> LENGTH: 867
<212> TYPE: PRT
<213> ORGANISM: Artificial Sequence
<220> FEATURE:
<223> OTHER INFORMATION: Description of Artificial Sequence: TV1.8_2

<400> SEQUENCE: 3

Met Arg Val Met Gly Thr Gln Lys Asn Cys Gln Gln Trp Trp Ile Trp
1               5                   10                  15

Gly Ile Leu Gly Phe Trp Met Leu Met Ile Cys Asn Thr Glu Asp Leu
                20                  25                  30

Trp Val Thr Val Tyr Tyr Gly Val Pro Val Trp Arg Asp Ala Lys Thr
            35                  40                  45
```

```
Thr Leu Phe Cys Ala Ser Asp Ala Lys Ala Tyr Glu Thr Glu Val His
 50                  55                  60

Asn Val Trp Ala Thr His Ala Cys Val Pro Thr Asp Pro Asn Pro Gln
 65                  70                  75                  80

Glu Ile Val Leu Gly Asn Val Thr Glu Asn Phe Asn Met Trp Lys Asn
                 85                  90                  95

Asp Met Ala Asp Gln Met His Glu Asp Val Ile Ser Leu Trp Asp Gln
            100                 105                 110

Ser Leu Lys Pro Cys Val Lys Leu Thr Pro Leu Cys Val Thr Leu Asn
        115                 120                 125

Cys Thr Asp Thr Asn Val Thr Gly Asn Arg Thr Val Thr Gly Asn Ser
    130                 135                 140

Thr Asn Asn Thr Asn Gly Thr Gly Ile Tyr Asn Ile Glu Glu Met Lys
145                 150                 155                 160

Asn Cys Ser Phe Asn Ala Thr Thr Glu Leu Arg Asp Lys Lys His Lys
                165                 170                 175

Glu Tyr Ala Leu Phe Tyr Arg Leu Asp Ile Val Pro Leu Asn Glu Asn
            180                 185                 190

Ser Asp Asn Phe Thr Tyr Arg Leu Ile Asn Cys Asn Thr Ser Thr Ile
        195                 200                 205

Thr Gln Ala Cys Pro Lys Val Ser Phe Asp Pro Ile Pro Ile His Tyr
    210                 215                 220

Cys Ala Pro Ala Gly Tyr Ala Ile Leu Lys Cys Asn Asn Lys Thr Phe
225                 230                 235                 240

Asn Gly Thr Gly Pro Cys Tyr Asn Val Ser Thr Val Gln Cys Thr His
                245                 250                 255

Gly Ile Lys Pro Val Val Ser Thr Gln Leu Leu Leu Asn Gly Ser Leu
            260                 265                 270

Ala Glu Glu Gly Ile Ile Ile Arg Ser Glu Asn Leu Thr Glu Asn Thr
        275                 280                 285

Lys Thr Ile Ile Val His Leu Asn Glu Ser Val Glu Ile Asn Cys Thr
    290                 295                 300

Arg Pro Asn Asn Asn Thr Arg Lys Ser Val Arg Ile Gly Pro Gly Gln
305                 310                 315                 320

Ala Phe Tyr Ala Thr Asn Asp Val Ile Gly Asn Ile Arg Gln Ala His
                325                 330                 335

Cys Asn Ile Ser Thr Asp Arg Trp Asn Lys Thr Leu Gln Gln Val Met
            340                 345                 350

Lys Lys Leu Gly Glu His Phe Pro Asn Lys Thr Ile Gln Phe Lys Pro
        355                 360                 365

His Ala Gly Gly Asp Leu Glu Ile Thr Met His Ser Phe Asn Cys Arg
    370                 375                 380

Gly Glu Phe Phe Tyr Cys Asn Thr Ser Asn Leu Phe Asn Ser Thr Tyr
385                 390                 395                 400

His Ser Asn Asn Gly Thr Tyr Lys Tyr Asn Gly Asn Ser Ser Ser Pro
                405                 410                 415

Ile Thr Leu Gln Cys Lys Ile Lys Gln Ile Val Arg Met Trp Gln Gly
            420                 425                 430

Val Gly Gln Ala Thr Tyr Ala Pro Pro Ile Ala Gly Asn Ile Thr Cys
        435                 440                 445

Arg Ser Asn Ile Thr Gly Ile Leu Leu Thr Arg Asp Gly Gly Phe Asn
    450                 455                 460

Thr Thr Asn Asn Thr Glu Thr Phe Arg Pro Gly Gly Gly Asp Met Arg
465                 470                 475                 480
```

Asp Asn Trp Arg Ser Glu Leu Tyr Lys Tyr Lys Val Glu Ile Lys
            485                 490                 495

Pro Leu Gly Ile Ala Pro Thr Lys Ala Lys Arg Arg Val Val Gln Arg
        500                 505                 510

Glu Lys Arg Ala Val Gly Ile Gly Ala Val Phe Leu Gly Phe Leu Gly
    515                 520                 525

Ala Ala Gly Ser Thr Met Gly Ala Ala Ser Ile Thr Leu Thr Val Gln
530                 535                 540

Ala Arg Gln Leu Leu Ser Gly Ile Val Gln Gln Gln Ser Asn Leu Leu
545                 550                 555                 560

Lys Ala Ile Glu Ala Gln Gln His Met Leu Gln Leu Thr Val Trp Gly
                565                 570                 575

Ile Lys Gln Leu Gln Ala Arg Val Leu Ala Ile Glu Arg Tyr Leu Lys
            580                 585                 590

Asp Gln Gln Leu Leu Gly Ile Trp Gly Cys Ser Gly Arg Leu Ile Cys
        595                 600                 605

Thr Thr Ala Val Pro Trp Asn Ser Ser Trp Ser Asn Lys Ser Glu Lys
    610                 615                 620

Asp Ile Trp Asp Asn Met Thr Trp Met Gln Trp Asp Arg Glu Ile Ser
625                 630                 635                 640

Asn Tyr Thr Gly Leu Ile Tyr Asn Leu Leu Glu Asp Ser Gln Asn Gln
                645                 650                 655

Gln Glu Lys Asn Glu Lys Asp Leu Leu Glu Leu Asp Lys Trp Asn Asn
            660                 665                 670

Leu Trp Asn Trp Phe Asp Ile Ser Asn Trp Pro Trp Tyr Ile Lys Ile
        675                 680                 685

Phe Ile Met Ile Val Gly Gly Leu Ile Gly Leu Arg Ile Ile Phe Ala
    690                 695                 700

Val Leu Ser Ile Val Asn Arg Val Arg Gln Gly Tyr Ser Pro Leu Ser
705                 710                 715                 720

Phe Gln Thr Leu Thr Pro Ser Pro Arg Gly Leu Asp Arg Leu Gly Gly
                725                 730                 735

Ile Glu Glu Glu Gly Gly Glu Gln Asp Arg Asp Arg Ser Ile Arg Leu
            740                 745                 750

Val Ser Gly Phe Leu Ser Leu Ala Trp Asp Asp Leu Arg Asn Leu Cys
        755                 760                 765

Leu Phe Ser Tyr His Arg Leu Arg Asp Phe Ile Leu Ile Ala Val Arg
    770                 775                 780

Ala Val Glu Leu Leu Gly His Ser Ser Leu Arg Gly Leu Gln Arg Gly
785                 790                 795                 800

Trp Glu Ile Leu Lys Tyr Leu Gly Ser Leu Val Gln Tyr Trp Gly Leu
                805                 810                 815

Glu Leu Lys Lys Ser Ala Ile Ser Leu Leu Asp Thr Ile Ala Ile Thr
            820                 825                 830

Val Ala Glu Gly Thr Asp Arg Ile Ile Glu Leu Val Gln Arg Ile Cys
        835                 840                 845

Arg Ala Ile Leu Asn Ile Pro Arg Arg Ile Arg Gln Gly Phe Glu Ala
    850                 855                 860

Ala Leu Leu
865

<210> SEQ ID NO 4
<211> LENGTH: 869
<212> TYPE: PRT

<213> ORGANISM: Artificial Sequence
<220> FEATURE:
<223> OTHER INFORMATION: Description of Artificial Sequence: TV1.8_5

<400> SEQUENCE: 4

```
Met Arg Val Met Gly Thr Gln Lys Asn Cys Gln Gln Trp Trp Ile Trp
 1               5                  10                  15

Gly Ile Leu Gly Phe Trp Met Leu Met Ile Cys Asn Thr Glu Asp Leu
             20                  25                  30

Trp Val Thr Val Tyr Tyr Gly Val Pro Val Trp Arg Glu Ala Lys Thr
         35                  40                  45

Thr Leu Phe Cys Ala Ser Asp Ala Lys Ala Tyr Glu Thr Glu Val His
     50                  55                  60

Asn Val Trp Ala Thr His Ala Cys Val Pro Thr Asp Pro Asn Pro Gln
 65                  70                  75                  80

Glu Ile Val Leu Gly Asn Val Thr Glu Asn Phe Asn Met Trp Lys Asn
                 85                  90                  95

Asn Met Ala Asp Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Thr Asp Thr Asn Val Thr Gly Asn Arg Thr Val Thr Gly Asn Thr
    130                 135                 140

Asn Asp Thr Asn Ile Ala Asn Ala Thr Tyr Lys Tyr Glu Glu Met Lys
145                 150                 155                 160

Asn Cys Ser Phe Asn Ala Thr Thr Glu Leu Arg Asp Lys Lys His Lys
                165                 170                 175

Glu Tyr Ala Leu Phe Tyr Lys Leu Asp Ile Val Pro Leu Asn Glu Asn
            180                 185                 190

Ser Asn Asn Phe Thr Tyr Arg Leu Ile Asn Cys Asn Thr Ser Thr Ile
        195                 200                 205

Thr Gln Ala Cys Pro Lys Val Ser Phe Asp Pro Ile Pro Ile His Tyr
    210                 215                 220

Cys Ala Pro Ala Asp Tyr Ala Ile Leu Lys Cys Asn Asn Lys Thr Phe
225                 230                 235                 240

Asn Gly Thr Gly Pro Cys Tyr Asn Val Ser Thr Val Gln Cys Thr His
                245                 250                 255

Gly Ile Lys Pro Val Val Ser Thr Gln Leu Leu Asn Gly Ser Leu
            260                 265                 270

Ala Glu Glu Gly Ile Ile Ile Arg Ser Glu Asn Leu Thr Glu Asn Thr
        275                 280                 285

Lys Thr Ile Ile Val His Leu Asn Glu Ser Val Glu Ile Asn Cys Thr
    290                 295                 300

Arg Pro Asn Asn Asn Thr Arg Lys Ser Val Arg Ile Gly Pro Gly Gln
305                 310                 315                 320

Ala Phe Tyr Ala Thr Asn Asp Val Ile Gly Asn Ile Arg Gln Ala His
                325                 330                 335

Cys Asn Ile Ser Thr Asp Arg Trp Asn Lys Thr Leu Gln Gln Val Met
            340                 345                 350

Lys Lys Leu Gly Glu His Phe Pro Asn Lys Thr Ile Lys Phe Glu Pro
        355                 360                 365

His Ala Gly Gly Asp Leu Glu Ile Thr Met His Ser Phe Asn Cys Arg
    370                 375                 380

Gly Glu Phe Phe Tyr Cys Asn Thr Ser Asn Leu Phe Asn Ser Thr Tyr
385                 390                 395                 400
```

```
Tyr Pro Lys Asn Gly Thr Tyr Lys Tyr Asn Gly Asn Ser Ser Leu Pro
            405                 410                 415
Ile Thr Leu Gln Cys Lys Ile Lys Gln Ile Val Arg Met Trp Gln Gly
        420                 425                 430
Val Gly Gln Ala Met Tyr Ala Pro Pro Ile Ala Gly Asn Ile Thr Cys
        435                 440                 445
Arg Ser Asn Ile Thr Gly Ile Leu Leu Thr Arg Asp Gly Gly Phe Asn
    450                 455                 460
Asn Thr Asn Asn Asp Thr Glu Glu Thr Phe Arg Pro Gly Gly Gly Asp
465                 470                 475                 480
Met Arg Asp Asn Trp Arg Ser Glu Leu Tyr Lys Tyr Lys Val Val Glu
                485                 490                 495
Ile Lys Pro Leu Gly Ile Ala Pro Thr Lys Ala Lys Arg Arg Val Val
            500                 505                 510
Gln Arg Lys Lys Arg Ala Val Gly Ile Gly Ala Val Phe Leu Gly Phe
        515                 520                 525
Leu Gly Ala Ala Gly Ser Thr Met Gly Ala Ala Ser Ile Thr Leu Thr
    530                 535                 540
Val Gln Ala Arg Gln Leu Leu Ser Gly Ile Val Gln Gln Gln Ser Asn
545                 550                 555                 560
Leu Leu Lys Ala Ile Glu Ala Gln Gln His Met Leu Gln Leu Thr Val
                565                 570                 575
Trp Gly Ile Lys Gln Leu Gln Ala Arg Val Leu Ala Ile Glu Arg Tyr
            580                 585                 590
Leu Lys Asp Gln Gln Leu Leu Gly Ile Trp Gly Cys Ser Gly Arg Leu
        595                 600                 605
Ile Cys Thr Thr Ala Val Pro Trp Asn Ser Ser Trp Ser Asn Lys Ser
    610                 615                 620
Glu Ala Asp Ile Trp Asp Asn Met Thr Trp Met Gln Trp Asp Arg Glu
625                 630                 635                 640
Ile Asn Asn Tyr Thr Glu Thr Ile Phe Arg Leu Leu Glu Asp Ser Gln
                645                 650                 655
Asn Gln Gln Glu Lys Asn Glu Lys Asp Leu Leu Glu Leu Asp Lys Trp
            660                 665                 670
Asn Asn Leu Trp Asn Trp Phe Asp Ile Ser Asn Trp Leu Trp Tyr Ile
        675                 680                 685
Lys Ile Phe Ile Met Ile Val Gly Gly Leu Ile Gly Leu Arg Ile Ile
    690                 695                 700
Phe Ala Val Leu Ser Ile Val Asn Arg Val Arg Gln Gly Tyr Ser Pro
705                 710                 715                 720
Leu Ser Phe Gln Thr Leu Thr Pro Ser Pro Arg Gly Leu Asp Arg Leu
                725                 730                 735
Gly Gly Ile Glu Glu Glu Gly Gly Glu Gln Asp Arg Asp Arg Ser Ile
            740                 745                 750
Arg Leu Val Ser Gly Phe Leu Ser Leu Ala Trp Asp Asp Leu Arg Ser
        755                 760                 765
Leu Cys Leu Phe Ser Tyr His Arg Leu Arg Asp Phe Ile Leu Ile Ala
    770                 775                 780
Val Arg Ala Val Glu Leu Leu Gly His Ser Ser Leu Arg Gly Leu Gln
785                 790                 795                 800
Arg Gly Trp Glu Ile Leu Lys Tyr Leu Gly Ser Leu Val Gln Tyr Trp
                805                 810                 815
Gly Leu Glu Leu Lys Lys Ser Ala Ile Ser Pro Leu Asp Thr Ile Ala
```

```
                        820                 825                 830
Ile Ala Val Ala Glu Gly Thr Asp Arg Ile Ile Glu Leu Val Gln Arg
            835                 840                 845

Ile Cys Arg Ala Ile Leu Asn Ile Pro Arg Arg Ile Arg Gln Gly Phe
            850                 855                 860

Glu Ala Ala Leu Leu
865

<210> SEQ ID NO 5
<211> LENGTH: 854
<212> TYPE: PRT
<213> ORGANISM: Artificial Sequence
<220> FEATURE:
<223> OTHER INFORMATION: Description of Artificial Sequence: TV2.12-5/1

<400> SEQUENCE: 5

Met Arg Ala Arg Gly Ile Leu Lys Asn Tyr Arg His Trp Trp Ile Trp
 1               5                  10                  15

Gly Ile Leu Gly Phe Trp Met Leu Met Cys Asn Val Lys Gly Leu
            20                  25                  30

Trp Val Thr Val Tyr Tyr Gly Val Pro Val Gly Arg Glu Ala Lys Thr
            35                  40                  45

Thr Leu Phe Cys Ala Ser Asp Ala Lys Ala Tyr Glu Lys Glu Val His
        50                  55                  60

Asn Val Trp Ala Thr His Ala Cys Val Pro Thr Asp Pro Asn Pro Gln
 65                  70                  75                  80

Glu Val Ile Leu Gly Asn Val Thr Glu Asn Phe Asn Met Trp Lys Asn
                85                  90                  95

Asp Met Val Asp Gln Met Gln Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Thr Asn Ala Thr Val Asn Tyr Asn Asn Thr Ser Lys Asp Met Lys
    130                 135                 140

Asn Cys Ser Phe Tyr Val Thr Thr Glu Leu Arg Asp Lys Lys Lys Lys
145                 150                 155                 160

Glu Asn Ala Leu Phe Tyr Arg Leu Asp Ile Val Pro Leu Asn Asn Arg
                165                 170                 175

Lys Asn Gly Asn Ile Asn Asn Tyr Arg Leu Ile Asn Cys Asn Thr Ser
            180                 185                 190

Ala Ile Thr Gln Ala Cys Pro Lys Val Ser Phe Asp Pro Ile Pro Ile
        195                 200                 205

His Tyr Cys Ala Pro Ala Gly Tyr Ala Pro Leu Lys Cys Asn Asn Lys
    210                 215                 220

Lys Phe Asn Gly Ile Gly Pro Cys Asp Asn Val Ser Thr Val Gln Cys
225                 230                 235                 240

Thr His Gly Ile Lys Pro Val Val Ser Thr Gln Leu Leu Leu Asn Gly
                245                 250                 255

Ser Leu Ala Glu Glu Glu Ile Ile Ile Arg Ser Glu Asn Leu Thr Asn
            260                 265                 270

Asn Val Lys Thr Ile Ile Val His Leu Asn Glu Ser Ile Glu Ile Lys
        275                 280                 285

Cys Thr Arg Pro Gly Asn Asn Thr Arg Lys Ser Val Arg Ile Gly Pro
    290                 295                 300

Gly Gln Ala Phe Tyr Ala Thr Gly Asp Ile Ile Gly Asp Ile Arg Gln
305                 310                 315                 320
```

```
Ala His Cys Asn Ile Ser Lys Asn Glu Trp Asn Thr Thr Leu Gln Arg
            325                 330                 335

Val Ser Gln Lys Leu Gln Glu Leu Phe Pro Asn Ser Thr Gly Ile Lys
            340                 345                 350

Phe Ala Pro His Ser Gly Gly Asp Leu Glu Ile Thr Thr His Ser Phe
            355                 360                 365

Asn Cys Gly Gly Glu Phe Phe Tyr Cys Asn Thr Thr Asp Leu Phe Asn
        370                 375                 380

Ser Thr Tyr Ser Asn Gly Thr Cys Thr Asn Gly Thr Cys Met Ser Asn
385                 390                 395                 400

Asn Thr Glu Arg Ile Thr Leu Gln Cys Arg Ile Lys Gln Ile Ile Asn
            405                 410                 415

Met Trp Gln Glu Val Gly Arg Ala Met Tyr Ala Pro Pro Ile Ala Gly
            420                 425                 430

Asn Ile Thr Cys Arg Ser Asn Ile Thr Gly Leu Leu Leu Thr Arg Asp
            435                 440                 445

Gly Gly Asp Asn Asn Thr Glu Thr Glu Thr Phe Arg Pro Gly Gly Gly
        450                 455                 460

Asp Met Arg Asp Asn Trp Arg Ser Glu Leu Tyr Lys Tyr Lys Val Val
465                 470                 475                 480

Glu Ile Lys Pro Leu Gly Val Ala Pro Thr Ala Ala Lys Arg Arg Val
            485                 490                 495

Val Glu Arg Glu Lys Arg Ala Val Gly Ile Gly Ala Val Phe Leu Gly
            500                 505                 510

Phe Leu Gly Ala Ala Gly Ser Thr Met Gly Ala Ala Ser Ile Thr Leu
            515                 520                 525

Thr Val Gln Ala Arg Gln Leu Leu Ser Gly Ile Val Gln Gln Gln Ser
            530                 535                 540

Asn Leu Leu Arg Ala Ile Glu Ala Gln Gln His Met Leu Gln Leu Thr
545                 550                 555                 560

Val Trp Gly Ile Lys Gln Leu Gln Ala Arg Val Leu Ala Ile Glu Arg
            565                 570                 575

Tyr Leu Gln Asp Gln Gln Leu Leu Gly Leu Trp Gly Cys Ser Gly Lys
            580                 585                 590

Leu Ile Cys Thr Thr Asn Val Leu Trp Asn Ser Ser Trp Ser Asn Lys
            595                 600                 605

Thr Gln Ser Asp Ile Trp Asp Asn Met Thr Trp Met Gln Trp Asp Arg
            610                 615                 620

Glu Ile Ser Asn Tyr Thr Asn Thr Ile Tyr Arg Leu Leu Glu Asp Ser
625                 630                 635                 640

Gln Ser Gln Gln Glu Arg Asn Glu Lys Asp Leu Leu Ala Leu Asp Arg
            645                 650                 655

Trp Asn Asn Leu Trp Asn Trp Phe Ser Ile Thr Asn Trp Leu Trp Tyr
            660                 665                 670

Ile Lys Ile Phe Ile Met Ile Val Gly Gly Leu Ile Gly Leu Arg Ile
            675                 680                 685

Ile Phe Ala Val Leu Ser Leu Val Asn Arg Val Arg Gln Gly Tyr Ser
            690                 695                 700

Pro Leu Ser Leu Gln Thr Leu Ile Pro Asn Pro Arg Gly Pro Asp Arg
705                 710                 715                 720

Leu Gly Gly Ile Glu Glu Glu Gly Gly Glu Gln Asp Ser Ser Arg Ser
            725                 730                 735

Ile Arg Leu Val Ser Gly Phe Leu Thr Leu Ala Trp Asp Asp Leu Arg
```

-continued

```
                740                 745                 750
Ser Leu Cys Leu Phe Cys Tyr His Arg Leu Arg Asp Phe Ile Leu Ile
            755                 760                 765

Val Val Arg Ala Val Glu Leu Leu Gly His Ser Ser Leu Arg Gly Leu
        770                 775                 780

Gln Arg Gly Trp Gly Thr Leu Lys Tyr Leu Gly Ser Leu Val Gln Tyr
785                 790                 795                 800

Trp Gly Leu Glu Leu Lys Lys Ser Ala Ile Asn Leu Leu Asp Thr Ile
            805                 810                 815

Ala Ile Ala Val Ala Glu Gly Thr Asp Arg Ile Leu Glu Phe Ile Gln
        820                 825                 830

Asn Leu Cys Arg Gly Ile Arg Asn Val Pro Arg Arg Ile Arg Gln Gly
            835                 840                 845

Phe Glu Ala Ala Leu Gln
    850

<210> SEQ ID NO 6
<211> LENGTH: 860
<212> TYPE: PRT
<213> ORGANISM: Artificial Sequence
<220> FEATURE:
<223> OTHER INFORMATION: Description of Artificial Sequence: consensus
      sequence

<400> SEQUENCE: 6

Met Arg Val Met Gly Thr Gln Lys Asn Cys Gln Gln Trp Trp Ile Trp
 1               5                  10                  15

Gly Ile Leu Gly Phe Trp Met Leu Met Ile Cys Asn Val Glu Asp Leu
            20                  25                  30

Trp Val Thr Val Tyr Tyr Gly Val Pro Val Trp Arg Glu Ala Lys Thr
        35                  40                  45

Thr Leu Phe Cys Ala Ser Asp Ala Lys Ala Tyr Glu Thr Glu Val His
    50                  55                  60

Asn Val Trp Ala Thr His Ala Cys Val Pro Thr Asp Pro Asn Pro Gln
65                  70                  75                  80

Glu Ile Val Leu Gly Asn Val Thr Glu Asn Phe Asn Met Trp Lys Asn
                85                  90                  95

Asn Met Val Asp Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Thr Asn Thr Asn Val Thr Gly Asn Arg Thr Val Thr Gly Asn Ser
    130                 135                 140

Asn Ser Asn Ala Ala Tyr Glu Glu Met Lys Asn Cys Ser Phe Asn Val
145                 150                 155                 160

Thr Thr Glu Leu Arg Asp Lys Lys His Lys Glu Tyr Ala Leu Phe Tyr
                165                 170                 175

Lys Leu Asp Ile Val Pro Leu Asn Asn Glu Asn Ser Asn Asn Phe Thr
            180                 185                 190

Tyr Arg Leu Ile Asn Cys Asn Thr Ser Thr Ile Thr Gln Ala Cys Pro
        195                 200                 205

Lys Val Ser Phe Asp Pro Ile Pro Ile His Tyr Cys Ala Pro Ala Gly
    210                 215                 220

Tyr Ala Ile Leu Lys Cys Asn Asn Lys Thr Phe Asn Gly Thr Gly Pro
225                 230                 235                 240

Cys Tyr Asn Val Ser Thr Val Gln Cys Thr His Gly Ile Lys Pro Val
```

```
                    245                 250                 255
Val Ser Thr Gln Leu Leu Asn Gly Ser Leu Ala Glu Glu Gly Ile
                260                 265                 270

Ile Ile Arg Ser Glu Asn Leu Thr Glu Asn Thr Lys Thr Ile Ile Val
                275                 280                 285

His Leu Asn Glu Ser Val Glu Ile Asn Cys Thr Arg Pro Asn Asn Asn
            290                 295                 300

Thr Arg Lys Ser Val Arg Ile Gly Pro Gly Gln Ala Phe Tyr Ala Thr
305                 310                 315                 320

Asn Asp Ile Ile Gly Asn Ile Arg Gln Ala His Cys Asn Ile Ser Thr
                325                 330                 335

Asp Arg Trp Asn Lys Thr Leu Gln Gln Val Met Lys Lys Leu Gln Glu
            340                 345                 350

His Phe Pro Asn Lys Thr Ile Lys Phe Lys Pro His Ala Gly Gly Asp
            355                 360                 365

Leu Glu Ile Thr Met His Ser Phe Asn Cys Arg Gly Glu Phe Phe Tyr
        370                 375                 380

Cys Asn Thr Ser Asn Leu Phe Asn Ser Thr Tyr His Asn Asn Gly Thr
385                 390                 395                 400

Tyr Lys Tyr Asn Gly Asn Ser Ser Pro Ile Thr Leu Gln Cys Lys Ile
                405                 410                 415

Lys Gln Ile Ile Arg Met Trp Gln Gly Val Gly Gln Ala Met Tyr Ala
            420                 425                 430

Pro Pro Ile Ala Gly Asn Ile Thr Cys Arg Ser Asn Ile Thr Gly Ile
            435                 440                 445

Leu Leu Thr Arg Asp Gly Gly Phe Asn Asn Thr Asn Thr Thr Glu Thr
        450                 455                 460

Phe Arg Pro Gly Gly Gly Asp Met Arg Asp Asn Trp Arg Ser Glu Leu
465                 470                 475                 480

Tyr Lys Tyr Lys Val Val Glu Ile Lys Pro Leu Gly Ile Ala Pro Thr
                485                 490                 495

Lys Ala Lys Arg Arg Val Val Gln Arg Glu Lys Arg Ala Val Gly Ile
            500                 505                 510

Gly Ala Val Phe Leu Gly Phe Leu Gly Ala Ala Gly Ser Thr Met Gly
            515                 520                 525

Ala Ala Ser Ile Thr Leu Thr Val Gln Ala Arg Gln Leu Leu Ser Gly
        530                 535                 540

Ile Val Gln Gln Gln Ser Asn Leu Leu Lys Ala Ile Glu Ala Gln Gln
545                 550                 555                 560

His Met Leu Gln Leu Thr Val Trp Gly Ile Lys Gln Leu Gln Ala Arg
                565                 570                 575

Val Leu Ala Ile Glu Arg Tyr Leu Lys Asp Gln Gln Leu Leu Gly Ile
            580                 585                 590

Trp Gly Cys Ser Gly Lys Leu Ile Cys Thr Thr Ala Val Pro Trp Asn
            595                 600                 605

Ser Ser Trp Ser Asn Lys Ser Glu Ala Asp Ile Trp Asp Asn Met Thr
        610                 615                 620

Trp Met Gln Trp Asp Arg Glu Ile Ser Asn Tyr Thr Asn Thr Ile Tyr
625                 630                 635                 640

Arg Leu Leu Glu Asp Ser Gln Asn Gln Gln Glu Lys Asn Glu Lys Asp
                645                 650                 655

Leu Leu Glu Leu Asp Lys Trp Asn Asn Leu Trp Asn Trp Phe Asp Ile
            660                 665                 670
```

-continued

```
Ser Asn Trp Leu Trp Tyr Ile Lys Ile Phe Ile Met Ile Val Gly Gly
        675                 680                 685

Leu Ile Gly Leu Arg Ile Ile Phe Ala Val Leu Ser Ile Val Asn Arg
    690                 695                 700

Val Arg Gln Gly Tyr Ser Pro Leu Ser Phe Gln Thr Leu Thr Pro Ser
705                 710                 715                 720

Pro Arg Gly Pro Asp Arg Leu Gly Gly Ile Glu Glu Glu Gly Gly Glu
                725                 730                 735

Gln Asp Arg Asp Arg Ser Ile Arg Leu Val Ser Gly Phe Leu Ser Leu
            740                 745                 750

Ala Trp Asp Asp Leu Arg Ser Leu Cys Leu Phe Ser Tyr His Arg Leu
        755                 760                 765

Arg Asp Phe Ile Leu Ile Ala Val Arg Ala Val Glu Leu Leu Gly His
    770                 775                 780

Ser Ser Leu Arg Gly Leu Gln Arg Gly Trp Glu Ile Leu Lys Tyr Leu
785                 790                 795                 800

Gly Ser Leu Val Gln Tyr Trp Gly Leu Glu Leu Lys Lys Ser Ala Ile
                805                 810                 815

Ser Leu Leu Asp Thr Ile Ala Ile Ala Val Ala Glu Gly Thr Asp Arg
            820                 825                 830

Ile Ile Glu Leu Val Gln Arg Ile Cys Arg Ala Ile Leu Asn Ile Pro
        835                 840                 845

Arg Arg Ile Arg Gln Gly Phe Glu Ala Ala Leu Leu
    850                 855                 860

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:
      catalytic center

<400> SEQUENCE: 7

Tyr Met Asp Asp
  1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:
      primer grip region

<400> SEQUENCE: 8

Trp Met Gly Tyr
  1

<210> SEQ ID NO 9
<211> LENGTH: 3999
<212> TYPE: DNA
<213> ORGANISM: Artificial Sequence
<220> FEATURE:
<223> OTHER INFORMATION: Description of Artificial Sequence:
      GagComplPolmut.SF2

<400> SEQUENCE: 9
gtcgacgcca ccatgggcgc cgcgccagc gtgctgagcg gcggcgagct ggacaagtgg      60
gagaagatcc gcctgcgccc cggcggcaag aagaagtaca gctgaagca catcgtgtgg     120 gccagccgcg agctggagcg cttcgccgtg aaccccggcc tgctggagac cagcgagggc    180
```

```
tgccgccaga tcctgggcca gctgcagccc agcctgcaga ccggcagcga ggagctgcgc    240
agcctgtaca acaccgtggc caccctgtac tgcgtgcacc agcgcatcga cgtcaaggac    300
accaaggagg ccctggagaa gatcgaggag gagcagaaca agtccaagaa gaaggcccag    360
caggccgccg ccgccgccgg caccggcaac agcagccagg tgagccagaa ctaccccatc    420
gtgcagaacc tgcagggcca gatggtgcac caggccatca gccccgcac cctgaacgcc     480 tgggtgaagg tggtggagga aaggccttc agccccgagg tgatccccat gttcagcgcc     540
ctgagcgagg gcgccacccc ccaggacctg aacacgatgt tgaacaccgt gggcggccac    600
caggccgcca tgcagatgct gaaggagacc atcaacgagg aggccgccga gtgggaccgc    660
gtgcaccccg tgcacgccgg ccccatcgcc cccggccaga tgcgcgagcc ccgcggcagc    720
gacatcgccg gcaccaccag caccctgcag gagcagatcg gctggatgac caacaacccc    780
cccatccccg tgggcgagat ctacaagcgg tggatcatcc tgggcctgaa caagatcgtg    840
cggatgtaca gccccaccag catcctggac atccgccagg gccccaagga gcccttccgc    900
gactacgtgg accgcttcta caagaccctg cgcgctgagc aggccagcca ggacgtgaag    960
aactggatga ccgagaccct gctggtgcag aacgccaacc ccgactgcaa gaccatcctg    1020
aaggctctcg gccccgcggc caccctggag gagatgatga ccgcctgcca gggcgtgggc   1080
ggccccggcc acaaggcccg cgtgctggcc gaggcgatga ccaggtgac gaacccggcg     1140 accatcatga tgcagcgcgg caacttccgc aaccagcgga agaccgtcaa gtgcttcaac    1200
tgcggcaagg agggccacac cgccaggaac tgccgcgccc ccgcaagaa gggctgctgg    1260 cgctgcggcc gcgagggcca ccagatgaag gactgcaccg agcgccaggc caacttcctg   1320
ggcaagatct ggcccagcta caagggccgc cccggcaact tcctgcagag ccgccccgag    1380
cccaccgccc ccccgagga gagcttccgc ttcggcgagg agaagaccac cccagccag     1440 aagcaggagc ccatcgacaa ggagctgtac cccctgacca gctgcgcag cctgttcggc    1500 aacgacccca gcagccagaa agaattcaag gcccgcgtgc tggccgaggc gatgagccag    1560
gtgacgaacc cggcgaccat catgatgcag cgcggcaact tccgcaacca gcggaagacc    1620
gtcaagtgct tcaactgcgg caaggagggc cacaccgcca ggaactgccg cgcccccgc     1680 aagaagggct gctggcgctg cggccgcgaa ggacaccaaa tgaaagattg cactgagaga    1740
caggctaatt tcttccgcga ggacctggcc ttcctgcagg gcaaggcccg cgagttcagc    1800
agcgagcaga cccgcgccaa cagccccacc cgccgcgagc tgcaggtgtg gggcggcgag    1860
aacaacagcc tgagcgaggc cggcgccgac cgccagggca ccgtgagctt caacttcccc    1920
cagatcaccc tgtggcagcg ccccctggtg accatcagga tcggcggcca gctcaaggag    1980
gcgctgctcg acaccggcgc cgacgacacc gtgctggagg agatgaacct gcccggcaag    2040
tggaagccca gatgatcgg cgggatcggg ggcttcatca aggtgcggca gtacgaccag     2100
atccccgtgg agatctgcgg ccacaaggcc atcggcaccg tgctggtggg ccccaccccc    2160
gtgaacatca tcggccgcaa cctgctgacc cagatcggct gcaccctgaa cttcccccatc   2220 agccccatcg agacggtgcc cgtgaagctg aagccgggga tggacggccc caaggtcaag    2280
cagtggcccc tgaccgagga aaagatcaag gccctggtgg agatctgcac cgagatggag    2340
aaggagggca gatcagcaa gatcggcccc gagaacccct acaacacccc cgtgttcgcc     2400
atcaagaaga aggacagcac caagtggcgc aagctggtgg acttccgcga gctgaacaag    2460
cgcacccagg acttctggga ggtgcagctg ggcatcccc accccgcggg cctgaagaag    2520
aagaagagcg tgaccgtgct ggacgtgggc gacgcctact tcagcgtgcc cctggacaag    2580
```

```
gacttccgca agtacaccgc cttcaccatc cccagcatca acaacgagac ccccggcatc    2640
cgctaccagt acaacgtgct gccccagggc tggaagggca gccccgccat cttccagagc    2700
agcatgacca agatcctgga gcccttccgc aagcagaacc ccgacatcgt gatctaccag    2760 gccccctgt acgtgggcag cgacctggag atcggccagc accgcaccaa gatcgaggag    2820
ctgcgccagc acctgctgcg ctggggcttc accacccccg acaagaagca ccagaaggag    2880 cccccttcc tgcccatcga gctgcacccc gacaagtgga ccgtgcagcc catcatgctg    2940
cccgagaagg acagctggac cgtgaacgac atccagaagc tggtgggcaa gctgaactgg    3000
gccagccaga tctacgccgg catcaaggtg aagcagctgt gcaagctgct gcgcggcacc    3060
aaggccctga ccgaggtgat ccccctgacc gaggaggccg agctggagct ggccgagaac    3120
cgcgagatcc tgaaggagcc cgtgcacgag gtgtactacg accccagcaa ggacctggtg    3180
gccgagatcc agaagcaggg ccagggccag tggacctacc agatctacca ggagcccttc    3240
aagaacctga agaccggcaa gtacgcccgc atgcgcggcg cccacaccaa cgacgtgaag    3300
cagctgaccg aggccgtgca gaaggtgagc accgagagca tcgtgatctg gggcaagatc    3360
cccaagttca gctgcccat ccagaaggag acctgggagg cctggtggat ggagtactgg    3420
caggccacct ggatccccga gtgggagttc gtgaacaccc cccccctggt gaagctgtgg    3480
taccagctgg agaaggagcc catcgtgggc gccgagacct tctacgtgga cggcgccgcc    3540
aaccgcgaga ccaagctggg caaggccggc tacgtgaccg accggggccg gcagaaggtg    3600
gtgagcatcg ccgacaccac caaccagaag accgagctgc aggccatcca cctggccctg    3660
caggacagcg gcctggaggt gaacatcgtg accgacagcc agtacgccct gggcatcatc    3720
caggcccagc ccgacaagag cgagagcgag ctggtgagcc agatcatcga gcagctgatc    3780
aagaaggaga aggtgtacct ggcctgggtg cccgcccaca agggcatcgg cggcaacgag    3840
caggtggaca gctggtgag cgccggcatc cgcaaggtgc tgttcctgaa cggcatcgat    3900
ggcggcatcg tgatctacca gtacatggac gacctgtacg tgggcagcgg cggccctagg    3960
atcgattaaa agcttcccgg ggctagcacc ggttctaga                          3999
```

<210> SEQ ID NO 10
<211> LENGTH: 3999
<212> TYPE: DNA
<213> ORGANISM: Artificial Sequence
<220> FEATURE:
<223> OTHER INFORMATION: Description of Artificial Sequence:
      GagComplPolmutAtt.SF2

<400> SEQUENCE: 10

```
gtcgacgcca ccatgggcgc ccgcgccagc gtgctgagcg gcggcgagct ggacaagtgg     60
gagaagatcc gcctgcgccc cggcggcaag aagaagtaca agctgaagca catcgtgtgg    120
gccagccgcg agctggagcg cttcgccgtg aaccccggcc tgctggagac cagcgagggc    180
tgccgccaga tcctgggcca gctgcagccc agcctgcaga ccggcagcga ggagctgcgc    240
agcctgtaca acaccgtggc caccctgtac tgcgtgcacc agcgcatcga cgtcaaggac    300
accaaggagg ccctggagaa gatcgaggag gagcagaaca gtccaagaa gaaggcccag    360 caggccgccg ccgccgccgg caccggcaac agcagccagg tgagccagaa ctaccccatc    420
gtgcagaacc tgcagggcca gatggtgcac caggccatca gccccgcac cctgaacgcc    480 tgggtgaagg tggtggagga aaggccttc agccccgagg tgatcccat gttcagcgcc    540 ctgagcgagg gcgccacccc ccaggacctg aacacgatgt tgaacaccgt gggcggccac    600
```

```
caggccgcca tgcagatgct gaaggagacc atcaacgagg aggccgccga gtgggaccgc    660
gtgcacccg tgcacgccgg ccccatcgcc cccggccaga tgcgcgagcc ccgcggcagc    720
gacatcgccg gcaccaccag caccctgcag gagcagatcg gctggatgac caacaaccc    780
cccatccccg tgggcgagat ctacaagcgg tggatcatcc tgggcctgaa caagatcgtg    840
cggatgtaca gccccaccag catcctggac atccgccagg ccccaagga gcccttccgc    900
gactacgtgg accgcttcta caagaccctg cgcgctgagc aggccagcca ggacgtgaag    960
aactggatga ccgagaccct gctggtgcag aacgccaacc ccgactgcaa gaccatcctg   1020
aaggctctcg ccccgcggc caccctggag gagatgatga ccgcctgcca gggcgtgggc   1080
ggccccggcc acaaggcccg cgtgctggcc gaggcgatga gccaggtgac gaacccggcg   1140
accatcatga tgcagcgcgg caacttccgc aaccagcgga agaccgtcaa gtgcttcaac   1200
tgcggcaagg agggccacac cgccaggaac tgccgcgccc ccgcaagaa gggctgctgg   1260
cgctgcggcc gcgagggcca ccagatgaag gactgcaccg agcgccaggc caacttcctg   1320
ggcaagatct ggcccagcta aagggccgc cccggcaact tcctgcagag ccgccccgag   1380
cccaccgccc ccccgagga gagcttccgc ttcggcgagg agaagaccac ccccagccag   1440
aagcaggagc ccatcgacaa ggagctgtac cccctgacca gcctgcgcag cctgttcggc   1500
aacgacccca gcagccagaa agaattcaag gcccgcgtgc tggccgaggc gatgagccag   1560
gtgacgaacc cggcgaccat catgatgcag cgcggcaact ccgcaacca gcggaagacc   1620
gtcaagtgct tcaactgcgg caaggagggc cacaccgcca ggaactgccg cgcccccgc   1680
aagaagggct gctggcgctg cggccgcgaa ggacaccaaa tgaaagattg cactgagaga   1740
caggctaatt tcttccgcga ggacctggcc ttcctgcagg gcaaggcccg cgagttcagc   1800
agcgagcaga cccgcgccaa cagccccacc cgccgcgagc tgcaggtgtg gggcggcgag   1860
aacaacagcc tgagcgaggc cggcgccgac cgccagggca ccgtgagctt caacttcccc   1920
cagatcaccc tgtggcagcg ccccctggtg accatcagga tcggcggcca gctcaaggag   1980
gcgctgctcg actccggcgc cgacgacacc gtgctggagg agatgaacct gcccggcaag   2040
tggaagccca agatgatcgg cgggatcggg ggcttcatca aggtgcggca gtacgaccag   2100
atccccgtgg agatctgcgg ccacaaggcc atcggcaccg tgctggtggg ccccacccc   2160
gtgaacatca tcggccgcaa cctgctgacc cagatcggct gcaccctgaa cttccccatc   2220
agccccatcg agacggtgcc cgtgaagctg aagccgggga tggacggccc caaggtcaag   2280
cagtggcccc tgaccgagga aagatcaag gccctggtgg agatctgcac cgagatggag   2340
aaggagggca agatcagcaa gatcggcccc gagaacccct acaacacccc cgtgttcgcc   2400
atcaagaaga aggacagcac caagtggcgc aagctggtgg acttccgcga gctgaacaag   2460
cgcacccagg acttctggga ggtgcagctg ggcatccccc accccgccgg cctgaagaag   2520
aagaagagcg tgaccgtgct ggacgtgggc gacgcctact tcagcgtgcc cctggacaag   2580
gacttccgca gtacaccgc cttcaccatc cccagcatca caacgagac ccccggcatc   2640
cgctaccagt acaacgtgct gccccagggc tggaagggca ccccgccat cttccagagc   2700
agcatgacca agatcctgga gcccttccgc aagcagaacc ccgacatcgt gatctaccag   2760
gccccctgt acgtgggcag cgacctggag atcggccagc accgcaccaa gatcgaggag   2820
ctgcgccagc acctgctgcg ctggggcttc accacccccg acaagaagca ccagaaggag   2880
ccccccttcc tgcccatcga gctgcacccc gacaagtgga ccgtcagcc catcatgctg   2940
cccgagaagg acagctggac cgtgaacgac atccagaagc tggtgggcaa gctgaactgg   3000
```

-continued

```
gccagccaga tctacgccgg catcaaggtg aagcagctgt gcaagctgct gcgcggcacc    3060
aaggccctga ccgaggtgat cccctgacc gaggaggccg agctggagct ggccgagaac    3120
cgcgagatcc tgaaggagcc cgtgcacgag gtgtactacg accccagcaa ggacctggtg    3180
gccgagatcc agaagcaggg ccagggccag tggacctacc agatctacca ggagcccttc    3240
aagaacctga agaccggcaa gtacgcccgc atgcgcggcg cccacaccaa cgacgtgaag    3300
cagctgaccg aggccgtgca gaaggtgagc accgagagca tcgtgatctg ggcaagatc     3360 cccaagttca agctgcccat ccagaaggag acctgggagg cctggtggat ggagtactgg    3420
caggccacct ggatcccgga gtgggagttc gtgaacaccc ccccctggt gaagctgtgg     3480 taccagctgg agaaggagcc catcgtgggc gccgagacct tctacgtgga cggcgccgcc    3540
aaccgcgaga ccaagctggg caaggccggc tacgtgaccg accggggccg gcagaaggtg    3600
gtgagcatcg ccgacaccac caaccagaag accgagctgc aggccatcca cctggccctg    3660
caggacagcg gcctggaggt gaacatcgtg accgacagcc agtacgccct gggcatcatc    3720
caggcccagc ccgacaagag cgagagcgag ctggtgagcc agatcatcga gcagctgatc    3780
aagaaggaga aggtgtacct ggcctgggtg cccgcccaca gggcatcgg cggcaacgag     3840 caggtggaca agctggtgag cgccggcatc cgcaaggtgc tgttcctgaa cggcatcgat    3900
ggcggcatcg tgatctacca gtacatggac gacctgtacg tgggcagcgg cggccctagg    3960
atcgattaaa agcttccgg ggctagcacc ggttctaga                            3999
```

<210> SEQ ID NO 11
<211> LENGTH: 3999
<212> TYPE: DNA
<213> ORGANISM: Artificial Sequence
<220> FEATURE:
<223> OTHER INFORMATION: Description of Artificial Sequence:
      GagComplPolmutIna.SF2

<400> SEQUENCE: 11

```
gtcgacgcca ccatgggcgc ccgcgccagc gtgctgagcg gcggcgagct ggacaagtgg     60
gagaagatcc gcctgcgccc cggcggcaag aagaagtaca agctgaagca catcgtgtgg    120
gccagccgcg agctggagcg cttcgccgtg aaccccggcc tgctggagac cagcgagggc    180
tgccgccaga tcctgggcca gctgcagccc agcctgcaga ccggcagcga ggagctgcgc    240
agcctgtaca cccgtggc caccctgtac tgcgtgcacc agcgcatcga cgtcaaggac     300
accaaggagg ccctggagaa gatcgaggag gagcagaaca gtccaagaa gaaggcccag    360 caggccgccg ccgccgccgg caccggcaac agcagccagg tgagccagaa ctaccccatc    420
gtgcagaacc tgcagggcca gatggtgcac caggccatca gccccgcac cctgaacgcc    480 tgggtgaagg tggtggagga aaggccttc agccccgagg tgatccccat gttcagcgcc    540
ctgagcgagg gcgccacccc ccaggacctg aacacgatgt gaacaccgt gggcggccac    600 caggccgcca tgcagatgct gaaggagacc atcaacgagg aggccgccga gtgggaccgc    660
gtgcaccccg tgcacgccgg ccccatcgcc ccggccaga tgcgcgagcc ccgcggcagc    720
gacatcgccg gcaccaccag caccctgcag gagcagatcg ctggatgac caacaacccc    780 cccatccccg tgggcgagat ctacaagcgg tggatcatcc tgggcctgaa caagatcgtg    840
cggatgtaca gccccaccag catcctggac atcgccagg cccaaggaa gcccttccgc    900 gactacgtgg accgcttcta caagaccctg cgcgctgagc aggccagcca ggacgtgaag    960
aactggatga ccgagaccct gctggtgcag aacgccaacc ccgactgcaa gaccatcctg    1020
aaggctctcg gccccgcggc caccctggag gagatgatga ccgcctgcca gggcgtgggc    1080
```

```
ggccccggcc acaaggcccg cgtgctggcc gaggcgatga gccaggtgac gaacccggcg    1140
accatcatga tgcagcgcgg caacttccgc aaccagcgga agaccgtcaa gtgcttcaac    1200
tgcggcaagg agggccacac cgccaggaac tgccgcgccc cccgcaagaa gggctgctgg    1260
cgctgcggcc gcgagggcca ccagatgaag gactgcaccg agcgccaggc caacttcctg    1320
ggcaagatct ggcccagcta caagggccgc cccggcaact tcctgcagag ccgccccgag    1380
cccaccgccc ccccgagga gagcttccgc ttcggcgagg agaagaccac ccccagccag    1440
aagcaggagc ccatcgacaa ggagctgtac cccctgacca gcctgcgcag cctgttcggc    1500
aacgacccca gcagccagaa agaattcaag gcccgcgtgc tggccgaggc gatgagccag    1560
gtgacgaacc cggcgaccat catgatgcag cgcggcaact cccgcaacca gcggaagacc    1620
gtcaagtgct tcaactgcgg caaggagggc cacaccgcca ggaactgccg cgccccccgc    1680
aagaagggct gctggcgctg cggccgcgaa ggacaccaaa tgaaagattg cactgagaga    1740
caggctaatt tcttccgcga ggacctggcc ttcctgcagg gcaaggcccg cgagttcagc    1800
agcgagcaga cccgcgccaa cagccccacc cgccgcgagc tgcaggtgtg gggcggcgag    1860
aacaacagcc tgagcgaggc cggcgccgac cgccagggca ccgtgagctt caacttcccc    1920
cagatcaccc tgtggcagcg cccccctggtg accatcagga tcggcggcca gctcaaggag    1980
gcgctgctcg ccaccggcgc cgacgacacc gtgctggagg agatgaacct gcccggcaag    2040
tggaagccca agatgatcgg cgggatcggg ggcttcatca aggtgcggca gtacgaccag    2100
atccccgtgg agatctgcgg ccacaaggcc atcggcaccg tgctggtggg ccccaccccc    2160
gtgaacatca tcggccgcaa cctgctgacc cagatcggct gcaccctgaa cttccccatc    2220
agccccatcg agacggtgcc cgtgaagctg aagccgggga tggacggccc caaggtcaag    2280
cagtggcccc tgaccgagga gaagatcaag gccctggtgg agatctgcac cgagatggag    2340
aaggagggca gatcagcaa gatcggcccc gagaacccct acaacacccc cgtgttcgcc    2400
atcaagaaga aggacagcac caagtggcgc aagctggtgg acttccgcga gctgaacaag    2460
cgcacccagg acttctggga ggtgcagctg ggcatccccc accccgccgg cctgaagaag    2520
aagaagagcg tgaccgtgct ggacgtgggc gacgcctact cagcgtgcc cctggacaag    2580
gacttccgca gtacaccgc cttcaccatc cccagcatca acaacgagac ccccggcatc    2640
cgctaccagt acaacgtgct gccccagggc tggaagggca gccccgccat cttccagagc    2700
agcatgacca agatcctgga gcccttccgc aagcagaacc ccgacatcgt gatctaccag    2760
gcccccctgt acgtgggcag cgacctggag atcggccagc accgcaccaa gatcgaggag    2820
ctgcgccagc acctgctgcg ctggggcttc accacccccg acaagaagca ccagaaggag    2880
ccccccttcc tgcccatcga gctgcacccc gacaagtgga ccgtgcagcc catcatgctg    2940
cccgagaagg acagctggac cgtgaacgac atccagaagc tggtgggcaa gctgaactgg    3000
gccagccaga tctacgccgg catcaaggtg aagcagctgt gcaagctgct gcgcggcacc    3060
aaggccctga ccgaggtgat ccccctgacc gaggaggccg agctggagct ggccgagaac    3120
cgcgagatcc tgaaggagcc cgtgcacgag gtgtactacg accccagcaa ggacctggtg    3180
gccgagatcc agaagcaggg ccagggccag tggacctacc agatctacca ggagcccttc    3240
aagaacctga gaccggcaa gtacgcccgc atgcgcggcg cccacaccaa cgacgtgaag    3300
cagctgaccg aggccgtgca gaaggtgagc accgagagca tcgtgatctg gggcaagatc    3360
cccaagttca agctgcccat ccagaaggag acctgggagg cctggtggat ggagtactgg    3420
caggccacct ggatccccga gtgggagttc gtgaacaccc ccccctggt gaagctgtgg    3480
```

| | |
|---|---:|
| taccagctgg agaaggagcc catcgtgggc gccgagacct tctacgtgga cggcgccgcc | 3540 |
| aaccgcgaga ccaagctggg caaggccggc tacgtgaccg accggggccg gcagaaggtg | 3600 |
| gtgagcatcg ccgacaccac caaccagaag accgagctgc aggccatcca cctggccctg | 3660 |
| caggacagcg gcctggaggt gaacatcgtg accgacagcc agtacgccct gggcatcatc | 3720 |
| caggcccagc ccgacaagag cgagagcgag ctggtgagcc agatcatcga gcagctgatc | 3780 |
| aagaaggaga aggtgtacct ggcctgggtg cccgcccaca gggcatcgg cggcaacgag | 3840 |
| caggtggaca gctggtgag cgccggcatc cgcaaggtgc tgttcctgaa cggcatcgat | 3900 |
| ggcggcatcg tgatctacca gtacatggac gacctgtacg tgggcagcgg cggccctagg | 3960 |
| atcgattaaa agcttcccgg ggctagcacc ggttctaga | 3999 |

<210> SEQ ID NO 12
<211> LENGTH: 5274
<212> TYPE: DNA
<213> ORGANISM: Artificial Sequence
<220> FEATURE:
<223> OTHER INFORMATION: Description of Artificial Sequence:
      gagCpolInaTatRevNef.opt_B

<400> SEQUENCE: 12

| | |
|---|---:|
| gtcgacgcca ccatgggcgc ccgcgccagc gtgctgagcg gcggcgagct ggacaagtgg | 60 |
| gagaagatcc gcctgcgccc cggcggcaag aagaagtaca agctgaagca catcgtgtgg | 120 |
| gccagccgcg agctggagcg cttcgccgtg aaccccggcc tgctggagac cagcgagggc | 180 |
| tgccgccaga tcctgggcca gctgcagccc agcctgcaga ccggcagcga ggagctgcgc | 240 |
| agcctgtaca caccgtggc caccctgtac tgcgtgcacc agcgcatcga cgtcaaggac | 300 |
| accaaggagg ccctggagaa gatcgaggag gagcagaaca gtccaagaa gaaggcccag | 360 |
| caggccgccg ccgccgccgg caccggcaac agcagccagg tgagccagaa ctaccccatc | 420 |
| gtgcagaacc tgcagggcca gatggtgcac caggccatca gcccccgcac cctgaacgcc | 480 |
| tgggtgaagg tggtggagga gaaggccttc agccccgagg tgatccccat gttcagcgcc | 540 |
| ctgagcgagg gcgccacccc ccaggacctg aacacgatgt tgaacaccgt gggcggccac | 600 |
| caggccgcca tgcagatgct gaaggagacc atcaacgagg aggccgccga gtgggaccgc | 660 |
| gtgcaccccg tgcacgccgg ccccatcgcc ccggccagga tgcgcgagcc ccgcggcagc | 720 |
| gacatcgccg gcaccaccag caccctgcag gagcagatcg gctggatgac caacaacccc | 780 |
| cccatccccg tgggcgagat ctacaagcgg tggatcatcc tgggcctgaa caagatcgtg | 840 |
| cggatgtaca gccccaccag catcctggac atccgccagg ccccaagga gcccttccgc | 900 |
| gactacgtgg accgcttcta caagaccctg cgcgctgagc aggccagcca ggacgtgaag | 960 |
| aactggatga ccgagaccct gctggtgcag aacgccaacc ccgactgcaa gaccatcctg | 1020 |
| aaggctctcg gccccgcggc caccctggag gagatgatga ccgcctgcca gggcgtgggc | 1080 |
| ggccccggcc acaaggcccg cgtgctggcc gaggcgatga gccaggtgac gaacccggcg | 1140 |
| accatcatga tgcagcgcgg caacttccgc aaccagcgga agaccgtcaa gtgcttcaac | 1200 |
| tgcggcaagg agggccacac cgccaggaac tgccgcgccc ccgcaagaa gggctgctgg | 1260 |
| cgctgcggcc gcgagggcca ccagatgaag gactgcaccg agcgccaggc caacttcctg | 1320 |
| ggcaagatct ggcccagcta caagggccgc cccggcaact tcctgcagag ccgccccgag | 1380 |
| cccaccgccc ccccgagga gagcttccgc ttcggcgagg agaagaccac ccccagccag | 1440 |
| aagcaggagc ccatcgacaa ggagctgtac cccctgacca gcctgcgcag cctgttcggc | 1500 |

-continued

| | |
|---|---|
| aacgacccca gcagccagaa agaattcaag gcccgcgtgc tggccgaggc gatgagccag | 1560 |
| gtgacgaacc cggcgaccat catgatgcag cgcggcaact tccgcaacca gcggaagacc | 1620 |
| gtcaagtgct tcaactgcgg caaggagggc cacaccgcca ggaactgccg cgcccccgc | 1680 |
| aagaagggct gctggcgctg cggccgcgaa ggacaccaaa tgaaagattg cactgagaga | 1740 |
| caggctaatt tcttccgcga ggacctggcc ttcctgcagg gcaaggcccg cgagttcagc | 1800 |
| agcgagcaga cccgcgccaa cagccccacc cgccgcgagc tgcaggtgtg gggcggcgag | 1860 |
| aacaacagcc tgagcgaggc cggcgccgac cgccagggca ccgtgagctt caacttcccc | 1920 |
| cagatcaccc tgtggcagcg ccccctggtg accatcagga tcggcggcca gctcaaggag | 1980 |
| gcgctgctcg ccaccggcgc cgacgacacc gtgctggagg agatgaacct gcccggcaag | 2040 |
| tggaagccca agatgatcgg cgggatcggg ggcttcatca aggtgcggca gtacgaccag | 2100 |
| atccccgtgg agatctgcgg ccacaaggcc atcggcaccg tgctggtggg ccccaccccc | 2160 |
| gtgaacatca tcggccgcaa cctgctgacc cagatcggct gcaccctgaa cttccccatc | 2220 |
| agccccatcg agacggtgcc cgtgaagctg aagccgggga tggacggccc caaggtcaag | 2280 |
| cagtggcccc tgaccgagga gaagatcaag gccctggtgg agatctgcac cgagatggag | 2340 |
| aaggagggca agatcagcaa gatcggcccc gagaacccct acaacacccc cgtgttcgcc | 2400 |
| atcaagaaga aggacagcac caagtggcgc aagctggtgg acttccgcga gctgaacaag | 2460 |
| cgcacccagg acttctggga ggtgcagctg ggcatccccc accccgccgg cctgaagaag | 2520 |
| aagaagagcg tgaccgtgct ggacgtgggc gacgcctact tcagcgtgcc cctggacaag | 2580 |
| gacttccgca gtacaccgc cttcaccatc cccagcatca caacgagac ccccggcatc | 2640 |
| cgctaccagt acaacgtgct gccccagggc tggaagggca gccccgccat cttccagagc | 2700 |
| agcatgacca agatcctgga gcccttccgc aagcagaacc ccgacatcgt gatctaccag | 2760 |
| gcccccctgt acgtgggcag cgacctggag atcggccagc accgcaccaa gatcgaggag | 2820 |
| ctgcgccagc acctgctgcg ctggggcttc accaccccg acaagaagca ccagaaggag | 2880 |
| cccccttcc tgcccatcga gctgcacccc gacaagtgga ccgtgcagcc catcatgctg | 2940 |
| cccgagaagg acagctggac cgtgaacgac atccagaagc tggtgggcaa gctgaactgg | 3000 |
| gccagccaga tctacgccgg catcaaggtg aagcagctgt gcaagctgct gcgcggcacc | 3060 |
| aaggccctga ccgaggtgat cccctgacc gaggaggccg agctggagct ggccgagaac | 3120 |
| cgcgagatcc tgaaggagcc cgtgcacgag gtgtactacg accccagcaa ggacctggtg | 3180 |
| gccgagatcc agaagcaggg ccagggccag tggacctacc agatctacca ggagcccttc | 3240 |
| aagaacctga gaccggcaa gtacgcccgc atgcgcggcg cccacaccaa cgacgtgaag | 3300 |
| cagctgaccg aggccgtgca gaaggtgagc accgagagca tcgtgatctg ggcaagatc | 3360 |
| cccaagttca agctgcccat ccagaaggag acctgggagg cctggtggat ggagtactgg | 3420 |
| caggccacct ggatccccga gtgggagttc gtgaacaccc ccccctggt gaagctgtgg | 3480 |
| taccagctgg agaaggagcc catcgtgggc gccgagacct tctacgtgga cggcgccgcc | 3540 |
| aaccgcgaga ccaagctggg caaggccggc tacgtgaccg accggggccg gcagaaggtg | 3600 |
| gtgagcatcg ccgacaccac caaccagaag accgagctgc aggccatcca cctggccctg | 3660 |
| caggacagcg gcctggaggt gaacatcgtg accgacagcc agtacgccct gggcatcatc | 3720 |
| caggcccagc ccgacaagag cgagagcgag ctggtgagcc agatcatcga gcagctgatc | 3780 |
| aagaaggaga aggtgtacct ggcctgggtg cccgcccaca gggcatcgg cggcaacgag | 3840 |
| caggtggaca agctggtgag cgccggcatc cgcaaggtgc tgttcctgaa cggcatcgat | 3900 |

| | |
|---|---:|
| ggcggcatcg tgatctacca gtacatggac gacctgtacg tgggcagcgg cggccctagg | 3960 |
| gagcccgtgg acccccgcct ggagccctgg aagcaccccg gcagccagcc caagaccgcc | 4020 |
| ggcaccaact gctactgcaa gaagtgctgc ttccactgcc aggtgagctt catcaccaag | 4080 |
| ggcctgggca tcagctacgg ccgcaagaag cgccgccagc cgccgccgcg ccccccgac | 4140 |
| agcgaggtgc accaggtgag cctgcccaag cagcccgcca gccagcccca gggcgacccc | 4200 |
| accggcccca aggagagcaa gaagaaggtg gagcgcgaga ccgagaccga ccccgtgcac | 4260 |
| cccggggccg gccgcagcgg cgacagcgac gaggagctgc tgcagaccgt gcgcttcatc | 4320 |
| aagttcctgt accagagcaa ccccctgccc agccccaagg gcaccgcca ggccgacctg | 4380 |
| aaccgccgcc gccgctggcg cgagcgccag cgccagatcc agagcatcag cgcctggatc | 4440 |
| atcagcaccc acctgggccg cagcaccgag cccgtgcccc tgcagctgcc ccccgacctg | 4500 |
| cgcctgaacc tggactgcag cgaggactgc ggcaccagcg gcacccaggg cgtgggcagc | 4560 |
| ccccaggtgc tgggcgagag ccccgccgtg ctggacagcg gcaccaagga gctcgaggcc | 4620 |
| ggcaagtgga gcaagcgcat gagcggctgg agcgccgtgc gcgagcgcat gaagcgcgcc | 4680 |
| gagcccgccg agcccgccgc cgacggcgtg ggcgccgtga ccgcgacct ggagaagcac | 4740 |
| ggcgccatca ccagcagcaa caccgccgcc aacaacgccg actgcgcctg gctggaggcc | 4800 |
| caggaggacg aggacgtggg cttccccgtg cgccccagg tgccctgcg ccccatgacc | 4860 |
| tacaaggccg ccctggacct gagccacttc ctgaaggaga agggcggcct ggagggcctg | 4920 |
| atctacagcc agaagcgcca ggacatcctg gacctgtgga tccaccacac ccagggctac | 4980 |
| ttccccggct ggcagaacta cacccccggc cccggcatcc gctacccct gaccttcggc | 5040 |
| tggtgcttca gctggtgcc cgtggacccc gactacgtgg aggaggccaa cgccggcgag | 5100 |
| aacaacagcc tgctgcaccc catgagccag cacggcatgg acgaccccga aaggaggtg | 5160 |
| ctggtgtggc gcttcgacag ccgcctggcc ttccaccaca tggcccgcga gctgcacccc | 5220 |
| gagtactaca aggactgcga ttaaaagctt cccggggcta gcaccggttc taga | 5274 |

<210> SEQ ID NO 13
<211> LENGTH: 3564
<212> TYPE: DNA
<213> ORGANISM: Artificial Sequence
<220> FEATURE:
<223> OTHER INFORMATION: Description of Artificial Sequence:
      GagPolmutAtt.SF2

<400> SEQUENCE: 13

| | |
|---|---:|
| gtcgacgcca ccatgggcgc ccgcgccagc gtgctgagcg gcggcgagct ggacaagtgg | 60 |
| gagaagatcc gcctgcgccc cggcggcaag aagaagtaca agctgaagca catcgtgtgg | 120 |
| gccagccgcg agctggagcg cttcgccgtg aaccccggcc tgctggagac cagcgagggc | 180 |
| tgccgccaga tcctgggcca gctgcagccc agcctgcaga ccggcagcga ggagctgcgc | 240 |
| agcctgtaca acaccgtggc caccctgtac tgcgtgcacc agcgcatcga cgtcaaggac | 300 |
| accaaggagg ccctggagaa gatcgaggag gagcagaaca agtccaagaa gaaggcccag | 360 |
| caggccgccg ccgccgccgg caccggcaac agcagccagg tgagccagaa ctaccccatc | 420 |
| gtgcagaacc tgcagggcca gatggtgcac caggccatca gccccgcac cctgaacgcc | 480 |
| tgggtgaagg tggtggagga aggccttc agccccgagt gatccccat gttcagcgcc | 540 |
| ctgagcgagg gcgccacccc ccaggacctg aacacgatgt gaacaccgt gggcggccac | 600 |
| caggccgcca tgcagatgct gaaggagacc atcaacgagg aggccgccga gtgggaccgc | 660 |
| gtgcaccccg tgcacgccgg ccccatcgcc cccggccaga tgcgcgagcc ccgcggcagc | 720 |

```
gacatcgccg gcaccaccag caccctgcag gagcagatcg gctggatgac caacaacccc    780
cccatccccg tgggcgagat ctacaagcgg tggatcatcc tgggcctgaa caagatcgtg    840
cggatgtaca gccccaccag catcctggac atccgccagg gccccaagga gcccttccgc    900
gactacgtgg accgcttcta caagaccctg cgcgctgagc aggccagcca ggacgtgaag    960
aactggatga ccgagaccct gctggtgcag aacgccaacc ccgactgcaa gaccatcctg   1020
aaggctctcg gccccgcggc caccctggag gagatgatga ccgcctgcca gggcgtgggc   1080
ggccccggcc acaaggcccg cgtgctggcc gaggcgatga gccaggtgac gaacccggcg   1140
accatcatga tgcagcgcgg caacttccgc aaccagcgga gaccgtcaa gtgcttcaac    1200
tgcggcaagg agggccacac cgccaggaac tgccgcgccc ccgcaagaa gggctgctgg    1260
cgctgcggcc gcgaaggaca ccaaatgaaa gattgcactg agagacaggc taatttcttc   1320
cgcgaggacc tggccttcct gcagggcaag gcccgcgagt tcagcagcga gcagacccgc   1380
gccaacagcc ccacccgccg cgagctgcag gtgtggggcg gcgagaacaa cagcctgagc   1440
gaggccggcg ccgaccgcca gggcaccgtg agcttcaact cccccagat caccctgtgg   1500
cagcgccccc tggtgaccat caggatcggc ggccagctca aggaggcgct gctcgactcc   1560
ggcgccgacg acaccgtgct ggaggagatg aacctgcccg gcaagtggaa gcccaagatg   1620
atcggcggga tcgggggctt catcaaggtg cggcagtacg accagatccc cgtggagatc   1680
tgcggccaca aggccatcgg caccgtgctg gtgggccca ccccgtgaa catcatcggc   1740
cgcaacctgc tgacccagat cggctgcacc ctgaacttcc ccatcagccc catcgagacg   1800
gtgcccgtga agctgaagcc ggggatggac ggccccaagg tcaagcagtg gcccctgacc   1860
gaggagaaga tcaaggccct ggtggagatc tgcaccgaga tggagaagga gggcaagatc   1920
agcaagatcg gccccgagaa cccctacaac accccgtgt tcgccatcaa gaagaaggac   1980
agcaccaagt ggcgcaagct ggtggacttc cgcgagctga acaagcgcac ccaggacttc   2040
tgggaggtgc agctgggcat ccccccaccc gccggcctga agaagaagaa gagcgtgacc   2100
gtgctggacg tgggcgacgc ctacttcagc gtgcccctgg acaaggactt ccgcaagtac   2160
accgccttca ccatccccag catcaacaac gagacccccg gcatccgcta ccagtacaac   2220
gtgctgcccc agggctggaa gggcagcccc gccatcttcc agagcagcat gaccaagatc   2280
ctggagcccc tccgcaagca gaaccccgac atcgtgatct accaggcccc cctgtacgtg   2340
ggcagcgacc tggagatcgg ccagcaccgc accaagatcg aggagctgcg ccagcacctg   2400
ctgcgctggg gcttcaccac ccccgacaag aagcaccaga aggagccccc cttcctgccc   2460
atcgagctgc accccgacaa gtggaccgtg cagcccatca tgctgcccga aggacagc   2520
tggaccgtga acgacatcca gaagctggtg ggcaagctga actgggccag ccagatctac   2580
gccggcatca aggtgaagca gctgtgcaag ctgctgcgcg gcaccaaggc cctgaccgag   2640
gtgatccccc tgaccgagga ggccgagctg gagctggccg agaaccgcga gatcctgaag   2700
gagcccgtgc acgaggtgta ctacgacccc agcaaggacc tggtggccga gatccagaag   2760
cagggccagg ccagtggac ctaccagatc taccaggagc ccttcaagaa cctgaagacc   2820
ggcaagtacg cccgcatgcg cggcgcccac accaacgacg tgaagcagct gaccgaggcc   2880
gtgcagaagg tgagcaccga gagcatcgtg atctgggca agatcccaa gttcaagctg   2940
cccatccaga aggagacctg ggaggcctgg tggatggagt actggcaggc cacctggatc   3000
cccgagtggg agttcgtgaa cacccccccc ctggtgaagc tgtggtacca gctggagaag   3060
gagcccatcg tgggcgccga gaccttctac gtggacggcg ccgccaaccg cgagaccaag   3120
```

```
ctgggcaagg ccggctacgt gaccgaccgg ggccggcaga aggtggtgag catcgccgac    3180
accaccaacc agaagaccga gctgcaggcc atccacctgg ccctgcagga cagcggcctg    3240
gaggtgaaca tcgtgaccga cagccagtac gccctgggca tcatccaggc ccagcccgac    3300
aagagcgaga gcgagctggt gagccagatc atcgagcagc tgatcaagaa ggagaaggtg    3360
tacctggcct gggtgcccgc ccacaagggc atcggcggca acgagcaggt ggacaagctg    3420
gtgagcgccg gcatccgcaa ggtgctgttc ctgaacggca tcgatggcgg catcgtgatc    3480
taccagtaca tggacgacct gtacgtgggc agcggcggcc ctaggatcga ttaaaagctt    3540
cccggggcta gcaccggtga attc                                          3564

<210> SEQ ID NO 14
<211> LENGTH: 3564
<212> TYPE: DNA
<213> ORGANISM: Artificial Sequence
<220> FEATURE:
<223> OTHER INFORMATION: Description of Artificial Sequence:
      GagPolmutIna.SF2

<400> SEQUENCE: 14
gtcgacgcca ccatgggcgc ccgcgccagc gtgctgagcg gcggcgagct ggacaagtgg      60
gagaagatcc gcctgcgccc cggcggcaag aagaagtaca agctgaagca catcgtgtgg     120
gccagccgcg agctggagcg cttcgccgtg aaccccggcc tgctggagac cagcgagggc     180
tgccgccaga tcctgggcca gctgcagccc agcctgcaga ccggcagcga ggagctgcgc     240
agcctgtaca acaccgtggc caccctgtac tgcgtgcacc agcgcatcga cgtcaaggac     300
accaaggagg ccctggagaa gatcgaggag gagcagaaca agtccaagaa gaaggcccag     360
caggccgccg ccgccgccgg caccggcaac agcagccagg tgagccagaa ctaccccatc     420
gtgcagaacc tgcagggcca gatggtgcac caggccatca gccccgcac cctgaacgcc     480 tgggtgaagg tggtggagga aaggccttc agccccgagg tgatccccat gttcagcgcc     540
ctgagcgagg gcgccacccc ccaggacctg aacacgatgt tgaacaccgt gggcggccac     600
caggccgcca tgcagatgct gaaggagacc atcaacgagg aggccgccga gtgggaccgc     660
gtgcaccccg tgcacgccgg ccccatcgcc cccggccaga tgcgcgagcc ccgcggcagc     720
gacatcgccg gcaccaccag caccctgcag gagcagatcg gctggatgac caacaacccc     780 cccatcccc tgggcgagat ctacaagcgg tggatcatcc tgggcctgaa caagatcgtg     840
cggatgtaca gccccaccag catcctggac atcgccagg gccccaagga gcccttccgc     900
gactacgtgg accgcttcta caagaccctg cgcgctgagc aggccagcca ggacgtgaag     960
aactggatga ccgagaccct gctggtgcag aacgccaacc ccgactgcaa gaccatcctg    1020
aaggctctcg gccccgcggc cacccctggag gagatgatga ccgcctgcca gggcgtgggc    1080
ggccccggcc acaaggcccg cgtgctggcc gaggcgatga ccaggtgac gaacccggcg    1140 accatcatga tgcagcgcgg caacttccgc aaccagcgga gaccgtcaa gtgcttcaac    1200 tgcggcaagg agggccacac cgccaggaac tgccgcgccc ccgcaagaa gggctgctgg    1260 cgctgcggcc gcgaaggaca ccaaatgaaa gattgcactg agacaggc taatttcttc    1320 cgcgaggacc tggccttcct gcagggcaag gccgcgagt tcagcagcga gcagacccgc    1380
gccaacagcc ccacccgccg cgagctgcag gtgtggggcg cgagaacaa cagcctgagc    1440 gaggccggcg ccgaccgcca gggcaccgtg agcttcaact tccccagat caccctgtgg    1500 cagcgccccc tggtgaccat caggatcggc ggccagctca aggaggcgct gctcgccacc    1560
```

```
ggcgccgacg acaccgtgct ggaggagatg aacctgcccg gcaagtggaa gcccaagatg      1620
atcggcggga tcgggggctt catcaaggtg cggcagtacg accagatccc cgtggagatc      1680
tgcggccaca aggccatcgg caccgtgctg gtgggcccca cccccgtgaa catcatcggc      1740
cgcaacctgc tgacccagat cggctgcacc ctgaacttcc ccatcagccc catcgagacg      1800
gtgcccgtga agctgaagcc ggggatggac ggccccaagg tcaagcagtg gcccctgacc      1860
gaggagaaga tcaaggccct ggtggagatc tgcaccgaga tggagaagga gggcaagatc      1920
agcaagatcg cccccgagaa cccctacaac acccccgtgt cgccatcaa gaagaaggac       1980 agcaccaagt ggcgcaagct ggtggacttc cgcgagctga acaagcgcac ccaggacttc      2040
tgggaggtgc agctgggcat ccccccacccc gccggcctga agaagaagaa gagcgtgacc     2100
gtgctggacg tgggcgacgc ctacttcagc gtgcccctgg acaaggactt ccgcaagtac      2160
accgccttca ccatccccag catcaacaac gagaccccg gcatccgcta ccagtacaac       2220
gtgctgcccc agggctggaa gggcagcccc gccatcttcc agagcagcat gaccaagatc      2280
ctggagccct tccgcaagca gaaccccgac atcgtgatct accaggcccc cctgtacgtg      2340
ggcagcgacc tggagatcgg ccagcaccgc accaagatcg aggagctgcg ccagcacctg      2400
ctgcgctggg gcttcaccac ccccgacaag aagcaccaga aggagccccc cttcctgccc      2460
atcgagctgc accccgacaa gtggaccgtg cagcccatca tgctgcccga aaggacagc      2520 tggaccgtga acgacatcca gaagctggtg ggcaagctga actgggccag ccagatctac      2580
gccggcatca aggtgaagca gctgtgcaag ctgctgcgcg gcaccaaggc cctgaccgag      2640
gtgatccccc tgaccgagga ggccgagctg gagctggccg agaaccgcga gatcctgaag      2700
gagcccgtgc acgaggtgta ctacgacccc agcaaggacc tggtggccga gatccagaag      2760
cagggccagg gccagtggac ctaccagatc taccaggagc ccttcaagaa cctgaagacc      2820
ggcaagtacg cccgcatgcg cggcgcccac accaacgacg tgaagcagct gaccgaggcc      2880
gtgcagaagg tgagcaccga gagcatcgtg atctggggca gatccccaa gttcaagctg      2940 cccatccaga aggagacctg ggaggcctgg tggatggagt actggcaggc cacctggatc      3000
cccgagtggg agttcgtgaa cacccccccc ctggtgaagc tgtggtacca gctggagaag      3060
gagcccatcg tgggcgccga gaccttctac gtggacggcg ccgccaaccg cgagaccaag      3120
ctgggcaagg ccggctacgt gaccgaccgg ggccggcaga ggtggtgag catcgccgac      3180 accaccaacc agaagaccga gctgcaggcc atccacctgg ccctgcagga cagcggcctg      3240
gaggtgaaca tcgtgaccga cagccagtac gccctgggca tcatccaggc ccagcccgac      3300
aagagcgaga gcgagctggt gagccagatc atcgagcagc tgatcaagaa ggagaaggtg      3360
tacctggcct gggtgcccgc ccacaagggc atcggcgga acgagcaggt ggacaagctg      3420
gtgagcgccg gcatccgcaa ggtgctgttc ctgaacggca tcgatggcgg catcgtgatc      3480
taccagtaca tggacgacct gtacgtgggc agcggcggcc ctaggatcga ttaaaagctt      3540
cccggggcta gcaccggtga attc                                             3564
```

<210> SEQ ID NO 15
<211> LENGTH: 3496
<212> TYPE: DNA
<213> ORGANISM: Artificial Sequence
<220> FEATURE:
<223> OTHER INFORMATION: Description of Artificial Sequence:
      GagProtInaRTmut.SF2

<400> SEQUENCE: 15

```
gccaccatgg gcgcccgcgc cagcgtgctg agcggcggcg agctggacaa gtgggagaag      60
```

```
atccgcctgc gccccggcgg caagaagaag tacaagctga agcacatcgt gtgggccagc    120
cgcgagctgg agcgcttcgc cgtgaacccc ggcctgctgg agaccagcga gggctgccgc    180
cagatcctgg ccagctgca gcccagcctg cagaccggca gcgaggagct gcgcagcctg     240
tacaacaccg tggccaccct gtactgcgtg caccagcgca tcgacgtcaa ggacaccaag    300
gaggccctgg agaagatcga ggaggagcag aacaagtcca agaagaaggc ccagcaggcc    360
gccgccgccg ccggcaccgg caacagcagc caggtgagcc agaactaccc catcgtgcag    420
aacctgcagg gccagatggt gcaccaggcc atcagccccc gcaccctgaa cgcctgggtg    480
aaggtggtgg aggagaaggc cttcagcccc gaggtgatcc ccatgttcag cgccctgagc    540
gagggcgcca ccccccagga cctgaacacg atgttgaaca ccgtgggcgg ccaccaggcc    600
gccatgcaga tgctgaagga gaccatcaac gaggaggccg ccgagtggga ccgcgtgcac    660
cccgtgcacg ccggccccat cgccccggc cagatgcgcg agccccgcgg cagcgacatc     720
gccggcacca ccagcaccct gcaggagcag atcggctgga tgaccaacaa ccccccatc     780 cccgtgggcg agatctacaa gcggtggatc atcctgggcc tgaacaagat cgtgcggatg    840
tacagcccca ccagcatcct ggacatccgc cagggcccca aggagccctt ccgcgactac    900
gtggaccgct tctacaagac cctgcgcgct gagcaggcca gccaggacgt gaagaactgg    960
atgaccgaga ccctgctggt gcagaacgcc aaccccgact gcaagaccat cctgaaggct    1020
ctcggccccg cggccaccct ggaggagatg atgaccgcct gccagggcgt gggcggcccc    1080
ggccacaagg cccgcgtgct ggccgaggcg atgagccagg tgacgaaccc ggcgaccatc    1140
atgatgcagc gcggcaactt ccgcaaccag cggaagaccg tcaagtgctt caactgcggc    1200
aaggagggcc acaccgccag gaactgccgc gccccccgca gaagggctg ctggcgctgc    1260 ggccgcgagg gccaccagat gaaggactgc accgagcgcc aggccaactt cctgggcaag    1320
atctggccca gctacaaggg ccgccccggc aacttcctgc agagccgccc cgagcccacc    1380
gccccccccg aggagagctt ccgcttcggc gaggagaaga ccaccccccag ccagaagcag    1440 gagcccatcg acaaggagct gtaccccctg accagcctgc gcagcctgtt cggcaacgac    1500
cccagcagcc agaaagaatt cccccagatc accctgtggc agcgcccct ggtgaccatc     1560 aggatcggcg gccagctcaa ggaggcgctg ctcgccaccg cgccgacga caccgtgctg    1620 gaggagatga acctgcccgg caagtggaag cccaagatga tcggcgggat cgggggcttc    1680
atcaaggtgc ggcagtacga ccagatcccc gtggagatct gcggcacaa ggccatcggc     1740 accgtgctgg tgggccccac ccccgtgaac atcatcggcc gcaacctgct gacccagatc    1800
ggctgcaccc tgaacttccc catcagcccc atcgagacgg tgcccgtgaa gctgaagccg    1860
gggatggacg gccccaaggt caagcagtgg cccctgaccg aggagaagat caaggccctg    1920
gtggagatct gcaccgagat ggagaaggag ggcaagatca gcaagatcgg ccccgagaac    1980
ccctacaaca ccccccgtgtt cgccatcaag aagaaggaca gcaccaagtg gcgcaagctg    2040
gtggacttcc gcgagctgaa caagcgcacc caggacttct gggaggtgca gctgggcatc    2100 ccccacccccg ccggcctgaa gaagaagaag agcgtgaccg tgctggacgt gggcgacgcc    2160
tacttcagcg tgcccctgga caaggacttc cgcaagtaca ccgccttcac catccccagc    2220
atcaacaacg agacccccgg catccgctac agtacaacg tgctgcccca gggctggaag    2280
ggcagccccg ccatcttcca gagcagcatg accaagatcc tggagccctt ccgcaagcag    2340
aaccccgaca tcgtgatcta ccaggccccc ctgtacgtgg cagcgacct ggagatcggc     2400 cagcaccgca ccaagatcga ggagctgcgc cagcacctgc tgcgctgggg cttcaccacc    2460
```

```
cccgacaaga agcaccagaa ggagccccccc ttcctgccca tcgagctgca ccccgacaag    2520
tggaccgtgc agcccatcat gctgcccgag aaggacagct ggaccgtgaa cgacatccag    2580
aagctggtgg gcaagctgaa ctgggccagc cagatctacg ccggcatcaa ggtgaagcag    2640
ctgtgcaagc tgctgcgcgg caccaaggcc ctgaccgagg tgatccccct gaccgaggag    2700
gccgagctgg agctggccga aaccgcgag atcctgaagg agcccgtgca cgaggtgtac    2760 tacgaccca gcaaggacct ggtggccgag atccagaagc agggccaggg ccagtggacc    2820
taccagatct accaggagcc cttcaagaac ctgaagaccg gcaagtacgc ccgcatgcgc    2880
ggcgcccaca ccaacgacgt gaagcagctg accgaggccg tgcagaaggt gagcaccgag    2940
agcatcgtga tctggggcaa gatccccaag ttcaagctgc ccatccagaa ggagacctgg    3000
gaggcctggt ggatggagta ctggcaggcc acctggatcc ccgagtggga gttcgtgaac    3060
accccccccc tggtgaagct gtggtaccag ctggagaagg agcccatcgt gggcgccgag    3120
accttctacg tggacggcgc cgccaaccgc gagaccaagc tgggcaaggc cggctacgtg    3180
accgaccggg gccggcagaa ggtggtgagc atcgccgaca ccaccaacca gaagaccgag    3240
ctgcaggcca tccacctggc cctgcaggac agcggcctgg aggtgaacat cgtgaccgac    3300
agccagtacg ccctgggcat catccaggcc cagcccgaca gagcgagag cgagctggtg    3360 agccagatca tcgagcagct gatcaagaag gagaaggtgt acctggcctg ggtgcccgcc    3420
cacaagggca tcggcggcaa cgagcaggtg acaagctgg tgagcgccgg catccgcaag    3480
gtgctctaaa tctaga                                                    3496
```

<210> SEQ ID NO 16
<211> LENGTH: 4773
<212> TYPE: DNA
<213> ORGANISM: Artificial Sequence
<220> FEATURE:
<223> OTHER INFORMATION: Description of Artificial Sequence:
      GagProtInaRTmutTatRevNef.opt_B

<400> SEQUENCE: 16

```
gccaccatgg gcgcccgcgc cagcgtgctg agcggcggcg agctggacaa gtgggagaag      60
atccgcctgc gccccggcgg caagaagaag tacaagctga gcacatcgt gtgggccagc     120 cgcgagctga gcgcttcgc cgtgaacccc ggcctgctgg agaccagcga gggctgccgc     180
cagatcctgg gccagctgca gcccagcctg cagaccggca gcgaggagct gcgcagcctg     240
tacaacaccg tggccaccct gtactgcgtg caccagcgca tcgacgtcaa ggacaccaag     300
gaggccctgg agaagatcga ggaggagcag aacaagtcca gaagaaggc ccagcaggcc     360 gccgccgccg ccggcaccgg caacagcagc caggtgagcc agaactaccc catcgtgcag     420
aacctgcagg gccagatggt gcaccaggcc atcagccccc gcaccctgaa cgcctgggtg     480
aaggtggtgg aggagaaggc cttcagcccc gaggtgatcc ccatgttcag cgccctgagc     540
gagggcgcca ccccccagga cctgaacacg atgttgaaca ccgtgggcgg ccaccaggcc     600
gccatgcaga tgctgaagga gaccatcaac gaggaggccg ccgagtggga ccgcgtgcac     660
cccgtgcacg ccggccccat cgccccggc cagatgcgcg agccccgcgg cagcgacatc     720
gccggcacca ccagcaccct gcaggagcag atcggctgga tgaccaacaa ccccccccatc     780 cccgtgggcg agatctacaa gcggtggatc atcctgggcc tgaacaagat cgtgcggatg     840
tacagcccca ccagcatcct ggacatccgc cagggcccca aggagccctt ccgcgactac     900
gtggaccgct tctacaagac cctgcgcgct gagcaggcca gcaggacgt gaagaactgg     960
```

```
atgaccgaga ccctgctggt gcagaacgcc aaccccgact gcaagaccat cctgaaggct    1020
ctcggccccg cggccaccct ggaggagatg atgaccgcct gccagggcgt gggcggcccc    1080
ggccacaagg cccgcgtgct ggccgaggcg atgagccagg tgacgaaccc ggcgaccatc    1140
atgatgcagc gcggcaactt ccgcaaccag cggaagaccg tcaagtgctt caactgcggc    1200
aaggagggcc acaccgccag gaactgccgc gccccccgca agaagggctg ctggcgctgc    1260
ggccgcgagg ccaccagat gaaggactgc accgagcgcc aggccaactt cctgggcaag    1320
atctggccca gctacaaggg ccgccccggc aacttcctgc agagccgccc cgagcccacc    1380 gcccccccg aggagagctt ccgcttcggc gaggagaaga ccaccccag ccagaagcag    1440 gagcccatcg acaaggagct gtaccccctg accagcctgc gcagcctgtt cggcaacgac    1500
cccagcagcc agaaagaatt cccccagatc accctgtggc agcgccccct ggtgaccatc    1560
aggatcggcg ccagctcaa ggaggcgctg ctcgccaccg gcgccgacga caccgtgctg    1620
gaggagatga acctgcccgg caagtggaag cccaagatga tcggcgggat cggggggcttc    1680 atcaaggtgc ggcagtacga ccagatcccc gtggagatct gcggccacaa ggccatcggc    1740
accgtgctgg tgggccccac ccccgtgaac atcatcggcc gcaacctgct gacccagatc    1800
ggctgcaccc tgaacttccc catcagcccc atcgagacgg tgcccgtgaa gctgaagccg    1860
gggatggacg gccccaaggt caagcagtgg cccctgaccg aggagaagat caaggccctg    1920
gtggagatct gcaccgagat ggagaaggag ggcaagatca gcaagatcgg ccccgagaac    1980
ccctacaaca ccccgtgtt cgccatcaag aagaaggaca gcaccaagtg cgcaagctg    2040 gtggacttcc gcgagctgaa caagcgcacc caggacttct gggaggtgca gctgggcatc    2100
ccccaccccg ccggcctgaa gaagaagaag agcgtgaccg tgctggacgt gggcgacgcc    2160
tacttcagcg tgcccctgga caaggacttc cgcaagtaca ccgccttcac catccccagc    2220
atcaacaacg agaccccgg catccgctac cagtacaacg tgctgcccca gggctggaag    2280
ggcagccccg ccatcttcca gagcagcatg accaagatcc tggagccctt ccgcaagcag    2340
aaccccgaca tcgtgatcta ccaggccccc ctgtacgtgg gcagcgacct ggagatcggc    2400
cagcaccgca ccaagatcga ggagctgcgc cagcacctgc tgcgctgggg cttcaccacc    2460
cccgacaaga agcaccagaa ggagcccccc ttcctgccca tcgagctgca ccccgacaag    2520
tggaccgtgc agcccatcat gctgcccgag aaggacagct ggaccgtgaa cgacatccag    2580
aagctggtgg gcaagctgaa ctgggccagc cagatctacg ccggcatcaa ggtgaagcag    2640
ctgtgcaagc tgctgcgcgg caccaaggcc ctgaccgagt gatcccccct gaccgaggag    2700
gccgagctgg agctggccga gaaccgcgag atcctgaagg agcccgtgca cgaggtgtac    2760 tacgaccca gcaaggacct ggtggccgag atccagaagc agggccaggg ccagtggacc    2820
taccagatct accaggagcc cttcaagaac ctgaagaccg gcaagtacgc ccgcatgcgc    2880
ggcgcccaca ccaacgacgt gaagcagctg accgaggccc tgcagaaggt gagcaccgag    2940
agcatcgtga tctgggcaa gatccccaag ttcaagctgc ccatccagaa ggagacctgg    3000
gaggcctggt ggatggagta ctggcaggcc acctggatcc ccgagtggga gttcgtgaac    3060 acccccccc tggtgaagct gtggtaccag ctggagaagg agcccatcgt gggcgccgag    3120
accttctacg tggacggcgc cgccaaccgc gagaccaagc tggcaaggc cggctacgtg    3180 accgaccggg gccggcagaa ggtggtgagc atcgccgaca ccaccaacca gaagaccgag    3240
ctgcaggcca tccacctggc cctgcaggac agcggcctgg aggtgaacat cgtgaccgac    3300
agccagtacg ccctgggcat catccaggcc cagcccgaca gagcgagag cgagctggtg    3360
```

| | |
|---|---|
| agccagatca tcgagcagct gatcaagaag gagaaggtgt acctggcctg ggtgcccgcc | 3420 |
| cacaagggca tcggcggcaa cgagcaggtg acaagctgg tgagcgccgg catccgcaag | 3480 |
| gtgctcaagc ttgagcccgt ggaccccgc ctggagccct ggaagcaccc cggcagccag | 3540 |
| cccaagaccg ccggcaccaa ctgctactgc aagaagtgct gcttccactg ccaggtgagc | 3600 |
| ttcatcacca agggcctggg catcagctac ggccgcaaga agcgccgcca gcgccgccgc | 3660 |
| gcccccccg acagcgaggt gcaccaggtg agcctgccca gcagcccgc cagccagccc | 3720 |
| cagggcgacc ccaccggccc caaggagagc aagaagaagg tggagcgcga gaccgagacc | 3780 |
| gaccccgtgc accccgggc cggccgcagc ggcgacagcg acgaggagct gctgcagacc | 3840 |
| gtgcgcttca tcaagttcct gtaccagagc aaccccctgc ccagccccaa gggcacccgc | 3900 |
| caggccgacc tgaaccgccg ccgccgctgg cgcgagcgcc agcgcagat ccagagcatc | 3960 |
| agcgcctgga tcatcagcac ccacctgggc cgcagcaccg agcccgtgcc cctgcagctg | 4020 |
| cccccgacc tgcgcctgaa cctggactgc agcgaggact gcggcaccag cggcacccag | 4080 |
| ggcgtgggca gccccaggt gctgggcgag agcccgccg tgctggacag cggcaccaag | 4140 |
| gagctcgagg ccggcaagtg gagcaagcgc atgagcggct ggagcgccgt gcgcgagcgc | 4200 |
| atgaagcgcg ccgagcccgc cgagcccgcc gccgacggcg tgggcgccgt gagccgcgac | 4260 |
| ctggagaagc acggcgccat caccagcagc aacaccgccg ccaacaacgc cgactgcgcc | 4320 |
| tggctggagg cccaggagga cgaggacgtg ggcttccccg tgcgccccca ggtgcccctg | 4380 |
| cgccccatga cctacaaggc cgccctggac ctgagccact tcctgaagga aagggcggc | 4440 |
| ctggagggcc tgatctacag ccagaagcgc caggacatcc tggacctgtg gatccaccac | 4500 |
| acccagggct acttccccgg ctggcagaac tacacccccg gccccggcat ccgctacccc | 4560 |
| ctgaccttcg gctggtgctt caagctggtg cccgtggacc ccgactacgt ggaggaggcc | 4620 |
| aacgccggcg agaacaacag cctgctgcac cccatgagcc agcacggcat ggacgacccc | 4680 |
| gagaaggagg tgctggtgtg cgcgttcgac agccgcctgg ccttccacca catggcccgc | 4740 |
| gagctgcacc ccgagtacta caaggactgc taa | 4773 |

<210> SEQ ID NO 17
<211> LENGTH: 3205
<212> TYPE: DNA
<213> ORGANISM: Artificial Sequence
<220> FEATURE:
<223> OTHER INFORMATION: Description of Artificial Sequence:
       GagRTmut.SF2

<400> SEQUENCE: 17

| | |
|---|---|
| gtcgacgcca ccatgggcgc ccgcgccagc gtgctgagcg gcggcgagct ggacaagtgg | 60 |
| gagaagatcc gcctgcgccc cggcggcaag aagaagtaca agctgaagca catcgtgtgg | 120 |
| gccagccgcg agctggagcg cttcgccgtg aaccccggcc tgctggagac cagcgagggc | 180 |
| tgccgccaga tcctgggcca gctgcagccc agcctgcaga ccggcagcga ggagctgcgc | 240 |
| agcctgtaca acaccgtggc caccctgtac tgcgtgcacc agcgcatcga cgtcaaggac | 300 |
| accaaggagg ccctggagaa gatcgaggag gagcagaaca gtccaagaa gaaggcccag | 360 |
| caggccgccg ccgccgccgg caccggcaac agcagccagg tgagccagaa ctaccccatc | 420 |
| gtgcagaacc tgcagggcca gatggtgcac caggccatca gcccccgcac cctgaacgcc | 480 |
| tgggtgaagg tggtggagga aaggccttc agccccgagg tgatccccat gttcagcgcc | 540 |
| ctgagcgagg gcgccacccc ccaggacctg aacacgatgt tgaacaccgt gggcggccac | 600 |
| caggccgcca tgcagatgct gaaggagacc atcaacgagg aggccgccga gtgggaccgc | 660 |

-continued

```
gtgcacccccg tgcacgccgg ccccatcgcc cccggccaga tgcgcgagcc ccgcggcagc   720
gacatcgccg gcaccaccag caccctgcag gagcagatcg gctggatgac caacaacccc   780
cccatccccg tgggcgagat ctacaagcgg tggatcatcc tgggcctgaa caagatcgtg   840
cggatgtaca gccccaccag catcctggac atccgccagg cccccaagga gcccttccgc   900
gactacgtgg accgcttcta caagaccctg cgcgctgagc aggccagcca ggacgtgaag   960
aactggatga ccgagaccct gctggtgcag aacgccaacc ccgactgcaa gaccatcctg   1020
aaggctctcg gccccgcggc caccctggag gagatgatga ccgcctgcca gggcgtgggc   1080
ggccccggcc acaaggcccg cgtgctggcc gaggcgatga gccaggtgac gaacccggcg   1140
accatcatga tgcagcgcgg caacttccgc aaccagcgga agaccgtcaa gtgcttcaac   1200
tgcggcaagg agggccacac cgccaggaac tgccgcgccc ccgcaagaa gggctgctgg    1260 cgctgcggcc gcgagggcca ccagatgaag gactgcaccg agcgccaggc caacttcctg   1320
ggcaagatct ggcccagcta caagggccgc cccggcaact tcctgcagag ccgccccgag   1380
cccaccgccc ccccgagga gagcttccgc ttcggcgagg agaagaccac ccccagccag    1440
aagcaggagc ccatcgacaa ggagctgtac cccctgacca gctgcgcag cctgttcggc     1500 aacgacccca gcagccagaa agaattcccc atcagcccca tcgagacggt gcccgtgaag   1560
ctgaagccgg ggatgacgg ccccaaggtc aagcagtggc ccctgaccga ggagaagatc    1620
aaggccctgg tggagatctg caccgagatg gagaaggagg caagatcag caagatcggc    1680 cccgagaacc cctacaacac ccccgtgttc gccatcaaga agaaggacag caccaagtgg   1740
cgcaagctgg tggacttccg cgagctgaac aagcgcaccc aggacttctg ggaggtgcag   1800
ctgggcatcc cccaccccgc cggcctgaag aagaagaaga gcgtgaccgt gctggacgtg   1860
ggcgacgcct acttcagcgt gccccctggac aaggacttcc gcaagtacac cgccttcacc   1920
atccccagca tcaacaacga ccccccggc atccgctacc agtacaacgt gctgcccag     1980 ggctggaagg gcagccccgc catcttccag agcagcatga ccaagatcct ggagcccttc   2040
cgcaagcaga accccgacat cgtgatctac caggcccccc tgtacgtggg cagcgacctg   2100
gagatcggcc agcaccgcac caagatcgag gagctgcgcc agcacctgct gcgctggggc   2160
ttcaccaccc ccgacaagaa gcaccagaag gagcccccct tcctgcccat cgagctgcac   2220
cccgacaagt ggaccgtgca gcccatcatg ctgcccgaga aggacagctg gaccgtgaac   2280
gacatccaga agctggtggg caagctgaac tgggccagcc agatctacgc cggcatcaag   2340
gtgaagcagc tgtgcaagct gctgcgcggc accaaggccc tgaccgaggt gatccccctg   2400
accgaggagg ccgagctgga gctggccgag aaccgcgaga tcctgaagga gcccgtgcac   2460
gaggtgtact acgaccccag caaggacctg gtggccgaga tccagaagca gggccagggc   2520
cagtggacct accagatcta ccaggagccc ttcaagaacc tgaagaccgg caagtacgcc   2580
cgcatgcgcg gcgcccacac caacgacgtg aagcagctga ccgaggccgt gcagaaggtg   2640
agcaccgaga gcatcgtgat ctggggcaag atccccaagt tcaagctgcc catccagaag   2700
gagacctggg aggcctggtg gatggagtac tggcaggcca cctggatccc cgagtgggag   2760
ttcgtgaaca ccccccccct ggtgaagctg tggtaccagc tggagaagga gcccatcgtg   2820
ggcgccgaga ccttctacgt ggacggcgcc gccaaccgcg agaccaagct gggcaaggcc   2880
ggctacgtga ccgaccgggg ccggcagaag gtggtgagca tcgccgacac caccaaccag   2940
aagaccgagc tgcaggccat ccacctggcc ctgcaggaca cgcggcctgga ggtgaacatc   3000 gtgaccgaca gccagtacgc cctgggcatc atccaggccc agcccgacaa gagcgagagc   3060
```

```
gagctggtga gccagatcat cgagcagctg atcaagaagg agaaggtgta cctggcctgg      3120
gtgcccgccc acaagggcat cggcggcaac gagcaggtgg acaagctggt gagcgccggc      3180
atccgcaagg tgctctaaat ctaga                                            3205
```

<210> SEQ ID NO 18
<211> LENGTH: 2799
<212> TYPE: DNA
<213> ORGANISM: Artificial Sequence
<220> FEATURE:
<223> OTHER INFORMATION: Description of Artificial Sequence:
      GagTatRevNef.opt_B

<400> SEQUENCE: 18

```
gccaccatgg cgcccgcgc cagcgtgctg agcggcggcg agctggacaa gtgggagaag        60
atccgcctgc gccccggcgg caagaagaag tacaagctga gcacatcgt gtgggccagc       120 cgcgagctga gcgcttcgc cgtgaacccc ggcctgctgg agaccagcga gggctgccgc       180
cagatcctgg ccagctgca gcccagcctg cagaccggca gcgaggagct gcgcagcctg       240
tacaacaccg tggccaccct gtactgcgtg caccagcgca tcgacgtcaa ggacaccaag       300
gaggccctgg agaagatcga ggaggagcag aacaagtcca agaagaaggc ccagcaggcc      360
gccgccgccg ccggcaccgg caacagcagc caggtgagcc agaactaccc catcgtgcag      420
aacctgcagg gccagatggt gcaccaggcc atcagccccc gcaccctgaa cgcctgggtg      480
aaggtggtgg aggagaaggc cttcagcccc gaggtgatcc ccatgttcag cgccctgagc      540
gagggcgcca ccccccagga cctgaacacg atgttgaaca ccgtgggcgg ccaccaggcc      600
gccatgcaga tgctgaagga gaccatcaac gaggaggccg ccgagtggga ccgcgtgcac      660
cccgtgcacg ccggccccat cgcccccggc cagatgcgcg agcccgcgg cagcgacatc       720 gccggcacca ccagcaccct gcaggagcag atcggctgga tgaccaacaa cccccccatc      780
cccgtgggcg agatctacaa gcggtggatc atcctgggcc tgaacaagat cgtgcggatg      840
tacagcccca ccagcatcct ggacatccgc cagggcccca aggagccctt ccgcgactac     900
gtggaccgct tctacaagac cctgcgcgct gagcaggcca gccaggacgt gaagaactgg      960
atgaccgaga ccctgctggt gcagaacgcc aaccccgact gcaagaccat cctgaaggct     1020
ctcggccccg cggccaccct ggaggagatg atgaccgcct gccagggcgt gggcggcccc     1080
ggccacaagg cccgcgtgct ggccgaggcg atgagccagg tgacgaaccc ggcgaccatc     1140
atgatgcagc gcggcaactt ccgcaaccag cggaagaccg tcaagtgctt caactgcggc     1200
aaggagggcc acaccgccag gaactgccgc gccccccgca agaagggctg ctggcgctgc     1260
ggccgcgagg gcaccagat gaaggactgc accgagcgcc aggccaactt cctgggcaag     1320
atctggccca gctacaaggg ccgcccccgg aacttcctgc agagccgccc cgagcccacc     1380
gccccccccg aggagagctt ccgcttcggc gaggagaaga ccaccccag ccagaagcag      1440 gagcccatcg acaaggagct gtaccccctg accagcctgc gcagcctgtt cggcaacgac     1500
cccagcagcc aggaattcga gcccgtggac cccgcctgg agcctggaa gcaccccggc      1560 agccagccca gaccgccgg caccaactgc tactgcaaga agtgctgctt ccactgccag     1620
gtgagcttca tcaccaaggg cctgggcatc agctacggcc gcaagaagcg ccgcagcgc      1680 cgccgcgcc cccccgacag cgaggtgcac caggtgagcc tgcccaagca gccgccagc     1740 cagcccagg gcgaccccac cggccccaag gagagcaaga agaaggtgga gcgcgagacc     1800
gagaccgacc ccgtgcaccc cggggccggc cgcagcggcg acagcgacga ggagctgctg     1860
```

```
cagaccgtgc gcttcatcaa gttcctgtac cagagcaacc ccctgcccag ccccaagggc    1920
acccgccagg ccgacctgaa ccgccgccgc cgctggcgcg agcgccagcg ccagatccag    1980
agcatcagcg cctggatcat cagcacccac ctgggccgca gcaccgagcc cgtgcccctg    2040
cagctgcccc ccgacctgcg cctgaacctg gactgcagcg aggactgcgg caccagcggc    2100
acccagggcg tgggcagccc ccaggtgctg ggcgagagcc ccgccgtgct ggacagcggc    2160
accaaggagc tcgaggccgg caagtggagc aagcgcatga gcggctggag cgccgtgcgc    2220
gagcgcatga agcgcgccga gcccgccgag cccgccgccg acggcgtggg cgccgtgagc    2280
cgcgacctgg agaagcacgg cgccatcacc agcagcaaca ccgccgccaa caacgccgac    2340
tgcgcctggc tggaggccca ggaggacgag gacgtgggct tccccgtgcg cccccaggtg    2400
cccctgcgcc ccatgaccta caaggccgcc ctggacctga ccacttcct gaaggagaag    2460 ggcggcctgg agggcctgat ctacagccag aagcgccagg acatcctgga cctgtggatc    2520
caccacaccc agggctactt ccccggctgg cagaactaca cccccggccc cggcatccgc    2580
taccccctga ccttcggctg gtgcttcaag ctggtgcccg tggaccccga ctacgtggag    2640
gaggccaacg ccggcgagaa caacagcctg ctgcacccca tgagccagca cggcatggac    2700
gaccccgaga aggaggtgct ggtgtggcgc ttcgacagcc gcctggcctt ccaccacatg    2760
gcccgcgagc tgcaccccga gtactacaag gactgctaa                           2799
```

<210> SEQ ID NO 19
<211> LENGTH: 2028
<212> TYPE: DNA
<213> ORGANISM: Artificial Sequence
<220> FEATURE:
<223> OTHER INFORMATION: Description of Artificial Sequence:
      gp140.modSF162.CwtLmod

<400> SEQUENCE: 19

```
atgcgcgtga tgggcaccca agaagaactgc cagcagtggt ggatctgggg catcctgggc      60
ttctggatgc tgatgatctg cagcgccgtg agaagctgt gggtgaccgt gtactacggc     120
gtgcccgtgt ggaaggaggc caccaccacc ctgttctgcg ccagcgacgc caaggcctac     180
gacaccgagg tgcacaacgt gtgggccacc cacgcctgcg tgcccaccga ccccaacccc     240
caggagatcg tgctggagaa cgtgaccgag aacttcaaca tgtggaagaa caacatggtg     300
gagcagatgc acgaggacat catcagcctg tgggaccaga gcctgaagcc ctgcgtgaag     360
ctgacccccc tgtgcgtgac cctgcactgc accaacctga agaacgccac caacaccaag     420
agcagcaact ggaaggagat ggaccgcggc gagatcaaga actgcagctt caaggtgacc     480
accagcatcc gcaacaagat gcagaaggag tacgccctgt tctacaagct ggacgtggtg     540
cccatcgaca cgacaacac cagctacaag ctgatcaact gcaacaccag cgtgatcacc     600
caggcctgcc ccaaggtgag cttcgagccc atccccatcc actactgcgc ccccgccggc     660
ttcgccatcc tgaagtgcaa cgacaagaag ttcaacggca gcggccctg caccaacgtg     720 agcaccgtgc agtgcaccca cggcatccgc cccgtggtga gcacccagct gctgctgaac     780
ggcagcctgg ccgaggaggg cgtggtgatc cgcagcgaga acttcaccga caacgccaag     840
accatcatcg tgcagctgaa ggagagcgtg gagatcaact gcacccgccc caacaacaac     900 accccgcaaga gcatcaccat cggcccggc cgcgccttct acgccaccgg cgacatcatc     960
ggcgacatcc gccaggccca ctgcaacatc agcggcgaga agtggaacaa caccctgaag    1020
cagatcgtga ccaagctgca ggcccagttc ggcaacaaga ccatcgtgtt caagcagagc    1080
agcggcggcg accccgagat cgtgatgcac agcttcaact gcggcggcga gttcttctac    1140
```
tgcaacagca cccagctgtt caacagcacc tggaacaaca ccatcggccc caacaacacc    1200
aacggcacca tcaccctgcc ctgccgcatc aagcagatca tcaaccgctg gcaggaggtg    1260
ggcaaggcca tgtacgcccc ccccatccgc ggccagatcc gctgcagcag caacatcacc    1320
ggcctgctgc tgacccgcga cggcggcaag gagatcagca acaccaccga gatcttccgc    1380
cccggcggcg cgacatgcg cgacaactgg cgcagcgagc tgtacaagta caaggtggtg    1440
aagatcgagc ccctgggcgt ggcccccacc aaggccaagc gccgcgtggt gcagcgcgag    1500
aagcgcgccg tgaccctggg cgccatgttc ctgggcttcc tgggcgccgc cggcagcacc    1560
atgggcgccc gcagcctgac cctgaccgtg caggcccgcc agctgctgag cggcatcgtg    1620
cagcagcaga caacctgct gcgcgccatc gaggcccagc agcacctgct gcagctgacc    1680 gtgtgggca tcaagcagct gcaggcccgc gtgctggccg tggagcgcta cctgaaggac    1740
cagcagctgc tgggcatctg gggctgcagc ggcaagctga tctgcaccac cgccgtgccc    1800
tggaacgcca gctggagcaa caagagcctg gaccagatct ggaacaacat gacctggatg    1860
gagtgggagc gcgagatcga caactacacc aacctgatct accctgat cgaggagagc    1920 cagaaccagc aggagaagaa cgagcaggag ctgctggagc tggacaagtg gccagcctg    1980 tggaactggt tcgacatcag caagtggctg tggtacatct aactcgag             2028

<210> SEQ ID NO 20
<211> LENGTH: 2033
<212> TYPE: DNA
<213> ORGANISM: Artificial Sequence
<220> FEATURE:
<223> OTHER INFORMATION: Description of Artificial Sequence:
      gp140.modSF162.CwtLnat

<400> SEQUENCE: 20
atgagagtga tggggacaca gaagaattgt caacaatggt ggatatgggg catcttaggc      60
ttctggatgc taatgatttg tagcgccgtg gagaagctgt gggtgaccgt gtactacggc     120
gtgcccgtgt ggaaggaggc caccaccacc ctgttctgcg ccagcgacgc caaggcctac     180
gacaccgagg tgcacaacgt gtgggccacc cacgcctgcg tgcccaccga ccccaacccc     240
caggagatcg tgctggagaa cgtgaccgag aacttcaaca tgtggaagaa caacatggtg     300
gagcagatgc acgaggacat catcagcctg tgggaccaga gcctgaagcc ctgcgtgaag     360 ctgaccccc tgtgcgtgac cctgcactgc accaacctga agaacgccac caacaccaag     420
agcagcaact ggaaggagat ggaccgcggc gagatcaaga ctgcagcttc caaggtgacc     480
accagcatcc gcaacaagat gcagaaggag tacgccctgt tctacaagct ggacgtggtg     540
cccatcgaca cgacaacac cagctacaag ctgatcaact gcaacaccag cgtgatcacc     600
caggcctgcc ccaaggtgag cttcgagccc atccccatcc actactgcgc cccgccggc     660 ttcgccatcc tgaagtgcaa cgacaagaag ttcaacggca cgcccctg caccaacgtg     720 agcaccgtgc agtgcaccca cggcatccgc cccgtggtga gcacccagct gctgctgaac     780
ggcagcctgg ccgaggaggg cgtggtgatc cgcagcgaga cttcaccga caacgccaag     840 accatcatcg tgcagctgaa ggagagcgtg gagatcaact gcacccgccc caacaacaac     900
acccgcaaga gcatcaccat cggccccggc cgcgccttct acgccaccgg cgacatcatc     960
ggcgacatcc gccaggccca ctgcaacatc agcgccgaga agtggaacaa cacctgaag    1020 cagatcgtga ccaagctgca ggcccagttc ggcaacaaga ccatcgtgtt caagcagagc    1080
agcggcggcg accccgagat cgtgatgcac agcttcaact gcggcggcga gttcttctac    1140

| | |
|---|---|
| tgcaacagca cccagctgtt caacagcacc tggaacaaca ccatcggccc caacaacacc | 1200 |
| aacggcacca tcaccctgcc ctgccgcatc aagcagatca tcaaccgctg caggaggtg | 1260 |
| ggcaaggcca tgtacgcccc ccccatccgc ggccagatcc gctgcagcag caacatcacc | 1320 |
| ggcctgctgc tgacccgcga cggcggcaag gagatcagca caccaccga gatcttccgc | 1380 |
| cccggcggcg gcgacatgcg cgacaactgg cgcagcgagc tgtacaagta caaggtggtg | 1440 |
| aagatcgagc ccctgggcgt ggcccccacc aaggccaagc gccgcgtggt gcagcgcgag | 1500 |
| aagcgcgccg tgaccctggg cgccatgttc ctgggcttcc tgggcgccgc cggcagcacc | 1560 |
| atgggcgccc gcagcctgac cctgaccgtg caggcccgcc agctgctgag cggcatcgtg | 1620 |
| cagcagcaga acaacctgct gcgcgccatc gaggcccagc agcacctgct gcagctgacc | 1680 |
| gtgtgggca tcaagcagct gcaggcccgc gtgctggccg tggagcgcta cctgaaggac | 1740 |
| cagcagctgc tgggcatctg gggctgcagc ggcaagctga tctgcaccac cgccgtgccc | 1800 |
| tggaacgcca gctggagcaa caagagcctg accagatct ggaacaacat gacctggatg | 1860 |
| gagtgggagc gcgagatcga caactacacc aacctgatct acaccctgat cgaggagagc | 1920 |
| cagaaccagc aggagaagaa cgagcaggag ctgctggagc tggacaagtg ggccagcctg | 1980 |
| tggaactggt tcgacatcag caagtggctg tggtacatct aactcgaggr sht | 2033 |

<210> SEQ ID NO 21
<211> LENGTH: 2453
<212> TYPE: DNA
<213> ORGANISM: Artificial Sequence
<220> FEATURE:
<223> OTHER INFORMATION: Description of Artificial Sequence: gp160.modSF162.delV2.mut7

<400> SEQUENCE: 21

| | |
|---|---|
| atggatgcaa tgaagagagg ctctgctgt gtgctgctgc tgtgtggagc agtcttcgtt | 60 |
| tcgcccagcg ccgtggagaa gctgtgggtg accgtgtact acggcgtgcc cgtgtggaag | 120 |
| gaggccacca ccaccctgtt ctgcgccagc gacgccaagg cctacgacac cgaggtgcac | 180 |
| aacgtgtggg ccacccacgc ctgcgtgccc accgacccca ccccagga gatcgtgctg | 240 |
| gagaacgtga ccgagaactt caacatgtgg aagaacaaca tggtggagca gatgcacgag | 300 |
| gacatcatca gcctgtggga ccagagcctg aagcccctgcg tgaagctgac ccccctgtgc | 360 |
| gtgaccctgc actgcaccaa cctgaagaac gccaccaaca ccaagagcag caactggaag | 420 |
| gagatggacc gcggcgagat caagaactgc agcttcaagg tgggcgccgg caagctgatc | 480 |
| aactgcaaca ccagcgtgat cacccaggcc tgccccaagg tgagcttcga gcccatcccc | 540 |
| atccactact gcgcccccgc cggcttcgcc atcctgaagt gcaacgacaa gaagttcaac | 600 |
| ggcagcggcc cctgcaccaa cgtgagcacc gtgcagtgca cccacggcat ccgccccgtg | 660 |
| gtgagcaccc agctgctgct gaacggcagc ctggccgagg agggcgtggt gatccgcagc | 720 |
| gagaacttca ccgacaacgc caagaccatc atcgtgcagc tgaaggagag cgtggagatc | 780 |
| aactgcaccc gccccaacaa caacacccgc aagagcatca ccatcggccc cggccgcgcc | 840 |
| ttctacgcca ccgcgacat catcggcgac atccgccagg cccactgcaa catcagcggc | 900 |
| gagaagtgga caacaccct gaagcagatc gtgaccaagc tgcaggccca gttcggcaac | 960 |
| aagaccatcg tgttcaagca gagcagcggc ggcgacccccg gatcgtgat gcacagcttc | 1020 |
| aactgcggcg gcgagttctt ctactgcaac agcacccagc tgttcaacag cacctggaac | 1080 |
| aacaccatcg gccccaacaa caccaacggc accatcaccc tgccctgccg catcaagcag | 1140 |
| atcatcaacc gctggcagga ggtgggcaag gccatgtacg ccccccccat ccgcggccag | 1200 |

```
atccgctgca gcagcaacat caccggcctg ctgctgaccc gcgacggcgg caaggagatc    1260
agcaacacca ccgagatctt ccgccccggc ggcggcgaca tgcgcgacaa ctggcgcagc    1320
gagctgtaca agtacaaggt ggtgaagatc gagcccctgg gcgtggcccc caccaaggcc    1380
atcagcagcg tggtgcagag cgagaagagc gccgtgaccc tgggcgccat gttcctgggc    1440
ttcctgggcg ccgccggcag caccatgggc gcccgcagcc tgaccctgac cgtgcaggcc    1500
cgccagctgc tgagcggcat cgtgcagcag cagaacaacc tgctgcgcgc catcgaggcc    1560
cagcagcacc tgctgcagct gaccgtgtgg ggcatcaagc agctgcaggc ccgcgtgctg    1620
gccgtggagc gctacctgaa ggaccagcag ctgctgggca tctggggctg cagcggcaag    1680
ctgatctgca ccaccgccgt gccctggaac gccagctgga gcaacaagag cctggaccag    1740
atctggaaca acatgacctg gatggagtgg gagcgcgaga tcgacaacta caccaacctg    1800
atctacaccc tgatcgagga gagccagaac cagcaggaga gaacgagca ggagctgctg    1860 gagctggaca agtgggccag cctgtggaac tggttcgaca tcagcaagtg gctgtggtac    1920
atcaagatct tcatcatgat cgtgggcggc ctggtgggcc tgcgcatcgt gttcaccgtg    1980
ctgagcatcg tgaaccgcgt gcgccagggc tacagccccc tgagcttcca gacccgcttc    2040
cccgcccccc gcggccccga ccgccccgag ggcatcgagg aggagggcgg cgagcgcgac    2100
cgcgaccgca gcgccccct ggtgcacggc ctgctggccc tgatctggga cgacctgcgc    2160
agcctgtgcc tgttcagcta ccaccgcctg cgcgacctga tcctgatcgc gcccgcatc    2220 gtggagctgc tgggccgccg cggctggag gccctgaagt actggggcaa cctgctgcag    2280
tactggatcc aggagctgaa gaacagcgcc gtgagcctgt cgacgccat cgccatcgcc    2340 gtggccgagg gcaccgaccg catcatcgag gtggcccagc gcatcggccg cgccttcctg    2400
cacatccccc gccgcatccg ccagggcttc gagcgcgccc tgctgtaagr sht           2453

<210> SEQ ID NO 22
<211> LENGTH: 2453
<212> TYPE: DNA
<213> ORGANISM: Artificial Sequence
<220> FEATURE:
<223> OTHER INFORMATION: Description of Artificial Sequence:
      gp160.modSF162.delV2.mut8

<400> SEQUENCE: 22
atggatgcaa tgaagagagg gctctgctgt gtgctgctgc tgtgtggagc agtcttcgtt      60
tcgcccagcg ccgtggagaa gctgtgggtg accgtgtact acggcgtgcc cgtgtggaag     120
gaggccacca ccaccctgtt ctgcgccagc gacgccaagg cctacgacac cgaggtgcac     180
aacgtgtggg ccaccacgc ctgcgtgccc accgacccca cccccagga gatcgtgctg     240 gagaacgtga ccgagaactt caacatgtgg aagaacaaca tggtggagca gatgcacgag     300
gacatcatca gcctgtggga ccagagcctg aagcccctgcg tgaagctgac cccctgtgc     360 gtgaccctgc actgcaccaa cctgaagaac gccaccaaca ccaagagcag caactggaag     420
gagatggacc gcggcgagat caagaactgc agcttcaagg tgggcgccgg caagctgatc     480
aactgcaaca ccagcgtgat cacccaggcc tgccccaagg tgagcttcga gcccatcccc     540
atccactact gcgcccccgc cggcttcgcc atcctgaagt gcaacgacaa gaagttcaac     600
ggcagcggcc cctgcaccaa cgtgagcacc gtgcagtgca cccacggcat ccgccccgtg     660
gtgagcaccc agctgctgct gaacggcagc ctggccgagg agggcgtggt gatccgcagc     720
gagaacttca ccgacaacgc caagaccatc atcgtgcagc tgaaggagag cgtggagatc     780
```

```
aactgcaccc gccccaacaa caacacccgc aagagcatca ccatcggccc cggccgcgcc      840
ttctacgcca ccggcgacat catccggcga catccgccag gcccactgca catcagcggc      900
gagaagtgga acaacaccct gaagcagatc gtgaccaagc tgcaggccca gttcggcaac      960
aagaccatcg tgttcaagca gagcagcggc ggcgaccccg agatcgtgat gcacagcttc     1020
aactgcggcg gcgagttctt ctactgcaac agcacccagc tgttcaacag cacctggaac     1080
aacaccatcg gccccaacaa caccaacggc accatcaccc tgccctgccg catcaagcag     1140
atcatcaacc gctggcagga ggtgggcaag gccatgtacg ccccccccat ccgcggccag     1200
atccgctgca gcagcaacat caccggcctg ctgctgaccc gcgacggcgg caaggagatc     1260
agcaacacca ccgagatctt ccgccccggc ggcggcgaca tgcgcgacaa ctggcgcagc     1320
gagctgtaca gtacaaggt ggtgaagatc gagcccctgg gcgtggcccc caccatcgcc      1380
atcagcagcg tggtgcagag cgagaagagc gccgtgaccc tgggcgccat gttcctgggc     1440
ttcctgggcg ccgccggcag caccatgggc gcccgcagcc tgaccctgac cgtgcaggcc     1500
cgccagctgc tgagcggcat cgtgcagcag cagaacaacc tgctgcgcgc catcgaggcc     1560
cagcagcacc tgctgcagct gaccgtgtgg ggcatcaagc agctgcaggc cgcgtgctg      1620 gccgtggagc gctacctgaa ggaccagcag ctgctgggca tctggggctg cagcggcaag     1680
ctgatctgca ccaccgccgt gccctggaac gccagctgga gcaacaagag cctggaccag     1740
atctggaaca acatgacctg gatggagtgg gagcgcgaga tcgacaacta caccaacctg     1800
atctacaccc tgatcgagga gagccagaac cagcaggaga gaacgagca ggagctgctg      1860 gagctggaca agtgggccag cctgtggaac tggttcgaca tcagcaagtg gctgtggtac     1920
atcaagatct tcatcatgat cgtgggcggc ctggtgggcc tgcgcatcgt gttcaccgtg     1980
ctgagcatcg tgaaccgcgt gcgccagggc tacagccccc tgagcttcca gacccgcttc     2040
cccgcccccc gcggccccga ccgccccgag ggcatcgagg aggagggcgg cgagcgcgac     2100
cgcgaccgca gcagccccct ggtgcacggc ctgctggccc tgatctggga cgacctgcgc     2160
agcctgtgcc tgttcagcta ccaccgcctg cgcgacctga tcctgatcgc cgcccgcatc     2220
gtggagctgc tgggccgccg cggctgggag gccctgaagt actggggcaa cctgctgcag     2280
tactggatcc aggagctgaa gaacagcgcc gtgagcctgt tcgacgccat cgccatcgcc     2340
gtggccgagg gcaccgaccg catcatcgag gtggcccagc gcatcggccg cgccttcctg     2400
cacatccccc gccgcatccg ccagggcttc gagcgcgccc tgctgtaagr sht            2453

<210> SEQ ID NO 23
<211> LENGTH: 866
<212> TYPE: DNA
<213> ORGANISM: Artificial Sequence
<220> FEATURE:
<223> OTHER INFORMATION: Description of Artificial Sequence:
      int.opt.mut.SF2

<400> SEQUENCE: 23
ttcctgaacg gcatcgacaa ggcccaggag gagcacgaga agtaccacag caactggcgc       60
gccatggcca gcgacttcaa cctgcccccc gtggtggcca aggagatcgt ggccagcgcc      120
gacaagtgcc agctgaaggg cgaggccatg cacggccagg tggactgcag ccccggcatc      180
tggcagctgg cctgcacca cctggagggc aagatcatcc tggtggccgt gcacgtggcc      240
agcggctaca tcgaggccga ggtgatcccc gccgagaccg ccaggagac cgcctacttc      300 ctgctgaagc tggccggccg ctggcccgtg aagaccatcg acaccgccaa cggcagcaac      360
ttcaccagca ccaccgtgaa ggccgcctgc tggtgggccg gcatcaagca ggagttcggc      420
```

```
atcccctaca accccccagag ccagggcgtg gtggcgagca tgaacaacga gctgaagaag    480
atcatcggcc aggtgcgcga ccaggccgag cacctgaaga ccgccgtgca gatggccgtg    540
ttcatccaca acttcaagcg caagggcggc atcggcggct acagcgccgg cgagcgcatc    600
gtggacatca tcgccaccga catccagacc aaggagctgc agaagcagat caccaagatc    660
cagaacttcc gcgtgtacta ccgcgacaac aaggacccccc tgaagggccc cgccaagctg    720
ctgtggaagg gcgagggcgc cgtggtgatc caggacaaca gcgacatcaa ggtggtgccc    780
cgccgcaagg ccaagatcat ccgcgactac ggcaagcaga tggccggcga cgactgcgtg    840
gccagccgcc aggacgagga cgrsht                                          866

<210> SEQ ID NO 24
<211> LENGTH: 869
<212> TYPE: DNA
<213> ORGANISM: Artificial Sequence
<220> FEATURE:
<223> OTHER INFORMATION: Description of Artificial Sequence: int.opt.SF2

<400> SEQUENCE: 24
ttcctgaacg gcatcgacaa ggcccaggag gagcacgaga gtaccacag caactggcgc       60 gccatggcca gcgacttcaa cctgccccccc gtggtggcca aggagatcgt ggccagctgc    120
gacaagtgcc agctgaaggg cgaggccatg cacggccagg tggactgcag ccccggcatc    180
tggcagctgg actgcacccca cctggagggc aagatcatcc tggtggccgt gcacgtggcc    240
agcggctaca tcgaggccga ggtgatcccc gccgagaccg gccaggagac cgcctacttc    300
ctgctgaagc tggccggccg ctggccccgtg aagaccatcc acaccgacaa cggcagcaac    360
ttcaccagca ccaccgtgaa ggccgcctgc tggtgggccg gcatcaagca ggagttcggc    420
atcccctaca accccagag ccagggcgtg gtggagagca tgaacaacga gctgaagaag     480
atcatcggcc aggtgcgcga ccaggccgag cacctgaaga ccgccgtgca gatggccgtg    540
ttcatccaca acttcaagcg caagggcggc atcggcggct acagcgccgg cgagcgcatc    600
gtggacatca tcgccaccga catccagacc aaggagctgc agaagcagat caccaagatc    660
cagaacttcc gcgtgtacta ccgcgacaac aaggacccccc tgtggaaggg ccccgccaag    720
ctgctgtgga agggcgaggg cgccgtggtg atccaggaca acagcgacat caaggtggtg    780
ccccgccgca aggccaagat catccgcgac tacggcaagc agatggccgg cgacgactgc    840
gtggccagcc gccaggacga ggacgrsht                                       869

<210> SEQ ID NO 25
<211> LENGTH: 629
<212> TYPE: DNA
<213> ORGANISM: Artificial Sequence
<220> FEATURE:
<223> OTHER INFORMATION: Description of Artificial Sequence:
      nef.D125G.-myr.opt.SF162

<400> SEQUENCE: 25
atggccggca gtggagcaa gcgcatgagc ggctggagcg ccgtgcgcga gcgcatgaag      60
cgcgccgagc ccgccgagcc cgccgccgac ggcgtgggcg ccgtgagccg cgacctggag   120
aagcacggcg ccatcaccag cagcaacacc gccgccaaca cgccgactg cgcctggctg    180 gaggcccagg aggacgagga cgtgggcttc cccgtgcgcc cccaggtgcc cctgcgcccc    240
atgacctaca aggccgccct ggacctgagc cacttcctga aggagaaggg cggcctggag    300
ggcctgatct acagccagaa gcgccaggac atcctggacc tgtggatcca ccacacccag    360
```

```
ggctacttcc ccggctggca gaactacacc cccggccccg gcatccgcta ccccctgacc      420
ttcggctggt gcttcaagct ggtgcccgtg accccgact acgtggagga ggccaacgcc       480
ggcgagaaca acagcctgct gcaccccatg agccagcacg gcatggacga ccccgagaag      540
gaggtgctgg tgtggcgctt cgacagccgc ctggccttcc accacatggc ccgcgagctg      600
caccccgagt actacaagga ctgcgrsht                                        629
```

<210> SEQ ID NO 26
<211> LENGTH: 570
<212> TYPE: DNA
<213> ORGANISM: Artificial Sequence
<220> FEATURE:
<223> OTHER INFORMATION: Description of Artificial Sequence:
      nef.D107G.-myr18.opt.SF162

<400> SEQUENCE: 26

```
atgaagcgcg ccgagcccgc cgagcccgcc gccgacggcg tgggcgccgt gagccgcgac       60
ctggagaagc acggcgccat caccagcagc aacaccgccg ccaacaacgc cgactgcgcc      120
tggctggagg cccaggagga cgaggacgtg ggcttccccg tgcgccccca ggtgcccctg      180
cgccccatga cctacaaggc cgccctggac ctgagccact cctgaaggaa gaaggggcggc    240 ctggagggcc tgatctacag ccagaagcgc caggacatcc tggacctgtg gatccaccac      300
acccagggct acttccccgg ctggcagaac tacaccccg gccccggcat ccgctacccc       360
ctgaccttcg gctggtgctt caagctggtg cccgtggacc ccgactacgt ggaggaggcc      420
aacgccggca gaacaacag cctgctgcac cccatgagcc agcacggcat ggacgacccc      480
gagaaggagg tgctggtgtg cgcttcgac agccgcctgg ccttccacca catggcccgc      540
gagctgcacc ccgagtacta caaggactgc                                       570
```

<210> SEQ ID NO 27
<211> LENGTH: 624
<212> TYPE: DNA
<213> ORGANISM: Artificial Sequence
<220> FEATURE:
<223> OTHER INFORMATION: Description of Artificial Sequence:
      nef.opt.D125G.SF162

<400> SEQUENCE: 27

```
atgggcggca gtggagcaa gcgcatgagc ggctggagcg ccgtgcgcga gcgcatgaag        60
cgcgccgagc ccgccgagcc cgccgccgac ggcgtgggcg ccgtgagccg cgacctggag      120
aagcacggcg ccatcaccag cagcaacacc gccgccaaca acgccgactg cgcctggctg      180
gaggcccagg aggacgagga cgtgggcttc cccgtgcgcc cccaggtgcc cctgcgcccc      240
atgacctaca aggccgccct ggacctgagc cacttcctga aggagaaggg cggcctggag      300
ggcctgatct acagccagaa gcgccaggac atcctggacc tgtggatcca cacccag        360 ggctacttcc ccggctggca gaactacacc cccggccccg gcatccgcta ccccctgacc     420
ttcggctggt gcttcaagct ggtgcccgtg accccgact acgtggagga ggccaacgcc       480
ggcgagaaca acagcctgct gcaccccatg agccagcacg gcatggacga ccccgagaag      540
gaggtgctgg tgtggcgctt cgacagccgc ctggccttcc accacatggc ccgcgagctg      600
caccccgagt actacaagga ctgc                                             624
```

<210> SEQ ID NO 28
<211> LENGTH: 624
<212> TYPE: DNA
<213> ORGANISM: Artificial Sequence
<220> FEATURE:

```
<223> OTHER INFORMATION: Description of Artificial Sequence:
      nef.opt.SF162

<400> SEQUENCE: 28
atgggcggca agtggagcaa gcgcatgagc ggctggagcg ccgtgcgcga gcgcatgaag      60
cgcgccgagc ccgccgagcc cgccgccgac ggcgtgggcg ccgtgagccg cgacctggag     120
aagcacggcg ccatcaccag cagcaacacc gccgccaaca cgccgactg cgcctggctg      180 gaggcccagg aggacgagga cgtgggcttc ccgtgcgcc cccaggtgcc cctgcgcccc      240
atgacctaca aggccgccct ggacctgagc cacttcctga aggagaaggg cggcctggag     300
ggcctgatct acagccagaa cgccaggac atcctggacc tgtggatcca ccacacccag      360
ggctacttcc ccgactggca gaactacacc cccggccccg gcatccgcta ccccctgacc     420
ttcggctggt gcttcaagct ggtgcccgtg accccgact acgtggagga ggccaacgcc      480
ggcgagaaca acagcctgct gcaccccatg agccagcacg gcatggacga ccccgagaag     540
gaggtgctgg tgtggcgctt cgacagccgc ctggccttcc accacatggc ccgcgagctg     600 cacccgagt actacaagga ctgc                                              624

<210> SEQ ID NO 29
<211> LENGTH: 360
<212> TYPE: DNA
<213> ORGANISM: Artificial Sequence
<220> FEATURE:
<223> OTHER INFORMATION: Description of Artificial Sequence:
      p15RnaseH.opt.SF2

<400> SEQUENCE: 29
tacgtggacg gcgccgccaa ccgcgagacc aagctgggca aggccggcta cgtgaccgac       60
cggggccggc agaaggtggt gagcatcgcc gacaccacca accagaagac cgagctgcag      120
gccatccacc tggccctgca ggacagcggc ctggaggtga acatcgtgac cgacagccag      180
tacgccctgg gcatcatcca ggcccagccc gacaagagcg agagcgagct ggtgagccag      240
atcatcgagc agctgatcaa gaaggagaag gtgtacctgg cctgggtgcc cgcccacaag     300
ggcatcggcg gcaacgagca ggtggacaag ctggtgagcg ccggcatccg caaggtgctg      360

<210> SEQ ID NO 30
<211> LENGTH: 2460
<212> TYPE: DNA
<213> ORGANISM: Artificial Sequence
<220> FEATURE:
<223> OTHER INFORMATION: Description of Artificial Sequence:
      p2Pol.opt.YMWM.SF2

<400> SEQUENCE: 30
gccaccatgg ccgaggcgat gagccaggtg acgaacccgg cgaccatcat gatgcagcgc       60
ggcaacttcc gcaaccagcg gaagaccgtc aagtgcttca actgcggcaa ggagggccac      120
accgccagga actgccgcgc cccccgcaag aagggctgct ggcgctgcgg ccgcgaagga     180
caccaaatga agattgcac tgagagacag gctaatttct ccgcgagga cctggccttc       240 ctgcagggca aggcccgcga gttcagcagc gagcagaccc gccaacag ccccaccgc        300 cgcgagctgc aggtgtgggg cggcgagaac aacagcctga gcgaggcgg cgccgaccgc      360 cagggcaccg tgagcttcaa cttcccccag atcccctgt ggcagcgccc cctggtgacc      420
atcaggatcg gcggccagct caaggaggcg ctgctcgcca ccggcgccga cgacaccgtg     480
ctggaggaga tgaacctgcc cggcaagtgg aagcccaaga tgatcggcgg gatcgggggc     540
ttcatcaagg tgcggcagta cgaccagatc cccgtggaga tctgcggcca caggccatc      600
```

```
ggcaccgtgc tggtgggccc caccccgtg aacatcatcg gccgcaacct gctgacccag    660
atcggctgca ccctgaactt ccccatcagc cccatcgaga cggtgcccgt gaagctgaag    720
ccggggatgg acggcccaa ggtcaagcag tggcccctga ccgaggagaa gatcaaggcc    780
ctggtggaga tctgcaccga gatggagaag gagggcaaga tcagcaagat cggccccgag    840
aacccctaca caccccgt gttcgccatc aagaagaagg acagcaccaa gtggcgcaag    900
ctggtggact ccgcgagct gaacaagcgc acccaggact ctgggaggt gcagctgggc    960 atccccacc ccgccggcct gaagaagaag aagagcgtga ccgtgctgga cgtgggcgac   1020
gcctacttca gcgtgcccct ggacaaggac ttccgcaagt acaccgcctt caccatcccc   1080
agcatcaaca cgagaccccc cggcatccgc taccagtaca cgtgctgcc ccagggctgg   1140 aagggcagcc ccgccatctt ccagagcagc atgaccaaga tcctggagcc cttccgcaag   1200
cagaaccccg acatcgtgat ctaccaggcc cccctgtacg tgggcagcga cctggagatc   1260
ggccagcacc gcaccaagat cgaggagctg cgccagcacc tgctgcgctg ggcttcacc   1320 acccccgaca agaagcacca gaaggagccc cccttcctgc ccatcgagct gcaccccgac   1380
aagtggaccg tgcagcccat catgctgccc gagaaggaca ctggaccgt gaacgacatc   1440 cagaagctgg tgggcaagct gaactgggcc agccagatct acgccggcat caaggtgaag   1500
cagctgtgca gctgctgcg cggcaccaag gccctgaccg aggtgatccc cctgaccgag   1560
gaggccgagc tggagctggc cgagaaccgc gagatcctga aggagcccgt gcacgaggtg   1620
tactacgacc ccagcaagga cctggtggcc gagatccaga gcagggcca gggccagtgg   1680 acctaccaga tctaccagga gcccttcaag aacctgaaga ccggcaagta cgcccgcatg   1740
cgcggcgccc acaccaacga cgtgaagcag ctgaccgagg ccgtgcagaa ggtgagcacc   1800
gagagcatcg tgatctgggg caagatcccc aagttcaagc tgcccatcca aggagacc   1860 tgggaggcct ggtggatgga gtactggcag gccacctgga tccccgagtg ggagttcgtg   1920 aacaccccc ccctggtgaa gctgtggtac cagctggaga aggagcccat cgtgggcgcc   1980
gagaccttct acgtggacgg cgccgccaac cgcgagacca gctgggcaa ggccggctac   2040 gtgaccgacc ggggccggca aaggtggtg agcatcgccg acaccaccaa ccagaagacc   2100
gagctgcagg ccatccacct ggccctgcag gacagcggcc tggaggtgaa catcgtgacc   2160
gacagccagt acgccctggg catcatccag gcccagcccg acaagagcga gagcgagctg   2220
gtgagccaga tcatcgagca gctgatcaag aaggagaagg tgtacctggc ctgggtgccc   2280
gcccacaagg gcatcggcgg caacgagcag gtggacaagc tggtgagcgc cggcatccgc   2340
aaggtgctgt tcctgaacgg catcgatggc ggcatcgtga tctaccagta catggacgac   2400
ctgtacgtgg gcagcggcgg ccctaggatc gattaaaagc ttcccggggc tagcaccggt   2460
```

<210> SEQ ID NO 31
<211> LENGTH: 2466
<212> TYPE: DNA
<213> ORGANISM: Artificial Sequence
<220> FEATURE:
<223> OTHER INFORMATION: Description of Artificial Sequence:
      p2PolInaopt.YM.SF2

<400> SEQUENCE: 31

```
gccaccatgg ccgaggcgat gagccaggtg acgaacccgg cgaccatcat gatgcagcgc     60
ggcaacttcc gcaaccagcg gaagaccgtc aagtgcttca actgcggcaa ggagggccac    120
accgccagga actgccgcgc ccccgcaag aagggctgct ggcgctgcgg ccgcgaagga    180
```

```
caccaaatga aagattgcac tgagagacag gctaatttct tccgcgagga cctggccttc    240
ctgcagggca aggcccgcga gttcagcagc gagcagaccc gcgccaacag ccccacccgc    300
cgcgagctgc aggtgtgggg cggcgagaac aacagcctga gcgaggccgg cgccgaccgc    360
cagggcaccg tgagcttcaa cttcccccag atcaccctgt ggcagcgccc cctggtgacc    420
atcaggatcg gcggccagct caaggaggcg ctgctcgcca ccggcgccga cgacaccgtg    480
ctggaggaga tgaacctgcc cggcaagtgg aagcccaaga tgatcggcgg gatcgggggc    540
ttcatcaagg tgcggcagta cgaccagatc cccgtggaga tctgcggcca aaggccatc     600 ggcaccgtgc tggtgggccc cacccccgtg aacatcatcg gccgcaacct gctgacccag    660
atcggctgca ccctgaactt ccccatcagc ccatcgaga cggtgcccgt gaagctgaag      720
ccggggatgg acgcccccaa ggtcaagcag tggcccctga ccgaggagaa gatcaaggcc    780
ctggtggaga tctgcaccga gatggagaag gagggcaaga tcagcaagat cggccccgag    840 aaccccctaca cacccccgt gttcgccatc aagaagaagg acagcaccaa gtggcgcaag     900
ctggtggact tccgcgagct gaacaagcgc acccaggact tctgggaggt gcagctgggc    960
atcccccacc ccgccggcct gaagaagaag aagagcgtga ccgtgctgga cgtgggcgac   1020
gcctacttca gcgtgcccct ggacaaggac ttccgcaagt acaccgcctt caccatcccc   1080
agcatcaaca cgagaccccc cggcatccgc taccagtaca cgtgctgcc ccagggctgg      1140 aagggcagcc ccgccatctt ccagagcagc atgaccaaga tcctggagcc cttccgcaag   1200
cagaaccccg acatcgtgat ctaccaggcc cccctgtacg tgggcagcga cctggagatc   1260
ggccagcacc gcaccaagat cgaggagctg cgccagcacc tgctgcgctg gggcttcacc   1320 accccccgaca agaagcacca gaaggagccc cccttcctgt ggatgggcta cgagctgcac   1380
cccgacaagt ggaccgtgca gcccatcatg ctgcccgaga aggacagctg gaccgtgaac   1440
gacatccaga gctggtggg caagctgaac tgggccagcc agatctacgc cggcatcaag      1500
gtgaagcagc tgtgcaagct gctgcgcggc accaaggccc tgaccgaggt gatccccctg   1560
accgaggagg ccgagctgga gctggccgag aaccgcgaga tcctgaagga gcccgtgcac   1620
gaggtgtact acgaccccag caaggacctg gtggccgaga tccagaagca gggccagggc   1680
cagtggacct accagatcta ccaggagccc ttcaagaacc tgaagaccgg caagtacgcc   1740
cgcatgcgcg cgcccacac caacgacgtg aagcagctga ccgaggccgt gcagaaggtg   1800
agcaccgaga gcatcgtgat ctggggcaag atccccaagt tcaagctgcc catccagaag   1860
gagacctggg aggcctggtg gatggagtac tggcaggcca cctggatccc cgagtgggag   1920
ttcgtgaaca ccccccccct ggtgaagctg tggtaccagc tggagaagga gcccatcgtg   1980
ggcgccgaga ccttctacgt ggacggcgcc gccaaccgcg agaccaagct gggcaaggcc   2040
ggctacgtga ccgaccgggg ccggcagaag gtggtgagca tcgccgacac caccaaccag   2100
aagaccgagc tgcaggccat ccacctggcc ctgcaggaca cggcctgga ggtgaacatc     2160 gtgaccgaca gccagtacgc cctgggcatc atccaggccc agcccgacaa gagcgagagc   2220
gagctggtga gccagatcat cgagcagctg atcaagaagg agaaggtgta cctggcctgg   2280
gtgcccgccc acaagggcat cggcggcaac gagcaggtgg acaagctggt gagcgccggc   2340
atccgcaagg tgctgttcct gaacggcatc gatggcggca tcgtgatcta ccagtacatg   2400
gacgacctgt acgtgggcag cggcggccct aggatcgatt aaaagcttcc gggggctagc   2460
accggt                                                               2466
```

<210> SEQ ID NO 32

<211> LENGTH: 2472
<212> TYPE: DNA
<213> ORGANISM: Artificial Sequence
<220> FEATURE:
<223> OTHER INFORMATION: Description of Artificial Sequence: p2Polopt.SF2

<400> SEQUENCE: 32

| | |
|---|---|
| gccaccatgg ccgaggcgat gagccaggtg acgaacccgg cgaccatcat gatgcagcgc | 60 |
| ggcaacttcc gcaaccagcg gaagaccgtc aagtgcttca actgcggcaa ggagggccac | 120 |
| accgccagga actgccgcgc cccccgcaag aagggctgct ggcgctgcgg ccgcgaagga | 180 |
| caccaaatga agattgcac tgagagacag gctaatttct tccgcgagga cctggccttc | 240 |
| ctgcagggca aggcccgcga gttcagcagc gagcagaccc gcgccaacag ccccacccgc | 300 |
| cgcgagctgc aggtgtgggg cggcgagaac aacagcctga gcgaggccgg cgccgaccgc | 360 |
| cagggcaccg tgagcttcaa cttcccccag atcaccctgt ggcagcgccc cctggtgacc | 420 |
| atcaggatcg gcgccagct caaggaggcg ctgctcgaca ccggcgccga cgacaccgtg | 480 |
| ctggaggaga tgaacctgcc cggcaagtgg aagcccaaga tgatcggcgg gatcggggc | 540 |
| ttcatcaagg tgcggcagta cgaccagatc cccgtgagga tctgcggcca caaggccatc | 600 |
| ggcaccgtgc tggtgggccc cacccccgtg aacatcatcg gccgcaacct gctgacccag | 660 |
| atcggctgca ccctgaactt ccccatcagc cccatcgaga cggtgcccgt gaagctgaag | 720 |
| ccggggatgg acggccccaa ggtcaagcag tggcccctga ccgaggagaa gatcaaggcc | 780 |
| ctggtggaga tctgcaccga gatggagaag gagggcaaga tcagcaagat cggcccccgag | 840 |
| aaccccctaca cacccccgt gttcgccatc aagaagaagg acagcaccaa gtggcgcaag | 900 |
| ctggtggact ccgcgagct gaacaagcgc acccaggact ctgggaggt gcagctgggc | 960 |
| atccccacc ccgccggcct gaagaagaag aagagcgtga ccgtgctgga cgtgggcgac | 1020 |
| gcctacttca gcgtgcccct ggacaaggac ttccgcaagt acaccgcctt caccatcccc | 1080 |
| agcatcaaca acgagacccc cggcatccgc taccagtaca acgtgctgcc ccagggctgg | 1140 |
| aagggcagcc ccgccatctt ccagagcagc atgaccaaga tcctggagcc cttccgcaag | 1200 |
| cagaaccccg acatcgtgat ctaccagtac atggacgacc tgtacgtggg cagcgacctg | 1260 |
| gagatcggcc agcaccgcac caagatcgag gagctgcgcc agcacctgct cgcctggggc | 1320 |
| ttcaccaccc ccgacaagaa gcaccagaag gagcccccct tcctgtggat gggctacgag | 1380 |
| ctgcacccg acaagtggac cgtgcagccc atcatgctgc ccgagaagga cagctggacc | 1440 |
| gtgaacgaca tccagaagct ggtgggcaag ctgaactggg ccagccagat ctacgccggc | 1500 |
| atcaaggtga gcagctgtg caagctgctg cgcggcacca aggccctgac cgaggtgatc | 1560 |
| cccctgaccg aggaggccga gctggagctg gccgagaacc gcgagatcct gaaggagccc | 1620 |
| gtgcacgagg tgtactacga ccccagcaag gacctggtgg ccgagatcca gaagcagggc | 1680 |
| cagggccagt ggacctacca gatctaccag gagcccttca gaacctgaa gaccggcaag | 1740 |
| tacgcccgca tgcgcggcgc ccacaccaac gacgtgaagc agctgaccga ggccgtgcag | 1800 |
| aaggtgagca ccgagagcat cgtgatctgg ggcaagatcc ccaagttcaa gctgccatc | 1860 |
| cagaaggaga cctgggaggc ctggtggatg gagtactggc aggccacctg gatccccgag | 1920 |
| tgggagttcg tgaacacccc cccctggtg aagctgtggt accagctgga aggagccc | 1980 |
| atcgtgggcg ccgagacctt ctacgtggac ggcgccgcca accgcgagac caagctgggc | 2040 |
| aaggccggct acgtgaccga ccggggccgg cagaaggtgg tgagcatcgc cgacaccacc | 2100 |
| aaccagaaga ccgagctgca ggccatccac ctggccctgc aggacagcgg cctggaggtg | 2160 |

| | |
|---|---:|
| aacatcgtga ccgacagcca gtacgccctg ggcatcatcc aggcccagcc cgacaagagc | 2220 |
| gagagcgagc tggtgagcca gatcatcgag cagctgatca agaaggagaa ggtgtacctg | 2280 |
| gcctgggtgc ccgcccacaa gggcatcggc ggcaacgagc aggtggacaa gctggtgagc | 2340 |
| gccggcatcc gcaaggtgct gttcctgaac ggcatcgatg gcggcatcgt gatctaccag | 2400 |
| tacatggacg acctgtacgt gggcagcggc ggccctagga tcgattaaaa gcttcccggg | 2460 |
| gctagcaccg gt | 2472 |

<210> SEQ ID NO 33
<211> LENGTH: 3639
<212> TYPE: DNA
<213> ORGANISM: Artificial Sequence
<220> FEATURE:
<223> OTHER INFORMATION: Description of Artificial Sequence:
    p2PolTatRevNef.opt.native_B

<400> SEQUENCE: 33

| | |
|---|---:|
| atggccgagg cgatgagcca ggtgacgaac ccggcgacca tcatgatgca gcgcggcaac | 60 |
| ttccgcaacc agcggaagac cgtcaagtgc ttcaactgcg gcaaggaggg ccacaccgcc | 120 |
| aggaactgcc gcgccccccg caagaagggc tgctggcgct gcggccgcga aggacaccaa | 180 |
| atgaaagatt gcactgagag acaggctaat ttcttccgcg aggacctggc cttcctgcag | 240 |
| ggcaaggccc gcgagttcag cagcgagcag acccgcgcca cagccccac cgccgcgag | 300 |
| ctgcaggtgt ggggcggcga gaacaacagc ctgagcgagg ccggcgccga ccgccagggc | 360 |
| accgtgagct tcaacttccc ccagatcacc ctgtggcagc gccccctggt gaccatcagg | 420 |
| atcggcggcc agctcaagga ggcgctgctc gacaccggcg ccgacgacac cgtgctggag | 480 |
| gagatgaacc tgcccggcaa gtggaagccc aagatgatcg gcgggatcgg ggcttcatc | 540 |
| aaggtgcggc agtacgacca gatccccgtg gagatctgcg ccacaaggc catcggcacc | 600 |
| gtgctggtgg gccccacccc cgtgaacatc atcggccgca acctgctgac ccagatcggc | 660 |
| tgcaccctga acttccccat cagccccatc gagacggtgc ccgtgaagct gaagccgggg | 720 |
| atggacggcc ccaaggtcaa gcagtggccc ctgaccgagg agaagatcaa ggccctggtg | 780 |
| gagatctgca ccgagatgga aggagggc aagatcagca agatcggccc cgagaacccc | 840 |
| tacaacaccc ccgtgttcgc catcaagaag aaggacagca ccaagtggcg caagctggtg | 900 |
| gacttccgcg agctgaacaa gcgcacccag gacttctggg aggtgcagct gggcatcccc | 960 |
| cacccccgcg gcctgaagaa gaagaagagc gtgaccgtgc tggacgtggg cgacgcctac | 1020 |
| ttcagcgtgc ccctggacaa ggacttccgc aagtacaccg ccttcaccat ccccagcatc | 1080 |
| aacaacgaga cccccggcat ccgctaccag tacaacgtgc tgccccaggg ctggaagggc | 1140 |
| agccccgcca tcttccagag cagcatgacc aagatcctgg agcccttccg caagcagaac | 1200 |
| cccgacatcg tgatctacca gtacatggac gacctgtacg tgggcagcga cctggagatc | 1260 |
| ggccagcacc gcaccaagat cgaggagctg cgccagcacc tgctgcgctg ggcttcacc | 1320 |
| accccgaca gaagcacca gaaggagccc cccttcctgt ggatgggcta cgagctgcac | 1380 |
| cccgacaagt ggaccgtgca gcccatcatg ctgcccgaga aggacagctg gaccgtgaac | 1440 |
| gacatccaga gctggtggg caagctgaac tgggccagcc agatctacgc cggcatcaag | 1500 |
| gtgaagcagc tgtgcaagct gctgcgcggc accaaggccc tgaccgaggt gatccccctg | 1560 |
| accgaggagg ccgagctgga gctggccgag aaccgcgaga tcctgaagga gcccgtgcac | 1620 |
| gaggtgtact acgaccccag caaggacctg gtggccgaga tccagaagca gggccagggc | 1680 |

```
cagtggacct accagatcta ccaggagccc ttcaagaacc tgaagaccgg caagtacgcc    1740
cgcatgcgcg cgcccacac caacgacgtg aagcagctga ccgaggccgt gcagaaggtg    1800
agcaccgaga gcatcgtgat ctggggcaag atccccaagt tcaagctgcc catccagaag    1860
gagacctggg aggcctggtg gatggagtac tggcaggcca cctggatccc cgagtgggag    1920
ttcgtgaaca cccccccct ggtgaagctg tggtaccagc tggagaagga gcccatcgtg    1980
ggcgccgaga ccttctacgt ggacggcgcc gccaaccgcg agaccaagct gggcaaggcc    2040
ggctacgtga ccgaccgggg ccggcagaag gtggtgagca tcgccgacac caccaaccag    2100
aagaccgagc tgcaggccat ccacctggcc ctgcaggaca cgggcctgga ggtgaacatc    2160
gtgaccgaca gccagtacgc cctgggcatc atccaggccc agcccgacaa gagcgagagc    2220
gagctggtga ccagatcat cgagcagctg atcaagaagg agaaggtgta cctggcctgg    2280
gtgcccgccc acaagggcat cggcggcaac gagcaggtgg acaagctggt gagcgccggc    2340
atccgcaagg tgctggaatt cgagcccgtg accccccgcc tggagccctg gaagcacccc    2400
ggcagccagc ccaagaccgc ctgcaccaac tgctactgca agaagtgctg cttccactgc    2460
caggtgtgct tcatcaccaa gggcctgggc atcagctacg ccgcaagaa cgccgccag    2520 cgccgccgcg ccccccccga cagcgaggtg caccaggtga gcctgcccaa gcagcccgcc    2580
agccagcccc agggcgaccc caccggcccc aaggagagca agaagaaggt ggagcgcgag    2640
accgagaccg accccgtgca cccggggcc ggccgcagcg gcgacagcga cgaggagctg    2700
ctgcagaccg tgcgcttcat caagttcctg taccagagca ccccctgcc cagccccaag    2760 ggcacccgcc aggcccgccg caaccgccgc cgccgctggc gcgagcgcca gcgccagatc    2820
cagagcatca gcgcctggat catcagcacc cacctgggcc gcagcaccga gcccgtgccc    2880
ctgcagctgc ccccctgga gcgcctgaac ctggactgca gcgaggactg cggcaccagc    2940
ggcacccagg gcgtgggcag cccccaggtc ctgggcgaga gccccgccgt gctggacagc    3000
ggcaccaagg agctcgaggg cggcaagtgg agcaagcgca tgagcggctg gagcgccgtg    3060
cgcgagcgca tgaagcgcgc cgagcccgcc gagcccgccg ccgacggcgt gggcgccgtg    3120
agccgcgacc tggagaagca cggcgccatc accagcagca caccgccgc caacaacgcc    3180 gactgcgcct ggctggaggc ccaggaggac gaggacgtgg gcttccccgt gcgcccccag    3240
gtgcccctgc gccccatgac ctacaaggcc gccctggacc tgagccactt cctgaaggag    3300
aagggcggcc tggagggcct gatctacagc cagaagcgcc aggacatcct ggacctgtgg    3360
atccaccaca cccagggcta cttccccgac tggcagaact acaccccgg ccccggcatc    3420 cgctacccc tgaccttcgg ctggtgcttc aagctggtgc ccgtggaccc cgactacgtg    3480
gaggaggcca cgccggcga gaacaacagc ctgctgcacc ccatgagcca gcacggcatg    3540
gacgaccccg agaaggaggt gctggtgtgg cgcttcgaca ccgcctggc cttccaccac    3600 atggcccgcg agctgcaccc cgagtactac aaggactgc                          3639
```

<210> SEQ ID NO 34
<211> LENGTH: 3735
<212> TYPE: DNA
<213> ORGANISM: Artificial Sequence
<220> FEATURE:
<223> OTHER INFORMATION: Description of Artificial Sequence:
      p2PolTatRevNef.opt_B

<400> SEQUENCE: 34

```
gccaccatgg ccgaggcgat gagccaggtg acgaacccgg cgaccatcat gatgcagcgc      60
ggcaacttcc gcaaccagcg gaagaccgtc aagtgcttca actgcggcaa ggagggccac     120
```

```
accgccagga actgccgcgc cccccgcaag aagggctgct ggcgctgcgg ccgcgaagga    180
caccaaatga aagattgcac tgagagacag gctaatttct tccgcgagga cctggccttc    240
ctgcagggca aggcccgcga gttcagcagc gagcagaccc gcgccaacag ccccacccgc    300
cgcgagctgc aggtgtgggg cggcgagaac aacagcctga gcgaggccgg cgccgaccgc    360
cagggcaccg tgagcttcaa cttcccccag atcaccctgt ggcagcgccc cctggtgacc    420
atcaggatcg gcggccagct caaggaggcg ctgctcgcca ccggcgccga cgacaccgtg    480
ctggaggaga tgaacctgcc cggcaagtgg aagcccaaga tgatcggcgg gatcggggc    540 ttcatcaagg tgcggcagta cgaccagatc cccgtggaga tctgcggcca caaggccatc    600
ggcaccgtgc tggtgggccc caccccgtg aacatcatcg gccgcaacct gctgacccag    660
atcggctgca ccctgaactt ccccatcagc ccatcgaga cggtgcccgt gaagctgaag    720
ccggggatgg acggcccaa ggtcaagcag tggcccctga ccgaggagaa gatcaaggcc    780
ctggtggaga tctgcaccga gatggagaag gagggcaaga tcagcaagat cggccccgag    840
aacccctaca cacccccgt gttcgccatc aagaagaagg acagcaccaa gtggcgcaag    900
ctggtggact tccgcgagct gaacaagcgc acccaggact tctgggaggt gcagctgggc    960
atcccccacc ccgccggcct gaagaagaag aagagcgtga ccgtgctgga cgtgggcgac    1020
gcctacttca gcgtgcccct ggacaaggac ttccgcaagt acaccgcctt caccatcccc    1080
agcatcaaca acgagacccc cggcatccgc taccagtaca acgtgctgcc ccagggctgg    1140
aagggcagcc ccgccatctt ccagagcagc atgaccaaga tcctggagcc cttccgcaag    1200
cagaaccccg acatcgtgat ctaccaggcc cccctgtacg tgggcagcga cctggagatc    1260
ggccagcacc gcaccaagat cgaggagctg cgccagcacc tgctgcgctg ggcttcacc    1320 acccccgaca agaagcacca agggagccc cccttcctgc ccatcgagct gcaccccgac    1380
aagtggaccg tgcagcccat catgctgccc gagaaggaca gctggaccgt gaacgacatc    1440
cagaagctgg tgggcaagct gaactgggcc agccagatct cgccggcat caaggtgaag    1500 cagctgtgca agctgctgcg cggcaccaag gccctgaccg aggtgatccc cctgaccgag    1560
gaggccgagc tggagctggc cgagaaccgc gagatcctga aggagcccgt gcacgaggtg    1620
tactacgacc ccagcaagga cctggtggcc gagatccaga agcagggcca gggccagtgg    1680
acctaccaga tctaccagga gcccttcaag aacctgaaga ccggcaagta cgcccgcatg    1740
cgcggcgccc acaccaacga cgtgaagcag ctgaccgagg ccgtgcagaa ggtgagcacc    1800
gagagcatcg tgatctgggg caagatcccc aagttcaagc tgcccatcca gaaggagacc    1860
tgggaggcct ggtggatgga gtactggcag gccacctgga tccccgagtg ggagttcgtg    1920
aacacccccc ccctggtgaa gctgtggtac cagctggaga aggagcccat cgtgggcgcc    1980
gagaccttct acgtggacgg cgccgccaac cgcgagacca gctgggcaa ggccggctac    2040 gtgaccgacc ggggccggca aaggtggtg agcatcgccg acaccaccaa ccagaagacc    2100
gagctgcagg ccatccacct ggccctgcag gacagcggcc tggaggtgaa catcgtgacc    2160
gacagccagt acgccctggg catcatccag gcccagcccg acaagagcga gagcgagctg    2220
gtgagccaga tcatcgagca gctgatcaag aaggagaagg tgtacctggc ctgggtgccc    2280
gcccacaagg gcatcggcgg caacgagcag gtggacaagc tggtgagcgc cggcatccgc    2340
aaggtgctgt tcctgaacgg catcgatggc ggcatcgtga tctaccagta catggacgac    2400
ctgtacgtgg gcagcggcgg ccctagggag cccgtggacc cccgcctgga gccctggaag    2460 cacccccggca gccagcccaa gaccgccggc accaactgct actgcaagaa gtgctgcttc    2520
```

| | |
|---|---|
| cactgccagg tgagcttcat caccaagggc ctgggcatca gctacggccg caagaagcgc | 2580 |
| cgccagcgcc gccgcgcccc ccccgacagc gaggtgcacc aggtgagcct gcccaagcag | 2640 |
| cccgccagcc agcccagggc gaccccacc ggccccaagg agagcaagaa gaaggtggag | 2700 |
| cgcgagaccg agaccgaccc cgtgcacccc ggggccggcc gcagcggcga cagcgacgag | 2760 |
| gagctgctgc agaccgtgcg cttcatcaag ttcctgtacc agagcaaccc cctgcccagc | 2820 |
| cccaagggca cccgccaggc cgacctgaac cgccgccgcc gctggcgcga cgccagcgc | 2880 |
| cagatccaga gcatcagcgc ctggatcatc agcacccacc tgggccgcag caccgagccc | 2940 |
| gtgcccctgc agctgccccc cgacctgcgc ctgaacctgg actgcagcga ggactgcggc | 3000 |
| accagcggca cccagggcgt gggcagcccc caggtgctgg gcgagagccc cgccgtgctg | 3060 |
| gacagcggca ccaaggagct cgaggccggc aagtggagca gcgcatgag cggctggagc | 3120 |
| gccgtgcgcg agcgcatgaa gcgcgccgag cccgccgagc ccgccgccga cggcgtgggc | 3180 |
| gccgtgagcc gcgacctgga gaagcacggc gccatcacca gcagcaacac cgccgccaac | 3240 |
| aacgccgact cgcctggct ggaggccag gaggacgagg acgtgggctt ccccgtgcgc | 3300 |
| ccccaggtgc cctgcgccc catgacctac aaggccgccc tggacctgag ccacttcctg | 3360 |
| aaggagaagg gcggcctgga gggcctgatc tacagccaga gcgccagga catcctggac | 3420 |
| ctgtggatcc accacaccca gggctacttc cccggctggc agaactacac ccccggcccc | 3480 |
| ggcatccgct acccctgac cttcggctgg tgcttcaagc tggtgcccgt ggaccccgac | 3540 |
| tacgtggagg aggccaacgc cggcgagaac aacagcctgc tgcacccat gagccagcac | 3600 |
| ggcatggacg accccgagaa ggaggtgctg gtgtggcgct cgacagccg cctggccttc | 3660 |
| caccacatgg cccgcgagct gcaccccgag tactacaagg actgcgatta aaagcttccc | 3720 |
| ggggctagca ccggt | 3735 |

<210> SEQ ID NO 35
<211> LENGTH: 2145
<212> TYPE: DNA
<213> ORGANISM: Artificial Sequence
<220> FEATURE:
<223> OTHER INFORMATION: Description of Artificial Sequence: pol.opt.SF2

<400> SEQUENCE: 35

| | |
|---|---|
| ttcttccgcg aggacctggc cttcctgcag ggcaaggccc gcgagttcag cagcgagcag | 60 |
| acccgcgcca acagccccac ccgccgcgag ctgcaggtgt ggggcggcga gaacaacagc | 120 |
| ctgagcgagg ccggcgccga ccgccagggc accgtgagct tcaacttccc ccagatcacc | 180 |
| ctgtggcagc gccccctggt gaccatcagg atcggcggcc agctcaagga ggcgctgctc | 240 |
| gacaccggcg ccgacgacac cgtgctggag gagatgaacc tgcccggcaa gtggaagccc | 300 |
| aagatgatcg gcgggatcgg gggcttcatc aaggtgcggc agtacgacca gatccccgtg | 360 |
| gagatctgcg gccacaaggc catcggcacc gtgctggtgg gccccacccc cgtgaacatc | 420 |
| atcggccgca acctgctgac ccagatcggc tgcaccctga acttccccat cagccccatc | 480 |
| gagacggtgc ccgtgaagct gaagccgggg atggacggcc ccaaggtcaa gcagtggccc | 540 |
| ctgaccgagg agaagatcaa ggccctggtg gagatctgca ccgagatgga aggagggc | 600 |
| aagatcagca agatcggccc cgagaacccc tacaacaccc ccgtgttcgc catcaagaag | 660 |
| aaggacagca ccaagtggcg caagctggtg gacttccgcg agctgaacaa gcgcacccag | 720 |
| gacttctggg aggtgcagct gggcatcccc caccccgccg gctgaagaa gaagaagagc | 780 |
| gtgaccgtgc tggacgtggg cgacgcctac ttcagcgtgc ccctggacaa ggacttccgc | 840 |

-continued

```
aagtacaccg ccttcaccat ccccagcatc aacaacgaga cccccggcat ccgctaccag      900
tacaacgtgc tgccccaggg ctggaagggc agccccgcca tcttccagag cagcatgacc      960
aagatcctgg agcccttccg caagcagaac cccgacatcg tgatctacca gtacatggac     1020
gacctgtacg tgggcagcga cctggagatc ggccagcacc gcaccaagat cgaggagctg     1080
cgccagcacc tgctgcgctg gggcttcacc accccgaca agaagcacca gaaggagccc     1140
cccttcctgt ggatgggcta cgagctgcac cccgacaagt ggaccgtgca gcccatcatg     1200
ctgcccgaga aggacagctg gaccgtgaac gacatccaga agctggtggg caagctgaac     1260
tgggccagcc agatctacgc cggcatcaag gtgaagcagc tgtgcaagct gctgcgcggc     1320
accaaggccc tgaccgaggt gatcccctg accgaggagg ccgagctgga gctggccgag     1380
aaccgcgaga tcctgaagga gcccgtgcac gaggtgtact acgaccccag caaggacctg     1440
gtggccgaga tccagaagca gggccagggc cagtggacct accagatcta ccaggagccc     1500
ttcaagaacc tgaagaccgg caagtacgcc cgcatgcgcg cgcccacac caacgacgtg     1560 aagcagctga ccgaggccgt gcagaaggtg agcaccgaga gcatcgtgat ctggggcaag     1620
atccccaagt tcaagctgcc catccagaag gagacctggg aggcctggtg gatggagtac     1680
tggcaggcca cctggatccc cgagtgggag ttcgtgaaca cccccccct ggtgaagctg     1740 tggtaccagc tggagaagga gcccatcgtg ggcgccgaga ccttctacgt ggacggcgcc     1800
gccaaccgcg agaccaagct gggcaaggcc ggctacgtga ccgaccgggg ccggcagaag     1860
gtggtgagca tcgccgacac caccaaccag aagaccgagc tgcaggccat ccacctggcc     1920
ctgcaggaca gcggcctgga ggtgaacatc gtgaccgaca gccagtacgc cctgggcatc     1980
atccaggccc agcccgacaa gagcgagagc gagctggtga gccagatcat cgagcagctg     2040
atcaagaagg agaaggtgta cctggcctgg gtgcccgccc acaagggcat cggcggcaac     2100
gagcaggtgg acaagctggt gagcgccggc atccgcaagg tgctg                    2145
```

<210> SEQ ID NO 36
<211> LENGTH: 297
<212> TYPE: DNA
<213> ORGANISM: Artificial Sequence
<220> FEATURE:
<223> OTHER INFORMATION: Description of Artificial Sequence:
    prot.opt.SF2

<400> SEQUENCE: 36

```
ccccagatca ccctgtggca gcgcccctg gtgaccatca ggatcggcgg ccagctcaag       60
gaggcgctgc tcgacaccgg cgccgacgac accgtgctgg aggagatgaa cctgcccggc     120
aagtggaagc ccaagatgat cggcgggatc gggggcttca tcaaggtgcg gcagtacgac     180
cagatccccg tggagatctg cggccacaag gccatcggca ccgtgctggt gggcccccacc     240 cccgtgaaca tcatcggccg caacctgctg acccagatcg gctgcaccct gaacttc       297
```

<210> SEQ ID NO 37
<211> LENGTH: 297
<212> TYPE: DNA
<213> ORGANISM: Artificial Sequence
<220> FEATURE:
<223> OTHER INFORMATION: Description of Artificial Sequence:
    protIna.opt.SF2

<400> SEQUENCE: 37

```
ccccagatca ccctgtggca gcgcccctg gtgaccatca ggatcggcgg ccagctcaag       60
gaggcgctgc tcgccaccgg cgccgacgac accgtgctgg aggagatgaa cctgcccggc     120
```

```
aagtggaagc ccaagatgat cggcgggatc gggggcttca tcaaggtgcg gcagtacgac    180
cagatccccg tggagatctg cggccacaag gccatcggca ccgtgctggt gggccccacc    240
cccgtgaaca tcatcggccg caacctgctg acccagatcg gctgcaccct gaacttc      297
```

<210> SEQ ID NO 38  
<211> LENGTH: 1971  
<212> TYPE: DNA  
<213> ORGANISM: Artificial Sequence  
<220> FEATURE:  
<223> OTHER INFORMATION: Description of Artificial Sequence: protInaRT.YM.opt.SF2

<400> SEQUENCE: 38

```
ccccagatca ccctgtggca gcgcccctg  gtgaccatca ggatcggcgg ccagctcaag      60
gaggcgctgc tcgccaccgg cgccgacgac accgtgctgg aggagatgaa cctgcccggc     120
aagtggaagc ccaagatgat cggcgggatc gggggcttca tcaaggtgcg gcagtacgac    180
cagatccccg tggagatctg cggccacaag gccatcggca ccgtgctggt gggccccacc    240
cccgtgaaca tcatcggccg caacctgctg acccagatcg gctgcaccct gaacttcccc    300
atcagcccca tcgagacggt gcccgtgaag ctgaagccgg ggatggacgg ccccaaggtc    360
aagcagtggc ccctgaccga ggagaagatc aaggccctgg tggagatctg caccgagatg    420
gagaaggagg gcaagatcag caagatcggc ccagagaacc cctacaacac ccccgtgttc    480
gccatcaaga gaaggacag caccaagtgg cgcaagctgg tggacttccg cgagctgaac    540
aagcgcaccc aggacttctg ggaggtgcag ctgggcatcc cccaccccgc cggcctgaag    600
aagaagaaga gcgtgaccgt gctggacgtg ggcgacgcct acttcagcgt gcccctggac    660
aaggacttcc gcaagtacac cgccttcacc atccccagca tcaacaacga gaccccggc     720 atccgctacc agtacaacgt gctgcccag  ggctggaagg gcagccccgc catcttccag    780
agcagcatga ccaagatcct ggagcccttc cgcaagcaga ccccgacat  cgtgatctac    840 caggcccccc tgtacgtggg cagcgacctg gagatcggcc agcaccgcac caagatcgag    900
gagctgcgcc agcacctgct gcgctggggc ttcaccaccc ccgacaagaa gcaccagaag    960 gagccccct   tcctgtggat gggctacgag ctgcaccccg acaagtggac cgtgcagccc   1020
atcatgctgc ccgagaagga cagctggacc gtgaacgaca tccagaagct ggtgggcaag   1080
ctgaactggg ccagccagat ctacgccggc atcaaggtga agcagctgtg caagctgctg   1140
cgcggcacca aggccctgac cgaggtgatc cccctgaccg aggaggccga gctggagctg   1200
gccgagaacc gcgagatcct gaaggagccc gtgcacgagg tgtactacga ccccagcaag   1260
gacctggtgg ccgagatcca gaagcaggc  cagggccagt ggacctacca gatctaccag   1320
gagcccttca gaacctgaa gaccggcaag tacgcccgca tgcgcggcgc ccacaccaac   1380
gacgtgaagc agctgaccga ggccgtgcag aaggtgagca ccgagagcat cgtgatctgg   1440
ggcaagatcc ccaagttcaa gctgcccatc cagaaggaga cctgggaggc ctggtggatg   1500
gagtactggc aggccacctg gatccccgag tgggagttcg tgaacacccc ccccctggtg   1560
aagctgtggt accagctgga gaaggagccc atcgtgggcg ccgagacctt ctacgtggac   1620
ggcgccgcca ccgcgagac caagctgggc aaggccggct acgtgaccga ccggggccgg   1680
cagaaggtgg tgagcatcgc cgacaccacc aaccagaaga ccgagctgca ggccatccac   1740
ctggccctgc aggacagcgg cctggaggtg aacatcgtga ccgacagcca gtacgccctg   1800
ggcatcatcc aggcccagcc cgacaagagc gagagcgagc tggtgagcca gatcatcgag   1860
```

```
cagctgatca agaaggagaa ggtgtacctg gcctgggtgc ccgcccacaa gggcatcggc    1920
ggcaacgagc aggtggacaa gctggtgagc gccggcatcc gcaaggtgct g             1971

<210> SEQ ID NO 39
<211> LENGTH: 2262
<212> TYPE: DNA
<213> ORGANISM: Artificial Sequence
<220> FEATURE:
<223> OTHER INFORMATION: Description of Artificial Sequence:
      protInaRT.YMWM.opt.SF2

<400> SEQUENCE: 39
ccccagatca ccctgtggca gcgcccctg gtgaccatca ggatcggcgg ccagctcaag      60
gaggcgctgc tcgccaccgg cgccgacgac accgtgctgg aggagatgaa cctgcccggc    120
aagtggaagc ccaagatgat cggcgggatc gggggcttca tcaaggtgcg gcagtacgac    180
cagatccccg tggagatctg cggccacaag gccatcggca ccgtgctggt gggccccacc    240
cccgtgaaca tcatcggccg caacctgctg acccagatcg gctgcaccct gaacttcccc    300
cagatcaccc tgtggcagcg ccccctggtg accatcagga tcggcggcca gctcaaggag    360
gcgctgctcg acaccggcgc cgacgacacc gtgctgagg atgaacct gcccggcaag      420 tggaagccca agatgatcgg cgggatcggg gcttcatca aggtgcggca gtacgaccag    480
atccccgtgg agatctgcgg ccacaaggcc atcggcaccg tgctggtggg ccccaccccc    540
gtgaacatca tcggccgcaa cctgctgacc cagatcggct gcaccctgaa cttccccatc    600
agccccatcg acgcgtgcc cgtgaagctg aagccgggga tggacggccc caaggtcaag    660
cagtggcccc tgaccgagga agatcaag gccctggtgg agatctgcac cgagatggag    720
aaggagggca agatcagcaa gatcggcccc gagaacccct acaacacccc cgtgttcgcc    780
atcaagaaga aggacagcac caagtggcgc aagctggtgg acttccgcga gctgaacaag    840
cgcacccagg acttctggga ggtgcagctg ggcatccccc accccgccgg cctgaagaag    900
aagaagagcg tgaccgtgct ggacgtgggc gacgcctact cagcgtgcc cctggacaag    960 gacttccgca gtacaccgc cttcaccatc cccagcatca acaacgagac ccccggcatc   1020
cgctaccagt acaacgtgct gccccagggc tggaagggca gccccgccat cttccagagc   1080
agcatgacca agatcctgga gcccttccgc aagcagaacc ccgacatcgt gatctaccag   1140
gcccccctgt acgtgggcag cgacctggag atcggccagc accgcaccaa gatcgaggag   1200
ctgcgccagc acctgctgcg ctggggcttc accaccccg acaagaagca ccagaaggag   1260
ccccccttcc tgcccatcga gctgcacccc gacaagtgga ccgtgcagcc catcatgctg   1320
cccgagaagg acagctggac cgtgaacgac atccagaagc tggtgggcaa gctgaactgg   1380
gccagccaga tctacgccgg catcaaggtg aagcagctgt gcaagctgct gcgcggcacc   1440
aaggccctga ccgaggtgat cccccctgacc gaggaggccg agctggagct ggccgagaac   1500
cgcgagatcc tgaaggagcc cgtgcacgag gtgtactacg accccagcaa ggacctggtg   1560
gccgagatcc agaagcaggg ccagggccag tggacctacc agatctacca ggagcccttc   1620
aagaacctga gaccggcaa gtacgcccgc atgcgcggcg cccacaccaa cgacgtgaag   1680
cagctgaccg aggccgtgca gaaggtgagc accgagagca tcgtgatctg gggcaagatc   1740
cccaagttca gctgcccat ccagaaggag acctgggagg cctggtggat ggagtactgg   1800
caggccacct ggatccccga gtgggagttc gtgaacaccc cccctggt gaagctgtgg   1860 taccagctgg agaaggagcc catcgtgggc gccgagacct tctacgtgga cggcgccgcc   1920
aaccgcgaga ccaagctggg caaggccggc tacgtgaccg accggggccg gcagaaggtg   1980
```

| gtgagcatcg ccgacaccac caaccagaag accgagctgc aggccatcca cctggccctg | 2040 |
| caggacagcg gcctggaggt gaacatcgtg accgacagcc agtacgccct gggcatcatc | 2100 |
| caggcccagc ccgacaagag cgagagcgag ctggtgagcc agatcatcga gcagctgatc | 2160 |
| aagaaggaga aggtgtacct ggcctgggtg cccgcccaca agggcatcgg cggcaacgag | 2220 |
| caggtggaca agctggtgag cgccggcatc cgcaaggtgc tg | 2262 |

<210> SEQ ID NO 40
<211> LENGTH: 1990
<212> TYPE: DNA
<213> ORGANISM: Artificial Sequence
<220> FEATURE:
<223> OTHER INFORMATION: Description of Artificial Sequence:
      ProtInaRTmut.SF2

<400> SEQUENCE: 40

| gtcgacgcca ccatgcccca gatcaccctg tggcagcgcc ccctggtgac catcaggatc | 60 |
| ggcggccagc tcaaggaggc gctgctcgcc accggcgccg acgacaccgt gctggaggag | 120 |
| atgaacctgc ccggcaagtg gaagcccaag atgatcggcg ggatcggggg cttcatcaag | 180 |
| gtgcggcagt acgaccagat ccccgtggag atctgcggcc acaaggccat cggcaccgtg | 240 |
| ctggtgggcc ccaccccgt gaacatcatc ggccgcaacc tgctgaccca gatcggctgc | 300 |
| accctgaact tccccatcag ccccatcgag acggtgcccg tgaagctgaa gccggggatg | 360 |
| gacggcccca ggtcaagca gtggcccctg accgaggaga gatcaaggc cctggtggag | 420 |
| atctgcaccg agatggagaa ggagggcaag atcagcaaga tcggccccga gaacccctac | 480 |
| aacacccccg tgttcgccat caagaagaag acagcacca gtggcgcaa gctggtggac | 540 |
| ttccgcgagc tgaacaagcg cacccaggac ttctgggagg tgcagctggg catccccac | 600 |
| cccgccggcc tgaagaagaa gaagagcgtg accgtgctgg acgtgggcga cgcctacttc | 660 |
| agcgtgcccc tggacaagga cttccgcaag tacaccgcct tcaccatccc cagcatcaac | 720 |
| aacgagaccc ccggcatccg ctaccagtac aacgtgctgc cccagggctg gaagggcagc | 780 |
| cccgccatct tccagagcag catgaccaag atcctggagc ccttccgcaa gcagaacccc | 840 |
| gacatcgtga tctaccaggc ccccctgtac gtgggcagcg acctggagat cggccagcac | 900 |
| cgcaccaaga tcgaggagct gcgccagcac ctgctgcgct ggggcttcac cacccccgac | 960 |
| aagaagcacc agaaggagcc ccccttcctg cccatcgagc tgcaccccga caagtggacc | 1020 |
| gtgcagccca tcatgctgcc cgagaaggac agctggaccg tgaacgacat ccagaagctg | 1080 |
| gtgggcaagc tgaactgggc cagccagatc tacgccggca tcaaggtgaa gcagctgtgc | 1140 |
| aagctgctgc gcggcaccaa ggccctgacc gaggtgatcc ccctgaccga ggaggccgag | 1200 |
| ctggagctgg ccgagaaccg cgagatcctg aaggagcccg tgcacgaggt gtactacgac | 1260 |
| cccagcaagg acctggtggc cgagatccag aagcagggcc agggccagtg gacctaccag | 1320 |
| atctaccagg agcccttcaa gaacctgaag accggcaagt acgcccgcat gcgcggcgcc | 1380 |
| cacaccaacg acgtgaagca gctgaccgag gccgtgcaga aggtgagcac cgagagcatc | 1440 |
| gtgatctggg gcaagatccc caagttcaag ctgcccatcc agaaggagac ctgggaggcc | 1500 |
| tggtggatgg agtactggca ggccacctgg atccccgagt gggagttcgt gaacaccccc | 1560 |
| cccctggtga gctgtggta ccagctggag aaggagccca tcgtgggcgc cgagaccttc | 1620 |
| tacgtggacg gcgccgccaa ccgcgagacc aagctgggca aggccggcta cgtgaccgac | 1680 |
| cggggccggc agaaggtggt gagcatcgcc gacaccacca ccagaagac cgagctgcag | 1740 |

-continued

| | |
|---|---|
| gccatccacc tggccctgca ggacagcggc ctggaggtga acatcgtgac cgacagccag | 1800 |
| tacgccctgg gcatcatcca ggcccagccc gacaagagcg agagcgagct ggtgagccag | 1860 |
| atcatcgagc agctgatcaa gaaggagaag gtgtacctgg cctgggtgcc cgcccacaag | 1920 |
| ggcatcggcg gcaacgagca ggtggacaag ctggtgagcg ccggcatccg caaggtgctc | 1980 |
| taaatctaga | 1990 |

<210> SEQ ID NO 41
<211> LENGTH: 1977
<212> TYPE: DNA
<213> ORGANISM: Artificial Sequence
<220> FEATURE:
<223> OTHER INFORMATION: Description of Artificial Sequence:
    protRT.opt.SF2

<400> SEQUENCE: 41

| | |
|---|---|
| ccccagatca ccctgtggca gcgccccctg gtgaccatca ggatcggcgg ccagctcaag | 60 |
| gaggcgctgc tcgacaccgg cgccgacgac accgtgctgg aggagatgaa cctgcccggc | 120 |
| aagtggaagc ccaagatgat cggcgggatc gggggcttca tcaaggtgcg gcagtacgac | 180 |
| cagatccccg tggagatctg cggccacaag gccatcggca ccgtgctggt gggccccacc | 240 |
| cccgtgaaca tcatcggccg caacctgctg acccagatcg gctgcaccct gaacttcccc | 300 |
| atcagcccca tcgagacggt gcccgtgaag ctgaagccgg ggatggacgg ccccaaggtc | 360 |
| aagcagtggc ccctgaccga ggagaagatc aaggccctgg tggagatctg caccgagatg | 420 |
| gagaaggagg gcaagatcag caagatcggc cccgagaacc cctacaacac ccccgtgttc | 480 |
| gccatcaaga gaaggacag caccaagtgg cgcaagctgg tggacttccg cgagctgaac | 540 |
| aagcgcaccc aggacttctg ggaggtgcag ctgggcatcc ccaccccgc cggcctgaag | 600 |
| aagaagaaga gcgtgaccgt gctggacgtg ggcgacgcct acttcagcgt gcccctggac | 660 |
| aaggacttcc gcaagtacac cgccttcacc atccccagca tcaacaacga ccccccggc | 720 |
| atccgctacc agtacaacgt gctgccccag ggctggaagg gcagccccgc catcttccag | 780 |
| agcagcatga ccaagatcct ggagcccttc cgcaagcaga accccgacat cgtgatctac | 840 |
| cagtacatgg acgacctgta cgtgggcagc gacctggaga tcggccagca ccgcaccaag | 900 |
| atcgaggagc tgcgccagca cctgctgcgc tggggcttca ccaccccga caagaagcac | 960 |
| cagaaggagc ccccttcct gtggatgggc tacgagctgc accccgacaa gtggaccgtg | 1020 |
| cagcccatca tgctgcccga gaaggacagc tggaccgtga acgacatcca gaagctggtg | 1080 |
| ggcaagctga actgggccag ccagatctac gccggcatca aggtgaagca gctgtgcaag | 1140 |
| ctgctgcgcg gcaccaaggc cctgaccgag gtgatccccc tgaccgagga ggccgagctg | 1200 |
| gagctggccg agaaccgcga gatcctgaag gagcccgtgc acgaggtgta ctacgacccc | 1260 |
| agcaaggacc tggtggccga gatccagaag cagggccagg gccagtggac ctaccagatc | 1320 |
| taccaggagc ccttcaagaa cctgaagacc ggcaagtacg cccgcatgcg cggcgcccac | 1380 |
| accaacgacg tgaagcagct gaccgaggcc gtgcagaagg tgagcaccga gagcatcgtg | 1440 |
| atctggggca gatcccccaa gttcaagctg cccatccaga aggagacctg ggaggcctgg | 1500 |
| tggatggagt actggcaggc cacctggatc cccgagtggg agttcgtgaa cacccccccc | 1560 |
| ctggtgaagc tgtggtacca gctggagaag gagcccatcg tgggcgccga ccttctac | 1620 |
| gtggacggcg ccgccaaccg cgagaccaag ctgggcaagg ccggctacgt gaccgaccgg | 1680 |
| ggccggcaga aggtggtgag catcgccgac accaccaacc agaagaccga gctgcaggcc | 1740 |
| atccacctgg ccctgcagga cagcggcctg gaggtgaaca tcgtgaccga cagccagtac | 1800 |

```
gccctgggca tcatccaggc ccagcccgac aagagcgaga gcgagctggt gagccagatc   1860
atcgagcagc tgatcaagaa ggagaaggtg tacctggcct gggtgcccgc ccacaagggc   1920
atcggcggca acgagcaggt ggacaagctg gtgagcgccg gcatccgcaa ggtgctg      1977
```

<210> SEQ ID NO 42
<211> LENGTH: 3252
<212> TYPE: DNA
<213> ORGANISM: Artificial Sequence
<220> FEATURE:
<223> OTHER INFORMATION: Description of Artificial Sequence:
     ProtRT.TatRevNef.opt_B

<400> SEQUENCE: 42

```
atgccccaga tcaccctgtg gcagcgcccc ctggtgacca tcaggatcgg cggccagctc     60
aaggaggcgc tgctcgccac cggcgccgac gacaccgtgc tggaggagat gaacctgccc    120
ggcaagtgga gcccaagat gatcggcggg atcgggggct tcatcaaggt gcggcagtac    180
gaccagatcc ccgtggagat ctgcggccac aaggccatcg gcaccgtgct ggtgggcccc    240
acccccgtga acatcatcgg ccgcaacctg ctgacccaga tcggctgcac cctgaacttc    300
cccatcagcc ccatcgagac ggtgcccgtg aagctgaagc cggggatgga cggccccaag    360
gtcaagcagt ggcccctgac cgaggagaag atcaaggccc tggtggagat ctgcaccgag    420
atggagaagg agggcaagat cagcaagatc ggcccccgaga acccctacaa cacccccgtg    480
ttcgccatca gaagaaggga cagcaccaag tggcgcaagc tggtggactt ccgcgagctg    540
aacaagcgca cccaggactt ctgggaggtg cagctgggca tcccccaccc cgccggcctg    600
aagaagaaga gagcgtgac cgtgctggac gtgggcgacg cctacttcag cgtgcccctg    660
gacaaggact tccgcaagta caccgccttc accatcccca gcatcaacaa cgagaccccc    720
ggcatccgct accagtacaa cgtgctgccc cagggctgga agggcagccc cgccatcttc    780
cagagcagca tgaccaagat cctggagccc ttccgcaagc agaaccccga catcgtgatc    840
taccaggccc ccctgtacgt gggcagcgac ctggagatcg gccagcaccg caccaagatc    900
gaggagctgc gccagcacct gctgcgctgg ggcttcacca cccccgacaa gaagcaccag    960
aaggagcccc ccttcctgcc catcgagctg caccccgaca gtggaccgt gcagcccatc    1020 atgctgcccg agaaggacag ctggaccgtg aacgacatcc agaagctggt gggcaagctg    1080
aactgggcca gccagatcta cgccggcatc aaggtgaagc agctgtgcaa gctgctgcgc    1140
ggcaccaagg ccctgaccga ggtgatcccc ctgaccgagg aggccgagct ggagctggcc    1200
gagaaccgcg agatcctgaa ggagcccgtg cacgaggtgt actacgaccc cagcaaggac    1260
ctggtggccg agatccagaa gcagggccag ggccagtgga cctaccagat ctaccaggag    1320
cccttcaaga acctgaagac cggcaagtac gcccgcatgc gcggcgccca caccaacgac    1380
gtgaagcagc tgaccgaggc cgtgcagaag gtgagcaccg agagcatcgt gatctggggc    1440
aagatcccca gttcaagct gcccatccag aaggagacct gggaggcctg gtggatggag    1500
tactggcagg ccacctggat ccccgagtgg gagttcgtga acacccccc cctggtgaag    1560 ctgtggtacc agctggagaa ggagcccatc gtgggcgccg agaccttcta cgtggacggc    1620
gccgccaacc gcgagaccaa gctgggcaag gccggctacg tgaccgaccg gggccggcag    1680
aaggtggtga gcatcgccga caccaccaac cagaagaccg agctgcaggc catccacctg    1740
gccctgcagg acagcggcct ggaggtgaac atcgtgaccg acagccagta cgccctgggc    1800
atcatccagg cccagcccga caagagcgag agcgagctgg tgagccagat catcgagcag    1860
```

-continued

| | |
|---|---|
| ctgatcaaga aggagaaggt gtacctggcc tgggtgcccg cccacaaggg catcggcggc | 1920 |
| aacgagcagg tggacaagct ggtgagcgcc ggcatccgca aggtgctcga attcgagccc | 1980 |
| gtggaccccc gcctggagcc ctggaagcac cccggcagcc agcccaagac cgccggcacc | 2040 |
| aactgctact gcaagaagtg ctgcttccac tgccaggtga gcttcatcac caagggcctg | 2100 |
| ggcatcagct acggccgcaa gaagcgccgc cagcgccgcc gcgcccccc cgacagcgag | 2160 |
| gtgcaccagg tgagcctgcc caagcagccc gccagccagc ccagggcga ccccaccggc | 2220 |
| cccaaggaga gcaagaagaa ggtggagcgc gagaccgaga ccgaccccgt gcaccccggg | 2280 |
| gccgccgca gcggcgacag cgacgaggag ctgctgcaga ccgtgcgctt catcaagttc | 2340 |
| ctgtaccaga gcaacccct gcccagcccc aagggcaccc gccaggccga cctgaaccgc | 2400 |
| cgccgccgct ggcgcgagcg ccagcgccag atccagagca tcagcgcctg gatcatcagc | 2460 |
| acccacctgg gccgcagcac cgagcccgtg cccctgcagc tgcccccga cctgcgcctg | 2520 |
| aacctggact gcagcgagga ctgcggcacc agcggcaccc agggcgtggg cagccccag | 2580 |
| gtgctgggcg agagccccgc cgtgctggac agcggcacca aggagctcga ggccggcaag | 2640 |
| tggagcaagc gcatgagcgg ctggagcgcc gtgcgcgagc gcatgaagcg cgccgagccc | 2700 |
| gccgagcccg ccgccgacgg cgtgggcgcc gtgagccgcg acctggagaa gcacggcgcc | 2760 |
| atcaccagca gcaacaccgc cgccaacaac gccgactgcg cctggctgga ggcccaggag | 2820 |
| gacgaggacg tgggcttccc cgtgcgcccc caggtgcccc tgcgcccat gacctacaag | 2880 |
| gccgccctgg acctgagcca cttcctgaag gagaagggcg gcctggaggg cctgatctac | 2940 |
| agccagaagc gccaggacat cctggacctg tggatccacc acacccaggg ctacttcccc | 3000 |
| ggctggcaga actacacccc cggccccggc atccgctacc ccctgacctt cggctggtgc | 3060 |
| ttcaagctgg tgcccgtgga ccccgactac gtggaggagg ccaacgccgg cgagaacaac | 3120 |
| agcctgctgc accccatgag ccagcacggc atggacgacc ccgagaagga ggtgctggtg | 3180 |
| tggcgcttcg acagccgcct ggccttccac cacatggccc gcgagctgca ccccgagtac | 3240 |
| tacaaggact gc | 3252 |

<210> SEQ ID NO 43
<211> LENGTH: 3264
<212> TYPE: DNA
<213> ORGANISM: Artificial Sequence
<220> FEATURE:
<223> OTHER INFORMATION: Description of Artificial Sequence:
ProtRTTatRevNef.opt_B

<400> SEQUENCE: 43

| | |
|---|---|
| gccaccatgc cccagatcac cctgtggcag cgcccctgg tgaccatcag gatcggcggc | 60 |
| cagctcaagg aggcgctgct cgccaccggc gccgacgaca ccgtgctgga ggagatgaac | 120 |
| ctgcccggca gtggaagcc caagatgatc ggcgggatcg ggggcttcat caaggtgcgg | 180 |
| cagtacgacc agatccccgt ggagatctgc ggccacaagg ccatcggcac cgtgctggtg | 240 |
| ggcccacccc ccgtgaacat catcggccgc aacctgctga cccagatcgg ctgcaccctg | 300 |
| aacttcccca tcagccccat cgagacggtg cccgtgaagc tgaagccggg gatggacggc | 360 |
| cccaaggtca gcagtggcc cctgaccgag gagaagatca ggccctggt ggagatctgc | 420 |
| accgagatgg agaaggaggg caagatcagc aagatcggcc ccgagaaccc ctacaacacc | 480 |
| cccgtgttcg ccatcaagaa gaaggacagc accaagtggc gcaagctggt ggacttccgc | 540 |
| gagctgaaca gcgcaccca ggacttctgg gaggtgcagc tggcatccc caccccgcc | 600 |
| ggcctgaaga gaagaagag cgtgaccgtg ctggacgtgg gcgacgccta cttcagcgtg | 660 |

```
cccctggaca aggacttccg caagtacacc gccttcacca tccccagcat caacaacgag    720
acccccggca tccgctacca gtacaacgtg ctgccccagg gctggaaggg cagcccccgcc   780
atcttccaga gcagcatgac caagatcctg gagcccttcc gcaagcagaa ccccgacatc    840
gtgatctacc aggcccccct gtacgtgggc agcgacctgg agatcggcca gcaccgcacc    900
aagatcgagg agctgcgcca gcacctgctg cgctggggct tcaccacccc cgacaagaag    960
caccagaagg agccccccct cctgcccatc gagctgcacc ccgacaagtg gaccgtgcag    1020
cccatcatgc tgcccgagaa ggacagctgg accgtgaacg acatccagaa gctggtgggc    1080
aagctgaact gggccagcca gatctacgcc ggcatcaagg tgaagcagct gtgcaagctg    1140
ctgcgcggca ccaaggccct gaccgaggtg atcccccctga ccgaggaggc cgagctggag    1200
ctggccgaga accgcgagat cctgaaggag cccgtgcacg aggtgtacta cgaccccagc    1260
aaggacctgg tggccgagat ccagaagcag ggccagggcc agtggaccta ccagatctac    1320
caggagccct tcaagaacct gaagaccggc aagtacgccc gcatgcgcgg cgcccacacc    1380
aacgacgtga agcagctgac cgaggccgtg cagaaggtga gcaccgagag catcgtgatc    1440
tggggcaaga tccccaagtt caagctgccc atccagaagg agacctggga ggcctggtgg    1500
atggagtact ggcaggccac ctggatcccc gagtgggagt tcgtgaacac cccccccctg    1560
gtgaagctgt ggtaccagct ggagaaggag cccatcgtgg gcgccgagac cttctacgtg    1620
gacggcgccg ccaaccgcga gaccaagctg ggcaaggccg gctacgtgac cgaccggggc    1680
cggcagaagg tggtgagcat cgccgacacc accaaccaga gaccgagct gcaggccatc     1740
cacctggccc tgcaggacag cggcctggag gtgaacatcg tgaccgacag ccagtacgcc    1800
ctgggcatca tccaggccca gcccgacaag agcgagagcg agctggtgag ccagatcatc    1860
gagcagctga tcaagaagga gaaggtgtac ctggcctggg tgcccgccca agggcatc      1920
ggcggcaacg agcaggtgga caagctggtg agcgccggca tccgcaaggt gctcgaattc    1980
gagcccgtgg accccgcct ggagccctgg aagcaccccg gcagccagcc caagaccgcc     2040
ggcaccaact gctactgcaa gaagtgctgc ttccactgcc aggtgagctt catcaccaag    2100
ggcctgggca tcagctacgg ccgcaagaag cgccgccagc cgccgcgcgc cccccccgac    2160
agcgaggtgc accaggtgag cctgcccaag cagcccgcca gcagccccca gggcgacccc    2220
accggcccca aggagagcaa gaagaaggtg gagcgcgaga ccgagaccga ccccgtgcac    2280
cccgggggccg gccgcagcgg cgacagcgac gaggagctgc tgcagaccgt gcgcttcatc    2340
aagttcctgt accagagcaa ccccctgccc agccccaagg gcacccgcca ggccgacctg    2400
aaccgccgcc gccgctggcg cgagcgccag cgccagatcc agagcatcag cgcctggatc    2460
atcagcaccc acctgggccg cagcaccgag cccgtgcccc tgcagctgcc cccgacctg     2520
cgcctgaacc tggactgcag cgaggactgc ggcaccagcg gcaccagggg cgtgggcagc    2580
ccccaggtgc tgggcgagag ccccgccgtg ctggacagcg gcaccaagga gctcgaggcc    2640
ggcaagtgga gcaagcgcat gagcggctgg agcgccgtgc gcgagcgcat gaagcgcgcc    2700
gagcccgccg agcccgccgc cgacggcgtg ggcgccgtga ccgcgacct ggagaagcac    2760
ggcgccatca ccagcagcaa caccgccgcc aacaacgccg actgcgcctg gctggaggcc    2820
caggaggacg aggacgtggg cttccccgtg cgccccagg tgcccctgcg ccccatgacc     2880
tacaaggccg ccctggacct gagccacttc ctgaaggaga agggcggcct ggagggcctg    2940
atctacagcc agaagcgcca ggacatcctg gacctgtgga tccaccacac ccagggctac    3000
ttccccggct ggcagaacta caccccccggc cccggcatcc gctaccccct gaccttcggc   3060
```

```
tggtgcttca agctggtgcc cgtggacccc gactacgtgg aggaggccaa cgccggcgag    3120
aacaacagcc tgctgcaccc catgagccag cacggcatgg acgaccccga aaggaggtg    3180 ctggtgtggc gcttcgacag ccgcctggcc ttccaccaca tggcccgcga gctgcacccc   3240
gagtactaca aggactgcga ttaa                                          3264
```

<210> SEQ ID NO 44
<211> LENGTH: 348
<212> TYPE: DNA
<213> ORGANISM: Artificial Sequence
<220> FEATURE:
<223> OTHER INFORMATION: Description of Artificial Sequence:
      rev.exon1_2.M5-10.opt.SF162

<400> SEQUENCE: 44

```
atggccggcc gcagcggcga cagcgacgag gagctgctgc agaccgtgcg cttcatcaag    60
ttcctgtacc agagcaaccc cctgccagcc cccaagggca cccgccaggc cgacctgaac   120
cgccgccgcc gctggcgcga cgccagcgcg cagatccaga gcatcagcgc ctggatcatc   180
agcacccacc tggccgcag caccgagccc gtgcccctgc agctgccccc cgacctgcgc    240
ctgaacctgg actgcagcga ggactgcggc accagcggca cccagggcgt gggcagcccc   300
caggtgctgg gcgagagccc cgccgtgctg gacagcggca ccaaggag               348
```

<210> SEQ ID NO 45
<211> LENGTH: 348
<212> TYPE: DNA
<213> ORGANISM: Artificial Sequence
<220> FEATURE:
<223> OTHER INFORMATION: Description of Artificial Sequence: description

<400> SEQUENCE: 45

```
atggccggcc gcagcggcga cagcgacgag gagctgctgc agaccgtgcg cttcatcaag    60
ttcctgtacc agagcaaccc cctgccagcc cccaagggca cccgccaggc ccgccgcaac   120
cgccgccgcc gctggcgcga cgccagcgcg cagatccaga gcatcagcgc ctggatcatc   180
agcacccacc tgggccgcag caccgagccc gtgcccctgc agctgccccc cctggagcgc   240
ctgaacctgg actgcagcga ggactgcggc accagcggca cccagggcgt gggcagcccc   300
caggtgctgg gcgagagccc cgccgtgctg gacagcggca ccaaggag               348
```

<210> SEQ ID NO 46
<211> LENGTH: 1977
<212> TYPE: DNA
<213> ORGANISM: Artificial Sequence
<220> FEATURE:
<223> OTHER INFORMATION: Description of Artificial Sequence: RT.opt.SF2
      (mutant)

<400> SEQUENCE: 46

```
gccaccatgc cccagatcac cctgtggcag cgcccctgg tgaccatcag gatcggcggc    60
cagctcaagg aggcgctgct cgccaccggc gccgacgaca ccgtgctgga ggagatgaac   120
ctgcccggca gtggaagcc caagatgatc ggcgggatcg ggggcttcat caaggtgcgg   180
cagtacgacc agatccccgt ggagatctgc ggccacaagg ccatcggcac cgtgctggtg   240
ggccccaccc ccgtgaacat catcggccgc aacctgctga cccagatcgg ctgcaccctg   300
aacttcccca tcagccccat cgagacggtg cccgtgaagc tgaagccggg gatggacggc   360
cccaaggtca gcagtggcc cctgaccgag gagaagatca ggcccctggt ggagatctgc   420
accgagatgg agaaggaggg caagatcagc aagatcggcc ccgagaaccc ctacaacacc   480
```

-continued

```
cccgtgttcg ccatcaagaa gaaggacagc accaagtggc gcaagctggt ggacttccgc      540
gagctgaaca agcgcaccca ggacttctgg gaggtgcagc tgggcatccc ccaccccgcc      600
ggcctgaaga agaagaagag cgtgaccgtg ctggacgtgg cgacgccta cttcagcgtg       660 cccctggaca aggacttccg caagtacacc gccttcacca tccccagcat caacaacgag      720 accccggca tccgctacca gtacaacgtg ctgccccagg ctggaaggg cagccccgcc        780 atcttccaga gcagcatgac caagatcctg gagcccttcc gcaagcagaa ccccgacatc      840
gtgatctacc aggccccct gtacgtgggc agcgacctgg agatcggcca gcaccgcacc      900
aagatcgagg agctgcgcca gcacctgctg cgctggggct tcaccacccc cgacaagaag      960
caccagaagg agccccctt cctgcccatc gagctgcacc ccgacaagtg gaccgtgcag      1020
cccatcatgc tgcccgagaa ggacagctgg accgtgaacg acatccagaa gctggtgggc     1080
aagctgaact gggccagcca gatctacgcc ggcatcaagg tgaagcagct gtgcaagctg     1140
ctgcgcggca ccaaggccct gaccgaggtg atccccctga ccgaggaggc cgagctggag     1200
ctggccgaga accgcgagat cctgaaggag cccgtgcacg aggtgtacta cgaccccagc     1260
aaggacctgg tggccgagat ccagaagcag ggccagggcc agtggaccta ccagatctac     1320
caggagccct tcaagaacct gaagaccggc aagtacgccc gcatgcgcgg cgcccacacc     1380
aacgacgtga agcagctgac cgaggccgtg cagaaggtga gcaccgagag catcgtgatc     1440
tggggcaaga tccccaagtt caagctgccc atccagaagg agacctggga ggcctggtgg     1500
atggagtact ggcaggccac ctggatcccc gagtgggagt cgtgaacac ccccccctg      1560 gtgaagctgt ggtaccagct ggagaaggag cccatcgtgg gcgccgagac cttctacgtg     1620
gacggcgccg ccaaccgcga gaccaagctg ggcaaggccg gctacgtgac cgaccggggc     1680
cggcagaagg tggtgagcat cgccgacacc accaaccaga gaccgagct gcaggccatc      1740 cacctggccc tgcaggacag cggcctggag gtgaacatcg tgaccgacag ccagtacgcc     1800
ctgggcatca tccaggccca gcccgacaag agcgagagcg agctggtgag ccagatcatc     1860
gagcagctga tcaagaagga gaaggtgtac ctggcctggg tgcccgccca aagggcatc      1920 ggcggcaacg agcaggtgga caagctggtg agcgccggca tccgcaaggt gctctaa        1977
```

<210> SEQ ID NO 47
<211> LENGTH: 1989
<212> TYPE: DNA
<213> ORGANISM: Artificial Sequence
<220> FEATURE:
<223> OTHER INFORMATION: Description of Artificial Sequence: description

<400> SEQUENCE: 47

```
gccaccatgc cccagatcac cctgtggcag cgccccctgg tgaccatcag gatcggcggc      60
cagctcaagg aggcgctgct cgacaccggc gccgacgaca ccgtgctgga ggagatgaac     120
ctgcccggca gtggaagcc caagatgatc ggcgggatcg ggggcttcat caaggtgcgg      180
cagtacgacc agatccccgt ggagatctgc ggccacaagg ccatcggcac cgtgctggtg     240 ggcccccaccc ccgtgaacat catcggccgc aacctgctga cccagatcgg ctgcaccctg    300
aacttcccca tcagccccat cgagacggtg cccgtgaagc tgaagccggg gatggacggc     360
cccaaggtca gcagtggcc cctgaccgag gagaagatca aggccctggt ggagatctgc     420
accgagatgg agaaggaggg caagatcagc aagatcggcc ccgagaaccc ctacaacacc     480
cccgtgttcg ccatcaagaa gaaggacagc accaagtggc gcaagctggt ggacttccgc     540
gagctgaaca agcgcaccca ggacttctgg gaggtgcagc tgggcatccc ccaccccgcc     600
```

```
ggcctgaaga agaagaagag cgtgaccgtg ctggacgtgg cgacgccta cttcagcgtg    660 cccctggaca aggacttccg caagtacacc gccttcacca tccccagcat caacaacgag    720 accccggca tccgctacca gtacaacgtg ctgccccagg ctggaaggg cagccccgcc    780 atcttccaga gcagcatgac caagatcctg gagcccttcc gcaagcagaa ccccgacatc    840
gtgatctacc agtacatgga cgacctgtac gtgggcagcg acctggagat cggccagcac    900
cgcaccaaga tcgaggagct gcgccagcac ctgctgcgct ggggcttcac cacccccgac    960
aagaagcacc agaaggagcc ccccttcctg tggatgggct acgagctgca ccccgacaag   1020
tggaccgtgc agcccatcat gctgcccgag aaggacagct ggaccgtgaa cgacatccag   1080
aagctggtgg gcaagctgaa ctgggccagc cagatctacg ccggcatcaa ggtgaagcag   1140
ctgtgcaagc tgctgcgcgg caccaaggcc ctgaccgagt gatccccct gaccgaggag   1200 gccgagctgg agctgccga gaaccgcgag atcctgaagg agcccgtgca cgaggtgtac   1260
tacgacccca gcaaggacct ggtggccgag atccagaagc agggccaggg ccagtggacc   1320
taccagatct accaggagcc cttcaagaac ctgaagaccg gcaagtacgc ccgcatgcgc   1380
ggcgcccaca ccaacgacgt gaagcagctg accgaggccg tgcagaaggt gagcaccgag   1440
agcatcgtga tctggggcaa gatccccaag ttcaagctgc ccatccagaa ggagacctgg   1500
gaggcctggt ggatggagta ctggcaggcc acctggatcc ccgagtggga gttcgtgaac   1560
accccccccc tggtgaagct gtggtaccag ctggagaagg agcccatcgt gggcgccgag   1620
accttctacg tggacggcgc cgccaaccgc gagaccaagc tgggcaaggc cggctacgtg   1680
accgaccggg gccggcagaa ggtggtgagc atcgccgaca ccaccaacca gaagaccgag   1740
ctgcaggcca tccacctggc cctgcaggac agcggcctgg aggtgaacat cgtgaccgac   1800
agccagtacg ccctgggcat catccaggcc cagcccgaca gagcgagag cgagctggtg   1860 agccagatca tcgagcagct gatcaagaag gagaaggtgt acctggcctg ggtgcccgcc   1920
cacaagggca tcggcggcaa cgagcaggtg gacaagctgg tgagcgccgg catccgcaag   1980
gtgctgtaa                                                          1989

<210> SEQ ID NO 48
<211> LENGTH: 1693
<212> TYPE: DNA
<213> ORGANISM: Artificial Sequence
<220> FEATURE:
<223> OTHER INFORMATION: Description of Artificial Sequence: RTmut.SF2

<400> SEQUENCE: 48
gtcgacgcca ccatgcccat cagccccatc gagacggtgc ccgtgaagct gaagccgggg     60
atggacggcc ccaaggtcaa gcagtggccc ctgaccgagg agaagatcaa ggccctggtg    120
gagatctgca ccgagatgga aaggagggc aagatcagca gatcggccc cgagaacccc    180 tacaacaccc ccgtgttcgc catcaagaag aaggacagca ccaagtggcg caagctggtg    240
gacttccgcg agctgaacaa gcgcacccag gacttctggg aggtgcagct gggcatcccc    300
cacccccgcg gcctgaagaa gaagaagagc gtgaccgtgc tggacgtggg cgacgcctac    360
ttcagcgtgc cctggacaa ggacttccgc aagtacaccg ccttcaccat ccccagcatc    420
aacaacgaga ccccggcat ccgctaccag tacaacgtgc tgccccaggg ctggaaggc    480 agccccgcca tcttccagag cagcatgacc aagatcctgg agcccttccg caagcagaac    540
cccgacatct gatctacca ggccccctg tacgtgggca gcgacctgga gatcggccag    600
caccgcacca agatcgagga gctgcgccag cacctgctgc gctggggctt caccacccc    660
```

```
gacaagaagc accagaagga gcccccttc ctgcccatcg agctgcaccc cgacaagtgg      720
accgtgcagc ccatcatgct gcccgagaag gacagctgga ccgtgaacga catccagaag    780
ctggtgggca agctgaactg ggccagccag atctacgccg gcatcaaggt gaagcagctg    840
tgcaagctgc tgcgcggcac caaggccctg accgaggtga tcccctgac cgaggaggcc    900 gagctggagc tggccgagaa ccgcgagatc ctgaaggagc ccgtgcacga ggtgtactac    960
gaccccagca aggacctggt ggccgagatc cagaagcagg gccagggcca gtggacctac   1020
cagatctacc aggagccctt caagaacctg aagaccggca gtacgcccg catgcgcggc   1080 gcccacacca cgacgtgaa gcagctgacc gaggccgtgc agaaggtgag caccgagagc   1140
atcgtgatct ggggcaagat ccccaagttc aagctgccca tccagaagga gacctgggag   1200
gcctggtgga tggagtactg gcaggccacc tggatccccg agtgggagtt cgtgaacacc   1260 cccccctgg tgaagctgtg gtaccagctg gagaaggagc ccatcgtggg cgccgagacc   1320
ttctacgtgg acgcgccgc caaccgcgag accaagctgg gcaaggccgg ctacgtgacc   1380
gaccggggcc ggcagaaggt ggtgagcatc gccgacacca ccaaccagaa gaccgagctg   1440
caggccatcc acctggccct gcaggacagc ggcctggagg tgaacatcgt gaccgacagc   1500
cagtacgccc tgggcatcat ccaggcccag cccgacaaga gcgagagcga gctggtgagc   1560
cagatcatcg agcagctgat caagaaggag aaggtgtacc tggcctgggt gcccgcccac   1620
aagggcatcg gcggcaacga gcaggtggac aagctggtga gcgccggcat ccgcaaggtg   1680
ctctaaagaa ttc                                                     1693

<210> SEQ ID NO 49
<211> LENGTH: 303
<212> TYPE: DNA
<213> ORGANISM: Artificial Sequence
<220> FEATURE:
<223> OTHER INFORMATION: Description of Artificial Sequence:
      tat.exon1_2.opt.C22-37.SF2

<400> SEQUENCE: 49
atggagcccg tggaccccg cctggagccc tggaagcacc ccggcagcca gcccaagacc      60
gccggcacca actgctactg caagaagtgc tgcttccact gccaggtgag cttcatcacc    120
aagggcctgg gcatcagcta cggccgcaag aagcgccgcc agcgccgccg cgcccccccc    180
gacagcgagg tgcaccaggt gagcctgccc aagcagcccg ccagccagcc cagggcgac   240 cccaccggcc ccaaggagag caagaagaag gtggagcgcg agaccgagac cgaccccgtg   300
cac                                                                303

<210> SEQ ID NO 50
<211> LENGTH: 303
<212> TYPE: DNA
<213> ORGANISM: Artificial Sequence
<220> FEATURE:
<223> OTHER INFORMATION: Description of Artificial Sequence: description

<400> SEQUENCE: 50
atggagcccg tggaccccg cctggagccc tggaagcacc ccggcagcca gcccaagacc      60
gcctgcacca actgctactg caagaagtgc tgcttccact gccaggtgag cttcatcacc    120
aagggcctgg gcatcagcta cggccgcaag aagcgccgcc agcgccgccg cgcccccccc    180
gacagcgagg tgcaccaggt gagcctgccc aagcagcccg ccagccagcc cagggcgac   240 cccaccggcc ccaaggagag caagaagaag gtggagcgcg agaccgagac cgaccccgtg   300
```

| | |
|---|---|
| cac | 303 |

<210> SEQ ID NO 51
<211> LENGTH: 1281
<212> TYPE: DNA
<213> ORGANISM: Artificial Sequence
<220> FEATURE:
<223> OTHER INFORMATION: Description of Artificial Sequence:
      TatRevNef.opt.native.SF162

<400> SEQUENCE: 51

| | |
|---|---|
| atggagcccg tggacccccg cctggagccc tggaagcacc ccggcagcca gcccaagacc | 60 |
| gcctgcacca actgctactg caagaagtgc tgcttccact gccaggtgtg cttcatcacc | 120 |
| aagggcctgg gcatcagcta cggccgcaag aagcgccgcc agcgccgccg cgccccccc | 180 |
| gacagcgagg tgcaccaggt gagcctgccc aagcagcccg ccagccagcc cagggcgac | 240 |
| cccaccggcc ccaaggagag caagaagaag gtggagcgcg agaccgagac cgaccccgtg | 300 |
| cacccggggg ccggccgcag cggcgacagc gacgaggagc tgctgcagac cgtgcgcttc | 360 |
| atcaagttcc tgtaccagag caaccccctg cccagcccca agggcacccg ccaggcccgc | 420 |
| cgcaaccgcc gccgccgctg gcgcgagcgc cagcgccaga tccagagcat cagcgcctgg | 480 |
| atcatcagca cccacctggg ccgcagcacc gagcccgtgc ccctgcagct gccccccctg | 540 |
| gagcgcctga acctggactg cagcgaggac tgcggcacca gcggcaccca gggcgtgggc | 600 |
| agcccccagg tgctgggcga gagccccgcc gtgctggaca gcggcaccaa ggagctcgag | 660 |
| ggcggcaagt ggagcaagcg catgagcggc tggagcgccg tgcgcgagcg catgaagcgc | 720 |
| gccgagcccg ccgagcccgc cgccgacggc gtgggcgccg tgagccgcga cctggagaag | 780 |
| cacggcgcca tcaccagcag caacaccgcc gccaacaacg ccgactgcgc ctggctggag | 840 |
| gcccaggagg acgaggacgt gggcttcccc gtgcgccccc aggtgcccct gcgccccatg | 900 |
| acctacaagg ccgccctgga cctgagccac ttcctgaagg agaagggcgg cctggagggc | 960 |
| ctgatctaca gccagaagcg ccaggacatc ctggacctgt ggatccacca cacccagggc | 1020 |
| tacttccccg actggcagaa ctacaccccc ggccccggca tccgctaccc cctgaccttc | 1080 |
| ggctggtgct tcaagctggt gcccgtggac cccgactacg tggaggaggc caacgccggc | 1140 |
| gagaacaaca gcctgctgca ccccatgagc cagcacggca tggacgaccc cgagaaggag | 1200 |
| gtgctggtgt ggcgcttcga cagccgcctg gccttccacc acatggcccg cgagctgcac | 1260 |
| cccgagtact acaaggactg c | 1281 |

<210> SEQ ID NO 52
<211> LENGTH: 1281
<212> TYPE: DNA
<213> ORGANISM: Artificial Sequence
<220> FEATURE:
<223> OTHER INFORMATION: Description of Artificial Sequence:
      TatRevNef.opt.SF162

<400> SEQUENCE: 52

| | |
|---|---|
| atggagcccg tggacccccg cctggagccc tggaagcacc ccggcagcca gcccaagacc | 60 |
| gccggcacca actgctactg caagaagtgc tgcttccact gccaggtgag cttcatcacc | 120 |
| aagggcctgg gcatcagcta cggccgcaag aagcgccgcc agcgccgccg cgccccccc | 180 |
| gacagcgagg tgcaccaggt gagcctgccc aagcagcccg ccagccagcc cagggcgac | 240 |
| cccaccggcc ccaaggagag caagaagaag gtggagcgcg agaccgagac cgaccccgtg | 300 |
| cacccggggg ccggccgcag cggcgacagc gacgaggagc tgctgcagac cgtgcgcttc | 360 |

|                                                      |      |
|------------------------------------------------------|------|
| atcaagttcc tgtaccagag caacccctg cccagccca agggcacccg ccaggccgac | 420 |
| ctgaaccgcc gccgccgctg gcgcgagcgc cagcgccaga tccagagcat cagcgcctgg | 480 |
| atcatcagca cccacctggg ccgcagcacc gagcccgtgc ccctgcagct gcccccgac | 540 |
| ctgcgcctga acctggactg cagcgaggac tgcggcacca gcggcaccca gggcgtgggc | 600 |
| agcccccagg tgctgggcga gagccccgcc gtgctggaca gcggcaccaa ggagctcgag | 660 |
| gccggcaagt ggagcaagcg catgagcggc tggagcgccg tgcgcgagcg catgaagcgc | 720 |
| gccgagcccg ccgagcccgc cgccgacggc gtgggcgccg tgagccgcga cctggagaag | 780 |
| cacggcgcca tcaccagcag caacaccgcc gccaacaacg ccgactgcgc ctggctggag | 840 |
| gcccaggagg acgaggacgt gggcttcccc gtgcgccccc aggtgcccct gcgccccatg | 900 |
| acctacaagg ccgccctgga cctgagccac ttcctgaagg agaagggcgg cctggagggc | 960 |
| ctgatctaca gccagaagcg ccaggacatc ctggacctgt ggatccacca cacccagggc | 1020 |
| tacttccccg gctggcagaa ctacaccccc ggccccggca tccgctaccc cctgaccttc | 1080 |
| ggctggtgct tcaagctggt gcccgtggac cccgactacg tggaggaggc caacgccggc | 1140 |
| gagaacaaca gcctgctgca ccccatgagc cagcacggca tggacgaccc cgagaaggag | 1200 |
| gtgctggtgt ggcgcttcga cagccgcctg gccttccacc acatggcccg cgagctgcac | 1260 |
| cccgagtact acaaggactg c | 1281 |

<210> SEQ ID NO 53
<211> LENGTH: 2799
<212> TYPE: DNA
<213> ORGANISM: Artificial Sequence
<220> FEATURE:
<223> OTHER INFORMATION: Description of Artificial Sequence:
      TatRevNefGag B

<400> SEQUENCE: 53

|                                                      |      |
|------------------------------------------------------|------|
| gccaccatgg agcccgtgga ccccgcctg gagccctgga agcacccggg cagccagccc | 60 |
| aagaccgccg gcaccaactg ctactgcaag aagtgctgct ccactgcca ggtgagcttc | 120 |
| atcaccaagg gcctgggcat cagctacggc cgcaagaagc gccgcagcg ccgccgcgcc | 180 |
| ccccccgaca gcgaggtgca ccaggtgagc ctgcccaagc agcccgccag ccagccccag | 240 |
| ggcgacccca ccggccccaa ggagagcaag aagaaggtgg agcgcgagac cgagaccgac | 300 |
| cccgtgcacc ccggggccgg ccgcagcggc gacagcgacg aggagctgct gcagaccgtg | 360 |
| cgcttcatca gttcctgta ccagagcaac ccctgccca gccccaaggg cacccgccag | 420 |
| gccgacctga accgccgccg ccgctggcgc gagcgccagc gccagatcca gagcatcagc | 480 |
| gcctggatca tcagcaccca cctgggccgc agcaccgagc ccgtgcccct gcagctgccc | 540 |
| cccgacctgc gcctgaacct ggactgcagc gaggactgcg gcaccagcgg cacccagggc | 600 |
| gtgggcagcc ccaggtgct gggcgagagc ccgccgtgc tggacagcgg caccaaggag | 660 |
| ctcgaggccg gcaagtggag caagcgcatg agcggctgga gcgccgtgcg cgagcgcatg | 720 |
| aagcgcgccg agcccgccga gcccgccgcc gacggcgtgg gcgccgtgag ccgcgacctg | 780 |
| gagaagcacg gcgccatcac cagcagcaac accgccgcca acaacgccga ctgcgcctgg | 840 |
| ctggaggccc aggaggacga ggacgtgggc ttccccgtgc gccccaggt gccctgcgc | 900 |
| cccatgacct acaaggccgc cctggacctg agccacttcc tgaaggagaa gggcggcctg | 960 |
| gagggcctga tctacagcca gaagcgccag gacatcctgg acctgtggat ccaccacacc | 1020 |
| cagggctact tccccggctg gcagaactac accccggcc ccggcatccg ctaccccctg | 1080 |
| accttcggct ggtgcttcaa gctggtgccc gtggacccg actacgtgga ggaggccaac | 1140 |

```
gccggcgaga acaacagcct gctgcacccc atgagccagc acggcatgga cgaccccgag    1200
aaggaggtgc tggtgtggcg cttcgacagc cgcctggcct tccaccacat ggcccgcgag    1260
ctgcaccccg agtactacaa ggactgcgaa ttcggcgccc gcgccagcgt gctgagcggc    1320
ggcgagctgg acaagtggga agatccgc ctgcgcccg cggcaagaa gaagtacaag        1380
```

```
gccggcgaga acaacagcct gctgcacccc atgagccagc acggcatgga cgaccccgag    1200
aaggaggtgc tggtgtggcg cttcgacagc cgcctggcct tccaccacat ggcccgcgag    1260
ctgcaccccg agtactacaa ggactgcgaa ttcggcgccc gcgccagcgt gctgagcggc    1320
ggcgagctgg acaagtggga agatccgc  ctgcgcccg gcggcaagaa gaagtacaag     1380
ctgaagcaca tcgtgtgggc cagccgcgag ctggagcgct tcgccgtgaa ccccggcctg    1440
ctggagacca gcgagggctg ccgccagatc ctgggccagc tgcagcccag cctgcagacc    1500
ggcagcgagg agctgcgcag cctgtacaac accgtggcca ccctgtactg cgtgcaccag    1560
cgcatcgacg tcaaggacac caaggaggcc ctggagaaga tcgaggagga gcagaacaag    1620
tccaagaaga aggcccagca ggccgccgcc gccgccggca ccggcaacag cagccaggtg    1680
agccagaact accccatcgt gcagaacctg cagggccaga tggtgcacca ggccatcagc    1740
ccccgcaccc tgaacgcctg ggtgaaggtg gtggaggaga aggccttcag ccccgaggtg    1800
atccccatgt tcagcgccct gagcgagggc gccaccccc  aggacctgaa cacgatgttg    1860
aacaccgtgg gcggccacca ggccgccatg cagatgctga aggagaccat caacgaggag    1920
gccgccgagt gggaccgcgt gcaccccgtg cacgccggcc ccatcgcccc cggccagatg    1980
cgcgagcccc gcggcagcga catcgccggc accaccagca ccctgcagga gcagatcggc    2040
tggatgacca caaccccccc catccccgtg ggcgagatct acaagcggtg gatcatcctg    2100
ggcctgaaca agatcgtgcg gatgtacagc cccaccagca tcctggacat ccgccagggc    2160
cccaaggagc ccttccgcga ctacgtggac cgcttctaca agaccctgcg cgctgagcag    2220
gccagccagg acgtgaagaa ctggatgacc gagaccctgc tggtgcagaa cgccaacccc    2280
gactgcaaga ccatcctgaa ggctctcggc cccgcggcca ccctggagga gatgatgacc    2340
gcctgccagg gcgtgggcgg ccccggccac aaggcccgcg tgctggccga ggcgatgagc    2400
caggtgacga cccggcgac  catcatgatg cagcgcggca cttccgcaa ccagcggaag     2460
accgtcaagt gcttcaactg cggcaaggag ggccacaccg ccaggaactg ccgcgccccc    2520
cgcaagaagg gctgctggcg ctgcggccgc gagggcacc  agatgaagga ctgcaccgag    2580
cgccaggcca acttcctggg caagatctgg cccagctaca agggccgccc cggcaacttc    2640
ctgcagagcc gccccgagcc caccgccccc cccgaggaga gcttccgctt cggcgaggag    2700
aagaccaccc ccagccagaa gcaggagccc atcgacaagg agctgtaccc cctgaccagc    2760
ctgcgcagcc tgttcggcaa cgaccccagc agccagtaa                          2799
```

<210> SEQ ID NO 54
<211> LENGTH: 5283
<212> TYPE: DNA
<213> ORGANISM: Artificial Sequence
<220> FEATURE:
<223> OTHER INFORMATION: Description of Artificial Sequence: description

<400> SEQUENCE: 54

```
gtcgacgcca ccatggagcc cgtggacccc cgcctggagc cctggaagca ccccggcagc      60
cagcccaaga ccgccggcac caactgctac tgcaagaagt gctgcttcca ctgccaggtg     120
agcttcatca ccaagggcct gggcatcagc tacggccgca agaagcgccg ccagcgccgc     180
cgcgcccccc ccgacagcga ggtgcaccag gtgagcctgc caagcagcc  cgccagccag     240
ccccaggggcg accccaccgg ccccaaggag agcaagaaga aggtggagcg cgagaccgag     300
accgaccccg tgcaccccgg ggccggccgc agcggcgaca cgacgaggac gctgctgcag     360
accgtgcgct tcatcaagtt cctgtaccag agcaacccc  tgcccagccc caagggcacc     420
```

```
cgccaggccg acctgaaccg ccgccgccgc tggcgcgagc gccagcgcca gatccagagc    480
atcagcgcct ggatcatcag cacccacctg ggccgcagca ccgagcccgt gcccctgcag    540
ctgcccccg  acctgcgcct gaacctggac tgcagcgagg actgcggcac cagcggcacc    600
cagggcgtgg gcagccccca ggtgctgggc gagagccccg ccgtgctgga cagcggcacc    660
aaggagctcg aggccggcaa gtggagcaag cgcatgagcg gctggagcgc cgtgcgcgag    720
cgcatgaagc gcgccgagcc ccgccgagcc ccgccgacg  gcgtgggcgc cgtgagccgc    780
gacctggaga agcacggcgc catcaccagc agcaacaccg ccgccaacaa cgccgactgc    840
gcctggctgg aggcccagga ggacgaggac gtgggcttcc ccgtgcgccc ccaggtgccc    900
ctgcgcccca tgacctacaa ggccgccctg acctgagcc  acttcctgaa ggagaagggc    960
ggcctggagg gcctgatcta cagccagaag cgccaggaca tcctggacct gtggatccac   1020
cacacccagg gctacttccc cggctggcag aactacaccc ccggccccgg catccgctac   1080
cccctgacct tcggctggtg cttcaagctg gtgcccgtgg accccgacta cgtggaggag   1140
gccaacgccg gcgagaacaa cagcctgctg cacccatga  ccagcacggc catggacgac   1200
cccgagaagg aggtgctggt gtggcgcttc gacagccgcc tggccttcca ccacatggcc   1260
cgcgagctgc accccgagta ctacaaggac tgcctcgagg gcgcccgcgc cagcgtgctg   1320
agcggcggcg agctggacaa gtgggagaag atccgcctgc gccccggcgg caagaagaag   1380
tacaagctga agcacatcgt gtgggccagc cgcgagctgg agcgcttcgc cgtgaacccc   1440
ggcctgctgg agaccagcga gggctgccgc cagatcctgg ccagctgca  gcccagcctg   1500
cagaccggca gcgaggagct gcgcagcctg tacaacaccg tggccaccct gtactgcgtg   1560
caccagcgca tcgacgtcaa ggacaccaag gaggccctgg agaagatcga ggaggagcag   1620
aacaagtcca gaagaaggc  ccagcaggcc gccgccgccg ccggcaccgg caacagcagc   1680
caggtgagcc agaactaccc catcgtgcag aacctgcagg gccagatggt gcaccaggcc   1740
atcagccccc gcaccctgaa cgcctgggtg aaggtggtgg aggagaaggc cttcagcccc   1800
gaggtgatcc ccatgttcag cgccctgagc gagggcgcca ccccccagga cctgaacacg   1860
atgttgaaca ccgtgggcgg ccaccaggcc gccatgcaga tgctgaagga gaccatcaac   1920
gaggaggccg ccgagtggga ccgcgtgcac cccgtgcacg ccggcccat  cgccccggc    1980
cagatgcgcg agccccgcgg cagcgacatc gccggcacca ccagcaccct gcaggagcag   2040
atcggctgga tgaccaacaa ccccccatc  cccgtgggcg agatctacaa gcggtggatc   2100
atcctgggcc tgaacaagat cgtgcggatg tacagcccca ccagcatcct ggacatccgc   2160
cagggccca  aggagccctt ccgcgactac gtggaccgct tctacaagac cctgcgcgct   2220
gagcaggcca gccaggacgt gaagaactgg atgaccgaga ccctgctggt gcagaacgcc   2280
aaccccgact gcaagaccat cctgaaggct ctcggccccg cggccaccct ggaggagatg   2340
atgaccgcct gccagggcgt gggcggcccc ggccacaagg cccgcgtgct ggccgaggcg   2400
atgagccagg tgacgaaccc ggcgaccatc atgatgcagc gcggcaactt ccgcaaccag   2460
cggaagaccg tcaagtgctt caactgcggc aaggagggcc acaccgccag gaactgccgc   2520
gccccccgca gaagggctg ctggcgctgc ggccgcgagg ccaccagat  gaaggactgc   2580
accgagcgca aggccaactt cctgggcaag atctggccca gctacaaggg ccgccccggc   2640
aacttcctgc agagccgccc cgagccacc  gccccccg   aggagagctt ccgcttcggc   2700
gaggagaaga ccaccccag  ccagaagcag gagcccatcg acaaggagct gtaccccctg   2760
accagcctgc gcagcctgtt cggcaacgac cccagcagcc agaaagaatt caaggcccgc   2820
```

```
gtgctggccg aggcgatgag ccaggtgacg aacccggcga ccatcatgat gcagcgcggc    2880
aacttccgca accagcggaa gaccgtcaag tgcttcaact gcggcaagga gggccacacc    2940
gccaggaact gccgcgcccc ccgcaagaag ggctgctggc gctgcggccg cgaaggacac    3000
caaatgaaag attgcactga gagacaggct aatttcttcc gcgaggacct ggccttcctg    3060
cagggcaagg cccgcgagtt cagcagcgag cagacccgcg ccaacagccc cacccgccgc    3120
gagctgcagg tgtgggcgg cgagaacaac agcctgagcg aggccggcgc cgaccgccag    3180
ggcaccgtga gcttcaactt cccccagatc cccctgtggc agcgccccct ggtgaccatc    3240
aggatcggcg gccagctcaa ggaggcgctg ctcgccaccg gcgccgacga caccgtgctg    3300
gaggagatga acctgcccgg caagtggaag cccaagatga tcggcgggat cgggggcttc    3360
atcaaggtgc ggcagtacga ccagatcccc gtggagatct gcgccacaa ggccatcggc    3420 accgtgctgg tgggccccac ccccgtgaac atcatcggcc gcaacctgct gacccagatc    3480
ggctgcaccc tgaacttccc catcagcccc atcgagacg tgcccgtgaa gctgaagccg    3540
gggatggacg gccccaaggt caagcagtgg ccctgaccg aggagaagat caaggccctg    3600
gtggagatct gcaccgagat ggagaaggag gcaagatca gcaagatcgg ccccgagaac    3660
ccctacaaca cccccgtgtt cgccatcaag aagaaggaca gcaccaagtg gcgcaagctg    3720
gtggacttcc gcgagctgaa caagcgcacc caggacttct gggaggtgca gctgggcatc    3780
ccccaccccg ccggcctgaa gaagaagaag agcgtgaccg tgctggacgt gggcgacgcc    3840
tacttcagcg tgcccctgga caaggacttc cgcaagtaca ccgccttcac catcccccagc    3900 atcaacaacg agacccccgg catccgctac cagtacaacg tgctgcccca gggctggaag    3960
ggcagccccg ccatcttcca gagcagcatg accaagatcc tggagccctt ccgcaagcag    4020
aaccccgaca tcgtgatcta ccaggccccc ctgtacgtgg gcagcgacct ggagatcggc    4080
cagcaccgca ccaagatcga ggagctgcgc cagcacctgc tgcgctgggg cttcaccacc    4140
cccgacaaga gcaccagaa ggagccccc ttcctgccca tcgagctgca ccccgacaag    4200
tggaccgtgc agcccatcat gctgcccgag aaggacagct ggaccgtgaa cgacatccag    4260
aagctggtgg gcaagctgaa ctgggccagc cagatctacg ccggcatcaa ggtgaagcag    4320
ctgtgcaagc tgctgcgcgg caccaaggcc ctgaccgagg tgatccccct gaccgaggag    4380
gccgagctgg agctggccga aaccgcgag atcctgaagg agcccgtgca cgaggtgtac    4440 tacgaccccca gcaaggacct ggtggccgag atccagaagc agggccaggg ccagtggacc    4500
taccagatct accaggagcc cttcaagaac ctgaagaccg gcaagtacgc ccgcatgcgc    4560
ggcgcccaca ccaacgacgt gaagcagctg accgaggccg tgcagaaggt gagcaccgag    4620
agcatcgtga tctgggcaa gatccccaag ttcaagctgc ccatccagaa ggagacctgg    4680
gaggcctggt ggatggagta ctggcaggcc acctggatcc ccgagtggga gttcgtgaac    4740 acccccccc tggtgaagct gtggtaccag ctggagaagg agcccatcgt gggcgccgag    4800
accttctacg tggacggcgc cgccaaccgc gagaccaagc tgggcaaggc cggctacgtg    4860
accgaccggg gccggcagaa ggtggtgagc atcgccgaca ccaccaacca gaagaccgag    4920
ctgcaggcca tccacctggc cctgcaggac agcggcctgg aggtgaacat cgtgaccgac    4980
agccagtacg ccctgggcat catccaggcc cagcccgaca gagcgagag cgagctggtg    5040 agccagatca tcgagcagct gatcaagaag gagaaggtgt acctggcctg ggtgccggc    5100 cacaagggca tcggcggcaa cgagcaggtg gacaagctgg tgagcgccgg catccgcaag    5160
gtgctgttcc tgaacggcat cgatggcggc atcgtgatct accagtacat ggacgacctg    5220
```

```
tacgtgggca gcggcggccc taggatcgat taaaagcttc ccggggctag caccggttct    5280
aga                                                                  5283

<210> SEQ ID NO 55
<211> LENGTH: 4773
<212> TYPE: DNA
<213> ORGANISM: Artificial Sequence
<220> FEATURE:
<223> OTHER INFORMATION: Description of Artificial Sequence:
      TatRevNefGagProtInaRTmut B

<400> SEQUENCE: 55
gccaccatgg agcccgtgga cccccgcctg gagccctgga agcaccccgg cagccagccc      60
aagaccgccg gcaccaactg ctactgcaag aagtgctgct ccactgcca  ggtgagcttc     120 atcaccaagg gcctgggcat cagctacggc cgcaagaagc gccgccagcg ccgccgcgcc     180 cccccgaca  gcgaggtgca ccaggtgagc ctgcccaagc agcccgccag ccagccccag     240
ggcgacccca ccggccccaa ggagagcaag aagaaggtgg agcgcgagac cgagaccgac     300
cccgtgcacc ccggggccgg ccgcagcggc gacagcgacg aggagctgct gcagaccgtg     360
cgcttcatca gttcctgta  ccagagcaac cccctgccca gccccaaggg cacccgccag     420
gccgacctga accgccgccg ccgctggcgc gagcgccagc gccagatcca gagcatcagc     480
gcctggatca tcagcaccca cctgggccgc agcaccgagc ccgtgcccct gcagctgccc     540
cccgacctgc gcctgaacct ggactgcagc gaggactgcg gcaccagcgg cacccagggc     600
gtgggcagcc cccaggtgct gggcgagagc cccgccgtgc tggacagcgg caccaaggag     660
ctcgaggccg gcaagtggag caagcgcatg gccggctgga gcgccgtgcg cgagcgcatg     720
aagcgcgccg agcccgccga ccccgccgcc gacggcgtgg gcgccgtgag ccgcgacctg     780
gagaagcacg gcgccatcac cagcagcaac accgccgcca caacgccga  ctgcgcctgg     840 ctggaggccc aggaggacga ggacgtgggc ttccccgtgc gccccaggt  gcccctgcgc     900 cccatgacct acaaggccgc cctggacctg agccacttcc tgaaggagaa gggcggcctg     960
gagggcctga tctacagcca gaagcgccag gacatcctgg acctgtggat ccaccacacc    1020
cagggctact cccccggctg gcagaactac acccccggcc ccggcatccg ctacccctg     1080 accttcggct ggtgcttcaa gctggtgccc gtgaccccg  actacgtgga ggaggccaac    1140
gccggcgaga caacagcct  gctgcacccc atgagccagc acggcatgga cgaccccgag    1200
aaggaggtgc tggtgtggcg cttcgacagc cgcctggcct tccaccacat ggcccgcgag    1260
ctgcaccccg agtactacaa ggactgcaag cttggcgccc gcgccagcgt gctgagcggc    1320
ggcgagctgg acaagtggga aagatccgc  ctgcgcccg  cggcaagaa  gaagtacaag    1380 ctgaagcaca tcgtgtgggc cagccgcgag ctggagcgct cgccgtgaa  ccccggcctg    1440 ctggagacca gcgagggctg ccgccagatc ctggccagc  tgcagcccag cctgcagacc    1500
ggcagcgagg agctgcgcag cctgtacaac accgtggcca ccctgtactg cgtgcaccag    1560
cgcatcgacg tcaaggacac caaggaggcc ctggagaaga tcgaggagga gcagaacaag    1620
tccaagaaga aggcccagca ggccgccgcc gccgccggca ccggcaacag cagccaggtg    1680
agccagaact  accccatcgt gcagaacctg cagggccaga tggtgcacca ggccatcagc    1740
ccccgcaccc tgaacgcctg ggtgaaggtg gtggaggaga aggccttcag ccccgaggtg    1800
atccccatgt tcagcgccct gagcgagggc gccaccccc  aggacctgaa cacgatgttg    1860
aacaccgtgg gcggccacca ggccgccatg cagatgctga aggagaccat caacgaggag    1920
```

```
gccgccgagt gggaccgcgt gcaccccgtg cacgccggcc ccatcgcccc cggccagatg    1980
cgcgagcccc gcggcagcga catcgccggc accaccagca ccctgcagga gcagatcggc    2040
tggatgacca acaaccccc catccccgtg ggcgagatct acaagcggtg gatcatcctg     2100
ggcctgaaca agatcgtgcg gatgtacagc cccaccagca tcctggacat ccgccagggc    2160
cccaaggagc ccttccgcga ctacgtggac cgcttctaca agaccctgcg cgctgagcag    2220
gccagccagg acgtgaagaa ctggatgacc gagaccctgc tggtgcagaa cgccaacccc    2280
gactgcaaga ccatcctgaa ggctctcggc cccgcggcca ccctggagga tgatgatgacc   2340
gcctgccagg gcgtgggcgg ccccggccac aaggcccgcg tgctggccga ggcgatgagc    2400
caggtgacga acccggcgac catcatgatg cagcgcggca acttccgcaa ccagcggaag    2460
accgtcaagt gcttcaactg cggcaaggag ggccacaccg ccaggaactg ccgcgccccc    2520
cgcaagaagg gctgctggcg ctgcggccgc gagggccacc agatgaagga ctgcaccgag    2580
cgccaggcca acttcctggg caagatctgg cccagctaca agggccgccc cggcaacttc    2640
ctgcagagcc gccccgagcc caccgccccc ccgaggaga gcttccgctt cggcgaggag     2700
aagaccaccc ccagccagaa gcaggagccc atcgacaagg agctgtaccc cctgaccagc    2760
ctgcgcagcc tgttcggcaa cgaccccagc agccagaaag aattcccca gatcaccctg     2820
tggcagcgcc ccctggtgac catcaggatc ggcggccagc tcaaggaggc gctgctcgcc    2880
accggcgccg acgacaccgt gctggaggag atgaacctgc ccggcaagtg aagcccaag     2940
atgatcggcg ggatcggggg cttcatcaag gtgcggcagt acgaccagat ccccgtggag    3000
atctgcggcc acaaggccat cggcaccgtg ctggtgggcc caccccgt gaacatcatc      3060
ggccgcaacc tgctgaccca gatcggctgc accctgaact tccccatcag ccccatcgag    3120
acggtgcccg tgaagctgaa gccggggatg gacggcccca aggtcaagca gtggcccctg    3180
accgaggaga gatcaaggc cctggtggag atctgcaccg agatggagaa ggagggcaag     3240
atcagcaaga tcggccccga gaaccccta aacacccccg tgttcgccat caagaagaag    3300
gacagcacca gtggcgcaa gctggtggac ttccgcgagc tgaacaagcg cacccaggac    3360
ttctggagg tgcagctggg catccccac cccgccggcc tgaagaagaa gagagcgtg     3420
accgtgctgg acgtgggcga cgcctacttc agcgtgcccc tggacaagga cttccgcaag    3480
tacaccgcct tcaccatccc cagcatcaac aacgagaccc ccggcatccg ctaccagtac    3540
aacgtgctgc cccagggctg gaagggcagc cccgccatct tccagagcag catgaccaag    3600
atcctggagc ccttccgcaa gcagaacccc gacatcgtga tctaccaggc cccctgtac     3660
gtgggcagcg acctggagat cggccagcac cgcaccaaga tcgaggagct gcgccagcac    3720
ctgctgcgct ggggcttcac cacccccgac aagaagcacc agaaggagcc cccttcctg     3780
cccatcgagc tgcaccccga caagtggacc gtgcagccca tcatgctgcc cgagaaggac    3840
agctggaccg tgaacgacat ccagaagctg gtgggcaagc tgaactgggc cagccagatc    3900
tacgccggca tcaaggtgaa gcagctgtgc aagctgctgc gcggcaccaa ggccctgacc    3960
gaggtgatcc ccctgaccga ggaggccgag ctggagctgg ccgagaaccg cgagatcctg    4020
aaggagcccg tgcacgaggt gtactacgac cccagcaagg acctggtggc cgagatccag    4080
aagcagggca gggccagtg gacctaccag atctaccagg agcccttcaa gaacctgaag    4140
accggcaagt acgcccgcat gcgcggcgcc cacaccaacg acgtgaagca gctgaccgag    4200
gccgtgcaga aggtgagcac cgagagcatc gtgatctggg gcaagatccc caagttcaag    4260
ctgcccatcc agaaggagac ctgggaggcc tggtggatgg agtactggca ggccacctgg    4320
```

```
atccccgagt gggagttcgt gaacacccccc cccctggtga agctgtggta ccagctggag    4380
aaggagccca tcgtgggcgc cgagaccttc tacgtggacg gcgccgccaa ccgcgagacc    4440
aagctgggca aggccggcta cgtgaccgac cggggccggc agaaggtggt gagcatcgcc    4500
gacaccacca accagaagac cgagctgcag gccatccacc tggccctgca ggacagcggc    4560
ctggaggtga acatcgtgac cgacagccag tacgccctgg gcatcatcca ggcccagccc    4620
gacaagagcg agagcgagct ggtgagccag atcatcgagc agctgatcaa gaaggagaag    4680
gtgtacctgg cctgggtgcc cgcccacaag ggcatcggcg gcaacgagca ggtggacaag    4740
ctggtgagcg ccggcatccg caaggtgctc taa                                 4773
```

<210> SEQ ID NO 56
<211> LENGTH: 3636
<212> TYPE: DNA
<213> ORGANISM: Artificial Sequence
<220> FEATURE:
<223> OTHER INFORMATION: Description of Artificial Sequence:
      TatRevNefp2Pol.opt_B

<400> SEQUENCE: 56

```
gccaccatgg agcccgtgga cccccgcctg gagccctgga agcaccccgg cagccagccc      60
aagaccgccg gcaccaactg ctactgcaag aagtgctgct ccactgccca ggtgagcttc     120
atcaccaagg gcctgggcat cagctacggc cgcaagaagc gccgccagcg ccgccgcgcc     180 cccccccgaca gcgaggtgca caggtgagc ctgcccaagc agcccgccag ccagccccag     240
ggcgacccca ccgccccaa ggagagcaag aagaaggtgg agcgcgagac cgagaccgac     300
cccgtgcacc ccggggccgg ccgcagcggc gacagcgacg aggagctgct gcagaccgtg     360
cgcttcatca gttcctgta ccagagcaac cccctgccca gccccaaggg cacccgccag     420
gccgacctga accgccgccg ccgctggcgc gagcgccagc gccagatcca gagcatcagc     480
gcctggatca tcagcaccca cctgggccgc agcaccgagc ccgtgccct gcagctgccc     540 cccgacctgc gcctgaacct ggactgcagc gaggactgcg gcaccagcgg caccccagggc     600 gtgggcagcc ccaggtgct gggcgagagc cccgccgtgc tggacagcgg caccaaggag     660
ctcgaggccg gcaagtggag caagcgcatg agcggctgga gcgccgtgcg cgagcgcatg     720
aagcgcgccg agcccgccga gccgccgcc gacggcgtgg gcgccgtgag ccgcgacctg     780
gagaagcacg gcgccatcac cagcagcaac accgccgcca caacgccga ctgcgcctgg     840 ctggaggccc aggaggacga ggacgtgggc ttccccgtgc gccccaggt gcccctgcgc     900 cccatgacct acaaggccgc cctggacctg agccacttcc tgaaggagaa gggcggcctg     960
gagggcctga tctacagcca gaagcgccag gacatcctgg acctgtggat ccaccacacc    1020
cagggctact ccccggctg gcagaactac acccccggcc ccggcatccg ctaccccctg    1080
accttcggct ggtgcttcaa gctggtgccc gtggaccccg actacgtgga ggaggccaac    1140
gccggcgaga caacagcct gctgcacccc atgagccagc acggcatgga cgaccccgag    1200
aaggaggtgc tggtgtggcg cttcgacagc cgcctggcct tccaccacat ggcccgcgag    1260
ctgcaccccg agtactacaa ggactgcgaa ttcgccgagg cgatgagcca ggtgacgaac    1320
ccggcgacca tcatgatgca gcgcggcaac ttccgcaacc agcggaagac cgtcaagtgc    1380
ttcaactgcg gcaaggaggg ccacaccgcc aggaactgcc gcgcccccg caagaagggc    1440 tgctggcgct gcggccgcga aggacaccaa atgaaagatt gcactgagag acaggctaat    1500
ttcttccgcg aggacctggc cttcctgcag ggcaaggccc gcgagttcag cagcgagcag    1560
acccgcgcca acagccccac ccgccgcgag ctgcaggtgt ggggcggcga gaacaacagc    1620
```

```
ctgagcgagg ccggcgccga ccgccagggc accgtgagct tcaacttccc ccagatcacc    1680
ctgtggcagc gccccctggt gaccatcagg atcggcggcc agctcaagga ggcgctgctc    1740
gccaccggcg ccgacgacac cgtgctggag gagatgaacc tgcccggcaa gtggaagccc    1800
aagatgatcg gcgggatcgg gggcttcatc aaggtgcggc agtacgacca gatccccgtg    1860
gagatctgcg gccacaaggc catcggcacc gtgctggtgg cccccacccc cgtgaacatc    1920
atcggccgca acctgctgac ccagatcggc tgcaccctga acttccccat cagccccatc    1980
gagacggtgc ccgtgaagct gaagccgggg atggacggcc ccaaggtcaa gcagtggccc    2040
ctgaccgagg agaagatcaa ggccctggtg gagatctgca ccgagatgga aaggagggc    2100
aagatcagca agatcggccc cgagaacccc tacaacaccc ccgtgttcgc catcaagaag    2160
aaggacagca ccaagtggcg caagctggtg gacttccgcg agctgaacaa gcgcacccag    2220
gacttctggg aggtgcagct gggcatcccc caccccgccg gcctgaagaa gaagaagagc    2280
gtgaccgtgc tggacgtggg cgacgcctac ttcagcgtgc ccctgacaa ggacttccgc    2340
aagtacaccg ccttcaccat ccccagcatc aacaacgaga ccccccggcat ccgctaccag    2400
tacaacgtgc tgccccaggg ctggaagggc agccccgcca tcttccagag cagcatgacc    2460
aagatcctgg agcccttccg caagcagaac cccgacatcg tgatctacca ggcccccctg    2520
tacgtgggca gcgacctgga gatcggccag caccgcacca gatcgagga gctgcgccag    2580
cacctgctgc gctggggctt caccaccccc gacaagaagc accagaagga gccccccttc    2640
ctgcccatcg agctgcaccc cgacaagtgg accgtgcagc ccatcatgct gcccgagaag    2700
gacagctgga ccgtgaacga catccagaag ctggtgggca gctgaactg gccagccag    2760
atctacgccg gcatcaaggt gaagcagctg tgcaagctgc tgcgcggcac caaggccctg    2820
accgaggtga tccccctgac cgaggaggcc gagctggagc tggccgagaa ccgcgagatc    2880
ctgaaggagc ccgtgcacga ggtgtactac gaccccagca aggacctggt ggccgagatc    2940
cagaagcagg gccagggcca gtggacctac cagatctacc aggagccctt caagaacctg    3000
aagaccggca gtacgcccg catgcgcggc gcccacacca cgacgtgaa gcagctgacc    3060
gaggccgtgc agaaggtgag caccgagagc atcgtgatct ggggcaagat ccccaagttc    3120
aagctgccca tccagaagga gacctgggag gcctggtgga tggagtactg gcaggccacc    3180
tggatccccg agtgggagtt cgtgaacacc ccccccctgg tgaagctgtg gtaccagctg    3240
gagaaggagc ccatcgtggg cgccgagacc ttctacgtgg acggcgccgc caaccgcgag    3300
accaagctgg gcaaggccgg ctacgtgacc gaccggggcc ggcagaaggt ggtgagcatc    3360
gccgacacca ccaaccagaa gaccgagctg caggccatcc acctggccct gcaggacagc    3420
ggcctggagg tgaacatcgt gaccgacagc cagtacgccc tgggcatcat ccaggcccag    3480
cccgacaaga gcgagagcga gctggtgagc cagatcatcg agcagctgat caagaaggag    3540
aaggtgtacc tggcctgggt gcccgcccac aagggcatcg gcggcaacga gcaggtggac    3600
aagctggtga gcgccggcat ccgcaaggtg ctgtaa                              3636
```

<210> SEQ ID NO 57
<211> LENGTH: 3261
<212> TYPE: DNA
<213> ORGANISM: Artificial Sequence
<220> FEATURE:
<223> OTHER INFORMATION: Description of Artificial Sequence:
      TatRevNefprotRTopt B

<400> SEQUENCE: 57

```
gccaccatgg agcccgtgga cccccgcctg gagccctgga agcaccccgg cagccagccc      60
aagaccgccg gcaccaactg ctactgcaag aagtgctgct tccactgcca ggtgagcttc     120
atcaccaagg gcctgggcat cagctacggc cgcaagaagc gccgccagcg ccgccgcgcc     180 cccccgaca gcgaggtgca ccaggtgagc ctgcccaagc agcccgccag ccagccccag     240
ggcgacccca ccggccccaa ggagagcaag aagaaggtgg agcgcgagac cgagaccgac     300
cccgtgcacc ccggggccgg ccgcagcggc gacagcgacg aggagctgct gcagaccgtg     360
cgcttcatca agttcctgta ccagagcaac cccctgccca gccccaaggg cacccgccag     420
gccgacctga accgccgccg ccgctggcgc gagcgccagc gccagatcca gagcatcagc     480
gcctggatca tcagcaccca cctgggccgc agcaccgagc ccgtgcccct gcagctgccc     540
cccgacctgc gcctgaacct ggactgcagc gaggactgcg gcaccagcgg cacccagggc     600
gtgggcagcc cccaggtgct gggcgagagc cccgccgtgc tggacagcgg caccaaggag     660
ctcgaggccg gcaagtggag caagcgcatg agcggctgga gcgccgtgcg cgagcgcatg     720
aagcgcgccg agcccgccga gccgccgcc gacgcgtgg gcgccgtgag ccgcgacctg     780
gagaagcacg gcgccatcac cagcagcaac accgccgcca caacgccga ctgcgcctgg     840 ctggaggccc aggaggacga ggacgtgggc ttccccgtgc gcccccaggt gcccctgcgc     900
cccatgacct acaaggccgc cctggacctg agccacttcc tgaaggagaa gggcggcctg     960
gagggcctga tctacagcca gaagcgccag gacatcctgg acctgtggat ccaccacacc    1020
cagggctact cccccggctg gcagaactac accccggcc ccggcatccg ctaccccctg    1080
accttcggct ggtgcttcaa gctggtgccc gtggaccccg actacgtgga ggaggccaac    1140
gccggcgaga caacagcct gctgcacccc atgagccagc acggcatgga cgaccccgag    1200
aaggaggtgc tggtgtggcg cttcgacagc cgcctggcct tccaccacat ggcccgcgag    1260
ctgcaccccg agtactacaa ggactgcgaa ttccccagg atcaccctgtg gcagcgcccc    1320 ctggtgacca tcaggatcgg cggccagctc aaggaggcgc tgctcgccac cggcgccgac    1380
gacaccgtgc tggaggagat gaacctgccc ggcaagtgga agcccaagat gatcggcggg    1440
atcgggggct tcatcaaggt gcggcagtac gaccagatcc ccgtggagat ctgcggccac    1500
aaggccatcg gcaccgtgct ggtgggcccc acccccgtga acatcatcgg ccgcaacctg    1560
ctgacccaga tcggctgcac cctgaacttc cccatcagcc catcgagac ggtgcccgtg    1620 aagctgaagc cggggatgga cggccccaag gtcaagcagt ggcccctgac cgaggagaag    1680
atcaaggccc tggtggagat ctgcaccgag atggagaagg agggcaagat cagcaagatc    1740
ggccccgaga acccctacaa cacccccgtg ttcgccatca agaagaagga cagcaccaag    1800
tggcgcaagc tggtggactt ccgcgagctg aacaagcgca cccaggactt ctggaggtg     1860 cagctgggca tcccccaccc cgccggcctg aagaagaaga gagcgtgac cgtgctggac    1920 gtgggcgacg cctacttcag cgtgcccctg gacaaggact ccgcaagta caccgccttc    1980 accatcccca gcatcaacaa cgagaccccc ggcatccgct accagtacaa cgtgctgccc    2040
cagggctgga gggcagccc cgccatcttc cagagcagca tgaccaagat cctggagccc    2100
ttccgcaagc agaaccccga catcgtgatc taccaggccc ccctgtacgt gggcagcgac    2160
ctggagatcg gccagcaccg caccaagatc gaggagctgc gccagcacct gctgcgctgg    2220
ggcttcacca ccccgacaa gaagcaccag aaggagcccc ccttcctgcc catcgagctg    2280
caccccgaca gtggaccgt gcagcccatc atgctgcccg agaaggacag ctggaccgtg    2340
aacgacatcc agaagctggt gggcaagctg aactgggcca gccagatcta cgccggcatc    2400
```

```
aaggtgaagc agctgtgcaa gctgctgcgc ggcaccaagg ccctgaccga ggtgatcccc    2460
ctgaccgagg aggccgagct ggagctggcc gagaaccgcg agatcctgaa ggagcccgtg    2520
cacgaggtgt actacgaccc cagcaaggac ctggtggccg agatccagaa gcagggccag    2580
ggccagtgga cctaccagat ctaccaggag cccttcaaga acctgaagac cggcaagtac    2640
gcccgcatgc gcggcgccca ccaacgac gtgaagcagc tgaccgaggc cgtgcagaag      2700
gtgagcaccg agagcatcgt gatctgcggc aagatcccca agttcaagct gcccatccag    2760
aaggagacct gggaggcctg gtggatggag tactggcagg ccacctggat ccccgagtgg    2820
gagttcgtga caccccccc cctggtgaag ctgtggtacc agctggagaa ggagcccatc     2880
gtgggcgccg agaccttcta cgtggacggc gccgccaacc gcgagaccaa gctgggcaag    2940
gccggctacg tgaccgaccg gggccggcag aaggtggtga gcatcgccga caccaccaac    3000
cagaagaccg agctgcaggc catccacctg gccctgcagg acagcggcct ggaggtgaac    3060
atcgtgaccg acagccagta cgccctgggc atcatccagg cccagcccga caagagcgag    3120
agcgagctgg tgagccagat catcgagcag ctgatcaaga aggagaaggt gtacctggcc    3180
tgggtgcccg cccacaaggg catcggcggc aacgagcagg tggacaagct ggtgagcgcc    3240
ggcatccgca aggtgctcta a                                              3261

<210> SEQ ID NO 58
<211> LENGTH: 576
<212> TYPE: DNA
<213> ORGANISM: Artificial Sequence
<220> FEATURE:
<223> OTHER INFORMATION: Description of Artificial Sequence: vif.opt.SF2

<400> SEQUENCE: 58
atggagaacc gctggcaggt gatgatcgtg tggcaggtgg accgcatgcg catccgcacc      60
tggaagagcc tggtgaagca ccacatgtac atcagcaaga aggccaaggg ctggttctac    120
cgccaccact acgagagcac ccaccccgc gtgagcagcg aggtgcacat ccccctgggc     180
gacgccaagc tggtgatcac cacctactgg ggcctgcaca ccggcgagcg cgagtggcac    240
ctgggccagg gcgtggccat cgagtggcgc aagaagaagt acagcaccca ggtggacccc    300
ggcctggccg accagctgat ccacctgcac tacttcgact gcttcagcga gagcgccatc    360
aagaacgcca tcctgggcta ccgcgtgagc ccccgctgcg agtaccaggc cggccacaac    420
aaggtgggca gcctgcagta cctggcctg gccgccctga tcacccccaa gaagaccaag    480
ccccccctgc ccagcgtgaa gaagctgacc gaggaccgct ggaacaagcc ccagaagacc    540
aagggccacc gcggcagcca ccatgaacgg ccac                                576

<210> SEQ ID NO 59
<211> LENGTH: 291
<212> TYPE: DNA
<213> ORGANISM: Artificial Sequence
<220> FEATURE:
<223> OTHER INFORMATION: Description of Artificial Sequence: vpr.opt.SF2

<400> SEQUENCE: 59
atggagcagg cccccgagga ccagggcccc cagcgcgagc cctacaacga gtggaccctg      60
gagctgctgg aggagctgaa gcgcgaggcc gtgcgccact cccccgccc ctggctgcac     120 agcctgggcc agtacatcta cgagacctac ggcgacacct gggccggcgt ggaggccatc    180
atccgcatcc tgcagcagct gctgttcatc cacttccgca tcggctgcca gcacagccgc    240
atcggcatca tccagcagcg ccgcgcccgc cgcaacggcg ccagccgcag c              291
```

<210> SEQ ID NO 60
<211> LENGTH: 243
<212> TYPE: DNA
<213> ORGANISM: Artificial Sequence
<220> FEATURE:
<223> OTHER INFORMATION: Description of Artificial Sequence:
      vpu.opt.SF162

<400> SEQUENCE: 60

```
atgcagcccc tgcagatcct ggccatcgtg ccctggtgg tggccgccat catcgccatc      60
gtggtgtgga ccatcgtgta catcgagtac cgcaagatcc tgcgccagcg caagatcgac    120
cgcctgatcg accgcatcac cgagcgcgcc gaggacagcg caacgagag cgagggcgac     180 caggaggagc tgagcgccct ggtggagcgc ggccacctgg cccctggga cgtggacgac    240 ctg                                                                   243
```

<210> SEQ ID NO 61
<211> LENGTH: 2007
<212> TYPE: DNA
<213> ORGANISM: Artificial Sequence
<220> FEATURE:
<223> OTHER INFORMATION: Description of Artificial Sequence:
      gp140modSF162.GM135-154-186-195

<400> SEQUENCE: 61

```
atggatgcaa tgaagagagg ctctgctgt gtgctgctgc tgtgtggagc agtcttcgtt      60
tcgcccagcg ccgtggagaa gctgtgggtg accgtgtact acggcgtgcc cgtgtggaag    120
gaggccacca ccacctgtt ctgcgccagc gacgccaagg cctacgacac cgaggtgcac    180
aacgtgtggg ccacccacgc ctgcgtgccc accgacccca cccccagga gatcgtgctg    240 gagaacgtga ccgagaactt caacatgtgg aagaacaaca tggtggagca gatgcacgag    300
gacatcatca gcctgtggga ccagagcctg aagcccgcg tgaagctgac ccccctgtgc    360
gtgaccctgc actgcaccaa cctgaagcag gccaccaaca ccaagagcag caactggaag    420
gagatggacc gcggcgagat caagcagtgc agcttcaagg tgaccaccag catccgcaac    480
aagatgcaga aggagtacgc cctgttctac aagctggacg tggtgccat cgacaacgac    540 cagaccagct acaagctgat caactgccag accagcgtga tcacccaggc ctgccccaag    600
gtgagcttcg agcccatccc catccactac tgcgcccccg ccggcttcgc catcctgaag    660
tgcaacgaca agaagttcaa cggcagcggc ccctgcacca acgtgagcac cgtgcagtgc    720
acccacggca tccgccccgt ggtgagcacc cagctgctgc tgaacggcag cctggccgag    780
gagggcgtgg tgatccgcag cgagaacttc accgacaacg ccaagaccat catcgtgcag    840
ctgaaggaga gcgtggagat caactgcacc cgccccaaca caacacccg caagagcatc    900 accatcggcc ccggccgcgc cttctacgcc accggcgaca tcatcggcga catccgccag    960
gcccactgca acatcagcgg cgagaagtgg aacaacaccc tgaagcagat cgtgaccaag   1020
ctgcaggccc agttcggcaa caagaccatc gtgttcaagc agagcagcgg cggcgacccc   1080
gagatcgtga tgcacagctt caactgcggc ggcgagttct tctactgcaa cagcacccag   1140
ctgttcaaca gcacctggaa caccatc ggccccaaca caccaacgg caccatcacc   1200 ctgcctgcc gcatcaagca gatcatcaac cgctggcagg aggtgggcaa ggccatgtac   1260
gcccccccca tccgcggcca gatccgctgc agcagcaaca tcaccggcct gctgctgacc   1320
cgcgacggcg gcaaggagat cagcaacacc accgagatct tccgcccggg cggcggcgac   1380
atgcgcgaca ctggcgcag cgagctgtac aagtacaagg tggtgaagat cgagcccctg   1440
```

```
ggcgtggccc ccaccaaggc caagcgccgc gtggtgcagc gcgagaagcg cgccgtgacc    1500
ctgggcgcca tgttcctggg cttcctgggc gccgccggca gcaccatggg cgcccgcagc    1560
ctgaccctga ccgtgcaggc ccgccagctg ctgagcggca tcgtgcagca gcagaacaac    1620
ctgctgcgcg ccatcgaggc ccagcagcac ctgctgcagc tgaccgtgtg gggcatcaag    1680
cagctgcagg cccgcgtgct ggccgtggag cgctacctga aggaccagca gctgctgggc    1740
atctggggct gcagcggcaa gctgatctgc accaccgccg tgccctggaa cgccagctgg    1800
agcaacaaga gcctggacca gatctggaac aacatgacct ggatggagtg ggagcgcgag    1860
atcgacaact acaccaacct gatctacacc ctgatcgagg agagccagaa ccagcaggag    1920
aagaacgagc aggagctgct ggagctggac aagtgggcca gcctgtggaa ctggttcgac    1980
atcagcaagt ggctgtggta catctaa                                        2007
```

<210> SEQ ID NO 62
<211> LENGTH: 2007
<212> TYPE: DNA
<213> ORGANISM: Artificial Sequence
<220> FEATURE:
<223> OTHER INFORMATION: Description of Artificial Sequence:
      gp140modSF162.GM154

<400> SEQUENCE: 62

```
atggatgcaa tgaagagagg gctctgctgt gtgctgctgc tgtgtggagc agtcttcgtt     60
tcgcccagcg ccgtggagaa gctgtgggtg accgtgtact acggcgtgcc cgtgtggaag    120
gaggccacca ccaccctgtt ctgcgccagc gacgccaagg cctacgacac cgaggtgcac    180
aacgtgtggg ccacccacgc ctgcgtgccc accgacccca cccccaggga gatcgtgctg    240
gagaacgtga ccgagaactt caacatgtgg aagaacaaca tggtggagca gatgcacgag    300
gacatcatca gcctgtggga ccagagcctg aagccctgcg tgaagctgac cccctgtgc    360 gtgaccctgc actgcaccaa cctgaagaac gccaccaaca ccaagagcag caactggaag    420
gagatggacc gcggcgagat caagcagtgc agcttcaagg tgaccaccag catccgcaac    480
aagatgcaga aggagtacgc cctgttctac aagctggacg tggtgcccat cgacaacgac    540
aacaccagct acaagctgat caactgcaac accagcgtga tcacccaggc ctgccccaag    600
gtgagcttcg agcccatccc catccactac tgcgcccccg ccggcttcgc catcctgaag    660
tgcaacgaca agaagttcaa cggcagcggc ccctgcacca cgtgagcac cgtgcagtgc    720 acccacggca tccgccccgt ggtgagcacc cagctgctgc tgaacggcag cctggccgag    780
gagggcgtgg tgatccgcag cgagaacttc accgacaacg ccaagaccat catcgtgcag    840
ctgaaggaga gctggagat caactgcacc cgccccaaca caacacccg caagagcatc    900 accatcggcc ccggccgcgc cttctacgcc accggcgaca tcatcggcga catccgccag    960
gcccactgca acatcagcgg cgagaagtgg aacaacaccc tgaagcagat cgtgaccaag    1020
ctgcaggccc agttcggcaa caagaccatc gtgttcaagc agagcagcgg cggcgaccc    1080 gagatcgtga tgcacagctt caactgcggc ggcgagttct tctactgcaa cagcacccag    1140
ctgttcaaca gcacctggaa caacaccatc ggccccaaca caccaacgg caccatcacc    1200 ctgccctgcc gcatcaagca gatcatcaac cgctggcagg aggtgggcaa ggccatgtac    1260
gcccccccca tccgcggcca gatccgctgc agcagcaaca tcaccggcct gctgctgacc    1320
cgcgacggcg gcaaggagat cagcaacacc accgagatct ccgcccggg cggcggcgac    1380 atgcgcgaca ctggcgcag cgagctgtac aagtacaagg tggtgaagat cgagcccctg    1440
ggcgtggccc ccaccaaggc caagcgccgc gtggtgcagc gcgagaagcg cgccgtgacc    1500
```

```
ctgggcgcca tgttcctggg cttcctgggc gccgccggca gcaccatggg cgcccgcagc   1560
ctgaccctga ccgtgcaggc ccgccagctg ctgagcggca tcgtgcagca gcagaacaac   1620
ctgctgcgcg ccatcgaggc ccagcagcac ctgctgcagc tgaccgtgtg gggcatcaag   1680
cagctgcagg cccgcgtgct ggccgtggag cgctacctga aggaccagca gctgctgggc   1740
atctggggct gcagcggcaa gctgatctgc accaccgccg tgccctggaa cgccagctgg   1800
agcaacaaga gcctggacca gatctggaac aacatgacct ggatggagtg ggagcgcgag   1860
atcgacaact acaccaacct gatctacacc ctgatcgagg agagccagaa ccagcaggag   1920
aagaacgagc aggagctgct ggagctggac aagtgggcca gcctgtggaa ctggttcgac   1980
atcagcaagt ggctgtggta catctaa                                        2007

<210> SEQ ID NO 63
<211> LENGTH: 2007
<212> TYPE: DNA
<213> ORGANISM: Artificial Sequence
<220> FEATURE:
<223> OTHER INFORMATION: Description of Artificial Sequence:
      gp140modSF162.GM154-186-195

<400> SEQUENCE: 63
atggatgcaa tgaagagagg gctctgctgt gtgctgctgc tgtgtggagc agtcttcgtt     60
tcgcccagcg ccgtggagaa gctgtgggtg accgtgtact acggcgtgcc cgtgtggaag    120
gaggccacca ccaccctgtt ctgcgccagc gacgccaagg cctacgacac cgaggtgcac    180
aacgtgtggg ccacccacgc ctgcgtgccc accgacccca cccccaggga gatcgtgctg    240
gagaacgtga ccgagaactt caacatgtgg aagaacaaca tggtggagca gatgcacgag    300
gacatcatca gcctgtggga ccagagcctg aagccctgcg tgaagctgac cccctgtgc    360 gtgaccctgc actgcaccaa cctgaagaac gccaccaaca ccaagagcag caactggaag    420
gagatggacc gcggcgagat caagagtgc agcttcaagg tgaccaccag catccgcaac    480
aagatgcaga aggagtacgc cctgttctac aagctggacg tggtgcccat cgacaacgac    540
cagaccagct acaagctgat caactgccag accagcgtga tcacccaggc ctgccccaag    600
gtgagcttcg agcccatccc catccactac tgcgccccc ccggcttcgc catcctgaag    660
tgcaacgaca agaagttcaa cggcagcggc ccctgcacca cgtgagcac cgtgcagtgc    720 acccacggca tccgccccgt ggtgagcacc cagctgctgc tgaacggcag cctggccgag    780
gagggcgtgg tgatccgcag cgagaacttc accgacaacg ccaagaccat catcgtgcag    840
ctgaaggaga gcgtggagat caactgcacc cgccccaaca caacacccg caagagcatc    900 accatcggcc ccgccgcgc cttctacgcc ccggcgaca tcatcggcga catccgccag    960
gcccactgca acatcagcgg cgagaagtgg aacaacaccc tgaagcagat cgtgaccaag   1020
ctgcaggccc agttcggcaa caagaccatc gtgttcaagc agagcagcgg cggcgacccc   1080
gagatcgtga tgcacagctt caactgcggc ggcgagttct tctactgcaa cagcacccag   1140
ctgttcaaca gcacctggaa caacaccatc ggccccaaca caccaacgg caccatcacc   1200 ctgccctgcc gcatcaagca gatcatcaac cgctggcagg aggtgggcaa ggccatgtac   1260
gcccccccca tccgcggcca gatccgctgc agcagcaaca tcaccggcct gctgctgacc   1320
cgcgacggcg gcaaggagat cagcaacacc accgagatct ccgccccgg cggcggcgac   1380 atgcgcgaca ctggcgcag cgagctgtac aagtacaagg tggtgaagat cgagcccctg   1440
ggcgtggccc ccaccaaggc caagcgccgc gtggtgcagc gcgagaagcg cgccgtgacc   1500
```

```
ctgggcgcca tgttcctggg cttcctgggc gccgccggca gcaccatggg cgcccgcagc    1560
ctgaccctga ccgtgcaggc cgccagctg ctgagcggca tcgtgcagca gcagaacaac    1620
ctgctgcgcg ccatcgaggc ccagcagcac ctgctgcagc tgaccgtgtg gggcatcaag    1680
cagctgcagg cccgcgtgct ggccgtggag cgctacctga aggaccagca gctgctgggc    1740
atctggggct gcagcggcaa gctgatctgc accaccgccg tgccctggaa cgccagctgg    1800
agcaacaaga gcctggacca gatctggaac aacatgacct ggatggagtg ggagcgcgag    1860
atcgacaact acaccaacct gatctacacc ctgatcgagg agagccagaa ccagcaggag    1920
aagaacgagc aggagctgct ggagctggac aagtgggcca gcctgtggaa ctggttcgac    1980
atcagcaagt ggctgtggta catctaa                                        2007

<210> SEQ ID NO 64
<211> LENGTH: 2007
<212> TYPE: DNA
<213> ORGANISM: Artificial Sequence
<220> FEATURE:
<223> OTHER INFORMATION: Description of Artificial Sequence:
      gp140mut7.modSF162.GM154

<400> SEQUENCE: 64
atggatgcaa tgaagagagg gctctgctgt gtgctgctgc tgtgtggagc agtcttcgtt      60
tcgcccagcg ccgtgagaa gctgtgggtg accgtgtact acggcgtgcc cgtgtggaag     120
gaggccacca ccaccctgtt ctgcgccagc gacgccaagg cctacgacac cgaggtgcac     180
aacgtgtggg ccaccacgc ctgcgtgccc accgacccca ccccaggag atcgtgctg      240 gagaacgtga ccgagaactt caacatgtgg aagaacaaca tggtggagca gatgcacgag     300
gacatcatca gcctgtggga ccagagcctg aagcccctgc gtgaagctga ccccctgtgc     360
gtgaccctgc actgcaccaa cctgaagaac gccaccaaca ccaagagcag caactggaag     420
gagatggacc gcggcgagat caagcagtgc agcttcaagg tgaccaccag catccgcaac     480
aagatgcaga aggagtacgc cctgttctac aagctggacg tggtgcccat cgacaacgac     540
aacaccagct acaagctgat caactgcaac accagcgtga tcacccaggc ctgccccaag     600
gtgagcttcg agcccatccc catccactac tgcgcccccg ccggcttcgc catcctgaag     660
tgcaacgaca agaagttcaa cggcagcggc ccctgcacca acgtgagcac cgtgcagtgc     720
acccacggca tccgccccgt ggtgagcacc cagctgctgc tgaacggcag cctggccgag     780
gagggcgtgg tgatccgcag cgagaacttc accgacaacg ccaagaccat catcgtgcag     840
ctgaaggaga gcgtggagat caactgcacc cgccccaaca acaacacccg caagagcatc     900
accatcggcc ccggccgcgc cttctacgcc accggcgaca tcatcggcga catccgccag     960
gcccactgca acatcagcgg cgagaagtgg aacaacaccc tgaagcagat cgtgaccaag    1020
ctgcaggccc agttcggcaa caagaccatc gtgttcaagc agagcagcgg cggcgacccc    1080
gagatcgtga tgcacagctt caactgcggc ggcgagttct tctactgcaa cagcacccag    1140
ctgttcaaca gcacctggaa caacaccatc ggccccaaca acaccaacgg caccatcacc    1200
ctgccctgcc gcatcaagca gatcatcaac cgctggcagg aggtgggcaa ggccatgtac    1260 gccccccca tccgcggcca gatccgctgc agcagcaaca tcaccggcct gctgctgacc    1320
cgcgacggcg gcaaggagat cagcaacacc accgagatct ccgccccgg cggcggcgac    1380 atgcgcgaca actggcgcag cgagctgtac aagtacaagg tggtgaagat cgagcccctg    1440
ggcgtggccc ccaccaaggc catcagcagc gtggtgcaga gcgagaagag cgccgtgacc    1500
ctgggcgcca tgttcctggg cttcctgggc gccgccggca gcaccatggg cgcccgcagc    1560
```

```
ctgaccctga ccgtgcaggc ccgccagctg ctgagcggca tcgtgcagca gcagaacaac    1620
ctgctgcgcg ccatcgaggc ccagcagcac ctgctgcagc tgaccgtgtg gggcatcaag    1680
cagctgcagg cccgcgtgct ggccgtggag cgctacctga aggaccagca gctgctgggc    1740
atctggggct gcagcggcaa gctgatctgc accaccgccg tgccctggaa cgccagctgg    1800
agcaacaaga gcctggacca gatctggaac aacatgacct ggatggagtg ggagcgcgag    1860
atcgacaact acaccaacct gatctacacc ctgatcgagg agagccagaa ccagcaggag    1920
aagaacgagc aggagctgct ggagctggac aagtgggcca gcctgtggaa ctggttcgac    1980
atcagcaagt ggctgtggta catctaa                                        2007
```

```
<210> SEQ ID NO 65
<211> LENGTH: 100
<212> TYPE: PRT
<213> ORGANISM: Artificial Sequence
<220> FEATURE:
<223> OTHER INFORMATION: Description of Artificial Sequence:
      gp140modSF162

<400> SEQUENCE: 65

Asp Ile Ile Ser Leu Trp Asp Gln Ser Leu Lys Pro Cys Val Lys Leu
 1               5                  10                  15

Thr Pro Leu Cys Val Thr Leu His Cys Thr Asn Leu Lys Asn Ala Thr
             20                  25                  30

Asn Thr Lys Ser Ser Asn Trp Lys Glu Met Asp Arg Gly Glu Ile Lys
         35                  40                  45

Asn Cys Ser Phe Lys Val Thr Thr Ser Ile Arg Asn Lys Met Gln Lys
     50                  55                  60

Glu Tyr Ala Leu Phe Tyr Lys Leu Asp Val Val Pro Ile Asp Asn Asp
 65                  70                  75                  80

Asn Thr Ser Tyr Lys Leu Ile Asn Cys Asn Thr Ser Val Ile Thr Gln
                 85                  90                  95

Ala Cys Pro Lys
            100

<210> SEQ ID NO 66
<211> LENGTH: 100
<212> TYPE: PRT
<213> ORGANISM: Artificial Sequence
<220> FEATURE:
<223> OTHER INFORMATION: Description of Artificial Sequence:
      gp140.modSF162.GM154

<400> SEQUENCE: 66

Asp Ile Ile Ser Leu Trp Asp Gln Ser Leu Lys Pro Cys Val Lys Leu
 1               5                  10                  15

Thr Pro Leu Cys Val Thr Leu His Cys Thr Asn Leu Lys Asn Ala Thr
             20                  25                  30

Asn Thr Lys Ser Ser Asn Trp Lys Glu Met Asp Arg Gly Glu Ile Lys
         35                  40                  45

Gln Cys Ser Phe Lys Val Thr Thr Ser Ile Arg Asn Lys Met Gln Lys
     50                  55                  60

Glu Tyr Ala Leu Phe Tyr Lys Leu Asp Val Val Pro Ile Asp Asn Asp
 65                  70                  75                  80

Asn Thr Ser Tyr Lys Leu Ile Asn Cys Asn Thr Ser Val Ile Thr Gln
                 85                  90                  95

Ala Cys Pro Lys
            100
```

<210> SEQ ID NO 67
<211> LENGTH: 100
<212> TYPE: PRT
<213> ORGANISM: Artificial Sequence
<220> FEATURE:
<223> OTHER INFORMATION: Description of Artificial Sequence:
gp140.modSF162.GM154-186-195

<400> SEQUENCE: 67

```
Asp Ile Ile Ser Leu Trp Asp Gln Ser Leu Lys Pro Cys Val Lys Leu
  1               5                  10                  15

Thr Pro Leu Cys Val Thr Leu His Cys Thr Asn Leu Lys Asn Ala Thr
             20                  25                  30

Asn Thr Lys Ser Ser Asn Trp Lys Glu Met Asp Arg Gly Glu Ile Lys
         35                  40                  45

Gln Cys Ser Phe Lys Val Thr Thr Ser Ile Arg Asn Lys Met Gln Lys
     50                  55                  60

Glu Tyr Ala Leu Phe Tyr Lys Leu Asp Val Val Pro Ile Asp Asn Asp
 65                  70                  75                  80

Gln Thr Ser Tyr Lys Leu Ile Asn Cys Gln Thr Ser Val Ile Thr Gln
                 85                  90                  95

Ala Cys Pro Lys
            100
```

<210> SEQ ID NO 68
<211> LENGTH: 100
<212> TYPE: PRT
<213> ORGANISM: Artificial Sequence
<220> FEATURE:
<223> OTHER INFORMATION: Description of Artificial Sequence:
gp140.modSF162.GM135-154-186-195

<400> SEQUENCE: 68

```
Asp Ile Ile Ser Leu Trp Asp Gln Ser Leu Lys Pro Cys Val Lys Leu
  1               5                  10                  15

Thr Pro Leu Cys Val Thr Leu His Cys Thr Asn Leu Lys Gln Ala Thr
             20                  25                  30

Asn Thr Lys Ser Ser Asn Trp Lys Glu Met Asp Arg Gly Glu Ile Lys
         35                  40                  45

Gln Cys Ser Phe Lys Val Thr Thr Ser Ile Arg Asn Lys Met Gln Lys
     50                  55                  60

Glu Tyr Ala Leu Phe Tyr Lys Leu Asp Val Val Pro Ile Asp Asn Asp
 65                  70                  75                  80

Gln Thr Ser Tyr Lys Leu Ile Asn Cys Gln Thr Ser Val Ile Thr Gln
                 85                  90                  95

Ala Cys Pro Lys
            100
```

The invention claimed is:

1. An expression cassette comprising a polynucleotide sequence which has at least 90% sequence identity to SEQ ID NO:42.

2. The expression cassette of claim 1 wherein the nucleotide sequence has at least 95% identity.

3. The expression cassette of claim 1 wherein the nucleotide sequence has at least 98% identity.

4. The expression cassette of claim 1 wherein the nucleotide sequence is SEQ ID NO:42.

5. The expression cassette of claim 1 which is in a gene delivery vector.

6. The expression cassette of claim 5 wherein the gene delivery vector is a non-viral vector.

7. The expression cassette of claim 5 wherein the vector is coated on a gold or tungsten particle.

8. The expression cassette of claim 5 wherein the vector is encapsulated in a liposome preparation.

9. The expression cassette of claim 5 wherein the vector is a viral vector.

10. The expression cassette of claim 9 wherein the viral vector is selected from the group consisting of a retroviral vector, an alphaviral vector, and a lentiviral vector.

* * * * *